US012553061B2

(12) United States Patent
Mathew et al.

(10) Patent No.: US 12,553,061 B2
(45) Date of Patent: Feb. 17, 2026

(54) METHODS AND COMPOSITIONS FOR MODIFYING CYTOKININ RECEPTOR HISTIDINE KINASE GENES IN PLANTS

(71) Applicant: Pairwise Plants Services, Inc., Durham, NC (US)

(72) Inventors: Lolita George Mathew, Cary, NC (US); Xiaoyu Zhang, Cary, NC (US); Devin O'Connor, Hillsborough, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 312 days.

(21) Appl. No.: 17/819,975

(22) Filed: Aug. 16, 2022

(65) Prior Publication Data

US 2023/0063927 A1 Mar. 2, 2023

Related U.S. Application Data

(60) Provisional application No. 63/234,000, filed on Aug. 17, 2021.

(51) Int. Cl.
*C12N 15/82* (2006.01)
*C12N 9/22* (2006.01)
*C12N 15/11* (2006.01)

(52) U.S. Cl.
CPC ........... *C12N 15/8261* (2013.01); *C12N 9/22* (2013.01); *C12N 15/11* (2013.01); *C12N 15/8213* (2013.01); *C12N 2310/20* (2017.05)

(58) Field of Classification Search
None
See application file for complete search history.

(56) References Cited

U.S. PATENT DOCUMENTS

2009/0183270 A1* 7/2009 Adams .............. C12N 15/8247 800/312
2015/0082481 A1 3/2015 La Rosa et al.

FOREIGN PATENT DOCUMENTS

CN 103484472 A * 1/2014
WO 02099079 A2 12/2002
WO WO-2013072832 A1 * 5/2013 ......... C12N 15/8261
WO 2019193143 A1 10/2019

OTHER PUBLICATIONS

Taylor, Isaiah, et al. "Mechanism and function of root circumnutation." Proceedings of the National Academy of Sciences 118.8 (2021): e2018940118. (Year: 2021).*
Ding, Wona, et al. "Isolation, characterization and transcriptome analysis of a cytokinin receptor mutant Osckt1 in rice." Frontiers in Plant Science 8 (2017): 88. (Year: 2017).*
Burr, Christian A., et al. "The HK5 and HK6 cytokinin receptors mediate diverse developmental pathways in rice." Development 147.20 (2020): dev191734. (Year: 2020).*
Burr, Christian A., et al. "The HK5 and HK6 cytokinin receptors mediate diverse developmental pathways in rice." Development 147.20 (2020): dev191734. Supplemental Materials (Year: 2020).*
Yamada, Hisami, et al. "The *Arabidopsis* AHK4 histidine kinase is a cytokinin-binding receptor that transduces cytokinin signals across the membrane." Plant and Cell Physiology 42.9 (2001): 1017-1023 (Year: 2001).*
Liu, Yun, et al. "Research progress on the roles of cytokinin in plant response to stress." International journal of molecular sciences 21.18 (2020): 6574 (Year: 2020).*
English Translation of CN 103484472 A (Year: 2014).*
International Search Report and Written Opinion for International Application No. PCT/US2022/074991 dated Jan. 12, 2023 (28 pages).
Uniprot Database accession No. A0A445JCK0. RecName: Histidine kinase {EC0:00002561ARBA:ARBA00012438}; EC=2.7.13.3 {EC0:00002561ARBA:ARBA00012438} (Apr. 2021).
Bartrina, Isabel, et al., "Gain-of-function mutants of the cytokinin receptors AHK2 and AHK3 regulate plant organ size, flowering time and plant longevity", Plant Physiol, 173, 2017, 1783-1797.
Heyl, Alexander, et al., "Evolutionary proteomics identifies amino acids essential for ligand-binding of the cytokinin receptor CHASE domain", BMC Evolutionary Biology 7, 2007, 1-8.
Miwa, Kumiko, et al., "Identification of amino acid substitutions that render the *Arabidopsis* cytokinin receptor histidine kinase AHK4 constitutively active", Plant Cell Physiol. 48, 2007, 1809-1814.
Muszynski, Michael G., et al., "The Maize Hairy Sheath Frayed1 (Hsf1) Mutation Alters Leaf Patterning Through Increased Cytokinin Signaling", Plant Cell, 32, 2020.
Niemann, Michael C.E., et al., "*Arabidopsis* ROCK1 transports UDP-GlcNAc/UDP-GalNAc and regulates ER protein quality control and cytokinin activity", Proc Natl Acad Sci USA 112, 2015, 291-296.
Nongpiur, Ramsong, et al., "Histidine kinases in plants: Cross talk between hormone and stress responses", Plant Signaling & Behavior. 7(10):1230-1237 (2012).
Romanov, Georgy A., et al., "Biochemical characteristics and ligand-binding properties of *Arabidopsis* cytokinin receptor AHK3 compared to CRE1/AHK4 as revealed by a direct binding assay", J. Exp. Bot. 57, 2006, 4051-4058.
Saucedo, Manuel, et al., "An altered hydrotropic response (ahrl) mutant of *Arabidopsis* recovers root hydrotropism with cytokinin", Journal of Experimental Botany. 63(10):3587-3602 (2012).
Steklov, Mikhail Yu, et al., "Structural basis for cytokinin receptor signaling: an evolutionary approach", Plant Cell Rep. 32, 2013, 781-793.

(Continued)

*Primary Examiner* — Amjad Abraham
*Assistant Examiner* — Kelsey L McWilliams
(74) *Attorney, Agent, or Firm* — Myers Bigel, P.A.

(57) ABSTRACT

This invention relates to compositions and methods for modifying Cytokinin Receptor Histidine Kinase (HK) genes in plants, optionally to improve yield traits, the HK genes encoding a histidine kinase (HK) polypeptide. The invention further relates to plants having increased improved yield traits produced using the methods and compositions of the invention.

17 Claims, No Drawings

Specification includes a Sequence Listing.

(56) References Cited

OTHER PUBLICATIONS

Stolz, Andrea, et al., "The specificity of cytokinin signalling in *Arabidopsis thaliana* is mediated by differing ligand affinities and expression profiles of the receptors", Plant J. 67, 2011, 157-168.
Tirichine, Leila, et al., "A Gain-of-Function Mutation in a Cytokinin Receptor Triggers Spontaneous Root Nodule Organogenesis", Science, 315, 2007, 104-107.

* cited by examiner

SEQUENCE LISTING

```
Sequence total quantity: 261
SEQ ID NO: 1           moltype = AA  length = 1228
FEATURE                Location/Qualifiers
REGION                 1..1228
                       note = Lachnospiraceae bacterium
source                 1..1228
                       mol_type = protein
                       organism = unidentified
SEQUENCE: 1
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
```

```
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 2           moltype = AA  length = 1307
FEATURE                Location/Qualifiers
source                 1..1307
                       mol_type = protein
                       organism = Acidaminococcus sp.
SEQUENCE: 2
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN               1307

SEQ ID NO: 3           moltype = AA  length = 1241
FEATURE                Location/Qualifiers
source                 1..1241
                       mol_type = protein
                       organism = Butyrivibrio proteoclasticus
SEQUENCE: 3
MLLYENYTKR NQITKSLRLE LRPQGKTLRN IKELNLLEQD KAIYALLERL KPVIDEGIKD  60
IARDTLKNCE LSFEKLYEHF LSGDKKAYAK ESERLKKEIV KTLIKNLPEG IGKISEINSA  120
KYLNGVLYDF IDKTHKDSEE KQNILSDILE TKGYLALFSK FLTSRITTLE QSMPKRVIEN  180
FEIYAANIPK MQDALERGAV SFAIEYESIC SVDYYNQILS QEDIDSYNRL ISGIMDEDGA  240
KEKGINQTIS EKNIKIKSEH LEEKPFRILK QLHKQILEER EKAFTIDHID SDEEVVQVTK  300
EAFEQTKEQW ENIKKINGFY AKDPGDITLF IVVGPNQTHV LSQLIYGEHD RIRLLLEEYE  360
KNTLEVLPRR TKSEDARYDK FVNAVPKKVA KESHTFDGLQ KMTGDDRLFI LYRDELARNY  420
MRIKEAYGTF ERDILKSRRG IKGNRDVQES LVSFYDELTK FRSALRIINS GNDEKADPIF  480
YNTFDGIFEK ANRTYKAENL CRNYVTKSPA DDARIMASCL GTPARLRTHW WNGEENFAIN  540
DVAMIRRGDE YYYFVLTPDV KPVDLKTKDE TDAQIFVQRK GAKSFLGLPK ALFKCILEPY  600
FESPEHKNDK NCVIEEYVSK PLTIDRRAYD IFKNGTFKKT NIGIDGLTEE KFKDDCRYLI  660
DVYKEFIAVY TRYSCFNMSG LKRADEYNDI GEFFSDVDTR LCTMEWIPVS FERINDMVDK  720
KEGLLFLVRS MFLYNRPRKP YERTFIQLFS DSNMEHTSML LNSRAMIQYR AASLPRRVTH  780
KKGSILVALR DSNGEHIPMH IREAIYKMKN NFDISSEDFI MAKAYLAEHD VAIKKANEDI  840
IRNRRYTEDK FFLSLSYTKN ADISARTLDY INDKVEEDTQ DSRMAVIVTR NLKDLTYVAV  900
VDEKNNVLEE KSLNEIDGVN YRELLKERTK IKYHDKTRLW QYDVSSKGLK EAYVELAVTQ  960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
LLEDKAVFDG NMAEKFLDKT AISGKSVELI YKWFANALYG IITKKDGEKI YRSPITGTEI  1200
DVSKNTTYNF GKKFMFKQEY RGDGDFLDAF LNYMQAQDIA V                      1241

SEQ ID NO: 4           moltype = AA  length = 1238
FEATURE                Location/Qualifiers
source                 1..1238
                       mol_type = protein
                       organism = Candidatus Methanoplasma termitum
SEQUENCE: 4
MNNYDEFTKL YPIQKTIRFE LKPQGRTMEH LETFNFFEED RDRAEKYKIL KEAIDEYHKK  60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD IVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIDRTG NNDAFNEYIS  420
KMRTAREKID AARKEMKFIS EKISGDEESI HIIKTLLDSV QQFLHFFNLF KARQDIPLDG  480
```

```
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLR PVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                         1238

SEQ ID NO: 5            moltype = AA  length = 1281
FEATURE                 Location/Qualifiers
source                  1..1281
                        mol_type = protein
                        organism = Eubacterium eligens
SEQUENCE: 5
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                           1281

SEQ ID NO: 6            moltype = AA  length = 1300
FEATURE                 Location/Qualifiers
source                  1..1300
                        mol_type = protein
                        organism = Francisella novicida
SEQUENCE: 6
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKVNY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 7            moltype = AA  length = 1206
FEATURE                 Location/Qualifiers
source                  1..1206
                        mol_type = protein
                        note = Lachnospiraceae sp.
                        organism = unidentified
SEQUENCE: 7
```

```
MYYESLTKQY PVSKTIRNEL IPIGKTLDNI RQNNILESDV KRKQNYEHVK GILDEYHKQL  60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                             1206

SEQ ID NO: 8           moltype = AA  length = 1233
FEATURE                Location/Qualifiers
source                 1..1233
                       mol_type = protein
                       note = Lachnospiraceae sp.
                       organism = unidentified
SEQUENCE: 8
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKKLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDRE TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                               1233

SEQ ID NO: 9           moltype = AA  length = 1227
FEATURE                Location/Qualifiers
source                 1..1227
                       mol_type = protein
                       note = Lachnospiraceae sp.
                       organism = unidentified
SEQUENCE: 9
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI ANINKCPKNI FKINTEVRVL LKHDDNPYVI GIDRGERNLL  840
YIVVVDGKGN IVEQYSLNEI INNFNGIRIK TDYHSLLDKK EKERFEARQN WTSIENIKEL  900
KAGYISQVVH KICELVEKYD AVIALEDLNS GFKNSRVKVE KQVYQKFEKM LIDKLNYMVD  960
KKSNPCATGG ALKGYQITNK FESFKSMSTQ NGFIFYIPAW LTSKIDPSTG FVNLLKTKYT  1020
SIADKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IASNKEWLEY AQTSVKH                                      1227
```

```
SEQ ID NO: 10          moltype = AA  length = 1264
FEATURE                Location/Qualifiers
source                 1..1264
                       mol_type = protein
                       organism = Leptospira inadai
SEQUENCE: 10
MEDYSGFVNI YSIQKTLRFE LKPVGKTLEH IEKKGFLKKD KIRAEDYKAV KKIIDKYHRA  60
YIEEVFDSVL HQKKKKDKTR FSTQFIKEIK EFSELYYKTE KNIPDKERLE ALSEKLRKML  120
VGAFKGEFSE EVAEKYNKNL FSKELIRNEI EKFCETDEER KQVSNFKSFT TYFTGFHSNR  180
QNIYSDEKKS TAIGYRIIHQ NLPKFLDNLK IIESIQRRFK DFPWSDLKKN LKKIDKNIKL  240
TEYFSIDGFV NVLNQKGIDA YNTILGGKSE ESGEKIQGLN EYINLYRQKN NIDRKNPLNV  300
KILFKQILGD RETKSFIPEA FPDDQSVLNS ITEFAKYLKL DKKKKSIIAE LKKFLSSFNR  360
YELDGIYLAN DNSLASISTF LFDDWSFIKK SVSFKYDESV GDPKKKIKSP LKYEKEKEKW  420
LKQKYYTISF LNDAIESYSK SQDEKRVKIR LEAYFAEFKS KDDAKKQFDL LERIEEAYAI  480
VEPLLGAEYP RDRNLKADKK EVGKIKDFLD SIKSLQFFLK PLLSAEIFDE KDLGFYNQLE  540
GYYEEIDISG HLYNKVRNYL TGKIYSKEKF KLNFENSTLL KGWDENREVA NLCVIFREDQ  600
KYYLGVMDKE NNTILSDIPK VKPNELFYEK MVYKLIPTPH MQLPRIIFSS DNLSIYNPSK  660
SILKIREAKS FKEGKNFKLK DCHKFIDFYK ESISKNEDWS RFDFKFSKTS SYENISEFYR  720
EVERQGYNLD FKKVSKFYID SLVEDGKLYL FQIYNKDFSI FSKGKPNLHT IYFRSLFSKE  780
NLKDVCLKLN GEAEMFFRKK SINYDEKKKR EGHHPELFEK LKYPILKDKR YSEDKFQFHL  840
PISLNFKSKE RLNFNLKVNE FLKRNKDINI IGIDRGERNL LYLVMINQKG EILKQTLLDS  900
MQSGKGRPEI NYKEKLQEKE IERDKARKSW GTVENIKELK EGYLSIVIHQ ISKLMVENNA  960
IVVLEDLNIG FKRGRQKVER QVYQKFEKML IDKLNFLVFK ENKPTEPGGV LKAYQLTDEF  1020
QSFEKLSKQT GFLFYVPSWN TSKIDPRTGF IDFLHPAYEN IEKAKQWINK FDSIRFNSKM  1080
DWFEFTADTR KFSENLMLGK NRVWVICTTN VERYFTSKTA NSSIQYNSIQ ITEKLKELFV  1140
DIPFSNGQDL KPEILRKNDA VFFKSLLFYI KTTLSLRQNN GKKGEEEKDF ILSPVVDSKG  1200
RFFNSLEASD DEPKDADANG AYHIALKGLM NLLVLNETKE ENLSRPKWKI KNKDWLEFVW  1260
ERNR                                                              1264

SEQ ID NO: 11          moltype = AA  length = 1373
FEATURE                Location/Qualifiers
source                 1..1373
                       mol_type = protein
                       organism = Moraxella bovoculi
SEQUENCE: 11
MLFQDFTHLY PLSKTVRFEL FIDRTLEHIH AKNFLSQDET MADMHQKVKV ILDDYHRDFI  60
ADMMGEVKLT KLAEFYDVYL KFRKNPKDDE LQKAQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFKD  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQKDFMLHV PITMNFGVQG  960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373

SEQ ID NO: 12          moltype = AA  length = 1352
FEATURE                Location/Qualifiers
source                 1..1352
                       mol_type = protein
                       note = Parcubacteria bacterium
                       organism = unidentified
SEQUENCE: 12
MENIFDQFIG KYSLSKTLRF ELKPVGKTED FLKINKVFEK DQTIDDSYNQ AKFYFDSLHQ  60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
MGNAKGDNAN RYQKMIYKQI ADASKDVPRL LLTSKKAMEK FKPSQEILRI KKEKTFKRES  720
```

```
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 13          moltype = AA  length = 1260
FEATURE                Location/Qualifiers
source                 1..1260
                       mol_type = protein
                       organism = Porphyromonas crevioricanis
SEQUENCE: 13
MDSLKDFTNL YPVSKTLRFE LKPVGKTLEN IEKAGILKED EHRAESYRRV KKIIDTYHKV  60
FIDSSLENMA KMGIENEIKA MLQSFCELYK KDHRTEGEDK ALDKIRAVLR GLIVGAFTGV  120
CGRRENTVQN EKYESLFKEK LIKEILPDFV LSTEAESLPF SVEEATRSLK EFDSFTSYFA  180
GFYENRKNIY STKPQSTAIA YRLIHENLPK FIDNILVFQK IKEPIAKELE HIRADFSAGG  240
YIKKDERLED IFSLNYYIHV LSQAGIEKYN ALIGKIVTEG DGEMKGLNEH INLYNQQRGR  300
EDRLPLFRPL YKQILSDREQ LSYLPESFEK DEELLRALKE FYDHIAEDIL GRTQQLMTSI  360
SEYDLSRIYV RNDSQLTDIS KKMLGDWNAI YMARERAYDH EQAPKRITAK YERDRIKALK  420
GEESISLANL NSCIAFLDNV RDCRVDTYLS TLGQKEGPHG LSNLVENVFA SYHEAEQLLS  480
FPYPEENNLI QDKDNVVLIK NLLDNISDLQ RFLKPLWGMG DEPDKDERFY GEYNYIRGAL  540
DQVIPLYNKV RNYLTRKPYS TRKVKLNFGN SQLLSGWDRN KEKDNSCVIL RKGQNFYLAI  600
MNNRHKRSFE NKMLPEYKEG EPYFEKMDYK FLPDPNKMLP KVFLSKKGIE IYKPSPKLLE  660
QYGHGTHKKG DTFSMDDLHE LIDFFKHSIE AHEDWKQFGF KFSDTATYEN VSSFYREVED  720
QGYKLSFRKV SESYVYSLID QGKLYLFQIY NKDFSPCSKG TPNLHTLYWR MLFDERNLAD  780
VIYKLDGKAE IFFREKSLKN DHPTHPAGKP IKKKSRQKKG EESLFEYDLV KDRRYTMDKF  840
QFHVPITMNF KCSAGSKVND MVNAHIREAK DMHVIGIDRG ERNLLYICVI DSRGTILDQI  900
SLNTINDIDY HDLLESRDKD RQQEHRNWQT IEGIKELKQG YLSQAVHRIA ELMVAYKAVV  960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 14          moltype = AA  length = 664
FEATURE                Location/Qualifiers
source                 1..664
                       mol_type = protein
                       organism = Prevotella disiens
SEQUENCE: 14
NSYKEDKKRL NKVIIAYIEQ IKQTNIKKSI IESISKYPNI SDDDKVTPSS LLEKIKKVSI  60
DSYNGILSFK SFQSVNKEVI DNLLKTISPL KNKAEFLDLI NKDYQIFTEV QAVIDEICKQ  120
KTFIYFPISN VELEKEMGDK DKPLCLFQIS NKDLSFAKTF SANLRKKRGA ENLHTMLFKA  180
LMEGNQDNLD LGSGAIFYRA KSLDGNKPTH PANEAIKCRN VANKDKVSLF TYDIYKNRRY  240
MENKFLFHLS IVQNYKAAND SAQLNSSATE YIRKADDLHI IGIDRGERNL LYYSVIDMKG  300
NIVEQDSLNI IRNNDLETDY HDLLDKREKE RKANRQNWEA VEGIKDLKKG YLSQAVHQIA  360
QLMLKYNAII ALEDLGQMFV TRGQKIEKAV YQQFEKSLVD KLSYLVDKKR PYNELGGILK  420
AYQLASSITK NNSDKQNGFL FYVPAWNTSK IDPVTGFTDL LRPKAMTIKE AQDFFGAFDN  480
ISYNDKGYFE FETNYDKFKI RMKSAQTRWT ICTFGNRIKR KKDKNYWNYE EVELTEEFKK  540
LFKDSNIDYE NCNLKEEIQN KDNRKFFDDL IKLLQLTLQM RNSDDKGNDY IISPVANAEG  600
QFFDSRNGDK KLPLDADANG AYNIARKGLW NIRQIKQTKN KDDLNLSISS TEWLDFVREK  660
PYLK                                                               664

SEQ ID NO: 15          moltype = AA  length = 1484
FEATURE                Location/Qualifiers
SITE                   1073
                       note = misc_feature - Xaa can be any naturally occurring
                        amino acid
source                 1..1484
                       mol_type = protein
                       note = Peregrinibacteria bacterium
                       organism = unidentified
SEQUENCE: 15
MSNFFKNFTN LYELSKTLRF ELKPVGDTLT NMKDHLEYDE KLQTFLKDQN IDDAYQALKP  60
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYYFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
SDKYFANYHD LQDRLKEAKV FQKADKKSED DIKIPEAIEL SGLFGVLDSL ADWQTTLFKS  480
SILSNEKLKI ITDSQTPSEA LLKMIFNDIE KNMESFLKET NDIITLKKYK GNKEGTEKIK  540
QWFDYTLAIN RMLKYFLVKE NKIKGNSLDT NISEALKTLI YSDDAEWFKW YDALRNYLTQ  600
```

```
KPQDEAKENK LKLNFDNPSL AGGWDVNKEC SNFCVILKDK NEKKYLAMIK KGENTLFQKE  660
WTEGRGKNLT KKSNPLFEIN NCEILSKMEY DFWADVSKMI PKCSTQLKAV VNHFKQSDNE  720
FIFPIGYKVT SGEKFREECK ISKQDFELNN KVFNKNELSV TAMRYDLSST QEKQYIKAFQ  780
KEYWELLFKQ EKRDTKLTNN EIFNEWINFC NKKYSELLSW ERKYKDALTN WINFCKYFLS  840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT  960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
DYYFEYDKGE FVDEKTGEIK PKKWRLYSGE NGKSLDRFRG EREKDKYEWK IDKIDIVKIL  1320
DDLFVNFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                  1484

SEQ ID NO: 16          moltype = AA  length = 1245
FEATURE                Location/Qualifiers
source                 1..1245
                       mol_type = protein
                       organism = Porphyromonas macacae
SEQUENCE: 16
MKTQHFFEDF TSLYSLSKTI RFELKPIGKT LENIKKNGLI RRDEQRLDDY EKLKKVIDEY  60
HEDFIANILS SFSFSEEILQ SYIQNLSISE ARAKIEKTMR DTLAKAFSED ERYKSIFKKE  120
LVKKDIPVWC PAYKSLCKKF DNFTTSLVPF HENRKNLYTS NEITASIPYR IVHVNLPKFI  180
QNIEALCELQ KKMGADLYLE MMENLRNVWP SFVKTPDDLC NLKTYNHLMV QSSISEYNRF  240
VGGYSTEDGT KHQGINEWIN IYRQRNKEMR LPGLVFLHKQ ILAKVDSSSF ISDTLENDDQ  300
VFCVLRQFRK LFWNTVSSKE DDAASLKDLF CGLSGYDPEA IYVSDAHLAT ISKNIFDRWN  360
YISDAIRRKT EVLMPRKKES VERYAEKISK QIKKRQSYSL AELDDLLAHY SEESLPAGFS  420
LLSYFTSLGG QKYLVSDGEV ILYEEGSNIW DEVLIAFRDL QVILDKDFTE KKLGKDEEAV  480
SVIKKALDSA LRLRKFFDLL SGTGAEIRRD SSFYALYTDR MDKLKGLLKM YDKVRNYLTK  540
KPYSIEKFKL HFDNPSLLSG WDKNKELNNL SVIFRQNGYY YLGIMTPKGK NLFKTLPKLG  600
AEEMFYEKME YKQIAEPMLM LPKVFFPKKT KPAFAPDQSV VDIYNKKTFK TGQKGFNKKD  660
LYRLIDFYKE ALTVHEWKLF NFSFSPTEQY RNIGEFFDEV REQAYKVSMV NVPASYIDEA  720
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQHGIDR GERNLLYISR IDTRGNLLEQ FSLNVIESDK GDLRTDYQKI  900
LGDREQERLR RRQEWKSIES IKDLKDGYMS QVVHKICNMV VEHKAIVVLE NLNLSFMKGR  960
KKVEKSVYEK FERMLVDKLN YLVVDKKNLS NEPGGLYAAY QLTNPLFSFE ELHRYPQSGI  1020
LFFVDPWNTS LTDPSTGFVN LLGRINYTNV GDARKFFDRF NAIRYDGKGN ILFDLDLSRF  1080
DVRVETQRKL WTLTTFGSRI AKSKKSGKWM VERIENLSLC FLELFEQFNI GYRVEKDLKK  1140
AILSQDRKEF YVRLIYLFNL MMQIRNSDGE EDYILSPALN EKNLQFDSRL IEAKDLPVDA  1200
DANGAYNVAR KGLMVVQRIK RGDHESIHRI GRAQWLRYVQ EGIVE                 1245

SEQ ID NO: 17          moltype = AA  length = 1250
FEATURE                Location/Qualifiers
source                 1..1250
                       mol_type = protein
                       organism = Smithella sp.
SEQUENCE: 17
MQTLFENFTN QYPVSKTLRF ELIPQGKTKD FIEQKGLLKK DEDRAEKYKK VKNIIDEYHK  60
DFIEKSLNGL KLDGLEKYKT LYLKQEKDDK DKKAFDKEKE NLRKQIANAF RNNEKFKTLF  120
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTDKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI  1020
FYVPAWNTSK TDPATGFIDF LKPRYENLNQ AKDFFEKFDS IRLNSKADYF EFAFDFKNFT  1080
EKADGGRTKW TVCTTNEDRY QWNRALNNNR GSQEKYDITA ELKSLFDGKV DYKSGKDLKQ  1140
QIASQESADF FKALMKNLSI TLSLRHNNGE KGDNEQDYIL SPVADSKGRF FDSRKADDDM  1200
PKNADANGAY HIALKGLWCL EQISKTDDLK KVKLAISNKE WLEFVQTLKG             1250

SEQ ID NO: 18          moltype = DNA  length = 3987
FEATURE                Location/Qualifiers
source                 1..3987
                       mol_type = other DNA
                       organism = synthetic construct
SEQUENCE: 18
atggccggga gcaagaagcg ccggataaag caggacacgc agttcgaggg cttcaccaac  60
```

-continued

```
ctgtaccaag tctccaagac gctccggttc gagcttatcc cgcaagggaa gaccctgaaa  120
cacatccagg aacaaggttt catcgaggag gacaaggccc gcaacgacca ctacaaggag  180
ctcaagccca taatcgatcg gatctacaag acgtacgccg accagtgcct ccaactggtg  240
cagctcgact gggagaacct gagcgccgcc attgacagct accgcaagga aaagacggag  300
gagacgcgca acgcccttat tgaggagcaa gccacctacc gcaacgccat ccacgactac  360
ttcatcgggc gcaccgacaa cctgacggac gcgatcaaca agcgccacgc ggaaatctac  420
aagggccttt tcaaggccga gctcttcaac gggaaggtcc taaaacagct cgggactgtc  480
acgacaaccg agcatgagaa cgccctcctt cgcagcttcg acaagttcac cacatacttc  540
tcgggcttct accggaaccg caagaacgtt ttcagcgccg aggacatctc caccgccatc  600
ccgcacagga tcgtccagga caacttcccc aagttcaagg agaactgcca catcttcacg  660
cgcctgatta cagccgtacc ttcacttcgt gagcacttcg agaacgtcaa aaaggccatc  720
gggatcttcg tctccacgtc catcgaggag gtattctctt tcccgttcta taaccagctc  780
ctgacccaga cgcagatcga cctctacaac cagctactgg gcggcatcag ccgggaggcc  840
gggaccgaga aaataaaggg cctcaacgaa gttctcaacc tggccatcca gaagaacgac  900
gagaccgcgc atatcatcgc atccctgccg catcgcttca ttcctttgtt caagcagata  960
ttgagcgacc ggaacaccct ctcgttcatc ctcgaagaat tcaagagcga cgaggaggtc  1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacggagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg acccggagtt ctccgcgcgc ctcacgggta ttaagctgga gatggagcca  1560
agcttaagct tctacaacaa ggcccgcaac tacgcgacca aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgcca agatgatccc gaagtgctcc  1860
acgcagctca aagccgtcac ggcccacttc cagacgcata ccacgccgat acttctgagc  1920
aacaacttca ttgagccgct agagatcacg aaggagatat acgacctaaa caaccccgaa  1980
aaggagccca agaagttcca gacagcctac gctaagaaga caggtgatca gaagggatat  2040
agggaggcac tctgcaagtg gatcgacttc acgcgcgact tcctgtcgaa atatacaaag  2100
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgg acgcggtgga gacggggaaa ctatacctgt tccaaatata taacaaggac  2280
ttcgctaaag ggcaccacgg gaagcccaac ctgcacacac tctactggac gggcttgttt  2340
tcgccagaaa atttggccaa gacttcgatc aagctcaacg gccaggcgga gttgttttac  2400
cgtcccaagt ctcgcatgaa gcgcatggcg catcgcctcg gagagaaaat gcttaacaag  2460
aagctcaagg atcagaagac gcccatacct gatacgttgt accaggaatt gtacgactac  2520
gtgaaccacc gcctatcgca cgacctctca gacgaggccc gcgccctcct cccaaacgtg  2580
attactaagg aggtttccca tgaaataatc aaggaccgac ggttcaccag cgacaaattt  2640
tttttccacg tgcctatcac gctcaattac caggcggcca actccccatc gaagttcaac  2700
cagcgcgtga acgcctacct taaggagcac ccggagaccc caatcatcgg gatcgaccgt  2760
ggcgagcgga acctgatcta tattacggtg atcgatagca ccgggaagat cctggagcag  2820
cgctccctga acacaatcca gcagtttgac taccagaaga aactcgacaa ccgggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
gtcgtgctgg agaacctcaa cttcgggttt aagtccaagc gcaccggcat cgcggagaag  3060
gcggtgtacc agcagttcga gaagatgctg atcgacaagc tgaactgcct ggtgctcaag  3120
gactaccctg cggagaaggt cggcggggtc ttgaacccgt accagctaac cgaccagttc  3180
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag ggcttcgact tcctgcatta cgacgttaag  3360
acaggcgact tcatcctgca cttcaagatg aaccgcaacc tgtcgttcca gaggggcctg  3420
cccggcttca tgcccgcctg ggatatcgtc tttgagaaga atgagacgca gttcgacgcg  3480
aaggggacgc cgttcatcgc tggaaagcgg atcgtgccgg tcatcgagaa ccaccgcttc  3540
acgggtcgct accgagattt atacccgcc aacgaactaa ttgcgctgct ggaggagaag  3600
gggatcgtgt tccgagatgg cagcaacatt ctcccgaagc tgctggagaa cgacgactcg  3660
cacgctattg acacgatggt cgccctcata cggagcgtgc ttcagatgcg gaacagtaac  3720
gctgccacgg gcgaggacta cattaactcc cccgtccgcg acctcaacgg ggtctgcttc  3780
gatagccgct tccagaaccc ggagtggcct atggatgcgg acgcgaacgg ggcctaccac  3840
atcgccctca agggccaact cctgctcaac cacttgaagg aaagcaaaga cctcaaattg  3900
cagaatggca tcagtaacca ggactggctc gcgtacatcc aggaactgag aaacgggtcc  3960
aagaagcggc gtatcaagca agattga                                      3987
```

```
SEQ ID NO: 19          moltype = DNA  length = 3987
FEATURE                Location/Qualifiers
source                 1..3987
                       mol_type = other DNA
                       organism = synthetic construct
SEQUENCE: 19
atggcgggaa gcaaaaagcg ccggattaag caagacacgc agttcgaggg cttcacgaac  60
ctctaccaag tcagcaagac cctccggttc gagctgatac cacagggaaa gacgctcaag  120
cacatccagg aacagggctt catcgaggag gacaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga gaagactgag  300
gagacccgca acgccctgat cgaggagcaa gcaacctacc ggaacgccat ccacgactac  360
```

```
ttcatcggcc gcaccgacaa cctcaccgac gcgatcaaca agcggcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg agaacgtcaa aaaggcaatt  720
gggatcttcg tctcgaccag cattgaggag gtgttcagct tccccttcta caaccagctc  780
ctcacccaga cgcagatcga cctgtacaat cagttgctcg gcgggataag ccgcgaggcg  840
ggaaccgaaa aaatcaaggg gctgaacgaa gtgttgaacc tcgccatcca gaagaacgac  900
gagaccgcgc acatcatcgc ctccctgccc caccggttca tcccgctgtt caagcagatc  960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgctc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg agcgaaatcc tgtcccacgc gcacgcggcc  1380
ctggatcagc ctctgccgac gaccctcaag aaacaagaag aaaaggaaat cctcaagtcg  1440
cagctcgact cgctgctggg cctgtaccat ctcctcgact ggttcgccgt ggacgagagc  1500
aacgaggtgg accccgagtt ctccgcgcgg cttacgggga tcaagctgga gatggagccc  1560
agcctgtcct tctacaacaa ggcgcgcaac tacgccacca agaagcccta cagcgtggag  1620
aagttcaagc tcaacttcca gatgcccact ctcgcacgtg ggtgggacgt caaccgcgaa  1680
aaaaataatg gggcgatcct gttcgtcaag aacggcctgt actacttggg catcatgccg  1740
aaacagaagg gccgctacaa ggccctgagc ttcgaaccga ccgagaaaac gagcgagggg  1800
ttcgacaaga tgtactacga ctacttcccc gacgccgcga agatgattcc aaagtgctcc  1860
acgcagctta aggccgtgac ggcccacttc cagacgcaca cgaccccgat cctcctcagc  1920
aacaacttca tcgagcccct ggagatcacg aaggagatat acgacctgaa caacccggag  1980
aaggagccca agaaattcca gaccgcctac gccaagaaga caggcgacca aaagggttac  2040
agggaggccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccagcgcat cgcggagaag  2220
gagatcatgg acgcagtgga gacgggcaag ctatacctat ttcagatata caacaaagac  2280
ttcgctaagg gacaccacgg caagcctaac ctgcacaccc tctactggac ggggctcttc  2340
agcccggaga acctcgccaa gacctcgatc aagctcaacg gccaggccga gctgttctac  2400
cggcccaagt cccgcatgaa gcggatggcc caccggctcg gggagaaaat gctcaacaag  2460
aaattgaagg accaaaaaac gccgataccc gacaccctat accaggagct gtacgactat  2520
gtgaaccacc gcctgagcca cgacctcagc gacgaggcgc gggccctcct gccgaacgtc  2580
atcacaaagg aggtcagcca cgagatcatc aaggaccggc gcttcacctc cgacaagttt  2640
ttctttcacg tgcccatcac gctcaactac caggccgcca actcgccgtc caagttcaac  2700
cagcgcgtga acgcctacct caaggagcac cccgagaccc cgatcatcgg gattgaccga  2760
ggggagcgga acctcatcta catcaccgtc atcgacagca ccgggaagat ccttgaacag  2820
cggtcgctca acaccatcca gcagttcgac taccagaaga aactcgacaa ccgggagaag  2880
gagagagtgg cggcccgcca ggcttggtcc gtcgtcggga cgattaagga cttgaaacaa  2940
ggttacctgt cgcaagtgat ccacgagatc gttgacctga tgatccacta ccaagccgtc  3000
gtggtcctgg agaacctcaa cttcggcttc aagagcaaac gaaccggcat cgcggagaag  3060
gccgtgtacc agcagttcga aaaaatgctg atcgacaagc tgaactgcct cgtgctcaag  3120
gactaccccg ctgagaaggt cggcggggtg ctgaacccgt accagctcac tgaccagttc  3180
accagcttcg caaagatggg cacccagtcc ggcttcctgt tctacgtgcc tgcgccatac  3240
acctcgaaga tcgacccgct caccgggttc gtggacccct tcgtctggaa gaccatcaag  3300
aaccacgaga gccgcaagca cttcctggag ggcttcgact tcctccacta cgacgtcaag  3360
accggggact tcatcctgca cttcaagatg aaccgcaacc tcagtttcca gcgcggcctg  3420
ccggggttca tgcccgcttg ggatatagtc ttcgagaaga atgagacgca gttcgacgcg  3480
aagggcaccc cgttcatcgc cgggaagcgc atcgtgccgg tcatcgagaa ccaccggttc  3540
accgggcgct accgcgacct atacccggcg aacgagttga tcgccctcct ggaggagaag  3600
ggcatcgtgt tccgcgacgg ctccaacatc ctcccgaagc tgctcgaaaa cgacgactcc  3660
cacgccatcg acacgatggt cgcgctgatc cggtcggtgc tccagatgcg gaactccaac  3720
gccgcgacgg gcgaggacta catcaacagt ccggtccgcg atctgaacgg cgtctgcttc  3780
gactcccggt tccagaaccc cgagtggccg atggacgcgg acgcgaacgg cgcataccac  3840
atcgccctaa aagggcaatt gctgctcaac cacctcaagg aatccaaaga cctaaagctc  3900
cagaacggca tctccaacca ggactggctg gcgtacatcc aggaactgcg gaacgggagc  3960
aaaaaacgtc ggatcaagca agattga                                     3987
```

```
SEQ ID NO: 20          moltype = DNA  length = 3987
FEATURE                Location/Qualifiers
source                 1..3987
                       mol_type = other DNA
                       organism = synthetic construct
SEQUENCE: 20
atggcgggct ccaagaaacg ccggattaag caagataccc agttcgaggg gttcacgaac  60
ctctaccaag tgagcaagac cctccgattc gaactgattc ctcaggggaa gaccctcaag  120
cacatccagg agcaagggtt catcgaggag gacaaggcgc ggaacgacca ctacaaggaa  180
ctcaaaccca tcatcgaccg catctacaag acctacgccg atcagtgcct ccagctcgtg  240
cagttggact gggagaacct cagcgcggcc attgactcct accggaagga gaaaacggag  300
gagacgcgca acgcgctcat cgaggaacag gcaacctatc gcaacgccat ccacgactac  360
ttcatcggga ggactgacaa cctcactgac gcgattaaca agcgccacgc ggagatatac  420
aagggactct tcaaagcgga gctgtttaac ggcaaggttc tcaagcaact cggcactgtg  480
accacgaccg agcatgagaa cgccctgctc cgctccttcg acaagttcac cacctacttc  540
tccgggttct accgcaaccg caagaatgtc ttcagcgcgg aggacatcag cacggccatt  600
ccacatcgaa tcgtccaaga taacttcccg aagttcaagg agaactgcca catcttcacc  660
```

```
cgactcatta ctgctgtacc gtcgttacgc gaacacttcg agaacgtcaa gaaggcaatt  720
ggaatcttcg tctctacgtc aatagaggag gtgttcagct tccctttcta caaccagctc  780
cttacgcaga cccagataga cctgtacaat cagctcctcg gtgggatcag ccgggaggcg  840
gggactgaga agattaaagg gctcaacgag gtcttgaacc tggccatcca aaaaaacgat  900
gagacggcgc acatcatcgc ctcgctgccc caccggttca tcccgctgtt caagcagatc  960
ctcagtgaca ggaacacctt gagctttatc ctagaggagt tcaagagcga cgaggaggtg  1020
atccagagct tctgcaagta caaaaccctg ctgaggaacg agaacgtcct ggagacggcg  1080
gaggcgctgt tcaacgagct gaactctatc gacttaactc acatattcat ctcgcacaag  1140
aagctggaga ctattagctc tgcactctgc gaccactggg acaccctccg caacgcgctc  1200
tacgagcgcc gcatctcgga gctgaccggg aagatcacca aatccgcgaa ggaaaaggtc  1260
cagcgttccc tcaaacacga ggatattaac ttacaggaga ttatctcagc ggctgggaag  1320
gagttgtcag aggcgttcaa gcagaaaact tccgagatcc tgagccacgc gcacgcagcg  1380
ctcgaccagc ctctgcccac caccctcaaa aagcaggaag aaaaagagat cctcaagagc  1440
cagttggact ccctgctggg gctctatcac cttctcgact ggttcgccgt cgatgagtcg  1500
aacgaggtgg accccgagtt ctccgcccgg ctgaccggca tcaagctaga gatggagccg  1560
tccctcagct tctacaataa ggcccgcaac tacgcgacca aaaaacccta cagcgtggag  1620
aagttcaagc tgaacttcca gatgccgacc ttagcacgcg gttgggacgt aaacagggag  1680
aagaacaatg gagccatcct gttcgtcaag aacgggcttt actacctcgg gataatgccc  1740
aagcagaagg gccgctacaa ggccctttcc ttcgagccga cggagaaaac ctccgagggg  1800
ttcgacaaga tgtactacga ctacttcccc gacgccgcca agatgatccc gaagtgctca  1860
acgcagctaa aagccgtgac cgcccacttc cagacccaca cgacgccgat cctgctgagc  1920
aacaacttca tcgagcccct tgagatcact aaggagatat acgacctgaa caaccccgag  1980
aaggagccca agaagtttca aaccgcctac gccaaaaaaa ctggcgacca aaagggctac  2040
agggaggcgc tgtgtaagtg gatcgacttc acacgcgact tcctttcgaa gtatacgaag  2100
acaacctcta ttgacctgag cagcctgcgt cctagctccc agtacaaaga tttgggcgag  2160
tactacgcgg agcttaatcc actactctac cacatctcat tccagcgcat cgctgagaag  2220
gaaatcatgg acgcggtgga gacaggcaaa ctgtacctct tccagatata caacaaagac  2280
ttcgctaagg ggcaccacgg gaagcccaac cttcatacgc tctactggac gggcctattc  2340
agccccgaaa atctggccaa gacctccatc aagctgaacg gccaagcgga gctgttctac  2400
agacccaaga gccggatgaa gcggatggcc cacaggctcg gcgagaaaat gcttaacaaa  2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca cgagatcatc aaggaccggc ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cgggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
ggttatctgt cccaagtcat ccacgagatc gttgatctga tgatccacta tcaggcagtg  3000
gtggtgctgg agaatctcaa cttcggcttc aagagtaagc ggacgggaat cgccgagaag  3060
gccgtgtacc agcagttcga gaagatgctg atcgacaagc tcaactgcct tgtgctgaaa  3120
gactacccgg ccgagaaggt cggcggcgtc ctcaacccgt accaacttac cgaccagttc  3180
acctccttcg ccaagatggg cactcagtcc gggttcttgt tctacgtccc cgcaccttac  3240
acctctaaga tcgaccctct gactggcttc gtagatccat tcgtgtggaa gaccattaag  3300
aaccacgaga gccgcaagca cttcctggag ggcttcgact tcctgcacta cgacgtgaag  3360
accggggact tcatccttca cttcaagatg aaccggaacc tcagcttcca gcggggcctg  3420
ccggggttca tgcccgcctg ggacatcgtg ttcgagaaga acgagaccca gttcgacgcg  3480
aagggcacgc ccttcatcgc cgggaagcgt atcgtgccgg tgatcgagaa ccatcgtttc  3540
acgggtcgct accgtgacct ctacccggcg aacgagctta tcgcactcct ggaggagaag  3600
ggcatcgtct tccgggacgg ctccaacatc ctcccgaaac tgctggaaaa cgacgactct  3660
cacgccatcg acacgatggt ggccctcatc cggtccgtgc tccaaatgcg gaacagcaac  3720
gccgccaccg gtgaggacta catcaacagc ccggtccggg atctgaacgg ggtgtgcttc  3780
gattcgcggt tccagaatcc tgagtggccg atggacgcgg atgcaaacgg ggcgtaccac  3840
atcgcgctca agggccagtt acttctgaac caccttaagg agtctaaaga tttgaaactc  3900
cagaacggga tctcgaacca ggactggctg gcctacatcc aagagttgcg gaacggcagc  3960
aagaagcggc ggattaagca agattag                                    3987
```

```
SEQ ID NO: 21           moltype = DNA  length = 1592
FEATURE                 Location/Qualifiers
source                  1..1592
                        mol_type = other DNA
                        organism = Medicago truncatula
SEQUENCE: 21
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaattta ttttaataat cacatgtact  600
attttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtccacgtgt cacgttttaa ttggaagagg tgccgttggc gtaatataac  960
```

```
agccaatcga tttttgctat aaaagcaaat caggtaaact aaacttcttc attcttttct  1020
tccccatcgc tacaaaaccg gttcctttgg aaaagagatt cattcaaacc tagcacccaa  1080
ttccgtttca aggtataatc tactttctat tcttcgatta ttttattatt attagctact  1140
atcgtttaat cgatcttttc ttttgatccg tcaaatttaa attcaattag ggttttgttc  1200
ttttctttca tctgattgaa atccttctga attgaaccgt ttacttgatt ttactgttta  1260
ttgtatgatt taatcctttg tttttcaaag acagtcttta gattgtgatt aggggttcat  1320
ataaattttt agatttggat ttttgtattg tatgattcaa aaaatacgtc ctttaattag  1380
attagtacat ggatattttt tacccgattt attgattgtc agggagaatt tgatgagcaa  1440
gttttttgga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                                1592

SEQ ID NO: 22          moltype = DNA  length = 2000
FEATURE                Location/Qualifiers
source                 1..2000
                       mol_type = other DNA
                       organism = Zea mays
SEQUENCE: 22
gtcgtgcccc tctctagaga taaagagcat tgcatgtcta aagtataaaa aattaccaca  60
tattttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttttg caaatagctt gacctatata  300
atacttcatc cattttatta gtacatccat ttaggattta gggttgatgg tttctataga  360
ctaattttta gtacatccat tttattcttt ttagtctcta aattttttaa aactaaaact  420
ctattttagt ttttattta ataatttaga tataaaatga aataaaataa attgactaca  480
aataaaacaa atacccttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                              2000

SEQ ID NO: 23          moltype = AA  length = 228
FEATURE                Location/Qualifiers
source                 1..228
                       mol_type = protein
                       organism = Rattus norvegicus
SEQUENCE: 23
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK                228

SEQ ID NO: 24          moltype = AA  length = 199
FEATURE                Location/Qualifiers
source                 1..199
                       mol_type = protein
                       organism = Homo sapiens
SEQUENCE: 24
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199

SEQ ID NO: 25          moltype = DNA  length = 621
FEATURE                Location/Qualifiers
source                 1..621
                       mol_type = other DNA
```

```
                        organism = Petromyzon marinus
SEQUENCE: 25
acagatgcag agtatgtgag aattcacgaa aagctggaca tctatacctt caagaagcag  60
ttctttaaca ataagaagtc tgtgagccat aggtgctacg tgctgttcga gctgaagaga  120
aggggtgaaa gaagggcatg tttttggggg tatgctgtga acaagcccca gtctggaact  180
gagagaggca ttcacgccga aattttcagc atcagaaagg tggaggaata cctgagggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg gtgtggggct gaacgtgatg gtgtccgagc actatcagtg ctgtagaaag  480
attttcattc agtcctcaca taatcagctg aacgagaata gatggctgga aaagactctg  540
aagagggctg agaagagaag gtccgaactg tcaattatga tccaggtgaa gatcctgcac  600
accactaagt cacctgccgt g                                            621

SEQ ID NO: 26           moltype = AA  length = 160
FEATURE                 Location/Qualifiers
source                  1..160
                        mol_type = protein
                        organism = synthetic construct
SEQUENCE: 26
FERNYDPREL RKETYLLYEI KWGKSGKLWR HWCQNNRTQH AEVYFLENIF NARRFNPSTH  60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                       160

SEQ ID NO: 27           moltype = AA  length = 207
FEATURE                 Location/Qualifiers
source                  1..207
                        mol_type = protein
                        organism = synthetic construct
SEQUENCE: 27
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WVCKLYYEKN ARNQIGLWNL RDNGVGLNVM VSEHYQCCRK IFIQSSHNQL NENRWLEKTL  180
KRAEKRRSEL SIMFQVKILH TTKSPAV                                      207

SEQ ID NO: 28           moltype = AA  length = 228
FEATURE                 Location/Qualifiers
source                  1..228
                        mol_type = protein
                        organism = synthetic construct
SEQUENCE: 28
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH  120
LANPRNRQGL RDLISSGVTI QIMTEQESGY CWHNFVNYSP SNESHWPRYP HLWVRLYVLE  180
LYCIILGLPP CLNILRRKQS QLTSFTIALQ SCHYQRLPPH ILWATGLK               228

SEQ ID NO: 29           moltype = AA  length = 162
FEATURE                 Location/Qualifiers
source                  1..162
                        mol_type = protein
                        organism = synthetic construct
SEQUENCE: 29
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YPENERNRQG LRDLVNSGVT  120
IRIMDLPDYN YCWKTFVSDQ GGDEDYWPGH FAPWIKQYSL KL                     162

SEQ ID NO: 30           moltype = AA  length = 166
FEATURE                 Location/Qualifiers
source                  1..166
                        mol_type = protein
                        organism = Escherichia coli
SEQUENCE: 30
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTD                 166

SEQ ID NO: 31           moltype = AA  length = 166
FEATURE                 Location/Qualifiers
source                  1..166
                        mol_type = protein
                        organism = synthetic construct
SEQUENCE: 31
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM PRQVFNAQKK AQSSTD                 166

SEQ ID NO: 32           moltype = AA  length = 166
FEATURE                 Location/Qualifiers
source                  1..166
```

```
                         mol_type = protein
                         organism = synthetic construct
SEQUENCE: 32
SEVEFSHEYW MRHALTLAKR AWDEREVPVG AVLVLNNRVI GEGWNRSIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM RRQVFNAQKK AQSSTD                 166

SEQ ID NO: 33            moltype = AA  length = 166
FEATURE                  Location/Qualifiers
source                   1..166
                         mol_type = protein
                         organism = synthetic construct
SEQUENCE: 33
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM RRQVFNAQKK AQSSTD                 166

SEQ ID NO: 34            moltype = AA  length = 166
FEATURE                  Location/Qualifiers
source                   1..166
                         mol_type = protein
                         organism = synthetic construct
SEQUENCE: 34
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM PRQVFNAQKK AQSSTD                 166

SEQ ID NO: 35            moltype = AA  length = 1763
FEATURE                  Location/Qualifiers
source                   1..1763
                         mol_type = protein
                         organism = synthetic construct
SEQUENCE: 35
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTDSGGSSG GSSGSETPGT SESATPESSG GSSGGSDKKY SIGLAIGTNS VGWAVITDEY  420
KVPSKKFKVL GNTDRHSIKK NLIGALLFDS GETAEATRLK RTARRRYTRR KNRICYLQEI  480
FSNEMAKVDD SFFHRLEESF LVEEDKKHER HPIFGNIVDE VAYHEKYPTI YHLRKKLVDS  540
TDKADLRLIY LALAHMIKFR GHFLIEGDLN PDNSDVDKLF IQLVQTYNQL FEENPINASG  600
VDAKAILSAR LSKSRRLENL IAQLPGEKKN GLFGNLIALS LGLTPNFKSN FDLAEDAKLQ  660
LSKDTYDDDL DNLLAQIGDQ YADLFLAAKN LSDAILLSDI LRVNTEITKA PLSASMIKRY  720
DEHHQDLTLL KALVRQQLPE KYKEIFFDQS KNGYAGYIDG GASQEEFYKF IKPILEKMDG  780
TEELLVKLNR EDLLRKQRTF DNGSIPHQIH LGELHAILRR QEDFYPFLKD NREKIEKILT  840
FRIPYYVGPL ARGNSRFAWM TRKSEETITP WNFEEVVDKG ASAQSFIERM TNFDKNLPNE  900
KVLPKHSLLY EYFTVYNELT KVKYVTEGMR KPAFLSGEQK KAIVDLLFKT NRKVTVKQLK  960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRNFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                          1763

SEQ ID NO: 36            moltype = AA  length = 1565
FEATURE                  Location/Qualifiers
source                   1..1565
                         mol_type = protein
                         organism = synthetic construct
SEQUENCE: 36
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
```

```
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 37          moltype = AA  length = 1565
FEATURE                Location/Qualifiers
source                 1..1565
                       mol_type = protein
                       organism = synthetic construct
SEQUENCE: 37
SEVEFSHEYW MRHALTLAKR ARDEREVPVG AVLVLNNRVI GEGWNRAIGL HDPTAHAEIM  60
ALRQGGLVMQ NYRLYDATLY STFEPCVMCA GAMIHSRIGR VVFGVRNAKT GAAGSLMDVL  120
HHPGMNHRVE ITEGILADEC AALLCRFFRM PRRVFNAQKK AQSSTDSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 38          moltype = AA  length = 364
FEATURE                Location/Qualifiers
source                 1..364
                       mol_type = protein
                       organism = synthetic construct
SEQUENCE: 38
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTD                                                              364

SEQ ID NO: 39          moltype = AA  length = 167
FEATURE                Location/Qualifiers
source                 1..167
                       mol_type = protein
                       organism = synthetic construct
SEQUENCE: 39
MSEVEFSHEY WMRHALTLAK RARDEREVPV GAVLVLNNRV IGEGWNRAIG LHDPTAHAEI  60
MALRQGGLVM QNYRLYDATL YSTFEPCVMC AGAMIHSRIG RVVFGVRNAK TGAAGSLMDV  120
LHHPGMNHRV EITEGILADE CAALLCRFFR MPRRVFNAQK KAQSSTD                167

SEQ ID NO: 40          moltype = AA  length = 167
FEATURE                Location/Qualifiers
```

```
source                  1..167
                        mol_type = protein
                        organism = synthetic construct
SEQUENCE: 40
MSEVEFSHEY WMRHALTLAK RARDEREVPV GAVLVLNNRV IGEGWNRAIG LHDPTAHAEI  60
MALRQGGLVM QNYRLIDATL YVTFEPCVMC AGAMIHSRIG RVVFGVRNSK RGAAGSLMNV  120
LNYPGMNHRV EITEGILADE CAALLCDFYR MPRQVFNAQK KAQSSIN                167

SEQ ID NO: 41           moltype = AA  length = 83
FEATURE                 Location/Qualifiers
source                  1..83
                        mol_type = protein
                        organism = Bacillus phage AR9
SEQUENCE: 41
TNLSDIIEKE TGKQLVIQES ILMLPEEVEE VIGNKPESDI LVHTAYDEST DENVMLLTSD  60
APEYKPWALV IQDSNGENKI KML                                          83

SEQ ID NO: 42           moltype = AA  length = 24
FEATURE                 Location/Qualifiers
source                  1..24
                        mol_type = protein
                        organism = synthetic construct
SEQUENCE: 42
EELLSKNYHL ENEVARLKKG SGSG                                         24

SEQ ID NO: 43           moltype = AA  length = 241
FEATURE                 Location/Qualifiers
source                  1..241
                        mol_type = protein
                        organism = synthetic construct
SEQUENCE: 43
EEELLSKNYH LENEVARLKK GSGSGEELLS KNYHLENEVA RLKKGSGSGE ELLSKNYHLE  60
NEVARLKKGS GSGEELLSKN YHLENEVARL KKGSGSGEEL LSKNYHLENE VARLKKGSGS  120
GEELLSKNYH LENEVARLKK GSGSGEELLS KNYHLENEVA RLKKGSGSGE ELLSKNYHLE  180
NEVARLKKGS GSGEELLSKN YHLENEVARL KKGSGSGEEL LSKNYHLENE VARLKKGSGS  240
G                                                                  241

SEQ ID NO: 44           moltype = AA  length = 277
FEATURE                 Location/Qualifiers
source                  1..277
                        mol_type = protein
                        organism = synthetic construct
SEQUENCE: 44
MGPDIVMTQS PSSLSASVGD RVTITCRSST GAVTTSNYAS WVQEKPGKLF KGLIGGTNNR  60
APGVPSRFSG SLIGDKATLT ISSLQPEDFA TYFCALWYSN HWVFGQGTKV ELKRGGGGSG  120
GGGSGGGGSS GGGSEVKLLE SGGGLVQPGG SLKLSCAVSG FSLTDYGVNW VRQAPGRGLE  180
WIGVIWGDGI TDYNSALKDR FIISKDNGKN TVYLQMSKVR SDDTALYYCV TGLFDYWGQG  240
TLVTVSSYPY DVPDYAGGGG GSGGGGSGGG GSGGGGS                           277

SEQ ID NO: 45           moltype = DNA  length = 66
FEATURE                 Location/Qualifiers
source                  1..66
                        mol_type = other DNA
                        organism = Saccharomyces bayanus
SEQUENCE: 45
ttcttgtcgt acttatagat cgctacgtta tttcaatttt gaaaatctga gtcctgggag  60
tgcgga                                                             66

SEQ ID NO: 46           moltype = AA  length = 605
FEATURE                 Location/Qualifiers
source                  1..605
                        mol_type = protein
                        organism = Homo sapiens
SEQUENCE: 46
MSGWESYYKT EGDEEAEEEQ EENLEASGDY KYSGRDSLIF LVDASKAMFE SQSEDELTPF  60
DMSIQCIQSV YISKIISSDR DLLAWFYGTE KDKNSVNFKI YVLQELDNPG AKRILELDQF  120
KGQQGQKRFQ DMMGHGSDYS LSEVLWVCAN LFSDVQFKMS HKRIMLFTNE DNPHGNDSAK  180
ASRARTKAGD LRDTGIFLDL HLKKPGGFDI SLFYRDIISI AEDEDLRVHF EESSKLEDLL  240
RKVRAKETRK RALSRLKLKL NKDIVISVGI YNLVQKALKP PPIKLYRETN EPVKTKTRTF  300
NTSTGGLLLP SDTKRSQIYG SRQIILEKEE TEELKRFDDP GLMLMGFKPL VLLKKHHYLR  360
PSLFVYPEES LVIGSSTLFS ALLIKCLEKE VAALCRYTPR RNIPPYFVAL VPQEEELDDQ  420
KIQVTPPGFQ LVFLPFADDK RKMPFTEKIM ATPEQVGKMK AIVEKLRFTY RSDSFENPVL  480
QQHFRNLEAL ALDLMEPEQA VDLTLPKVEA MNKRLGSLVD EFKELVYPPD YNPEGKVTKR  540
KHDNEGSGSK RPKVEYSEEE LKTHISKGTL GKFTVPLKEA CRAYGLKSGL KKQELLEALT  600
KHFQD                                                              605

SEQ ID NO: 47           moltype = AA  length = 482
FEATURE                 Location/Qualifiers
source                  1..482
```

```
                         mol_type = protein
                         organism = synthetic construct
SEQUENCE: 47
MVRSGNKAAW LCMDVGFTMS NSIPGIESPF EQAKKVITMF VQRQVFAENK DEIALVLFGT  60
DGTDNPLSGG DQYQNITVHR HLMLPDFDLL EDIESKIQPG SQQADFLDAL IVSMDVIQHE  120
TIGKKFEKRH IEIFTDLSSR FSKSQLDIII HSLKKCDISE RHSIHWPCRL TIGSNLSIRI  180
AAYKSILQER VKKTTWDAKT LKKEDIQKET VYCLNDDDET EVLKEDIIQG FRYGSDIVPF  240
SKVDEEQMKY KSEGKCFSVL GFCKSSQVQR RFFMGNQVLK VFAARDDEAA AVALSSLIHA  300
LDDLDIWAIV RYAYDKRANP QVGVAFPHIK HNYECLVYVQ LPFMEDLRQY MFSSLKNSKK  360
YAPTEAQLNA VDALIDSMSL AKKDEKTDTL EDLFPTTKIP NPRFQRLFQC LLHRALHPRE  420
PLPPIQQHIW NMLNPPAEVT TKSQIPLSKI KTLFPLIEAK KKDQVTAQEI FQDNHEDGPT  480
AK                                                                482

SEQ ID NO: 48            moltype = DNA  length = 10
FEATURE                  Location/Qualifiers
source                   1..10
                         mol_type = other DNA
                         organism = Methanobacterium thermoautotrophicum
SEQUENCE: 48
aatttttgga                                                        10

SEQ ID NO: 49            moltype = AA  length = 83
FEATURE                  Location/Qualifiers
source                   1..83
                         mol_type = protein
                         organism = Methanobacterium thermoautotrophicum
SEQUENCE: 49
GSVIDVSSQR VNVQRPLDAL GNSLNSPVII KLKGDREFRG VLKSFDLHMN LVLNDAEELE  60
DGEVTRRLGT VLIRGDNIVY ISP                                         83

SEQ ID NO: 50            moltype = DNA  length = 25
FEATURE                  Location/Qualifiers
source                   1..25
                         mol_type = other DNA
                         organism = Bacteriophage MS2
SEQUENCE: 50
gcgcacatga ggatcaccca tgtgc                                       25

SEQ ID NO: 51            moltype = AA  length = 116
FEATURE                  Location/Qualifiers
source                   1..116
                         mol_type = protein
                         organism = Bacteriophage MS2
SEQUENCE: 51
MASNFTQFVL VDNGGTGDVT VAPSNFANGI AEISSNSRSQ AYKVTCSVRQ SSAQNRKYTI  60
KVEVPKGAWR SYLNMELTIP IFATNSDCEL IVKAMQGLLK DGNPIPSAIA ANSGIY     116

SEQ ID NO: 52            moltype = DNA  length = 26
FEATURE                  Location/Qualifiers
source                   1..26
                         mol_type = other DNA
                         organism = Bacteriophage PP7
SEQUENCE: 52
ataaggagtt tatatggaaa ccctta                                      26

SEQ ID NO: 53            moltype = AA  length = 127
FEATURE                  Location/Qualifiers
source                   1..127
                         mol_type = protein
                         organism = Bacteriophage PP7
SEQUENCE: 53
MSKTIVLSVG EATRTLTEIQ STADRQIFEE KVGPLVGRLR LTASLRQNGA KTAYRVNLKL  60
DQADWDCSTS VCGELPKVRY TQVWSHDVTI VANSTEASRK SLYDLTKSLV ATSQVEDLVV  120
NLVPLGR                                                           127

SEQ ID NO: 54            moltype = DNA  length = 19
FEATURE                  Location/Qualifiers
source                   1..19
                         mol_type = other DNA
                         organism = Shigella phage
SEQUENCE: 54
ctgaatgcct gcgagcatc                                              19

SEQ ID NO: 55            moltype = AA  length = 62
FEATURE                  Location/Qualifiers
source                   1..62
                         mol_type = protein
                         organism = Shigella phage
SEQUENCE: 55
```

```
MKSIRCKNCN KLLFKADSFD HIEIRCPRCK RHIIMLNACE HPTEKHCGKR EKITHSDETV  60
RY                                                                  62

SEQ ID NO: 56          moltype = AA  length = 1367
FEATURE                Location/Qualifiers
source                 1..1367
                       mol_type = protein
                       organism = synthetic construct
SEQUENCE: 56
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 57          moltype = AA  length = 1367
FEATURE                Location/Qualifiers
source                 1..1367
                       mol_type = protein
                       organism = synthetic construct
SEQUENCE: 57
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLADDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 58          moltype = DNA  length = 4101
FEATURE                Location/Qualifiers
source                 1..4101
                       mol_type = other DNA
                       organism = synthetic construct
SEQUENCE: 58
gacaagaagt acagcatcgg gctggcgatc gggaccaact ccgtcggctg ggctgtgatt  60
accgacgagt acaaggtgcc atccaagaag ttcaaggtcc tcggcaacac tgaccggcac  120
agcattaaga agaacctgat tggggcgctg ctgttcgatt cgggggagac tgcggaggcg  180
accaggctga agcggactgc gcgccggagg tacaccagga ggaagaatcg gatctgctac  240
ctccaggaga ttttctcgaa tgagatggcc aaggtggacg attccttctt ccatcgcctg  300
gaggagtcgt tcctcgttga ggaggacaag aagcatgaga ggcatcccat tttcgggaat  360
atcgttgacg aggtggctta ccatgagaag tacccgacca tctaccatct gcggaagaag  420
ctcgtcgatt cgaccgataa ggccgacctg cggctgatct acctggccct cgcgcacatg  480
attaagttcc ggggccattt cctcatcgag ggcgacctca acccggacaa ctcggacgtg  540
gataagctct tcattcagct cgtgcagaca tacaaccagc tcttcgagga gaatcccatt  600
```

```
aacgcctcgg gggtcgacgc taaggctatt ctctcggctc ggctgtcgaa gtcgcgccgg  660
ctggagaatc tcattgccca gctcccaggc gagaagaaga acggcctctt cggcaacctg  720
attgccctgt cgctggggct cacaccgaat ttcaagtcga acttcgacct cgccgaggac  780
gctaagctcc agctcagcaa ggatacttac gatgatgacc tcgataacct gctcgcccag  840
attggggatc agtacgcgga tctgttcctc gcggccaaga atctcagcga tgctattctc  900
ctgtcggaca ttctccgcgt caacacagag attactaagg ccccactgtc ggcgagcatg  960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcggcgcgtc ccaggaggag ttctacaagt tcattaagcc catcctggag  1140
aagatggacg ggaccgagga gctgctggtg aagctcaatc gggaggacct gctccggaag  1200
cagcgcacat tcgacaatgg ctcgattcct caccagattc acctgggcga gctgcacgcc  1260
attctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgagattagc  1740
ggggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcagctg aagcgcaggc ggtacacagg gtgggggcgg  1980
ctgagccgga agctgatcaa cggattcgg gataagcagt ccgggaagac aattctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga agggcattct gcaaaccgtc  2220
aaggtggttg atgagctggt caaggtcatg gggcggcata agccagagaa tattgtcatc  2280
gagatggcgc gggagaatca gaccacacag aaggggcaga agaactcacg ggagcggatg  2340
aagcgcatcg aggagggcat caaggagctg gggtcgcaga tcctgaagga gcatcccgtg  2400
gagaacactc agctgcaaaa tgagaagctg tacctctact acctccagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcgggggcct gagcgagctg gacaaggcgg ggttcattaa gaggcagctg  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcgc atgatgccta cctcaacgcg gtcgtgggga ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg gaagaggccc  3180
ctcatcgaga caaatgggga gacaggggag attgtctggg ataaggggcg ggatttcgcg  3240
accgtccgga aggtcctgtc gatgccccag gttaatattg tcaagaagac tgaggtccag  3300
actggcggct tctcaaagga gtcgattctc ccaaagagga actccgataa gctcattgct  3360
cggaagaagg attgggaccc caagaagtac ggggggattcg actcccccac tgttgcttac  3420
tctgttctgg ttgttgctaa ggtggagaag gggaagtcga agaagctgaa gagcgtgaag  3480
gagctgctcg ggattacaat tatggagagg tcatccttcg agaagaatcc catcgacttc  3540
ctggaggcca agggctacaa ggaggtgaag aaggacctga ttattaagct gcccaagtac  3600
tcgctcttcg agctggagaa tgggcggaag cggatgctgg cgtccgcggg ggagctgcaa  3660
aaggggaacg agctggcgct cccctccaag tatgtgaact tcctctacct ggcgtcgcac  3720
tacgagaagc tgaagggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcgggggcga c                                            4101
```

```
SEQ ID NO: 59          moltype = DNA  length = 4101
FEATURE                Location/Qualifiers
source                 1..4101
                       mol_type = other DNA
                       organism = synthetic construct
SEQUENCE: 59
gacaagaagt actccattgg cctggcgatt gggacaaact cggtggggtg ggccgtgatt  60
acggatgagt acaaggttcc aagcaagaag ttcaaggtcc tcgggaacac agatcggcat  120
tcgattaaga agaatctcat tgggcgctc ctcttcgact cgggggagac agcggaggct  180
accaggctca agcggacagc caggcggcgg tacacaaggc ggaagaatcg catctgctac  240
ctccaggaga ttttctcgaa tgagatggcg aaggtggacg acagcttctt ccatcggctg  300
gaggagtcct tcctggtgga ggaggataag aagcacgaga ggcatccaat tttcgggaac  360
atcgtggacg aggttgcgta ccatgagaag taccctacaa tctaccatct gcggaagaag  420
ctggttgact ccacagacaa ggcggacctg aggctgatct acctcgctct ggcccacatg  480
attaagttcc gcgggcattt cctgatcgag ggggacctga atcccgacaa ttcggatgtg  540
gacaagctct tcatccagct ggtgcagacc tacaaccagc tgttcgagga gaatcccatc  600
aatgcgtcgg gcgttgacgc taaggccatt ctgtccgcta ggctgtcgaa gagcaggagg  660
ctggagaacc tgatcgccca gctgccaggc gagaagaaga atgggctctt cgggaatctg  720
attgcgctct ccctggggct gacaccgaac ttcaagagca atttcgatct ggctgaggac  780
```

```
gcgaagctcc agctctcgaa ggacacttac gacgatgacc tcgataacct cctcgcgcag  840
atcggggacc agtacgctga tctcttcctc gccgctaaga acctctcgga tgctatcctg  900
ctctccgaca ttctccgggt taataccgag attacaaagg ccccactgtc ggcgtccatg  960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg ggacagagga gctgctggtg aagctcaacc gggaggatct gctcaggaag  1200
cagcggacgt tcgacaacgg gtcgattccc catcagatcc acctggggga gctgcacgcg  1260
atcctgcgcc ggcaggagga tttctaccct ttcctgaagg ataatcggga gaagatcgag  1320
aagattctca ccttccggat tccctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagcccgc gttcctgtcc  1620
ggcgagcaga agaaggccat tgtggacctc ctgttcaaga ccaatcgcaa ggtcacagtc  1680
aagcagctca aggaggatta cttcaagaag atcgagtgct tcgactcggt tgagattagc  1740
ggggtggagg atcggttcaa cgcgagcctc ggcacttacc acgacctcct gaagatcatc  1800
aaggataagg acttcctcga caacgaggag aacgaggata ttctggagga catcgtgctc  1860
accctgacgc tgttcgagga tcgggagatg atcgaggagc gcctgaagac ctacgctcat  1920
ctcttcgatg ataaggtcat gaagcagctg aagaggaggc ggtacaccgg gtggggccgc  1980
ctgagcagga agctcattaa cgggatcagg gacaagcaga gcggcaagac catcctggac  2040
ttcctcaaga gcgatggctt cgccaaccgg aatttcatgc agctcatcca cgacgactcc  2100
ctcaccttca aggaggacat tcagaaggct caggtcagcg gccagggcga ctcgctgcat  2160
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcgc gggagaatca gaccactcag aagggccaga agaactcgcg ggagcgcatg  2340
aagaggatcg aggaggggat taaggagctg ggcagccaga ttctcaagga gcaccccgtg  2400
gagaataccc agctccagaa cgagaagctg tacctctact acctccagaa tgggcgggac  2460
atgtatgttg atcaggagct ggacatcaat cgcctctcgg attacgacgt ggaccacatc  2520
gtgccccaga gcttcctgaa ggatgatagc atcgacaata aggtcctgac ccgctccgac  2580
aagaatcgcg gcaagagcga caacgtgccg agcgaggagg tcgtgaagaa gatgaagaac  2640
tactggcggc agctgctgaa cgcgaagctc attacacagc ggaagttcga taacctgacg  2700
aaggcggaga ggggcggcct ctccgagctg gacaaggcgg gcttcattaa gaggcagctc  2760
gtggagactc gccagatcac caagcacgtg gctcagatcc tcgatagccg gatgaatacg  2820
aagtacgatg agaatgacaa gctcatccgg gaggtgaagg taatcaccct gaagtcaaag  2880
ctcgttagcg atttccggaa ggacttccag ttctacaagg tgcgggagat taacaactac  2940
catcatgcgc acgatgcgta cctcaatgcg gtggtgggca cagccctgat taagaagtac  3000
cccaagctgg agagcgagtt cgtctacggg gactacaagg tgtacgatgt tcggaagatg  3060
atcgccaaga gcgagcagga gattgggaag gccaccgcta agtacttctt ctactcgaat  3120
attatgaatt tcttcaagac cgagatcaca ctcgctaatg gggagattcg gaagcggccc  3180
ctcatcgaga ctaacgggga gactggcgag attgtgtggg acaaggggcg cgacttcgct  3240
accgtgcgca aggtcctctc gatgccccag gttaatattg ttaagaagac agaggtgcag  3300
acgggcgggt tctccaagga gtctatcctg ccgaagcgga actcggacaa gctgatcgcc  3360
cgcaagaagg attgggaccc caagaagtac gggggattcg atagcccaac cgtggcttac  3420
agcgtcctgg tggtcgccaa ggttgagaag gggaagtcga agaagctcaa gagcgttaag  3480
gagctgctgg gcatcaccat catggagcgg tccagcttcg agaagaatcc tatcgacttc  3540
ctggaggcta aggggtacaa ggaggtcaag aaggacctga tcattaagct gcccaagtac  3600
tctctgttcg agctggagaa cgggaggaag cggatgctgg cgtctgctgg cgagctacag  3660
aagggcaatg agctggcgct cccctcgaag tatgtcaact tcctctacct ggcttcccat  3720
tacgagaagc tgaagggctc gcccgaggat aatgagcaga agcagctctt cgtggagcag  3780
cacaagcact acctcgacga gatcattgag cagatttcgg agttctcgaa gcgggtcatt  3840
ctcgcggacg cgaacctcga caaggtcctc tcggcgtaca acaagcaccg ggacaagccc  3900
atccgggagc aggccgagaa cattatccac ctcttcacac tgaccaacct cggcgctccc  3960
gccgcgttca agtacttcga caccaccatt gaccgcaaga gatacacatc caccaaggag  4020
gtgctggacg cgaccctcat ccaccagagc atcacaggcc tctacgagac acggatcgac  4080
ctctcgcagc tcgggggcga t                                           4101
```

```
SEQ ID NO: 60          moltype = DNA  length = 4092
FEATURE                Location/Qualifiers
source                 1..4092
                       mol_type = other DNA
                       organism = synthetic construct
SEQUENCE: 60
gacaagaagt actcgatcgg cctggcgatt ggcacaaaca gcgtggggtg ggctgtgatc  60
actgatgagt acaaggtgcc atcgaagaag ttcaaggtgc tggggaatac agaccggcat  120
tcgatcaaga agaatctcat tggcgctctc ctcttcgatt ccggcgagac tgctgaggcg  180
acccgcctga agcgcaccgc ccggcggcgc tacactcggc ggaagaatag gatttgctac  240
ctccaggaga ttttctcgaa tgagatggcc aaggtggatg acagcttctt ccaccgcctg  300
gaggagtcgt tcctggtcga ggaggacaag aagcatgagc ggcaccctat cttcgggaat  360
atcgttgatg aggtcgccta ccacgagaag taccccacta tctaccatct ccgcaagaag  420
ctcgtggaca gcacagataa ggccgacctc cgcctgatct acctcgccct cgcgcacatg  480
attaagttcc gggggcactt cctcattgag gggggatctga atcccgataa ctccgacgtg  540
gacaagctgt tcatccagct ggtgcagaca tacaaccagc tgttcgagga gaatcccatc  600
aacgcgagcg gcgtggacgc taaggccatt ctgtcggcta ggctctcgaa gtcgaggcgg  660
ctggagaacc tgattgcgca gctccccggc gagaagaaga acgggctgtt cgggaatctc  720
atcgccctct ccctcggcct cacaccaaac ttcaagagca atttcgacct ggctgaggac  780
gctaagctgc aactctcaaa ggatacatac gatgacgacc tggacaatct cctggctcag  840
atcggcgacc agtacgctga cctgttcctc gcggccaaga atctgtcgga cgcgattctc  900
ctcagcgaca tcctgcgcgt caataccgag attacgaagg ctccactgtc tgcgtcaatg  960
```

```
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg gggcgcgag ccaggaggag ttctacaagt tcatcaagcc catcctggag  1140
aagatggacg gcaccgagga gctactcgtg aagctcaatc gggaggatct cctccggaag  1200
cagcggacat tcgataacgg gtctatccca caccagatcc acctcggcga gctgcatgcg  1260
attctgcggc ggcaggagga tttctaccct ttcctgaagg acaaccggga gaagatcgag  1320
aagatcctca cattccggat tccatactac gtcggccccc tggcgagggg caatagccgg  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctccccaacg agaaggtcct gccgaagcat agcctcctgt acgagtactt caccgtctac  1560
aatgagctaa ctaaggtcaa gtatgtgaca gagggcatga ggaagccagc cttcctctca  1620
ggcgagcaga agaaggccat tgtggacctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg ggacttacc acgacctgct gaagattatt  1800
aaggacaagg acttcctgga taacgaggag aatgaggaca tcctggagga tattgtgctc  1860
accctcaccc tgttcgagga cagggagatg attgaggaga ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agctgatcca cgacgactcc  2100
ctcaccttca aggaggacat tcagaaggcc caggttagcg gccaggggga ctcactccac  2160
gagcatattg ccaatctggc cggctctcca gctatcaaga agggcatcct gcaaacagtt  2220
aaggttgttg acgagctggt taaggtcatg ggcggcata agcccgagaa cattgtcatc  2280
gagatggctc gggagaacca gacaactcag aagggccaga agaactccag ggagcgcatg  2340
aagcggattg aggagggcat taaggagctg gggtcccaga tcctcaagga gcaccctgtc  2400
gagaacactc agctgcaaaa cgagaagctc tacctgtact acctccagaa cgggcgggat  2460
atgtatgtgg atcaggagct ggacatcaac aggctctccg actacgacgt ggatcacatt  2520
gtcccacagt ctttcctcaa ggatgattcc atcgacaaca aggtgctgac gcgcagcgac  2580
aagaataggg ggaagtcgga caacgttccg agcgaggagg tcgtgaagaa gatgaagaat  2640
tactggaggc agctcctgaa tgcgaagctg atcactcaga ggaagttcga caatctgaca  2700
aaggcggaga ggggcgggct ctcggagctg gataaggcgg gcttcatcaa gcggcagctc  2760
gttgaaaccc ggcagatcac caagcatgtc gcccagatcc tcgatagccg catgaacacc  2820
aagtacgatg agaacgacaa gctcattcgg gaggttaagg tcattacgct gaagtccaag  2880
ctcgtcagcg acttcaggaa ggatttccag ttctacaagg ttcgggagat taacaactac  2940
caccacgcgc atgatgcgta cctgaacgct gttgtcggca ctgctctcat caagaagtac  3000
ccaaagctgg agtccgagtt cgtctacggg gactacaagg tctacgatgt ccggaagatg  3060
atcgccaagt cggagcagga gatcgggaag gctactgcga agtacttctt ctacagcaac  3120
attatgaatt tcttcaagac ggagattacg ctggcgaacg gggagattag gaagaggccc  3180
ctcattgaga ctaatgggga gacaggcgag attgtttggg acaagggccg cgacttcgcg  3240
actgtgcgga aggtcctgtc catgccacag gtgaatattg ttaagaagac agaggtgcag  3300
actgggggct tctcgaagga gagcattctc ccaaagcgga acagcgataa gctcatcgcg  3360
cgcaagaagg attgggaccc taagaagtac ggcggcttcg attctcccac tgtggcctac  3420
tccgttctcg tggttgccaa ggttgagaag gggaagtcga agaagctgaa gtcggtcaag  3480
gagctgctcg ggattacaat catggagcgg agcagcttcg agaagaaccc tattgatttc  3540
ctggaggcca agggctacaa ggaggttaag aaggatctca ttatcaagct ccctaagtac  3600
tctctgttcg agctggagaa tggccggaag aggatgctgg cctcggctgg cgagctacag  3660
aaggggaatg agctggccct cccgtcgaag tatgtgaatt tcctgtacct cgcgtcgcac  3720
tacgagaagc tcaagggcag cccggaggat aatgagcaga agcagctctt cgtggagcag  3780
cataagcact acctggacga gatcattgag cagatcagcg agttctcgaa gcgggttatt  3840
ctggctgatg ctaacctgga caaggttctg agcgcctaca ataagcatcg cgacaagccg  3900
attcgcgagc aggcggagaa tattatccac ctgttcaccc tcactaacct cggggctccc  3960
gcggccttca agtacttcga taccacaata gataggaagc ggtacacctc gacgaaggag  4020
gtcctcgacg ccacactcat ccatcagtcg attacaggcc tgtacgagac acggattgac  4080
ctctcgcagc tg                                                     4092
```

```
SEQ ID NO: 61          moltype = DNA  length = 4101
FEATURE                Location/Qualifiers
source                 1..4101
                       mol_type = other DNA
                       organism = synthetic construct
SEQUENCE: 61
gacaagaagt attccatagg cctggctatc ggcaccaaca gcgtgggctg ggccgtcatc  60
accgacgagt acaaagtgcc gagtaaaaag ttcaaagtgc tcggcaacac cgaccgccac  120
tccataaaga aaaacctgat cggggcgctc ctgttcgaca gcggcgagac ggcggaggcc  180
acccgcttga aacgcacggc ccgacggcgc tacacgcggc gcaagaaccg gatctgttac  240
ctacaggaga ttttctctaa cgagatggcg aaggtggacg actcgttctt tcaccgcctc  300
gaagagtcct tcctcgtgga ggaggacaag aaacacgagc gccacccgat cttcggcaac  360
atcgtggacg aggtggccta ccacgagaag tacccgacca tctaccacct ccggaagaaa  420
ctcgtggaca gcacggacaa ggccgacctg aggctcatct acctcgccct ggcgcacatg  480
attaagttcc ggggccactt cctgatcgag ggcgacctga acccggacaa cagcgacgtg  540
gacaagctgt tcatccagct agtccagacc tacaaccagc ttttcgagga aaaccccatc  600
aacgccagcg gggtggacgc gaaggcgatc ctgtccgccc ggctgagcaa gtcccggcgg  660
ctggagaacc tcatcgcgca gttgcccggc gagaagaaga acgggctgtt cgggaacctg  720
atcgccctct ccctggggct caccccgaac ttcaagtcca acttcgacct cgccgaggac  780
gccaaactac agctgagcaa ggacacctac gacgacgacc tcgacaacct gctggcccag  840
atcggggacc agtacgcaga cctgttcctc gccgccaaga acctctccga cgccatcctg  900
ctgtcggaca tcctgcgggt gaacacggag atcacgaagg ccccgctctc ggcctcgatg  960
attaaacgct acgacgagca ccaccaggac ttgaccctcc tcaaggcgct ggtccgccag  1020
cagcttcccg agaagtacaa ggaaatcttt ttcgatcaga gcaagaacgg gtacgccggg  1080
tacatcgacg gcggggcgtc ccaggaggag ttctacaagt tcatcaagcc catcctggag  1140
```

```
aaaatggacg ggaccgagga gctgctcgtg aagctcaacc gcgaagattt gctccgcaag  1200
cagcgcacgt tcgacaacgg gtcgatcccg caccagatcc acctgggcga gctgcacgcg  1260
atcctcaggc gtcaggaaga cttctacccc ttcctcaagg acaaccgcga gaagatagag  1320
aagattctga ccttcagaat tccttattac gtgggcccgc tggctcgggg caactcgcgc  1380
ttcgcctgga tgacgcgcaa gtccgaggag accatcaccc cgtggaactt cgaggaggtg  1440
gtggataagg gtgcctcggc ccagtccttc atcgagcgga tgaccaactt cgacaagaac  1500
ctgccgaacg agaaggtgct ccccaagcac agcctgctct acgaatattt cacggtgtac  1560
aacgagctga cgaaggtcaa gtacgtgacc gagggaatga ggaaacctgc attcctctcc  1620
ggggagcaga agaaagccat agtcgacctc ctgttcaaga ccaaccggaa ggtcaccgtc  1680
aagcagctca aggaggacta cttcaagaag atcgagtgct tcgattcagt ggagatcagc  1740
ggcgtcgagg accggttcaa cgccagcctg ggcacctacc acgacctgct caagatcatc  1800
aaggacaagg acttcctcga caacgaggag aacgaggaca tcctggagga catcgtgctg  1860
accctgacgc tcttcgagga ccgcgagatg atcgaggagc gcctcaagac ctacgcccac  1920
ctgttcgacg acaaggtgat gaagcagctc aagcggcgga gatatactgg gtggggccgc  1980
ctctcccgga agctcattaa cggtatcagg gataagcagt ccgggaagac gatcctcgac  2040
ttcctcaagt cggacgggtt cgccaaccgc aacttcatgc agctcatcca cgacgactcc  2100
ctgacgttca aggaggacat ccagaaggcc caagtgtctg gtcaaggtga ctcgctccac  2160
gagcacatcg ccaacctcgc gggcagcccg gccatcaaga agggaatact ccagaccgtc  2220
aaggtggtgg acgagctggt gaaggtcatg ggccgccaca agccggagaa catcgtcatc  2280
gagatggcgc gggagaacca gaccacgcag aaggggcaga aaaatagccg tgagcgcatg  2340
aagcgcatcg aggaggggat taaggagttg ggcagccaga tcctcaagga gcaccctgtg  2400
gagaacacgc agttgcaaaa cgagaagctc tacctgtact acctccagaa cgggagggat  2460
atgtacgtgg accaagaact ggacatcaac cgcctgtccg actacgacgt ggaccacatc  2520
gtgccgcaga gcttcctcaa ggacgacagc atcgacaaca aggtgctcac ccggtccgac  2580
aagaatcggg gcaagtccga caacgtgccc agcgaggagg tcgtcaaaaa gatgaaaaac  2640
tactggcgac aactactgaa cgccaagctc atcacccagc gcaagttcga caacctcaca  2700
aaagccgagc gcggcgggtt gagcgagctg gacaaggccg ggttcatcaa gcgccagctc  2760
gtcgagacgc gccagatcac gaagcacgtc gcgcagatac tcgacagccg gatgaacacc  2820
aagtacgacg agaacgacaa gctcatccgg gaggtgaagg tcatcaccct caagtcgaag  2880
ctcgtgagcg acttccgcaa ggacttccag ttctacaagg tccgggagat caacaactac  2940
caccacgccc acgatgctta tcttaacgcc gtggtgggga cggccctcat taagaaatac  3000
ccgaagctgg agtcggagtt cgtgtacggc gactacaagg tgtacgacgt caggaagatg  3060
atcgccaagt ccgaacagga gatcgggaag gccacggcga aatacttctt ctacagcaac  3120
atcatgaact tcttcaagac cgagatcacc ctcgccaacg gcgagatccg caagcgcccg  3180
ctcatcgaga cgaacgggga gaccggcgag atcgtctggg acaaggggcg cgacttcgcc  3240
actgtgcgga aggtgctgtc gatgccccag gtcaacatcg tcaagaagac ggaggtccag  3300
acgggcgggt tcagcaagga gagcatcctg ccgaagcgca acagcgacaa gctgatcgcc  3360
cgcaaaaagg actgggatcc aaaaaagtac ggcggcttcg acagccccac cgtcgcctac  3420
agcgtcctcg tcgtcgctaa agtcgagaag ggcaagtcca aaaagctcaa gagcgtcaag  3480
gagctgctcg ggatcaccat catggagcgg tccagcttcg agaagaaccc aattgatttc  3540
ctggaggcga agggctacaa ggaggtcaag aaagacctca tcataaagct gccgaagtac  3600
tcactcttcg agctggagaa cggcgcaag cggatgctgg cgtcggccgg agagctccaa  3660
aagggcaacg agctggcgct gccgagcaag tacgtgaact tcctctacct ggcgtcccac  3720
tacgagaagc tcaagggcag tccagaggat aacgagcaga agcagctatt cgtggagcag  3780
cacaagcact acctggacga gatcatcgag cagatcagcg agttctccaa gcgcgtcatc  3840
ctggcggacg ccaacctgga caaggtgctg tccgcgtaca acaagcaccg cgacaagccg  3900
atccgcgagc aagccgagaa catcatccac ctgttcaccc tcacgaacct cggggcaccc  3960
gccgccttca aatatttcga cacgaccatc gaccgcaagc gctacaccag cacgaaggag  4020
gtgctcgacg ccaccctgat ccaccagagc atcaccgggc tgtacgagac ccgcatcgac  4080
ctctcgcagc tcggcgggga c                                            4101
```

```
SEQ ID NO: 62           moltype = DNA  length = 4101
FEATURE                 Location/Qualifiers
source                  1..4101
                        mol_type = other DNA
                        organism = synthetic construct
SEQUENCE: 62
gacaagaagt acagtattgg attggccatc gggacgaaca gcgtgggctg ggccgtcatc  60
accgacgagt acaaggtgcc atccaagaag tttaaggttc tggggaatac cgaccgccac  120
tcgatcaaga aaaatctcat cggggcgctg cttttcgaca gcggcgagac ggcggaagcg  180
acgcggctca agcggacggc tcgtcgccgt tacacccggc gtaagaaccg catctgttac  240
ctccaggaga tattcagcaa cgagatggcg aaggtggacg actccttttt ccaccgtctt  300
gaggagtcct tcctggtcga ggaggacaag aagcacgagc gccaccccgat cttcgggaac  360
atcgtggacg aggtggccta ccacgagaag taccccacga tctaccacct ccgcaaaaaa  420
ctcgtggact caactgacaa ggccgatttg aggcttatct acctcgccct cgcccacatg  480
attaagttcc gtgggcactt cctaatcgag ggtgacctca accccgacaa ctctgacgtg  540
gacaagctgt tcatccagct tgtgcagacc tacaatcagc tctttgagga gaatccgatc  600
aacgcatctg gtgtggacgc aaaggccatc ctcagcgcgc ggctgagcaa gtctaggcgg  660
ttggagaacc tgatcgccca actgcccggc gagaagaaaa atggcctctt cggcaacctg  720
atcgccctgt cgctggggct cacgccgaac ttcaagagta actttgacct ggcggaggac  780
gctaagctcc agctatctaa ggacacatac gacgacgacc tggacaacct gctggcccag  840
atcggcgacc agtacgccga cctcttccta gccgccaaga acctgtccga cgccatcctc  900
ctcagcgaca tcctgcgcgt gaacacggag atcacgaagg ctccgctcag cgcctccatg  960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
```

```
aaaatcctga cgtttcgcat accctactac gtcggcccgc tggcgcgcgg caactcccgg  1380
ttcgcctgga tgacccgtaa gagcgaggag acgatcaccc cgtggaactt cgaggaggtc  1440
gtggacaagg gcgcgagcgc gcagagcttc atcgagcgca tgaccaactt cgacaagaac  1500
ctcccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc caagtgagcg gtcaagggga cagcctccac  2160
gagcacattg cgaaccttgc tgggagccct gcgatcaaga aggggatatt gcaaaccgtg  2220
aaggtcgtgg acgagttggt gaaggtcatg gggcgacaca agcccgagaa catcgtgatc  2280
gagatggcca gggaaaatca gaccacgcag aagggccaaa aaaacagccg cgagcggatg  2340
aagcggatcg aggagggcat caaggagctg gggtcgcaga tcctcaagga gcacccggtg  2400
gagaacacgc agctccagaa cgagaagctg tacctctatt acctacagaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
aaggctgaac gtggtgggct cagcgagcta gacaaggcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtggtgggga cggcgcttat taagaaatat  3000
cccaagctgg aaagcgagtt cgtttacggc gactacaagg tgtacgacgt ccgcaagatg  3060
atcgcaaagt cggaacagga aatcggaaag gcgacggcca aatatttctt ttactccaac  3120
atcatgaatt tttttaagac ggagatcacc ctggcgaacg gggagatccg caagcggccc  3180
ctcatcgaga ccaacgggga gacgggcgag atcgtctggg acaagggccg ggacttcgcc  3240
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actcgccgac cgtcgcctac  3420
agcgtcctcg tggtggctaa ggtcgagaag ggcaagagca aaaagctaaa gtcggtgaag  3480
gagctgctgg gcatcaccat catggagcgc tcgtctttcg agaagaatcc aatcgacttc  3540
ctagaggcga aggggtacaa ggaggtcaaa aaggatctta tcatcaaact gccgaagtac  3600
agtctgttcg agctggagaa cgggcggaag cggatgctgg ctagtgcggg cgagttgcag  3660
aagggcaacg agttggcact gccctccaag tacgtgaact tcctgtacct ggcctcccac  3720
tacgagaagc tcaaggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca acaagcacag ggacaagcca  3900
atcagggaac aggccgagaa catcatccac ctgttcaccc tgaccaacct gggtgcaccg  3960
gctgccttca agtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                            4101
```

```
SEQ ID NO: 63           moltype = DNA  length = 4092
FEATURE                 Location/Qualifiers
source                  1..4092
                        mol_type = other DNA
                        organism = synthetic construct
SEQUENCE: 63
gacaaaaagt attccattgg actcgctatc ggcacgaaca gcgtcgggtg ggcggtcatc  60
actgacgagt acaaggtgcc gagcaagaag tttaaggtgc tgggaaacac cgacaggcac  120
tcgatcaaga aaaatcttat cggggcccta ctcttcgact ccggagaaac cgccgaggcc  180
acccggttga agcgcacggc ccgccgtcgc tacaccaggc gcaagaaccg gatctgctac  240
ctccaggaga tattcagcaa tgagatggcg aaggtggacg actcgttttt tcacaggcta  300
gaggagtctt tcctcgtgga ggaggacaag aaacacgagc gccaccccat cttcggcaac  360
atcgtggatg aggtggcata tcacgagaag tacccaacca tctaccacct ccgcaaaaag  420
ctcgtggact ctaccgacaa ggccgacctc cgtctgatct acctcgcgct ggcccacatg  480
attaagttcc gaggacactt tctgatcgag ggcgacctga acccagacaa cagcgacgtg  540
gacaagctgt tcatccaact tgtccagacc tacaatcagc tcttcgagga gaaccctatc  600
aacgcctcgg gcgtggacgc gaaggccatc ctgtccgccc gcctgagcaa gtcgcggcgg  660
ctggagaacc tgatcgccca gctccccggc gaaaaaaaga acggcctctt cggcaacctc  720
atcgcgttgt cgctggggct caccccgaac ttcaagtcca acttcgacct ggccgaggac  780
gctaaactcc agctctcgaa ggatacctac gacgacgacc tcgacaacct gctggcccag  840
atcggcgacc agtacgcgga ccttttcctg gcggccaaga acctgagcga cgcgatcctc  900
cttagcgaca tactccgtgt gaacaccgag atcacgaagg ccccgctctc cgcgtccatg  960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
aaaatggacg ggaccgagga gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcgggcccc ttgcgagggg caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
```

```
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
ggcgagcaga agaaagccat tgtggatctc ctgttcaaga ccaaccgcaa ggtgacggtg  1680
aaacagctca aagaggacta cttcaagaag atcgagtgct tcgactccgt agagatcagc  1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctcccgca agctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgagcg gccagggaga ctcgctacac  2160
gagcatatcg ccaacctggc tggcagcccg gcgattaaga aaggaatcct ccaaaccgtc  2220
aaagtggtgg acgagctggt gaaggtgatg ggccgccaca agcccgagaa cattgtgatc  2280
gagatggcgc gggagaacca gacgacgcag aagggccaaa aaaatagcag ggaaaggatg  2340
aagcgaatag aggaggggat caaggagctg ggagccaga ttctcaaaga gcacccggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca aagtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagg tcattaccct taaatcgaag  2880
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgcccg  3180
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                     4092
```

```
SEQ ID NO: 64           moltype = DNA  length = 4101
FEATURE                 Location/Qualifiers
source                  1..4101
                        mol_type = other DNA
                        organism = synthetic construct
SEQUENCE: 64
gacaagaagt atagtattgg actcgccatc ggaaccaact ctgtggggtg ggctgttatt  60
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggttg  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctg  720
atcgctcttt cattggggtt gacacccaac tttaagagta actttgactt ggcagaagat  780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttagggt taataccgaa attacaaagg cccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg gggcgcaag tcaagaagaa ttttacaaat tcatcaagcc aattcttgaa  1140
aagatggacg ggactgagga attgctggtg aaactgaata gagaggacct tcttagaaaa  1200
cagaggacat ttgacaatgg gtccatccca caccagattc atctggggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttat  1560
aacgaattga ccaaggtgaa gtatgtgacc gagggaatga ggaagccagc atttttgtcc  1620
ggggagcaaa agaaagcaat cgttgatctt ctcttcaaga ccaacagaaa agtgaccgtg  1680
```

```
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaagac tatcctcgat  2040
ttccttaaga gtgatggctt tgcaaatagg aattttatgc agctgattca tgacgactca  2100
cttaccttca aagaagacat ccaaaaagct caggtgtctg ggcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatggcaa gggaaaatca aacaacccag aagggacaga agaacagtag ggaaaggatg  2340
aaaaggatag aagaggggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggacctta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact tttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca acaaacacag ggataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                           4101

SEQ ID NO: 65          moltype = DNA  length = 4101
FEATURE                Location/Qualifiers
source                 1..4101
                       mol_type = other DNA
                       organism = synthetic construct
SEQUENCE: 65
gacaaaaagt attccatcgg gcttgctatc ggaaccaact ctgtggggtg ggcagttatt  60
accgacgaat acaaggtgcc cagcaagaag tttaaggttc tggggaacac agatagacat  120
agcataaaga aaaacctgat aggcgcactg ttgttcgact ccggggaaac agccgaagct  180
accaggctga agagaactgc aagaagaagg tacaccagaa gaaaaaacag aatatgttat  240
ctccaagaga ttttctctaa cgagatggcc aaggtggacg actcattctt tcacagactg  300
gaagaatctt tccttgtgga agaagataag aaacacgaga ggcaccctat ttttggcaat  360
atcgtggatg aggtggctta ccacgaaaaa taccctacaa tataccacct caggaaaaaa  420
ttggttgata gtacagacaa ggccgacctc aggctcatct atttggccct ggcccatatg  480
attaaattca gggggcactt tctcatcgag ggagatttga accccgacaa cagtgatgtt  540
gataagctct ttattcagct cgtgcagact tacaatcagt tgtttgagga aaaccccatt  600
aatgcttccg gggtggacgc caaggcaatc ctttctgcaa gactctcaaa gtcaaggaga  660
ctcgaaaatc tgatagcaca gcttccagga gagaagaaga acgggctctt tggaaacctg  720
atcgctctgt cactcggact cacacccaat ttcaaaagca attttgattt ggcagaggac  780
gctaagctgc aactcagtaa ggatacctac gacgatgact tggataatct gctcgcacaa  840
attggggacc agtatgcaga cctgtttctc gcagctaaga acttgagtga cgccatattg  900
ctcagtgaca tcctcagggt taataccgag attacaaaag ctccactctc tgcaagcatg  960
atcaagaggt atgacgagca ccatcaagac ctgacactcc ttaaggcgtt ggttaggcag  1020
caacttcctg aaaagtataa ggaaatcttc ttcgatcaaa gcaaaaacgg ctacgccggc  1080
tatatagacg gggagcatc ccaagaagaa ttttataagt tcataaaacc tatattggag  1140
aagatggacg ggacagagga attgctcgtg aaactgaaca gggaggatct cctcaggaag  1200
caaaggacct tcgacaatgg ctccatccca catcagattc acctcggcga actgcacgca  1260
atactgagaa gacaagagga cttttatcct ttcctgaagg acaacaggga gaaaatcgag  1320
aaaatcttga cattcagaat cccatactac gttgggcctc tggccagagg taacagtagg  1380
ttcgcctgga tgactaggaa atcagaggag actattacac cctggaactt tgaagaagtt  1440
gttgataagg gagcttcagc acaatcattc atcgaaagaa tgacaaactt tgacaaaaat  1500
ctgcctaatg agaaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
aagcagctta aggaagacta ctttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa aacgaagata tactggagga catagttctg  1860
```

```
acacttactt tgttcgagga tagggagatg atcgaggaaa gactgaaaac atatgctcac  1920
cttttcgacg acaaagttat gaaacaactc aagagaagga gatatacagg gtgggggaga  1980
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aacccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagg tgtacgacgt tagaaaaatg  3060
attgcaaagt cagagcagga gatagggaaa gccactgcaa aatatttctt ttatagcaat  3120
atcatgaatt tctttaagac agaaatcaca ctggccaatg gggaaataag gaagaggccc  3180
ctgatcgaaa ctaatggcga gacaggggag attgtgtggg ataaaggtag ggactttgca  3240
acagtgagga aagtgctgag catgccccaa gttaatatcg ttaaaaagac cgaggttcaa  3300
acagggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagagca agaaactgaa gtcagttaag  3480
gaactccttg gtatcactat catggaaaga agctcctttg agaagaaccc tattgacttc  3540
ctggaggcta aagggtacaa agaggttaag aaagacctta tcattaaatt gcccaaatat  3600
agtcttttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caaatttctg agttttcaaa aagggtaatc  3840
ttggctgacg caaatctcga caaagttttg tcagcttaca acaaacatag agataagcca  3900
attagagagc aagctgagaa tatcatccat ctgtttaccc tgactaacct tggagcgcct  3960
gctgctttta aatatttcga caccacaatc gacaggaaga ggtacactag cactaaggaa  4020
gttctcgacg ccaccctcat ccaccagagt attacaggcc tgtacgagac aagaattgat  4080
ctttctcaac ttggtggtga c                                           4101

SEQ ID NO: 66           moltype = DNA  length = 4101
FEATURE                 Location/Qualifiers
source                  1..4101
                        mol_type = other DNA
                        organism = synthetic construct
SEQUENCE: 66
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaatttgat tggagcactc ctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct ttcttgttga agaggacaaa aagcatgaaa ggcatcccat cttcggcaat  360
atagttgatg aggttgcata ccatgagaag taccccacaa tctaccacct cagaaagaaa  420
cttgtggact ccacagataa agcagacctg aggctcatat acctcgcact cgcacacatg  480
atcaagttca gagggcactt tctcatcgaa ggtgacctga atccagataa ttcagatgtg  540
gataaactgt ttatacagct ggtgcaaaca tacaaccaac ttttcgagga aaacccaatc  600
aatgcctccg gtgttgatgc aaaggccatc ctgtcagcaa gactcagcaa aagcaggcgg  660
ctcgaaaacc tcatcgccca gcttcccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
atcggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagccct cgttagacag  1020
cagttgccag aaaagtacaa agaaatattc tttgatcaat caaaaaacgg atatgcaggg  1080
tacatcgacg gtggggcaag ccaggaagag ttctacaaat tcatcaaacc tatcctggaa  1140
aagatggatg ggacagaaga gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca tttttgaagg acaataggga gaaaatcgaa  1320
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg gtgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga agaaagctat tgtggacctc ctgttcaaga caaatagaaa agtgacagtt  1680
aagcaactca aagaggatta cttcaaaaag atcgaatgtt ttgactctgt ggagatcagc  1740
ggggtggagg atagattcaa cgccagcctg ggtacatatc atgatctcct gaaaatcatt  1800
aaagacaagg acttccttga caacgaggag aacgaggaca ttctggaaga cattgttctg  1860
accctcacac tctttgagga tagggagatg attgaggaaa gactgaagac ctacgcccac  1920
ctctttgacg ataaagtgat gaaacagctc aagagaagaa ggtatacagg ttgggggaga  1980
ctgagcagga agttgatcaa tgggattagg gacaaacagt ccgggaaaac aatcctcgat  2040
```

```
tttctgaagt cagacggttt cgcaaacaga aattttatgc agctcattca cgatgacagc  2100
ttgacattca aggaagacat ccaaaaggct caagtgagcg gccaagggga tagcctccac  2160
gagcatattg caaatctggc aggttcacca gccatcaaaa agggcatact tcagacagtt  2220
aaggttgtgg acgaattggt taaagttatg ggcaggcata agccagagaa tatcgttatc  2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca aagttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa aagacagctg  2760
gttgagacaa ggcagatcac aaaacatgtg gcacagatcc ttgactcaag gatgaatacc  2820
aagtatgatg agaatgataa gttgatcagg gaggttaaag ttatcacact caaatccaaa  2880
ctggtgtcag acttcaggaa agactttcaa ttttataagg tgagggagat caataactac  2940
caccatgcac atgacgccta cctgaacgca gtggtgggta cagcattgat taaaaaatac  3000
cctaagctgg agtctgagtt tgtgtacggg gactacaagg tgtacgacgt gaggaaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggattttgct  3240
actgttagaa aagttctgag tatgccacaa gtgaatattg tgaaaaagac agaagttcag  3300
acaggtgggt tctccaaaga atccatcctg cccaagagaa attcagacaa gctcatcgca  3360
agaaagaagg actgggaccc taagaagtac ggaggatttg acagccccac cgtggcctat  3420
tccgtgcttg ttgtggcaaa ggtggagaaa gggaagagca aaaaactgaa atccgtgaaa  3480
gaactgctgg gaattaccat catggaaaga agctcctttg agaagaaccc aatcgacttc  3540
ctggaagcaa aaggatataa ggaagtgaaa aaggacctca ttatcaagct cccaaaatac  3600
tcacttttcg agttggagaa cggtagaaag aggatgctgg caagcgcagg ggaacttcag  3660
aaaggcaatg agctggcatt gccatcaaag tatgtgaact tcctctactt ggccagccat  3720
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata ataagcatag agacaagcca  3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                            4101

SEQ ID NO: 67          moltype = DNA  length = 3307
FEATURE                Location/Qualifiers
source                 1..3307
                       mol_type = other DNA
                       organism = synthetic construct
SEQUENCE: 67
gagcaaggac acctacgacg acgacttgga caacctattg gcccagatag gtgaccagta  60
tgcagacctc ttccttgcgg ccaagaactt gagtgacgct atactgctca gtgacatcct  120
gagggtgaac actgagatca ctaaggcccc tctctctgcc tcaatgatta agcgttacga  180
cgagcatcac caggatctca ccctgcttaa ggcccttgtt cggcagcagc tccctgagaa  240
gtacaaggag atatttttg accagtctaa gaacggctac gccggttaca ttgacggtgg  300
ggcaagccag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaatacct tactacgtgg ggccccttgc tcggggaaac tccagattcg catggatgac  600
caggaagtca gaggagacca tcacaccctg gaactttgag gaggtggttg acaaaggtgc  660
ttctgcccag tccttcattg agcggatgac taacttcgac aagaacctgc ccaacgagaa  720
ggtgctgcca aagcacagcc tgctctacga atactttact gtgtacaatg agctgacgaa  780
ggtgaagtac gtgacagagg ggatgcggaa gcccgctttc ctgagcggcg agcaaaaaaa  840
agcaatcgtg gacctactgt tcaagaccaa ccgaaaggtg acagtgaagc agctcaagga  900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg ggaagactct cccgaaaact  1200
gataaacggc atcagggaca agcagtcagg gaagacgatc ttggacttcc tgaaatccga  1260
cgggttcgcc aaccgcaact tcatgcagct cattcacgac gactcactaa cgttcaaaga  1320
ggacattcag aaggctcaag tcagtggaca aggcgactcc ctgcacgagc acattgcaaa  1380
ccttgcgggc tccccggcga ttaaaaaggg cattctccaa acggttaagg tggtggacga  1440
gctggtgaag gtgatgggcc gacacaagcc tgagaacatc gtgatcgaga tggccaggga  1500
gaaccagact acccagaagg gtcagaagaa ctctcgggaa cgtatgaagc gtattgagga  1560
ggggattaag gagttgggct ctcaaatcct caaggagcac cctgtggaga acactcagct  1620
ccaaaacgag aagctgtacc tgtactacct gcaaaacggg cgcgatatgt acgtggatca  1680
ggagttggac atcaacaggc ttagcgatta cgacgtggac cacatcgtgc cacagtcatt  1740
cttaaaggac gacagcatcg acaacaaggt tctgacgagg agcgacaaga atcgagggaa  1800
aagtgacaat gttccatccg aggaggtggt caagaaaatg aagaactatt ggcgtcagct  1860
tctgaacgcc aagctcatca cccagcggaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
cgacaagctc atcagggagg tgaaggtcat tacccttaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca agttggagtc  2220
```

```
ggagttcgtt tacggggact acaaggtgta cgacgttcgg aagatgatcg ccaagtctga  2280
acaggagatc gggaaagcaa ccgccaagta tttcttctat agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca agaggaactc agacaagctc atagcacgca aaaaagactg  2580
ggatccaaag aaatacggcg ggttcgactc gccgacagtc gcatactccg tgttagtggt  2640
ggctaaagtg gaaaagggga agtccaagaa gctcaagtcc gtcaaggagt tgctcgggat  2700
caccattatg gaacggtcct cattcgagaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggagag cttcagaagg ggaacgagct  2880
tgcactgcct tccaagtacg tgaacttcct gtacctcgcc tctcattacg agaagttgaa  2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata  3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                            3307

SEQ ID NO: 68          moltype = DNA  length = 4101
FEATURE                Location/Qualifiers
source                 1..4101
                       mol_type = other DNA
                       organism = synthetic construct
SEQUENCE: 68
gacaaaaaat actcaattgg tctggcaatt gggaccaaca gtgtcggatg ggccgtgatt  60
accgacgagt acaaggtgcc gtccaaaaaa ttcaaggtgc ttgggaacac cgaccgccac  120
tcgatcaaga aaaacctaat cggtgcgttg cttttcgaca gtggggagac cgccgaggca  180
acacgcttaa aacgcacagc taggaggaga tatacacggc gcaagaaccg aatatgctac  240
ttacaggaga tattctccaa tgagatggcg aaggtggacg actctttctt ccatcggctt  300
gaggaatcct tcctggtcga ggaggacaag aagcacgagc gacacccgat attcgggaac  360
atcgttgatg aggtggcgta ccacgagaag tacccaacga tataccactt acgcaagaag  420
ctcgtggact ctacggacaa ggccgacttg cgccttatct acttggcact ggcccacatg  480
attaagttcc gaggccactt ccttatcgag ggtgacctga accccgataa ctccgacgtg  540
gacaagctct tcatccaact cgtccagaca tacaaccagc tattcgagga gaatcctatc  600
aacgcctctg ggtggacgc taaagctatc ctctcagccc gcctgtcaaa gtcgaggagg  660
ttggagaacc taatcgccca gcttccaggc gagaagaaaa atgggctgtt cggaaacctt  720
atcgcactct cactgggcct aaccccgaac ttcaagtcca acttcgacct ggcagaggac  780
gcgaaattgc agttgtcgaa agacacctat gacgatgacc tggacaacct gttggcccag  840
ataggggacc agtacgccga cctgttccta gcggccaaga acctgtccga cgccatcttg  900
ctgtcggata tactgcgggt gaacaccgag atcactaaag cacctctctc cgccagcatg  960
attaagcgtt acgacgagca ccaccaagat ttgaccctgc taaaggcact tgtacggcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgag  1320
aagatactga ccttcagaat accttactac gtcggaccccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaacac agcctcctct acgaatattt cacagtgtac  1560
aacgagctta ctaaagttaa gtatgttact gagggcatga ggaaacccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg ggcgacacaa agcccgagaa catcgtgatc  2280
gagatggcca gggagaacca gaccacccag aaggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggga ccgcgcttat taaaaagtac  3000
cctaagttgg agtcagagtt cgtttatggg gactacaagg tgtacgacgt ccggaagatg  3060
attgcaaagt ctgaacagga aatcgggaag gccaccgcca aatatttctt ctacagtaac  3120
attatgaatt tttttaagac tgaaattact ctcgcaaacg gcgagatcag gaagcgtccc  3180
```

```
ctcatcgaga caaacgggga gaccggggag atagtctggg acaaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                             4101

SEQ ID NO: 69          moltype = DNA  length = 6117
FEATURE                Location/Qualifiers
source                 1..6117
                       mol_type = genomic DNA
                       organism = Glycine max
SEQUENCE: 69
atgagcttgc tccatgtagt tgggtttggt cttaaagtgg ggcatctact tttggtgcta  60
tgttgctggg ttgtgtctgt ggtttatctt aactggtttc tcagcagtgg aattattatg  120
gacaccaaga tgggtggtgg aggtggtggt ggtagcaaga tgtggcacaa aaaatggtgg  180
gagaagatct cagggcaggg ttgcaaaatc caccaacagt actaccagta tattggctcc  240
aagaaagtta agagagcgtt gtggaggaag cttttgctga catgggtagt gggttggttc  300
atagtatctt tgcggatctt ctgctacatg agctcgcaag gtactgagaa gaggaaagaa  360
actcttgcaa gcatgtgtga tgaaagggct aggatgctgc aggatcagtt taatgtcagt  420
atgaaccata tccaagccat gtccattcta atctccactt tccaccatgc taagagcccc  480
tcagccatcg atcaggtact agtctttact ttgttgttgc aaatcaggac ctaattcact  540
aattccccac cttttgcttt tagtctttgt ttattttggc ttaattttta ttcacatagg  600
tttctgagtt gtttcattgt cattaatttt agtgtctaat agcattattt tgtctaatac  660
acaacacctt ttttgtggag aatttattgg ggttttagta ttatatgttt tgctgacaag  720
gttactgaac ttgagctgct ggaacatgac ctgatttcct tggttcctcc ccttcttgtc  780
ggatagaaaa gatcccactt tcttttatcc ttcgatcttt agtctcatct ctgcaaatta  840
atctaacttc caaaacttgc agaaaacttt tgcaaagtac acagaaagaa cagcttttga  900
gagacctctt acaagtggtg ttgcgtatgc tgtaagggtg ctccattctg aaagggaaca  960
atttgaaaag cagcaaggtt ggactatcaa gaggatggat actctagagc agaacccggt  1020
tcataaggac gattatgccc cagaggcact ggagccatcc cctgttcagg aagaatatgc  1080
tcctgtcatc tttgcacagg atacaattgc acacgtgatt tctgttaatg tgctttctgg  1140
aaaggtaggt ttctgatact tgtataattt tatttgtgga gctagtctga gccatatatt  1200
gttaattatg aaaattgtga aaatgctata cagtagactt tgatgtcttg atgataattt  1260
taatccatcc attctaagct ttttattcct ggtagtatgg tttttgactg gtctttagtg  1320
gtcattaatt ttttttccgg agaatgttta tgaagaaaaa actatctatg ttgccatatt  1380
gcttgttttt gtacccttgt tcttcctttc tcttgcttgt gatgatggga ttgctcctga  1440
tggagaatag tacacatgaa tagactctaa ttttgtgaat atcacaaagc tgaattgaga  1500
cacgttgttc atgtttgata tctaaaatct atggcaattt atttggattt atgattgtca  1560
cagttattca cttgttcatc aacaggaaga ccgtgaaaat gtgctgcgtg caagagaatc  1620
aggcaaaggg gttttaactg cgccctttag gctgctcaaa acaaatcgac taggggttat  1680
cctgaccttt gctgtttaca agagagatct cccatcaaat acaaccccaa atgaaaggat  1740
tcaagcaact gacgggtgtg cctagttttt gaattttttt gcatctgaca ttcattagct  1800
tttttggtca atttttatga ttttttatca ttcatataat ttagcttatt ccattttggt  1860
catctaaagc tttgaagtac tactaagtaa ctaatcactg tattcaaatt ttcagagaag  1920
attcatgaaa tctattaatg tgagaagagt gaataattat tggctctccc ttgtgataat  1980
tagaagcttt gaagttataa atctactttt aaattcaata aagccaatgg gaaaatgaaa  2040
aaaaatcatg aacacagtta aagagagcag catttttatg tcttcactac tgcttgctgg  2100
gcaggtatct tgggggagtc tttgatgttg agtcattagt ggagaaatta cttcagcaac  2160
ttgctagcaa gcaaactgta attgttcatg tatatgatac tacaaatcgt actcatccaa  2220
ttgccatgta tggctcaaat gaatcagggg atttttttcta tcacgtcagc actcttaact  2280
ttggagaccc ttttaggaag catgagatgc actgcaggta agagtaatgc tactgaagaa  2340
gtctaatatc tccgtcctcc ttaatgctca gtgtagtttg taagaataac agtgggtcac  2400
cttgaaatag gtagaggata tattaaatac acggtttatt attgtattaa tgtcacatga  2460
cttaatactt cacaatctag tggttttgct gctagcgata cctagtctag agttctttta  2520
tctggacttg tcatactttt ttagggtcat tgaatcttaa ctatttttat taatacatta  2580
caatgaaaat gtacaagttg tcaaagacga actattcatg aaaattaagc ttgatgctaa  2640
tgcaggttca agcagaagcc accatggcca tgggtggcaa taactacttc tattggtatc  2700
cttgttattg cactccttgt tggatatatt ttccatgcca ctgtgaatcg aattgccaaa  2760
gtagaagatg attaccgtga gatgatggaa cttaaaaaac gagctgaggc ggctgatgtt  2820
gcaaaatccc aggtatggaa cttttttttta aaatttattt gttgaactta ttttggctta  2880
actcatactg atcatgtggg ctttatcaat tgtaaccgca gtttcttgct actgtttccc  2940
atgagatcag aacaccaatg aatggtgttt tgggtgagtt gtcttctgtc tacggcttag  3000
tctattatcc aatttttatc tatattattt ccacagaaaa gaagagcttc ttcagccatg  3060
accctgctct aaattggatt ttcagggatg ttgcatatgc ttatggacac agatctagat  3120
gtaacccaac aggaatatgt caggacagca caggaaagtg gaaaagctct ggtgtcactt  3180
ataaatgagg ttttggatca ggctaagatt gagtttggta agctagagct tgaggctgtg  3240
ctcttcgaca tacgggcaat tttggatgat gtattgtctc tattttctga gaagtctcaa  3300
ggaaaaagag tagaggtaat atctctctca tctactgttg atttttttatc atgatggaat  3360
```

```
tttcaaaatg tgcgtagtct aatagttaat ggctcttcat aatttttgtg gtaactgcag  3420
ttggcagttt atgtgtcaga tcatgttcct gaattactta taggtgatcc aggaagattt  3480
cgacaaataa ttaccaatct catgggtaac tcaattaagg taagtttatg gtagagagaa  3540
gaacattatg tataattcaa gttacttagt ctgatatcct tcatataagt tacttagaga  3600
tgttcccttg tcctacatcc ttgccttata gacatgctac ggtcatcata gtctcatgaa  3660
aaaaaatctt ctatttagtg ttctagccaa gcatgactat tagtagagca aagttgatgt  3720
gtatttcttg aaaatattat taaaactgat tctgtaattg tttggcagtt cacggacaaa  3780
ggacatattt ttgtcacaat ccatcttgtt gaggaggttg tccgttcaat agaggttgac  3840
aaagaatcca actcagaaaa taccttgagt ggttcgcccg ttgctgatag tcgccggagc  3900
tgggaaggat tcaaggcttt cagtcaagag ggacctcttg gttccttctc atcccctcca  3960
atgatcttgt caatttgatt gtatctgttg aagatacagg tgaaggtatt cctcttgaat  4020
ctcagccact catcttcacc ccattcatgc aggtaggttc atccatctcc cgaaagcatg  4080
gaggaacagg cattggccta agcattagca aatgtttggt tggcctcatg aatggggaaa  4140
ttggatttgt gagcataccc aagattgggt ccacattcac ttttactgct gtattcacca  4200
atggacaccg tagttcaagt gagtgtaaaa ttcagcaaat caacaaccaa cctcagtctg  4260
catcttcaga atttgagggg atgactgcat taattattga cccaagatct gttagagcag  4320
aagtgtctgg atatcacatc caacggcttg gcattcatgt tgaaatggtt tcagatttaa  4380
aacaaggttt gtcaaccata agcaatggga atgtagttgt taatatggtc ctgattgagc  4440
aggaggtttg ggatagagat ttaggcttgt catctcactt tgtcaataac acgaggagaa  4500
ttgatcatgg ggttcctcca aagctgttca ttcttgttaa ttctagtagt tcttttaaag  4560
ctagcgtaaa cttgggtgtt cataatccta ctgtgatcac caaacctctg agagcaagta  4620
tgcttgctgc ctcactacaa cgagccatgg gtgtccaaaa caagggagct cctcatagag  4680
agctccaaag tttgtctctt cgccatcttc ttcgtggcag gaaaattcta attgtagacg  4740
acaatggtgt gaaccgtgca gtagcagctg gtgcattgaa aaagtatgga gcagatgtgg  4800
tttgtgttag cagtggaaaa gatgccatct cttccttgaa gccaccccat cagtttgatg  4860
cctgtttcat ggatattcaa atgccagaaa tggatgggta tgtatgcacc tggaatactt  4920
tctttcagaa tctgatattt ttaatatctg gagtaatatt tgaaatttct acaaacatag  4980
aaaagagttt ttaattcttt tattgatcta acagaataat tgaaaatatc ttacttaaca  5040
gttttaacat caaaggaaaa cttattgcac tgcaaagatt tgtgaaacaa actaatgtat  5100
attaagcaca caaggtgttt ggagtctata attcatttga caattctatg acaaaaatag  5160
tcttgtctca ttaagtgagg tttgatacat gatgccattg agcttggtta aaaaccaaat  5220
tctaagggat gctatttacc ataaatctct tttgataatt ttctttagtt tcctttttgg  5280
tgctgtgtct agctccttta actttcccta tgtaccaaag tttacatcct gtagtgtctt  5340
actccttgac ttcttctcca acctatttag tttcttgaaa acatgtgatg tgaatccttt  5400
tccaaatcat gatgtccacc accttcagag aattatcttt caatgtacca atattccaag  5460
caccaaatct aatcaggcac aactagtcta gttgctttac ccacatttgt ctacaaaaat  5520
gtgaaaactc ttgcttattt aatacatttg aaagtttctg tagcagctct agctcattta  5580
acactgtact caaggcattc aaagtgttat ttttgggtta cgacctagca ttggcacaca  5640
taatccattg ttagtgatcc atgcttgggc tttcaacaag ttttatgttg gttgtcaagg  5700
gcctaacaca accctcttcc tttgtcaggc tttggaacca gctatgagcc cataagcgga  5760
gtcaattcat ttcacaattc taaataaaaa attatttgaa aatttattta tctactttct  5820
atttataaac ccagaattat cattatatta caattttgct aataacaatt ctttcccaac  5880
agatttgaag ctacaaagcg aattagggag atggaagata gtgtgaacag agaagtatct  5940
atggatgact ttgagaatat tacaaactgg catgtaccca ttttagccat gaccgcagat  6000
gtgatacagg ctacacacga ggaatgccta aggtgtggca tggatggata tgtttcaaaa  6060
ccatttgaag ctgaacagct gtatagagaa gtctcacggt tttccagtc atcttga      6117
```

```
SEQ ID NO: 70          moltype = DNA  length = 3039
FEATURE                Location/Qualifiers
source                 1..3039
                       mol_type = other DNA
                       organism = Glycine max
SEQUENCE: 70
atgagcttgc tccatgtagt tgggtttggt cttaaagtgg ggcatctact tttggtgcta  60
tgttgctggg ttgtgtctgt ggtttatctt aactggtttc tcagcagtgg aattattatg  120
gacaccaaga tgggtggtgg aggtggtggt ggtagcaaga tgtggcacaa aaaatggtgg  180
gagaagatct cagggcaggg ttgcaaaatc caccaacagt actaccagta tattggctcc  240
aagaaagtta agagagcgtt gtggaggaag cttttgctga catgggtagt gggttggttc  300
atagtatctt tgcggatctt ctgctacatg agctcgcaag gtactgagaa gaggaaagaa  360
actcttgcaa gcatgtgtga tgaaagggct aggatgctgc aggatcagtt taatgtcagt  420
atgaaccata tccaagccat gtccattcta atctccactt tccaccatgc taagagcccc  480
tcagccatcg atcagaaaac ttttgcaaag tacacagaaa gaacagcttt tgagagacct  540
cttacaagtg gtgttgcgta tgctgtaagg gtgctccatt ctgaaaggga acaatttgaa  600
aagcagcaag gttggactat caagaggatg gatactctag agcagaaccc ggttcataag  660
gacgattatg ccccagaggc actggagcca tcccctgttc aggaagaata tgctcctgtc  720
atctttgcac aggatacaat tgcacacgtg atttctgtta atgtgctttc tggaaaggaa  780
gaccgtgaaa atgtgctgcg tgcaagagaa tcaggcaaag gggttttaac tgcgcccttt  840
aggctgctca aaacaaatcg actaggggtt atcctgacct ttgctgttta caagagagat  900
ctcccatcaa atacaacccc aaatgaaagg attcaagcaa ctgacgggta tcttgggggga  960
gtctttgatg ttgagtcatt agtggagaaa ttacttcagc aacttgctag caagcaaact  1020
gtaattgttc atgtatatga tactacaaat cgtactcatc caattgccat gtatggctca  1080
aatgaatcag gggatttttt ctatcacgtc agcactctta actttggaga ccctttttagg  1140
aagcatgaga tgcactgcag gttcaagcag aagccaccat ggccatgggt ggcaataact  1200
acttctattg gtatccttgt tattgcactc cttgttggat atattttcca tgccactgtg  1260
aatcgaattg ccaaagtaga agatgattac cgtgagatga tggaacttaa aaaacgagct  1320
gaggcggctg atgttgcaaa atcccagttt cttgctactg tttcccatga gatcagaaca  1380
ccaatgaatg gtgttttggg gatgttgcat atgcttatgg acacagatct agatgtaacc  1440
caacaggaat atgtcaggac agcacaggaa agtggaaaag ctctggtgtc acttataaat  1500
gaggttttgg atcaggctaa gattgagttt ggtaagctag agcttgaggc tgtgctcttc  1560
```

```
gacatacggg caattttgga tgatgtattg tctctatttt ctgagaagtc tcaaggaaaa  1620
agagtagagt tggcagttta tgtgtcagat catgttcctg aattacttat aggtgatcca  1680
ggaagatttc gacaaataat taccaatctc atgggtaact caattaagtt cacggacaaa  1740
ggacatattt ttgtcacaat ccatcttgtt gaggaggttg tccgttcaat agaggttgac  1800
aaagaatcca actcagaaaa taccttgagt ggttcgcccg ttgctgatag tcgccggagc  1860
tgggaaggat tcaaggcttt cagtcaagag ggacctcttg atacaggtga aggtattcct  1920
cttgaatctc agccactcat cttcaccccca ttcatgcagg taggttcatc catctcccga  1980
aagcatggag gaacaggcat tggcctaagc attagcaaat gtttggttgg cctcatgaat  2040
ggggaaattg gatttgtgag catacccaag attgggtcca cattcacttt tactgctgta  2100
ttcaccaatg gacaccgtag ttcaagtgag tgtaaaattc agcaaatcaa caaccaacct  2160
cagtctgcat cttcagaatt tgaggggatg actgcattaa ttattgaccc aagatctgtt  2220
agagcagaag tgtctggata tcacatccaa cggcttggca ttcatgttga aatggtttca  2280
gatttaaaac aaggtttgtc aaccataagc aatgggaatg tagttgttaa tatggtcctg  2340
attgagcagg aggtttggga tagagattta ggcttgtcat ctcactttgt caataacacg  2400
aggagaattg atcatggggt tcctccaaag ctgttcattc ttgttaattc tagtagttct  2460
tttaaagcta gcgtaaactt gggtgttcat aatcctactg tgatcaccaa acctctgaga  2520
gcaagtatgc ttgctgcctc actacaacga gccatgggtg tccaaaacaa gggagctcct  2580
catagagagc tccaaagttt gtctcttcgc catcttcttc gtggcaggaa aattctaatt  2640
gtagacgaca atggtgtgaa ccgtgcagta gcagctggtg cattgaaaaa gtatggagca  2700
gatgtggttt gtgttagcag tggaaaagat gccatctctt ccttgaagcc accccatcag  2760
tttgatgcct gtttcatgga tattcaaatg ccagaaatgg atggatttga agctacaaag  2820
cgaattaggg agatggaaga tagtgtgaac agagaagtat ctatggatga ctttgagaat  2880
attacaaact ggcatgtacc cattttagcc atgaccgcag atgtgataca ggctacacac  2940
gaggaatgcc taaggtgtgg catggatgga tatgtttcaa aaccatttga agctgaacag  3000
ctgtatagag aagtctcacg gtttttccag tcatcttga                         3039

SEQ ID NO: 71          moltype = AA  length = 1030
FEATURE                Location/Qualifiers
source                 1..1030
                       mol_type = protein
                       organism = Glycine max
SEQUENCE: 71
MSLLHVVGFG LKVGHLLLVL CCWVVSVVYL NWFLSSGIIM DTKMGGGGGG GSKMWHKKWW  60
EKISGQGCKI HQQYYQYIGS KKVKRALWRK LLLTWVVGWF IVSLRIFCYM SSQGTEKRKE  120
TLASMCDERA RMLQDQFNVS MNHIQAMSIL ISTFHHAKSP SAIDQKTFAK YTERTAFERP  180
LTSGVAYAVR VLHSEREQFE KQQGWTIKRM DTLEQNPVHK DDYAPEALEP SPVQEEYAPV  240
IFAQDTIAHV ISVNVLSGKE DRENVLRARE SGKGVLTAPF RLLKTNRLGV ILTFAVYKRD  300
LPSNTTPNER IQATDGYLGG VFDVESLVEK LLQQLASKQT VIVHVYDTTN RTHPIAMYGS  360
NESGDFFYHV STLNFGDPFR KHEMHCRFKQ KPPWPWVAIT TSIGILVIAL LVGYIFHATV  420
NRIAKVEDDY REMMELKKRA EADVAKSQF LATVSHEIRT PMNGVLGMLH MLMDTDLDVT  480
QQEYVRTAQE SGKALVSLIN EVLDQAKIEF GKLELEAVLF DIRAILDDVL SLFSEKSQGK  540
RVELAVYVSD HVPELLIGDP GRFRQIITNL MGNSIKFTDK GHIFVTIHLV EEVVRSIEVD  600
KESNSENTLS GSPVADSRRS WEGFKAFSQE GPLGSFSSPS NDLVNLIVSV EDTGEGIPLE  660
SQPLIFTPFM QVGSSISRKH GGTGIGLSIS KCLVGLMNGE IGFVSIPKIG STFTFTAVFT  720
NGHRSSSECK IQQINNQPQS ASSEFEGMTA LIIDPRSVRA EVSGYHIQRL GIHVEMVSDL  780
KQGLSTISNG NVVVNMVLIE QEVWDRDLGL SSHFVNNTRR IDHGVPPKLF ILVNSSSSFK  840
ASVNLGVHNP TVITKPLRAS MLAASLQRAM GVQNKGAPHR ELQSLSLRHL LRGRKILIVD  900
DNGVNRAVAA GALKKYGADV VCVSSGKDAI SSLKPPHQFD ACFMDIQMPE MDGFEATKRI  960
REMEDSVNRE VSMDDFENIT NWHVPILAMT ADVIQATHEE CLRCGMDGYV SKPFEAEQLY  1020
REVSRFFQSS                                                         1030

SEQ ID NO: 72          moltype = DNA  length = 1751
FEATURE                Location/Qualifiers
source                 1..1751
                       mol_type = genomic DNA
                       organism = Glycine max
SEQUENCE: 72
tcagccatcg atcaggtact agtctttact ttgttgttgc aaatcaggac ctaattcact  60
aattccccac cttttgcttt tagtctttgt ttattttggc ttaattttta ttcacatagg  120
tttctgagtt gtttcattgt cattaatttt agtgtctaat agcattattt tgtctaatac  180
acaacacctt ttttgtggag aatttattgg ggttttagta ttatatgttt tgctgacaag  240
gttactgaac ttgagctgct ggaacatgac ctgatttcct tggttcctcc ccttcttgtc  300
ggatagaaaa gatcccactt tcttttatcc ttcgatcttt agtctcatct ctgcaaatta  360
atctaacttc caaaacttgc agaaaacttt tgcaaagtac acagaaagaa cagcttttga  420
gagacctctt acaagtggtg ttgcgtatgc tgtaagggtg ctccattctg aaagggaaca  480
atttgaaaag cagcaaggtt ggactatcaa gaggatggat actctagagc agaacccggt  540
tcataaggac gattatgccc cagaggcact ggagccatcc cctgttcagg aagaatatgc  600
tcctgtcatc tttgcacagg atacaattgc acacgtgatt tctgttaatg tgctttctgg  660
aaaggtaggt ttctgatact tgtataattt tatttgtgga gctagtctga gccatatatt  720
gttaattatg aaaattgtga aaatgctata cagtagactt tgatgtcttg atgataattt  780
taatccatcc attctaagct ttttattcct ggtagtatgg tttttgactg gtctttagtg  840
gtcattaatt ttttttccgg agaatgttta tgaagaaaaa actatctatg ttgccatatt  900
gcttgttttt gtacccttgt tcttcctttc tcttgcttgt gatgatggga ttgctcctga  960
tggagaatag tacacatgaa tagactctaa ttttgtgaat atcacaaagc tgaattgaga  1020
cacgttgttc atgtttgata tctaaaatct atggcaattt atttggattt atgattgtca  1080
cagttattca cttgttcatc aacaggaaga ccgtgaaaat gtgctgcgtg caagagaatc  1140
aggcaaaggg gttttaactg cgccctttag gctgctcaaa acaaatcgac taggggttat  1200
cctgaccttt gctgtttaca agagagatct cccatcaaat acaaccccaa atgaaaggat  1260
tcaagcaact gacgggtgtg cctagttttt gaattttttt gcatctgaca ttcattagct  1320
```

```
tttttggtca atttttatga ttttttatca ttcatataat ttagcttatt ccattttggt  1380
catctaaagc tttgaagtac tactaagtaa ctaatcactg tattcaaatt ttcagagaag  1440
attcatgaaa tctattaatg tgagaagagt gaataattat tggctctccc ttgtgataat  1500
tagaagcttt gaagttataa atctactttt aaattcaata aagccaatgg gaaaatgaaa  1560
aaaaatcatg aacacagtta aagagagcag catttttatg tcttcactac tgcttgctgg  1620
gcaggtatct tgggggagtc tttgatgttg agtcattagt ggagaaatta cttcagcaac  1680
ttgctagcaa gcaaactgta attgttcatg tatatgatac tacaaatcgt actcatccaa  1740
ttgccatgta t                                                      1751

SEQ ID NO: 73          moltype = DNA  length = 1095
FEATURE                Location/Qualifiers
source                 1..1095
                       mol_type = genomic DNA
                       organism = Glycine max
SEQUENCE: 73
gttcctcccc ttcttgtcgg atagaaaaga tcccactttc ttttatcctt cgatctttag  60
tctcatctct gcaaattaat ctaacttcca aaacttgcag aaaacttttg caaagtacac  120
agaaagaaca gcttttgaga gacctcttac aagtggtgtt gcgtatgctg taagggtgct  180
ccattctgaa agggaacaat ttgaaaagca gcaaggttgg actatcaaga ggatggatac  240
tctagagcag aacccggttc ataaggacga ttatgcccca gaggcactgg agccatcccc  300
tgttcaggaa gaatatgctc ctgtcatctt tgcacaggat acaattgcac acgtgatttc  360
tgttaatgtg ctttctggaa aggtaggttt ctgatacttg tataatttta tttgtggagc  420
tagtctgagc catatattgt taattatgaa aattgtgaaa atgctataca gtagactttg  480
atgtcttgat gataatttta atccatccat tctaagcttt ttattcctgg tagtatggtt  540
tttgactggt ctttagtggt cattaatttt ttttccggag aatgtttatg aagaaaaaac  600
tatctatgtt gccatattgc ttgtttttgt acccttgttc ttcctttctc ttgcttgtga  660
tgatgggatt gctcctgatg gagaatagta cacatgaata gactctaatt ttgtgaatat  720
cacaaagctg aattgagaca cgttgttcat gtttgatatc taaaatctat ggcaatttat  780
ttggatttat gattgtcaca gttattcact tgttcatcaa caggaagacc gtgaaaatgt  840
gctgcgtgca agagaatcag gcaaaggggt tttaactgcg ccctttaggc tgctcaaaac  900
aaatcgacta ggggttatcc tgacctttgc tgtttacaag agagatctcc catcaaatac  960
aaccccaaat gaaaggattc aagcaactga cgggtgtgcc tagtttttga atttttttgc  1020
atctgacatt cattagcttt tttggtcaat ttttatgatt ttttatcatt catataattt  1080
agcttattcc atttt                                                  1095

SEQ ID NO: 74          moltype = DNA  length = 895
FEATURE                Location/Qualifiers
source                 1..895
                       mol_type = genomic DNA
                       organism = Glycine max
SEQUENCE: 74
aaaacttttg caaagtacac agaaagaaca gcttttgaga gacctcttac aagtggtgtt  60
gcgtatgctg taagggtgct ccattctgaa agggaacaat ttgaaaagca gcaaggttgg  120
actatcaaga ggatggatac tctagagcag aacccggttc ataaggacga ttatgcccca  180
gaggcactgg agccatcccc tgttcaggaa gaatatgctc ctgtcatctt tgcacaggat  240
acaattgcac acgtgatttc tgttaatgtg ctttctggaa aggtaggttt ctgatacttg  300
tataatttta tttgtggagc tagtctgagc catatattgt taattatgaa aattgtgaaa  360
atgctataca gtagactttg atgtcttgat gataatttta atccatccat tctaagcttt  420
ttattcctgg tagtatggtt tttgactggt ctttagtggt cattaatttt ttttccggag  480
aatgtttatg aagaaaaaac tatctatgtt gccatattgc ttgtttttgt acccttgttc  540
ttcctttctc ttgcttgtga tgatgggatt gctcctgatg gagaatagta cacatgaata  600
gactctaatt ttgtgaatat cacaaagctg aattgagaca cgttgttcat gtttgatatc  660
taaaatctat ggcaatttat ttggatttat gattgtcaca gttattcact tgttcatcaa  720
caggaagacc gtgaaaatgt gctgcgtgca agagaatcag gcaaaggggt tttaactgcg  780
ccctttaggc tgctcaaaac aaatcgacta ggggttatcc tgacctttgc tgtttacaag  840
agagatctcc catcaaatac aaccccaaat gaaaggattc aagcaactga cgggt      895

SEQ ID NO: 75          moltype = DNA  length = 503
FEATURE                Location/Qualifiers
source                 1..503
                       mol_type = genomic DNA
                       organism = Glycine max
SEQUENCE: 75
tctcatctct gcaaattaat ctaacttcca aaacttgcag aaaacttttg caaagtacac  60
agaaagaaca gcttttgaga gacctcttac aagtggtgtt gcgtatgctg taagggtgct  120
ccattctgaa agggaacaat ttgaaaagca gcaaggttgg actatcaaga ggatggatac  180
tctagagcag aacccggttc ataaggacga ttatgcccca gaggcactgg agccatcccc  240
tgttcaggaa gaatatgctc ctgtcatctt tgcacaggat acaattgcac acgtgatttc  300
tgttaatgtg ctttctggaa aggtaggttt ctgatacttg tataatttta tttgtggagc  360
tagtctgagc catatattgt taattatgaa aattgtgaaa atgctataca gtagactttg  420
atgtcttgat gataatttta atccatccat tctaagcttt ttattcctgg tagtatggtt  480
tttgactggt ctttagtggt cat                                         503

SEQ ID NO: 76          moltype = DNA  length = 463
FEATURE                Location/Qualifiers
source                 1..463
                       mol_type = genomic DNA
                       organism = Glycine max
SEQUENCE: 76
```

```
ctaacttcca aaacttgcag aaaactttttg caaagtacac agaaagaaca gcttttgaga  60
gacctcttac aagtggtgtt gcgtatgctg taagggtgct ccattctgaa agggaacaat  120
ttgaaaagca gcaaggttgg actatcaaga ggatggatac tctagagcag aacccggttc  180
ataaggacga ttatgcccca gaggcactgg agccatcccc tgttcaggaa gaatatgctc  240
ctgtcatctt tgcacaggat acaattgcac acgtgatttc tgttaatgtg ctttctggaa  300
aggtaggttt ctgatacttg tataatttta tttgtggagc tagtctgagc catatattgt  360
taattatgaa aattgtgaaa atgctataca gtagactttg atgtcttgat gataatttta  420
atccatccat tctaagcttt ttattcctgg tagtatggtt ttt                   463

SEQ ID NO: 77          moltype = DNA  length = 233
FEATURE                Location/Qualifiers
source                 1..233
                       mol_type = genomic DNA
                       organism = Glycine max
SEQUENCE: 77
gttcctcccc ttcttgtcgg atagaaaaga tcccactttc ttttatcctt cgatctttag  60
tctcatctct gcaaattaat ctaacttcca aaacttgcag aaaactttttg caaagtacac  120
agaaagaaca gcttttgaga gacctcttac aagtggtgtt gcgtatgctg taagggtgct  180
ccattctgaa agggaacaat ttgaaaagca gcaaggttgg actatcaaga gga        233

SEQ ID NO: 78          moltype = DNA  length = 113
FEATURE                Location/Qualifiers
source                 1..113
                       mol_type = genomic DNA
                       organism = Glycine max
SEQUENCE: 78
tctcatctct gcaaattaat ctaacttcca aaacttgcag aaaactttttg caaagtacac  60
agaaagaaca gcttttgaga gacctcttac aagtggtgtt gcgtatgctg taa        113

SEQ ID NO: 79          moltype = DNA  length = 73
FEATURE                Location/Qualifiers
source                 1..73
                       mol_type = genomic DNA
                       organism = Glycine max
SEQUENCE: 79
ctaacttcca aaacttgcag aaaactttttg caaagtacac agaaagaaca gcttttgaga  60
gacctcttac aag                                                    73

SEQ ID NO: 80          moltype = DNA  length = 223
FEATURE                Location/Qualifiers
source                 1..223
                       mol_type = genomic DNA
                       organism = Glycine max
SEQUENCE: 80
tataatttta tttgtggagc tagtctgagc catatattgt taattatgaa aattgtgaaa  60
atgctataca gtagactttg atgtcttgat gataatttta atccatccat tctaagcttt  120
ttattcctgg tagtatggtt tttgactggt ctttagtggt cattaatttt ttttccggag  180
aatgtttatg aagaaaaaac tatctatgtt gccatattgc ttg                   223

SEQ ID NO: 81          moltype = DNA  length = 143
FEATURE                Location/Qualifiers
source                 1..143
                       mol_type = genomic DNA
                       organism = Glycine max
SEQUENCE: 81
taattatgaa aattgtgaaa atgctataca gtagactttg atgtcttgat gataatttta  60
atccatccat tctaagcttt ttattcctgg tagtatggtt tttgactggt ctttagtggt  120
cattaatttt ttttccggag aat                                         143

SEQ ID NO: 82          moltype = DNA  length = 104
FEATURE                Location/Qualifiers
source                 1..104
                       mol_type = genomic DNA
                       organism = Glycine max
SEQUENCE: 82
atgctataca gtagactttg atgtcttgat gataatttta atccatccat tctaagcttt  60
ttattcctgg tagtatggtt tttgactggt ctttagtggt catt                  104

SEQ ID NO: 83          moltype = DNA  length = 64
FEATURE                Location/Qualifiers
source                 1..64
                       mol_type = genomic DNA
                       organism = Glycine max
SEQUENCE: 83
atgtcttgat gataatttta atccatccat tctaagcttt ttattcctgg tagtatggtt  60
tttg                                                              64

SEQ ID NO: 84          moltype = DNA  length = 250
FEATURE                Location/Qualifiers
```

```
source                  1..250
                        mol_type = genomic DNA
                        organism = Glycine max
SEQUENCE: 84
ttttaaattc aataaagcca atgggaaaat gaaaaaaaat catgaacaca gttaaagaga  60
gcagcatttt tatgtcttca ctactgcttg ctgggcaggt atcttggggg agtctttgat  120
gttgagtcat tagtggagaa attacttcag caacttgcta gcaagcaaac tgtaattgtt  180
catgtatatg atactacaaa tcgtactcat ccaattgcca tgtatggctc aaatgaatca  240
ggggattttt                                                         250

SEQ ID NO: 85           moltype = DNA  length = 170
FEATURE                 Location/Qualifiers
source                  1..170
                        mol_type = genomic DNA
                        organism = Glycine max
SEQUENCE: 85
catgaacaca gttaaagaga gcagcatttt tatgtcttca ctactgcttg ctgggcaggt  60
atcttggggg agtctttgat gttgagtcat tagtggagaa attacttcag caacttgcta  120
gcaagcaaac tgtaattgtt catgtatatg atactacaaa tcgtactcat             170

SEQ ID NO: 86           moltype = DNA  length = 130
FEATURE                 Location/Qualifiers
source                  1..130
                        mol_type = genomic DNA
                        organism = Glycine max
SEQUENCE: 86
gcagcatttt tatgtcttca ctactgcttg ctgggcaggt atcttggggg agtctttgat  60
gttgagtcat tagtggagaa attacttcag caacttgcta gcaagcaaac tgtaattgtt  120
catgtatatg                                                         130

SEQ ID NO: 87           moltype = DNA  length = 90
FEATURE                 Location/Qualifiers
source                  1..90
                        mol_type = genomic DNA
                        organism = Glycine max
SEQUENCE: 87
ctactgcttg ctgggcaggt atcttggggg agtctttgat gttgagtcat tagtggagaa  60
attacttcag caacttgcta gcaagcaaac                                   90

SEQ ID NO: 88           moltype = DNA  length = 69
FEATURE                 Location/Qualifiers
source                  1..69
                        mol_type = genomic DNA
                        organism = Glycine max
SEQUENCE: 88
tatcttgggg gagtctttga tgttgagtca ttagtggaga aattacttca gcaacttgct  60
agcaagcaa                                                          69

SEQ ID NO: 89           moltype = DNA  length = 60
FEATURE                 Location/Qualifiers
source                  1..60
                        mol_type = genomic DNA
                        organism = Glycine max
SEQUENCE: 89
aaaacttttg caaagtacac agaaagaaca gcttttgaga gacctcttac aagtggtgtt  60

SEQ ID NO: 90           moltype = DNA  length = 594
FEATURE                 Location/Qualifiers
source                  1..594
                        mol_type = other DNA
                        organism = Glycine max
SEQUENCE: 90
tcagccatcg atcagaaaac ttttgcaaag tacacagaaa gaacagcttt tgagagacct  60
cttacaagtg gtgttgcgta tgctgtaagg gtgctccatt ctgaaaggga acaatttgaa  120
aagcagcaag gttggactat caagaggatg gatactctag agcagaaccc ggttcataag  180
gacgattatg ccccagaggc actggagcca tcccctgttc aggaagaata tgctcctgtc  240
atctttgcac aggatacaat tgcacacgtg atttctgtta atgtgctttc tggaaaggaa  300
gaccgtgaaa atgtgctgcg tgcaagagaa tcaggcaaag gggttttaac tgcgcccttt  360
aggctgctca aaacaaatcg actaggggtt atcctgacct ttgctgttta caagagagat  420
ctcccatcaa atacaacccc aaatgaaagg attcaagcaa ctgacgggta tcttggggga  480
gtctttgatg ttgagtcatt agtggagaaa ttacttcagc aacttgctag caagcaaact  540
gtaattgttc atgtatatga tactacaaat cgtactcatc caattgccat gtat        594

SEQ ID NO: 91           moltype = DNA  length = 123
FEATURE                 Location/Qualifiers
source                  1..123
                        mol_type = other DNA
                        organism = Glycine max
SEQUENCE: 91
```

```
cactttccac catgctaaga gcccctcagc catcgatcag aaaactttg caaagtacac  60
agaaagaaca gcttttgaga gacctcttac aagtggtgtt gcgtatgctg taagggtgct  120
cca                                                               123

SEQ ID NO: 92          moltype = DNA  length = 164
FEATURE                Location/Qualifiers
source                 1..164
                       mol_type = other DNA
                       organism = Glycine max
SEQUENCE: 92
gagatctccc atcaaataca accccaaatg aaaggattca agcaactgac gggtatcttg  60
ggggagtctt tgatgttgag tcattagtgg agaaattact tcagcaactt gctagcaagc  120
aaactgtaat tgttcatgta tatgatacta caaatcgtac tcat                  164

SEQ ID NO: 93          moltype = DNA  length = 123
FEATURE                Location/Qualifiers
source                 1..123
                       mol_type = other DNA
                       organism = Glycine max
SEQUENCE: 93
ccccaaatga aaggattcaa gcaactgacg ggtatcttgg gggagtcttt gatgttgagt  60
cattagtgga gaaattactt cagcaacttg ctagcaagca aactgtaatt gttcatgtat  120
atg                                                               123

SEQ ID NO: 94          moltype = DNA  length = 84
FEATURE                Location/Qualifiers
source                 1..84
                       mol_type = other DNA
                       organism = Glycine max
SEQUENCE: 94
agcaactgac gggtatcttg ggggagtctt tgatgttgag tcattagtgg agaaattact  60
tcagcaactt gctagcaagc aaac                                        84

SEQ ID NO: 95          moltype = AA  length = 198
FEATURE                Location/Qualifiers
source                 1..198
                       mol_type = protein
                       organism = Glycine max
SEQUENCE: 95
SAIDQKTFAK YTERTAFERP LTSGVAYAVR VLHSEREQFE KQQGWTIKRM DTLEQNPVHK  60
DDYAPEALEP SPVQEEYAPV IFAQDTIAHV ISVNVLSGKE DRENVLRARE SGKGVLTAPF  120
RLLKTNRLGV ILTFAVYKRD LPSNTTPNER IQATDGYLGG VFDVESLVEK LLQQLASKQT  180
VIVHVYDTTN RTHPIAMY                                               198

SEQ ID NO: 96          moltype = AA  length = 20
FEATURE                Location/Qualifiers
source                 1..20
                       mol_type = protein
                       organism = Glycine max
SEQUENCE: 96
KTFAKYTERT AFERPLTSGV                                             20

SEQ ID NO: 97          moltype = AA  length = 11
FEATURE                Location/Qualifiers
source                 1..11
                       mol_type = protein
                       organism = Glycine max
SEQUENCE: 97
TFAKYTERTA F                                                      11

SEQ ID NO: 98          moltype = AA  length = 11
FEATURE                Location/Qualifiers
source                 1..11
                       mol_type = protein
                       organism = Glycine max
SEQUENCE: 98
ERTAFERPLT S                                                      11

SEQ ID NO: 99          moltype = AA  length = 23
FEATURE                Location/Qualifiers
source                 1..23
                       mol_type = protein
                       organism = Glycine max
SEQUENCE: 99
YLGGVFDVES LVEKLLQQLA SKQ                                         23

SEQ ID NO: 100         moltype = AA  length = 11
FEATURE                Location/Qualifiers
source                 1..11
```

```
                        mol_type = protein
                        organism = Glycine max
SEQUENCE: 100
GVFDVESLVE K                                                          11

SEQ ID NO: 101          moltype = AA  length = 11
FEATURE                 Location/Qualifiers
source                  1..11
                        mol_type = protein
                        organism = Glycine max
SEQUENCE: 101
LVEKLLQQLA S                                                          11

SEQ ID NO: 102          moltype = DNA  length = 8099
FEATURE                 Location/Qualifiers
source                  1..8099
                        mol_type = genomic DNA
                        organism = Glycine max
SEQUENCE: 102
acacagattt gtgaatggca tttcccagtt tttcttttc catttcaacc tctttctcac  60
tcttttctgt gttcttccga cccccttaaaa ttggacacac aaaaaggtaa aaagaaaaaa  120
aaagtgagag acccagggga gaaaaaaatg attcattttg agaatcagaa aaccacttat  180
ggaccacaca gaaaaattgc actctagagc agtagtgaag tgagtaatat agaaaaaata  240
aataacataa accaaagaaa aaaaaaacag tgtttctgt gtttggttca gtttgttgtt  300
ggttccatca ctcactggtc aacaaaggtt gcttttttcc atcatcctgt gaacatggtg  360
tttctatttt cagcttctca cctcagcaat gagaactgag gaaggggaga cactgttggt  420
gtgaaatgcg ttagtgttag tgccataaat agaaagagag atatagagaa aatagaaaag  480
agaaaatgag agttgcaaga aagaaagaag ggctggtact agtagtagtg tatagactaa  540
tgtattactt aattaattaa taattatttt tgagtttttt ttttatcatg aagctcgtgg  600
gagacgagcg tatcaaggga aatcctacaa attcgatttt ttcttatctg ttaataatat  660
aaatataaat aaaaaaaagt gacaacagag aaaagtagca taaaataaaa gcagcagtgt  720
gtagtgtaga gagagagaca cggatttgga ccaaccaaaa tttggttcct atggttcatt  780
gtacagccac cctttctttc ctgttacagg taaacaaaca taaacattat tgtttctttc  840
tttccttttt tctacaaaaa tgcctcattc atttctacta agactctctt tcattgggtt  900
ctgtgtgttt gtgttttggg gtcagtgtct ctggcttgga atattatatg caagagggtg  960
tgtgaactag tttcacgcct acatagcatg attattggtt agagttctct tgttttttt  1020
aatgtgatcc tcagtacaca aaagtgtgaa acaaggccaa gtattggagg ggtgtagggt  1080
gagagtgaaa gcgaggtggt gagggatgtg gtagctcttt gaaatttgag ctatttcccc  1140
atcttttgag acccatgctt gtgtgttgag cttggaaagt ttcatttttt ttttgtttta  1200
attctgggtt acttgtctct ctttctctct ctctctctct ctctctctct ctctctccct  1260
ctctctctat tgatttcttt ttgttttggt gatttttgat gaagtgcgtt ttgcttgtta  1320
ggagagagaa agagagggaa ttggccaatc cttcattatg cttagtgtgt ttgtgcttgc  1380
cctttctcat gttttgaatc acgcaaaaca atgctgtgat gatgctttta catggagttt  1440
tgttctgtga tccctttttct tttctagcac caacagagaa aagtgtctgc aatttcgtca  1500
taactttaaa gaaagctaac tctactatgt gagcactaac tataaatttc tcttcttggg  1560
gcttctctaa ggcagaaggt gagcaaggga acataacagc ccagggaaac tagggagagt  1620
gtgaattact tgctgatggg tcttagtttg aagatgcaga gccaccatcc tgtggctttg  1680
aggttacatg atcaaatggg gtctaagaga aagtacacat tcattcaggc tcatagagct  1740
tggcttccaa agtttctgct gctgtggatc ctgctaatgg ctttgatcag ttggtgcatc  1800
tatagcaaaa tggatgatga cactaaagtc cgaaggaaag aggttttggg tagcctctgt  1860
gatcaaaggg caagaatgtt gcaagaccag tttagtgtta gtgttaacca tgtccatgcc  1920
cttgccatcc ttgtttcaac cttccattac tacagatacc cttctgccat tgaccaggtt  1980
agagcttgat cttccacttt aatcttgatt tgatacaagc taagcatgat attatatgta  2040
atggtttgaa agaaatgaaa tgctatttgg gattttcaca cttctactta ttgctcaaat  2100
tgtgtaaata actaaatatc tccatccatt gttcataata aaataggaaa cctttgctga  2160
gtacactgcc cggacagcat ttgaacggcc gttactgagt ggtgtggcct atgcgcaaag  2220
agttgttaac tctgagaggg agagatttga gaaagaacat ggatgggtta taaaaacaat  2280
ggaaagaaag tcttcactgg ttagagatga gtatgcaccg gtgatattcg cgcaagaaac  2340
tgtctcatat cttgagtctc ttgatatgat gtctggggag gtagattaca acactgccga  2400
acattattct atttactgct tatatattgt taaattttca ctcaaaattt tgcctttgca  2460
tgttcaggag gaccgagaaa acattttaag ggctagagcc actgggaagg cggttctgac  2520
tagtcctttc agtcttttgg gttctcacca tctcggtgtg gttttaacat tccctgtgta  2580
caaatctaag ctccctcaga agccaacagt ggaagaacgc attgaagcaa ctgcagggtg  2640
ggttttagtt tcacttctat ttgtttttca agttttcttt tgtgatatac ttggcgattc  2700
tttgtgttaa atgacatata gtatattttt tagttgttat gcttgtatgt tattttcata  2760
ccctaaataa taatgacaac actgtgtgtc aaataatatc acatttttct actaatcaat  2820
gaaagctgct gcggcttctt tctccattag atcatgactg atgctaacta ttaaagctgt  2880
gaccactaca ttttaatggt atcagtatca caatacctgc cactttgtgc taccagtttt  2940
atttccatca ataccacctt gggtgccata gccatttccc ctgatcacta tcagagagtt  3000
tgaggacaac tgttggcgat gcaaatggca caaccaatta actggttaat gtttattaat  3060
taacaattta tttaacattc aatatagtta accaattaaa tttttattat tcctatttta  3120
ccaataattc ctcttcttta aaattgttct tttggttttt gtattttcat ggccctcaat  3180
tattgaattc agagctgtat gtaagaggca ggatgcttgt gttgtgtggt ttgcatcctg  3240
tcctgtctaa aatgtagttt taacttttag ttctatagtt gcttacatcg acaagcctct  3300
ttaccttgtt tcaatcttgt ggctttatgt ttacactaag cttcttagtg tcctaatgta  3360
ttgaataaat ttctaattga catcagatat gttggaggat cctttgatgt tgagtccctt  3420
gtaaagaatt tacttgggca acttgatggt aaccaagcaa ttttggtgaa tgtatatgat  3480
attacaaact atactaatcc cctagtcatg tatgggaacc tatatgaaga aggcgatatg  3540
tctcttgtgc atgaaagcaa gcttgatttt ggagatccat acaggaaaca tcagatgata  3600
```

```
tgtaggtagg tgcttctggc tgctgtactt ttttctgtaa ggacctttaa tgtttttact  3660
tgtcaactga tagttatcat caaatttttg aacaggtacc atcagaaggc accgacaaac  3720
tggatagctc ttaccacggc attcctattc tttgtgattc ttttttttagt gggttacatt  3780
ttatatggtg ctggaaacca tattgtcaaa gttgaagatg atttccatgc aatggaggaa  3840
ttgaaagtcc gagcagaagc agctgatatt gccaagtccc aggtaatttt tctggcatat  3900
tgttatcagg gttcattatt tccaggatta cttgctgatc acaattacct aaattttgtt  3960
tttaatttca gtttctagct acggtctctc atgaaattag aacacccatg aatggtattt  4020
taggtaactt caagaatctg tttctctatc ttattaacaa aagtgtgata tatgctttca  4080
taacttttgc ttttctattg atgttggtat catttaactt aaaattactg taggaatgct  4140
tgctctgctt ctagatacag aattgagttc aacccaacga gattatgctc agactgctca  4200
agcatgtgga aaggcactca taacattaat aaatgaggtg cttgaccgtg ctaaaattga  4260
agctggcaag ctagagctgg aggctgttcc atttgatctt cgttccataa ttgatgatgt  4320
tctttctctt ttttctgaga aatctagaca caaaggttta gaggtatgtt taattgttga  4380
ttaacctact ataaatgcca tatcataggt ttgctttgtc aaagttataa aatttcacca  4440
ttctattttt ttgattgatg aacttatact gttctttcat ctctttgtca cctttttggt  4500
gtcttatgcc actcgatttt catgttcctg atgctcatac tgaacctcaa cctgaactca  4560
tattgtcaat tgtggaagta aagctggctg tgtttgtttc tgacaaagtt ccggatattg  4620
tcatgggaga tcctgggaga ttcagacaaa taataacaaa tcttgttggc aactctgtta  4680
aagtaagtgg aattttcata gtttgttcat ctgttggatg ttatttgcat ttggaaatgc  4740
cattctaagt ttctaactgt ttcaatcttc ttcacttttc ttctcccccc cccccccccac  4800
agtgagcagc tgtggaagaa agcattgata ttgatgcttg aatccttcat atttattctc  4860
tcccttgtgt acgccaaatt ttattcacaa ggtacttgtt gataacatta ctaattaatt  4920
tgcacatctt gcagtttact gaacaagggc atatatttgt taaagttcat ctagcagaca  4980
atcgaaagtc cataatgaat ggaaaacacg atacttttct aaatggagaa tcagatgaag  5040
ttttccatat atctggtgat tatcatttca aaaccttaag tggatgtgaa gctgccgatg  5100
aacggaatag ttgggataat tttaagcatc taatcgctga cgaagaatat ggccttgatt  5160
cttctagaga aacaatggct gcttgtgaat cttctgagca agtcaccttg agggtgtgcg  5220
tggaggacac tggaattgga attcctttct cagctcagga tgggatattc atgccatttg  5280
tgcaggctga cagctcaacc tcacgaaatt atgggggtac tggtattggc ttgagtatca  5340
gtaaatgtct ggttgagcta atgggtggtc agataaactt cataagtcga ccccaggttg  5400
ggagcacctt ttcttttact gcagtttgtg aagcatttaa gaaaagttca gttaccaaca  5460
agaagaaaaa tttggaagat ctgccttcaa gttttagagg gatgaaagtc attgtggttg  5520
atgggaagcc tgttagagct gctgtgacta gataccattt gaagagacta gggatactag  5580
ttaaagttgc aaataggatc agtaaggctg ttgctttatg tggtaagagt ggttctttga  5640
aatcggggta agttctatta ttccatctct attttgattt ttttttctta tagacagaat  5700
tggtgttaat tatgaagaaa ctgaaagtga ttataaacaa agtggtatca acattttgct  5760
attgttgtaa catatgcttg tgaaaaaaaa aacctttaaa ttgactttgc aagtttattg  5820
gaaaacatat tctgcagttt tatcagggtg tctatcctct gctatggtcc cactactaga  5880
ttttagggtt tgtgtttgat atataaaaag gcgtaatggc atagtcatgt ctcaatggct  5940
aagtttcaat gtagctattt ttcaatccca gtgaggtttc aaatgtcttt tggttatgtt  6000
tcagttatct tcaatttgaa atcaattcat ggtgtatttc ttggatgtgc ctttacaaag  6060
cttaatgttg attttgatat tttagttgtt ctagttttc ctttataagg cttgcattat  6120
tctttaaagt tatatcgtga aactgctttt gactattttt tttttccacg agagagggag  6180
taggggagga agaaaagaaa agaaaatgga agatactatg tttcattatt ttcatatttc  6240
tattcagaca tcaaatgcta aggaatttgt tttttaataa atgaatgaca tttgaagaat  6300
atatgctatt attttttttct tctatggttt aagttgcttg gttcagttta ttcactgagt  6360
gaaactactt ggatgtggca gaatgttcca gcctgatatt atcatggttg agaaggacac  6420
atggataact ggagaggatg gcattttcaa tacatggaaa cataatggtc gtacgattaa  6480
gatgcctaaa atgatccttc tggcaaccaa tattagtaat gccgaatttg ataaagctaa  6540
gttcacgggt ttcactgata ctgtgatcat gaagcctctg agagctagta tggtggctgc  6600
ttgtcttcag caagttttgg gtatggggaa gaagaggcag ctagggaaag acatgcctaa  6660
tggttttcta catagccttc tctatggaaa gaaaattttg gtggttgatg acaatggggt  6720
aaaccggagg gttgcagcag gtgcactaaa gaagtttgga gctgatgtga agtgtgctga  6780
aagtggcaaa gtcgcccttg aaatgctgca attgcctcac aattttgatg cttgcttcat  6840
ggacatccaa atgccagaaa tggacgggta cacatttata ttggctatta ttgcttcttt  6900
tcttgcttta tatgttggaa atattttata cttaatagat tcgtgtatca catgataaat  6960
gcctttagtg tccacctgtt aattgctagt gtctaggaag ttgcacttag ttaatattag  7020
ccgggagtat agcctttgtc aagatgcatc acatataaca ggattgacgc tatgagaaat  7080
gctagcgacg ctctctttct aacacactct atgattgatt gaaatatact aaaaatcacc  7140
aattttggta ggactcactc ctcatttaat aattcttct cttgattaat aagtggaacc  7200
atcagaattg atgatttcca ataaaattca acctatcata gagagtatta gaaagagtgt  7260
tagagagcgt taaaatcagc tcatataaat tgcattcctc ttgaggctat tattgactat  7320
tatgttaaaa taagctcaaa tataaattgt actttgtac tacatagctt tggcttcgta  7380
attaagcttg gttgtaaaga tttttgatgc ctcattcaat ttagaatgaa aaaaggatgg  7440
agtataggga aaaagtgggt tggcaaaata agatactgat ctcacagcat tctgtatggt  7500
tcttctcttc atgttccaac cataaaagat agaccaagct ggcaagatgt gaaagttcga  7560
atacatggaa ttttatactt ttaatccata tgtattatca tattatgtat tcataagagt  7620
ttgttacatg tgaggaaaat gtgttgattc atgtgaggaa aattgagata tgcatggact  7680
tggggaaacc atctaaacag atgttacaca ttttgcagat ttgaagcaac tagtagaatt  7740
cggatgatgg agagcaaggc aaatgaggag atgaatggca gtgagtggca tgtacctata  7800
ctggccatga cagctgatgt gatccttgct acgtacgaca agtgcgtgaa atgtggcatg  7860
gatggatacg tctcaaagcc atttgaggaa gagaatctgt atcaggaagt tgcaaagttt  7920
ttcaaatcca agaccatctc agactcatga caatgtgctt tgaacttggc aaccaactag  7980
aagattgatt ggagacaaca cattttagtt tttttatttt atcattacta gcactttcac  8040
atgtcacttg taactagtta cttatgcatg ctctcatgcc tagagtaatg cttgttttc   8099
```

```
SEQ ID NO: 103          moltype = DNA  length = 2964
FEATURE                 Location/Qualifiers
source                  1..2964
```

```
                       mol_type = other DNA
                       organism = Glycine max
SEQUENCE: 103
atgggtctta gtttgaagat gcagagccac catcctgtgg ctttgaggtt acatgatcaa  60
atggggtcta agagaaagta cacattcatt caggctcata gagcttggct tccaaagttt  120
ctgctgctgt ggatcctgct aatggctttg atcagttggt gcatctatag caaaatggat  180
gatgacacta aagtccgaag gaaagaggtt ttgggtagcc tctgtgatca aagggcaaga  240
atgttgcaag accagtttag tgttagtgtt aaccatgtcc atgcccttgc catccttgtt  300
tcaaccttcc attactacag atacccttct gccattgacc aggaaacctt tgctgagtac  360
actgcccgga cagcatttga acggccgtta ctgagtggtg tggcctatgc gcaaagagtt  420
gttaactctg agagggagag atttgagaaa gaacatggat gggttataaa aacaatggaa  480
agaaagtctt cactggttag agatgagtat gcaccggtga tattcgcgca agaaactgtc  540
tcatatcttg agtctcttga tatgatgtct ggggaggagg accgagaaaa cattttaagg  600
gctagagcca ctgggaaggc ggttctgact agtcctttca gtcttttggg ttctcaccat  660
ctcggtgtgg ttttaacatt ccctgtgtac aaatctaagc tccctcagaa gccaacagtg  720
gaagaacgca ttgaagcaac tgcaggatat gttggaggat cctttgatgt tgagtccctt  780
gtaaagaatt tacttgggca acttgatggt aaccaagcaa ttttggtgaa tgtatatgat  840
attacaaact atactaatcc cctagtcatg tatgggaacc tatatgaaga aggcgatatg  900
tctcttgtgc atgaaagcaa gcttgatttt ggagatccat acaggaaaca tcagatgata  960
tgtaggtacc atcagaaggc accgacaaac tggatagctc ttaccacggc attcctattc  1020
tttgtgattc ttttttagt gggttacatt ttatatggtg ctggaaacca tattgtcaaa  1080
gttgaagatg atttccatgc aatggaggaa ttgaaagtcc gagcagaagc agctgatatt  1140
gccaagtccc agtttctagc tacggtctct catgaaatta gaacacccat gaatggtatt  1200
ttaggaatgc ttgctctgct tctagataca gaattgagtt caacccaacg agattatgct  1260
cagactgctc aagcatgtgg aaaggcactc ataacattaa taaatgaggt gcttgaccgt  1320
gctaaaattg aagctggcaa gctagagctg gaggctgttc catttgatct tcgttccata  1380
attgatgatg ttctttctct tttttctgag aaatctagac acaaaggttt agagctggct  1440
gtgtttgttt ctgacaaagt tccggatatt gtcatgggag atcctgggag attcagacaa  1500
ataataacaa atcttgttgg caactctgtt aaatttactg aacaagggca tatatttgtt  1560
aaagttcatc tagcagacaa tcgaaagtcc ataatgaatg gaaaacacga tacttttcta  1620
aatggagaat cagatgaagt tttccatata tctggtgatt atcatttcaa aaccttaagt  1680
ggatgtgaag ctgccgatga acggaatagt tgggataatt ttaagcatct aatcgctgac  1740
gaagaatatg gccttgattc ttctagagaa acaatggctg cttgtgaatc ttctgagcaa  1800
gtcaccttga gggtgtgcgt ggaggacact ggaattggaa ttcctttctc agctcaggat  1860
gggatattca tgccatttgt gcaggctgac agctcaacct cacgaaatta tgggggtact  1920
ggtattggct tgagtatcag taaatgtctg gttgagctaa tgggtggtca gataaacttc  1980
ataagtcgac cccaggttgg gagcaccttt tcttttactg cagtttgtga agcatttaag  2040
aaaagttcag ttaccaacaa gaagaaaaat ttggaagatc tgccttcaag ttttagaggg  2100
atgaaagtca ttgtggttga tgggaagcct gttagagctg ctgtgactag ataccatttg  2160
aagagactag ggatactagt taaagttgca aataggatca gtaaggctgt tgctttatgt  2220
ggtaagagtg gttctttgaa atcgggaatg ttccagcctg atattatcat ggttgagaag  2280
gacacatgga taactggaga ggatggcatt ttcaatacat ggaaacataa tggtcgtacg  2340
attaagatgc ctaaaatgat ccttctggca accaatatta gtaatgccga atttgataaa  2400
gctaagttca cgggtttcac tgatactgtg atcatgaagc ctctgagagc tagtatggtg  2460
gctgcttgtc ttcagcaagt tttgggtatg gggaagaaga ggcagctagg gaaagacatg  2520
cctaatggtt ttctacatag ccttctctat ggaaagaaaa ttttggtggt tgatgacaat  2580
ggggtaaacc ggagggttgc agcaggtgca ctaaagaagt ttggagctga tgtgaagtgt  2640
gctgaaagtg gcaaagtcgc ccttgaaatg ctgcaattgc ctcacaattt tgatgcttgc  2700
ttcatggaca tccaaatgcc agaaatggac ggatttgaag caactagtag aattcggatg  2760
atggagagca aggcaaatga ggagatgaat ggcagtgagt ggcatgtacc tatactggcc  2820
atgacagctg atgtgatcct tgctacgtac gacaagtgcg tgaaatgtgg catggatgga  2880
tacgtctcaa agccatttga ggaagagaat ctgtatcagg aagttgcaaa gtttttcaaa  2940
tccaagacca tctcagactc atga                                      2964

SEQ ID NO: 104         moltype = AA  length = 993
FEATURE                Location/Qualifiers
source                 1..993
                       mol_type = protein
                       organism = Glycine max
SEQUENCE: 104
MGLSLKMQSH HPVGAGHIVA LRLHDQMGSK RKYTFIQAHR AWLPKFLLLW ILLMALISWC  60
IYSKMDDDTK VRRKEVLGSL CDQRARMLQD QFSVSVNHVH ALAILVSTFH YYRYPSAIDQ  120
ETFAEYTART AFERPLLSGV AYAQRVVNSE RERFEKEHGW VIKTMERKSS LVRDEYAPVI  180
FAQETVSYLE SLDMMSGEED RENILRARAT GKAVLTSPFS LLGSHHLGVV LTFPVYKSKL  240
PQKPTVEERI EATAGYVGGS FDVESLVKNL LGQLDGNQAI LVNVYDITNY TNPLVMYGNL  300
YEEGDMSLVH ESKLDFGDPY RKHQMICRYH QKAPTNWIAL TTAFLFFVIL FLVGYILYGA  360
GNHIVKVEDD FHAMEELKVR AEAADIAKSQ FLATVSHEIR TPMNGILGML ALLLDTELSS  420
TQRDYAQTAQ ACGKALITLI NEVLDRAKIE AGKLELEAVP FDLRSIIDDV LSLFSEKSRH  480
KGLELAVFVS DKVPDIVMGD PGRFRQIITN LVGNSVKFTE QGHIFVKVHL ADNRKSIMNG  540
KHDTFLNGES DEVFHISGDY HFKTLSGCEA ADERNSWDNF KHLIADEEYG LDSSRETMAA  600
CESSEQVTLR VCVEDTGIGI PFSAQDGIFM PFVQADSSTS RNYGGTGIGL SISKCLVELM  660
GGQINFISRP QVGSTFSFTA VCEAFKKSSV TNKKKNLEDL PSSFRGMKVI VVDGKPVRAA  720
VTRYHLKRLG ILVKVANRIS KAVALCGKSG SLKSGMFQPD IIMVEKDTWI TGEDGIFNTW  780
KHNGRTIKMP KMILLATNIS NAEFDKAKFT GFTDTVIMKP LRASMVAACL QQVLGMGKKR  840
QLGKDMPNGF LHSLLYGKKI LVVDDNGVNR RVAAGALKKF GADVKCAESG KVALEMLQLP  900
HNFDACFMDI QMPEMDGFEA TSRIRMMESK ANEEMNGSEW HVPILAMTAD VILATYDKCV  960
KCGMDGYVSK PFEEENLYQE VAKFFKSKTI SDS                             993

SEQ ID NO: 105         moltype = DNA  length = 1744
```

```
FEATURE                 Location/Qualifiers
source                  1..1744
                        mol_type = genomic DNA
                        organism = Glycine max
SEQUENCE: 105
tggcttccaa agtttctgct gctgtggatc ctgctaatgg ctttgatcag ttggtgcatc  60
tatagcaaaa tggatgatga cactaaagtc cgaaggaaag aggttttggg tagcctctgt  120
gatcaaaggg caagaatgtt gcaagaccag tttagtgtta gtgttaacca tgtccatgcc  180
cttgccatcc ttgtttcaac cttccattac tacagatacc cttctgccat tgaccaggtt  240
agagcttgat cttccacttt aatcttgatt tgatacaagc taagcatgat attatatgta  300
atggtttgaa agaaatgaaa tgctatttgg gattttcaca cttctactta ttgctcaaat  360
tgtgtaaata actaaatatc tccatccatt gttcataata aaataggaaa cctttgctga  420
gtacactgcc cggacagcat ttgaacggcc gttactgagt ggtgtggcct atgcgcaaag  480
agttgttaac tctgagaggg agagatttga gaaagaacat ggatgggtta taaaaacaat  540
ggaaagaaag tcttcactgg ttagagatga gtatgcaccg gtgatattcg cgcaagaaac  600
tgtctcatat cttgagtctc ttgatatgat gtctggggag gtagattaca acactgccga  660
acattattct atttactgct tatatattgt taaattttca ctcaaaattt tgcctttgca  720
tgttcaggag gaccgagaaa acattttaag ggctagagcc actgggaagg cggttctgac  780
tagtcctttc agtcttttgg gttctcacca tctcggtgtg gttttaacat tccctgtgta  840
caaatctaag ctccctcaga agccaacagt ggaagaacgc attgaagcaa ctgcagggtg  900
ggtttttagtt tcacttctat ttgtttttca agtttcttt tgtgatatac ttggcgattc  960
tttgtgttaa atgacatata gtatattttt tagttgttat gcttgtatgt tattttcata  1020
ccctaaataa taatgacaac actgtgtgtc aaataatatc acatttttct actaatcaat  1080
gaaagctgct gcggcttctt tctccattag atcatgactg atgctaacta ttaaagctgt  1140
gaccactaca ttttaatggt atcagtatca caatacctgc cactttgtgc taccagtttt  1200
atttccatca ataccacctt gggtgccata gccatttccc ctgatcacta tcagagagtt  1260
tgaggacaac tgttggcgat gcaaatggca caaccaatta actggttaat gtttattaat  1320
taacaattta tttaacattc aatatagtta accaattaaa tttttattat tcctatttta  1380
ccaataattc ctcttcttta aaattgttct tttggttttt gtattttcat ggccctcaat  1440
tattgaattc agagctgtat gtaagaggca ggatgcttgt gttgtgtggt ttgcatcctg  1500
tcctgtctaa aatgtagttt taacttttag ttctatagtt gcttacatcg acaagcctct  1560
ttaccttgtt tcaatcttgt ggctttatgt ttacactaag cttcttagtg tcctaatgta  1620
ttgaataaat ttctaattga catcagatat gttggaggat cctttgatgt tgagtccctt  1680
gtaaagaatt tacttgggca acttgatggt aaccaagcaa ttttggtgaa tgtatatgat  1740
atta                                                               1744

SEQ ID NO: 106          moltype = DNA  length = 899
FEATURE                 Location/Qualifiers
source                  1..899
                        mol_type = genomic DNA
                        organism = Glycine max
SEQUENCE: 106
tggcttccaa agtttctgct gctgtggatc ctgctaatgg ctttgatcag ttggtgcatc  60
tatagcaaaa tggatgatga cactaaagtc cgaaggaaag aggttttggg tagcctctgt  120
gatcaaaggg caagaatgtt gcaagaccag tttagtgtta gtgttaacca tgtccatgcc  180
cttgccatcc ttgtttcaac cttccattac tacagatacc cttctgccat tgaccaggtt  240
agagcttgat cttccacttt aatcttgatt tgatacaagc taagcatgat attatatgta  300
atggtttgaa agaaatgaaa tgctatttgg gattttcaca cttctactta ttgctcaaat  360
tgtgtaaata actaaatatc tccatccatt gttcataata aaataggaaa cctttgctga  420
gtacactgcc cggacagcat ttgaacggcc gttactgagt ggtgtggcct atgcgcaaag  480
agttgttaac tctgagaggg agagatttga gaaagaacat ggatgggtta taaaaacaat  540
ggaaagaaag tcttcactgg ttagagatga gtatgcaccg gtgatattcg cgcaagaaac  600
tgtctcatat cttgagtctc ttgatatgat gtctggggag gtagattaca acactgccga  660
acattattct atttactgct tatatattgt taaattttca ctcaaaattt tgcctttgca  720
tgttcaggag gaccgagaaa acattttaag ggctagagcc actgggaagg cggttctgac  780
tagtcctttc agtcttttgg gttctcacca tctcggtgtg gttttaacat tccctgtgta  840
caaatctaag ctccctcaga agccaacagt ggaagaacgc attgaagcaa ctgcagggt   899

SEQ ID NO: 107          moltype = DNA  length = 233
FEATURE                 Location/Qualifiers
source                  1..233
                        mol_type = genomic DNA
                        organism = Glycine max
SEQUENCE: 107
tgaaagaaat gaaatgctat ttgggatttt cacacttcta cttattgctc aaattgtgta  60
aataactaaa tatctccatc cattgttcat aataaaatag gaaacctttg ctgagtacac  120
tgcccggaca gcatttgaac ggccgttact gagtggtgtg gcctatgcgc aaagagttgt  180
taactctgag agggagagat ttgagaaaga acatggatgg gttataaaaa caa         233

SEQ ID NO: 108          moltype = DNA  length = 153
FEATURE                 Location/Qualifiers
source                  1..153
                        mol_type = genomic DNA
                        organism = Glycine max
SEQUENCE: 108
cttattgctc aaattgtgta aataactaaa tatctccatc cattgttcat aataaaatag  60
gaaacctttg ctgagtacac tgcccggaca gcatttgaac ggccgttact gagtggtgtg  120
gcctatgcgc aaagagttgt taactctgag agg                               153
```

```
SEQ ID NO: 109          moltype = DNA  length = 103
FEATURE                 Location/Qualifiers
source                  1..103
                        mol_type = genomic DNA
                        organism = Glycine max
SEQUENCE: 109
tatctccatc cattgttcat aataaaatag gaaacctttg ctgagtacac tgcccggaca  60
gcatttgaac ggccgttact gagtggtgtg gcctatgcgc aaa                    103

SEQ ID NO: 110          moltype = DNA  length = 62
FEATURE                 Location/Qualifiers
source                  1..62
                        mol_type = genomic DNA
                        organism = Glycine max
SEQUENCE: 110
ataaaatagg aaacctttgc tgagtacact gcccggacag catttgaacg gccgttactg  60
ag                                                                 62

SEQ ID NO: 111          moltype = DNA  length = 223
FEATURE                 Location/Qualifiers
source                  1..223
                        mol_type = genomic DNA
                        organism = Glycine max
SEQUENCE: 111
tgcttatata ttgttaaatt ttcactcaaa attttgcctt tgcatgttca ggaggaccga  60
gaaaacattt taagggctag agccactggg aaggcggttc tgactagtcc tttcagtctt  120
ttgggttctc accatctcgg tgtggtttta acattccctg tgtacaaatc taagctccct  180
cagaagccaa cagtggaaga acgcattgaa gcaactgcag ggt                    223

SEQ ID NO: 112          moltype = DNA  length = 143
FEATURE                 Location/Qualifiers
source                  1..143
                        mol_type = genomic DNA
                        organism = Glycine max
SEQUENCE: 112
tgcatgttca ggaggaccga gaaaacattt taagggctag agccactggg aaggcggttc  60
tgactagtcc tttcagtctt ttgggttctc accatctcgg tgtggtttta acattccctg  120
tgtacaaatc taagctccct cag                                          143

SEQ ID NO: 113          moltype = DNA  length = 103
FEATURE                 Location/Qualifiers
source                  1..103
                        mol_type = genomic DNA
                        organism = Glycine max
SEQUENCE: 113
gaaaacattt taagggctag agccactggg aaggcggttc tgactagtcc tttcagtctt  60
ttgggttctc accatctcgg tgtggtttta acattccctg tgt                    103

SEQ ID NO: 114          moltype = DNA  length = 63
FEATURE                 Location/Qualifiers
source                  1..63
                        mol_type = genomic DNA
                        organism = Glycine max
SEQUENCE: 114
agccactggg aaggcggttc tgactagtcc tttcagtctt ttgggttctc accatctcgg  60
tgt                                                                63

SEQ ID NO: 115          moltype = DNA  length = 239
FEATURE                 Location/Qualifiers
source                  1..239
                        mol_type = genomic DNA
                        organism = Glycine max
SEQUENCE: 115
tttaccttgt ttcaatcttg tggctttatg tttacactaa gcttcttagt gtcctaatgt  60
attgaataaa tttctaattg acatcagata tgttggagga tcctttgatg ttgagtccct  120
tgtaaagaat ttacttgggc aacttgatgg taaccaagca attttggtga atgtatatga  180
tattacaaac tatactaatc ccctagtcat gtatgggaac ctatatgaag aaggcgata   239

SEQ ID NO: 116          moltype = DNA  length = 161
FEATURE                 Location/Qualifiers
source                  1..161
                        mol_type = genomic DNA
                        organism = Glycine max
SEQUENCE: 116
gcttcttagt gtcctaatgt attgaataaa tttctaattg acatcagata tgttggagga  60
tcctttgatg ttgagtccct tgtaaagaat ttacttgggc aacttgatgg taaccaagca  120
attttggtga atgtatatga tattacaaac tatactaatc c                      161

SEQ ID NO: 117          moltype = DNA  length = 120
```

```
FEATURE                 Location/Qualifiers
source                  1..120
                        mol_type = genomic DNA
                        organism = Glycine max
SEQUENCE: 117
attgaataaa tttctaattg acatcagata tgttggagga tcctttgatg ttgagtccct  60
tgtaaagaat ttacttgggc aacttgatgg taaccaagca attttggtga atgtatatga  120

SEQ ID NO: 118          moltype = DNA  length = 79
FEATURE                 Location/Qualifiers
source                  1..79
                        mol_type = genomic DNA
                        organism = Glycine max
SEQUENCE: 118
acatcagata tgttggagga tcctttgatg ttgagtccct tgtaaagaat ttacttgggc  60
aacttgatgg taaccaagc                                               79

SEQ ID NO: 119          moltype = DNA  length = 736
FEATURE                 Location/Qualifiers
source                  1..736
                        mol_type = genomic DNA
                        organism = Glycine max
SEQUENCE: 119
tggcttccaa agtttctgct gctgtggatc ctgctaatgg ctttgatcag ttggtgcatc  60
tatagcaaaa tggatgatga cactaaagtc cgaaggaaag aggttttggg tagcctctgt  120
gatcaaaggg caagaatgtt gcaagaccag tttagtgtta gtgttaacca tgtccatgcc  180
cttgccatcc ttgtttcaac cttccattac tacagatacc cttctgccat tgaccaggaa  240
acctttgctg agtacactgc ccggacagca tttgaacggc cgttactgag tggtgtggcc  300
tatgcgcaaa gagttgttaa ctctgagagg gagagatttg agaaagaaca tggatgggtt  360
ataaaaacaa tggaaagaaa gtcttcactg gttagagatg agtatgcacc ggtgatattc  420
gcgcaagaaa ctgtctcata tcttgagtct cttgatatga tgtctgggga ggaggaccga  480
gaaaacattt taagggctag agccactggg aaggcggttc tgactagtcc tttcagtctt  540
ttgggttctc accatctcgg tgtggtttta acattccctg tgtacaaatc taagctccct  600
cagaagccaa cagtggaaga acgcattgaa gcaactgcag gatatgttgg aggatccttt  660
gatgttgagt cccttgtaaa gaatttactt gggcaacttg atggtaacca agcaattttg  720
gtgaatgtat atgata                                                  736

SEQ ID NO: 120          moltype = DNA  length = 519
FEATURE                 Location/Qualifiers
source                  1..519
                        mol_type = genomic DNA
                        organism = Glycine max
SEQUENCE: 120
cttctgccat tgaccaggaa acctttgctg agtacactgc ccggacagca tttgaacggc  60
cgttactgag tggtgtggcc tatgcgcaaa gagttgttaa ctctgagagg gagagatttg  120
agaaagaaca tggatgggtt ataaaaacaa tggaaagaaa gtcttcactg gttagagatg  180
agtatgcacc ggtgatattc gcgcaagaaa ctgtctcata tcttgagtct cttgatatga  240
tgtctgggga ggaggaccga gaaaacattt taagggctag agccactggg aaggcggttc  300
tgactagtcc tttcagtctt ttgggttctc accatctcgg tgtggtttta acattccctg  360
tgtacaaatc taagctccct cagaagccaa cagtggaaga acgcattgaa gcaactgcag  420
gatatgttgg aggatccttt gatgttgagt cccttgtaaa gaatttactt gggcaacttg  480
atggtaacca agcaattttg gtgaatgtat atgatatta                         519

SEQ ID NO: 121          moltype = AA  length = 245
FEATURE                 Location/Qualifiers
source                  1..245
                        mol_type = protein
                        organism = Glycine max
SEQUENCE: 121
WLPKFLLLWI LLMALISWCI YSKMDDDTKV RRKEVLGSLC DQRARMLQDQ FSVSVNHVHA  60
LAILVSTFHY YRYPSAIDQE TFAEYTARTA FERPLLSGVA YAQRVVNSER ERFEKEHGWV  120
IKTMERKSSL VRDEYAPVIF AQETVSYLES LDMMSGEEDR ENILRARATG KAVLTSPFSL  180
LGSHHLGVVL TFPVYKSKLP QKPTVEERIE ATAGYVGGSF DVESLVKNLL GQLDGNQAIL  240
VNVYD                                                              245

SEQ ID NO: 122          moltype = AA  length = 166
FEATURE                 Location/Qualifiers
source                  1..166
                        mol_type = protein
                        organism = Glycine max
SEQUENCE: 122
SAIDQETFAE YTARTAFERP LLSGVAYAQR VVNSERERFE KEHGWVIKTM ERKSSLVRDE  60
YAPVIFAQET VSYLESLDMM SGEEDRENIL RARATGKAVL TSPFSLLGSH HLGVVLTFPV  120
YKSKLPQKPT VEERIEATAG YVGGSFDVES LVKNLLGQLD GNQAIL                 166

SEQ ID NO: 123          moltype = AA  length = 37
FEATURE                 Location/Qualifiers
source                  1..37
                        mol_type = protein
```

```
                        organism = Glycine max
SEQUENCE: 123
YRYPSAIDQE TFAEYTARTA FERPLLSGVA YAQRVVN                         37

SEQ ID NO: 124          moltype = AA  length = 31
FEATURE                 Location/Qualifiers
source                  1..31
                        mol_type = protein
                        organism = Glycine max
SEQUENCE: 124
NILRARATGK AVLTSPFSLL GSHHLGVVLT F                               31

SEQ ID NO: 125          moltype = AA  length = 38
FEATURE                 Location/Qualifiers
source                  1..38
                        mol_type = protein
                        organism = Glycine max
SEQUENCE: 125
RIEATAGYVG GSFDVESLVK NLLGQLDGNQ AILVNVYD                        38

SEQ ID NO: 126          moltype = AA  length = 19
FEATURE                 Location/Qualifiers
source                  1..19
                        mol_type = protein
                        organism = Glycine max
SEQUENCE: 126
ETFAEYTART AFERPLLSG                                             19

SEQ ID NO: 127          moltype = AA  length = 11
FEATURE                 Location/Qualifiers
source                  1..11
                        mol_type = protein
                        organism = Glycine max
SEQUENCE: 127
TFAEYTARTA F                                                     11

SEQ ID NO: 128          moltype = AA  length = 11
FEATURE                 Location/Qualifiers
source                  1..11
                        mol_type = protein
                        organism = Glycine max
SEQUENCE: 128
ARTAFERPLL S                                                     11

SEQ ID NO: 129          moltype = AA  length = 18
FEATURE                 Location/Qualifiers
source                  1..18
                        mol_type = protein
                        organism = Glycine max
SEQUENCE: 129
KAVLTSPFSL LGSHHLGV                                              18

SEQ ID NO: 130          moltype = AA  length = 11
FEATURE                 Location/Qualifiers
source                  1..11
                        mol_type = protein
                        organism = Glycine max
SEQUENCE: 130
AVLTSPFSLL G                                                     11

SEQ ID NO: 131          moltype = AA  length = 21
FEATURE                 Location/Qualifiers
source                  1..21
                        mol_type = protein
                        organism = Glycine max
SEQUENCE: 131
YVGGSFDVES LVKNLLGQLD G                                          21

SEQ ID NO: 132          moltype = AA  length = 18
FEATURE                 Location/Qualifiers
source                  1..18
                        mol_type = protein
                        organism = Glycine max
SEQUENCE: 132
GSFDVESLVK NLLGQLDG                                              18

SEQ ID NO: 133          moltype = AA  length = 13
FEATURE                 Location/Qualifiers
source                  1..13
```

```
                        mol_type = protein
                        organism = Glycine max
SEQUENCE: 133
GSFDVESLVK NLL                                                        13

SEQ ID NO: 134          moltype = AA  length = 9
FEATURE                 Location/Qualifiers
source                  1..9
                        mol_type = protein
                        organism = Glycine max
SEQUENCE: 134
FDVESLVKN                                                             9

SEQ ID NO: 135          moltype = AA  length = 9
FEATURE                 Location/Qualifiers
source                  1..9
                        mol_type = protein
                        organism = Glycine max
SEQUENCE: 135
VKNLLGQLD                                                             9

SEQ ID NO: 136          moltype = DNA  length = 27660
FEATURE                 Location/Qualifiers
source                  1..27660
                        mol_type = genomic DNA
                        organism = Zea mays
SEQUENCE: 136
attggtaaag taaaatatca ggtcaccata tggttatttg attcttaaat atcatttgtt  60
attgacttat tgcatgatcc atgaccatat tactcgtcaa ctgttacaaa gttgcattga  120
tctcattttt gtttccaatg tttctagccg gacgaatgtg acttatgtgc tggaatcagt  180
ggcgtgaatg tggtccagaa tattgggtca agttctaatc gcacaataat attatgtcta  240
tctgcttttt tggggagcat tgtgatatca atagttaaaa ctacgcacaa aagagggatt  300
caaacccaca agctttatgc agatgagaaa gttctccagg caccaagtac taaaataagt  360
cgaaagtggt caaagagagc cctgcttatt ggtgtcttat ttgggctctg tagctctgta  420
tgcatatttt catgcatgta tgccgatgtt gttgctcgga gaattgagaa tcttgctaat  480
atgtgtgatg agagagcaag gatgttacag gatcagttta atgtaagcat gaaccatgtg  540
catgcgttgg ctatactggt ctcatcattt caccatggga aggatccttc tgctattgat  600
caggtaccca tcacatcatg cattgcaagg tgctcctccc ataagcatgg tgaataaaaa  660
acttccaatt tttggtaaaa agagttgttg ctgcccacta ctcacacaca cagcccggtt  720
cttacaaaaa tgaccgtagg ccaaccggct gatctacggg aaccaaacat tacatgttgc  780
aaaaaggaag cggagtctat taatatgtgt gtcatatcgt aagagcagaa cagtaaattt  840
gagaacaggt caatgggaac catattatta tgtgtagtga aatcaaacta tccttagttc  900
agttcctgct tagcaccatt taatactagc ctccggaaca atgatgcctc tattaagatt  960
gcatatttta tcaattcgac cttcatgtta gtatatttac ttgggtaagt catgtacaat  1020
tcttcttttg gtaacattgt agttacccta ctggatatca tgatatctat cagcgttgtg  1080
ccctagtgat caagggaaca taatttgatc tcttgaagta gatggattcc ttaggagcca  1140
tctaaatcta tatcttaaaa atgaaagaca tcttaattgc tgacactatg agcaaaacca  1200
caaggttttt ttgaattggg aaacaagtaa tgtggttcaa agatggaatg cagagttgca  1260
tctaagtgaa taagtgttat ttatctcaga cacattggag agctgtgtat cattgtgatt  1320
ttttttcgca gacacgtagg agaactgtgt atcattgcat taaggataag tatatgaaaa  1380
cctacacatg cccccaaaac agattctatc gccacttata aaggttaatt atgaccaaaa  1440
gtgcatgcag cccctaaatc aagcatctca tgtatgctga ccacatcttc agatcattgt  1500
cctttgatcc tcaaggtcag agagggctgc ttggggaaaa gacggtttca ttttgagagt  1560
ttctggccca aatttcctgg ttttctggag gtggtgggtg cgtcctggag cttgccagtt  1620
gggggctcat gcccgttgga gcaggtgtct ttgaagctta aaaggttagc tcgcgcattg  1680
cagtcctggg ggcataaaga agtgggtaat gtaaggttgc agctggggct tgtcagagaa  1740
gtgttgcata ggctggaaat ggcgcaggat atcagaattc tgtccagtgg agaagtttgg  1800
ttgctaaact tgttgaagca gcggtgtctt agcctcgcgt ctcttgaaag gactgttgct  1860
cggttgagat cacggatcca ctatctaaag gagggtgatg ccaacactaa gttctttcat  1920
tcgcaggcat gttatcgaaa gaaaaagaat ttcatctcca aaattgaggg agatggaaga  1980
ttggctacca accatgatga tatgcaacaa attcttgagg agtattttcg taacctgctg  2040
ggggctgatt tgcagaggcc atttactatt gatctgagta attgtcacag ggctgcgatg  2100
gatctaactg ttttggagca gcctttttca gagaaggagg ttagggacac cattgctagt  2160
ctcccttctg ataaggcccc tgggcctgat ggttttacag gaaaatttta taagacatgc  2220
tgggacatca ttaaggtcga cataatggct gctcttaatt ccctttacca tggtgatgcc  2280
tataaacttg acttgctgaa ctcagcgtat ctcattcttc ttccaaagag ggaagatgct  2340
tcctcagcta gtgattttcg accaattagc ttgattcata gttttgctaa gctggtcact  2400
aagatcctcg ctaatcgttt gggaccatat cttcaggacc tagtggcagc taaccagagt  2460
gcttttatta gaggaaggtc aattcacgac aatttcatgc tagtgcaaca atcgattaag  2520
ttccttcata agaggaagat ctctagtttg ctgttgaaac tggacatttc caaggctttc  2580
gactcagtct cgtgggcgtt tttattggag attttggcac atttggggtt tggtcctgtt  2640
tggcgtaatc tgatctccaa cctgttattc acttcttcta ctcaggtgct cctgaatggc  2700
tcgcctggta atcatatttt tcatcggaga ggtcttcgcc agggagatcc tctttctccc  2760
atgctatttg tgatggtttt ggatgtgctt agcagcttgt tccgggttgc tgaaaataga  2820
ggcttgttgc agggccttgg gggagctgat gtccgcagta gagtctccat ctatgcggat  2880
gatgtggtcc ttttcataaa gccaattgaa gcagatctga attgtgctaa aataatacta  2940
aactgttttg gttcggcttc tggtctggta accaatatgc tcaagagcag tgctattcca  3000
attagatgtg atgatcagca ggtgcttgct ggttgcagtg tgctgcattg cagtcccgct  3060
gcgtttcctt gcaagtatct ggggctgccc atatctgata aaaaattgag gaaatgtgac  3120
```

```
cttaagttat ggattgagaa gattgcagat cgtctgccta actggaaggc tcggctgctc  3180
aatctggctg ggcggactgc gttggtgaag tttgttctat cggccattcc gacttatctt  3240
cttattgcaa tcaatgtccc tcagtgggtt attaaatcaa ttgataaaat tcggcgagga  3300
tttctttgga gaggaagaaa ggaagttaat ggtggtagct gtcttgttcc atgggaagtt  3360
gtcacgaggc ctctgaagct tggtgggctt gggatcccta accttaagct caaaagctga  3420
gcattgcagg caaaatggtt atggttggaa aagacggatc taagcagacc ttggcgtggg  3480
ctgtcccttc cagtgcaacg tcaggttaga cagttctttg atttgtcggt tgttaccatt  3540
ttagggaatg gggctactac tctcttctgg tcggatagat ggattcatgg gaataatatc  3600
caggacattg cccctgaggt ggtgggtatg gttggccgca aggcgtattc ttccagaacg  3660
gtggcacagg ctctggataa ttggcattgg gtcagtgata ttcgtggtgc tctttccttg  3720
agtgggttgc agcaatatct gttgttatgg gatactttgg gggaagttag gctttctcat  3780
gatgctgaca gacatgtttg gatgcactct tcttctggga tgttctcctc aaagtcttgc  3840
tataaggctt ttttcatggg ttcaatttcg tttgagccat ggaaacgttt gtggaaatcc  3900
tgggctcccc caaaatgcaa gttctttctc tggctggcga taaggaataa gtgttggact  3960
gctgatagat taaggaggag agggctgcaa cacccggttg tttgtgttct ttgtgaccaa  4020
gagcaggaaa cagtgcaaca tcttctgtgt acttgcagtt ttgccaggca attttggcat  4080
gctattcttg ttcccttgtg tcttggggat ctcattcctg ctgttcatga aatctcattt  4140
gctgattggt ggaggaaggt gcttaagaag gtgcccaaaa acagaaagaa aggcttcaac  4200
agtctcatta tcttggggtc ttggtgccta tggctgacta ggaacaaagc tgtttttgat  4260
ggtgtaaacc cttccctgtg ttttgttaaa agcttatttc tgaatgagtt aagttgttgg  4320
gagagggctg gggctaaaca gctagcaagt tttggtcttc ctgctatcat gagtagggtc  4380
tagattgtgg tcaagtgttc tgtttgccct acgggcattg tactttggtc ctcttggacc  4440
tttttcctct cttaatataa tgacgtgcag tcctcctgcg cgttcgagaa aaaaaacagc  4500
aatacctgcc tcccaaggat tatctggatt tacttaataa ttaggtggta ctccgtagca  4560
acaaacacca gaaacttgtt atagctgaaa actggagaca ccaccctatt tctggtttca  4620
atttacttgt tatatgggct ttttttctcg aaaaacgcag gagagctgca catcattgta  4680
ttaataagaa ggggaaatta aggtccaaga ggaccagtac aaaaaaccac actatggtgg  4740
ccagcaacaa gcataaataa aactatccat aggactagga tacaaaaaga cgaccaagga  4800
aaaaattagg tcgggcctgc tgcgcctaga gcagcagcaa gcccaaggct tccgaggtgt  4860
ttggcaccag ccagcaccca taaggatagc tcgtcgatga agcttctatg caccttgcca  4920
atggttggta aatctccatc gaaaataact ctgtttctat gcaaccaaag gcaccatgct  4980
cccaaaataa tggcactgtt gactcccttt ctcttgcttc tgtgcacctg aatggtcact  5040
agtccccacc aatcagcaaa attagtatct tctggtcctg gagttaagtg gcccatacca  5100
aagggggaga ggatgttatg ccaaaactgc ctggcgaaga cacaaccagt caacagatgc  5160
tgaactgttt cttgctcttg ttcacagaaa gggcatgctt ccggatgggg aagacctctt  5220
ttttgcagcc tgtcagctgt ccaacactta ttctgcatgg ctaaccataa aaaggtcttg  5280
cacttaggag gagcccacga tttccaaagt cttttctaag gttcgaaggt gatggagccc  5340
aaaaacagaa ccttgtagca ggacctagaa gagaaaaggc ccgaagactc gaatctccac  5400
atatggtgat cctcctgaga agtgagcacg atctcaccca gggtgtccca aagcgtaaga  5460
tattgttgta tccctacaag ggagagggtt ggcttgatgt ccctgaccca cgacatgccc  5520
tctaaggctt gatgcactgt cctggtagag gcaacctttt tatccacctt tgagatcact  5580
tcaggtgcca gctcagcgat agagcaccca tttatccatc tgtccctcca aaaaagggtg  5640
ttattgccat ttcccacatt agtgtacatc gaactggcca ctagtttcct tacttgtgac  5700
tgaacaggga gatccaatcc actccaaggc ctattcgggt cagtcttgga gagccaaagc  5760
catttagctt gcaacgccca actcttatat attagatttg ggataccaag tccaccaagg  5820
tccagcggtc tggtgacttt atcccacgcc accaggcaat gcccaccttt cacatctttt  5880
ctacccttcc acaagaaacc tcgccgaatt ttgtcaatag cactgataac ccacttggga  5940
acgttcatgg cgatgaaaag atatacaggg attgcagaga gcacgaacct gaccaaggat  6000
gccctgccag caaggtttag cagtggagcc ttccaaccgg gcagccggtt agctatcttg  6060
tcaacccact gcaaaaggtc ccttttccct aacttcttat cagaaacagg cagccccaaa  6120
tagttgcatg gaaaagaagc cgagttgcac tgcaaaattt tacagctgtc ctgaaccgtc  6180
tgatcatcac aactgagagg gatagcacaa ctttttcgca aattcacaac taagcccgag  6240
gcctctccaa agcaatccag gatcattttg acacaagtaa gatcatcaac tgcaggcttg  6300
acaaaaagaa ccacatcatc tgcgtaaatc gagagcctag atttcacgtt tctgatggcc  6360
aggtcctgca gcaatcctct ttcctcagca tgcttgaata agctactaag cacatccatc  6420
acgattatga aaagcatagg agataagggg tcgccttggc gcagccccct ccgatgacga  6480
atataatccc ccggagctcc gttcaatagc acttgtgtgg aagaagtgga taacaaattg  6540
aacacgagac cacaccacct aggcccgaag cccagatggg ataatacttt taggagaaag  6600
gcccaggaca ctgaatcgaa agcttttgta atatctagct ttagaaacag accagcgatc  6660
ttcttcctgt gaaaggcctt gatagaatgt tgaaccaaca tgtagttatc atgaatggaa  6720
cgtcccttaa caaaggcact ttgatttgta gccaccaaat tttgaaggtg cggtgctaag  6780
cgattagcca agactttgga tatcaacttg gcgaagctgt gaataagact aattggcctg  6840
tagtccccgg ctgtcttggc atcaactttc ttagggataa gtgttaggta cgcagaattc  6900
atcatccaca atttgcgtgt gttaccttgg tgcagggtga taactgccgc catcagatca  6960
gccttaatta tgtgccaaca agttttataa aatcttcctg tataatcgtc tggccccagg  7020
gctttgtccg agggaaggct agcaatagtg gcccggacct cctcctctgt aatgggaagg  7080
tccaaggccc caaggtcaac atcagcactg tggcaaacct ccaaatctag agtgaactct  7140
cgctgcttcg ctacccccaa cagattggag aaaaaatcaa acaagacctc ctgcttttcc  7200
tcttgcgagg tggcgatctg gtccccatgc actaattcag agataaagtt tcgctttttc  7260
cgatagcaag cctgtagatg aaaaaaggaa gtgttggcat ctccctcttt cagatatttg  7320
atccgcgatc taagtctagc aattgtccat tccagagatg caagccccag gcagtgatgc  7380
ttaagccttc ctttcagcca tatctcgtcc ccacacaaca gtctattgtc ttgagcaatc  7440
tcaaatctgt gcaaaatttc cctggccagg ttaagctgaa atttaacatt tccgatcctt  7500
ttatggctcc acgactgcaa agcctttgca agccttttca actttagagc taatctttcc  7560
aagggacaag aaatcataac tggctgctcc caagaggtag ccaccgtctc caaaaaatct  7620
ggaaacttgg tccaaaaact ctcaaagtgg aatctccgtt tccctttgac attctcatta  7680
agatgcaggg ctaagggaaa ggaaagaatg cctgcctcta ataattgtac atccatttct  7740
aaaagagtac taccaattgc caaataatag ggatactgtt tgggggataa cctaaatcaa  7800
ctgtatttgg aactgtgaag agattcgtaa acgtgagata tgtagtttcg aactatattt  7860
```

```
tatatgcatt aattagctat ggtttgtagg ggaaaatcat cttatttttc atactgcttg  7920
aacacatgta cacttttcaa tgagcataaa cctttgctaa tgtcaactca tgcagaaaac  7980
atttgaggac ttcacagcaa ggacaacatt tgaaaggcca ttgatgagtg gtgtcgccta  8040
tgcattgaag gtattacaca atgaaagaca acagtttgag gaacaacatg gatggaagat  8100
taagaagatg gaagatggag atcagtccct tgttcatgac tacaaccttg aaaagcttga  8160
accatcacca gttcaagatg agtatgcgcc tgttattttc tctcaggaaa ctgtgaagca  8220
cattatatct gtagatatga tgtctgggaa ggtagtagga tattcgtaag cctttacagt  8280
aaatacttac tattttatct atcctgagtt ccttactact atttttgtta taaaacgaag  8340
aaatttctgg ctcttcttct aactttcaat attattagga ttaaacatgt gtagaacttc  8400
tcggtcaaaa aagacacttt agaacttata tttttatttt aattagaatt tgatgtataa  8460
aaattaatca tttttacaat gagtgttata gtaatataag ttgttatgtg tcttgttcaa  8520
tgtgttaatt actatagcat gttccataga aatactgtgc aggctgttac taattctctc  8580
ttattctgtc tttgtggaaa ttacataatt actaaacctc atagtaataa taataataac  8640
taagactcca tttttctgct aacattacaa ccttgatttc aggaagatca tgacaatata  8700
ttacgttcct ggtcaacagg taaaggggcc ctaacatccc cttttaagct tctgaagtcc  8760
aaccatctcg gtgtggtgct tacattcact gtatataaat atgatctgcc tccaaatgca  8820
acaccacagg agcgtattca tgctacattg gggtaaaatg ttttgcaaag tttcaagttg  8880
aagctatata ggaatacact attttttctt taggagactt aaccttgtgg ttattgacac  8940
tttgcagcta tcttggtgcc tcatttgatg tcccttctct ggttgataaa ctcctagaac  9000
aactcgctag caaacgaaag atagtagtta atttatatga caccacaaat catacctctc  9060
ctattgaaat gtatggttct gattttactc catctggtga tctgcatatt agtagcattg  9120
attttggaga cccaacacgc aaacatgaga tgcattgcag gtagaaaact ttttttttgat 9180
gcgaattata caatgctttt gttcttcaga tatgctcagt gctttctctt tcaaacttct  9240
ctttcagatt taaacatgaa ccttcactgc catggtctgc aataataata tcaacagctg  9300
tagctataat tgttttgctt gttggacata ttatttatgc aactctgaac tcccttgaaa  9360
aggctgaaca tgattataga gtaatgagag aacttaaagg acaagctgaa gctgcagata  9420
tagcaaaatc tcaggttcat tctacctctt ccagtgtctt catcctatgc attggtttgt  9480
tatctcattt gttctacttt tctctttttg tcggctgagt cattattgat tgtcttgcag  9540
tttctagcaa ctgtttccca tgagattcgg actccaatga atggtgtttt aggtctgtac  9600
ttctgatatt tctttttttgt ctattaatac ataccgcagt tatttgtgtt tatgttttaa  9660
tcaaagacaa ctaaataaat tttgaaaagg atttcttctt gaattaggta tgctgcagat  9720
gctaatggac actgaacttg atacaactca gcaggatttt gtagtcaccg ctcaagaaag  9780
tggaaaggta ttaataaact taataaatga agtccttgat ctggctaaga tagagtcagg  9840
aaggattgag ctggaagcag tgccttttga tgtccgtgat attcttgaca atgtgatatc  9900
tcttttctac gataaatcac aagctaaagg catagaggtg agtcctaatt tagaacttgt  9960
attgtttgct aagctctgaa tattgtttgt gccatgggac ctaaaataat gtgtaattct  10020
tttttgaggg tagttggccg tgcttgtatc tgaccaagtt cctgatgtcc taattgggga  10080
tccatggcgg ttccggcaga tcattacgaa ccttgtgggg aattctatga aggttagatt  10140
caaatatgtg gtagcttcat tatttcagct tgctggcaag ttgtaactgt gtctagtcaa  10200
tcccaccatt tagcttatac aacaatatac tttgtaggaa acgtgacaac ttactaaaat  10260
attaatgtca tgagcttttg aatttgagat gtgtagaaga caattggtag aattggtcaa  10320
ttgtgtcgct gagctcgtgg gcagattata catgagtaca ttcacttgga tggcaagaaa  10380
cctccctaaa gataagaagt caggattaca tgaccctaat ctagcatatt taaagatatt  10440
ccaatataat ataccacccc ccatattttt ctcgaacgtg caggaaagct gcacatcttt  10500
atattaagaa gataaaaggt ccaaaatgga ccaaaacagg tatagataca aggcacctca  10560
cgtggccaaa aacaaaagta caaaaaaaac agtccataac tttttttttt tagataatgg  10620
aaaaatcatc cgaccttggc ctcaaatgag gttacggcca tttattacaa gggacggaag  10680
catattgcca aaacacctcc tatgaccact tcagagaacc ccaactagcc aaattaaaga  10740
acttcagcta tcgaaccaca gctactacat atttaaacgc aacgcagacc cccatccaaa  10800
attgctaaag aactgtagta gcaccctctc cacattacga catgaagact ttattaactc  10860
ttggtcctcc cttctaggct gaagctgaga ccagaagcgg caccaatatg ttgccctgaa  10920
ggttacctgc acacatgatt taggagatga attattgaac accacatcat ttctacttaa  10980
ccaaatagcc caacaaattg ccgatgcaac ggttaatagt aagtttcgaa ctctgggaag  11040
cctcccgctc gcccaaaccc caaacaaatc attaacatcc cgaggaggtc tcaaccccgt  11100
gcttatctga atcaaccgcc aaatgaatga cgcatacaaa caactgaaaa ataggtgctt  11160
tattgtctcc ggtctactac aaaagcaaca tatcttatta ccattccaat gcctcctagc  11220
caagttatcc tttgttaatg ttacccctct tttgaggtac cacataaaaa tcttaatttt  11280
cagaggaagc ctaagtttcc aaaggtcctt attatgcacc cccaacccat tgttaagaga  11340
tgccagatac agagacttaa ccgtaaacat cccgttggcg gtcaagttcc atctgaacaa  11400
gtccctgttt gaattcaaat tggtatgcgc aacaagtgag accaattgaa cccattggtc  11460
cctcaattgt tgagccaaac ccctccgaaa ggatatattt aagggcaccg tggagaacac  11520
acaggcaaca gtagagttct tcctcctcgc taggttataa agagacggaa aacgaagttt  11580
taacgttccc gacccgagcc aatcatcctc ccagaaacgc acctgggacc catcatgaat  11640
cacaaaggtt ccttttactaa tgaatgtgtc cttaactttc ataagaccac tccagaagtg 11700
tgaatcagtg gccctacgct gcgcctggga taaggttcga ttggccagat atttacgtct  11760
caataatgat tgccacatcc cttcttcatt gagaagttta tacaaccatt tgcttaagag  11820
gcatttattt tgaacctcta aattcaaaat gcctagcccg ccaacctcct taggttgaca  11880
aattacatcc catttggcca gcctatattt tttcttatga ccctcccctt gccagaaaaa  11940
acgcgatctg aaataatcta tcttctccag cacacctttt ggtacctcaa agaaagacat  12000
cataaacatc gctagactgg tcaacacaga attaattaat acgagccgcc ctcctactga  12060
cataagtttt cctttccagc tgctgagctt tttctcgaat ttggcctcca ctgttttcca  12120
ctcaccaatt gtcaatcgac ggtggtgcat aggaatccca agatatctga agggcagccc  12180
accagaactg caaccaaaca gccgtgtgta cctcccttca tcctcttttg ccttcccata  12240
acagaatatc tcactcttgt gaaagtttat tttaagacca gataactgct caaaggcaca  12300
taatatgagc ttcatattcg ttgccttttc cagatcgtga tccataaaca aaattgtatc  12360
atcagcgtat tgcagaatgg atagccccca tctaccaaat gcggcaccaa gcccttgatc  12420
tggccatttt cctttgctct attaatcagg gtagcaagca tgtccactac caagttaaag  12480
agaataggag acagcggatc gccctgcctc accctctat gggtctggaa aaaaggaccc  12540
atgtgatcat taactctaac cgcaacatgg cccccttca tgaaagactc gatccaccta  12600
```

-continued

```
caccaggtac ttgaaaaacc tttcatacga agggattgtt gaacaaagct ccacttcacc  12660
ttatcataag ctttctcgaa gtcgattttg aaaatgaccc catccctttt cttcgtatgt  12720
agctcatgaa tagtctcatg taagaccacc accccttcca tgatatttct tcctggcagg  12780
aacgcagtct gcaggggact gattacattc tgcgcaacct ccgtgatcct cttagtcgcc  12840
acctttgtga agattttgaa actgacattt agtagacaaa ttggtcggta ttgttgaacc  12900
gagattgcct cccgagtctt aggaagcaaa atgatagtcc caaagttaag actatacaaa  12960
gggagatttc ctgagtggaa ctcacgaaac aaagccataa gatcatcttt aataacatcc  13020
caacagattt gataaaattc cgccgggaat ccatcaggac ctggagcctt gttatgttcc  13080
atactaaaaa ccaccgcttt tacttcatct tcagaaaatg gctgggtgag cttctcgttc  13140
tcaacttgag taacttgtat tatatcatct ctaagatcct catccagact aaaagacgtg  13200
ttttctgggg ggccaaagag atttttataa taaccagtta tatgactctt taattctttc  13260
tcgtcgtata acatacgagc tccatccgtc atctggaaga tgcgattctt cctgaatttt  13320
ccattggcta tcatctgaaa atatttagta ttactatccc cctccaggag ctccttgacc  13380
ttcgctcttt gataccactt tatttcctcc tcccggagta gctgagcaag cctgttctgt  13440
aagtagttat gcagatccaa ctccgaagta ctcaacagaa ctacttcagc tctcttatct  13500
aaatcatcaa gcttagctat gatctccttt ttttcctttt tcaacaaccc cgaagtgtgc  13560
attgcccaac cccttaagtg ttggcgcacc ttcctaatcc tggcttgcca tttctccaaa  13620
ggagtagaac cacttgtctc atttacccaa atatctttta ccatatccac aaaaccatcc  13680
ctcagaaacc agcctagttc taacttgaac ggaggaattg tatgggcggt tacaacacct  13740
gtgctaagaa gcagaggagt atgatcggat atatttctcg acaaggcatg taccgaagct  13800
ctagggtatt ttccctccca ttctgtagct accaaaatcc gatccaactt ctcataagtc  13860
ggaatatccc tagtattagc ccaggtgtac cttcgccccg acatctgcaa ttctcttaga  13920
tcaagaccat caattaccgc attgaaaagg aacggccaac gatgatcaaa tctatcatta  13980
tttttctcag atggagatcg taaaatatta aaatctcccc caatgagaat aggtaaagtt  14040
tctgtattgc tcacacggac tagctcagaa aggaattctt gtttgaagca gtcctgggca  14100
gggccataca ccgagacaag agcccattta aaaccatctg ctttatcaag caaattaaac  14160
ttaataaaga aatccccttc cgtgatggca ccaacatcaa agacatcagc gtcaattcct  14220
aacaacatcc ccccagatct accatgaggt tctttgcaat gccagataaa atttttccca  14280
gcacacaaat tccttagtag atgatctggg aaggatttgc ggcctgtttc agagagggca  14340
ataaaattga gaccatgttc tttggtcaga tccgaaatgt atctaagttt tttcaaatcc  14400
ttgaacccat tgctgttcca aaagattcct ttcattggta aacaattaat taataatcaa  14460
gcccgacctt ttttcttaga acacaacgaa ccctgactag atggttttgt acagactgac  14520
ttaatcagcc catcagtgcc atccgtctct tcatgcataa tatccccaca caaatgattt  14580
aaaatgaaat gatcaaactc ttcgtcctct actactccct ttcccataaa atcagataaa  14640
tcagcctcgt tcttacccac tagctgatcc tgaactctat taatctctaa ttttttcaac  14700
tgaccaatag aggaagcaac tgaactagga ttagaacccg ctaaaatgcc aatattttta  14760
aaagaatcca gaatataatt atcgggtaaa ctaataaagg aaacattgtt acctttagtc  14820
ggctgatcgt ccaggttgta tcccgctttc agccgaatcg ctcgaactag cgagtcttca  14880
ctcaccgaat cagagcggcg cgagctacga cgcagtgcat gcacttttcc tgtcaacgcc  14940
tccgggatac tgcccaactt ttcaatacta acagcattga ccgagagaca ggtaccctga  15000
gattgatcca gatccagctg tgtagggcca gcgcacaccg atttcccact ggacgtgttg  15060
ctgttcagca tagaatccga caccttatta actgcccctg ctgaatcctt tgatgttccc  15120
ttcaagctcg ccccccttatt ccctctttca cctatattgt gatccttgtt ttgatcctga  15180
aattcatcat catcattatc cccgatatga tccatatcca tcggcaaagg ctggtcacct  15240
tcagctgctg actccaccct gaatttcagt tcatataagt agtctccaat taccacatca  15300
actacttgcg gaatcaaatt cgggtcaagc acggccacct tcagccttgc cctgtcaaac  15360
ttccgagtaa acaacatatc cacctctttt gagatgccta gcatagaacc aaccgcccag  15420
attaccgagt actctctaag ttccttaggt aaaccagtga actgcaccca agccttaggc  15480
atctcatatt ttatttcctc tccaaacccc tcttccttga caagcatctg tgcaccaaat  15540
tttgtatgaa cagttcccca ctcgatcata cggtgaagtt cacccctgga agggaaacac  15600
gtcgagaaca cattgttccc cacacacttc acacaccagt cccaatcagc agccaccaac  15660
cttttaagct cattcaaaat ctgctcttca ttcatggaac cctccacaat agacactgta  15720
ccattgcagc caccttgcct ctgctttact ggaatgggtt ggggtataaa gtaaaacccc  15780
aatccctcca ccgcataccc gcaaggtatt gcaaaagttt tgcaggcacg aaccaccgga  15840
catttcgaag ttaagtgagt tttgacatca caaatttcac aaaatagctc aatattacag  15900
tcactcaact gatgaccttt atttttgcac ctgaaacaaa acggcacttt ctcttttgaa  15960
cttgaaatca cagaagaacc caccttgtca tccaagtggg ttggagtaga caattctttg  16020
atggtctcca actttgaact gtgttgggac ccaatattcg gacctgctgg attcccccctc  16080
gagttctgaa tgtgctggct cttccccaca gactgctgca gcaaggaaac aatctgttcc  16140
atggtactat ctggaacagg cctgacagcg ctaccgttgc caattgatgt tgtaattgcc  16200
tgttggagca agtccacagc gtttgatact tgaggagtca ccgaagaagc ccctgaacct  16260
cccagaccct gtccagcgac catcacagag gaagcccctc catttgaaaa cctgctgtga  16320
acacctccgc ccccagactg ggttggcaaa gtacgaccac catagaaccg gcctccggca  16380
gaagcacctc ttccaccacg ccacgctcca gcacggccct gtccacctcc ccgacgtcca  16440
aaaggacggc gtccgccacc ataaccagga tggaacactg gttgggatcc accgcgtcca  16500
aagtcagtgt tcagtcccaa accagcgaca tatcctcccg tgcccccaag cagttgctga  16560
ccggtggaaa aacctgcagc gccctcggac tgatgctggc cgcgactgcc tccacgccct  16620
ccagtatcac caaccggcgc cattgcgttc cttacagcct cgacgaaggt gccaggagcc  16680
acaccccggg aggaaatgtg aaccgccctg gcagcagaag aactggtgcc tgagcgggag  16740
aacaaggaag ccagcccagc agttggccta taaggaatcc taggactgag aatcatatgt  16800
tgggccctcc cattccaacg gggacaagca ctaattaagc caacattcct tgattccagc  16860
acaggatccg catgagaatc ccagaatatc gcctgacttg catccatacc aaaatcattc  16920
aaattcaaac catcagctaa ccgctccgct gataccgctc ccattgaaga cgtcttcttc  16980
aacctttggc cgtggcacct tccaggggag cagcgccatt gcgctttttc tagtgcatgt  17040
ccaactgtga actccggcga acgtcgtggc gacggcaatt tgccctgcca tggcttcacc  17100
ttattcctag aagaagtgct cggactagga gaatgcaagc atgtactcaa cgtcggtcct  17160
ggtcccgacc tgcatacacc gccgactacc tctcctacct gttcgagagc ttcattccaa  17220
atagattttg gtggcgcgga actgcagtca attagcttgc cgtcaacaca ggacagagac  17280
ccgttcacga aaacagagag ccgaccaccc tcaggtgtcc gtccgctatt tgccgaaccg  17340
```

```
gccagatcac caacctcctg atccagctga acctgacaat cagcaacctc cgccagtggg  17400
cggacgacca ccgcatcggt gggcgccagc gtctttcgac gacgaccctt ccgagcgtac  17460
gtggccaagc aacgtcgctg catagcgcag agaacgaacg aacaaccact ggcgggagac  17520
cggcctagat ggccgcctcc cacctctggt gtcccactcc gccgagacag agggaagagc  17580
acttaccggg ttacgccgcg cgcctagccg ggacgcccac gcggcctaga ccgccttgcc  17640
gtggtcaccg cagagaagaa actcgagcgc cagggtccac cgcggcctgc gatgctctct  17700
gatgagcagc gggaagttgc ggcgtgcgaa gcgaccggcc cagcagttga gcacggcgtc  17760
gacggcgtcc gcgtcggcac gaggcagcgc gagcaagcgc gcgacgacct cggacacctt  17820
ccagtcccgc tgccaccggt tgccctccac gcggaggcgg tgtcacgcaa tcaaaaacag  17880
tccataacta gagagctaac aacagaacag ctacaaccct gccaggggag tgtattgggc  17940
atcaacacgg actgaggcag ggtgatcctc tatcgcctat gctgtttatt cttgtaatgg  18000
atgtcttgaa tctgcttgtg cagcgagcct ctgaggaagg gtttcttcag cctctttctt  18060
ctaggaatat gcagcatcgt atctcgctgt acgcggatga tgcaatgtta tttctatgtc  18120
ctactgcccc ggatatcagt atggttatgg atattcttca tttatttggt tcaacttcag  18180
gtctaaggac taatgtccag aagagcagtg tgttcccaat ctgatgtggg gaagaagagg  18240
tgaattgttt acaggacttg ctgctatgca atatttcagt ttttccctgt aagtacctcg  18300
gtttgccttt gtctcccaag aaactcacaa gggaccaggt tcaagccatt gttgaaagag  18360
tggccagcct tttgccagga tggaaagctg aacttatgac cagggctggt agagctattc  18420
atgtgcagtt tgtcatgacg gctaagatga tatatgcagc tctggcactt gaccttcctg  18480
tatgggccat caaagcaatc gataagctga ggaagggctt cctctggagg ggtaggaaag  18540
agttccgtgg tggtcactgc ctcttggctt ggcctaaggt tacccgtccc aaggagttgg  18600
gtggtcttgg gattagtgag ttaaagaacc tctgttgggc tttgagagct cgctggccat  18660
ggctgcagaa aacagacccc agtaggcctt gggcggactt ccccattcat gtttgtaagg  18720
tggttaaaaa tctgattgct gcagccatta ttactaagct cggtgatgga gccaataccc  18780
ttttctggaa ggacagatgg ttggagggga gatgtattaa ggacatagct cctgcgttgt  18840
ttgatttggt gcccttgcgt cttgccaaca aacggttggt caaagatact ctccctaatt  18900
tccattggct ctcagatgtg caaggggcaa tctcagtcag agtcattgct gaattcctgg  18960
aactttgtga agtgcttgat gcagttgtgc tccagcctgg aataagggat cgatatttat  19020
ggaaattcag cgcttcaggt gattatacat ctagttctgc ttataatgct ctcttccttg  19080
gttcagttca gttcgaacca gcagagcggc tatggaaatc ttgggctcct gggaagtgca  19140
agttctttat atggcttgtg gaacataata ggtgctggac tgctgacagg ctcagaaaaa  19200
gagggctaga ccgaccagag cagtgcccct tgtgcgacca agaggttgaa accataaatc  19260
atttgctggt caagtgtgtt tttgctaagc agttctggtt tgatttcctt aattcagtgg  19320
ggttgcggga tctgtatcca gctcatgagg aatcctttga gtcgtggtgg aagtctagca  19380
gctccggcat cggatcttgt gagaaaaggt ttcaattctt tagtgatcct aggtgcttgg  19440
accatttgga agcataggaa taggtgtgtt ttttatggtt gtaatcccag cttgctcacg  19500
acccttagga tggctaggga agaggcggtg ctctggtcca tgactggtgc caaggccttg  19560
tccttcctcc aagtcgatga gttgctggct taaaacagcg gtgtgggtcg tgtttcctcc  19620
atgttttagt cagtgatccg tagttagtct ctagtggtgt atgtgctgta ttggggttct  19680
ctcccccttt cttttcttct attaatacaa agatgcgcag ctctcctgcg tattccagaa  19740
aaaaaagaaa aaaaaaacaa ccctgggata ggggctgcta ggagatccaa attcttggcc  19800
ccagccagca cccacaaatc cctctcctcc ttagcttttc taatagccgg tgagagcggc  19860
acagatggtg agaccagaga agctgaaggt tgtaagacga cgagttgaca tcccccaaag  19920
tcatagtggt caatgtgtcg catatgctgt agctagagtg ctcaagcaag gcagaagctc  19980
tttgtgccga tgttgaggta gtcgagcacg agggtgagta gccatggttg aggatgccat  20040
ctttacgcca tggtgatggt cgaggcgcgt cgagacagtc cattgtataa gggggtgatg  20100
ttgaggtcaa tgtagtcaag gccatcgagg atgtcgacga aaatagcgac acagtcaagg  20160
caggtcatca tggaggaagc atacaccgga tttgctaggc ctgagaacgt gtcctggaga  20220
acggcacgct acactgccaa tataagacat gctagttaga gagccccaac aatgtgtcaa  20280
catccgagcg accttggaag agagtgcctc aacgatggtt gattgtggtg cccaaaacaa  20340
ctgagcacaa ggtgtcgatg tatcccacaa ttgtcaaatt agatgatata tgtgggaaag  20400
agacaatgat gctggcgatg tggttatgct gaatgaagaa ggaacagtgc gggagtgaac  20460
gctcctaccc gaaggggagt agtttgggcc gacgtccttg gccaaggcaa tggtccagac  20520
ataaggtaca gtgtgcccaa aggcagtggt ccagaagcaa ggtatggcgt caaaaacagt  20580
gttcgctgtt ggtgatgaag agcacaaaaa gtttgatgaa gaccaagtgc atcctggtgg  20640
tgcgcaagag gtgcaacaca attatcgatg tacatggagc gacaatgtag atgcattgtt  20700
gtatgccaac catggataga ggcatgccta tgagggtgtc tcaattagag aatctctaac  20760
attgccttaa atcaattctc tatcttataa tatagtgctt aacttataaa aaactgctcc  20820
aacagtgctc tattttacat ttttatcaaa aaatataggg cagaccataa agtgaccaaa  20880
atatactaca ctctggatta gggcttaact gttgcaacac aatttgtttt tagtgcctta  20940
aacactttaa atgatgtagt attgtaattt ttggaacatt attttgaggg gcagcgagtg  21000
tagcgtagag acagtttatg aggggcagta gcggaagtgt tgggatagca agcacaacca  21060
aatacacgga gttgggttgt gtcgtacaag gcgaagtagg tggtggggtg gctcaccacc  21120
ttcgatggga ggcgattgag gaggtgggtg gcggtgtgca aggcctctgc ccagtagttg  21180
gcagggagag acgcctgaaa gagaaggcaa caaatcatgt tggtggtggt gcgaatcatt  21240
cgctcggccc gaccgttttg ggcagaggtg taggggcacg agagatgcaa ttgaacgcca  21300
ctggcgagga agaacgaccg agaggcatgg ttgtcgaact cgcggccatt gtcacactgc  21360
agtgcatgga ccgggcgaca gaactgggtg gagacccagg cgaagaagtg agtgagggtg  21420
gtaaacgtgt cggatttcat tcgaaaagga aaagtccata ggaaatggga aaaatcgtcc  21480
aaaatcacca aatagtattt gtatcctgac agactgagta ccggggaggt ccatagatca  21540
caatgaacca ggtcaaaagc ctgttcagcc ctagaagaag atgtagtgaa aggaagacgg  21600
gtatgtcggt caagctgaca tgcatgacag aggccctcaa aatgtcccct attacaagaa  21660
gaatctaaag tgctggaaag cttggtcatg acctagatcc tgggtggccg agacgacgat  21720
gccaagtggt ggaggtggtg gtggagacca ggacgggagg tggagacacg ccggtggacg  21780
acgaccggag tgtgtagagg ggcccgacgc tgtcacatcg ggcgagtggg gtcctggtgg  21840
ccagatcctt tacagaaaaa ccagtagggt caaactcaat ggaacacgaa ttgtcggtgg  21900
tgaaccaacg gacagaaaga agattgtgag tgatgtgagg ggctacgaga acgtcgttga  21960
ggtagaacag tccagggaga accgaggcac ctactgaggt gactagaaga gtggaaccgt  22020
ttcgaacgac gatcgaggta gggtgtgtgg ggggaggtgg gtgtgagcga gagcatgcct  22080
```

-continued

```
agggtggggg tggtgtgata ggatgcaccg gagtcgatga cccagtcaga aggcggtggg  22140
gccaacgcca tggtgctgta tgcggcagcg agggcaacag ggtcccaacc tgcaacgaac  22200
gaggaccatg gtgtcgtggt agacggtctc gtaggcggga gttgaggcgg gccccgggtc  22260
ggtcggggca cgccgtatgg aggcatgttg taggcgggcg gcgtagtcag gagagccgga  22320
ggacgggagg cgctggggc ctgacccagc cacatggaga taatgccggt ccaggggttg  22380
tagaacgacg gccaactctg gtcgccaccc ctatcggtgg aacctccacg agaggagctg  22440
ccgcccccat gtccgccctt gtaggggcga cggccgccgt cgatggtgga atgctgacga  22500
gggtccgtag gagccgcggt gaagggccga gcgggggtcc tggttgacgg agcgcggggg  22560
gcgagtcctc cggaagacgc ctgggcacca ggggtggcgc tgtagagtgc cggagtggga  22620
gcctcgatcg tcatggtgag ctcctcgaga agaagttcat tgcgcacggc gtggaaggtg  22680
ggaaaaggta cggtcctctt gatgagagcc ttcaggtggc cgtagagggg gctgaggcca  22740
cacaggaggt ttagcaccaa ggtacggtcc gccagcgact cgccaaggtc gcggagggag  22800
tctgctaggc ccttcatctg gcggcagtac tcccgcacag agaggtcccc ctgggagaat  22860
tggtggaact gatcatcgat ttgaagggcc cgagcgtccc ggttcccgag gaattgttcc  22920
tcgagggcga gccacgcctg gcgggccgtg tccgccttgt cgcagatgat gtcctggagc  22980
tcgacggtga tagtgtcgtg gagccaaaag agcacgactg tgtccatcag ggaccaggcc  23040
atgggcggtg gggtgacgat gtcgtcgagg acgtggtcgg cgagagcgta gcgccgcagg  23100
gtgaggacct gcccccgaca gcgagggtag tgggaggacg ccgggtctag cacgattgac  23160
acgagggacc atatgttgtg gagaccggca gcctgcgcat gaagggcggc gatgtggtcg  23220
gcgtcgagtc caggggcgat gggtgcctgg ggttgggtgg aggtgcctcc ggggtgaccg  23280
gaggatgccc gaggaggagt cgctgagcgg tagccatttg ggcggtcaga gcagcgctca  23340
tggcacgctc ttgctacagg gcgagggtcg cagcgcgctc gcggtcgagg gaagcctcca  23400
cggctgcctg gatagtggcg atggccgtga ccagcgccga cgaggccgtc gggggggcgg  23460
gggggggcag tgacgtcagc ccatgtggcg gtggtgtggg cccggaggag aatcgcggcg  23520
tcgttgagca gcgagggtgg catcgggtag gggcccgaga tcggcgatgt gggcccctcc  23580
ccaacagcga ggtcgctagg ggtgccgagt ccggcagtgg cgagggcggc ggtagccgcg  23640
gcgctgcgtg ctggtggggc cacagtggca gtggccgcag ggagggccgc gcgtggctgc  23700
tgggcagcag cagtcgtagc ggcagccggg gtgtaggggg aatgaggtgg tgtcgacatg  23760
gcggcaccag gtggttgggc ggccgacgct gcggggttga cggcggcggt ggaggaagga  23820
ccggtgcgag cggccgaggt ggctggatgg ccggcgcggt gcccagtgag ggggtccggc  23880
gggggcagcc cttgctgctg ggcggcggcg caggaggagg cgccgcggcg gccagcctgg  23940
ggaggagcgg cgaccggtgg gaggaagggg agcggcgatc gggcctgggg ggagggagaa  24000
ggggggagcg gtggctgcca cggactggcg gcggcaggga gggtgggagg gaattagtgt  24060
ggctctgata ccatgtagaa ctatggaaaa ccctaaccct agaatagggt tgggcagtgt  24120
attaatagac caaataactg ggctaggccc attacaaggg acgggtatct aaaaaaatag  24180
actgcggctt ttttttaga taatggatac tagtccagct tctcctcgtt tggaggatta  24240
gccaacacac caaaagtttt tacatggagt agtcacacga ctagctgctt tatttgtcct  24300
tttcatttat gcaacctagg aattatttga cttgtctcca tcttaatgtg tctgctttta  24360
aatacagttt actgaacagg gccacatctt tgttcaagtc catttggtca aggaactaaa  24420
caggaaagga aacaattttt gtgatgtttc tgctcataac agagaaattc tgtatgattc  24480
tgacaactcg atgctatgga acacactaag cggacttgaa gtagcagata gctggaggtc  24540
cttggagaat tttacgatgt tcaagaattc aaatggtgaa acagatacaa ttaggttagc  24600
tgtcagagtt gaagacaccg gcataggaat aacaaaagat gctcaaatgc gtatttttac  24660
acctttcatg caagctgaca gttccacctc acgaacatat ggtggaactg gaattggctt  24720
gagtattaca aaacgtttag ttgaattgat gggtggagaa atagggttta ctagtaaatc  24780
aggagttggt agtacatttt cttttactgc cattttcaag gagaacagag gatgtcctgg  24840
agatatgaaa agatactatt ctgaacctac tccgttggat tttcaaggaa tgagggctct  24900
tattattgat ggaaggagtg cacgtgcaga ggttactatg taccatcttc gtagacttgg  24960
aatacagtgc agtcttgttg ccacatctga atctgaatct gcatcttcag ctttgatgaa  25020
agcctgcacc tcaaggttca tttccttgtg tagtttactg tttgatttac ttctacaagt  25080
tttagaaatt agaagttatt ttgttcaaat aaatgtaaca ttccttgcat ttataaactt  25140
ttgtcatctt aacacatggc tttgctatat tttctttagt tggttgtgtg ctatttcttt  25200
gaatattttc catattgtcg atcccaaaac aaggtttcgt aacttctcat gaactgaaga  25260
aaagtaggag aaacagagtg aaaccttcgt tggtttgagt ttagaaactg aaataggata  25320
gttcgattct aaataacttg tgaattcatt cagttgttgc tgtcatcatt ataacatatc  25380
aatttgttca tggccagcaa cctacacttg tcctcagtat tacgacccaa caaaatcaat  25440
gcataatgtc gccatcatca ctttccatgt atgcattttc ttttctaagc actgttgatg  25500
ccttacttgt tgatgttatc atttatattt tacatgttga gcagcaaaaa caatccggac  25560
atggtccttg ttgatacaga agcttggggt aaaggttcag gtttggcatt ctatcatcgt  25620
tttgtagatt gtcaactaaa gggcgcacac aagttttctc agcccatgcc aaagactatt  25680
cttttgggaa gctcaataag ccctgttgaa tctgattatt taagattgac aggatttggt  25740
gattgcataa ggaaacccct ccgtcttagt actattgttg cctgtcttcg caaaacctta  25800
ggggttgggg ttacaaggca gcagagtaga gaccaatctt tggttcttca aagtgtacta  25860
actggaaaac agattctggt tgtggatgat aatgcagtca accgtaaagt tgcagctggt  25920
tctttgaaga aatatggatc taaagttaca tgtgttgata gtgggagtga tgcaattgat  25980
atgctcaagc cacctcacac atttgatgct tgcttcatgg atgttcagat gcccgagatg  26040
gacgggtaat gttcctttcc aatgagttac taatgaaaaa gagcgcagat ttgctgccca  26100
ggcgttctca ttatctaaaa taccatgttg caatatttca aaaatcatca caaaaatcat  26160
gtatgcagta cacaaagtta ggtatagccg caacacttca gattgaaatt tcttcctaga  26220
tgccaagaac caaaatagac aagcagtcaa cctggcagtg ttcatcatgt gctgacagtg  26280
agactttgtt ttttaatctc agcatcaaag atgaacttta ttgaattctt gaggctacac  26340
ttaaggtgta cttgcacaca tgttttttgt gatgattgtt gaaacattgc aatacggtat  26400
tttagaatgt gggcgccaat ttccctgggc gccatatgat ttccaatgga aaattgtcat  26460
atgttattta cttgcgggat atactataag agttcaatat gtaaaagatt ctttgtgcag  26520
aagtcactct tggaacatct tacgttagtt cacatggaag catgtcttta gttttaggta  26580
tgtgcttctt ttggattttg tggaatcatc ggaacagatg catctttgat ggcctttccc  26640
ctaatgttgc taattttcta atccatgtgg gggatgagcg ccgtctgtgg gagactgccg  26700
gggccaaggg gttgacatcc cttgttgcct ccctctctca tgtagcctag agttttatag  26760
atgagtcagt ctatgctagt ttcgttcagg ccgccgtaag gcgtcagttg taccccggtc  26820
```

```
tattttagac cttgtttatt tgttctttta atataatgat acgcagctct cctgcgtgtt  26880
cgagaaaaaa agagaaagtt attttttggt cctcaaataa caacacttgt caaatgtatg  26940
catctcctca tgttattagc aagcactctc ataggagtat cactgaggat aatctctctt  27000
ttgttttcac atccagtcct tgcttaaaaa aatgcactgt agcctcacat gcttgtgttt  27060
gctttcctat gggttataac aagtggttgc atctactttg atcacttgta gatccactgt  27120
aggactacca ttaacaatat tcacattcaa ttgcaggttt gaagctacaa gattaatccg  27180
gtccatagag aaaaaaataa acgatatgat catgatgggt gaaatatccg ctaataatta  27240
tggaaataag gcccattggc atgtaccaat attagctatg acggcagatg taatccaagc  27300
gacttttgaa aaatgtatgc agtgtggaat ggatggatat gtgtcaaagc catttgaaga  27360
acagcagctc tactttgctg ttgctcattt cttagagact gatgaaacag aataacaaat  27420
ccaacttcgt aggagattga tttgccgcaa cactgtttca acatctgcca aaagaccatc  27480
tgttcaacag gttctgaaaa acagcgatcg gcagcatatt tggtgatttc ctctacatgc  27540
tttttaagag caagctaatg caattaaata tttccccatg cagttctaca agcttatgca  27600
tttacattct ttgtggagcg ataaaacttt gcttgtatac ttgtctgcca aatatctact  27660
```

```
SEQ ID NO: 137          moltype = DNA  length = 2823
FEATURE                 Location/Qualifiers
source                  1..2823
                        mol_type = other DNA
                        organism = Zea mays
SEQUENCE: 137
atgtatgccg atgttgttgc tcggagaatt gagaatcttg ctaatatgtg tgatgagaga  60
gcaaggatgt tacaggatca gtttaatgta agcatgaacc atgtgcatgc gttggctata  120
ctggtctcat catttcacca tgggaaggat ccttctgcta ttgatcagaa aacatttgag  180
gacttcacag caaggacaac atttgaaagg ccattgatga gtggtgtcgc ctatgcattg  240
aaggtattac acaatgaaag acaacagttt gaggaacaac atggatggaa gattaagaag  300
atggaagatg gagatcagtc ccttgttcat gactacaacc ttgaaaagct tgaaccatca  360
ccagttcaag atgagtatgc gcctgttatt ttctctcagg aaactgtgaa gcacattata  420
tctgtagata tgatgtctgg gaaggaagat catgacaata tattacgttc ctggtcaaca  480
ggtaaagggg ccctaacatc cccttttaag cttctgaagt ccaaccatct cggtgtggtg  540
cttacattca ctgtatataa atatgatctg cctccaaatg caacaccaca ggagcgtatt  600
catgctacat tgggctatct tggtgcctca tttgatgtcc cttctctggt tgataaactc  660
ctagaacaac tcgctagcaa acgaaagata gtagttaatt tatatgacac cacaaatcat  720
acctctccta ttgaaatgta tggttctgat tttactccat ctggtgatct gcatattagt  780
agcattgatt ttggagaccc aacacgcaaa catgagatgc attgcagatt taaacatgaa  840
ccttcactgc catggtctgc aataataata tcaacagctg tagctataat tgttttgctt  900
gttggacata ttatttatgc aactctgaac tcccttgaaa aggctgaaca tgattataga  960
gtaatgagag aacttaaagg acaagctgaa gctgcagata tagcaaaatc tcagtttcta  1020
gcaactgttt cccatgagat tcggactcca atgaatggtg ttttaggtat gctgcagatg  1080
ctaatggaca ctgaacttga tacaactcag caggatttgg tagtcaccgc tcaagaaagt  1140
ggaaaggtat taataaactt aataaatgaa gtccttgatc tggctaagat agagtcagga  1200
aggattgagc tggaagcagt gccttttgat gtccgtgata ttcttgacaa tgtgatatct  1260
cttttctacg ataaatcaca agctaaaggc atagagttgg ccgtgcttgt atctgaccaa  1320
gttcctgatg tcctaattgg ggatccatgg cggttccggc agatcattac gaaccttgtg  1380
gggaattcta tgaagtttac tgaacagggc cacatctttg ttcaagtcca tttggtcaag  1440
gaactaaaca ggaaaggaaa caatttttgt gatgtttctg ctcataacag agaaattctg  1500
tatgattctg acaactcgat gctatggaac acactaagcg gacttgaagt agcagatagc  1560
tggaggtcct tggagaattt tacgatgttc aagaattcaa atggtgaaac agatacaatt  1620
aggttagctg tcagagttga agacaccggc ataggaataa caaaagatgc tcaaatgcgt  1680
atttttacac ctttcatgca agctgacagt tccacctcac gaacatatgg tggaactgga  1740
attggcttga gtattacaaa acgtttagtt gaattgatgg gtggagaaat agggtttact  1800
agtaaatcag gagttggtag tacattttct tttactgcca ttttcaagga gaacagagga  1860
tgtcctggag atatgaaaag atactattct gaacctactc cgttggattt tcaaggaatg  1920
agggctctta ttattgatgg aaggagtgca cgtgcagagg ttactatgta ccatcttcgt  1980
agacttggaa tacagtgcag tcttgttgcc acatctgaat ctgaatctgc atcttcagct  2040
ttgatgaaag cctgcacctc aagcaaaaac aatccggaca tggtccttgt tgatacagaa  2100
gcttggggta aaggttcagg tttggcattc tatcatcgtt ttgtagattg tcaactaaag  2160
ggcgcacaca agttttctca gcccatgcca aagactattc ttttgggaag ctcaataagc  2220
cctgttgaat ctgattattt aagattgaca ggatttggtg attgcataag gaaacccctc  2280
cgtcttagta ctattgttgc ctgtcttcgc aaaaccttag ggttggggt tacaaggcag  2340
cagagtagag accaatcttt ggttcttcaa agtgtactaa ctggaaaaca gattctggtt  2400
gtggatgata atgcagtcaa ccgtaaagtt gcagctggtt ctttgaagaa atatggatct  2460
aaagttacat gtgttgatag tgggagtgat gcaattgata tgctcaagcc acctcacaca  2520
tttgatgctt gcttcatgga tgttcagatg cccgagatgg acgggtttga agctacaaga  2580
ttaatccggt ccatagagaa aaaaataaac gatatgatca tgatgggtga aatatccgct  2640
aataattatg gaaataaggc ccattggcat gtaccaatat tagctatgac ggcagatgta  2700
atccaagcga cttttgaaaa atgtatgcag tgtggaatgg atggatatgt gtcaaagcca  2760
tttgaagaac agcagctcta ctttgctgtt gctcatttct tagagactga tgaaacagaa  2820
taa                                                                2823
```

```
SEQ ID NO: 138          moltype = AA  length = 693
FEATURE                 Location/Qualifiers
source                  1..693
                        mol_type = protein
                        organism = Zea mays
SEQUENCE: 138
MYADVVARRI ENLANMCDER ARMLQDQFNV SMNHVHALAI LVSSFHHGKD PSAIDQKTFE  60
DFTARTTFER PLMSGVAYAL KVLHNERQQF EEQHGWKIKK MEDGDQSLVH DYNLEKLEPS  120
PVQDEYAPVI FSQETVKHII SVDMMSGKED HDNILRSWST GKGALTSPFK LLKSNHLGVV  180
```

```
LTFTVYKYDL PPNATPQERI HATLGYLGAS FDVPSLVDKL LEQLASKRKI VVNLYDTTNH  240
TSPIEMYGSD FTPSGDLHIS SIDFGDPTRK HEMHCRFKHE PSLPWSAIII STAVAIIVLL  300
VGHIIYATLN SLEKAEHDYR VMRELKGQAE AADIAKSQFL ATVSHEIRTP MNGVLGMLQM  360
LMDTELDTTQ QDFVVTAQES GKVLINLINE VLDLAKIESG RIELEAVPFD VRDILDNVIS  420
LFYDKSQAKG IELAVLVSDQ VPDVLIGDPW RFRQIITNLV GNSMKFTEQG HIFVQVHLVK  480
ELNRKGNNFC DVSAHNREIL YDSDNSMLWN TLSGLEVADS WRSLENFTMF KNSNGETDTI  540
RLAVRVEDTG IGITKDAQMR IFTPFMQADS STSRTYGGTG IGLSITKRLV ELMGGEIGFT  600
SKSGVGSTFS FTAIFKENRG CPGDMKRYYS EPTPLDFQGM RALIIDGRSA RAEVTMYHLR  660
RLGIQCSLVA TSESESASSA LMKACTSSYF YKF                               693

SEQ ID NO: 139          moltype = DNA  length = 1256
FEATURE                 Location/Qualifiers
source                  1..1256
                        mol_type = genomic DNA
                        organism = Zea mays
SEQUENCE: 139
gtaggggaaa atcatcttat ttttcatact gcttgaacac atgtacactt ttcaatgagc  60
ataaaccttt gctaatgtca actcatgcag aaaacatttg aggacttcac agcaaggaca  120
acatttgaaa ggccattgat gagtggtgtc gcctatgcat tgaaggtatt acacaatgaa  180
agacaacagt ttgaggaaca acatggatgg aagattaaga agatggaaga tggagatcag  240
tcccttgttc atgactacaa ccttgaaaag cttgaaccat caccagttca agatgagtat  300
gcgcctgtta ttttctctca ggaaactgtg aagcacatta tatctgtaga tatgatgtct  360
gggaaggtag taggatattc gtaagccttt acagtaaata cttactattt tatctatcct  420
gagttcctta ctactatttt tgttataaaa cgaagaaatt tctggctctt cttctaactt  480
tcaatattat taggattaaa catgtgtaga acttctcggt caaaaaagac actttagaac  540
ttatattttt attttaatta gaatttgatg tataaaaatt aatcattttt acaatgagtg  600
ttatagtaat ataagttgtt atgtgtcttg ttcaatgtgt taattactat agcatgttcc  660
atagaaatac tgtgcaggct gttactaatt ctctcttatt ctgtctttgt ggaaattaca  720
taattactaa acctcatagt aataataata ataactaaga ctccattttt ctgctaacat  780
tacaaccttg atttcaggaa gatcatgaca atatattacg ttcctggtca acaggtaaag  840
gggccctaac atccccttt aagcttctga agtccaacca tctcggtgtg gtgcttacat  900
tcactgtata taaatatgat ctgcctccaa atgcaacacc acaggagcgt attcatgcta  960
cattggggta aaatgttttg caaagtttca agttgaagct atataggaat acactatttt  1020
ttctttagga gacttaacct tgtggttatt gacactttgc agctatcttg gtgcctcatt  1080
tgatgtccct tctctggttg ataaactcct agaacaactc gctagcaaac gaaagatagt  1140
agttaattta tatgacacca caaatcatac ctctcctatt gaaatgtatg gttctgattt  1200
tactccatct ggtgatctgc atattagtag cattgatttt ggagacccaa cacgca      1256

SEQ ID NO: 140          moltype = DNA  length = 367
FEATURE                 Location/Qualifiers
source                  1..367
                        mol_type = genomic DNA
                        organism = Zea mays
SEQUENCE: 140
gtaggggaaa atcatcttat ttttcatact gcttgaacac atgtacactt ttcaatgagc  60
ataaaccttt gctaatgtca actcatgcag aaaacatttg aggacttcac agcaaggaca  120
acatttgaaa ggccattgat gagtggtgtc gcctatgcat tgaaggtatt acacaatgaa  180
agacaacagt ttgaggaaca acatggatgg aagattaaga agatggaaga tggagatcag  240
tcccttgttc atgactacaa ccttgaaaag cttgaaccat caccagttca agatgagtat  300
gcgcctgtta ttttctctca ggaaactgtg aagcacatta tatctgtaga tatgatgtct  360
gggaagg                                                            367

SEQ ID NO: 141          moltype = DNA  length = 232
FEATURE                 Location/Qualifiers
source                  1..232
                        mol_type = genomic DNA
                        organism = Zea mays
SEQUENCE: 141
gtaggggaaa atcatcttat ttttcatact gcttgaacac atgtacactt ttcaatgagc  60
ataaaccttt gctaatgtca actcatgcag aaaacatttg aggacttcac agcaaggaca  120
acatttgaaa ggccattgat gagtggtgtc gcctatgcat tgaaggtatt acacaatgaa  180
agacaacagt ttgaggaaca acatggatgg aagattaaga agatggaaga tg          232

SEQ ID NO: 142          moltype = DNA  length = 152
FEATURE                 Location/Qualifiers
source                  1..152
                        mol_type = genomic DNA
                        organism = Zea mays
SEQUENCE: 142
atgtacactt ttcaatgagc ataaaccttt gctaatgtca actcatgcag aaaacatttg  60
aggacttcac agcaaggaca acatttgaaa ggccattgat gagtggtgtc gcctatgcat  120
tgaaggtatt acacaatgaa agacaacagt tt                                152

SEQ ID NO: 143          moltype = DNA  length = 112
FEATURE                 Location/Qualifiers
source                  1..112
                        mol_type = genomic DNA
                        organism = Zea mays
SEQUENCE: 143
```

```
ataaaccttt gctaatgtca actcatgcag aaaacatttg aggacttcac agcaaggaca  60
acatttgaaa ggccattgat gagtggtgtc gcctatgcat tgaaggtatt ac          112

SEQ ID NO: 144         moltype = DNA  length = 72
FEATURE                Location/Qualifiers
source                 1..72
                       mol_type = genomic DNA
                       organism = Zea mays
SEQUENCE: 144
actcatgcag aaaacatttg aggacttcac agcaaggaca acatttgaaa ggccattgat  60
gagtggtgtc gc                                                      72

SEQ ID NO: 145         moltype = DNA  length = 243
FEATURE                Location/Qualifiers
source                 1..243
                       mol_type = genomic DNA
                       organism = Zea mays
SEQUENCE: 145
aagtttcaag ttgaagctat ataggaatac actatttttt ctttaggaga cttaaccttg  60
tggttattga cactttgcag ctatcttggt gcctcatttg atgtcccttc tctggttgat  120
aaactcctag aacaactcgc tagcaaacga aagatagtag ttaatttata tgacaccaca  180
aatcatacct ctcctattga aatgtatggt tctgatttta ctccatctgg tgatctgcat  240
att                                                                243

SEQ ID NO: 146         moltype = DNA  length = 163
FEATURE                Location/Qualifiers
source                 1..163
                       mol_type = genomic DNA
                       organism = Zea mays
SEQUENCE: 146
ctttaggaga cttaaccttg tggttattga cactttgcag ctatcttggt gcctcatttg  60
atgtcccttc tctggttgat aaactcctag aacaactcgc tagcaaacga aagatagtag  120
ttaatttata tgacaccaca aatcatacct ctcctattga aat                    163

SEQ ID NO: 147         moltype = DNA  length = 123
FEATURE                Location/Qualifiers
source                 1..123
                       mol_type = genomic DNA
                       organism = Zea mays
SEQUENCE: 147
tggttattga cactttgcag ctatcttggt gcctcatttg atgtcccttc tctggttgat  60
aaactcctag aacaactcgc tagcaaacga aagatagtag ttaatttata tgacaccaca  120
aat                                                                123

SEQ ID NO: 148         moltype = DNA  length = 83
FEATURE                Location/Qualifiers
source                 1..83
                       mol_type = genomic DNA
                       organism = Zea mays
SEQUENCE: 148
ctatcttggt gcctcatttg atgtcccttc tctggttgat aaactcctag aacaactcgc  60
tagcaaacga aagatagtag tta                                          83

SEQ ID NO: 149         moltype = DNA  length = 660
FEATURE                Location/Qualifiers
source                 1..660
                       mol_type = genomic DNA
                       organism = Zea mays
SEQUENCE: 149
tgtgatgaga gagcaaggat gttacaggat cagtttaatg taagcatgaa ccatgtgcat  60
gcgttggcta tactggtctc atcatttcac catgggaagg atccttctgc tattgatcag  120
aaaacatttg aggacttcac agcaaggaca acatttgaaa ggccattgat gagtggtgtc  180
gcctatgcat tgaaggtatt acacaatgaa agacaacagt ttgaggaaca acatggatgg  240
aagattaaga agatggaaga tggagatcag tcccttgttc atgactacaa ccttgaaaag  300
cttgaaccat caccagttca agatgagtat gcgcctgtta ttttctctca ggaaactgtg  360
aagcacatta tatctgtaga tatgatgtct gggaaggaag atcatgacaa tatattacgt  420
tcctggtcaa caggtaaagg ggccctaaca tccccttttta agcttctgaa gtccaaccat  480
ctcggtgtgg tgcttacatt cactgtatat aaatatgatc tgcctccaaa tgcaacacca  540
caggagcgta ttcatgctac attgggctat cttggtgcct catttgatgt cccttctctg  600
gttgataaac tcctagaaca actcgctagc aaacgaaaga tagtagttaa tttatatgac  660

SEQ ID NO: 150         moltype = DNA  length = 557
FEATURE                Location/Qualifiers
source                 1..557
                       mol_type = genomic DNA
                       organism = Zea mays
SEQUENCE: 150
cttctgctat tgatcagaaa acatttgagg acttcacagc aaggacaaca tttgaaaggc  60
cattgatgag tggtgtcgcc tatgcattga aggtattaca caatgaaaga caacagtttg  120
```

```
aggaacaaca tggatggaag attaagaaga tggaagatgg agatcagtcc cttgttcatg  180
actacaacct tgaaaagctt gaaccatcac cagttcaaga tgagtatgcg cctgttattt  240
tctctcagga aactgtgaag cacattatat ctgtagatat gatgtctggg aaggaagatc  300
atgacaatat attacgttcc tggtcaacag gtaaaggggc cctaacatcc ccttttaagc  360
ttctgaagtc caaccatctc ggtgtggtgc ttacattcac tgtatataaa tatgatctgc  420
ctccaaatgc aacaccacag gagcgtattc atgctacatt gggctatctt ggtgcctcat  480
ttgatgtccc ttctctggtt gataaactcc tagaacaact cgctagcaaa cgaaagatag  540
tagttaattt atatgac                                                 557

SEQ ID NO: 151         moltype = AA  length = 220
FEATURE                Location/Qualifiers
source                 1..220
                       mol_type = protein
                       organism = Zea mays
SEQUENCE: 151
CDERARMLQD QFNVSMNHVH ALAILVSSFH HGKDPSAIDQ KTFEDFTART TFERPLMSGV  60
AYALKVLHNE RQQFEEQHGW KIKKMEDGDQ SLVHDYNLEK LEPSPVQDEY APVIFSQETV  120
KHIISVDMMS GKEDHDNILR SWSTGKGALT SPFKLLKSNH LGVVLTFTVY KYDLPPNATP  180
QERIHATLGY LGASFDVPSL VDKLLEQLAS KRKIVVNLYD                        220

SEQ ID NO: 152         moltype = AA  length = 185
FEATURE                Location/Qualifiers
source                 1..185
                       mol_type = protein
                       organism = Zea mays
SEQUENCE: 152
SAIDQKTFED FTARTTFERP LMSGVAYALK VLHNERQQFE EQHGWKIKKM EDGDQSLVHD  60
YNLEKLEPSP VQDEYAPVIF SQETVKHIIS VDMMSGKEDH DNILRSWSTG KGALTSPFKL  120
LKSNHLGVVL TFTVYKYDLP PNATPQERIH ATLGYLGASF DVPSLVDKLL EQLASKRKIV  180
VNLYD                                                              185

SEQ ID NO: 153         moltype = AA  length = 34
FEATURE                Location/Qualifiers
source                 1..34
                       mol_type = protein
                       organism = Zea mays
SEQUENCE: 153
SAIDQKTFED FTARTTFERP LMSGVAYALK VLHN                              34

SEQ ID NO: 154         moltype = AA  length = 34
FEATURE                Location/Qualifiers
source                 1..34
                       mol_type = protein
                       organism = Zea mays
SEQUENCE: 154
RIHATLGYLG ASFDVPSLVD KLLEQLASKR KIVV                              34

SEQ ID NO: 155         moltype = AA  length = 16
FEATURE                Location/Qualifiers
source                 1..16
                       mol_type = protein
                       organism = Zea mays
SEQUENCE: 155
EDFTARTTFE RPLMSG                                                  16

SEQ ID NO: 156         moltype = AA  length = 12
FEATURE                Location/Qualifiers
source                 1..12
                       mol_type = protein
                       organism = Zea mays
SEQUENCE: 156
FTARTTFERP LM                                                      12

SEQ ID NO: 157         moltype = AA  length = 16
FEATURE                Location/Qualifiers
source                 1..16
                       mol_type = protein
                       organism = Zea mays
SEQUENCE: 157
ASFDVPSLVD KLLEQL                                                  16

SEQ ID NO: 158         moltype = AA  length = 11
FEATURE                Location/Qualifiers
source                 1..11
                       mol_type = protein
                       organism = Zea mays
SEQUENCE: 158
SFDVPSLVDK L                                                       11
```

```
SEQ ID NO: 159          moltype = DNA  length = 9926
FEATURE                 Location/Qualifiers
source                  1..9926
                        mol_type = genomic DNA
                        organism = Zea mays
SEQUENCE: 159
gcaacagaaa aaaacaacga aacacgcaac gtgcgggggc agatgcggca attccccgct  60
cacggcgcgc acatggaacg ccttcgcttt cctcctccct ccctccgtcc cgtcccgtgc  120
cccctctgc cttctctcac cgccacggcc actggcattg gccgcgctcg ccgcccaccg  180
cccaccgccc ccgcgccgct gtaggagcgc gcgcttgctt tagcgtaggc catggcccac  240
tactagcggg tgattagcct tgattagcgg gcaccactcc actgttacgg gaggcgcgtt  300
gttttaatcg cgggcgcgcg acgcccgtcg cctgtctcga atatctgctg ccgccgccaa  360
aagtgcggat tcctcctcct ccccgtcggg cggcctcgcc ccccctggtg cctactgggc  420
gctggcggag tgggagtgga tcgacgtgtt gcggccgcgg agtggaggca ataaagggaa  480
agctgggcgg agtgctcggg taccgtagcc ggattagtta ttaatgcccg cgagcagcta  540
gtcgtaggcg taactatttt aaggcagctg tcgccgctgg ggacttgcga aagcttcgcc  600
tcttttgaga agctctgcac cacgcctggc tccgccccgc tccccctcca cctccaggct  660
tccttcacag tctcgctgtt gctagtgctg ccttgctgct agtgataggg gtcccggggc  720
cctcaagttc tgggtgggcg gcaaacatat ggtgggcacc gggcggggga ataaggagga  780
agagaaagag gaggaggagc ggcagtagat ttgggccgca caggcaggga tggggggcaa  840
gtaccgcgcg gcgaggacga agaggtggtg gagggggctg gcagcggccg ggtgggtgct  900
aaccgcggtg gtctgctccg cggtgatgca ctggaccctg cgccgggaca gcatggaccg  960
cgccgaggag cgcctcgtca gcatgtgcga ggagagggcc aggatgctgc aggagcagtt  1020
cggggtcacc gtcaaccacg tccacgccat cgccattctc atctccacct tcaacttcga  1080
gaagtcccct ccagccatcg accaggttcg taaccattcg cccccaccct cttctccgcc  1140
attgctcttg tatgttgcaa tgccgcggca tcaattgaca gttggttcag caatggcgga  1200
cggacccccg agatcctgca cgttgttctc ccggttgtct ctgtcttttc tttaaggagc  1260
aaacaaaaaa aaaggaaaag aggagagaga gatgaagatg cgttctggtt tgttgaagct  1320
cacagtcgtt gcggcgctag tcgtctagct ggacatgatt gctgtggttg gctgggagcc  1380
tgggacaggt gctgtccatt gtcttgtgga aagaaaaaaa tgcccattcc tgcggtgggg  1440
aaggcgggga ttttttaggg tttaaagacg tcacggaact gaactactgg gttggtgcca  1500
cattgtttgt tcatagagtg gttagtgtgt tcgttgcaaa caccatctgg aggtcacttt  1560
gacaaccatt gggggcgctc ttttggcaac cttttgatcc cttagtttat tcttagaaag  1620
gtcactgtcg cagagattaa taatgttgca agctgctctc tgcctttctt ttttctttag  1680
cttagattat taatcgtcga agccgtcctt tactgcattt acagttcgtt tctcttcccc  1740
tttttgttga tttaccaata gtttagttta ggctcacagt gccgaaggcc catggtattt  1800
gaagacatgt tcattttttt tgcatactaa agtgatgata caatgaccaa tcaggttcat  1860
tgcatcatta cttttggtaa atcaacaaaa tttcttctgc tggttcttgc aatttatagt  1920
acattgctgc tcactgtttt ttttattctg gattaataaa cattgtccac tacaggacac  1980
ctttgcaaaa tacacggcaa ggacatcatt tgagcgacca ctgctcaatg gggtggcatt  2040
cgcacagcgt gtattccatc atgagaggga aatgtttgaa agccagcagg gatgggttat  2100
gaatacgatg cagcgggagc ctgcacctcc gcaggttgaa tacgccccag tgattttctc  2160
tcaggatacg gtttcctacc ttgcacgcat tgacatgatg tctggggagg tacagttact  2220
tctgtttgat tgttctttgt atccattggg ggggtgtttc tcgcgctttg atgcctcttt  2280
agtgaaatct atctatttat ttccaatata ggaggaccga gaaaacattt tccgggccag  2340
gactactggc aaagctgtgt taacaaaccc attccggttg cttggatcaa accacttggg  2400
agtagttctc acgtttgctg tgtaccgccc tgatctccct gctgatgcat cagttgagca  2460
acgtgtggaa gcaactattg ggtgagatgt tctaactcac ttccttcgtt gttttatttt  2520
ttggaccaaa tatttatagt attctcacct ttaagacttg tgtgtagcat ccatacttca  2580
gtaaaatgtg gatatgaaca aaattacacg catgattatt tgaccatgta atatcttgtc  2640
atcatgtatg ataccacatt tgtggttcac tatgatgacc tcgacatgtt tagtaacagg  2700
tgattatagg aacgacatgt ttctttttaa caaaaggcat aatgtgttaa tgatatagac  2760
atttagtaat ggcaaatact gcggtgcaat taacgttccc gtgcaattgc catgcaatca  2820
aactaccaag ggtcatgaaa aactctcgaa aattttatag atgcacttca ttatttcctc  2880
taccaatata tcaaatcttg agttctaatt catactatgt taagaaatat aaaaaataga  2940
aaattatgca ctatgcttat ctaattctaa agagaataat ttgttgtgtg ttgtacaaaa  3000
gtatgcatct gttgactatt gtggtaaaat ctaatcaagt tccctactaa tagatatctt  3060
ggtggagcct ttgatgtgga gtcacttgtg gagaatttgt tgagcaaact tgctggcaat  3120
caggatattg tggtaaatgt ctatgatgtc acaaatgctt cagatgctat ggttttgtat  3180
ggaccttcaa gtttggacga gcaagtgcct ttcttgcatg ttagcatgtt ggattttgga  3240
gatccattta ggaagcatga aatgagatgc aggttggtag tccttaccgg taaatcttag  3300
ctgtgttgtc tgcttttatt ttgcactaac gctgtcaacc atgcaggtat agacaaaaac  3360
ttcctatgcc gtggtctgcc atcaccaatc ctttgggcac atttgtcata tggatgcttc  3420
tagggtatag cattgctgct gcatattctc gatatgacaa agttactgaa gattgcagaa  3480
agatggaaga gctaaaaaca caggcagaag ctgctgatgt tgcaaaatct caggtttggc  3540
ctatacttta gcgctctctt ttgctaggca ttctagcata tgcaatcatg tatgacttat  3600
ctatgtttgt ctcaggcctt gttctgttgt atatggaatt aggggtcgaa ggtgattgag  3660
ggggattaaa tcttttctat ttaattttga ctagcaaggg attcaattcc cttcaatccc  3720
ctttaatcca tccctaacca aacaagccct tagagagttt atatcattcc ctgtttaggt  3780
gattggctgg ttgccttatg tgcctgatct ctcgcaccac ctccctaatc tgatttctat  3840
aaatcaggta gaggaagatc actggtaaag atctatatat tatgctccta gtattcagtt  3900
gactgcaaac aatattcaca ttatgatggt atcaatagac catcgtgatc atgtgacaat  3960
tcgctttcgc caagcctcag ctgcctgcat cgccttccta gcgccgtgtc atcaccatgc  4020
cacatgccat taaaccttgc cgttgccgct gatgccccgc aacgtgcaga ggacgaggac  4080
gcacaataga agacctgcta ggacttggtt ggtgtagccg atgaggttgc caaggccacc  4140
gtcgctgcta aggatcttgt acgtgccgcc taggatgttg ttgcaaagga acaacatacc  4200
actgttctcg caaaggaaca acatacactg ccgcctagga cccttcacca ttgataataa  4260
ttgttctatt gaatttgact tgtttggcct ctctgaagga tctcaatcct aggggtgatc  4320
gccagctgca atagttttag accccttttgg cctctacact caccgtcctg tcccatggag  4380
```

```
tcatgcgccc ttgttgcaac agctgccttc accacttggc atcattgttt cgggcatcct  4440
aggcagtcca aacttgttag tacctccacc atcaattgga aaaaatacta gtgattctct  4500
ttgtcacatg tgccaagttg ggcgtcatat tagattacct ttcggaacct cctctccttg  4560
ctaactctta agaattttga tttgattcat tgtgatgtgt ggacctcccc tattactagt  4620
gtctagttac aaatattatc ttgttactct tgattgcttg cacttccttt tgacatttcc  4680
gctttgagtc aaatttgaga cgtttcccgc cttggctcac ttttttctct tatgggaaga  4740
catagttcgg ctacaccatt cgaaatgttc aatgtgacaa tggccgcaag tttgataact  4800
cctcaactca cacctttctc accaaaggtg tcctgctcag gatgtcgtgc tcctacacac  4860
cctctcaaaa cagtaaagtc gactgtatga ttcgttccat taataacatc atatgtccat  4920
gctccttcaa gcctcccttg cctcgctata ctaggtgaag gtcttcacac tgctacatac  4980
cttgtcaatc gactagccac caaaacactg acatttggca cccccacttt gccctgtttg  5040
gttcacgtac ctcctacgac cacctcagtg tgtttggttg tgcatgctac caaaacatgt  5100
tcgccgtcgt gcctcacaag tcacaagctt gcttcccggt tgagtcaaca gaatcatgcg  5160
ggaagcaagc ttgtgacgtg tgaggcactc tgcaggcaac gatgacttgc tctcgaacaa  5220
cacatgggat cttgtcccat gtcctttcgg tgccaacatc gtctctgaca agtcattttt  5280
ctgctacaag ttccacgccg aaggttccct tgataaatat gaatcttgtt gggtcctcta  5340
tggcttcaca cagcccccta gtatggatta tgacgagact tttagtttag cggtctagcc  5400
tacgattgtt catactattt tgtatttttg ttcattacac tctcttagta atggctagtt  5460
catcagctcg atgtcaagaa tgccttcttg catgacatgc tttgtcgttt gtcatctcaa  5520
caagtccata tatatggtcc gaagcaggtg cctcgcgctt ggtgtagtcg ctttgctgca  5580
tgcttgctca ctttggaatt cactaaggcc aggtttgaca ccttgttcat atatccccac  5640
ataacagaca ggacacattt actgctatag gtggatgata ttgtcctcac tactctagtt  5700
aggatctcct ttgttgcatc atcactgcac tttaggagga attctccata atgatcttga  5760
tgtcatccat cacttcctgg gtgtggctgt tcagcagcgt tttgagtgcc atttctttca  5820
caacgacaat acactttgga tgtgattgag cacgctggca tgatcaactg caaatcgtgc  5880
agcacaccct tcgacactca tgtcaaggtc tcctccatag tcggtgcacc tatcaatgac  5940
cccactcagg atcatagttt ggttggtgca ttgcacacct tcatcggccc gctatctctt  6000
atgcggtcca gcaggtgtct ccacatttat gatcttcatg acattcacct ctttgttgtt  6060
aaacccatcc tgcggctgca aggggtacct agtcatggtc ttcttttgtg cttgtcgacg  6120
acctctgctc ttcttgtcta cgtggatgct gattgggctg tttgtgtgga cactcacaag  6180
tctacctcaa gctacaccat gttccttggt gatgatctgg ttttctagtc ctccaagcag  6240
tagaacagtg tcctactcca cggctctagt gccgaggctg agtaccagac atcaccaatg  6300
gcgtggccaa ggattgctga cttcgacaat tgctacgagg acatgccccc taacgaagat  6360
caccttggtc cgttatgata cttgtcgacc aaccctgctc agcatcaacg caagatcggt  6420
ctgcacttca tctgcaagcg tgttgctatt ggtgatgttt gtgttctcca tgtcctgaat  6480
cctgatgaca taccaatttt ctgacatctt caccaagggg cttctactta tgtcctatag  6540
atgttctgac tatggggtgt gtgtgtgtgt gtgttagaga gtttatctcc ttccctcttt  6600
aggtgattgg ctggttacct taggcgcccc ttctctgttt aggtgtttgg ctggtagtct  6660
tatttccttg ttcagttgat tgtctggttg ttttatgtgc ctgatctcct ggatcacctc  6720
cctgatcttg tttctataaa tcaggtagag gaagatcatt ggtagaggtc tatatattgt  6780
acttctgata ttcagttgaa tgcaagcaat attcacactc tacatctctc ttgcagttcc  6840
tggcaactgt gtcacatgag atcagaacac ctatgaatgg cgtccttggt acttatgcat  6900
ttattttgat tctacttaat cttcagttcc atgggcctgg caatctaaaa tttctgcctt  6960
ctggtgtagg aatgctggat atgcttttag gaacagatct aactatgaca cagaaggatt  7020
atgctcaaac tgctcaaatg tgtggcagag cattgattac actgataaat gatgtccttg  7080
atcgagcaaa gatcgaggct ggaaagttag agcttgaagc ggtgcctttt gacctgcgtt  7140
ctctcatgga tgatgttgtt tccttgtttt cttcaaagtc acgggagaag tgcattgagg  7200
tatgctactg ctaatgctta aagtaggaaa tgatgtttcc tgggccgtca cttgaatgga  7260
tgttgattgc ttttagttct agtttttggc tgatcaactg acaaataatg cagttctgca  7320
tgaatcaatc tgtcactata cttctatact tctctatggc agatactttc cctgattttt  7380
ttccttcttg ctgcagcttg cagtatttgt atgtgacaat gttccaaagg ttgttattgg  7440
agatccttgg aggtttcgac agatattgac aaatttggtc gggaatgcag tcaaagtaag  7500
cagccaattt tggtatttgg tatcctcaca ctacaacttc aaatgatgtt ggttagaagt  7560
atttgataag tctgtcatca aatacatgca caaaaatgca ctgatatatc tattgtctgt  7620
tccagttcac agaacgaggt catgtatttg tgcgggtctg tttggctgaa aactcaaatg  7680
tggaagccaa tcaggtccta catggagcca tgaatggcaa aggtggtaga gttgagtcaa  7740
caactaatgg tgccttcaat actttgagtg ggtttgaagc agcagacaga cgaaatagtt  7800
ggcaatattt taaactgctc ctctccgata aggagtcact tttggatgat cttgagggcg  7860
aaaattctaa tcaaagtgat tcaaatcatg tcacactagc aataagtatt gaggacacag  7920
gtgtcgggat accactgcaa gcacaagatc gtgtttttac accgtttatg caggctgaca  7980
gttcaacttc aaggaattat ggcggtactg gcatcggttt aagcatcagc aagtgtctag  8040
ctgaacttat gggtgggcag ataagtttca ctagccatcc ttctgttgga agcacgttca  8100
ctttctcagc cacactgaag cactcataca aagatatttc ggtcgattca agtaggagct  8160
tgacagaggc actaccaact gcttttaagg gaatgaaggc catcttggta gatgggagac  8220
ctgtacgtag tgctgttaca agatatcacc tcaagaggtt gggaatactt cttcaagttg  8280
tgaacaatat gaatgcagta gtaaaagctt tcccaggaca aaatggagca accggttcta  8340
ggtgagtgtt cttaagttag tttattaaat gctgttcata caattggctg agcaaggctt  8400
cacattccag tactttccct cacgtggagg ctgcctcaac ttcaaccctt atatgtggaa  8460
tgggagtagg gaacatttct tttattaaat tgtgtgacaa aagattcaaa ctcagacctg  8520
gccttgttac catgttgagc tgcatgcact catggcctca acaaaaaccc taagcaagga  8580
actcacttat aatttactag atatcataga tattctgtct gtttaatcag cttgtaccga  8640
ataagctatt cgcaaattgt ttttgagaat acagaatagc ataaaacatt attaaaacac  8700
cagatatgca ccttatactt gtttgtatga ccttcgaaat catcccattt attttcttgt  8760
agggaaaaag catcaattct ttttattgag agtgacttct ggaggcctga gacagatgtt  8820
cagttattga accatctacg cgagcagaag aacggtcagt tgtcggatgg gcacaaggta  8880
gttcttttgg tcacctctga agccgacaag gacaaatatg gatccatatt tgatattgtg  8940
atgtgtaagc ctataagggc aagcacaatc gcttcatcta ttcaacaact gctcaaagta  9000
gagatagccg aaagaaaaga taatcaaaac cggccgtcgt ttcttcgaag cttgctggtt  9060
gggaagaata tattggtcgt agacgataat aaagtcaacc tcagagttgc tgcggctgca  9120
```

```
ctcaagaaat atggtgctaa tgttagctgt gttgaaagcg gcaaggatgc tatcagtcta  9180
cttcaacccc cgcatcgctt cgatgcatgt tttatggatg ttcagatgcc agagatggac  9240
gggtatgtgg atgaaataaa caaagtcgtt ttccatttcc atcctgctgt ttgaagtttg  9300
tttgctagtt gaataaaaaa aatgtttcca ctgaccagca gttctcgatt gttacttttg  9360
taggtttgag gcaaccggac aaataaggca aatggagttg aaagcgaacg aggaaaggaa  9420
gaacaagttg gcttcgattg aaggctcgac aactgccgag taccatctgc ctgttctggc  9480
aatgacagcc gatgttatcc aggcaactta cgaagagtgc ataaaatcgg gaatggatgg  9540
atacgtatct aaacccttcg acgaggagca gctataccaa gcagtctcca gattggtagt  9600
gggaacgacg gattcggctg tttgatgttc aaaatacgat ggacctgact tctcattcat  9660
cgaagtgaag catcaccatc ttgcctctgt ccagctgact ctatatccct tgacaatggg  9720
cctctgacat ggcctctcac aagactagat gaaaaaagaa gatgaaagtg ccgtgagtta  9780
ggtacgtgtc acacatgaca tgaagttgct gcggcagccc agaggagtgt aggtagatca  9840
ccctgtaact ctcttgttct ttgatgttta taggctgttg tgtcttctga caattcattg  9900
gaaataccac atctcgttgc aatccc                                      9926
```

```
SEQ ID NO: 160          moltype = DNA  length = 3226
FEATURE                 Location/Qualifiers
source                  1..3226
                        mol_type = other DNA
                        organism = Zea mays
SEQUENCE: 160
atggggggca agtaccgcgc ggcgaggacg aagaggtggt ggaggggggct ggcagcggcc  60
gggtgggtgc taaccgcggt ggtctgctcc gcggtgatgc actggaccct gcgccgggac  120
agcatggacc gcgccgagga gcgcctcgtc agcatgtgcg aggagagggc caggatgctg  180
caggagcagt tcggggtcac cgtcaaccac gtccacgcca tcgccattct catctccacc  240
ttcaacttcg agaagtcccc tccagccatc gaccaggaca cctttgcaaa atacacggca  300
aggacatcat ttgagcgacc actgctcaat ggggtggcat tcgcacagcg tgtattccat  360
catgagaggg aaatgtttga aagccagcag ggatgggtta tgaatacgat gcagcgggag  420
cctgcacctc cgcaggttga atacgcccca gtgattttct ctcaggatac ggtttcctac  480
cttgcacgca ttgacatgat gtctggggag gaggaccgag aaaacatttt ccgggccagg  540
actactggca aagctgtgtt aacaaaccca ttccggttgc ttggatcaaa ccacttggga  600
gtagttctca cgtttgctgt gtaccgccct gatctccctg ctgatgcatc agttgagcaa  660
cgtgtggaag caactattgg atatcttggt ggagcctttg atgtggagtc acttgtggag  720
aatttgttga gcaaacttgc tggcaatcag gatattgtgg taaatgtcta tgatgtcaca  780
aatgcttcag atgctatggt tttgtatgga ccttcaagtt tggacgagca agtgcctttc  840
ttgcatgtta gcatgttgga ttttggagat ccatttagga agcatgaaat gagatgcagg  900
tatagacaaa aacttcctat gccgtggtct gccatcacca atcctttggg cacatttgtc  960
atatggatgc ttctagggta tagcattgct gctgcatatt ctcgatatga caaagttact  1020
gaagattgca gaaagatgga agagctaaaa acacaggcag aagctgctga tgttgcaaaa  1080
tctcagttcc tggcaactgt gtcacatgag atcagaacac ctatgaatgg cgtccttgga  1140
atgctggata tgcttttagg aacagatcta actatgacac agaaggatta tgctcaaact  1200
gctcaaatgt gtggcagagc attgattaca ctgataaatg atgtccttga tcgagcaaag  1260
atcgaggctg gaaagttaga gcttgaagcg gtgccttttg acctgcgttc tctcatggat  1320
gatgttgttt ccttgttttc ttcaaagtca cgggagaagt gcattgagct tgcagtattt  1380
gtatgtgaca atgttccaaa ggttgttatt ggagatcctt ggaggtttcg acagatattg  1440
acaaatttgg tcgggaatgc agtcaaattc acagaacgag gtcatgtatt tgtgcgggtc  1500
tgtttggctg aaaactcaaa tgtggaagcc aatcaggtcc tacatggagc catgaatggc  1560
aaaggtggta gagttgagtc aacaactaat ggtgccttca atactttgag tgggtttgaa  1620
gcagcagaca gacgaaatag ttggcaatat tttaaactgc tcctctccga taaggagtca  1680
cttttggatg atcttgaggg cgaaaattct aatcaaagtg attcaaatca tgtcacacta  1740
gcaataagta ttgaggacac aggtgtcggg ataccactgc aagcacaaga tcgtgttttt  1800
acaccgttta tgcaggctga cagttcaact tcaaggaatt atggcggtac tggcatcggt  1860
ttaagcatca gcaagtgtct agctgaactt atgggtgggc agataagttt cactagccat  1920
ccttctgttg gaagcacgtt cactttctca gccacactga agcactcata caaagatatt  1980
tcggtcgatt caagtaggag cttgacagag gcactaccaa ctgcttttaa gggaatgaag  2040
gccatcttgg tagatgggag acctgtacgt agtgctgtta caagatatca cctcaagagg  2100
ttgggaatac ttcttcaagt tgtgaacaat atgaatgcag tagtaaaagc tttcccagga  2160
caaaatggag caaccggttc tagggaaaaa gcatcaattc tttttattga gagtgacttc  2220
tggaggcctg agacagatgt tcagttattg aaccatctac gcgagcagaa gaacggtcag  2280
ttgtcggatg ggcacaaggt agttcttttg gtcacctctg aagccgacaa ggacaaatat  2340
ggatccatat ttgatattgt gatgtgtaag cctataaggg caagcacaat cgcttcatct  2400
attcaacaac tgctcaaagt agagatagcc gaaagaaaag ataatcaaaa ccggccgtcg  2460
tttcttcgaa gcttgctggt tgggaagaat atattggtcg tagacgataa taaagtcaac  2520
ctcagagttg ctgcggctgc actcaagaaa tatggtgcta atgttagctg tgttgaaagc  2580
ggcaaggatg ctatcagtct acttcaaccc ccgcatcgct tcgatgcatg ttttatggat  2640
gttcagatgc cagagatgga cggtttgag gcaaccggac aaataaggca aatggagttg  2700
aaagcgaacg aggaaaggaa gaacaagttg gcttcgattg aaggctcgac aactgccgag  2760
taccatctgc ctgttctggc aatgacagcc gatgttatcc aggcaactta cgaagagtgc  2820
ataaaatcgg gaatggatgg atacgtatct aaacccttcg acgaggagca gctataccaa  2880
gcagtctcca gattggtagt gggaacgacg gattcggctg tttgatgttc aaaatacgat  2940
ggacctgact tctcattcat cgaagtgaag catcaccatc ttgcctctgt ccagctgact  3000
ctatatccct tgacaatggg cctctgacat ggcctctcac aagactagat gaaaaaagaa  3060
gatgaaagtg ccgtgagtta ggtacgtgtc acacatgaca tgaagttgct gcggcagccc  3120
agaggagtgt aggtagatca ccctgtaact ctcttgttct ttgatgttta taggctgttg  3180
tgtcttctga caattcattg gaaataccac atctcgttgc aatccc                3226
```

```
SEQ ID NO: 161          moltype = AA  length = 974
FEATURE                 Location/Qualifiers
source                  1..974
```

```
                        mol_type = protein
                        organism = Zea mays
SEQUENCE: 161
MGGKYRAART KRWWRGLAAA GWVLTAVVCS AVMHWTLRRD SMDRAEERLV SMCEERARML  60
QEQFGVTVNH VHAIAILIST FNFEKSPPAI DQDTFAKYTA RTSFERPLLN GVAFAQRVFH  120
HEREMFESQQ GWVMNTMQRE PAPPQVEYAP VIFSQDTVSY LARIDMMSGE EDRENIFRAR  180
TTGKAVLTNP FRLLGSNHLG VVLTFAVYRP DLPADASVEQ RVEATIGYLG GAFDVESLVE  240
NLLSKLAGNQ DIVVNVYDVT NASDAMVLYG PSSLDEQVPF LHVSMLDFGD PFRKHEMRCR  300
YRQKLPMPWS AITNPLGTFV IWMLLGYSIA AAYSRYDKVT EDCRKMEELK TQAEAADVAK  360
SQFLATVSHE IRTPMNGVLG MLDMLLGTDL TMTQKDYAQT AQMCGRALIT LINDVLDRAK  420
IEAGKLELEA VPFDLRSLMD DVVSLFSSKS REKCIELAVF VCDNVPKVVI GDPWRFRQIL  480
TNLVGNAVKF TERGHVFVRV CLAENSNVEA NQVLHGAMNG KGGRVESTTN GAFNTLSGFE  540
AADRRNSWQY FKLLLSDKES LLDDLEGENS NQSDSNHVTL AISIEDTGVG IPLQAQDRVF  600
TPFMQADSST SRNYGGTGIG LSISKCLAEL MGGQISFTSH PSVGSTFTFS ATLKHSYKDI  660
SVDSSRSLTE ALPTAFKGMK AILVDGRPVR SAVTRYHLKR LGILLQVVNN MNAVVKAFPG  720
QNGATGSREK ASILFIESDF WRPETDVQLL NHLREQKNGQ LSDGHKVVLL VTSEADKDKY  780
GSIFDIVMCK PIRASTIASS IQQLLKVEIA ERKDNQNRPS FLRSLLVGKN ILVVDDNKVN  840
LRVAAAALKK YGANVSCVES GKDAISLLQP PHRFDACFMD VQMPEMDGFE ATGQIRQMEL  900
KANEERKNKL ASIEGSTTAE YHLPVLAMTA DVIQATYEEC IKSGMDGYVS KPFDEEQLYQ  960
AVSRLVVGTT DSAV                                                    974

SEQ ID NO: 162          moltype = DNA  length = 1311
FEATURE                 Location/Qualifiers
source                  1..1311
                        mol_type = genomic DNA
                        organism = Zea mays
SEQUENCE: 162
caaaatttct tctgctggtt cttgcaattt atagtacatt gctgctcact gttttttta  60
ttctggatta ataaacattg tccactacag gacacctttg caaaatacac ggcaaggaca  120
tcatttgagc gaccactgct caatggggtg gcattcgcac agcgtgtatt ccatcatgag  180
agggaaatgt ttgaaagcca gcagggatgg gttatgaata cgatgcagcg ggagcctgca  240
cctccgcagg ttgaatacgc cccagtgatt ttctctcagg atacggtttc ctaccttgca  300
cgcattgaca tgatgtctgg ggaggtacag ttacttctgt ttgattgttc tttgtatcca  360
ttgggggggt gtttctcgcg ctttgatgcc tctttagtga aatctatcta tttatttcca  420
atataggagg accgagaaaa cattttccgg gccaggacta ctggcaaagc tgtgttaaca  480
aacccattcc ggttgcttgg atcaaaccac ttgggagtag ttctcacgtt tgctgtgtac  540
cgccctgatc tccctgctga tgcatcagtt gagcaacgtg tggaagcaac tattgggtga  600
gatgttctaa ctcacttcct tcgttgtttt atttttgga ccaaatattt atagtattct  660
cacctttaag acttgtgtgt agcatccata cttcagtaaa atgtggatat gaacaaaatt  720
acacgcatga ttatttgacc atgtaatatc ttgtcatcat gtatgatacc acatttgtgg  780
ttcactatga tgacctcgac atgtttagta acaggtgatt ataggaacga catgtttctt  840
tttaacaaaa ggcataatgt gttaatgata tagacattta gtaatggcaa atactgcggt  900
gcaattaacg ttcccgtgca attgccatgc aatcaaacta ccaagggtca tgaaaaactc  960
tcgaaaattt tatagatgca cttcattatt tcctctacca atatatcaaa tcttgagttc  1020
taattcatac tatgttaaga aatataaaaa atagaaaatt atgcactatg cttatctaat  1080
tctaaagaga ataatttgtt gtgtgttgta caaaagtatg catctgttga ctattgtggt  1140
aaaatctaat caagttccct actaatagat atcttggtgg agcctttgat gtggagtcac  1200
ttgtggagaa tttgttgagc aaacttgctg gcaatcagga tattgtggta aatgtctatg  1260
atgtcacaaa tgcttcagat gctatggttt tgtatggacc ttcaagtttg g           1311

SEQ ID NO: 163          moltype = DNA  length = 223
FEATURE                 Location/Qualifiers
source                  1..223
                        mol_type = genomic DNA
                        organism = Zea mays
SEQUENCE: 163
caaaatttct tctgctggtt cttgcaattt atagtacatt gctgctcact gttttttta  60
ttctggatta ataaacattg tccactacag gacacctttg caaaatacac ggcaaggaca  120
tcatttgagc gaccactgct caatggggtg gcattcgcac agcgtgtatt ccatcatgag  180
agggaaatgt ttgaaagcca gcagggatgg gttatgaata cga                    223

SEQ ID NO: 164          moltype = DNA  length = 143
FEATURE                 Location/Qualifiers
source                  1..143
                        mol_type = genomic DNA
                        organism = Zea mays
SEQUENCE: 164
gctgctcact gttttttta ttctggatta ataaacattg tccactacag gacacctttg  60
caaaatacac ggcaaggaca tcatttgagc gaccactgct caatggggtg gcattcgcac  120
agcgtgtatt ccatcatgag agg                                          143

SEQ ID NO: 165          moltype = DNA  length = 103
FEATURE                 Location/Qualifiers
source                  1..103
                        mol_type = genomic DNA
                        organism = Zea mays
SEQUENCE: 165
ttctggatta ataaacattg tccactacag gacacctttg caaaatacac ggcaaggaca  60
tcatttgagc gaccactgct caatggggtg gcattcgcac agc                    103
```

```
SEQ ID NO: 166          moltype = DNA  length = 63
FEATURE                 Location/Qualifiers
source                  1..63
                        mol_type = genomic DNA
                        organism = Zea mays
SEQUENCE: 166
tccactacag gacacctttg caaaatacac ggcaaggaca tcatttgagc gaccactgct  60
caa                                                                 63

SEQ ID NO: 167          moltype = DNA  length = 223
FEATURE                 Location/Qualifiers
source                  1..223
                        mol_type = genomic DNA
                        organism = Zea mays
SEQUENCE: 167
ctctttagtg aaatctatct atttatttcc aatataggag gaccgagaaa acattttccg  60
ggccaggact actggcaaag ctgtgttaac aaacccattc cggttgcttg gatcaaacca  120
cttgggagta gttctcacgt ttgctgtgta ccgccctgat ctccctgctg atgcatcagt  180
tgagcaacgt gtggaagcaa ctattgggtg agatgttcta act                     223

SEQ ID NO: 168          moltype = DNA  length = 143
FEATURE                 Location/Qualifiers
source                  1..143
                        mol_type = genomic DNA
                        organism = Zea mays
SEQUENCE: 168
gaccgagaaa acattttccg ggccaggact actggcaaag ctgtgttaac aaacccattc  60
cggttgcttg gatcaaacca cttgggagta gttctcacgt ttgctgtgta ccgccctgat  120
ctccctgctg atgcatcagt tga                                           143

SEQ ID NO: 169          moltype = DNA  length = 103
FEATURE                 Location/Qualifiers
source                  1..103
                        mol_type = genomic DNA
                        organism = Zea mays
SEQUENCE: 169
ggccaggact actggcaaag ctgtgttaac aaacccattc cggttgcttg gatcaaacca  60
cttgggagta gttctcacgt ttgctgtgta ccgccctgat ctc                     103

SEQ ID NO: 170          moltype = DNA  length = 63
FEATURE                 Location/Qualifiers
source                  1..63
                        mol_type = genomic DNA
                        organism = Zea mays
SEQUENCE: 170
ctgtgttaac aaacccattc cggttgcttg gatcaaacca cttgggagta gttctcacgt  60
ttg                                                                 63

SEQ ID NO: 171          moltype = DNA  length = 231
FEATURE                 Location/Qualifiers
source                  1..231
                        mol_type = genomic DNA
                        organism = Zea mays
SEQUENCE: 171
tctaaagaga ataatttgtt gtgtgttgta caaaagtatg catctgttga ctattgtggt  60
aaaatctaat caagttccct actaatagat atcttggtgg agcctttgat gtggagtcac  120
ttgtggagaa tttgttgagc aaacttgctg gcaatcagga tattgtggta aatgtctatg  180
atgtcacaaa tgcttcagat gctatggttt tgtatggacc ttcaagtttg g            231

SEQ ID NO: 172          moltype = DNA  length = 151
FEATURE                 Location/Qualifiers
source                  1..151
                        mol_type = genomic DNA
                        organism = Zea mays
SEQUENCE: 172
catctgttga ctattgtggt aaaatctaat caagttccct actaatagat atcttggtgg  60
agcctttgat gtggagtcac ttgtggagaa tttgttgagc aaacttgctg gcaatcagga  120
tattgtggta aatgtctatg atgtcacaaa t                                  151

SEQ ID NO: 173          moltype = DNA  length = 111
FEATURE                 Location/Qualifiers
source                  1..111
                        mol_type = genomic DNA
                        organism = Zea mays
SEQUENCE: 173
aaaatctaat caagttccct actaatagat atcttggtgg agcctttgat gtggagtcac  60
ttgtggagaa tttgttgagc aaacttgctg gcaatcagga tattgtggta a            111
```

```
SEQ ID NO: 174         moltype = DNA  length = 71
FEATURE                Location/Qualifiers
source                 1..71
                       mol_type = genomic DNA
                       organism = Zea mays
SEQUENCE: 174
actaatagat atcttggtgg agcctttgat gtggagtcac ttgtggagaa tttgttgagc  60
aaacttgctg g                                                       71

SEQ ID NO: 175         moltype = DNA  length = 690
FEATURE                Location/Qualifiers
source                 1..690
                       mol_type = genomic DNA
                       organism = Zea mays
SEQUENCE: 175
tgctccgcgg tgatgcactg gaccctgcgc cgggacagca tggaccgcgc cgaggagcgc  60
ctcgtcagca tgtgcgagga gagggccagg atgctgcagg agcagttcgg ggtcaccgtc  120
aaccacgtcc acgccatcgc cattctcatc tccaccttca acttcgagaa gtcccctcca  180
gccatcgacc aggacacctt tgcaaaatac acggcaagga catcatttga gcgaccactg  240
ctcaatgggg tggcattcgc acagcgtgta ttccatcatg agagggaaat gtttgaaagc  300
cagcagggat gggttatgaa tacgatgcag cgggagcctg cacctccgca ggttgaatac  360
gccccagtga ttttctctca ggatacggtt tcctaccttg cacgcattga catgatgtct  420
ggggaggagg accgagaaaa cattttccgg gccaggacta ctggcaaagc tgtgttaaca  480
aacccattcc ggttgcttgg atcaaaccac ttgggagtag ttctcacgtt tgctgtgtac  540
cgccctgatc tccctgctga tgcatcagtt gagcaacgtg tggaagcaac tattggatat  600
cttggtggag cctttgatgt ggagtcactt gtggagaatt tgttgagcaa acttgctggc  660
aatcaggata ttgtggtaaa tgtctatgat                                   690

SEQ ID NO: 176         moltype = AA  length = 230
FEATURE                Location/Qualifiers
source                 1..230
                       mol_type = protein
                       organism = Zea mays
SEQUENCE: 176
CSAVMHWTLR RDSMDRAEER LVSMCEERAR MLQEQFGVTV NHVHAIAILI STFNFEKSPP  60
AIDQDTFAKY TARTSFERPL LNGVAFAQRV FHHEREMFES QQGWVMNTMQ REPAPPQVEY  120
APVIFSQDTV SYLARIDMMS GEEDRENIFR ARTTGKAVLT NPFRLLGSNH LGVVLTFAVY  180
RPDLPADASV EQRVEATIGY LGGAFDVESL VENLLSKLAG NQDIVVNVYD             230

SEQ ID NO: 177         moltype = AA  length = 34
FEATURE                Location/Qualifiers
source                 1..34
                       mol_type = protein
                       organism = Zea mays
SEQUENCE: 177
PPAIDQDTFA KYTARTSFER PLLNGVAFAQ RVFH                              34

SEQ ID NO: 178         moltype = AA  length = 31
FEATURE                Location/Qualifiers
source                 1..31
                       mol_type = protein
                       organism = Zea mays
SEQUENCE: 178
NIFRARTTGK AVLTNPFRLL GSNHLGVVLT F                                 31

SEQ ID NO: 179         moltype = AA  length = 33
FEATURE                Location/Qualifiers
source                 1..33
                       mol_type = protein
                       organism = Zea mays
SEQUENCE: 179
RVEATIGYLG GAFDVESLVE NLLSKLAGNQ DIV                               33

SEQ ID NO: 180         moltype = AA  length = 18
FEATURE                Location/Qualifiers
source                 1..18
                       mol_type = protein
                       organism = Zea mays
SEQUENCE: 180
DTFAKYTART SFERPLLN                                                18

SEQ ID NO: 181         moltype = AA  length = 14
FEATURE                Location/Qualifiers
source                 1..14
                       mol_type = protein
                       organism = Zea mays
SEQUENCE: 181
KYTARTSFER PLLN                                                    14
```

```
SEQ ID NO: 182          moltype = AA  length = 8
FEATURE                 Location/Qualifiers
source                  1..8
                        mol_type = protein
                        organism = Zea mays
SEQUENCE: 182
ARTSFERP                                                                  8

SEQ ID NO: 183          moltype = AA  length = 17
FEATURE                 Location/Qualifiers
source                  1..17
                        mol_type = protein
                        organism = Zea mays
SEQUENCE: 183
AVLTNPFRLL GSNHLGV                                                        17

SEQ ID NO: 184          moltype = AA  length = 11
FEATURE                 Location/Qualifiers
source                  1..11
                        mol_type = protein
                        organism = Zea mays
SEQUENCE: 184
AVLTNPFRLL G                                                              11

SEQ ID NO: 185          moltype = AA  length = 17
FEATURE                 Location/Qualifiers
source                  1..17
                        mol_type = protein
                        organism = Zea mays
SEQUENCE: 185
LGGAFDVESL VENLLSK                                                        17

SEQ ID NO: 186          moltype = AA  length = 13
FEATURE                 Location/Qualifiers
source                  1..13
                        mol_type = protein
                        organism = Zea mays
SEQUENCE: 186
GAFDVESLVE NLL                                                            13

SEQ ID NO: 187          moltype = DNA  length = 6363
FEATURE                 Location/Qualifiers
source                  1..6363
                        mol_type = genomic DNA
                        organism = Zea mays
SEQUENCE: 187
gcccgcagcc cgctcttccc cgctccacct ccaggcttcc agtctctcac tctcccgcgc  60
ctcttgctgc tgctgctggc gatagggatc ccagcgcctt caagttcggg tgggcggcta  120
gcgcggcgcg tgtcggcgag catatggtgg gcattgggcg ggggaaggag gaggaggagc  180
ggcaatagat ttgtgggcgc agaggcgggg atggggggca acaagtactg cgcggcgatg  240
acgaagagga gatggagggg gctggcagcg gccgcgtggg tgctagtcgc ggtggcttgc  300
tccgcggtga tgcactggac catgcgccgg gagagcatgg accgcgccga ggagcgcctc  360
gtcagcatgt gcgaggagag ggccaggatg ctgcaggagc agttcggggt caccgtcaac  420
cacgtccacg cgatcgccat tctcatcgcc accttcaact acgataagtc cccttccgct  480
atcgaccagg ttcgtcacca ttcgcccccc tcttctccgc cattgctctt gtagattgct  540
atgccacggt atcaattggc agttggttta gcaatagcgg accccgagat cctacacatt  600
gttctgtggg ttgtctcttt tctttaaagg agcaaacaga aaaaaaaggg gagaaataga  660
gatatagaga tgcgttgttg tttgttgacg cttaccgtcg tttagcacgc catgattgct  720
gtggttggct gggacaggtg ctgttcatag tcttgtggaa agaaaaaaaa tgtccattcc  780
tgcggcggtt aggcggggat tttttaggct tattggagac gtagctgaac tgaactgttg  840
ggttggtggc acattgtttg ttcatagagt gattagtgtg ttcgctgcaa aaccatctgg  900
gggttacttt gacatccatt ggggtgtgct cttttgccaa ccttttgatt ccttgtttat  960
tctgagaaag gtccctgtcg cagagattaa attatgttag aagctgcttt ctgcctctct  1020
tttcttttgc ttagattatt gatcctcaaa gccgtccttt cctgcatcta cacttcgttt  1080
ctcttccccc ccttttttttt tgtcgattta cctatagttt aggcgtgcag tgtcatgggc  1140
ccatgttatt tgaagacgtg ctcgtttttg catacaatga ccaatcttat tcgttgcatc  1200
attacttttg gtaaatcaac aagatgtctt cttctgattc ttgcaattta tagcatatta  1260
ttgtccagta ttctattttg gcttaataat taatgtccga cacaggacac ttttgcaaaa  1320
tacacggcaa ggacatcatt tgagcgaccg ctactcaatg gggtggcata tgcacagcgt  1380
gtattccatc atgagaggga aatgtttgaa agccagcagg gatggattat gaatacaatg  1440
cagcgggagc ctgcaccccc gcaggttgaa tatgctccag tgattttctc tcaggatact  1500
gtttcctacc tcgcacgcat tgacatgatg tctggagagg tatggttcta tttgatcgat  1560
cttagtattc attggggtgt ttatgaccct ttgatgtctc tttagtgaaa gcaatctatt  1620
tatttacgat acaggaggac cgagaaaaca ttttgcgggc caggactact ggcaaagctg  1680
tgttaacaaa cccatttcgg ttgcttggat caaaccactt gggagtagtt ctcacttttg  1740
ctgtgtaccg ccctgatctc cccgctgatg catcagttga gcaacgtgtg gaagcaacta  1800
ttgggtgaga tgttctaact cacatccttt gttgttttat ttttaaccaa atattctagc  1860
attgtcgcct ttaagactca tgtttaacat gtgggtatga ataaaatttt gtgcactatt  1920
atttgatcat gtaatatctt gtcatcgtgt atcatgccac atttgtggtt cactgatcaa  1980
```

```
tactgaattt aggttgacta tgatgacctt aacatgtcta gtaacaggtg ataatagaaa  2040
caatgtgttt cttttttaaa aaaggtatag cgtgcttatg gcagttatgg caggcacatt  2100
tagtaataga tcatgcaggt tataatcatt gcagcttgtc tcaatttaat caaatgatac  2160
tctatgctta tctaattttc aagagaataa tttgctgtgt gctcccagat atcttggtgg  2220
agcgtttgat gtggagtcac ttgtggagaa tttgctgagc aaacttgctg gcaatcagga  2280
tattgtggtg aatgtctatg atgtcacaaa tgcttcagag gctatggttt tgtatggacc  2340
ttctagttcg gatgagcgcg tgcctttctt gcatgttagc atgttggatt ttggagatcc  2400
gtttaggagg catgaaatga ggtgcaggtt ggtagtcctt atctgtaaat cttaattttc  2460
ttggctgctt ttgttttcca ctaatgttgt caacctgcag gtatagacaa aagcttccta  2520
tgcagtggtc tgccataacc aatcctttgg gcacatttgt catatggatg cttctggggt  2580
atagcattgc cgctgcatat tctcgatatg acaaagttac agaagattgt agaaagatgg  2640
aagagctaaa aacgcaggca gaagctgctg atgttgcaaa gtctcaggtt tggcctgttc  2700
tttagcactc tcatttacta ggcattctag catatgcatc atgtatggct tagcttatct  2760
atgtttgtct ctcttgcagt tcctggcaac tgtgtcacat gagatcagaa cacctatgaa  2820
tggcgtcctt ggtacttatg catttatttt gatattactt aatcttcagt tccgtgggcc  2880
tatcaatcta attttttcc ttctggcgta ggaatgctgg atatgctttt aggaacagat  2940
ctaactatga cacagaagga ttatgctcaa actgctcaaa tgtgtggcag agcattgata  3000
acgttgataa atgatgtcct tgatcgagca aagattgaag ctggaaagtt agagcttgaa  3060
gcggtgcctt ttgacctgcg ttctctcatg gatgatgtta tttccttatt ttcttcaaag  3120
tcacgggaga agtgcattga ggtatgttac tgttaatgct tgaagtagga aatgatgttg  3180
cctgggccat cacttgaatg gatattgatt gcttttagtc ctagtttttg gctgagcaac  3240
tgacgaataa tgcagtttg cctgaaccaa tctgtcacta tacattgtgg catatacttt  3300
tcctgatcct tttccttctt gctgcagctt gcagtatttg tatgtgacaa tgttccgaag  3360
gatgttcttg gagatccttg gaggtttcgg cagatactaa caaatttggt cggcaatgca  3420
gtcaaagtaa gcaaccattt atggtatttg gtatcctcac actacaactt cgaatgatgt  3480
tggttaagtc gtagataagt ctgtcatcaa atacattcag aaaaatgcgc tgatatattt  3540
atcgtgtgtt ccagttcaca gaacggggtc atgtatttgt gcgggtctgt ttggctgata  3600
actcaaatat ggaagccggt caggtcctaa atggagccat gaatgggaaa gatggtagag  3660
ttgattcaac aactaatggt gccttcaata ctctgagtgg gtttgaagca gcagacagac  3720
gaaatagttg gcaatatttt aagatgctcc tctctgataa ggagtccctt ttggatgatc  3780
ttgagggaac aaattctgat caaagtgatt cagaccatgt cacactagcg ataagtattg  3840
aggacacagg tgttgggata ccattgcaag cacaagatcg tgtttttaca ccgtttatgc  3900
aggctgatag ttcaacttca aggaattatg gtggtactgg catcggttta agcattagca  3960
agtgcctagc tgaacttatg ggtgggcaga taagttttgt cagccgtcct tttgttggaa  4020
gtacattcac tttctccacc acactgaagc gctcatacaa agatatttca gttgattcaa  4080
gtaggagctt gttagaggca ctaccaactg cttttaaggg aatgaaggcc atcttgatag  4140
atgggagacc tgtacgtagt gctgttacaa gatatcacct caagaggttg ggaataattg  4200
ttcaagttgt gaacaatatg agtgcagtag taaaagcttt ccctggacaa aatggagcaa  4260
ctgtttctag gtgagtgttc ttaagttagt ttattagatg ctggagatac aattggctga  4320
gcagtgattc acatttcagt actttccctc acatggaggc tccctcaacc gcaagcctta  4380
tatgtgaaat gggagctctg ttttaaaggc gacgtctagg cgccccaaca ctcctaggcg  4440
ttcccgtcgc gtagctaaat cagcaagagg gcagagagaa agaaggggcg gcgccgaatc  4500
aggccgccgg cggccgattc ggccccagcg acagctgaat cagggcggcg gcggccgaat  4560
cggggatggc ggcagcaaaa tcatgagtgg cggcggctga atcgtgtgag gagagaagga  4620
aaccacggct gaaaaagggg aggggagaag gaaagcagca gctcaatcga ggggggagag  4680
gggggaaaca gggggagata taggctggct tctttttctt cctcctccat gctgctgttt  4740
tatgctgctg ttttgttggt tctcatgttg ataaggtgtc accttgctcg tcttagttgt  4800
cgcctaggcg tccagaccag gtggtagttc aacgtcttat cttgccttac cgctttaaga  4860
accataaacg ggctagggaa catttctttt attaaattgt gtgactaaag atttgaattc  4920
gaaacctggt tttgttacca gcatgttaag ctgcatgcac tgacggcctc aacaaagacc  4980
ctaagggctg gtttggtgga cagggaaatg agatcccctc catttttctg tccaccaaac  5040
cagccctaaa ctggtgggaa aggcaggcaa ctcattaata tattttacta catataatag  5100
ataaaccgtc tatgccatca gtctgtcctg aataagctat tttctttttt gaaaaagtat  5160
aggaccctaa aatccttgac tgacctttta tccccaaact gttttgggga atagcataaa  5220
acattcttaa agcacctgaa tatgcacttt ataattgttt tgtatgacat ctgaaatcat  5280
cacatttatt ctcttgtagg gaaaaggcaa ccattctttt tattgagagt gacttttgga  5340
ggcccgagac agatgttcag ttattgaacc atctacgcga gcacaagaat cgtcagttgt  5400
ctgatgggca taaggtagtt cttttggtca cctccgaagc tgataaggac aagtatggat  5460
ccatatttga tattgtgatg tgcaagccta taagggcaag catgattgct tcatctattc  5520
aacaactgct caaagtagag atgcctgaaa gaagaaataa tcataatcgg ccatcatttc  5580
ttcgcagcct gctggttggg aagaatatat tggtagtaga tgataataaa gtcaatctta  5640
gagtcgctgc agctgcactc aaaaagtacg gtgctaatgt tagctgtgtt gagagtggca  5700
aagatgctat cagtctactt caacccccac attgctttga cgcatgtttt atggatgttc  5760
agatgccaga gatggatggg tatggattaa ataaatataa acacgtttgt catttccatc  5820
atgttgtttg aagtttgttt gctaggtgaa gtaaatctcc ccactgatca tcagttctca  5880
attattactt ttttaggttt gaggcaacaa gacaaataag gcaaacagag atgagagtta  5940
acgaggaaag gaagaataag ttggtgttga ttgaaggctc aacatttgtt gagtaccatt  6000
tgcctgtttt ggcgatgaca gccgatgtta tccaggcaac ttacgagaag tgtataaaat  6060
cgggaatgga tggatacgtg tctaaaccct tcgacgagga gcagctatac caagcagtct  6120
ccagattaat agtgggaacg acagattcga ctgtttaata tttagatggc tatgaatctg  6180
atttctcatt catcgaattg aagcacacca ccatgttgct tctgtccaag tttgactcta  6240
accctaaca attgtctgac ctggcctctc gcagcactag atgaaaagga tgaaagtgcc  6300
acgagttggc tatgtatcag caccacagat gaagttgcct caccccggag tgtaggttgg  6360
tag                                                               6363
```

SEQ ID NO: 188 moltype = DNA length = 2694
FEATURE Location/Qualifiers
source 1..2694
mol_type = other DNA

```
                        organism = Zea mays
SEQUENCE: 188
atggggggca acaagtactg cgcggcgatg acgaagagga gatggagggg gctggcagcg  60
gccgcgtggg tgctagtcgc ggtggcttgc tccgcggtga tgcactggac catgcgccgg  120
gagagcatgg accgcgccga ggagcgcctc gtcagcatgt gcgaggagag ggccaggatg  180
ctgcaggagc agttcggggt caccgtcaac cacgtccacg cgatcgccat tctcatcgcc  240
accttcaact acgataagtc cccttccgct atcgaccagg aggaccgaga aaacattttg  300
cgggccagga ctactggcaa agctgtgtta acaaacccat ttcggttgct tggatcaaac  360
cacttgggag tagttctcac ttttgctgtg taccgccctg atctccccgc tgatgcatca  420
gttgagcaac gtgtggaagc aactattgga tatcttggtg gagcgtttga tgtggagtca  480
cttgtggaga atttgctgag caaacttgct ggcaatcagg atattgtggt gaatgtctat  540
gatgtcacaa atgcttcaga ggctatggtt ttgtatggac cttctagttc ggatgagcgc  600
gtgcctttct tgcatgttag catgttggat tttggagatc cgtttaggag gcatgaaatg  660
aggtgcaggt atagacaaaa gcttcctatg cagtggtctg ccataaccaa tcctttgggc  720
acatttgtca tatggatgct tctggggtat agcattgccg ctgcatattc tcgatatgac  780
aaagttacag aagattgtag aaagatggaa gagctaaaaa cgcaggcaga agctgctgat  840
gttgcaaagt ctcagttcct ggcaactgtg tcacatgaga tcagaacacc tatgaatggc  900
gtccttggaa tgctggatat gcttttagga acagatctaa ctatgacaca gaaggattat  960
gctcaaactg ctcaaatgtg tggcagagca ttgataacgt tgataaatga tgtccttgat  1020
cgagcaaaga ttgaagctgg aaagttagag cttgaagcgg tgccttttga cctgcgttct  1080
ctcatggatg atgttatttc cttattttct tcaaagtcac gggagaagtg cattgagctt  1140
gcagtatttg tatgtgacaa tgttccgaag gatgttcttg gagatccttg gaggtttcgg  1200
cagatactaa caaatttggt cggcaatgca gtcaaattca cagaacgggg tcatgtattt  1260
gtgcgggtct gtttggctga taactcaaat atggaagccg gtcaggtcct aaatggagcc  1320
atgaatggga aagatggtag agttgattca acaactaatg gtgccttcaa tactctgagt  1380
gggtttgaag cagcagacag acgaaatagt tggcaatatt ttaagatgct cctctctgat  1440
aaggagtccc ttttggatga tcttgaggga acaaattctg atcaaagtga ttcagaccat  1500
gtcacactag cgataagtat tgaggacaca ggtgttggga taccattgca agcacaagat  1560
cgtgtttttta caccgtttat gcaggctgat agttcaactt caaggaatta tggtggtact  1620
ggcatcggtt taagcattag caagtgccta gctgaactta tgggtgggca gataagtttt  1680
gtcagccgtc cttttgttgg aagtacattc actttctcca ccacactgaa gcgctcatac  1740
aaagatattt cagttgattc aagtaggagc ttgttagagg cactaccaac tgcttttaag  1800
ggaatgaagg ccatcttgat agatgggaga cctgtacgta gtgctgttac aagatatcac  1860
ctcaagaggt tgggaataat tgttcaagtt gtgaacaata tgagtgcagt agtaaaagct  1920
ttccctggac aaaatggagc aactgtttct agggaaaagg caaccattct tttattgag  1980
agtgactttt ggaggcccga gacagatgtt cagttattga accatctacg cgagcacaag  2040
aatcgtcagt tgtctgatgg gcataaggta gttcttttgg tcacctccga agctgataag  2100
gacaagtatg gatccatatt tgatattgtg atgtgcaagc ctataagggc aagcatgatt  2160
gcttcatcta ttcaacaact gctcaaagta gagatgcctg aaagaagaaa taatcataat  2220
cggccatcat ttcttcgcag cctgctggtt gggaagaata tattggtagt agatgataat  2280
aaagtcaatc ttagagtcgc tgcagctgca ctcaaaaagt acggtgctaa tgttagctgt  2340
gttgagagtg gcaaagatgc tatcagtcta cttcaacccc cacattgctt tgacgcatgt  2400
tttatggatg ttcagatgcc agagatggat gggtttgagg caacaagaca aataaggcaa  2460
acagagatga gagttaacga ggaaaggaag aataagttgg tgttgattga aggctcaaca  2520
tttgttgagt accatttgcc tgttttggcg atgacagccg atgttatcca ggcaacttac  2580
gagaagtgta taaaatcggg aatggatgga tacgtgtcta aacccttcga cgaggagcag  2640
ctataccaag cagtctccag attaatagtg ggaacgacag attcgactgt ttaa        2694

SEQ ID NO: 189          moltype = AA  length = 897
FEATURE                 Location/Qualifiers
source                  1..897
                        mol_type = protein
                        organism = Zea mays
SEQUENCE: 189
MGGNKYCAAM TKRRWRGLAA AAWVLVAVAC SAVMHWTMRR ESMDRAEERL VSMCEERARM  60
LQEQFGVTVN HVHAIAILIA TFNYDKSPSA IDQEDRENIL RARTTGKAVL TNPFRLLGSN  120
HLGVVLTFAV YRPDLPADAS VEQRVEATIG YLGGAFDVES LVENLLSKLA GNQDIVVNVY  180
DVTNASEAMV LYGPSSSDER VPFLHVSMLD FGDPFRRHEM RCRYRQKLPM QWSAITNPLG  240
TFVIWMLLGY SIAAAYSRYD KVTEDCRKME ELKTQAEAAD VAKSQFLATV SHEIRTPMNG  300
VLGMLDMLLG TDLTMTQKDY AQTAQMCGRA LITLINDVLD RAKIEAGKLE LEAVPFDLRS  360
LMDDVISLFS SKSREKCIEL AVFVCDNVPK DVLGDPWRFR QILTNLVGNA VKFTERGHVF  420
VRVCLADNSN MEAGQVLNGA MNGKDGRVDS TTNGAFNTLS GFEAADRRNS WQYFKMLLSD  480
KESLLDDLEG TNSDQSDSDH VTLAISIEDT GVGIPLQAQD RVFTPFMQAD SSTSRNYGGT  540
GIGLSISKCL AELMGGQISF VSRPFVGSTF TFSTTLKRSY KDISVDSSRS LLEALPTAFK  600
GMKAILIDGR PVRSAVTRYH LKRLGIIVQV VNNMSAVVKA FPGQNGATVS REKATILFIE  660
SDFWRPETDV QLLNHLREHK NRQLSDGHKV VLLVTSEADK DKYGSIFDIV MCKPIRASMI  720
ASSIQQLLKV EMPERRNNHN RPSFLRSLLV GKNILVVDDN KVNLRVAAAA LKKYGANVSC  780
VESGKDAISL LQPPHCFDAC FMDVQMPEMD GFEATRQIRQ TEMRVNEERK NKLVLIEGST  840
FVEYHLPVLA MTADVIQATY EKCIKSGMDG YVSKPFDEEQ LYQAVSRLIV GTTDSTV     897

SEQ ID NO: 190          moltype = DNA  length = 1136
FEATURE                 Location/Qualifiers
source                  1..1136
                        mol_type = genomic DNA
                        organism = Zea mays
SEQUENCE: 190
tcaacaagat gtcttcttct gattcttgca atttatagca tattattgtc cagtattcta  60
ttttggctta ataattaatg tccgacacag gacacttttg caaaatacac ggcaaggaca  120
tcatttgagc gaccgctact caatggggtg gcatatgcac agcgtgtatt ccatcatgag  180
```

```
agggaaatgt ttgaaagcca gcagggatgg attatgaata caatgcagcg ggagcctgca  240
cccccgcagg ttgaatatgc tccagtgatt ttctctcagg atactgtttc ctacctcgca  300
cgcattgaca tgatgtctgg agaggtatgg ttctatttga tcgatcttag tattcattgg  360
ggtgtttatg accctttgat gtctctttag tgaaagcaat ctatttattt acgatacagg  420
aggaccgaga aaacattttg cgggccagga ctactggcaa agctgtgtta acaaacccat  480
ttcggttgct tggatcaaac cacttgggag tagttctcac ttttgctgtg taccgccctg  540
atctccccgc tgatgcatca gttgagcaac gtgtggaagc aactattggg tgagatgttc  600
taactcacat cctttgttgt tttattttta accaaatatt ctagcattgt cgcctttaag  660
actcatgttt aacatgtggg tatgaataaa attttgtgca ctattatttg atcatgtaat  720
atcttgtcat cgtgtatcat gccacatttg tggttcactg atcaatactg aatttaggtt  780
gactatgatg accttaacat gtctagtaac aggtgataat agaaacaatg tgtttctttt  840
ttaaaaaagg tatagcgtgc ttatggcagt tatggcaggc acatttagta atagatcatg  900
caggttataa tcattgcagc ttgtctcaat ttaatcaaat gatactctat gcttatctaa  960
ttttcaagag aataatttgc tgtgtgctcc cagatatctt ggtggagcgt ttgatgtgga  1020
gtcacttgtg gagaatttgc tgagcaaact tgctggcaat caggatattg tggtgaatgt  1080
ctatgatgtc acaaatgctt cagaggctat ggttttgtat ggaccttcta gttcgg      1136

SEQ ID NO: 191         moltype = DNA  length = 689
FEATURE                Location/Qualifiers
source                 1..689
                       mol_type = genomic DNA
                       organism = Zea mays
SEQUENCE: 191
tcaacaagat gtcttcttct gattcttgca atttatagca tattattgtc cagtattcta  60
ttttggctta ataattaatg tccgacacag gacacttttg caaaatacac ggcaaggaca  120
tcatttgagc gaccgctact caatggggtg gcatatgcac agcgtgtatt ccatcatgag  180
agggaaatgt ttgaaagcca gcagggatgg attatgaata caatgcagcg ggagcctgca  240
cccccgcagg ttgaatatgc tccagtgatt ttctctcagg atactgtttc ctacctcgca  300
cgcattgaca tgatgtctgg agaggtatgg ttctatttga tcgatcttag tattcattgg  360
ggtgtttatg accctttgat gtctctttag tgaaagcaat ctatttattt acgatacagg  420
aggaccgaga aaacattttg cgggccagga ctactggcaa agctgtgtta acaaacccat  480
ttcggttgct tggatcaaac cacttgggag tagttctcac ttttgctgtg taccgccctg  540
atctccccgc tgatgcatca gttgagcaac gtgtggaagc aactattggg tgagatgttc  600
taactcacat cctttgttgt tttattttta accaaatatt ctagcattgt cgcctttaag  660
actcatgttt aacatgtggg tatgaataa                                  689

SEQ ID NO: 192         moltype = DNA  length = 754
FEATURE                Location/Qualifiers
source                 1..754
                       mol_type = genomic DNA
                       organism = Zea mays
SEQUENCE: 192
ctctttagtg aaagcaatct atttatttac gatacaggag gaccgagaaa acattttgcg  60
ggccaggact actggcaaag ctgtgttaac aaacccattt cggttgcttg gatcaaacca  120
cttgggagta gttctcactt ttgctgtgta ccgccctgat ctccccgctg atgcatcagt  180
tgagcaacgt gtggaagcaa ctattgggtg agatgttcta actcacatcc tttgttgttt  240
tatttttaac caaatattct agcattgtcg cctttaagac tcatgtttaa catgtgggta  300
tgaataaaat tttgtgcact attatttgat catgtaatat cttgtcatcg tgtatcatgc  360
cacatttgtg gttcactgat caatactgaa tttaggttga ctatgatgac cttaacatgt  420
ctagtaacag gtgataatag aaacaatgtg tttctttttt aaaaaaggta tagcgtgctt  480
atggcagtta tggcaggcac atttagtaat agatcatgca ggttataatc attgcagctt  540
gtctcaattt aatcaaatga tactctatgc ttatctaatt ttcaagagaa taatttgctg  600
tgtgctccca gatatcttgg tggagcgttt gatgtggagt cacttgtgga gaatttgctg  660
agcaaacttg ctggcaatca ggatattgtg gtgaatgtct atgatgtcac aaatgcttca  720
gaggctatgg ttttgtatgg accttctagt tcgg                            754

SEQ ID NO: 193         moltype = DNA  length = 223
FEATURE                Location/Qualifiers
source                 1..223
                       mol_type = genomic DNA
                       organism = Zea mays
SEQUENCE: 193
tcaacaagat gtcttcttct gattcttgca atttatagca tattattgtc cagtattcta  60
ttttggctta ataattaatg tccgacacag gacacttttg caaaatacac ggcaaggaca  120
tcatttgagc gaccgctact caatggggtg gcatatgcac agcgtgtatt ccatcatgag  180
agggaaatgt ttgaaagcca gcagggatgg attatgaata caa                  223

SEQ ID NO: 194         moltype = DNA  length = 223
FEATURE                Location/Qualifiers
source                 1..223
                       mol_type = genomic DNA
                       organism = Zea mays
SEQUENCE: 194
ctctttagtg aaagcaatct atttatttac gatacaggag gaccgagaaa acattttgcg  60
ggccaggact actggcaaag ctgtgttaac aaacccattt cggttgcttg gatcaaacca  120
cttgggagta gttctcactt ttgctgtgta ccgccctgat ctccccgctg atgcatcagt  180
tgagcaacgt gtggaagcaa ctattgggtg agatgttcta act                  223

SEQ ID NO: 195         moltype = DNA  length = 223
```

```
FEATURE                Location/Qualifiers
source                 1..223
                       mol_type = genomic DNA
                       organism = Zea mays
SEQUENCE: 195
ttgcagcttg tctcaattta atcaaatgat actctatgct tatctaattt tcaagagaat  60
aatttgctgt gtgctcccag atatcttggt ggagcgtttg atgtggagtc acttgtggag  120
aatttgctga gcaaacttgc tggcaatcag gatattgtgg tgaatgtcta tgatgtcaca  180
aatgcttcag aggctatggt tttgtatgga ccttctagtt cgg                    223

SEQ ID NO: 196         moltype = DNA  length = 144
FEATURE                Location/Qualifiers
source                 1..144
                       mol_type = genomic DNA
                       organism = Zea mays
SEQUENCE: 196
tattattgtc cagtattcta ttttggctta ataattaatg tccgacacag gacacttttg  60
caaaatacac ggcaaggaca tcatttgagc gaccgctact caatggggtg gcatatgcac  120
agcgtgtatt ccatcatgag aggg                                         144

SEQ ID NO: 197         moltype = DNA  length = 104
FEATURE                Location/Qualifiers
source                 1..104
                       mol_type = genomic DNA
                       organism = Zea mays
SEQUENCE: 197
ttttggctta ataattaatg tccgacacag gacacttttg caaaatacac ggcaaggaca  60
tcatttgagc gaccgctact caatggggtg gcatatgcac agcg                   104

SEQ ID NO: 198         moltype = DNA  length = 63
FEATURE                Location/Qualifiers
source                 1..63
                       mol_type = genomic DNA
                       organism = Zea mays
SEQUENCE: 198
tccgacacag gacacttttg caaaatacac ggcaaggaca tcatttgagc gaccgctact  60
caa                                                                63

SEQ ID NO: 199         moltype = DNA  length = 143
FEATURE                Location/Qualifiers
source                 1..143
                       mol_type = genomic DNA
                       organism = Zea mays
SEQUENCE: 199
gaccgagaaa acattttgcg ggccaggact actggcaaag ctgtgttaac aaacccattt  60
cggttgcttg gatcaaacca cttgggagta gttctcactt ttgctgtgta ccgccctgat  120
ctccccgctg atgcatcagt tga                                          143

SEQ ID NO: 200         moltype = DNA  length = 103
FEATURE                Location/Qualifiers
source                 1..103
                       mol_type = genomic DNA
                       organism = Zea mays
SEQUENCE: 200
ggccaggact actggcaaag ctgtgttaac aaacccattt cggttgcttg gatcaaacca  60
cttgggagta gttctcactt ttgctgtgta ccgccctgat ctc                    103

SEQ ID NO: 201         moltype = DNA  length = 63
FEATURE                Location/Qualifiers
source                 1..63
                       mol_type = genomic DNA
                       organism = Zea mays
SEQUENCE: 201
ctgtgttaac aaacccattt cggttgcttg gatcaaacca cttgggagta gttctcactt  60
ttg                                                                63

SEQ ID NO: 202         moltype = DNA  length = 143
FEATURE                Location/Qualifiers
source                 1..143
                       mol_type = genomic DNA
                       organism = Zea mays
SEQUENCE: 202
tatctaattt tcaagagaat aatttgctgt gtgctcccag atatcttggt ggagcgtttg  60
atgtggagtc acttgtggag aatttgctga gcaaacttgc tggcaatcag gatattgtgg  120
tgaatgtcta tgatgtcaca aat                                          143

SEQ ID NO: 203         moltype = DNA  length = 103
FEATURE                Location/Qualifiers
source                 1..103
```

```
                        mol_type = genomic DNA
                        organism = Zea mays
SEQUENCE: 203
aatttgctgt gtgctcccag atatcttggt ggagcgtttg atgtggagtc acttgtggag  60
aatttgctga gcaaacttgc tggcaatcag gatattgtgg tga                    103

SEQ ID NO: 204          moltype = DNA  length = 62
FEATURE                 Location/Qualifiers
source                  1..62
                        mol_type = genomic DNA
                        organism = Zea mays
SEQUENCE: 204
tatcttggtg gagcgtttga tgtggagtca cttgtggaga atttgctgag caaacttgct  60
gg                                                                 62

SEQ ID NO: 205          moltype = DNA  length = 543
FEATURE                 Location/Qualifiers
source                  1..543
                        mol_type = genomic DNA
                        organism = Zea mays
SEQUENCE: 205
atggggggca acaagtactg cgcggcgatg acgaagagga gatggagggg gctggcagcg  60
gccgcgtggg tgctagtcgc ggtggcttgc tccgcggtga tgcactggac catgcgccgg  120
gagagcatgg accgcgccga ggagcgcctc gtcagcatgt gcgaggagag ggccaggatg  180
ctgcaggagc agttcggggt caccgtcaac cacgtccacg cgatcgccat tctcatcgcc  240
accttcaact acgataagtc cccttccgct atcgaccagg aggaccgaga aaacattttg  300
cgggccagga ctactggcaa agctgtgtta acaaacccat ttcggttgct tggatcaaac  360
cacttgggag tagttctcac ttttgctgtg taccgccctg atctccccgc tgatgcatca  420
gttgagcaac gtgtggaagc aactattgga tatcttggtg gagcgtttga tgtggagtca  480
cttgtggaga atttgctgag caaacttgct ggcaatcagg atattgtggt gaatgtctat  540
gat                                                                543

SEQ ID NO: 206          moltype = DNA  length = 279
FEATURE                 Location/Qualifiers
source                  1..279
                        mol_type = genomic DNA
                        organism = Zea mays
SEQUENCE: 206
tccgctatcg accaggagga ccgagaaaac attttgcggg ccaggactac tggcaaagct  60
gtgttaacaa acccatttcg gttgcttgga tcaaaccact tgggagtagt tctcactttt  120
gctgtgtacc gccctgatct ccccgctgat gcatcagttg agcaacgtgt ggaagcaact  180
attggatatc ttggtggagc gtttgatgtg gagtcacttg tggagaattt gctgagcaaa  240
cttgctggca atcaggatat tgtggtgaat gtctatgat                         279

SEQ ID NO: 207          moltype = AA  length = 181
FEATURE                 Location/Qualifiers
source                  1..181
                        mol_type = protein
                        organism = Zea mays
SEQUENCE: 207
MGGNKYCAAM TKRRWRGLAA AAWVLVAVAC SAVMHWTMRR ESMDRAEERL VSMCEERARM  60
LQEQFGVTVN HVHAIAILIA TFNYDKSPSA IDQEDRENIL RARTTGKAVL TNPFRLLGSN  120
HLGVVLTFAV YRPDLPADAS VEQRVEATIG YLGGAFDVES LVENLLSKLA GNQDIVVNVY  180
D                                                                  181

SEQ ID NO: 208          moltype = AA  length = 93
FEATURE                 Location/Qualifiers
source                  1..93
                        mol_type = protein
                        organism = Zea mays
SEQUENCE: 208
SAIDQEDREN ILRARTTGKA VLTNPFRLLG SNHLGVVLTF AVYRPDLPAD ASVEQRVEAT  60
IGYLGGAFDV ESLVENLLSK LAGNQDIVVN VYD                               93

SEQ ID NO: 209          moltype = AA  length = 32
FEATURE                 Location/Qualifiers
source                  1..32
                        mol_type = protein
                        organism = Zea mays
SEQUENCE: 209
VEATIGYLGG AFDVESLVEN LLSKLAGNQD IV                                32

SEQ ID NO: 210          moltype = AA  length = 22
FEATURE                 Location/Qualifiers
source                  1..22
                        mol_type = protein
                        organism = Zea mays
SEQUENCE: 210
GYLGGAFDVE SLVENLLSKL AG                                           22
```

```
SEQ ID NO: 211          moltype = AA  length = 12
FEATURE                 Location/Qualifiers
source                  1..12
                        mol_type = protein
                        organism = Zea mays
SEQUENCE: 211
AFDVESLVEN LL                                                     12

SEQ ID NO: 212          moltype = DNA  length = 7969
FEATURE                 Location/Qualifiers
source                  1..7969
                        mol_type = genomic DNA
                        organism = Glycine max
SEQUENCE: 212
tttgagtgga tagtttggaa agagataatg gcctataata atattttgaa aacatttgtg  60
ctgtgctacc gtattattct tatcatcttt gcctttccaa attctcctac tacctgaact  120
cgatgaacaa caactcattg ctttaaagct cttttcagct tcattctcca tgttcaagtg  180
accttttttt tacagtgtgc agctagcttc taagaaaaaa taaaaatctc tagaacacac  240
tcacgtgctt gtgttgttct tgtttggttc tagggccatg aagtgcgagc tagtagattt  300
tctttgctga gtgatagtga aaatcgaatc ttttgtaggt ttagttttga cccttccttt  360
ttgttctgcg ccttggttgg tagctgctgc tagctgacaa gataataagg agtatcaatt  420
tctgtttagc attagaaacc cagaatcttg tgattctttt attctttaaa gggtatttga  480
atttttctta tctgcctcta gtttcagtgt tcattttgca tttctgaatt ttaagctatt  540
ggggtggata agacagcatc ttatcaaggt cacatctctt attattattt ttattgaaga  600
tgtctttttt atttttcctt ccccttcaac ctacttgttt ttaggaattg ggtttctgtt  660
gttgttgttg ttcatcaaaa tctcgaattt tcttcaatca caagcctaaa aaacaaatct  720
tttagtgaat aggtgtgtgt tagccttgtg gggattctgt ggatttgaca gcggttctct  780
cctctcctct ctctctgtct ctgtctcggt ctctgtctct ctctctctct ctcacacaca  840
cacacaagcc tgcctggaat cagttagagt tgacacccgc aacctgtttg aactgtttct  900
ttttaacctg tgttggttac tgttgtggat gagtttgctc catgtagttg ggtttgctct  960
aaaagtgggg catctacttt tggtgctatg ttgctgggtt gtgtctgtcg tttaccttaa  1020
ctggtttatt agcagtggaa ttatggaaac caagatgatg ggtggtggtg gtggtggcgg  1080
tggcaagatg tggcacaaaa aatggtggga gaatatatca gggcagggtt gcaaaatcca  1140
ccaacagtac taccagtata ttggctctaa gaaagttaag agagcgttgt ggaggaagat  1200
tttgctgaca tgggtcgtgg gttggttcat agtatctttg tggatcttca gctacatgag  1260
cttgcaaggt actgagaaga ggaaagaaac tctcgcaagc atgtgtgatg aaagggctag  1320
gatgctgcag gatcagttta acgtcagtat gaaccatatc caagccatgt ccattctgat  1380
ctccaccttt caccatgcta agagccccctc agccatcgat caggtactag tctttacttt  1440
gttattgcaa atcaggacct aattcctcac cttttgcttt tagtctttgt ttgtgttacc  1500
ttaatttcta tacacatagg tttctgagtt gtttcattgt cattaatttt agtgtctaat  1560
agcattattc ccccctttt tgtggaaaat ttattgggat tttagtatta tatgttttgc  1620
taacaaggtt actgaacttg agctgctgga acatgacctg atttccttgt ttccccacct  1680
tcttgttgga tagaaaagat cccactttct tttatccttc aatctttagt ctcatctcta  1740
caaattaatc taacttccaa aactcgcaga aaacttttgc aaagtacaca gaaagaacag  1800
cttttgagag gcctcttaca agtggtgttg cgtatgctgt aagggtgctc cattctgaaa  1860
gggaacaatt tgaaaagcag caaggttgga ctatcaagag gatggatact ctagagcaga  1920
acccggttca taaggatgat tatgccccag aggcattgga gccatccccc gttcaggaag  1980
aatatgctcc tgtcatcttt gcacaggata caattgcaca tgtgatttct gttaatgtgc  2040
tttctggaaa ggtaggtttc tgatacttgc aaaattttat ttatggagct agtctgagcc  2100
atatattgtt aattatgaaa attgtgaaaa tgctatacaa taaactttga tgtcttgatc  2160
ataattttaa ttcatccatt ctaagctctt tattcctggt agtatggttt ttgactggtc  2220
ttttagtggt cattaatttt gttttgggag aatatttatg aagaaaaaac tatctatgct  2280
accatttgt accttgttc ttcctttgtc ttgcttgtcc tgatgggact gctcctgatg  2340
gagaatagta cacgtgaata gattctaatt ttgtgaatat cacaaagctg aattgagtca  2400
cgttgttcat gtttgatatc tgaaatctat ggcaatttat ttggaattat gattgtcaca  2460
gttattcact tgttcatcaa caggaagacc gtgaaaatgt gctgcgtgca agagaatcag  2520
gcaaaggcgt tttaactgcg cccttcaggc tgctcaaaac aaataggcta ggggttatcc  2580
tgacatttgc tgtctacaag agagatcttc catcaaatgc aaccccaaat gaaaggattc  2640
aagcaactga cgggtgtgcc taaattttga ttttttatg attttttatc attcatataa  2700
tttagcttat tccctttgg tcatctaaag ctttgaagta actagtctac taaataagta  2760
attgatgcat tcaaatttc agagagaaga ttatgaactc tattaatgta agaagggtga  2820
acaattattg gttcttccct gtgataatta gaagttttga agttacaaat ctacttttaa  2880
attcaataaa actgatggta aaaagaaaaa gaaatcatga acacagttaa agagagtagc  2940
atttttatgt cttcactact gcttgctggg caggtatctt gggggagtct ttgatgttga  3000
gtcattagtg gagaaattac ttcagcaact tgctagcaag caaagtgtaa ttgttaatgt  3060
gtatgatact acaaatcaca ctcatccaat tgccatgtat ggctcaaatg aatcagggga  3120
tgttttcttt cacgtcagca ctcttaactt tggagaccct tttaggaagc atgagatgca  3180
ctgcaggtaa gagttatgct acagaagaag tctaatattt ccgtcctcct taatgctctg  3240
tgtagtttgt aagaataaca gtgtgccaac ttgaaatagg tagaggatat attaaataca  3300
aggtgtatta atgtcatatg acttaatact tcacaatcta gtggttttgc tgctagcaat  3360
acctagtcta gagttctttt atctggagtt gtcatatttt ttagggtcat tgaatctaag  3420
tatttttatt ttaatatatt tcaattataa tgttcaaaat tgtcaaaaga cttgaactat  3480
tcatgaaaat taagcttgat gctaatgcag gttcaagcag aagccaccat ggccatgggt  3540
ggcaataact acttcaattg gtatccttgt tattgcactc cttgttggac atattttcca  3600
tgccactgtg aatcgaattg ccgaagtaga agatgattat cgtaaggaga tggaacttaa  3660
aaaacaagct gaggcggcag atgttgcaaa atcccaggta tgtaacttta tttatttatt  3720
tatttatttt gaacttgttt tggcttaact cacactgatc atgtgggctt tatcaattgt  3780
aaccacagtt tcttgctact gtttcccatg aaatcagaac accaatgaat ggtgttttag  3840
```

```
gtgagttgtc ttctgtctat ggtttagtcg attatccaat ttttaatttt taactatata  3900
cattccacaa aaaagaagag cttcttcagc catgaccctg ctctaaattg gattttcagg  3960
gatgttgcat atgcttatgg acacagatct agatgtcacc caacaggaat atgtcaggac  4020
agcacaggaa agtggaaaag ctctggtgtc acttataaac gaggttttgg atcaggctaa  4080
gattgaattt ggtaagctag agcttgaggc tgtgctcttc gacatacggg caattttgga  4140
tgatgtattg tcactatttt ctgagaagtc tcaaggaaaa ggagtagagg taatatatct  4200
ctcgtctact gttgcctttt tatcatgatg gaattttcaa aatgtgcata gtctaactat  4260
agttaatggc tcttcataat attttttgg gaactgcagt tggcagttta tgtgtcagat  4320
catgttccag aactactaat aggtgatcct ggaagatttc gacaaataat taccaatctc  4380
atgggtaact caattaaggt aagtttatgg tagagagaag aacattatgt ataattcaag  4440
ttatttagtc tgatatcctt catataagtt acttggagat gttcccttgt cctacatcct  4500
tgccttatag gcatgctacg gtcatcatag tctcatgaaa aaaaaattct atttactgtt  4560
ctagccaagc atatgactac tagtagagca aaattgatgt gtatttcttg aaaatattat  4620
taaaactgat tttgtaattg tttggcagtt cacggacaaa ggacatattt ttgtcacaat  4680
ccatcttgtt gaggaggttg tccgttcaat agaggttgac aaagaatcca actcagaaaa  4740
taccttgagt ggttcccctg ttgctgatag tcgccggagc tgggaaggat tcaaggcttt  4800
cagtcaagag ggacctcttg gttccttctc atccccctcc agtgatcttg tcaatttgat  4860
tgtatctgtt gaggatacag gtgaaggtat tcctcttgaa tctcagccac tcatctacac  4920
cccattcatg caggtaggtc catccatctc ccgaaagcat ggaggaacag gaattggcct  4980
aagcattagt aagtgtttgg ttggcctcat gaatggggaa attggatttg tgagtatacc  5040
caagactgga tccacattca cttttacagc tgtattcacc aatggacact gcagttcaaa  5100
tgagtgtaaa gttcagcaaa tcaacaacca acctcactct gcatcttcag aattcgaggg  5160
gatgactgca ttaattattg acccaagatc tgttagagca aaagtgtcta gatatcacat  5220
ccaacggctt ggcattcatg ttgagatggt ttcagattta aaacaaggtt tgtcaaccat  5280
aagcaatggg aatataatta ttaatatggt tttgattgag caggaggttt gggatagaga  5340
tttaggcttg tcatctcatt ttgtcaataa cacaaggaga attgatcagg gggttcctcc  5400
aaagctgttc attcttgtta attctagtag ttcttttaaa gctagtgtaa acttgggtgt  5460
tcataatcct attgtcatca ccaaacctct gagagcgagt atgcttgctg cctcactaca  5520
acgagccatg ggtgtccaaa ataagggagc tcctcataga gagctccaaa gtttgtctct  5580
tcgccatctt cttcgtggca ggaaaattct aattgtagat gacaatagtg tgaaccgtgc  5640
agtagcagct ggtgcattga aaaagtatgg agcagatgtg gtttgtgtta gtagtggtaa  5700
agatgccatc tcttccttga agccacccca tcagtttgat gcctgtttca tggatattca  5760
aatgccagaa atggatgggt atgtatgcac ctggagtact ttctttcaga atctgataat  5820
ttatcatttt ggagtaatat ttggaatttc tacaaacata gaaaagagtt tttagttctt  5880
ttattgatct aacagaataa ttgaaaatat tttactgaac agtttacatc aaaggaaaac  5940
tttttgcact gcaaagattt gtgaaacaaa ctaatgtata ttaagcacac aaggtgtttg  6000
gagtctaact tgctacagca atactataac tatgattcat ttgacaattc tacaacaaca  6060
atggccttgt ctcatgaagt gaggttgaat acatgtatca aatgatgcca ttgagctttg  6120
ttaaaaacca aattctaagg gatgttattt accataaaat ctcttttaat aatttccttt  6180
aatgtccttt ttggtctcct atccttttca caaggctaaa aaccatgcaa tgtactcttg  6240
tcattgtgcc tctaatgacc ttttttacat gtgtccaagc catcttagtc gatttttgt   6300
catcttgata ggtgttatac cagtatacca gtatctccta gtatacaatc attctatatc  6360
ttgtactttc ttgtgtagtc acacatccat cttcacatac tcattctata tcttatttct  6420
tactaaaatt gcaatgcata tattgtttta ctcctactga atctagtgtt tgtctccaaa  6480
actaaacttt atggttaact ttttcccttg attccctgat tttaagttat atcattcgca  6540
aaaagtatgc atttagtgat aaacatttgg gctattttcg ggtaacgact tagcattggc  6600
acacaatcca tcgctagtga tccacgtttg ggctttcaaa gttttatgtt gattgtcaag  6660
ggactatcca gcctttggaa ccagctatga gcccatacgt ggagtcaatt catttgacaa  6720
ttctaattaa aaaattattt gaagaattta cttatctact ttttatttct aaatcaagaa  6780
ttatcattgt gttacgattt tgctaataac aattcttttc caacagattt gaagctacaa  6840
agcgagttag ggagatggaa gatagtgtga acagagaagt atctatggat gactttgaga  6900
atattacaaa ctggcatgta cccattttag ccatgactgc agatgtgata catgctacac  6960
acgaggaatg cctaaagtgg ggcatggatg gatatgtttc aaaacccttt gaagctgaac  7020
agctgtatag agaagtctca cggtttttcc agtcatcttg aaaagaaaat acagtgctga  7080
tctaaaccag ataaactgat aatggaagca tagctgtttg tactccagga cactctgaag  7140
tgggtaaata ggttcagaag tctcctgaga gtaagttccc tatttaacag ccagtgcatg  7200
ttttagtatt tcaccacctc aaagtttggg ggttgttcac tagagactga agaatgttta  7260
tctatctcat ctgaaaggaa aaagaaaatg gaacaaaggg ggacaatatt gtagaagttc  7320
agaaatggtt cattctacct ttttgaccta ttttgttgtc ttttctgctg tgtgtgaagg  7380
tccctggttt aaaactttgt ttttgtggca gggagtgtac gtaggagcaa agtttgattg  7440
gttgcaattg agttgtaatt ggttgttaag ggtagcaaaa cccatattaa ttcttcttcc  7500
ttgtaaactc agcctctctt ctcattcgaa atgattgagg ctgattggaa gattagggtg  7560
tattataata caggttctgg agtctcctcc ttgtgtatgt aataatacaa cttatagtga  7620
tctagcctag gcacgttaca ttttatgtgt attgatgcat gtatcacaag ggcttgattc  7680
aggtgaaagg aagaaaatta gcttcttggc atcaaaggaa gctagcccat catcaatctt  7740
tgtatatgac tcacaataaa gatggtgatt gatgtatcac accaagcttg cttccttttg  7800
ttcttaacag tgctggaatt cggcttgcaa acatgtaact gatacattat actctagtgt  7860
ttgagtgatc caccattttt ttggcctatt tgtacatttc caatttctgg atttcctttg  7920
actcattgct cttgccttgc acatctcatg aaattattcc ttttatttt              7969

SEQ ID NO: 213          moltype = DNA  length = 4929
FEATURE                 Location/Qualifiers
source                  1..4929
                        mol_type = other DNA
                        organism = Glycine max
SEQUENCE: 213
tttgagtgga tagtttggaa agagataatg gcctataata atattttgaa aacatttgtg  60
ctgtgctacc gtattattct tatcatcttt gcctttccaa attctcctac tacctgaact  120
cgatgaacaa caactcattg ctttaaagct cttttcagct tcattctcca tgttcaagtg  180
```

acctttttttt tacagtgtgc agctagcttc taagaaaaaa taaaaatctc tagaacacac 240
tcacgtgctt gtgttgttct tgtttggttc tagggccatg aagtgcgagc tagtagattt 300
tctttgctga gtgatagtga aaatcgaatc ttttgtaggt ttagttttga cccttccttt 360
ttgttctgcg ccttggttgg tagctgctgc tagctgacaa gataataagg agtatcaatt 420
tctgtttagc attagaaacc cagaatcttg tgattctttt attctttaaa gggtatttga 480
atttttctta tctgcctcta gtttcagtgt tcattttgca tttctgaatt ttaagctatt 540
ggggtggata agacagcatc ttatcaaggt cacatctctt attattattt ttattgaaga 600
tgtcttttttt attttccttt ccccttcaac ctacttgttt ttaggaattg ggtttctgtt 660
gttgttgttg ttcatcaaaa tctcgaattt tcttcaatca caagcctaaa aaacaaatct 720
tttagtgaat aggtgtgtgt tagccttgtg gggattctgt ggatttgaca gcggttctct 780
cctctcctct ctctctgtct ctgtctcggt ctctgtctct ctctctctct ctcacacaca 840
cacacaagcc tgcctggaat cagttagagt tgacacccgc aacctgtttg aactgtttct 900
ttttaacctg tgttggttac tgttgtggat gagtttgctc catgtagttg ggtttgctct 960
aaaagtgggg catctacttt tggtgctatg ttgctgggtt gtgtctgtcg tttaccttaa 1020
ctggtttatt agcagtggaa ttatggaaac caagatgatg ggtggtggtg gtggtggcgg 1080
tggcaagatg tggcacaaaa aatggtggga gaatatatca gggcagggtt gcaaaatcca 1140
ccaacagtac taccagtata ttggctctaa gaaagttaag agagcgttgt ggaggaagat 1200
tttgctgaca tgggtcgtgg gttggttcat agtatctttg tggatcttca gctacatgag 1260
cttgcaaggt actgagaaga ggaaagaaac tctcgcaagc atgtgtgatg aaagggctag 1320
gatgctgcag gatcagttta acgtcagtat gaaccatatc caagccatgt ccattctgat 1380
ctccaccttt caccatgcta agagcccctc agccatcgat cagaaaactt ttgcaaagta 1440
cacagaaaga acagcttttg agaggcctct tacaagtggt gttgcgtatg ctgtaagggt 1500
gctccattct gaaagggaac aatttgaaaa gcagcaaggt tggactatca agaggatgga 1560
tactctagag cagaacccgg ttcataagga tgattatgcc ccagaggcat tggagccatc 1620
ccccgttcag gaagaatatg ctcctgtcat ctttgcacag gatacaattg cacatgtgat 1680
ttctgttaat gtgctttctg gaaaggaaga ccgtgaaaat gtgctgcgtg caagagaatc 1740
aggcaaaggc gttttaactg cgcccttcag gctgctcaaa acaaataggc taggggttat 1800
cctgacattt gctgtctaca agagagatct tccatcaaat gcaaccccaa atgaaaggat 1860
tcaagcaact gacgggtatc ttgggggagt ctttgatgtt gagtcattag tggagaaatt 1920
acttcagcaa cttgctagca agcaaagtgt aattgttaat gtgtatgata ctacaaatca 1980
cactcatcca attgccatgt atggctcaaa tgaatcaggg gatgttttct ttcacgtcag 2040
cactcttaac tttggagacc cttttaggaa gcatgagatg cactgcaggt tcaagcagaa 2100
gccaccatgg ccatgggtgg caataactac ttcaattggt atccttgtta ttgcactcct 2160
tgttggacat attttccatg ccactgtgaa tcgaattgcc gaagtagaag atgattatcg 2220
taaggagatg gaacttaaaa aacaagctga ggcggcagat gttgcaaaat cccagtttct 2280
tgctactgtt tcccatgaaa tcagaacacc aatgaatggt gttttaggga tgttgcatat 2340
gcttatggac acagatctag atgtcaccca acaggaatat gtcaggacag cacaggaaag 2400
tggaaaagct ctggtgtcac ttataaacga ggttttggat caggctaaga ttgaatttgg 2460
taagctagag cttgaggctg tgctcttcga catacgggca attttggatg atgtattgtc 2520
actattttct gagaagtctc aaggaaaagg agtagagttg gcagtttatg tgtcagatca 2580
tgttccagaa ctactaatag gtgatcctgg aagatttcga caaataatta ccaatctcat 2640
gggtaactca attaagttca cggacaaagg acatattttt gtcacaatcc atcttgttga 2700
ggaggttgtc cgttcaatag aggttgacaa agaatccaac tcagaaaata ccttgagtgg 2760
ttcccctgtt gctgatagtc gccggagctg ggaaggattc aaggctttca gtcaagaggg 2820
acctcttggt tccttctcat ccccctccag tgatcttgtc aatttgattg tatctgttga 2880
ggatacaggt gaaggtattc ctcttgaatc tcagccactc atctacaccc cattcatgca 2940
ggtaggtcca tccatctccc gaaagcatgg aggaacagga attggcctaa gcattagtaa 3000
gtgtttggtt ggcctcatga atggggaaat tggatttgtg agtataccca agactggatc 3060
cacattcact tttacagctg tattcaccaa tggacactgc agttcaaatg agtgtaaagt 3120
tcagcaaatc aacaaccaac ctcactctgc atcttcagaa ttcgagggga tgactgcatt 3180
aattattgac ccaagatctg ttagagcaaa agtgtctaga tatcacatcc aacggcttgg 3240
cattcatgtt gagatggttt cagatttaaa acaaggtttg tcaaccataa gcaatgggaa 3300
tataattatt aatatggttt tgattgagca ggaggtttgg gatagagatt taggcttgtc 3360
atctcatttt gtcaataaca caaggagaat tgatcagggg gttcctccaa agctgttcat 3420
tcttgttaat tctagtagtt cttttaaagc tagtgtaaac ttgggtgttc ataatcctat 3480
tgtcatcacc aaacctctga gagcgagtat gcttgctgcc tcactacaac gagccatggg 3540
tgtccaaaat aagggagctc ctcatagaga gctccaaagt ttgtctcttc gccatcttct 3600
tcgtggcagg aaaattctaa ttgtagatga caatagtgtg aaccgtgcag tagcagctgg 3660
tgcattgaaa aagtatggag cagatgtggt ttgtgttagt agtggtaaag atgccatctc 3720
ttccttgaag ccaccccatc agtttgatgc ctgtttcatg gatattcaaa tgccagaaat 3780
ggatggattt gaagctacaa agcgagttag ggagatggaa gatagtgtga acagagaagt 3840
atctatggat gactttgaga atattacaaa ctggcatgta cccattttag ccatgactgc 3900
agatgtgata catgctacac acgaggaatg cctaaagtgg ggcatggatg gatatgtttc 3960
aaaacccttt gaagctgaac agctgtatag agaagtctca cggtttttcc agtcatcttg 4020
aaaagaaaat acagtgctga tctaaaccag ataaactgat aatggaagca tagctgtttg 4080
tactccagga cactctgaag tgggtaaata ggttcagaag tctcctgaga gtaagttccc 4140
tatttaacag ccagtgcatg ttttagtatt tcaccacctc aaagtttggg ggttgttcac 4200
tagagactga agaatgttta tctatctcat ctgaaaggaa aaagaaaatg gaacaaaggg 4260
ggacaatatt gtagaagttc agaaatggtt cattctacct ttttgaccta ttttgttgtc 4320
ttttctgctg tgtgtgaagg tccctggttt aaaactttgt ttttgtggca gggagtgtac 4380
gtaggagcaa agtttgattg gttgcaattg agttgtaatt ggttgttaag ggtagcaaaa 4440
cccatattaa ttcttcttcc ttgtaaactc agcctctctt ctcattcgaa atgattgagg 4500
ctgattggaa gattagggtg tattataata caggttctgg agtctcctcc ttgtgtatgt 4560
aataatacaa cttatagtga tctagcctag gcacgttaca ttttatgtgt attgatgcat 4620
gtatcacaag ggcttgattc aggtgaaagg aagaaaatta gcttcttggc atcaaaggaa 4680
gctagcccat catcaatctt tgtatatgac tcacaataaa gatggtgatt gatgtatcac 4740
accaagcttg cttcctttttg ttcttaacag tgctggaatt cggcttgcaa acatgtaact 4800
gatacattat actctagtgt ttgagtgatc caccattttt ttggcctatt tgtacatttc 4860
caatttctgg atttcctttg actcattgct cttgccttgc acatctcatg aaattattcc 4920

```
ttttatttt                                                         4929

SEQ ID NO: 214          moltype = AA  length = 1030
FEATURE                 Location/Qualifiers
source                  1..1030
                        mol_type = protein
                        organism = Glycine max
SEQUENCE: 214
MSLLHVVGFA LKVGHLLLVL CCWVVSVVYL NWFISSGIME TKMMGGGGGG GGKMWHKKWW  60
ENISGQGCKI HQQYYQYIGS KKVKRALWRK ILLTWVVGWF IVSLWIFSYM SLQGTEKRKE  120
TLASMCDERA RMLQDQFNVS MNHIQAMSIL ISTFHHAKSP SAIDQKTFAK YTERTAFERP  180
LTSGVAYAVR VLHSEREQFE KQQGWTIKRM DTLEQNPVHK DDYAPEALEP SPVQEEYAPV  240
IFAQDTIAHV ISVNVLSGKE DRENVLRARE SGKGVLTAPF RLLKTNRLGV ILTFAVYKRD  300
LPSNATPNER IQATDGYLGG VFDVESLVEK LLQQLASKQS VIVNVYDTTN HTHPIAMYGS  360
NESGDVFFHV STLNFGDPFR KHEMHCRFKQ KPPWPWVAIT TSIGILVIAL LVGHIFHATV  420
NRIAEVEDDY RKEMELKKQA EAADVAKSQF LATVSHEIRT PMNGVLGMLH MLMDTDLDVT  480
QQEYVRTAQE SGKALVSLIN EVLDQAKIEF GKLELEAVLF DIRAILDDVL SLFSEKSQGK  540
GVELAVYVSD HVPELLIGDP GRFRQIITNL MGNSIKFTDK GHIFVTIHLV EEVVRSIEVD  600
KESNSENTLS GSPVADSRRS WEGFKAFSQE GPLGSFSSPS SDLVNLIVSV EDTGEGIPLE  660
SQPLIYTPFM QVGPSISRKH GGTGIGLSIS KCLVGLMNGE IGFVSIPKTG STFTFTAVFT  720
NGHCSSNECK VQQINNQPHS ASSEFEGMTA LIIDPRSVRA KVSRYHIQRL GIHVEMVSDL  780
KQGLSTISNG NIIINMVLIE QEVWDRDLGL SSHFVNNTRR IDQGVPPKLF ILVNSSSSFK  840
ASVNLGVHNP IVITKPLRAS MLAASLQRAM GVQNKGAPHR ELQSLSLRHL LRGRKILIVD  900
DNSVNRAVAA GALKKYGADV VCVSSGKDAI SSLKPPHQFD ACFMDIQMPE MDGFEATKRV  960
REMEDSVNRE VSMDDFENIT NWHVPILAMT ADVIHATHEE CLKWGMDGYV SKPFEAEQLY  1020
REVSRFFQSS                                                        1030

SEQ ID NO: 215          moltype = DNA  length = 223
FEATURE                 Location/Qualifiers
source                  1..223
                        mol_type = genomic DNA
                        organism = Glycine max
SEQUENCE: 215
ttcttgttgg atagaaaaga tcccactttc ttttatcctt caatctttag tctcatctct  60
acaaattaat ctaacttcca aaactcgcag aaaacttttg caaagtacac agaaagaaca  120
gcttttgaga ggcctcttac aagtggtgtt gcgtatgctg taagggtgct ccattctgaa  180
agggaacaat ttgaaaagca gcaaggttgg actatcaaga gga                    223

SEQ ID NO: 216          moltype = DNA  length = 143
FEATURE                 Location/Qualifiers
source                  1..143
                        mol_type = genomic DNA
                        organism = Glycine max
SEQUENCE: 216
caatctttag tctcatctct acaaattaat ctaacttcca aaactcgcag aaaacttttg  60
caaagtacac agaaagaaca gcttttgaga ggcctcttac aagtggtgtt gcgtatgctg  120
taagggtgct ccattctgaa agg                                          143

SEQ ID NO: 217          moltype = DNA  length = 103
FEATURE                 Location/Qualifiers
source                  1..103
                        mol_type = genomic DNA
                        organism = Glycine max
SEQUENCE: 217
acaaattaat ctaacttcca aaactcgcag aaaacttttg caaagtacac agaaagaaca  60
gcttttgaga ggcctcttac aagtggtgtt gcgtatgctg taa                    103

SEQ ID NO: 218          moltype = DNA  length = 63
FEATURE                 Location/Qualifiers
source                  1..63
                        mol_type = genomic DNA
                        organism = Glycine max
SEQUENCE: 218
aaactcgcag aaaacttttg caaagtacac agaaagaaca gcttttgaga ggcctcttac  60
aag                                                                63

SEQ ID NO: 219          moltype = DNA  length = 223
FEATURE                 Location/Qualifiers
source                  1..223
                        mol_type = genomic DNA
                        organism = Glycine max
SEQUENCE: 219
aactgatggt aaaaagaaaa agaaatcatg aacacagtta aagagagtag catttttatg  60
tcttcactac tgcttgctgg gcaggtatct tgggggagtc tttgatgttg agtcattagt  120
ggagaaatta cttcagcaac ttgctagcaa gcaaagtgta attgttaatg tgtatgatac  180
tacaaatcac actcatccaa ttgccatgta tggctcaaat gaa                    223

SEQ ID NO: 220          moltype = DNA  length = 143
FEATURE                 Location/Qualifiers
```

```
source                  1..143
                        mol_type = genomic DNA
                        organism = Glycine max
SEQUENCE: 220
aagagagtag catttttatg tcttcactac tgcttgctgg gcaggtatct tgggggagtc  60
tttgatgttg agtcattagt ggagaaatta cttcagcaac ttgctagcaa gcaaagtgta  120
attgttaatg tgtatgatac tac                                          143

SEQ ID NO: 221          moltype = DNA  length = 103
FEATURE                 Location/Qualifiers
source                  1..103
                        mol_type = genomic DNA
                        organism = Glycine max
SEQUENCE: 221
tcttcactac tgcttgctgg gcaggtatct tgggggagtc tttgatgttg agtcattagt  60
ggagaaatta cttcagcaac ttgctagcaa gcaaagtgta att                    103

SEQ ID NO: 222          moltype = DNA  length = 63
FEATURE                 Location/Qualifiers
source                  1..63
                        mol_type = genomic DNA
                        organism = Glycine max
SEQUENCE: 222
gcaggtatct tgggggagtc tttgatgttg agtcattagt ggagaaatta cttcagcaac  60
ttg                                                                63

SEQ ID NO: 223          moltype = DNA  length = 23
FEATURE                 Location/Qualifiers
source                  1..23
                        mol_type = other DNA
                        organism = synthetic construct
SEQUENCE: 223
atccatccat tctaagcttt tta                                          23

SEQ ID NO: 224          moltype = DNA  length = 20
FEATURE                 Location/Qualifiers
source                  1..20
                        mol_type = other DNA
                        organism = synthetic construct
SEQUENCE: 224
atccatccat tctaagcttt                                              20

SEQ ID NO: 225          moltype = DNA  length = 23
FEATURE                 Location/Qualifiers
source                  1..23
                        mol_type = other DNA
                        organism = synthetic construct
SEQUENCE: 225
ggggagtctt tgatgttgag tca                                          23

SEQ ID NO: 226          moltype = DNA  length = 23
FEATURE                 Location/Qualifiers
source                  1..23
                        mol_type = other DNA
                        organism = synthetic construct
SEQUENCE: 226
ctgaagtaat ttctccacta atg                                          23

SEQ ID NO: 227          moltype = DNA  length = 23
FEATURE                 Location/Qualifiers
source                  1..23
                        mol_type = other DNA
                        organism = synthetic construct
SEQUENCE: 227
atgttgagtc attagtggag aaa                                          23

SEQ ID NO: 228          moltype = DNA  length = 23
FEATURE                 Location/Qualifiers
source                  1..23
                        mol_type = other DNA
                        organism = synthetic construct
SEQUENCE: 228
ctgagtacac tgcccggaca gca                                          23

SEQ ID NO: 229          moltype = DNA  length = 23
FEATURE                 Location/Qualifiers
source                  1..23
                        mol_type = other DNA
                        organism = synthetic construct
```

```
SEQUENCE: 229
tgactagtcc tttcagtctt ttg                                            23

SEQ ID NO: 230         moltype = DNA  length = 21
FEATURE                Location/Qualifiers
source                 1..21
                       mol_type = other DNA
                       organism = synthetic construct
SEQUENCE: 230
tgactagtcc tttcagtctt t                                              21

SEQ ID NO: 231         moltype = DNA  length = 23
FEATURE                Location/Qualifiers
source                 1..23
                       mol_type = other DNA
                       organism = synthetic construct
SEQUENCE: 231
agtcccttgt aaagaattta ctt                                            23

SEQ ID NO: 232         moltype = DNA  length = 23
FEATURE                Location/Qualifiers
source                 1..23
                       mol_type = other DNA
                       organism = synthetic construct
SEQUENCE: 232
cccaagtaaa ttctttacaa ggg                                            23

SEQ ID NO: 233         moltype = DNA  length = 23
FEATURE                Location/Qualifiers
source                 1..23
                       mol_type = other DNA
                       organism = synthetic construct
SEQUENCE: 233
caaagtacac agaaagaaca gct                                            23

SEQ ID NO: 234         moltype = DNA  length = 23
FEATURE                Location/Qualifiers
source                 1..23
                       mol_type = other DNA
                       organism = synthetic construct
SEQUENCE: 234
tccactaatg actcaacatc aaa                                            23

SEQ ID NO: 235         moltype = DNA  length = 22
FEATURE                Location/Qualifiers
source                 1..22
                       mol_type = other DNA
                       organism = synthetic construct
SEQUENCE: 235
caagggactc aacatcaaag ga                                             22

SEQ ID NO: 236         moltype = DNA  length = 23
FEATURE                Location/Qualifiers
source                 1..23
                       mol_type = other DNA
                       organism = synthetic construct
SEQUENCE: 236
cagcaaggac aacatttgaa agg                                            23

SEQ ID NO: 237         moltype = DNA  length = 23
FEATURE                Location/Qualifiers
source                 1..23
                       mol_type = other DNA
                       organism = synthetic construct
SEQUENCE: 237
atgtcccttc tctggttgat aaa                                            23

SEQ ID NO: 238         moltype = DNA  length = 23
FEATURE                Location/Qualifiers
source                 1..23
                       mol_type = other DNA
                       organism = synthetic construct
SEQUENCE: 238
aggacttcac agcaaggaca aca                                            23

SEQ ID NO: 239         moltype = DNA  length = 23
FEATURE                Location/Qualifiers
source                 1..23
                       mol_type = other DNA
```

```
                      organism = synthetic construct
SEQUENCE: 239
ctagcgagtt gttctaggag ttt                                          23

SEQ ID NO: 240        moltype = DNA  length = 23
FEATURE               Location/Qualifiers
source                1..23
                      mol_type = other DNA
                      organism = synthetic construct
SEQUENCE: 240
atgtggagtc acttgtggag aat                                          23

SEQ ID NO: 241        moltype = DNA  length = 23
FEATURE               Location/Qualifiers
source                1..23
                      mol_type = other DNA
                      organism = synthetic construct
SEQUENCE: 241
caagtgactc cacatcaaag gct                                          23

SEQ ID NO: 242        moltype = DNA  length = 23
FEATURE               Location/Qualifiers
source                1..23
                      mol_type = other DNA
                      organism = synthetic construct
SEQUENCE: 242
caaaatacac ggcaaggaca tca                                          23

SEQ ID NO: 243        moltype = DNA  length = 23
FEATURE               Location/Qualifiers
source                1..23
                      mol_type = other DNA
                      organism = synthetic construct
SEQUENCE: 243
aagtggtttg atccaagcaa ccg                                          23

SEQ ID NO: 244        moltype = DNA  length = 7955
FEATURE               Location/Qualifiers
source                1..7955
                      mol_type = other DNA
                      organism = synthetic construct
SEQUENCE: 244
tgacaaatat tgttttttg agtggatagt ttggaaagag ataatggact ataataatgt  60
tgaaaacaat tgtgctatgc taccgtatta ttcttatcat cttgccttgc caaattctcc  120
tactacctga gctcgatgaa caacaactca ttgctttaaa gtccttgcca gcttcattct  180
ccacgttcaa gttaccttct tttttttttt ttacagtgtg cagctagctt ctaagaaata  240
aaagaaatct ttctggaaca cactcacgtg cttgtgttgt tcttgtttga ttctagggcc  300
atgaagtgca agctagaaga ccttctttgc tgagtgatag tgaagatcga atctttttgt  360
aggtttagtt ttggcccttc ctttttgttc tgcgtcttgg ttggtagctg ctgctagcta  420
acaagataat aaggagtatc aatttctgtt ttagaattag aaacccagaa tcttgtgatt  480
cttttattct ttaaagggta tttgaatttt tcttatctgt ctctagtttc agtgttcatt  540
tttgcattta tgaaatttta agctattggg gtggataaga cagcatctta tcaaggtcac  600
atcttctatt attatttcta tttttattat taagatgtct tttttatttt tccttccctt  660
caacctactt gtttttagtt tttgggaatt gggtttgtgt tattgttgtt cttctaaatc  720
ttgaatttcc ttcgatcaca agcctaacat cttttataat gaataggtgt gtgtgtgtta  780
gccttgtggg gattctgtgg atttgacagc ggttctttct tctctctctc taacacaagc  840
ctatacctgg aatcagctag agttgacacc cacaaactgt ttgaactgtg tctttttaac  900
ttgtgttggt tactgttgtg gatgagcttg ctccatgtag ttgggtttgg tcttaaagtg  960
gggcatctac ttttggtgct atgttgctgg gttgtgtctg tggtttatct taactggttt  1020
ctcagcagtg gaattattat ggacaccaag atgggtggtg gaggtggtgg tggtagcaag  1080
atgtggcaca aaaaatggtg ggagaagatc tcagggcagg gttgcaaaat ccaccaacag  1140
tactaccagt atattggctc caagaaagtt aagagagcgt tgtggaggaa gcttttgctg  1200
acatgggtag tgggttggtt catagtatct ttgcggatct tctgctacat gagctcgcaa  1260
ggtactgaga agaggaaaga aactcttgca agcatgtgtg atgaaagggc taggatgctg  1320
caggatcagt ttaatgtcag tatgaaccat atccaagcca tgtccattct aatctccact  1380
ttccaccatg ctaagagccc ctcagccatc gatcaggtac tagtctttac tttgttgttg  1440
caaatcagga cctaattcac taattcccca ccttttgctt ttagtctttg tttattttgg  1500
cttaattttt attcacatag gtttctgagt tgtttcattg tcattaattt tagtgtctaa  1560
tagcattatt ttgtctaata cacaacacct tttttgtgga gaatttattg gggttttagt  1620
attatatgtt ttgctgacaa ggttactgaa cttgagctgc tggaacatga cctgatttcc  1680
ttggttcctc cccttcttgt cggatagaaa agatcccact ttcttttatc cttcgatctt  1740
tagtctcatc tctgcaaatt aatctaactt ccaaaacttg cagaaaactt ttgcaaagta  1800
cacagaaaga acagcttttg agagacctct tacaagtggt gttgcgtatg ctgtaagggt  1860
gctccattct gaaagggaac aatttgaaaa gcagcaaggt tggactatca agaggatgga  1920
tactctagag cagaacccgg ttcataagga cgattatgcc ccagaggcac tggagccatc  1980
ccctgttcag gaagaatatg ctcctgtcat ctttgcacag gatacaattg cacacgtgat  2040
ttctgttaat gtgctttctg gaaaggtagg tttctgatac ttgtataatt ttatttgtgg  2100
agctagtctg agccatatat tgttaattat gaaaattgtg aaaatgctat acagtagact  2160
ttgatgtctt gatgataatt ttaatccatc cattctaagc tttttattcc tggtagtatg  2220
```

-continued

```
gtttttgact ggtctttagt ggtcattaat tttttttccg gagaatgttt atgaagaaaa  2280
aactatctat gttgccatat tgcttgtttt tgtacccttg ttcttccttt ctcttgcttg  2340
tgatgatggg attgctcctg atggagaata gtacacatga atagactcta attttgtgaa  2400
tatcacaaag ctgaattgag acacgttgtt catgtttgat atctaaaatc tatggcaatt  2460
tatttggatt tatgattgtc acagttattc acttgttcat caacaggaag accgtgaaaa  2520
tgtgctgcgt gcaagagaat caggcaaagg ggttttaact gcgcccttta ggctgctcaa  2580
aacaaatcga ctaggggtta tcctgacctt tgctgtttac aagagagatc tcccatcaaa  2640
tacaacccca aatgaaagga ttcaagcaac tgacgggtgt gcctagtttt tgaatttttt  2700
tgcatctgac attcattagc ttttttggtc aatttttatg attttttatc attcatataa  2760
tttagcttat tccattttgg tcatctaaag ctttgaagta ctactaagta actaatcact  2820
gtattcaaat tttcagagaa gattcatgaa atctattaat gtgagaagag tgaataatta  2880
ttggctctcc cttgtgataa ttagaagctt tgaagttata aatctacttt taaattcaat  2940
aaagccaatg ggaaaatgaa aaaaaatcat gaacacagtt aaagagagca gcatttttat  3000
gtcttcacta ctgcttgctg ggcaggtatc ttgggggagt ctttgttgag tcattagtgg  3060
agaaattact tcagcaactt gctagcaagc aaactgtaat tgttcatgta tatgatacta  3120
caaatcgtac tcatccaatt gccatgtatg gctcaaatga atcaggggat tttttctatc  3180
acgtcagcac tcttaacttt ggagaccctt ttaggaagca tgagatgcac tgcaggtaag  3240
agtaatgcta ctgaagaagt ctaatatctc cgtcctcctt aatgctcagt gtagtttgta  3300
agaataacag tgggtcacct tgaaataggt agaggatata ttaaatacac ggtttattat  3360
tgtattaatg tcacatgact taatacttca caatctagtg gttttgctgc tagcgatacc  3420
tagtctagag ttcttttatc tggacttgtc atactttttt agggtcattg aatcttaact  3480
atttttatta atacattaca atgaaaatgt acaagttgtc aaagacgaac tattcatgaa  3540
aattaagctt gatgctaatg caggttcaag cagaagccac catggccatg ggtggcaata  3600
actacttcta ttggtatcct tgttattgca ctccttgttg gatatatttt ccatgccact  3660
gtgaatcgaa ttgccaaagt agaagatgat taccgtgaga tgatggaact taaaaaacga  3720
gctgaggcgg ctgatgttgc aaaatcccag gtatggaact ttttttaaa atttatttgt  3780
tgaacttatt ttggcttaac tcatactgat catgtgggct ttatcaattg taaccgcagt  3840
ttcttgctac tgtttcccat gagatcagaa caccaatgaa tggtgttttg ggtgagttgt  3900
cttctgtcta cggcttagtc tattatccaa tttttatcta tattatttcc acagaaaaga  3960
agagcttctt cagccatgac cctgctctaa attggatttt cagggatgtt gcatatgctt  4020
atggacacag atctagatgt aacccaacag gaatatgtca ggacagcaca ggaaagtgga  4080
aaagctctgg tgtcacttat aaatgaggtt ttggatcagg ctaagattga gtttggtaag  4140
ctagagcttg aggctgtgct cttcgacata cgggcaattt tggatgatgt attgtctcta  4200
ttttctgaga agtctcaagg aaaaagagta gaggtaatat ctctctcatc tactgttgat  4260
tttttatcat gatggaattt tcaaaatgtg cgtagtctaa tagttaatgg ctcttcataa  4320
tttttgtggt aactgcagtt ggcagtttat gtgtcagatc atgttcctga attacttata  4380
ggtgatccag gaagatttcg acaaataatt accaatctca tgggtaactc aattaaggta  4440
agtttatggt agagagaaga acattatgta taattcaagt tacttagtct gatatccttc  4500
atataagtta cttagagatg ttcccttgtc ctacatcctt gccttataga catgctacgg  4560
tcatcatagt ctcatgaaaa aaaatcttct atttagtgtt ctagccaagc atgactatta  4620
gtagagcaaa gttgatgtgt atttcttgaa aatattatta aaactgattc tgtaattgtt  4680
tggcagttca cggacaaagg acatattttt gtcacaatcc atcttgttga ggaggttgtc  4740
cgttcaatag aggttgacaa agaatccaac tcagaaaata ccttgagtgg ttcgcccgtt  4800
gctgatagtc gccggagctg ggaaggattc aaggctttca gtcaagaggg acctcttggt  4860
tccttctcat cccctccaat gatcttgtca atttgattgt atctgttgaa gatacaggtg  4920
aaggtattcc tcttgaatct cagccactca tcttcacccc attcatgcag gtaggttcat  4980
ccatctcccg aaagcatgga ggaacaggca ttggcctaag cattagcaaa tgtttggttg  5040
gcctcatgaa tggggaaatt ggatttgtga gcatacccaa gattgggtcc acattcactt  5100
ttactgctgt attcaccaat ggacaccgta gttcaagtga gtgtaaaatt cagcaaatca  5160
acaaccaacc tcagtctgca tcttcagaat ttgaggggat gactgcatta attattgacc  5220
caagatctgt tagagcagaa gtgtctggat atcacatcca acggcttggc attcatgttg  5280
aaatggtttc agatttaaaa caaggtttgt caaccataag caatgggaat gtagttgtta  5340
atatggtcct gattgagcag gaggtttggg atagagattt aggcttgtca tctcactttg  5400
tcaataacac gaggagaatt gatcatgggg ttcctccaaa gctgttcatt cttgttaatt  5460
ctagtagttc ttttaaagct agcgtaaact tgggtgttca taatcctact gtgatcacca  5520
aacctctgag agcaagtatg cttgctgcct cactacaacg agccatgggt gtccaaaaca  5580
agggagctcc tcatagagag ctccaaagtt tgtctcttcg ccatcttctt cgtggcagga  5640
aaattctaat tgtagacgac aatggtgtga accgtgcagt agcagctggt gcattgaaaa  5700
agtatggagc agatgtggtt tgtgttagca gtggaaaaga tgccatctct tccttgaagc  5760
caccccatca gtttgatgcc tgtttcatgg atattcaaat gccagaaatg gatgggtatg  5820
tatgcacctg gaatactttc tttcagaatc tgatattttt aatatctgga gtaatattg  5880
aaatttctac aaacatagaa aagagttttt aattctttta ttgatctaac agaataattg  5940
aaaatatctt acttaacagt tttaacatca aaggaaaact tattgcactg caaagattg  6000
tgaaacaaac taatgtatat taagcacaca aggtgtttgg agtctataat tcatttgaca  6060
attctatgac aaaaatagtc ttgtctcatt aagtgaggtt tgatacatga tgccattgag  6120
cttggttaaa aaccaaattc taagggatgc tatttaccat aaatctcttt tgataatttt  6180
ctttagtttc ctttttggtg ctgtgtctag ctcctttaac tttccctatg taccaaagtt  6240
tacatcctgt agtgtcttac tccttgactt cttctccaac ctatttagtt tcttgaaaac  6300
atgtgatgtg aatcctttc caaatcatga tgtccaccac cttcagagaa ttatctttca  6360
atgtaccaat attccaagca ccaaatctaa tcaggcacaa ctagtctagt tgctttaccc  6420
acatttgtct acaaaaatgt gaaaactctt gcttatttaa tacatttgaa agtttctgta  6480
gcagctctag ctcatttaac actgtactca aggcattcaa agtgttattt ttgggttacg  6540
acctagcatt ggcacacata atccattgtt agtgatccat gcttgggctt tcaacaagtt  6600
ttatgttggt tgtcaagggc ctaacacaac cctcttcctt tgtcaggctt tggaaccagc  6660
tatgagccca taagcggagt caattcattt cacaattcta aataaaaaat tatttgaaaa  6720
tttatttatc tactttctat ttataaaccc agaattatca ttatattaca attttgctaa  6780
taacaattct ttcccaacag atttgaagct acaaagcgaa ttagggagat ggaagatagt  6840
gtgaacagag aagtatctat ggatgacttt gagaatatta caaactggca tgtacccatt  6900
ttagccatga ccgcagatgt gatacaggct acacacgagg aatgcctaag gtgtggcatg  6960
```

```
gatggatatg tttcaaaacc atttgaagct gaacagctgt atagagaagt ctcacggttt  7020
ttccagtcat cttgaaaaga aaatacggtg ccgagttaaa ccagaatatt tgataatgga  7080
agcgtagctg tccgtaatcc aggacactcc gaagtgggca aataggttcc gaagtctcct  7140
gagagtaagt tccctattta acagccagtg catgttttag tatttaacca cctcaaagct  7200
tggtggttgt tcactagaga cagaagaatg ctatctatct catctgaaag ataaaagaaa  7260
atggaacaaa gggggataat attgtagaag ttcagaaatg gttcattcta ccttttgac  7320
ctattttgtt gtcttttctg ctgtgtttga agggttcccg ttttaaaaca ttgtttttgt  7380
ggcagggagt gtacatagga gccaagtttg attggttgca attgagttgt aattggttgt  7440
taagggtacc aaaacccatt aattcttctt ccatgtaaag tcagccgaaa tgattgaggc  7500
tgattagaag actagggtgt attataatac aggttctgga gtctcatcct tgtgtatgta  7560
ataatacaac ttatagtaat ctagcctagg cgcgttacat ttttatgtgt attgatgcat  7620
gtatcacaag ggcttgattc aggtgaaagg aagaaaatta gcttcttggc atcaaagggg  7680
aggaaggaag caagtacaca ccatcaatct ttgtatatga ctcacaataa agatggtgat  7740
tcgatgtatc acagcaagct tgcttccttt tgttcttaac agtgctggaa ttcggcttgc  7800
aaacatgtaa ctgatacatt atactgtagt gtgagtgatc caccattttt tggccgattt  7860
ttatatttcc aattctggat ttcctttgac tcattgattt gccttgcaca tctcatgaaa  7920
ttattccttt tttttttaa tctcaatagt aaatt                              7955

SEQ ID NO: 245         moltype = DNA  length = 6111
FEATURE                Location/Qualifiers
source                 1..6111
                       mol_type = other DNA
                       organism = synthetic construct
SEQUENCE: 245
atgagcttgc tccatgtagt tgggtttggt cttaaagtgg ggcatctact tttggtgcta  60
tgttgctggg ttgtgtctgt ggtttatctt aactggtttc tcagcagtgg aattattatg  120
gacaccaaga tgggtggtgg aggtggtggt ggtagcaaga tgtggcacaa aaaatggtgg  180
gagaagatct cagggcaggg ttgcaaaatc caccaacagt actaccagta tattggctcc  240
aagaaagtta agagagcgtt gtggaggaag cttttgctga catgggtagt gggttggttc  300
atagtatctt tgcggatctt ctgctacatg agctcgcaag gtactgagaa gaggaaagaa  360
actcttgcaa gcatgtgtga tgaaagggct aggatgctgc aggatcagtt taatgtcagt  420
atgaaccata tccaagccat gtccattcta atctccactt tccaccatgc taagagcccc  480
tcagccatcg atcaggtact agtctttact ttgttgttgc aaatcaggac ctaattcact  540
aattccccac cttttgcttt tagtctttgt ttattttggc ttaattttta ttcacatagg  600
tttctgagtt gtttcattgt cattaatttt agtgtctaat agcattattt tgtctaatac  660
acaacacctt ttttgtggag aatttattgg ggttttagta ttatatgttt tgctgacaag  720
gttactgaac ttgagctgct ggaacatgac ctgatttcct tggttcctcc ccttcttgtc  780
ggatagaaaa gatcccactt tcttttatcc ttcgatcttt agtctcatct ctgcaaatta  840
atctaacttc caaaacttgc agaaaacttt tgcaaagtac acagaaagaa cagcttttga  900
gagacctctt acaagtggtg ttgcgtatgc tgtaagggtg ctccattctg aaagggaaca  960
atttgaaaag cagcaaggtt ggactatcaa gaggatggat actctagagc agaacccggt  1020
tcataaggac gattatgccc cagaggcact ggagccatcc cctgttcagg aagaatatgc  1080
tcctgtcatc tttgcacagg atacaattgc acacgtgatt tctgttaatg tgctttctgg  1140
aaaggtaggt ttctgatact tgtataattt tatttgtgga gctagtctga gccatatatt  1200
gttaattatg aaaattgtga aaatgctata cagtagactt tgatgtcttg atgataattt  1260
taatccatcc attctaagct ttttattcct ggtagtatgg tttttgactg gtctttagtg  1320
gtcattaatt ttttttccgg agaatgttta tgaagaaaaa actatctatg ttgccatatt  1380
gcttgttttt gtacccttgt tcttcctttc tcttgcttgt gatgatggga ttgctcctga  1440
tggagaatag tacacatgaa tagactctaa ttttgtgaat atcacaaagc tgaattgaga  1500
cacgttgttc atgtttgata tctaaaatct atggcaattt atttggattt atgattgtca  1560
cagttattca cttgttcatc aacaggaaga ccgtgaaaat gtgctgcgtg caagagaatc  1620
aggcaaaggg gttttaactg cgccctttag gctgctcaaa acaaatcgac taggggttat  1680
cctgaccttt gctgtttaca agagagatct cccatcaaat acaaccccaa atgaaaggat  1740
tcaagcaact gacgggtgtg cctagttttt gaatttttt gcatctgaca ttcattagct  1800
tttttggtca atttttatga ttttttatca ttcatataat ttagcttatt ccattttggt  1860
catctaaagc tttgaagtac tactaagtaa ctaatcactg tattcaaatt ttcagagaag  1920
attcatgaaa tctattaatg tgagaagagt gaataattat tggctctccc ttgtgataat  1980
tagaagcttt gaagttataa atctactttt aaattcaata aagccaatgg gaaaatgaaa  2040
aaaaatcatg aacacagtta aagagagcag catttttatg tcttcactac tgcttgctgg  2100
gcaggtatct tgggggagtc gttgagtcat tagtggagaa attacttcag caacttgcta  2160
gcaagcaaac tgtaattgtt catgtatatg atactacaaa tcgtactcat ccaattgcca  2220
tgtatggctc aaatgaatca ggggattttt tctatcacgt cagcactctt aactttggag  2280
acccttttag gaagcatgag atgcactgca ggtaagagta atgctactga agaagtctaa  2340
tatctccgtc ctccttaatg ctcagtgtag tttgtaagaa taacagtggg tcaccttgaa  2400
ataggtagag gatatattaa atacacggtt tattattgta ttaatgtcac atgacttaat  2460
acttcacaat ctagtggttt tgctgctagc gatacctagt ctagagttct tttatctgga  2520
cttgtcatac ttttttaggg tcattgaatc ttaactattt ttattaatac attacaatga  2580
aaatgtacaa gttgtcaaag acgaactatt catgaaaatt aagcttgatg ctaatgcagg  2640
ttcaagcaga agccaccatg gccatgggtg gcaataacta cttctattgg tatccttgtt  2700
attgcactcc ttgttggata tattttccat gccactgtga atcgaattgc caaagtagaa  2760
gatgattacc gtgagatgat ggaacttaaa aaacgagctg aggcggctga tgttgcaaaa  2820
tcccaggtat ggaacttttt tttaaaattt atttgttgaa cttattttgg cttaactcat  2880
actgatcatg tgggctttat caattgtaac cgcagtttct tgctactgtt tcccatgaga  2940
tcagaacacc aatgaatggt gttttgggtg agttgtcttc tgtctacggc ttagtctatt  3000
atccaatttt tatctatatt atttccacag aaaagaagag cttcttcagc catgaccctg  3060
ctctaaattg gattttcagg gatgttgcat atgcttatgg acacagatct agatgtaacc  3120
caacaggaat atgtcaggac agcacaggaa agtggaaaag ctctggtgtc acttataaat  3180
gaggttttgg atcaggctaa gattgagttt ggtaagctag agcttgaggc tgtgctcttc  3240
gacatacggg caattttgga tgatgtattg tctctatttt ctgagaagtc tcaaggaaaa  3300
```

```
agagtagagg taatatctct ctcatctact gttgattttt tatcatgatg gaattttcaa  3360
aatgtgcgta gtctaatagt taatggctct tcataatttt tgtggtaact gcagttggca  3420
gtttatgtgt cagatcatgt tcctgaatta cttataggtg atccaggaag atttcgacaa  3480
ataattacca atctcatggg taactcaatt aaggtaagtt tatggtagag agaagaacat  3540
tatgtataat tcaagttact tagtctgata tccttcatat aagttactta gagatgttcc  3600
cttgtcctac atccttgcct tatagacatg ctacggtcat catagtctca tgaaaaaaaa  3660
tcttctattt agtgttctag ccaagcatga ctattagtag agcaaagttg atgtgtattt  3720
cttgaaaata ttattaaaac tgattctgta attgtttggc agttcacgga caaaggacat  3780
atttttgtca caatccatct tgttgaggag gttgtccgtt caatagaggt tgacaaagaa  3840
tccaactcag aaaatacctt gagtggttcg cccgttgctg atagtcgccg gagctgggaa  3900
ggattcaagg ctttcagtca agagggacct cttggttcct tctcatcccc tccaatgatc  3960
ttgtcaattt gattgtatct gttgaagata caggtgaagg tattcctctt gaatctcagc  4020
cactcatctt caccccattc atgcaggtag gttcatccat ctcccgaaag catggaggaa  4080
caggcattgg cctaagcatt agcaaatgtt tggttggcct catgaatggg gaaattggat  4140
ttgtgagcat acccaagatt gggtccacat tcacttttac tgctgtattc accaatggac  4200
accgtagttc aagtgagtgt aaaattcagc aaatcaacaa ccaacctcag tctgcatctt  4260
cagaatttga ggggatgact gcattaatta ttgacccaag atctgttaga gcagaagtgt  4320
ctggatatca catccaacgg cttggcattc atgttgaaat ggtttcagat ttaaaacaag  4380
gtttgtcaac cataagcaat gggaatgtag ttgttaatat ggtcctgatt gagcaggagg  4440
tttgggatag agatttaggc ttgtcatctc actttgtcaa taacacgagg agaattgatc  4500
atggggttcc tccaaagctg ttcattcttg ttaattctag tagttctttt aaagctagcg  4560
taaacttggg tgttcataat cctactgtga tcaccaaacc tctgagagca agtatgcttg  4620
ctgcctcact acaacgagcc atgggtgtcc aaaacaaggg agctcctcat agagagctcc  4680
aaagtttgtc tcttcgccat cttcttcgtg gcaggaaaat tctaattgta gacgacaatg  4740
gtgtgaaccg tgcagtagca gctggtgcat tgaaaaagta tggagcagat gtggtttgtg  4800
ttagcagtgg aaaagatgcc atctcttcct tgaagccacc ccatcagttt gatgcctgtt  4860
tcatggatat tcaaatgcca gaaatggatg ggtatgtatg cacctggaat actttctttc  4920
agaatctgat atttttaata tctggagtaa tatttgaaat ttctacaaac atagaaaaga  4980
gtttttaatt cttttattga tctaacagaa taattgaaaa tatcttactt aacagtttta  5040
acatcaaagg aaaacttatt gcactgcaaa gatttgtgaa acaaactaat gtatattaag  5100
cacacaaggt gtttggagtc tataattcat ttgacaattc tatgacaaaa atagtcttgt  5160
ctcattaagt gaggtttgat acatgatgcc attgagcttg gttaaaaacc aaattctaag  5220
ggatgctatt taccataaat ctcttttgat aattttcttt agtttccttt ttggtgctgt  5280
gtctagctcc tttaactttc cctatgtacc aaagtttaca tcctgtagtg tcttactcct  5340
tgacttcttc tccaacctat ttagtttctt gaaaacatgt gatgtgaatc cttttccaaa  5400
tcatgatgtc caccaccttc agagaattat ctttcaatgt accaatattc caagcaccaa  5460
atctaatcag gcacaactag tctagttgct ttacccacat ttgtctacaa aaatgtgaaa  5520
actcttgctt atttaataca tttgaaagtt tctgtagcag ctctagctca tttaacactg  5580
tactcaaggc attcaaagtg ttatttttgg gttacgacct agcattggca cacataatcc  5640
attgttagtg atccatgctt gggctttcaa caagttttat gttggttgtc aagggcctaa  5700
cacaaccctc ttcctttgtc aggctttgga accagctatg agcccataag cggagtcaat  5760
tcatttcaca attctaaata aaaaattatt tgaaaattta tttatctact ttctatttat  5820
aaacccagaa ttatcattat attacaattt tgctaataac aattctttcc caacagattt  5880
gaagctacaa agcgaattag ggagatggaa gatagtgtga acagagaagt atctatggat  5940
gactttgaga atattacaaa ctggcatgta cccattttag ccatgaccgc agatgtgata  6000
caggctacac acgaggaatg cctaaggtgt ggcatggatg gatatgtttc aaaaccattt  6060
gaagctgaac agctgtatag agaagtctca cggtttttcc agtcatcttg a           6111
```

```
SEQ ID NO: 246          moltype = DNA  length = 7966
FEATURE                 Location/Qualifiers
source                  1..7966
                        mol_type = other DNA
                        organism = synthetic construct
SEQUENCE: 246
tttgagtgga tagtttggaa agagataatg gcctataata atattttgaa aacatttgtg  60
ctgtgctacc gtattattct tatcatcttt gcctttccaa attctcctac tacctgaact  120
cgatgaacaa caactcattg ctttaaagct cttttcagct tcattctcca tgttcaagtg  180
accttttttt tacagtgtgc agctagcttc taagaaaaaa taaaaatctc tagaacacac  240
tcacgtgctt gtgttgttct tgtttggttc tagggccatg aagtgcgagc tagtagattt  300
tctttgctga gtgatagtga aaatcgaatc ttttgtaggt ttagttttga cccttccttt  360
ttgttctgcg ccttggttgg tagctgctgc tagctgacaa gataataagg agtatcaatt  420
tctgtttagc attagaaacc cagaatcttg tgattctttt attctttaaa gggtatttga  480
atttttctta tctgcctcta gtttcagtgt tcattttgca tttctgaatt ttaagctatt  540
ggggtggata agacagcatc ttatcaaggt cacatctctt attattattt ttattgaaga  600
tgtctttttt atttttcctt ccccttcaac ctacttgttt ttaggaattg ggtttctgtt  660
gttgttgttg ttcatcaaaa tctcgaattt tcttcaatca caagcctaaa aaacaaatct  720
tttagtgaat aggtgtgtgt tagccttgtg gggattctgt ggatttgaca gcggttctct  780
cctctcctct ctctctgtct ctgtctcggt ctctgtctct ctctctctct ctcacacaca  840
cacacaagcc tgcctggaat cagttagagt tgacacccgc aacctgtttg aactgtttct  900
ttttaacctg tgttggttac tgttgtggat gagtttgctc catgtagttg ggtttgctct  960
aaaagtgggg catctacttt tggtgctatg ttgctgggtt gtgtctgtcg tttaccttaa  1020
ctggtttatt agcagtggaa ttatggaaac caagatgatg ggtggtggtg gtggtggcgg  1080
tggcaagatg tggcacaaaa aatggtggga gaatatatca gggcagggtt gcaaaatcca  1140
ccaacagtac taccagtata ttggctctaa gaaagttaag agagcgttgt ggaggaagat  1200
tttgctgaca tgggtcgtgg gttggttcat agtatctttg tggatcttca gctacatgag  1260
cttgcaaggt actgagaaga ggaaagaaac tctcgcaagc atgtgtgatg aaagggctag  1320
gatgctgcag gatcagttta acgtcagtat gaaccatatc caagccatgt ccattctgat  1380
ctccaccttt caccatgcta agagcccctc agccatcgat caggtactag tctttacttt  1440
gttattgcaa atcaggacct aattcctcac cttttgcttt tagtctttgt ttgtgttacc  1500
```

```
ttaatttcta tacacatagg tttctgagtt gtttcattgt cattaatttt agtgtctaat  1560
agcattattc cccccttttt tgtggaaaat ttattgggat tttagtatta tatgttttgc  1620
taacaaggtt actgaacttg agctgctgga acatgacctg atttccttgt ttccccacct  1680
tcttgttgga tagaaaagat cccactttct tttatccttc aatctttagt ctcatctcta  1740
caaattaatc taacttccaa aactcgcaga aaactttttgc aaagtacaca gaaagaacag  1800
cttttgagag gcctcttaca agtggtgttg cgtatgctgt aagggtgctc cattctgaaa  1860
gggaacaatt tgaaaagcag caaggttgga ctatcaagag gatggatact ctagagcaga  1920
acccggttca taaggatgat tatgccccag aggcattgga gccatccccc gttcaggaag  1980
aatatgctcc tgtcatcttt gcacaggata caattgcaca tgtgatttct gttaatgtgc  2040
tttctggaaa ggtaggtttc tgatacttgc aaaattttat ttatggagct agtctgagcc  2100
atatattgtt aattatgaaa attgtgaaaa tgctatacaa taaactttga tgtcttgatc  2160
ataattttaa ttcatccatt ctaagctctt tattcctggt agtatggttt ttgactggtc  2220
ttttagtggt cattaatttt gttttgggag aatatttatg aagaaaaaac tatctatgct  2280
accattttgt acccttgttc ttcctttgtc ttgcttgtcc tgatgggact gctcctgatg  2340
gagaatagta cacgtgaata gattctaatt ttgtgaatat cacaaagctg aattgagtca  2400
cgttgttcat gtttgatatc tgaaatctat ggcaatttat ttggaattat gattgtcaca  2460
gttattcact tgttcatcaa caggaagacc gtgaaaatgt gctgcgtgca agagaatcag  2520
gcaaaggcgt tttaactgcg cccttcaggc tgctcaaaac aaataggcta ggggttatcc  2580
tgacatttgc tgtctacaag agagatcttc catcaaatgc aaccccaaat gaaaggattc  2640
aagcaactga cgggtgtgcc taaattttga ttttttttatg atttttttatc attcatataa  2700
tttagcttat tccctttgg tcatctaaag ctttgaagta actagtctac taaataagta  2760
attgatgcat tcaaatttc agagagaaga ttatgaactc tattaatgta agaagggtga  2820
acaattattg gttcttccct gtgataatta gaagttttga agttacaaat ctacttttaa  2880
attcaataaa actgatggta aaaagaaaaa gaaatcatga acacagttaa agagagtagc  2940
atttttatgt cttcactact gcttgctggg caggtatctt gggggagtct ttgttgagtc  3000
attagtggag aaattacttc agcaacttgc tagcaagcaa agtgtaattg ttaatgtgta  3060
tgatactaca aatcacactc atccaattgc catgtatggc tcaaatgaat caggggatgt  3120
tttctttcac gtcagcactc ttaactttgg agaccctttt aggaagcatg agatgcactg  3180
caggtaagag ttatgctaca gaagaagtct aatatttccg tcctccttaa tgctctgtgt  3240
agtttgtaag aataacagtg tgccaacttg aaataggtag aggatatatt aaatacaagg  3300
tgtattaatg tcatatgact taatacttca caatctagtg gttttgctgc tagcaatacc  3360
tagtctagag ttcttttatc tggagttgtc atatttttta gggtcattga atctaagtat  3420
ttttatttta atatatttca attataatgt tcaaaattgt caaaagactt gaactattca  3480
tgaaaattaa gcttgatgct aatgcaggtt caagcagaag ccaccatggc catgggtggc  3540
aataactact tcaattggta tccttgttat tgcactcctt gttggacata ttttccatgc  3600
cactgtgaat cgaattgccg aagtagaaga tgattatcgt aaggagatgg aacttaaaaa  3660
acaagctgag gcggcagatg ttgcaaaatc ccaggtatgt aactttattt atttatttat  3720
ttattttgaa cttgttttgg cttaactcac actgatcatg tgggctttat caattgtaac  3780
cacagtttct tgctactgtt tcccatgaaa tcagaacacc aatgaatggt gttttaggtg  3840
agttgtcttc tgtctatggt ttagtcgatt atccaatttt taattttttaa ctatatacat  3900
tccacaaaaa agaagagctt cttcagccat gaccctgctc taaattggat tttcagggat  3960
gttgcatatg cttatggaca cagatctaga tgtcacccaa caggaatatg tcaggacagc  4020
acaggaaagt ggaaaagctc tggtgtcact tataaacgag gttttggatc aggctaagat  4080
tgaatttggt aagctagagc ttgaggctgt gctcttcgac atacgggcaa ttttggatga  4140
tgtattgtca ctattttctg agaagtctca aggaaaagga gtagaggtaa tatatctctc  4200
gtctactgtt gccttttttat catgatggaa ttttcaaaat gtgcatagtc taactatagt  4260
taatggctct tcataatatt tttttgggaa ctgcagttgg cagtttatgt gtcagatcat  4320
gttccagaac tactaatagg tgatcctgga agatttcgac aaataattac caatctcatg  4380
ggtaactcaa ttaaggtaag tttatggtag agagaagaac attatgtata attcaagtta  4440
tttagtctga tatccttcat ataagttact tggagatgtt cccttgtcct acatccttgc  4500
cttataggca tgctacggtc atcatagtct catgaaaaaa aaattctatt tactgttcta  4560
gccaagcata tgactactag tagagcaaaa ttgatgtgta tttcttgaaa atattattaa  4620
aactgatttt gtaattgttt ggcagttcac ggacaaagga catatttttg tcacaatcca  4680
tcttgttgag gaggttgtcc gttcaataga ggttgacaaa gaatccaact cagaaaatac  4740
cttgagtggt tcccctgttg ctgatagtcg ccggagctgg gaaggattca aggctttcag  4800
tcaagaggga cctcttggtt ccttctcatc cccctccagt gatcttgtca atttgattgt  4860
atctgttgag gatacaggtg aaggtattcc tcttgaatct cagccactca tctacacccc  4920
attcatgcag gtaggtccat ccatctcccg aaagcatgga ggaacaggaa ttggcctaag  4980
cattagtaag tgtttggttg gcctcatgaa tggggaaatt ggatttgtga gtatacccaa  5040
gactggatcc acattcactt ttacagctgt attcaccaat ggacactgca gttcaaatga  5100
gtgtaaagtt cagcaaatca acaaccaacc tcactctgca tcttcagaat tcgaggggat  5160
gactgcatta attattgacc caagatctgt tagagcaaaa gtgtctagat atcacatcca  5220
acggcttggc attcatgttg agatggtttc agatttaaaa caaggtttgt caaccataag  5280
caatgggaat ataattatta atatggtttt gattgagcag gaggtttggg atagagattt  5340
aggcttgtca tctcatttttg tcaataacac aaggagaatt gatcaggggg ttcctccaaa  5400
gctgttcatt cttgttaatt ctagtagttc ttttaaagct agtgtaaact tgggtgttca  5460
taatcctatt gtcatcacca aacctctgag agcgagtatg cttgctgcct cactacaacg  5520
agccatgggt gtccaaaata agggagctcc tcatagagag ctccaaagtt tgtctcttcg  5580
ccatcttctt cgtggcagga aaattctaat tgtagatgac aatagtgtga accgtgcagt  5640
agcagctggt gcattgaaaa agtatggagc agatgtggtt tgtgttagta gtggtaaaga  5700
tgccatctct tccttgaagc caccccatca gtttgatgcc tgtttcatgg atattcaaat  5760
gccagaaatg gatgggtatg tatgcacctg gagtactttc tttcagaatc tgataattta  5820
tcattttgga gtaatatttg gaatttctac aaacatagaa aagagttttt agttctttta  5880
ttgatctaac agaataattg aaaatatttt actgaacagt ttacatcaaa ggaaaacttt  5940
ttgcactgca aagatttgtg aaacaaacta atgtatatta agcacacaag gtgtttggag  6000
tctaacttgc tacagcaata ctataactat gattcatttg acaattctac aacaacaatg  6060
gccttgtctc atgaagtgag gttgaataca tgtatcaaat gatgccattg agctttgtta  6120
aaaaccaaat tctaagggat gttatttacc ataaaatctc ttttaataat ttcctttaat  6180
gtcctttttg gtctcctatc cttttcacaa ggctaaaaac catgcaatgt actcttgtca  6240
```

```
ttgtgcctct aatgaccttt tttacatgtg tccaagccat cttagtcgat tttttgtcat  6300
cttgataggt gttataccag tataccagta tctcctagta tacaatcatt ctatatcttg  6360
tactttcttg tgtagtcaca catccatctt cacatactca ttctatatct tatttcttac  6420
taaaattgca atgcatatat tgttttactc ctactgaatc tagtgtttgt ctccaaaact  6480
aaactttatg gttaactttt tcccttgatt ccctgatttt aagttatatc attcgcaaaa  6540
agtatgcatt tagtgataaa catttgggct attttcgggt aacgacttag cattggcaca  6600
caatccatcg ctagtgatcc acgtttgggc tttcaaagtt ttatgttgat tgtcaaggga  6660
ctatccagcc tttggaacca gctatgagcc catacgtgga gtcaattcat ttgacaattc  6720
taattaaaaa attatttgaa gaatttactt atctactttt tatttctaaa tcaagaatta  6780
tcattgtgtt acgattttgc taataacaat tcttttccaa cagatttgaa gctacaaagc  6840
gagttaggga gatggaagat agtgtgaaca gagaagtatc tatggatgac tttgagaata  6900
ttacaaactg gcatgtaccc attttagcca tgactgcaga tgtgatacat gctacacacg  6960
aggaatgcct aaagtggggc atggatggat atgtttcaaa accctttgaa gctgaacagc  7020
tgtatagaga agtctcacgg tttttccagt catcttgaaa agaaaataca gtgctgatct  7080
aaaccagata aactgataat ggaagcatag ctgtttgtac tccaggacac tctgaagtgg  7140
gtaaataggt tcagaagtct cctgagagta agttccctat ttaacagcca gtgcatgttt  7200
tagtatttca ccacctcaaa gtttgggggt tgttcactag agactgaaga atgtttatct  7260
atctcatctg aaaggaaaaa gaaaatggaa caaaggggga caatattgta gaagttcaga  7320
aatggttcat tctacctttt tgacctattt tgttgtcttt tctgctgtgt gtgaaggtcc  7380
ctggtttaaa actttgtttt tgtggcaggg agtgtacgta ggagcaaagt ttgattggtt  7440
gcaattgagt tgtaattggt tgttaagggt agcaaaaccc atattaattc ttcttccttg  7500
taaactcagc ctctcttctc attcgaaatg attgaggctg attggaagat tagggtgtat  7560
tataatacag gttctggagt ctcctccttg tgtatgtaat aatacaactt atagtgatct  7620
agcctaggca cgttacattt tatgtgtatt gatgcatgta tcacaagggc ttgattcagg  7680
tgaaaggaag aaaattagct tcttggcatc aaaggaagct agcccatcat caatctttgt  7740
atatgactca caataaagat ggtgattgat gtatcacacc aagcttgctt ccttttgttc  7800
ttaacagtgc tggaattcgg cttgcaaaca tgtaactgat acattatact ctagtgtttg  7860
agtgatccac catttttttg gcctatttgt acatttccaa tttctggatt tcctttgact  7920
cattgctctt gccttgcaca tctcatgaaa ttattccttt tatttt              7966
```

```
SEQ ID NO: 247          moltype = DNA  length = 6495
FEATURE                 Location/Qualifiers
source                  1..6495
                        mol_type = other DNA
                        organism = synthetic construct
SEQUENCE: 247
gcccgcagcc cgctcttccc cgctccacct ccaggcttcc agtctctcac tctcccgcgc  60
ctcttgctgc tgctgctggc gatagggatc ccagcgcctt caagttcggg tgggcggcta  120
gcgcggcgcg tgtcggcgag catatggtgg gcattgggcg ggggaaggag gaggaggagc  180
ggcaatagat ttgtgggcgc agaggcgggg atggggggca acaagtactg cgcggcgatg  240
acgaagagga gatggagggg gctggcagcg gccgcgtggg tgctagtcgc ggtggcttgc  300
tccgcggtga tgcactggac catgcgccgg gagagcatgg accgcgccga ggagcgcctc  360
gtcagcatgt gcgaggagag ggccaggatg ctgcaggagc agttcggggt caccgtcaac  420
cacgtccacg cgatcgccat tctcatcgcc accttcaact acgataagtc cccttccgct  480
atcgaccagg ttcgtcacca ttcgcccccc tcttctccgc cattgctctt gtagattgct  540
atgccacggt atcaattggc agttggttta gcaatagcgg accccgagat cctacacatt  600
gttctgtggg ttgtctcttt tctttaaagg agcaaacaga aaaaaaaggg gagaaataga  660
gatatagaga tgcgttgttg tttgttgacg cttaccgtcg tttagcacgc catgattgct  720
gtggttggct gggacaggtg ctgttcatag tcttgtggaa agaaaaaaaa tgtccattcc  780
tgcggcggtt aggcggggat tttttaggct tattggagac gtagctgaac tgaactgttg  840
ggttggtggc acattgtttg ttcatagagt gattagtgtg ttcgctgcaa aaccatctgg  900
gggttacttt gacatccatt ggggtgtgct cttttgccaa ccttttgatt ccttgtttat  960
tctgagaaag gtccctgtcg cagagattaa attatgttag aagctgcttt ctgcctctct  1020
tttctttgc ttagattatt gatcctcaaa gccgtccttt cctgcatcta cacttcgttt  1080
ctcttccccc cctttttttt tgtcgattta cctatagttt aggcgtgcag tgtcatgggc  1140
ccatgttatt tgaagacgtg ctcgtttttg catacaatga ccaatcttat tcgttgcatc  1200
attacttttg gtaaatcaac aagatgtctt cttctgattc ttgcaattta tagcatatta  1260
ttgtccagta ttctattttg gcttaataat taatgtccga cacaggacac ttttgcaaaa  1320
tacacggcaa ggacatcatt tgagcgaccg ctactcaatg ggtggcata tgcacagcgt  1380
gtattccatc atgagaggga aatgtttgaa agccagcagg gatggattat gaatacaatg  1440
cagcgggagc ctgcaccccc gcaggttgaa tatgctccag tgatttttctc tcaggatact  1500
gtttcctacc tcgcacgcat tgacatgatg tctggagagg tatggttcta tttgatcgat  1560
cttagtattc attggggtgt ttatgaccct ttgatgtctc tttagtgaaa gcaatctatt  1620
tatttacgat acaggaggac cgagaaaaca ttttgcgggc caggactact ggcaaagctg  1680
tgttaacaaa cccatttcgg ttgcttggat caaaccactt gggagtagtt ctcacttttg  1740
ctgtgtaccg ccctgatctc cccgctgatg catcagttga gcaacgtgtg gaagcaacta  1800
ttgggtgaga tgttctaact cacatccttt gttgttttat ttttaaccaa atattctagc  1860
attgtcgcct ttaagactca tgtttaacat gtgggtatga ataaaatttt gtgcactatt  1920
atttgatcat gtaatatctt gtcatcgtgt atcatgccac atttgtggtt cactgatcaa  1980
tactgaattt aggttgacta tgatgacctt aacatgtcta gtaacaggtg ataatagaaa  2040
caatgtgttt cttttttaaa aaaggtatag cgtgcttatg gcagttatgg caggcacatt  2100
tagtaataga tcatgcaggt tataatcatt gcagcttgtc tcaatttaat caaatgatac  2160
tctatgctta tctaattttc aagagaataa tttgctgtgt gctcccagat atcttggtgg  2220
agcgtttgat gtggagttac ttgtggagaa tttgctgagc aaacttgctg gcaatcagga  2280
tattgtggtg aatgtctatg atgtcacaaa tgcttcagag gctatggttt tgtatggacc  2340
ttctagttcg gatgagcgcg tgcctttctt gcatgttagc atgttggatt ttggagatcc  2400
gtttaggagg catgaaatga ggtgcaggtt ggtagtcctt atctgtaaat cttaattttc  2460
ttggctgctt ttgttttcca ctaatgttgt caacctgcag gtatagacaa aagcttccta  2520
tgcagtggtc tgccataacc aatcctttgg gcacatttgt catatggatg cttctggggt  2580
```

```
atagcattgc cgctgcatat tctcgatatg acaaagttac agaagattgt agaaagatgg  2640
aagagctaaa aacgcaggca gaagctgctg atgttgcaaa gtctcaggtt tggcctgttc  2700
tttagcactc tcatttacta ggcattctag catatgcatc atgtatggct tagcttatct  2760
atgtttgtct ctcttgcagt tcctggcaac tgtgtcacat gagatcagaa cacctatgaa  2820
tggcgtcctt ggtacttatg catttatttt gatattactt aatcttcagt tccgtgggcc  2880
tatcaatcta attttttttcc ttctggcgta ggaatgctgg atatgctttt aggaacagat  2940
ctaactatga cacagaagga ttatgctcaa actgctcaaa tgtgtggcag agcattgata  3000
acgttgataa atgatgtcct tgatcgagca aagattgaag ctggaaagtt agagcttgaa  3060
gcggtgcctt ttgacctgcg ttctctcatg gatgatgtta tttccttatt ttcttcaaag  3120
tcacgggaga agtgcattga ggtatgttac tgttaatgct tgaagtagga aatgatgttg  3180
cctgggccat cacttgaatg gatattgatt gcttttagtc ctagtttttg gctgagcaac  3240
tgacgaataa tgcagtttg cctgaaccaa tctgtcacta tacattgtgg catatacttt  3300
tcctgatcct tttccttctt gctgcagctt gcagtatttg tatgtgacaa tgttccgaag  3360
gatgttcttg gagatccttg gaggtttcgg cagatactaa caaatttggt cggcaatgca  3420
gtcaaagtaa gcaaccattt atggtatttg gtatcctcac actacaactt cgaatgatgt  3480
tggttaagtc gtagataagt ctgtcatcaa atacattcag aaaaatgcgc tgatatattt  3540
atcgtgtgtt ccagttcaca gaacggggtc atgtatttgt gcgggtctgt ttggctgata  3600
actcaaatat ggaagccggt caggtcctaa atggagccat gaatgggaaa gatggtagag  3660
ttgattcaac aactaatggt gccttcaata ctctgagtgg gtttgaagca gcagacagac  3720
gaaatagttg gcaatatttt aagatgctcc tctctgataa ggagtccctt ttggatgatc  3780
ttgagggaac aaattctgat caaagtgatt cagaccatgt cacactagcg ataagtattg  3840
aggacacagg tgttgggata ccattgcaag cacaagatcg tgtttttaca ccgtttatgc  3900
aggctgatag ttcaacttca aggaattatg gtggtactgg catcggttta agcattagca  3960
agtgcctagc tgaacttatg ggtgggcaga taagttttgt cagccgtcct tttgttggaa  4020
gtacattcac tttctccacc acactgaagc gctcatacaa agatatttca gttgattcaa  4080
gtaggagctt gttagaggca ctaccaactg cttttaaggg aatgaaggcc atcttgatag  4140
atgggagacc tgtacgtagt gctgttacaa gatatcacct caagaggttg ggaataattg  4200
ttcaagttgt gaacaatatg agtgcagtag taaaagcttt ccctggacaa aatggagcaa  4260
ctgtttctag gtgagtgttc ttaagttagt ttattagatg ctggagatac aattggctga  4320
gcagtgattc acatttcagt actttccctc acatggaggc tccctcaacc gcaagcctta  4380
tatgtgaaat gggagctctg ttttaaaggc gacgtctagg cgccccaaca ctcctaggcg  4440
ttcccgtcgc gtagctaaat cagcaagagg gcagagagaa agaaggggcg gcgccgaatc  4500
aggccgccgg cggccgattc ggccccagcg acagctgaat cagggcggcg gcggccgaat  4560
cggggatggc ggcagcaaaa tcatgagtgg cggcggctga atcgtgtgag gagagaagga  4620
aaccacggct gaaaaagggg aggggagaag gaaagcagca gctcaatcga ggggggagag  4680
gggggaaaca gggggagata taggctggct tctttttctt cctcctccat gctgctgttt  4740
tatgctgctg ttttgttggt tctcatgttg ataaggtgtc accttgctcg tcttagttgt  4800
cgcctaggcg tccagaccag gtggtagttc aacgtcttat cttgccttac cgctttaaga  4860
accataaacg ggctagggaa catttctttt attaaattgt gtgactaaag atttgaattc  4920
gaaacctggt tttgttacca gcatgttaag ctgcatgcac tgacggcctc aacaaagacc  4980
ctaagggctg gtttggtgga cagggaaatg agatcccctc catttttctg tccaccaaac  5040
cagccctaaa ctggtgggaa aggcaggcaa ctcattaata tattttacta catataatag  5100
ataaaccgtc tatgccatca gtctgtcctg aataagctat tttctttttt gaaaaagtat  5160
aggaccctaa aatccttgac tgacctttta tccccaaact gttttgggga atagcataaa  5220
acattcttaa agcacctgaa tatgcacttt ataattgttt tgtatgacat ctgaaatcat  5280
cacatttatt ctcttgtagg gaaaaggcaa ccattctttt tattgagagt gacttttgga  5340
ggcccgagac agatgttcag ttattgaacc atctacgcga gcacaagaat cgtcagttgt  5400
ctgatgggca taaggtagtt cttttggtca cctccgaagc tgataaggac aagtatggat  5460
ccatatttga tattgtgatg tgcaagccta taagggcaag catgattgct tcatctattc  5520
aacaactgct caaagtagag atgcctgaaa gaagaaataa tcataatcgg ccatcatttc  5580
ttcgcagcct gctggttggg aagaatatat tggtagtaga tgataataaa gtcaatctta  5640
gagtcgctgc agctgcactc aaaaagtacg gtgctaatgt tagctgtgtt gagagtggca  5700
aagatgctat cagtctactt caaccccccac attgctttga cgcatgtttt atggatgttc  5760
agatgccaga gatggatggg tatggattaa ataaatataa acacgtttgt catttccatc  5820
atgttgtttg aagtttgttt gctaggtgaa gtaaatctcc ccactgatca tcagttctca  5880
attattactt ttttaggttt gaggcaacaa gacaaataag gcaaacagag atgagagtta  5940
acgaggaaag gaagaataag ttggtgttga ttgaaggctc aacatttgtt gagtaccatt  6000
tgcctgtttt ggcgatgaca gccgatgtta tccaggcaac ttacgagaag tgtataaaat  6060
cgggaatgga tggatacgtg tctaaaccct tcgacgagga gcagctatac caagcagtct  6120
ccagattaat agtgggaacg acagattcga ctgtttaata tttagatggc tatgaatctg  6180
atttctcatt catcgaattg aagcacacca ccatgttgct tctgtccaag tttgactcta  6240
acccttaaca attgtctgac ctggcctctc gcagcactag atgaaaagga tgaaagtgcc  6300
acgagttggc tatgtatcag caccacagat gaagttgcct caccccggag tgtaggttgg  6360
tagatcactc tcttctttga tgtttatagg ttgttgtata tcttctgaca attcattgga  6420
aaccacatct cgttgcgaca ttggaggaca tcttcaatgc tggtaaattt gttataggaa  6480
tatcctttaa tgctg                                                  6495
```

```
SEQ ID NO: 248          moltype = DNA  length = 6495
FEATURE                 Location/Qualifiers
source                  1..6495
                        mol_type = other DNA
                        organism = synthetic construct
SEQUENCE: 248
gcccgcagcc cgctcttccc cgctccacct ccaggcttcc agtctctcac tctcccgcgc  60
ctcttgctgc tgctgctggc gatagggatc ccagcgcctt caagttcggg tgggcggcta  120
gcgcggcgcg tgtcggcgag catatggtgg gcattgggcg ggggaaggag gaggaggagc  180
ggcaatagat ttgtgggcgc agaggcgggg atggggggca acaagtactg cgcggcgatg  240
acgaagagga gatggagggg gctggcagcg gccgcgtggg tgctagtcgc ggtggcttgc  300
tccgcggtga tgcactggac catgcgccgg gagagcatgg accgcgccga ggagcgcctc  360
```

-continued

```
gtcagcatgt gcgaggagag ggccaggatg ctgcaggagc agttcggggt caccgtcaac  420
cacgtccacg cgatcgccat tctcatcgcc accttcaact acgataagtc cccttccgct  480
atcgaccagg ttcgtcacca ttcgcccccc tcttctccgc cattgctctt gtagattgct  540
atgccacggt atcaattggc agttggttta gcaatagcgg accccgagat cctacacatt  600
gttctgtggg ttgtctcttt tctttaaagg agcaaacaga aaaaaaaggg gagaaataga  660
gatatagaga tgcgttgttg tttgttgacg cttaccgtcg tttagcacgc catgattgct  720
gtggttggct gggacaggtg ctgttcatag tcttgtggaa agaaaaaaaa tgtccattcc  780
tgcggcggtt aggcggggat tttttaggct tattggagac gtagctgaac tgaactgttg  840
ggttggtggc acattgtttg ttcatagagt gattagtgtg ttcgctgcaa aaccatctgg  900
gggttacttt gacatccatt ggggtgtgct cttttgccaa ccttttgatt ccttgtttat  960
tctgagaaag gtccctgtcg cagagattaa attatgttag aagctgcttt ctgcctctct  1020
tttcttttgc ttagattatt gatcctcaaa gccgtccttt cctgcatcta cacttcgttt  1080
ctcttccccc ccttttttt tgtcgattta cctatagttt aggcgtgcag tgtcatgggc  1140
ccatgttatt tgaagacgtg ctcgttttttg catacaatga ccaatcttat tcgttgcatc  1200
attacttttg gtaaatcaac aagatgtctt cttctgattc ttgcaattta tagcatatta  1260
ttgtccagta ttctatttg gcttaataat taatgtccga cacaggacac ttttgcaaaa  1320
tacacggcaa ggacatcatt tgagcgaccg ctactcaatg gggtggcata tgcacagcgt  1380
gtattccatc atgagaggga aatgtttgaa agccagcagg gatggattat gaatacaatg  1440
cagcgggagc ctgcaccccc gcaggttgaa tatgctccag tgattttctc tcaggatact  1500
gtttcctacc tcgcacgcat tgacatgatg tctggagagg tatggttcta tttgatcgat  1560
cttagtattc attggggtgt ttatgaccct ttgatgtctc tttagtgaaa gcaatctatt  1620
tatttacgat acaggaggac cgagaaaaca ttttgcgggc caggactact ggcaaagctg  1680
tgttaacaaa cccatttcgg ttgcttggat caaaccactt gggagtagtt ctcacttttg  1740
ctgtgtaccg ccctgatctc cccgctgatg catcagttga gcaacgtgtg gaagcaacta  1800
ttgggtgaga tgttctaact cacatccttt gttgttttat ttttaaccaa atattctagc  1860
attgtcgcct ttaagactca tgtttaacat gtgggtatga ataaaatttt gtgcactatt  1920
atttgatcat gtaatatctt gtcatcgtgt atcatgccac atttgtggtt cactgatcaa  1980
tactgaattt aggttgacta tgatgacctt aacatgtcta gtaacaggtg ataatagaaa  2040
caatgtgttt ctttttaaa aaaggtatag cgtgcttatg gcagttatgg caggcacatt  2100
tagtaataga tcatgcaggt tataatcatt gcagcttgtc tcaatttaat caaatgatac  2160
tctatgctta tctaatttc aagagaataa tttgctgtgt gctcccagat atcttggtgg  2220
agcgtttgat gtggagttat ttgtggagaa tttgctgagc aaacttgctg gcaatcagga  2280
tattgtggtg aatgtctatg atgtcacaaa tgcttcagag gctatggttt tgtatggacc  2340
ttctagttcg gatgagcgcg tgcctttctt gcatgttagc atgttggatt ttggagatcc  2400
gtttaggagg catgaaatga ggtgcaggtt ggtagtcctt atctgtaaat cttaatttc  2460
ttggctgctt ttgttttcca ctaatgttgt caacctgcag gtatagacaa aagcttccta  2520
tgcagtggtc tgccataacc aatcctttgg gcacatttgt catatggatg cttctggggt  2580
atagcattgc cgctgcatat tctcgatatg acaaagttac agaagattgt agaaagatgg  2640
aagagctaaa aacgcaggca gaagctgctg atgttgcaaa gtctcaggtt tggcctgttc  2700
tttagcactc tcatttacta ggcattctag catatgcatc atgtatggct tagcttatct  2760
atgtttgtct ctcttgcagt tcctggcaac tgtgtcacat gagatcagaa cacctatgaa  2820
tggcgtcctt ggtacttatg catttatttt gatattactt aatcttcagt tccgtgggcc  2880
tatcaatcta attttttcc ttctggcgta ggaatgctgg atatgctttt aggaacagat  2940
ctaactatga cacagaagga ttatgctcaa actgctcaaa tgtgtggcag agcattgata  3000
acgttgataa atgatgtcct tgatcgagca aagattgaag ctggaaagtt agagcttgaa  3060
gcggtgcctt ttgacctgcg ttctctcatg gatgatgtta tttccttatt ttcttcaaag  3120
tcacgggaga agtgcattga ggtatgttac tgttaatgct tgaagtagga aatgatgttg  3180
cctgggccat cacttgaatg gatattgatt gcttttagtc ctagtttttg gctgagcaac  3240
tgacgaataa tgcagttttg cctgaaccaa tctgtcacta tacattgtgg catatacttt  3300
tcctgatcct tttccttctt gctgcagctt gcagtatttg tatgtgacaa tgttccgaag  3360
gatgttcttg gagatccttg gaggtttcgg cagatactaa caaatttggt cggcaatgca  3420
gtcaaagtaa gcaaccattt atggtatttg gtatcctcac actacaactt cgaatgatgt  3480
tggttaagtc gtagataagt ctgtcatcaa atacattcag aaaaatgcgc tgatatattt  3540
atcgtgtgtt ccagttcaca gaacggggtc atgtatttgt gcgggtctgt ttggctgata  3600
actcaaatat ggaagccggt caggtcctaa atggagccat gaatgggaaa gatggtagag  3660
ttgattcaac aactaatggt gccttcaata ctctgagtgg gtttgaagca gcagacagac  3720
gaaatagttg gcaatatttt aagatgctcc tctctgataa ggagtccctt ttggatgatc  3780
ttgagggaac aaattctgat caaagtgatt cagaccatgt cacactagcg ataagtattg  3840
aggacacagg tgttgggata ccattgcaag cacaagatcg tgtttttaca ccgtttatgc  3900
aggctgatag ttcaacttca aggaattatg gtggtactgg catcggttta agcattagca  3960
agtgcctagc tgaacttatg ggtgggcaga taagttttgt cagccgtcct tttgttggaa  4020
gtacattcac tttctccacc acactgaagc gctcatacaa agatatttca gttgattcaa  4080
gtaggagctt gttagaggca ctaccaactg cttttaaggg aatgaaggcc atcttgatag  4140
atgggagacc tgtacgtagt gctgttacaa gatatcacct caagaggttg ggaataattg  4200
ttcaagttgt gaacaatatg agtgcagtag taaaagcttt ccctggacaa aatggagcaa  4260
ctgtttctag gtgagtgttc ttaagttagt ttattagatg ctggagatac aattggctga  4320
gcagtgattc acatttcagt actttccctc acatggaggc tccctcaacc gcaagcctta  4380
tatgtgaaat gggagctctg ttttaaaggc gacgtctagg cgccccaaca ctcctaggcg  4440
ttcccgtcgc gtagctaaat cagcaagagg gcagagagaa agaaggggcg gcgccgaatc  4500
aggccgccgg cggccgattc ggccccagcg acagctgaat cagggcggcg gcggccgaat  4560
cggggatggc ggcagcaaaa tcatgagtgg cggcggctga atcgtgtgag gagagaagga  4620
aaccacggct gaaaaagggg aggggagaag gaaagcagca gctcaatcga gggggagag  4680
gggggaaaca gggggagata taggctggct tctttttctt cctcctccat gctgctgttt  4740
tatgctgctg ttttgttggt tctcatgttg ataaggtgtc accttgctcg tcttagttgt  4800
cgcctaggcg tccagaccag gtggtagttc aacgtcttat cttgccttac cgctttaaga  4860
accataaacg ggctagggaa catttctttt attaaattgt gtgactaaag atttgaattc  4920
gaaacctggt tttgttacca gcatgttaag ctgcatgcac tgacggcctc aacaaagacc  4980
ctaagggctg gtttggtgga cagggaaatg agatcccctc cattttctg tccaccaaac  5040
cagccctaaa ctggtgggaa aggcaggcaa ctcattaata tattttacta catataatag  5100
```

```
ataaaccgtc tatgccatca gtctgtcctg aataagctat tttctttttt gaaaaagtat  5160
aggaccctaa aatccttgac tgacctttta tccccaaact gttttgggga atagcataaa  5220
acattcttaa agcacctgaa tatgcacttt ataattgttt tgtatgacat ctgaaatcat  5280
cacatttatt ctcttgtagg gaaaaggcaa ccattctttt tattgagagt gacttttgga  5340
ggcccgagac agatgttcag ttattgaacc atctacgcga gcacaagaat cgtcagttgt  5400
ctgatgggca taaggtagtt cttttggtca cctccgaagc tgataaggac aagtatggat  5460
ccatatttga tattgtgatg tgcaagccta taagggcaag catgattgct tcatctattc  5520
aacaactgct caaagtagag atgcctgaaa gaagaaataa tcataatcgg ccatcatttc  5580
ttcgcagcct gctggttggg aagaatatat tggtagtaga tgataataaa gtcaatctta  5640
gagtcgctgc agctgcactc aaaaagtacg gtgctaatgt tagctgtgtt gagagtggca  5700
aagatgctat cagtctactt caaccccccac attgctttga cgcatgtttt atggatgttc  5760
agatgccaga gatggatggg tatggattaa ataaatataa acacgtttgt catttccatc  5820
atgttgtttg aagtttgttt gctaggtgaa gtaaatctcc ccactgatca tcagttctca  5880
attattactt ttttaggttt gaggcaacaa gacaaataag gcaaacagag atgagagtta  5940
acgaggaaag gaagaataag ttggtgttga ttgaaggctc aacatttgtt gagtaccatt  6000
tgcctgtttt ggcgatgaca gccgatgtta tccaggcaac ttacgagaag tgtataaaat  6060
cgggaatgga tggatacgtg tctaaaccct tcgacgagga gcagctatac caagcagtct  6120
ccagattaat agtgggaacg acagattcga ctgtttaata tttagatggc tatgaatctg  6180
atttctcatt catcgaattg aagcacacca ccatgttgct tctgtccaag tttgactcta  6240
acccttaaca attgtctgac ctggcctctc gcagcactag atgaaaagga tgaaagtgcc  6300
acgagttggc tatgtatcag caccacagat gaagttgcct caccccggag tgtaggttgg  6360
tagatcactc tcttctttga tgtttatagg ttgttgtata tcttctgaca attcattgga  6420
aaccacatct cgttgcgaca ttggaggaca tcttcaatgc tggtaaattt gttataggaa  6480
tatcctttaa tgctg                                                   6495
```

```
SEQ ID NO: 249         moltype = DNA  length = 9926
FEATURE                Location/Qualifiers
source                 1..9926
                       mol_type = other DNA
                       organism = synthetic construct
SEQUENCE: 249
gcaacagaaa aaaacaacga aacacgcaac gtgcgggggc agatgcggca attccccgct  60
cacggcgcgc acatggaacg ccttcgcttt cctcctccct ccctccgtcc cgtcccgtgc  120
ccccttctgc cttctctcac cgccacggcc actggcattg gccgcgctcg ccgcccaccg  180
cccaccgccc ccgcgccgct gtaggagcgc gcgcttgctt tagcgtaggc catggcccac  240
tactagcggg tgattagcct tgattagcgg gcaccactcc actgttacgg gaggcgcgtt  300
gttttaatcg cgggcgcgcg acgcccgtcg cctgtctcga atatctgctg ccgccgccaa  360
aagtgcggat tcctcctcct ccccgtcggg cggcctcgcc cccccctggtg cctactgggc  420
gctggcggag tgggagtgga tcgacgtgtt gcggccgcgg agtggaggca ataaagggaa  480
agctgggcgg agtgctcggg taccgtagcc ggattagtta ttaatgcccg cgagcagcta  540
gtcgtaggcg taactatttt aaggcagctg tcgccgctgg ggacttgcga aagcttcgcc  600
tcttttgaga agctctgcac cacgcctggc tccgccccgc tccccctcca cctccaggct  660
tccttcacag tctcgctgtt gctagtgctg ccttgctgct agtgataggg gtcccggggc  720
cctcaagttc tgggtgggcg gcaaacatat ggtgggcacc gggcggggga ataaggagga  780
agagaaagag gaggaggagc ggcagtagat ttgggccgca caggcaggga tggggggcaa  840
gtaccgcgcg gcgaggacga agaggtggtg gaggggggctg gcagcggccg ggtgggtgct  900
aaccgcggtg gtctgctccg cggtgatgca ctggaccctg cgccgggaca gcatggaccg  960
cgccgaggag cgcctcgtca gcatgtgcga ggagagggcc aggatgctgc aggagcagtt  1020
cggggtcacc gtcaaccacg tccacgccat cgccattctc atctccacct tcaacttcga  1080
gaagtcccct ccagccatcg accaggttcg taaccattcg cccccaccct cttctccgcc  1140
attgctcttg tatgttgcaa tgccgcggca tcaattgaca gttggttcag caatggcgga  1200
cggacccccg agatcctgca cgttgttctc ccggttgtct ctgtcttttc tttaaggagc  1260
aaacaaaaaa aaaggaaaag aggagagaga gatgaagatg cgttctggtt tgttgaagct  1320
cacagtcgtt gcggcgctag tcgtctagct ggacatgatt gctgtggttg gctgggagcc  1380
tgggacaggt gctgtccatt gtcttgtgga aagaaaaaaa tgcccattcc tgcggtgggg  1440
aaggcgggga ttttttaggg tttaaagacg tcacggaact gaactactgg gttggtgcca  1500
cattgtttgt tcatagagtg gttagtgtgt tcgttgcaaa caccatctgg aggtcacttt  1560
gacaaccatt gggggcgctc ttttggcaac cttttgatcc cttagtttat tcttagaaag  1620
gtcactgtcg cagagattaa taatgttgca agctgctctc tgcctttctt ttttctttag  1680
cttagattat taatcgtcga agccgtcctt tactgcattt acagttcgtt tctcttcccc  1740
tttttgttga tttaccaata gtttagttta ggctcacagt gccgaaggcc catggtattt  1800
gaagacatgt tcattttttt tgcatactaa agtgatgata caatgaccaa tcaggttcat  1860
tgcatcatta cttttggtaa atcaacaaaa tttcttctgc tggttcttgc aatttatagt  1920
acattgctgc tcactgtttt ttttattctg gattaataaa cattgtccac tacaggacac  1980
ctttgcaaaa tacacggcaa ggacatcatt tgagcgacca ctgctcaatg gggtggcatt  2040
cgcacagcgt gtattccatc atgagaggga aatgtttgaa agccagcagg gatgggttat  2100
gaatacgatg cagcgggagc ctgcacctcc gcaggttgaa tacgccccag tgattttctc  2160
tcaggatacg gtttcctacc ttgcacgcat tgacatgatg tctggggagg tacagttact  2220
tctgtttgat tgttctttgt atccattggg ggggtgtttc tcgcgctttg atgcctcttt  2280
agtgaaatct atctatttat ttccaatata ggaggaccga gaaaacattt tccgggccag  2340
gactactggc aaagctgtgt taacaaaccc attccggttg cttggatcaa accacttggg  2400
agtagttctc acgtttgctg tgtaccgccc tgatctccct gctgatgcat cagttgagca  2460
acgtgtggaa gcaactattg ggtgagatgt tctaactcac ttccttcgtt gttttatttt  2520
ttggaccaaa tatttatagt attctcacct ttaagacttg tgtgtagcat ccatacttca  2580
gtaaaatgtg gatatgaaca aaattacacg catgattatt tgaccatgta atatcttgtc  2640
atcatgtatg ataccacatt tgtggttcac tatgatgacc tcgacatgtt tagtaacagg  2700
tgattatagg aacgacatgt ttctttttaa caaaaggcat aatgtgttaa tgatatagac  2760
atttagtaat ggcaaatact gcggtgcaat taacgttccc gtgcaattgc catgcaatca  2820
aactaccaag ggtcatgaaa aactctcgaa aattttatag atgcacttca ttatttcctc  2880
```

```
taccaatata tcaaatcttg agttctaatt catactatgt taagaaatat aaaaaaataga  2940
aaattatgca ctatgcttat ctaattctaa agagaataat ttgttgtgtg ttgtacaaaa  3000
gtatgcatct gttgactatt gtggtaaaat ctaatcaagt tccctactaa tagatatctt  3060
ggtggagcct ttgatgtgga gttacttgtg gagaatttgt tgagcaaact tgctggcaat  3120
caggatattg tggtaaatgt ctatgatgtc acaaatgctt cagatgctat ggttttgtat  3180
ggaccttcaa gtttggacga gcaagtgcct ttcttgcatg ttagcatgtt ggattttgga  3240
gatccattta ggaagcatga aatgagatgc aggttggtag tccttaccgg taaatcttag  3300
ctgtgttgtc tgcttttatt ttgcactaac gctgtcaacc atgcaggtat agacaaaaac  3360
ttcctatgcc gtggtctgcc atcaccaatc ctttgggcac atttgtcata tggatgcttc  3420
tagggtatag cattgctgct gcatattctc gatatgacaa agttactgaa gattgcagaa  3480
agatggaaga gctaaaaaca caggcagaag ctgctgatgt tgcaaaatct caggtttggc  3540
ctatacttta gcgctctctt ttgctaggca ttctagcata tgcaatcatg tatgacttat  3600
ctatgtttgt ctcaggcctt gttctgttgt atatggaatt aggggtcgaa ggtgattgag  3660
ggggattaaa tcttttctat ttaattttga ctagcaaggg attcaattcc cttcaatccc  3720
ctttaatcca tccctaacca aacaagccct tagagagttt atatcattcc ctgtttaggt  3780
gattggctgg ttgccttatg tgcctgatct ctcgcaccac ctccctaatc tgatttctat  3840
aaatcaggta gaggaagatc actggtaaag atctatatat tatgctccta gtattcagtt  3900
gactgcaaac aatattcaca ttatgatggt atcaatagac catcgtgatc atgtgacaat  3960
tcgctttcgc caagcctcag ctgcctgcat cgccttccta gcgccgtgtc atcaccatgc  4020
cacatgccat taaaccttgc cgttgccgct gatgccccgc aacgtgcaga ggacgaggac  4080
gcacaataga agacctgcta ggacttggtt ggtgtagccg atgaggttgc caaggccacc  4140
gtcgctgcta aggatcttgt acgtgccgcc taggatgttg ttgcaaagga acaacatacc  4200
actgttctcg caaaggaaca acatacactg ccgcctagga cccttcacca ttgataataa  4260
ttgttctatt gaatttgact tgtttggcct ctctgaagga tctcaatcct aggggtgatc  4320
gccagctgca atagttttag accccttttgg cctctacact caccgtcctg tcccatggag  4380
tcatgcgccc ttgttgcaac agctgccttc accacttggc atcattgttt cgggcatcct  4440
aggcagtcca aacttgttag tacctccacc atcaattgga aaaaatacta gtgattctct  4500
ttgtcacatg tgccaagttg ggcgtcatat tagattacct ttcggaacct cctctccttg  4560
ctaactctta agaattttga tttgattcat tgtgatgtgt ggacctcccc tattactagt  4620
gtctagttac aaatattatc ttgttactct tgattgcttg cacttccttt tgacatttcc  4680
gctttgagtc aaatttgaga cgtttcccgc cttggctcac ttttttctct tatgggaaga  4740
catagttcgg ctacaccatt cgaaatgttc aatgtgacaa tggccgcaag tttgataact  4800
cctcaactca cacctttctc accaaaggtg tcctgctcag gatgtcgtgc tcctacacac  4860
cctctcaaaa cagtaaagtc gactgtatga ttcgttccat taataacatc atatgtccat  4920
gctccttcaa gcctcccttg cctcgctata ctaggtgaag gtcttcacac tgctacatac  4980
cttgtcaatc gactagccac caaaacactg acatttggca cccccacttt gccctgtttg  5040
gttcacgtac ctcctacgac cacctcagtg tgtttggttg tgcatgctac caaaacatgt  5100
tcgccgtcgt gcctcacaag tcacaagctt gcttcccggt tgagtcaaca gaatcatgcg  5160
ggaagcaagc ttgtgacgtg tgaggcactc tgcaggcaac gatgacttgc tctcgaacaa  5220
cacatgggat cttgtcccat gtcctttcgg tgccaacatc gtctctgaca agtcattttt  5280
ctgctacaag ttccacgccg aaggttccct tgataaatat gaatcttgtt gggtcctcta  5340
tggcttcaca cagcccccta gtatggatta tgacgagact tttagtttag cggtctagcc  5400
tacgattgtt catactattt tgtatttttg ttcattacac tctcttagta atggctagtt  5460
catcagctcg atgtcaagaa tgccttcttg catgacatgc tttgtcgttt gtcatctcaa  5520
caagtccata tatatggtcc gaagcaggtg cctcgcgctt ggtgtagtcg ctttgctgca  5580
tgcttgctca ctttggaatt cactaaggcc aggtttgaca ccttgttcat atatccccac  5640
ataacagaca ggacacattt actgctatag gtggatgata ttgtcctcac tactctagtt  5700
aggatctcct ttgttgcatc atcactgcac tttaggagga attctccata atgatcttga  5760
tgtcatccat cacttcctgg gtgtggctgt tcagcagcgt tttgagtgcc atttctttca  5820
caacgacaat acactttgga tgtgattgag cacgctggca tgatcaactg caaatcgtgc  5880
agcacaccct tcgacactca tgtcaaggtc tcctccatag tcggtgcacc tatcaatgac  5940
cccactcagg atcatagttt ggttggtgca ttgcacacct tcatcggccc gctatctctt  6000
atgcggtcca gcaggtgtct ccacatttat gatcttcatg acattcacct ctttgttgtt  6060
aaacccatcc tgcggctgca aggggtacct agtcatggtc ttcttttgtg cttgtcgacg  6120
acctctgctc ttcttgtcta cgtggatgct gattgggctg tttgtgtgga cactcacaag  6180
tctacctcaa gctacaccat gttccttggt gatgatctgg ttttctagtc ctccaagcag  6240
tagaacagtg tcctactcca cggctctagt gccgaggctg agtaccagac atcaccaatg  6300
gcgtggccaa ggattgctga cttcgacaat tgctacgagg acatgccccc taacgaagat  6360
caccttggtc cgttatgata cttgtcgacc aaccctgctc agcatcaacg caagatcggt  6420
ctgcacttca tctgcaagcg tgttgctatt ggtgatgttt gtgttctcca tgtcctgaat  6480
cctgatgaca taccaatttt ctgacatctt caccaagggg cttctactta tgtcctatag  6540
atgttctgac tatggggtgt gtgtgtgtgt gtgttagaga gtttatctcc ttccctcttt  6600
aggtgattgg ctggttacct taggcgcccc ttctctgttt aggtgtttgg ctggtagtct  6660
tatttccttg ttcagttgat tgtctggttg ttttatgtgc ctgatctcct ggatcacctc  6720
cctgatcttg tttctataaa tcaggtagag gaagatcatt ggtagaggtc tatatattgt  6780
acttctgata ttcagttgaa tgcaagcaat attcacactc tacatctctc ttgcagttcc  6840
tggcaactgt gtcacatgag atcagaacac ctatgaatgg cgtccttggt acttatgcat  6900
ttattttgat tctacttaat cttcagttcc atgggcctgg caatctaaaa tttctgcctt  6960
ctggtgtagg aatgctggat atgcttttag gaacagatct aactatgaca cagaaggatt  7020
atgctcaaac tgctcaaatg tgtggcagag cattgattac actgataaat gatgtccttg  7080
atcgagcaaa gatcgaggct ggaaagttag agcttgaagc ggtgcctttt gacctgcgtt  7140
ctctcatgga tgatgttgtt tccttgtttt cttcaaagtc acgggagaag tgcattgagg  7200
tatgctactg ctaatgctta aagtaggaaa tgatgtttcc tgggccgtca cttgaatgga  7260
tgttgattgc ttttagttct agtttttggc tgatcaactg acaaataatg cagttctgca  7320
tgaatcaatc tgtcactata cttctatact tctctatggc agatactttc cctgattttt  7380
ttccttcttg ctgcagcttg cagtatttgt atgtgacaat gttccaaagg ttgttattgg  7440
agatccttgg aggtttcgac agatattgac aaatttggtc gggaatgcag tcaaagtaag  7500
cagccaattt tggtatttgg tatcctcaca ctacaacttc aaatgatgtt ggttagaagt  7560
atttgataag tctgtcatca aatacatgca caaaaatgca ctgatatatc tattgtctgt  7620
```

```
tccagttcac agaacgaggt catgtatttg tgcgggtctg tttggctgaa aactcaaatg  7680
tggaagccaa tcaggtccta catggagcca tgaatggcaa aggtggtaga gttgagtcaa  7740
caactaatgg tgccttcaat actttgagtg ggtttgaagc agcagacaga cgaaatagtt  7800
ggcaatattt taaactgctc ctctccgata aggagtcact tttggatgat cttgagggcg  7860
aaaattctaa tcaaagtgat tcaaatcatg tcacactagc aataagtatt gaggacacag  7920
gtgtcgggat accactgcaa gcacaagatc gtgtttttac accgtttatg caggctgaca  7980
gttcaacttc aaggaattat ggcggtactg gcatcggttt aagcatcagc aagtgtctag  8040
ctgaacttat gggtgggcag ataagtttca ctagccatcc ttctgttgga agcacgttca  8100
ctttctcagc cacactgaag cactcataca aagatatttc ggtcgattca agtaggagct  8160
tgacagaggc actaccaact gcttttaagg gaatgaaggc catcttggta gatgggagac  8220
ctgtacgtag tgctgttaca agatatcacc tcaagaggtt gggaatactt cttcaagttg  8280
tgaacaatat gaatgcagta gtaaaagctt tcccaggaca aaatggagca accggttcta  8340
ggtgagtgtt cttaagttag tttattaaat gctgttcata caattggctg agcaaggctt  8400
cacattccag tactttccct cacgtggagg ctgcctcaac ttcaaccctt atatgtggaa  8460
tgggagtagg gaacatttct tttattaaat tgtgtgacaa aagattcaaa ctcagacctg  8520
gccttgttac catgttgagc tgcatgcact catggcctca acaaaaaccc taagcaagga  8580
actcacttat aatttactag atatcataga tattctgtct gtttaatcag cttgtaccga  8640
ataagctatt cgcaaattgt ttttgagaat acagaatagc ataaaacatt attaaaacac  8700
cagatatgca ccttatactt gtttgtatga ccttcgaaat catcccattt attttcttgt  8760
agggaaaaag catcaattct ttttattgag agtgacttct ggaggcctga gacagatgtt  8820
cagttattga accatctacg cgagcagaag aacggtcagt tgtcggatgg gcacaaggta  8880
gttcttttgg tcacctctga agccgacaag gacaaatatg gatccatatt tgatattgtg  8940
atgtgtaagc ctataagggc aagcacaatc gcttcatcta ttcaacaact gctcaaagta  9000
gagatagccg aaagaaaaga taatcaaaac cggccgtcgt ttcttcgaag cttgctggtt  9060
gggaagaata tattggtcgt agacgataat aaagtcaacc tcagagttgc tgcggctgca  9120
ctcaagaaat atggtgctaa tgttagctgt gttgaaagcg gcaaggatgc tatcagtcta  9180
cttcaacccc cgcatcgctt cgatgcatgt tttatggatg ttcagatgcc agagatggac  9240
gggtatgtgg atgaaataaa caaagtcgtt ttccatttcc atcctgctgt ttgaagtttg  9300
tttgctagtt gaataaaaaa aatgtttcca ctgaccagca gttctcgatt gttacttttg  9360
taggtttgag gcaaccggac aaataaggca aatggagttg aaagcgaacg aggaaaggaa  9420
gaacaagttg gcttcgattg aaggctcgac aactgccgag taccatctgc ctgttctggc  9480
aatgacagcc gatgttatcc aggcaactta cgaagagtgc ataaaaatcgg gaatggatgg  9540
atacgtatct aaacccttcg acgaggagca gctataccaa gcagtctcca gattggtagt  9600
gggaacgacg gattcggctg tttgatgttc aaaatacgat ggacctgact tctcattcat  9660
cgaagtgaag catcaccatc ttgcctctgt ccagctgact ctatatccct tgacaatggg  9720
cctctgacat ggcctctcac aagactagat gaaaaaagaa gatgaaagtg ccgtgagtta  9780
ggtacgtgtc acacatgaca tgaagttgct gcggcagccc agaggagtgt aggtagatca  9840
ccctgtaact ctcttgttct ttgatgttta taggctgttg tgtcttctga caattcattg  9900
gaaataccac atctcgttgc aatccc                                        9926
```

```
SEQ ID NO: 250          moltype = DNA  length = 19441
FEATURE                 Location/Qualifiers
source                  1..19441
                        mol_type = other DNA
                        organism = synthetic construct
SEQUENCE: 250
aaaacatttg aggacttcac agcaaggaga acatttgaaa ggccattgat gagtggtgtc  60
gcctatgcat tgaaggtatt acacaatgaa agacaacagt ttgaggaaca acatggatgg  120
aagattaaga agatggaaga tggagatcag tcccttgttc atgactacaa ccttgaaaag  180
cttgaaccat caccagttca agatgagtat gcgcctgtta ttttctctca ggaaactgtg  240
aagcacatta tatctgtaga tatgatgtct gggaaggtag taggatattc gtaagccttt  300
acagtaaata cttactattt tatctatcct gagttcctta ctactatttt tgttataaaa  360
cgaagaaatt tctggctctt cttctaactt tcaatattat taggattaaa catgtgtaga  420
acttctcggt caaaaaagac actttagaac ttatattttt attttaatta gaatttgatg  480
tataaaaatt aatcattttt acaatgagtg ttatagtaat ataagttgtt atgtgtcttg  540
ttcaatgtgt taattactat agcatgttcc atagaaatac tgtgcaggct gttactaatt  600
ctctcttatt ctgtctttgt ggaaattaca taattactaa acctcatagt aataataata  660
ataactaaga ctccattttt ctgctaacat tacaaccttg atttcaggaa gatcatgaca  720
atatattacg ttcctggtca acaggtaaag gggccctaac atccccttt aagcttctga   780
agtccaacca tctcggtgtg gtgcttacat tcactgtata taaatatgat ctgcctccaa  840
atgcaacacc acaggagcgt attcatgcta cattggggta aaatgttttg caaagtttca  900
agttgaagct atataggaat acactatttt ttctttagga gacttaacct tgtggttatt  960
gacactttgc agctatcttg gtgcctcatt tgatgtccct tctctggttg ataaactcct  1020
agaacaactc gctagcaaac gaaagatagt agttaattta tatgacacca caaatcatac  1080
ctctcctatt gaaatgtatg gttctgattt tactccatct ggtgatctgc atattagtag  1140
cattgatttt ggagacccaa cacgcaaaca tgagatgcat tgcaggtaga aaactttttt  1200
ttgatgcgaa ttatacaatg cttttgttct tcagatatgc tcagtgcttt ctctttcaaa  1260
cttctctttc agatttaaac atgaaccttc actgccatgg tctgcaataa taatatcaac  1320
agctgtagct ataattgttt tgcttgttgg acatattatt tatgcaactc tgaactccct  1380
tgaaaaggct gaacatgatt atagagtaat gagagaactt aaaggacaag ctgaagctgc  1440
agatatagca aaatctcagg ttcattctac ctcttccagt gtcttcatcc tatgcattgg  1500
tttgttatct catttgttct acttttctct ttttgtcggc tgagtcatta ttgattgtct  1560
tgcagtttct agcaactgtt tcccatgaga ttcggactcc aatgaatggt gttttaggtc  1620
tgtacttctg atatttcttt tttgtctatt aatacatacc gcagttattt gtgtttatgt  1680
tttaatcaaa gacaactaaa taaatttga aaaggatttc ttcttgaatt aggtatgctg   1740
cagatgctaa tggacactga acttgataca actcagcagg attttgtagt caccgctcaa  1800
gaaagtggaa aggtattaat aaacttaata aatgaagtcc ttgatctggc taagatagag  1860
tcaggaagga ttgagctgga agcagtgcct tttgatgtcc gtgatattct tgacaatgtg  1920
atatctcttt tctacgataa atcacaagct aaaggcatag aggtgagtcc taatttagaa  1980
```

```
cttgtattgt ttgctaagct ctgaatattg tttgtgccat gggacctaaa ataatgtgta  2040
attctttttt gagggtagtt ggccgtgctt gtatctgacc aagttcctga tgtcctaatt  2100
ggggatccat ggcggttccg gcagatcatt acgaaccttg tggggaattc tatgaaggtt  2160
agattcaaat atgtggtagc ttcattattt cagcttgctg gcaagttgta actgtgtcta  2220
gtcaatccca ccatttagct tatacaacaa tatactttgt aggaaacgtg acaacttact  2280
aaaatattaa tgtcatgagc ttttgaattt gagatgtgta gaagacaatt ggtagaattg  2340
gtcaattgtg tcgctgagct cgtgggcaga ttatacatga gtacattcac ttggatggca  2400
agaaacctcc ctaaagataa gaagtcagga ttacatgacc ctaatctagc atatttaaag  2460
atattccaat ataatatacc accccccata tttttctcga acgtgcagga aagctgcaca  2520
tctttatatt aagaagataa aaggtccaaa atggaccaaa acaggtatag atacaaggca  2580
cctcacgtgg ccaaaaacaa aagtacaaaa aaaacagtcc ataacttttt ttttttagat  2640
aatggaaaaa tcatccgacc ttggcctcaa atgaggttac ggccatttat tacaagggac  2700
ggaagcatat tgccaaaaca cctcctatga ccacttcaga gaaccccaac tagccaaatt  2760
aaagaacttc agctatcgaa ccacagctac tacatattta aacgcaacgc agacccccat  2820
ccaaaattgc taaagaactg tagtagcacc ctctccacat tacgacatga agactttatt  2880
aactcttggt cctcccttct aggctgaagc tgagaccaga agcggcacca atatgttgcc  2940
ctgaaggtta cctgcacaca tgatttagga gatgaattat tgaacaccac atcatttcta  3000
cttaaccaaa tagcccaaca aattgccgat gcaacggtta atagtaagtt tcgaactctg  3060
ggaagcctcc cgctcgccca aaccccaaac aaatcattaa catcccgagg aggtctcaac  3120
cccgtgctta tctgaatcaa ccgccaaatg aatgacgcat acaaacaact gaaaaatagg  3180
tgctttattg tctccggtct actacaaaag caacatatct tattaccatt ccaatgcctc  3240
ctagccaagt tatcctttgt taatgttacc cctcttttga ggtaccacat aaaaatctta  3300
attttcagag gaagcctaag tttccaaagg tccttattat gcacccccaa cccattgtta  3360
agagatgcca gatacagaga cttaaccgta aacatcccgt tggcggtcaa gttccatctg  3420
aacaagtccc tgtttgaatt caaattggta tgcgcaacaa gtgagaccaa ttgaacccat  3480
tggtccctca attgttgagc caaacccctc cgaaaggata tatttaaggg caccgtggag  3540
aacacacagg caacagtaga gttcttcctc ctcgctaggt tataaagaga cggaaaacga  3600
agttttaacg ttcccgaccc gagccaatca tcctcccaga aacgcacctg ggacccatca  3660
tgaatcacaa aggttccttt actaatgaat gtgtccttaa ctttcataag accactccag  3720
aagtgtgaat cagtggccct acgctgcgcc tgggataagg ttcgattggc cagatattta  3780
cgtctcaata atgattgcca catcccttct tcattgagaa gtttatacaa ccatttgctt  3840
aagaggcatt tattttgaac ctctaaattc aaaatgccta gcccgccaac ctccttaggt  3900
tgacaaatta catcccattt ggccagccta tattttttct tatgaccctc cccttgccag  3960
aaaaaacgcg atctgaaata atctatcttc tccagcacac cttttggtac ctcaaagaaa  4020
gacatcataa acatcgctag actggtcaac acagaattaa ttaatacgag ccgccctcct  4080
actgacataa gttttccttt ccagctgctg agctttttct cgaatttggc ctccactgtt  4140
ttccactcac caattgtcaa tcgacggtgg tgcataggaa tcccaagata tctgaagggc  4200
agcccaccag aactgcaacc aaacagccgt gtgtacctcc cttcatcctc ttttgccttc  4260
ccataacaga atatctcact cttgtgaaag tttattttaa gaccagataa ctgctcaaag  4320
gcacataata tgagcttcat attcgttgcc ttttccagat cgtgatccat aaacaaaatt  4380
gtatcatcag cgtattgcag aatggatagc cccccatcta ccaaatgcgg caccaagccc  4440
ttgatctggc cattttcctt tgctctatta atcagggtag caagcatgtc cactaccaag  4500
ttaaagagaa taggagacag cggatcgccc tgcctcaccc ctctatgggt ctggaaaaaa  4560
ggacccatgt gatcattaac tctaaccgca acatggcccc ccttcatgaa agactcgatc  4620
cacctacacc aggtacttga aaaacctttc atacgaaggg attgttgaac aaagctccac  4680
ttcaccttat cataagcttt ctcgaagtcg attttgaaaa tgaccccatc ccttttcttc  4740
gtatgtagct catgaatagt ctcatgtaag accaccaccc cttccatgat atttcttcct  4800
ggcaggaacg cagtctgcag gggactgatt acattctgcg caacctccgt gatcctctta  4860
gtcgccacct ttgtgaagat tttgaaactg acatttagta gacaaattgg tcggtattgt  4920
tgaaccgaga ttgcctcccg agtcttagga agcaaaatga tagtcccaaa gttaagacta  4980
tacaaaggga gatttcctga gtggaactca cgaaacaaag ccataagatc atctttaata  5040
acatcccaac agatttgata aaattccgcc gggaatccat caggacctgg agccttgtta  5100
tgttccatac taaaaaccac cgcttttact tcatcttcag aaaatggctg ggtgagcttc  5160
tcgttctcaa cttgagtaac ttgtattata tcatctctaa gatcctcatc cagactaaaa  5220
gacgtgtttt ctgggggggcc aaagagattt ttataataac cagttatatg actctttaat  5280
tctttctcgt cgtataacat acgagctcca tccgtcatct ggaagatgcg attcttcctg  5340
aattttccat tggctatcat ctgaaaatat ttagtattac tatccccctc caggagctcc  5400
ttgaccttcg ctctttgata ccactttatt tcctcctccc ggagtagctg agcaagcctg  5460
ttctgtaagt agttatgcag atccaactcc gaagtactca acagaactac ttcagctctc  5520
ttatctaaat catcaagctt agctatgatc tccttttttt ccttttttcaa caaccccgaa  5580
gtgtgcattg cccaacccct taagtgttgg cgcaccttcc taatcctggc ttgccatttc  5640
tccaaaggag tagaaccact tgtctcattt acccaaatat cttttaccat atccacaaaa  5700
ccatccctca gaaaccagcc tagttctaac ttgaacggag gaattgtatg ggcggttaca  5760
acacctgtgc taagaagcag aggagtatga tcggatatat ttctcgacaa ggcatgtacc  5820
gaagctctag ggtattttcc ctcccattct gtagctacca aaatccgatc caacttctca  5880
taagtcggaa tatccctagt attagcccag gtgtaccttc gccccgacat ctgcaattct  5940
cttagatcaa gaccatcaat taccgcattg aaaaggaacg gccaacgatg atcaaatcta  6000
tcattatttt tctcagatgg agatcgtaaa atattaaaat ctcccccaat gagaataggt  6060
aaagtttctg tattgctcac acggactagc tcagaaagga attcttgttt gaagcagtcc  6120
tgggcagggc catacaccga gacaagagcc catttaaaac catctgcttt atcaagcaaa  6180
ttaaacttaa taaagaaatc cccttccgtg atggcaccaa catcaaagac atcagcgtca  6240
attcctaaca acatcccccc agatctacca tgaggttctt tgcaatgcca gataaaattt  6300
ttcccagcac acaaattcct tagtagatga tctgggaagg atttgcggcc tgtttcagag  6360
agggcaataa aattgagacc atgttctttg gtcagatccg aaatgtatct aagttttttc  6420
aaatccttga acccattgct gttccaaaag attcctttca ttggtaaaca attaattaat  6480
aatcaagccc gacctttttt cttagaacac aacgaaccct gactagatgg ttttgtacag  6540
actgacttaa tcagcccatc agtgccatcc gtctcttcat gcataaatatc cccacacaaa  6600
tgatttaaaa tgaaatgatc aaactcttcg tcctctacta ctccctttcc cataaaatca  6660
gataaatcag cctcgttctt acccactagc tgatcctgaa ctctattaat ctctaatttt  6720
```

```
ttcaactgac caatagagga agcaactgaa ctaggattag aacccgctaa aatgccaata  6780
tttttaaaag aatccagaat ataattatcg ggtaaactaa taaaggaaac attgttacct  6840
ttagtcggct gatcgtccag gttgtatccc gctttcagcc gaatcgctcg aactagcgag  6900
tcttcactca ccgaatcaga gcggcgcgag ctacgacgca gtgcatgcac ttttcctgtc  6960
aacgcctccg ggatactgcc caacttttca atactaacag cattgaccga gagacaggta  7020
ccctgagatt gatccagatc cagctgtgta gggccagcgc acaccgattt cccactggac  7080
gtgttgctgt tcagcataga atccgacacc ttattaactg cccctgctga atcctttgat  7140
gttcccttca agctcgcccc cttattccct ctttcaccta tattgtgatc cttgttttga  7200
tcctgaaatt catcatcatc attatccccg atatgatcca tatccatcgg caaaggctgg  7260
tcaccttcag ctgctgactc caccctgaat ttcagttcat ataagtagtc tccaattacc  7320
acatcaacta cttgcggaat caaattcggg tcaagcacgg ccaccttcag ccttgccctg  7380
tcaaacttcc gagtaaacaa catatccacc tcttttgaga tgcctagcat agaaccaacc  7440
gcccagatta ccgagtactc tctaagttcc ttaggtaaac cagtgaactg cacccaagcc  7500
ttaggcatct catattttat ttcctctcca aacccctctt ccttgacaag catctgtgca  7560
ccaaattttg tatgaacagt tccccactcg atcatacggt gaagttcacc cctggaaggg  7620
aaacacgtcg agaacacatt gttccccaca cacttcacac accagtccca atcagcagcc  7680
accaaccttt taagctcatt caaaatctgc tcttcattca tggaaccctc cacaatagac  7740
actgtaccat tgcagccacc ttgcctctgc tttactggaa tgggttgggg tataaagtaa  7800
aaccccaatc cctccaccgc atacccgcaa ggtattgcaa aagttttgca ggcacgaacc  7860
accggacatt tcgaagttaa gtgagttttg acatcacaaa tttcacaaaa tagctcaata  7920
ttacagtcac tcaactgatg acctttattt ttgcacctga aacaaaacgg cactttctct  7980
tttgaacttg aaatcacaga agaacccacc ttgtcatcca agtgggttgg agtagacaat  8040
tctttgatgg tctccaactt tgaactgtgt tgggacccaa tattcggacc tgctggattc  8100
cccctcgagt tctgaatgtg ctggctcttc cccacagact gctgcagcaa ggaaacaatc  8160
tgttccatgg tactatctgg aacaggcctg acagcgctac cgttgccaat tgatgttgta  8220
attgcctgtt ggagcaagtc cacagcgttt gatacttgag gagtcaccga agaagcccct  8280
gaacctccca gaccctgtcc agcgaccatc acagaggaag cccctccatt tgaaaacctg  8340
ctgtgaacac ctccgccccc agactgggtt ggcaaagtac gaccaccata gaaccggcct  8400
ccggcagaag cacctcttcc accacgccac gctccagcac ggccctgtcc acctccccga  8460
cgtccaaaag gacggcgtcc gccaccataa ccaggatgga acactggttg ggatccaccg  8520
cgtccaaagt cagtgttcag tcccaaacca gcgacatatc ctcccgtgcc cccaagcagt  8580
tgctgaccgg tggaaaaacc tgcagcgccc tcggactgat gctggccgcg actgcctcca  8640
cgccctccag tatcaccaac cggcgccatt gcgttcctta cagcctcgac gaaggtgcca  8700
ggagccacac cccgggagga aatgtgaacc gccctggcag cagaagaact ggtgcctgag  8760
cgggagaaca aggaagccag cccagcagtt ggcctataag gaatcctagg actgagaatc  8820
atatgttggg ccctcccatt ccaacgggga caagcactaa ttaagccaac attccttgat  8880
tccagcacag gatccgcatg agaatcccag aatatcgcct gacttgcatc cataccaaaa  8940
tcattcaaat tcaaaccatc agctaaccgc tccgctgata ccgctcccat tgaagacgtc  9000
ttcttcaacc tttggccgtg gcaccttcca ggggagcagc gccattgcgc tttttctagt  9060
gcatgtccaa ctgtgaactc cggcgaacgt cgtggcgacg gcaatttgcc ctgccatggc  9120
ttcaccttat tcctagaaga agtgctcgga ctaggagaat gcaagcatgt actcaacgtc  9180
ggtcctggtc ccgacctgca tacaccgccg actacctctc ctacctgttc gagagcttca  9240
ttccaaatag attttggtgg cgcggaactg cagtcaatta gcttgccgtc aacacaggac  9300
agagacccgt tcacgaaaac agagagccga ccaccctcag gtgtccgtcc gctatttgcc  9360
gaaccggcca gatcaccaac ctcctgatcc agctgaacct gacaatcagc aacctccgcc  9420
agtgggcgga cgaccaccgc atcggtgggc gccagcgtct ttcgacgacg acccttccga  9480
gcgtacgtgg ccaagcaacg tcgctgcata gcgcagagaa cgaacgaaca accactggcg  9540
ggagaccggc ctagatggcc gcctcccacc tctggtgtcc cactccgccg agacagaggg  9600
aagagcactt accgggttac gccgcgcgcc tagccgggac gcccacgcgg cctagaccgc  9660
cttgccgtgg tcaccgcaga gaagaaactc gagcgccagg gtccaccgcg gcctgcgatg  9720
ctctctgatg agcagcggga agttgcggcg tgcgaagcga ccggcccagc agttgagcac  9780
ggcgtcgacg gcgtccgcgt cggcacgagg cagcgcgagc aagcgcgcga cgacctcgga  9840
caccttccag tcccgctgcc accggttgcc ctccacgcgg aggcggtgtc acgcaatcaa  9900
aaacagtcca taactagaga gctaacaaca gaacagctac aaccctgcca ggggagtgta  9960
ttgggcatca acacggactg aggcagggtg atcctctatc gcctatgctg tttattcttg  10020
taatggatgt cttgaatctg cttgtgcagc gagcctctga ggaagggttt cttcagcctc  10080
tttcttctag gaatatgcag catcgtatct cgctgtacgc ggatgatgca atgttatttc  10140
tatgtcctac tgccccggat atcagtatgg ttatggatat tcttcattta tttggttcaa  10200
cttcaggtct aaggactaat gtccagaaga gcagtgtgtt cccaatctga tgtggggaag  10260
aagaggtgaa ttgtttacag gacttgctgc tatgcaatat ttcagttttt ccctgtaagt  10320
acctcggttt gcctttgtct cccaagaaac tcacaaggga ccaggttcaa gccattgttg  10380
aaagagtggc cagcctttg ccaggatgga aagctgaact tatgaccagg gctggtagag  10440
ctattcatgt gcagtttgtc atgacggcta agatgatata tgcagctctg gcacttgacc  10500
ttcctgtatg ggccatcaaa gcaatcgata agctgaggaa gggcttcctc tggaggggta  10560
ggaaagagtt ccgtggtggt cactgcctct tggcttggcc taaggttacc cgtcccaagg  10620
agttgggtgg tcttgggatt agtgagttaa agaacctctg ttgggctttg agagctcgct  10680
ggccatggct gcagaaaaca gaccccagta ggccttgggc ggacttcccc attcatgttt  10740
gtaaggtggt taaaaatctg attgctgcag ccattattac taagctcggt gatggagcca  10800
ataccctttt ctggaaggac agatggttgg aggggagatg tattaaggac atagctcctg  10860
cgttgtttga tttggtgccc ttgcgtcttg ccaacaaacg gttggtcaaa gatactctcc  10920
ctaatttcca ttggctctca gatgtgcaag gggcaatctc agtcagagtc attgctgaat  10980
tcctggaact ttgtgaagtg cttgatgcag ttgtgctcca gcctggaata agggatcgat  11040
atttatggaa attcagcgct tcaggtgatt atacatctag ttctgcttat aatgctctct  11100
tccttggttc agttcagttc gaaccagcag agcggctatg gaaatcttgg gctcctggga  11160
agtgcaagtt ctttatatgg cttgtggaac ataataggtg ctggactgct gacaggctca  11220
gaaaaagagg gctagaccga ccagagcagt gccccttgtg cgaccaagag gttgaaacca  11280
taaatcattt gctggtcaag tgtgtttttg ctaagcagtt ctggtttgat ttccttaatt  11340
cagtggggtt gcgggatctg tatccagctc atgaggaatc ctttgagtcg tggtggaagt  11400
ctagcagctc cggcatcgga tcttgtgaga aaaggtttca attctttagt gatcctaggt  11460
```

-continued

```
gcttggacca tttggaagca taggaatagg tgtgtttttt atggttgtaa tcccagcttg  11520
ctcacgaccc ttaggatggc tagggaagag gcggtgctct ggtccatgac tggtgccaag  11580
gccttgtcct tcctccaagt cgatgagttg ctggcttaaa acagcggtgt gggtcgtgtt  11640
tcctccatgt tttagtcagt gatccgtagt tagtctctag tggtgtatgt gctgtattgg  11700
ggttctctcc ccctttcttt tcttctatta atacaaagat gcgcagctct cctgcgtatt  11760
ccagaaaaaa aagaaaaaaa aaacaaccct gggatagggg ctgctaggag atccaaattc  11820
ttggccccag ccagcaccca caaatccctc tcctccttag cttttctaat agccggtgag  11880
agcggcacag atggtgagac cagagaagct gaaggttgta agacgacgag ttgacatccc  11940
ccaaagtcat agtggtcaat gtgtcgcata tgctgtagct agagtgctca agcaaggcag  12000
aagctctttg tgccgatgtt gaggtagtcg agcacgaggg tgagtagcca tggttgagga  12060
tgccatcttt acgccatggt gatggtcgag gcgcgtcgag acagtccatt gtataagggg  12120
gtgatgttga ggtcaatgta gtcaaggcca tcgaggatgt cgacgaaaat agcgacacag  12180
tcaaggcagg tcatcatgga ggaagcatac accggatttg ctaggcctga gaacgtgtcc  12240
tggagaacgg cacgctacac tgccaatata agacatgcta gttagagagc cccaacaatg  12300
tgtcaacatc cgagcgacct tggaagagag tgcctcaacg atggttgatt gtggtgccca  12360
aaacaactga gcacaaggtg tcgatgtatc ccacaattgt caaattagat gatatatgtg  12420
ggaaagagac aatgatgctg gcgatgtggt tatgctgaat gaagaaggaa cagtgcggga  12480
gtgaacgctc ctacccgaag gggagtagtt tgggccgacg tccttggcca aggcaatggt  12540
ccagacataa ggtacagtgt gcccaaaggc agtggtccag aagcaaggta tggcgtcaaa  12600
aacagtgttc gctgttggtg atgaagagca caaaaagttt gatgaagacc aagtgcatcc  12660
tggtggtgcg caagaggtgc aacacaatta tcgatgtaca tggagcgaca atgtagatgc  12720
attgttgtat gccaaccatg gatagaggca tgcctatgag ggtgtctcaa ttagagaatc  12780
tctaacattg ccttaaatca attctctatc ttataatata gtgcttaact tataaaaaac  12840
tgctccaaca gtgctctatt ttacattttt atcaaaaaat atagggcaga ccataaagtg  12900
accaaaatat actacactct ggattagggc ttaactgttg caacacaatt tgtttttagt  12960
gccttaaaca ctttaaatga tgtagtattg taatttttgg aacattattt tgaggggcag  13020
cgagtgtagc gtagagacag tttatgaggg gcagtagcgg aagtgttggg atagcaagca  13080
caaccaaata cacggagttg ggttgtgtcg tacaaggcga agtaggtggt ggggtggctc  13140
accaccttcg atgggaggcg attgaggagg tgggtggcgg tgtgcaaggc ctctgcccag  13200
tagttggcag ggagagacgc ctgaaagaga aggcaacaaa tcatgttggt ggtggtgcga  13260
atcattcgct cggcccgacc gttttgggca gaggtgtagg ggcacgagag atgcaattga  13320
acgccactgg cgaggaagaa cgaccgagag gcatggttgt cgaactcgcg gccattgtca  13380
cactgcagtg catggaccgg gcgacagaac tgggtggaga cccaggcgaa gaagtgagtg  13440
agggtggtaa acgtgtcgga tttcattcga aaaggaaaag tccataggaa atgggaaaaa  13500
tcgtccaaaa tcaccaaata gtatttgtat cctgacagac tgagtaccgg ggaggtccat  13560
agatcacaat gaaccaggtc aaaagcctgt tcagccctag aagaagatgt agtgaaagga  13620
agacgggtat gtcggtcaag ctgacatgca tgacagaggc cctcaaaatg tcccctatta  13680
caagaagaat ctaaagtgct ggaaagcttg gtcatgacct agatcctggg tggccgagac  13740
gacgatgcca agtggtggag gtggtggtgg agaccaggac gggaggtgga gacacgccgg  13800
tggacgacga ccggagtgtg tagaggggcc cgacgctgtc acatcgggcg agtggggtcc  13860
tggtggccag atcctttaca gaaaaaccag tagggtcaaa ctcaatggaa cacgaattgt  13920
cggtggtgaa ccaacggaca gaaagaagat tgtgagtgat gtgaggggct acgagaacgt  13980
cgttgaggta gaacagtcca gggagaaccg aggcacctac tgaggtgact agaagagtgg  14040
aaccgtttcg aacgacgatc gaggtagggt gtgtgggggg aggtgggtgt gagcgagagc  14100
atgcctaggg tgggggtggt gtgataggat gcaccggagt cgatgaccca gtcagaaggc  14160
ggtggggcca acgccatggt gctgtatgcg gcagcgaggg caacagggtc ccaacctgca  14220
acgaacgagg accatggtgt cgtggtagac ggtctcgtag gcgggagttg aggcgggccc  14280
cgggtcggtc ggggcacgcc gtatggaggc atgttgtagg cgggcggcgt agtcaggaga  14340
gccggaggac gggaggcgct gggggcctga cccagccaca tggagataat gccggtccag  14400
gggttgtaga acgacggcca actctggtcg ccacccctat cggtggaacc tccacgagag  14460
gagctgccgc ccccatgtcc gcccttgtag gggcgacggc cgccgtcgat ggtggaatgc  14520
tgacgagggt ccgtaggagc cgcggtgaag ggccgagcgg gggtcctggt tgacggagcg  14580
cgggggggcga gtcctccgga agacgcctgg gcaccagggg tggcgctgta gagtgccgga  14640
gtgggagcct cgatcgtcat ggtgagctcc tcgagaagaa gttcattgcg cacggcgtgg  14700
aaggtgggaa aaggtacggt cctcttgatg agagccttca ggtggccgta gagggggctg  14760
aggccacaca ggaggtttag caccaaggta cggtccgcca gcgactcgcc aaggtcgcgg  14820
agggagtctg ctaggccctt catctggcgg cagtactccc gcacagagag gtcccccctgg  14880
gagaattggt ggaactgatc atcgatttga agggcccgag cgtcccggtt cccgaggaat  14940
tgttcctcga gggcgagcca cgcctggcgg gccgtgtccg ccttgtcgca gatgatgtcc  15000
tggagctcga cggtgatagt gtcgtggagc caaaagagca cgactgtgtc catcagggac  15060
caggccatgg gcggtggggt gacgatgtcg tcgaggacgt ggtcggcgag agcgtagcgc  15120
cgcagggtga ggacctgccc ccgacagcga gggtagtggg aggacgccgg gtctagcacg  15180
attgacacga gggaccatat gttgtggaga ccggcagcct gcgcatgaag ggcggcgatg  15240
tggtcggcgt cgagtccagg ggcgatgggt gcctggggtt gggtggaggt gcctccgggg  15300
tgaccggagg atgcccgagg aggagtcgct gagcggtagc catttgggcg gtcagagcag  15360
cgctcatggc acgctcttgc tacagggcga gggtcgcagc gcgctcgcgg tcgagggaag  15420
cctccacggc tgcctggata gtggcgatgg ccgtgaccag cgccgacgag gccgtcgggg  15480
gggcgggggg gggcagtgac gtcagcccat gtggcggtgg tgtgggcccg gaggagaatc  15540
gcggcgtcgt tgagcagcga gggtggcatc gggtaggggc ccgagatcgg cgatgtgggc  15600
ccctccccaa cagcgaggtc gctaggggtg ccgagtccgg cagtggcgag ggcggcggta  15660
gccgcggcgc tgcgtgctgg tggggccaca gtggcagtgg ccgcagggag ggccgcgcgt  15720
ggctgctggg cagcagcagt cgtagcggca gccggggtgt agggggaatg aggtggtgtc  15780
gacatggcgg caccaggtgg ttgggcggcc gacgctgcgg ggttgacggc ggcggtggag  15840
gaaggaccgg tgcgagcggc cgaggtggct ggatggccgg cgcggtgccc agtgaggggg  15900
tccggcgggg gcagcccttg ctgctgggcg gcggcgcagg aggaggcgcc gcggcggcca  15960
gcctggggag gagcggcgac cggtgggagg aaggggagcg gcgatcgggc ctggggggag  16020
ggagaagggg ggagcggtgg ctgccacgga ctggcggcgg cagggagggt gggagggaat  16080
tagtgtggct ctgataccat gtagaactat ggaaaaccct aaccctagaa tagggttggg  16140
cagtgtatta atagaccaaa taactgggct aggcccatta caagggacgg gtatctaaaa  16200
```

```
aaatagactg cggctttttt tttagataat ggatactagt ccagcttctc ctcgtttgga  16260
ggattagcca acacaccaaa agtttttaca tggagtagtc acacgactag ctgctttatt  16320
tgtccttttc atttatgcaa cctaggaatt atttgacttg tctccatctt aatgtgtctg  16380
cttttaaata cagtttactg aacagggcca catctttgtt caagtccatt tggtcaagga  16440
actaaacagg aaaggaaaca atttttgtga tgtttctgct cataacagag aaattctgta  16500
tgattctgac aactcgatgc tatggaacac actaagcgga cttgaagtag cagatagctg  16560
gaggtccttg gagaatttta cgatgttcaa gaattcaaat ggtgaaacag atacaattag  16620
gttagctgtc agagttgaag acaccggcat aggaataaca aaagatgctc aaatgcgtat  16680
ttttacacct ttcatgcaag ctgacagttc cacctcacga acatatggtg gaactggaat  16740
tggcttgagt attacaaaac gtttagttga attgatgggt ggagaaatag ggtttactag  16800
taaatcagga gttggtagta cattttcttt tactgccatt ttcaaggaga acagaggatg  16860
tcctggagat atgaaaagat actattctga acctactccg ttggattttc aaggaatgag  16920
ggctcttatt attgatggaa ggagtgcacg tgcagaggtt actatgtacc atcttcgtag  16980
acttggaata cagtgcagtc ttgttgccac atctgaatct gaatctgcat cttcagcttt  17040
gatgaaagcc tgcacctcaa ggttcatttc cttgtgtagt ttactgtttg atttacttct  17100
acaagtttta gaaattagaa gttattttgt tcaaataaat gtaacattcc ttgcatttat  17160
aaactttttgt catcttaaca catggctttg ctatattttc tttagttggt tgtgtgctat  17220
ttctttgaat attttccata ttgtcgatcc caaaacaagg tttcgtaact tctcatgaac  17280
tgaagaaaag taggagaaac agagtgaaac cttcgttggt ttgagtttag aaactgaaat  17340
aggatagttc gattctaaat aacttgtgaa ttcattcagt tgttgctgtc atcattataa  17400
catatcaatt tgttcatggc cagcaaccta cacttgtcct cagtattacg acccaacaaa  17460
atcaatgcat aatgtcgcca tcatcacttt ccatgtatgc attttctttt ctaagcactg  17520
ttgatgcctt acttgttgat gttatcattt atattttaca tgttgagcag caaaaacaat  17580
ccggacatgg tccttgttga tacagaagct tggggtaaag gttcaggttt ggcattctat  17640
catcgttttg tagattgtca actaaagggc gcacacaagt tttctcagcc catgccaaag  17700
actattcttt tgggaagctc aataagccct gttgaatctg attatttaag attgacagga  17760
tttggtgatt gcataaggaa acccctccgt cttagtacta ttgttgcctg tcttcgcaaa  17820
accttagggg ttggggttac aaggcagcag agtagagacc aatctttggt tcttcaaagt  17880
gtactaactg gaaaacagat tctggttgtg gatgataatg cagtcaaccg taaagttgca  17940
gctggttctt tgaagaaata tggatctaaa gttacatgtg ttgatagtgg gagtgatgca  18000
attgatatgc tcaagccacc tcacacattt gatgcttgct tcatggatgt tcagatgccc  18060
gagatggacg ggtaatgttc ctttccaatg agttactaat gaaaaagagc gcagatttgc  18120
tgcccaggcg ttctcattat ctaaaatacc atgttgcaat atttcaaaaa tcatcacaaa  18180
aatcatgtat gcagtacaca aagttaggta tagccgcaac acttcagatt gaaatttctt  18240
cctagatgcc aagaaccaaa atagacaagc agtcaacctg gcagtgttca tcatgtgctg  18300
acagtgagac tttgtttttt aatctcagca tcaaagatga actttattga attcttgagg  18360
ctacacttaa ggtgtacttg cacacatgtt ttttgtgatg attgttgaaa cattgcaata  18420
cggtatttta gaatgtgggc gccaatttcc ctgggcgcca tatgatttcc aatggaaaat  18480
tgtcatatgt tatttacttg cgggatatac tataagagtt caatatgtaa aagattcttt  18540
gtgcagaagt cactcttgga acatcttacg ttagttcaca tggaagcatg tctttagttt  18600
taggtatgtg cttcttttgg attttgtgga atcatcggaa cagatgcatc tttgatggcc  18660
tttcccctaa tgttgctaat tttctaatcc atgtgggggga tgagcgccgt ctgtgggaga  18720
ctgccggggc caaggggttg acatcccttg ttgcctccct ctctcatgta gcctagagtt  18780
ttatagatga gtcagtctat gctagtttcg ttcaggccgc cgtaaggcgt cagttgtacc  18840
ccggtctatt ttagaccttg tttatttgtt cttttaatat aatgatacgc agctctcctg  18900
cgtgttcgag aaaaaaagag aaagttattt tttggtcctc aaataacaac acttgtcaaa  18960
tgtatgcatc tcctcatgtt attagcaagc actctcatag gagtatcact gaggataatc  19020
tctcttttgt tttcacatcc agtccttgct taaaaaaatg cactgtagcc tcacatgctt  19080
gtgtttgctt tcctatgggt tataacaagt ggttgcatct actttgatca cttgtagatc  19140
cactgtagga ctaccattaa caatattcac attcaattgc aggtttgaag ctacaagatt  19200
aatccggtcc atagagaaaa aaataaacga tatgatcatg atgggtgaaa tatccgctaa  19260
taattatgga aataaggccc attggcatgt accaatatta gctatgacgg cagatgtaat  19320
ccaagcgact tttgaaaaat gtatgcagtg tggaatggat ggatatgtgt caaagccatt  19380
tgaagaacag cagctctact ttgctgttgc tcatttctta gagactgatg aaacagaata  19440
a                                                                  19441
```

```
SEQ ID NO: 251          moltype = DNA  length = 19441
FEATURE                 Location/Qualifiers
source                  1..19441
                        mol_type = other DNA
                        organism = synthetic construct
SEQUENCE: 251
aaaacatttg aggacttcac agcaaggata atatttgaaa ggccattgat gagtggtgtc  60
gcctatgcat tgaaggtatt acacaatgaa agacaacagt ttgaggaaca acatggatgg  120
aagattaaga agatggaaga tggagatcag tcccttgttc atgactacaa ccttgaaaag  180
cttgaaccat caccagttca agatgagtat gcgcctgtta ttttctctca ggaaactgtg  240
aagcacatta tatctgtaga tatgatgtct gggaaggtag taggatattc gtaagccttt  300
acagtaaata cttactattt tatctatcct gagttcctta ctactatttt tgttataaaa  360
cgaagaaatt tctggctctt cttctaactt tcaatattat taggattaaa catgtgtaga  420
acttctcggt caaaaaagac actttagaac ttatattttt attttaatta gaatttgatg  480
tataaaaatt aatcattttt acaatgagtg ttatagtaat ataagttgtt atgtgtcttg  540
ttcaatgtgt taattactat agcatgttcc atagaaatac tgtgcaggct gttactaatt  600
ctctcttatt ctgtctttgt ggaaattaca taattactaa acctcatagt aataataata  660
ataactaaga ctccattttt ctgctaacat tacaaccttg atttcaggaa gatcatgaca  720
atatattacg ttcctggtca acaggtaaag gggccctaac atccccttttt aagcttctga  780
agtccaacca tctcggtgtg gtgcttacat tcactgtata taaatatgat ctgcctccaa  840
atgcaacacc acaggagcgt attcatgcta cattggggta aaatgttttg caaagtttca  900
agttgaagct atataggaat acactatttt ttctttagga gacttaacct tgtggttatt  960
gacactttgc agctatcttg gtgcctcatt tgatgtccct tctctggttg ataaactcct  1020
```

-continued

```
agaacaactc gctagcaaac gaaagatagt agttaattta tatgacacca caaatcatac  1080
ctctcctatt gaaatgtatg gttctgattt tactccatct ggtgatctgc atattagtag  1140
cattgatttt ggagacccaa cacgcaaaca tgagatgcat tgcaggtaga aaactttttt  1200
ttgatgcgaa ttatacaatg cttttgttct tcagatatgc tcagtgcttt ctctttcaaa  1260
cttctctttc agatttaaac atgaaccttc actgccatgg tctgcaataa taatatcaac  1320
agctgtagct ataattgttt tgcttgttgg acatattatt tatgcaactc tgaactccct  1380
tgaaaaggct gaacatgatt atagagtaat gagagaactt aaaggacaag ctgaagctgc  1440
agatatagca aaatctcagg ttcattctac ctcttccagt gtcttcatcc tatgcattgg  1500
tttgttatct catttgttct acttttctct ttttgtcggc tgagtcatta ttgattgtct  1560
tgcagtttct agcaactgtt tcccatgaga ttcggactcc aatgaatggt gttttaggtc  1620
tgtacttctg atatttcttt tttgtctatt aatacatacc gcagttattt gtgtttatgt  1680
tttaatcaaa gacaactaaa taaattttga aaaggatttc ttcttgaatt aggtatgctg  1740
cagatgctaa tggacactga acttgataca actcagcagg attttgtagt caccgctcaa  1800
gaaagtggaa aggtattaat aaacttaata aatgaagtcc ttgatctggc taagatagag  1860
tcaggaagga ttgagctgga agcagtgcct tttgatgtcc gtgatattct tgacaatgtg  1920
atatctcttt tctacgataa atcacaagct aaaggcatag aggtgagtcc taatttagaa  1980
cttgtattgt ttgctaagct ctgaatattg tttgtgccat gggacctaaa ataatgtgta  2040
attctttttt gagggtagtt ggccgtgctt gtatctgacc aagttcctga tgtcctaatt  2100
ggggatccat ggcggttccg gcagatcatt acgaaccttg tggggaattc tatgaaggtt  2160
agattcaaat atgtggtagc ttcattattt cagcttgctg gcaagttgta actgtgtcta  2220
gtcaatccca ccatttagct tatacaacaa tatactttgt aggaaacgtg acaacttact  2280
aaaatattaa tgtcatgagc ttttgaattt gagatgtgta gaagacaatt ggtagaattg  2340
gtcaattgtg tcgctgagct cgtgggcaga ttatacatga gtacattcac ttggatggca  2400
agaaacctcc ctaaagataa gaagtcagga ttacatgacc ctaatctagc atatttaaag  2460
atattccaat ataatatacc acccccata tttttctcga acgtgcagga aagctgcaca  2520
tctttatatt aagaagataa aaggtccaaa atggaccaaa acaggtatag atacaaggca  2580
cctcacgtgg ccaaaaacaa aagtacaaaa aaaacagtcc ataacttttt tttttagat  2640
aatggaaaaa tcatccgacc ttggcctcaa atgaggttac ggccatttat tacaagggac  2700
ggaagcatat tgccaaaaca cctcctatga ccacttcaga gaaccccaac tagccaaatt  2760
aaagaacttc agctatcgaa ccacagctac tacatattta aacgcaacgc agacccccat  2820
ccaaaattgc taaagaactg tagtagcacc ctctccacat tacgacatga agactttatt  2880
aactcttggt cctcccttct aggctgaagc tgagaccaga agcggcacca atatgttgcc  2940
ctgaaggtta cctgcacaca tgatttagga gatgaattat tgaacaccac atcatttcta  3000
cttaaccaaa tagcccaaca aattgccgat gcaacggtta atagtaagtt tcgaactctg  3060
ggaagcctcc cgctcgccca aaccccaaac aaatcattaa catcccgagg aggtctcaac  3120
cccgtgctta tctgaatcaa ccgccaaatg aatgacgcat acaaacaact gaaaaatagg  3180
tgctttattg tctccggtct actacaaaag caacatatct tattaccatt ccaatgcctc  3240
ctagccaagt tatcctttgt taatgttacc cctcttttga ggtaccacat aaaaatctta  3300
attttcagag gaagcctaag tttccaaagg tccttattat gcacccccaa cccattgtta  3360
agagatgcca gatacagaga cttaaccgta aacatcccgt tggcggtcaa gttccatctg  3420
aacaagtccc tgtttgaatt caaattggta tgcgcaacaa gtgagaccaa ttgaacccat  3480
tggtccctca attgttgagc caaacccctc cgaaaggata tatttaaggg caccgtggag  3540
aacacacagg caacagtaga gttcttcctc ctcgctaggt tataaagaga cggaaaacga  3600
agttttaacg ttcccgaccc gagccaatca tcctcccaga aacgcacctg ggacccatca  3660
tgaatcacaa aggttccttt actaatgaat gtgtccttaa ctttcataag accactccag  3720
aagtgtgaat cagtggccct acgctgcgcc tgggataagg ttcgattggc cagatattta  3780
cgtctcaata atgattgcca catcccttct tcattgagaa gtttatacaa ccatttgctt  3840
aagaggcatt tattttgaac ctctaaattc aaaatgccta gcccgccaac ctccttaggt  3900
tgacaaatta catcccattt ggccagccta tattttttct tatgaccctc cccttgccag  3960
aaaaaacgcg atctgaaata atctatcttc tccagcacac cttttggtac ctcaaagaaa  4020
gacatcataa acatcgctag actggtcaac acagaattaa ttaatacgag ccgccctcct  4080
actgacataa gttttccttt ccagctgctg agctttttct cgaatttggc ctccactgtt  4140
ttccactcac caattgtcaa tcgacggtgg tgcataggaa tcccaagata tctgaagggc  4200
agcccaccag aactgcaacc aaacagccgt gtgtacctcc cttcatcctc ttttgccttc  4260
ccataacaga atatctcact cttgtgaaag tttattttaa gaccagataa ctgctcaaag  4320
gcacataata tgagcttcat attcgttgcc ttttccagat cgtgatccat aaacaaaatt  4380
gtatcatcag cgtattgcag aatggatagc cccccatcta ccaaatgcgg caccaagccc  4440
ttgatctggc cattttcctt tgctctatta atcagggtag caagcatgtc cactaccaag  4500
ttaaagagaa taggagacag cggatcgccc tgcctcaccc ctctatgggt ctggaaaaaa  4560
ggacccatgt gatcattaac tctaaccgca acatggcccc ccttcatgaa agactcgatc  4620
cacctacacc aggtacttga aaaacctttc atacgaaggg attgttgaac aaagctccac  4680
ttcaccttat cataagcttt ctcgaagtcg attttgaaaa tgaccccatc ccttttcttc  4740
gtatgtagct catgaatagt ctcatgtaag accaccaccc cttccatgat atttcttcct  4800
ggcaggaacg cagtctgcag gggactgatt acattctgcg caacctccgt gatcctctta  4860
gtcgccacct ttgtgaagat tttgaaactg acatttagta gacaaattgg tcggtattgt  4920
tgaaccgaga ttgcctcccg agtcttagga agcaaaatga tagtcccaaa gttaagacta  4980
tacaaaggga gatttcctga gtggaactca cgaaacaaag ccataagatc atctttaata  5040
acatcccaac agatttgata aaattccgcc gggaatccat caggacctgg agccttgtta  5100
tgttccatac taaaaaccac cgcttttact tcatcttcag aaaatggctg ggtgagcttc  5160
tcgttctcaa cttgagtaac ttgtattata tcatctctaa gatcctcatc cagactaaaa  5220
gacgtgtttt ctgggggcc aaagagattt ttataataac cagttatatg actctttaat  5280
tctttctcgt cgtataacat acgagctcca tccgtcatct ggaagatgcg attcttcctg  5340
aattttccat tggctatcat ctgaaaatat ttagtattac tatcccctc caggagctcc  5400
ttgaccttcg ctctttgata ccactttatt tcctcctccc ggagtagctg agcaagcctg  5460
ttctgtaagt agttatgcag atccaactcc gaagtactca acagaactac ttcagctctc  5520
ttatctaaat catcaagctt agctatgatc tccttttttt cctttttcaa caaccccgaa  5580
gtgtgcattg cccaacccct taagtgttgg cgcaccttcc taatcctggc ttgccatttc  5640
tccaaaggag tagaaccact tgtctcattt acccaaatat cttttaccat atccacaaaa  5700
ccatccctca gaaaccagcc tagttctaac ttgaacggag gaattgtatg ggcggttaca  5760
```

```
acacctgtgc taagaagcag aggagtatga tcggatatat ttctcgacaa ggcatgtacc  5820
gaagctctag ggtattttcc ctcccattct gtagctacca aaatccgatc caacttctca  5880
taagtcggaa tatccctagt attagcccag gtgtaccttc gccccgacat ctgcaattct  5940
cttagatcaa gaccatcaat taccgcattg aaaaggaacg gccaacgatg atcaaatcta  6000
tcattatttt tctcagatgg agatcgtaaa atattaaaat ctcccccaat gagaataggt  6060
aaagtttctg tattgctcac acggactagc tcagaaagga attcttgttt gaagcagtcc  6120
tgggcagggc catacaccga gacaagagcc catttaaaac catctgcttt atcaagcaaa  6180
ttaaacttaa taaagaaatc cccttccgtg atggcaccaa catcaaagac atcagcgtca  6240
attcctaaca acatcccccc agatctacca tgaggttctt tgcaatgcca gataaaattt  6300
ttcccagcac acaaattcct tagtagatga tctgggaagg atttgcggcc tgtttcagag  6360
agggcaataa aattgagacc atgttctttg gtcagatccg aaatgtatct aagtttttc  6420
aaatccttga acccattgct gttccaaaag attcctttca ttggtaaaca attaattaat  6480
aatcaagccc gaccttttt cttagaacac aacgaaccct gactagatgg ttttgtacag  6540
actgacttaa tcagcccatc agtgccatcc gtctcttcat gcataaatatc cccacacaaa  6600
tgatttaaaa tgaaatgatc aaactcttcg tcctctacta ctccctttcc cataaaatca  6660
gataaatcag cctcgttctt acccactagc tgatcctgaa ctctattaat ctctaatttt  6720
ttcaactgac caatagagga agcaactgaa ctaggattag aacccgctaa aatgccaata  6780
tttttaaaag aatccagaat ataattatcg ggtaaactaa taaaggaaac attgttacct  6840
ttagtcggct gatcgtccag gttgtatccc gctttcagcc gaatcgctcg aactagcgag  6900
tcttcactca ccgaatcaga gcggcgcgag ctacgacgca gtgcatgcac ttttcctgtc  6960
aacgcctccg ggatactgcc caacttttca atactaacag cattgaccga gagacaggta  7020
ccctgagatt gatccagatc cagctgtgta gggccagcgc acaccgattt cccactggac  7080
gtgttgctgt tcagcataga atccgacacc ttattaactg cccctgctga atcctttgat  7140
gttcccttca agctcgcccc cttattccct ctttcaccta tattgtgatc cttgttttga  7200
tcctgaaatt catcatcatc attatccccg atatgatcca tatccatcgg caaaggctgg  7260
tcaccttcag ctgctgactc caccctgaat ttcagttcat ataagtagtc tccaattacc  7320
acatcaacta cttgcggaat caaattcggg tcaagcacgg ccaccttcag ccttgccctg  7380
tcaaacttcc gagtaaacaa catatccacc tcttttgaga tgcctagcat agaaccaacc  7440
gcccagatta ccgagtactc tctaagttcc ttaggtaaac cagtgaactg cacccaagcc  7500
ttaggcatct catattttat ttcctctcca aacccctctt ccttgacaag catctgtgca  7560
ccaaattttg tatgaacagt tccccactcg atcatacggt gaagttcacc cctggaaggg  7620
aaacacgtcg agaacacatt gttccccaca cacttcacac accagtccca atcagcagcc  7680
accaaccttt taagctcatt caaaatctgc tcttcattca tggaaccctc cacaatagac  7740
actgtaccat tgcagccacc ttgcctctgc tttactggaa tgggttgggg tataaagtaa  7800
aaccccaatc cctccaccgc atacccgcaa ggtattgcaa aagttttgca ggcacgaacc  7860
accggacatt tcgaagttaa gtgagttttg acatcacaaa tttcacaaaa tagctcaata  7920
ttacagtcac tcaactgatg acctttattt ttgcacctga aacaaaacgg cactttctct  7980
tttgaacttg aaatcacaga agaacccacc ttgtcatcca agtgggttgg agtagacaat  8040
tctttgatgg tctccaactt tgaactgtgt tgggacccaa tattcggacc tgctggattc  8100
cccctcgagt tctgaatgtg ctggctcttc cccacagact gctgcagcaa ggaaacaatc  8160
tgttccatgg tactatctgg aacaggcctg acagcgctac cgttgccaat tgatgttgta  8220
attgcctgtt ggagcaagtc cacagcgttt gatacttgag gagtcaccga agaagcccct  8280
gaacctccca gaccctgtcc agcgaccatc acagaggaag cccctccatt tgaaaacctg  8340
ctgtgaacac ctccgccccc agactgggtt ggcaaagtac gaccaccata gaaccggcct  8400
ccggcagaag cacctcttcc accacgccac gctccagcac ggccctgtcc acctccccga  8460
cgtccaaaag gacggcgtcc gccaccataa ccaggatgga acactggttg ggatccaccg  8520
cgtccaaagt cagtgttcag tcccaaacca gcgacatatc ctcccgtgcc cccaagcagt  8580
tgctgaccgg tggaaaaacc tgcagcgccc tcggactgat gctggccgcg actgcctcca  8640
cgccctccag tatcaccaac cggcgccatt gcgttcctta cagcctcgac gaaggtgcca  8700
ggagccacac cccgggagga aatgtgaacc gccctggcag cagaagaact ggtgcctgag  8760
cgggagaaca aggaagccag cccagcagtt ggcctataag gaatcctagg actgagaatc  8820
atatgttggg ccctcccatt ccaacgggga caagcactaa ttaagccaac attccttgat  8880
tccagcacag gatccgcatg agaatcccag aatatcgcct gacttgcatc cataccaaaa  8940
tcattcaaat tcaaaccatc agctaaccgc tccgctgata ccgctcccat tgaagacgtc  9000
ttcttcaacc tttggccgtg gcaccttcca ggggagcagc gccattgcgc tttttctagt  9060
gcatgtccaa ctgtgaactc cggcgaacgt cgtggcgacg gcaatttgcc ctgccatggc  9120
ttcaccttat tcctagaaga agtgctcgga ctaggagaat gcaagcatgt actcaacgtc  9180
ggtcctggtc ccgacctgca tacaccgccg actacctctc ctacctgttc gagagcttca  9240
ttccaaatag attttggtgg cgcggaactg cagtcaatta gcttgccgtc aacacaggac  9300
agagacccgt tcacgaaaac agagagccga ccaccctcag gtgtccgtcc gctatttgcc  9360
gaaccggcca gatcaccaac ctcctgatcc agctgaacct gacaatcagc aacctccgcc  9420
agtgggcgga cgaccaccgc atcggtgggc gccagcgtct ttcgacgacg acccttccga  9480
gcgtacgtgg ccaagcaacg tcgctgcata gcgcagagaa cgaacgaaca accactggcg  9540
ggagaccggc ctagatggcc gcctcccacc tctggtgtcc cactccgccg agacagaggg  9600
aagagcactt accgggttac gccgcgcgcc tagccgggac gcccacgcgg cctagaccgc  9660
cttgccgtgg tcaccgcaga gaagaaactc gagcgccagg gtccaccgcg gcctgcgatg  9720
ctctctgatg agcagcggga agttgcggcg tgcgaagcga ccggcccagc agttgagcac  9780
ggcgtcgacg gcgtccgcgt cggcacgagg cagcgcgagc aagcgcgcga cgacctcgga  9840
caccttccag tcccgctgcc accggttgcc ctccacgcgg aggcggtgtc acgcaatcaa  9900
aaacagtcca taactagaga gctaacaaca gaacagctac aaccctgcca ggggagtgta  9960
ttgggcatca acacggactg aggcagggtg atcctctatc gcctatgctg tttattcttg  10020
taatggatgt cttgaatctg cttgtgcagc gagcctctga ggaagggttt cttcagcctc  10080
tttcttctag gaatatgcag catcgtatct cgctgtacgc ggatgatgca atgttatttc  10140
tatgtcctac tgccccggat atcagtatgg ttatggatat tcttcattta tttggttcaa  10200
cttcaggtct aaggactaat gtccagaaga gcagtgtgtt cccaatctga tgtggggaag  10260
aagaggtgaa ttgtttacag gacttgctgc tatgcaatat ttcagttttt ccctgtaagt  10320
acctcggttt gcctttgtct cccaagaaac tcacaaggga ccaggttcaa gccattgttg  10380
aaagagtggc cagccttttg ccaggatgga aagctgaact tatgaccagg gctggtagag  10440
ctattcatgt gcagtttgtc atgacggcta agatgatata tgcagctctg gcacttgacc  10500
```

```
ttcctgtatg ggccatcaaa gcaatcgata agctgaggaa gggcttcctc tggaggggta  10560
ggaaagagtt ccgtggtggt cactgcctct tggcttggcc taaggttacc cgtcccaagg  10620
agttgggtgg tcttgggatt agtgagttaa agaacctctg ttgggctttg agagctcgct  10680
ggccatggct gcagaaaaca gaccccagta ggccttgggc ggacttcccc attcatgttt  10740
gtaaggtggt taaaaatctg attgctgcag ccattattac taagctcggt gatggagcca  10800
ataccctttt ctggaaggac agatggttgg aggggagatg tattaaggac atagctcctg  10860
cgttgtttga tttggtgccc ttgcgtcttg ccaacaaacg gttggtcaaa gatactctcc  10920
ctaatttcca ttggctctca gatgtgcaag gggcaatctc agtcagagtc attgctgaat  10980
tcctggaact ttgtgaagtg cttgatgcag ttgtgctcca gcctggaata agggatcgat  11040
atttatggaa attcagcgct tcaggtgatt atacatctag ttctgcttat aatgctctct  11100
tccttggttc agttcagttc gaaccagcag agcggctatg gaaatcttgg gctcctggga  11160
agtgcaagtt ctttatatgg cttgtggaac ataataggtg ctggactgct gacaggctca  11220
gaaaaagagg gctagaccga ccagagcagt gccccttgtg cgaccaagag gttgaaacca  11280
taaatcattt gctggtcaag tgtgtttttg ctaagcagtt ctggtttgat ttccttaatt  11340
cagtggggtt gcgggatctg tatccagctc atgaggaatc ctttgagtcg tggtggaagt  11400
ctagcagctc cggcatcgga tcttgtgaga aaaggtttca attctttagt gatcctaggt  11460
gcttggacca tttggaagca taggaatagg tgtgtttttt atggttgtaa tcccagcttg  11520
ctcacgaccc ttaggatggc tagggaagag gcggtgctct ggtccatgac tggtgccaag  11580
gccttgtcct tcctccaagt cgatgagttg ctggcttaaa acagcggtgt gggtcgtgtt  11640
tcctccatgt tttagtcagt gatccgtagt tagtctctag tggtgtatgt gctgtattgg  11700
ggttctctcc ccctttcttt tcttctatta atacaaagat gcgcagctct cctgcgtatt  11760
ccagaaaaaa aagaaaaaaa aaacaaccct gggatagggg ctgctaggag atccaaattc  11820
ttggccccag ccagcaccca caaatccctc tcctccttag cttttctaat agccggtgag  11880
agcggcacag atggtgagac cagagaagct gaaggttgta agacgacgag ttgacatccc  11940
ccaaagtcat agtggtcaat gtgtcgcata tgctgtagct agagtgctca agcaaggcag  12000
aagctctttg tgccgatgtt gaggtagtcg agcacgaggg tgagtagcca tggttgagga  12060
tgccatcttt acgccatggt gatggtcgag gcgcgtcgag acagtccatt gtataagggg  12120
gtgatgttga ggtcaatgta gtcaaggcca tcgaggatgt cgacgaaaat agcgacacag  12180
tcaaggcagg tcatcatgga ggaagcatac accggattgg ctaggcctga gaacgtgtcc  12240
tggagaacgg cacgctacac tgccaatata agacatgcta gttagagagc cccaacaatg  12300
tgtcaacatc cgagcgacct tggaagagag tgcctcaacg atggttgatt gtggtgccca  12360
aaacaactga gcacaaggtg tcgatgtatc ccacaattgt caaattagat gatatatgtg  12420
ggaaagagac aatgatgctg gcgatgtggt tatgctgaat gaagaaggaa cagtgcggga  12480
gtgaacgctc ctacccgaag gggagtagtt tgggccgacg tccttggcca aggcaatggt  12540
ccagacataa ggtacagtgt gcccaaaggc agtggtccag aagcaaggta tggcgtcaaa  12600
aacagtgttc gctgttggtg atgaagagca caaaaagttt gatgaagacc aagtgcatcc  12660
tggtggtgcg caagaggtgc aacacaatta tcgatgtaca tggagcgaca atgtagatgc  12720
attgttgtat gccaaccatg gatagaggca tgcctatgag ggtgtctcaa ttagagaatc  12780
tctaacattg ccttaaatca attctctatc ttataatata gtgcttaact tataaaaaac  12840
tgctccaaca gtgctctatt ttacattttt atcaaaaaat atagggcaga ccataaagtg  12900
accaaaatat actacactct ggattagggc ttaactgttg caacacaatt tgtttttagt  12960
gccttaaaca ctttaaatga tgtagtattg taatttttgg aacattattt tgaggggcag  13020
cgagtgtagc gtagagacag tttatgaggg gcagtagcgg aagtgttggg atagcaagca  13080
caaccaaata cacggagttg ggttgtgtcg tacaaggcga agtaggtggt ggggtggctc  13140
accaccttcg atgggaggcg attgaggagg tgggtggcgg tgtgcaaggc ctctgcccag  13200
tagttggcag ggagagacgc ctgaaagaga aggcaacaaa tcatgttggt ggtggtgcga  13260
atcattcgct cggcccgacc gttttgggca gaggtgtagg ggcacgagag atgcaattga  13320
acgccactgg cgaggaagaa cgaccgagag gcatggttgt cgaactcgcg gccattgtca  13380
cactgcagtg catggaccgg gcgacagaac tgggtggaga cccaggcgaa gaagtgagtg  13440
agggtggtaa acgtgtcgga tttcattcga aaaggaaaag tccataggaa atgggaaaaa  13500
tcgtccaaaa tcaccaaata gtatttgtat cctgacagac tgagtaccgg ggaggtccat  13560
agatcacaat gaaccaggtc aaaagcctgt tcagccctag aagaagatgt agtgaaagga  13620
agacgggtat gtcggtcaag ctgacatgca tgacagaggc cctcaaaatg tcccctatta  13680
caagaagaat ctaaagtgct ggaaagcttg gtcatgacct agatcctggg tggccgagac  13740
gacgatgcca agtggtggag gtggtggtgg agaccaggac gggaggtgga gacacgccgg  13800
tggacgacga ccggagtgtg tagaggggcc cgacgctgtc acatcgggcg agtggggtcc  13860
tggtggccag atcctttaca gaaaaaccag tagggtcaaa ctcaatggaa cacgaattgt  13920
cggtggtgaa ccaacggaca gaaagaagat tgtgagtgat gtgaggggct acgagaacgt  13980
cgttgaggta gaacagtcca gggagaaccg aggcacctac tgaggtgact agaagagtgg  14040
aaccgtttcg aacgacgatc gaggtagggt gtgtgggggg aggtgggtgt gagcgagagc  14100
atgcctaggg tgggggtggt gtgataggat gcaccggagt cgatgaccca gtcagaaggc  14160
ggtggggcca acgccatggt gctgtatgcg gcagcgaggg caacagggtc ccaacctgca  14220
acgaacgagg accatggtgt cgtggtagac ggtctcgtag gcgggagttg aggcgggccc  14280
cgggtcggtc ggggcacgcc gtatggaggc atgttgtagg cgggcggcgt agtcaggaga  14340
gccggaggac gggaggcgct gggggcctga cccagccaca tggagataat gccggtccag  14400
gggttgtaga acgacggcca actctggtcg ccacccctat cggtggaacc tccacgagag  14460
gagctgccgc ccccatgtcc gcccttgtag gggcgacggc cgccgtcgat ggtggaatgc  14520
tgacgagggt ccgtaggagc cgcggtgaag ggccgagcgg gggtcctggt tgacggagcg  14580
cggggggcga gtcctccgga agacgcctgg gcaccagggg tggcgctgta gagtgccgga  14640
gtgggagcct cgatcgtcat ggtgagctcc tcgagaagaa gttcattgcg cacggcgtgg  14700
aaggtgggaa aaggtacggt cctcttgatg agagccttca ggtggccgta gagggggctg  14760
aggccacaca ggaggtttag caccaaggta cggtccgcca gcgactcgcc aaggtcgcgg  14820
agggagtctg ctaggccctt catctggcgg cagtactccc gcacagagag gtccccctgg  14880
gagaattggt ggaactgatc atcgatttga agggcccgag cgtcccggtt cccgaggaat  14940
tgttcctcga gggcgagcca cgcctggcgg gccgtgtccg ccttgtcgca gatgatgtcc  15000
tggagctcga cggtgatagt gtcgtggagc caaaagagca cgactgtgtc catcagggac  15060
caggccatgg gcggtggggt gacgatgtcg tcgaggacgt ggtcggcgag agcgtagcgc  15120
cgcagggtga ggacctgccc ccgacagcga gggtagtggg aggacgccgg gtctagcacg  15180
attgacacga gggaccatat gttgtggaga ccggcagcct gcgcatgaag ggcggcgatg  15240
```

```
tggtcggcgt cgagtccagg ggcgatgggt gcctggggtt gggtggaggt gcctccgggg  15300
tgaccggagg atgcccgagg aggagtcgct gagcggtagc catttgggcg gtcagagcag  15360
cgctcatggc acgctcttgc tacagggcga gggtcgcagc gcgctcgcgg tcgagggaag  15420
cctccacggc tgcctggata gtggcgatgg ccgtgaccag cgccgacgag gccgtcgggg  15480
gggcgggggg gggcagtgac gtcagcccat gtggcggtgg tgtgggcccg gaggagaatc  15540
gcggcgtcgt tgagcagcga gggtggcatc gggtaggggc ccgagatcgg cgatgtgggc  15600
ccctccccaa cagcgaggtc gctaggggtg ccgagtccgg cagtggcgag ggcggcggta  15660
gccgcggcgc tgcgtgctgg tggggccaca gtggcagtgg ccgcagggag ggccgcgcgt  15720
ggctgctggg cagcagcagt cgtagcggca gccggggtgt agggggaatg aggtggtgtc  15780
gacatggcgg caccaggtgg ttgggcggcc gacgctgcgg ggttgacggc ggcggtggag  15840
gaaggaccgg tgcgagcggc cgaggtggct ggatggccgg cgcggtgccc agtgaggggg  15900
tccggcgggg gcagcccttg ctgctgggcg gcggcgcagg aggaggcgcc gcggcggcca  15960
gcctggggag gagcggcgac cggtgggagg aaggggagcg gcgatcgggc ctggggggag  16020
ggagaagggg ggagcggtgg ctgccacgga ctggcggcgg cagggagggt gggagggaat  16080
tagtgtggct ctgataccat gtagaactat ggaaaaccct aaccctagaa tagggttggg  16140
cagtgtatta atagaccaaa taactgggct aggcccatta caagggacgg gtatctaaaa  16200
aaatagactg cggctttttt tttagataat ggatactagt ccagcttctc ctcgtttgga  16260
ggattagcca acacaccaaa agtttttaca tggagtagtc acacgactag ctgctttatt  16320
tgtccttttc atttatgcaa cctaggaatt atttgacttg tctccatctt aatgtgtctg  16380
cttttaaata cagtttactg aacagggcca catctttgtt caagtccatt tggtcaagga  16440
actaaacagg aaaggaaaca atttttgtga tgtttctgct cataacagag aaattctgta  16500
tgattctgac aactcgatgc tatggaacac actaagcgga cttgaagtag cagatagctg  16560
gaggtccttg gagaatttta cgatgttcaa gaattcaaat ggtgaaacag atacaattag  16620
gttagctgtc agagttgaag acaccggcat aggaataaca aaagatgctc aaatgcgtat  16680
ttttacacct ttcatgcaag ctgacagttc cacctcacga acatatggtg gaactggaat  16740
tggcttgagt attacaaaac gtttagttga attgatgggt ggagaaatag ggtttactag  16800
taaatcagga gttggtagta cattttcttt tactgccatt ttcaaggaga acagaggatg  16860
tcctggagat atgaaaagat actattctga acctactccg ttggattttc aaggaatgag  16920
ggctcttatt attgatggaa ggagtgcacg tgcagaggtt actatgtacc atcttcgtag  16980
acttggaata cagtgcagtc ttgttgccac atctgaatct gaatctgcat cttcagcttt  17040
gatgaaagcc tgcacctcaa ggttcatttc cttgtgtagt ttactgtttg atttacttct  17100
acaagtttta gaaattagaa gttattttgt tcaaataaat gtaacattcc ttgcatttat  17160
aaacttttgt catcttaaca catggctttg ctatattttc tttagttggt tgtgtgctat  17220
ttctttgaat attttccata ttgtcgatcc caaaacaagg tttcgtaact tctcatgaac  17280
tgaagaaaag taggagaaac agagtgaaac cttcgttggt ttgagtttag aaactgaaat  17340
aggatagttc gattctaaat aacttgtgaa ttcattcagt tgttgctgtc atcattataa  17400
catatcaatt tgttcatggc cagcaaccta cacttgtcct cagtattacg acccaacaaa  17460
atcaatgcat aatgtcgcca tcatcacttt ccatgtatgc attttctttt ctaagcactg  17520
ttgatgcctt acttgttgat gttatcattt atattttaca tgttgagcag caaaaacaat  17580
ccggacatgg tccttgttga tacagaagct tggggtaaag gttcaggttt ggcattctat  17640
catcgttttg tagattgtca actaaagggc gcacacaagt tttctcagcc catgccaaag  17700
actattcttt tgggaagctc aataagccct gttgaatctg attatttaag attgacagga  17760
tttggtgatt gcataaggaa acccctccgt cttagtacta ttgttgcctg tcttcgcaaa  17820
accttagggg ttggggttac aaggcagcag agtagagacc aatctttggt tcttcaaagt  17880
gtactaactg gaaaacagat tctggttgtg gatgataatg cagtcaaccg taaagttgca  17940
gctggttctt tgaagaaata tggatctaaa gttacatgtg ttgatagtgg gagtgatgca  18000
attgatatgc tcaagccacc tcacacattt gatgcttgct tcatggatgt tcagatgccc  18060
gagatggacg ggtaatgttc ctttccaatg agttactaat gaaaaagagc gcagatttgc  18120
tgcccaggcg ttctcattat ctaaaatacc atgttgcaat atttcaaaaa tcatcacaaa  18180
aatcatgtat gcagtacaca aagttaggta tagccgcaac acttcagatt gaaatttctt  18240
cctagatgcc aagaaccaaa atagacaagc agtcaacctg gcagtgttca tcatgtgctg  18300
acagtgagac tttgtttttt aatctcagca tcaaagatga actttattga attcttgagg  18360
ctacacttaa ggtgtacttg cacacatgtt ttttgtgatg attgttgaaa cattgcaata  18420
cggtatttta gaatgtgggc gccaatttcc ctgggcgcca tatgatttcc aatggaaaat  18480
tgtcatatgt tatttacttg cgggatatac tataagagtt caatatgtaa aagattcttt  18540
gtgcagaagt cactcttgga acatcttacg ttagttcaca tggaagcatg tctttagttt  18600
taggtatgtg cttcttttgg attttgtgga atcatcggaa cagatgcatc tttgatggcc  18660
tttcccctaa tgttgctaat tttctaatcc atgtggggga tgagcgccgt ctgtgggaga  18720
ctgccggggc caaggggttg acatcccttg ttgcctccct ctctcatgta gcctagagtt  18780
ttatagatga gtcagtctat gctagtttcg ttcaggccgc cgtaaggcgt cagttgtacc  18840
ccggtctatt ttagaccttg tttatttgtt cttttaatat aatgatacgc agctctcctg  18900
cgtgttcgag aaaaaaagag aaagttattt tttggtcctc aaataacaac acttgtcaaa  18960
tgtatgcatc tcctcatgtt attagcaagc actctcatag gagtatcact gaggataatc  19020
tctcttttgt tttcacatcc agtccttgct taaaaaaatg cactgtagcc tcacatgctt  19080
gtgtttgctt tcctatgggt tataacaagt ggttgcatct actttgatca cttgtagatc  19140
cactgtagga ctaccattaa caatattcac attcaattgc aggtttgaag ctacaagatt  19200
aatccggtcc atagagaaaa aaataaacga tatgatcatg atgggtgaaa tatccgctaa  19260
taattatgga aataaggccc attggcatgt accaatatta gctatgacgg cagatgtaat  19320
ccaagcgact tttgaaaaat gtatgcagtg tggaatggat ggatatgtgt caaagccatt  19380
tgaagaacag cagctctact ttgctgttgc tcatttctta gagactgatg aaacagaata  19440
a                                                                  19441
```

```
SEQ ID NO: 252         moltype = DNA  length = 19436
FEATURE                Location/Qualifiers
source                 1..19436
                       mol_type = other DNA
                       organism = synthetic construct
SEQUENCE: 252
aaaacatttg aggacttcac agcaaggaca acatttgaaa ggccattgat gagtggtgtc  60
```

```
gcctatgcat tgaaggtatt acacaatgaa agacaacagt ttgaggaaca acatggatgg  120
aagattaaga agatggaaga tggagatcag tcccttgttc atgactacaa ccttgaaaag  180
cttgaaccat caccagttca agatgagtat gcgcctgtta ttttctctca ggaaactgtg  240
aagcacatta tatctgtaga tatgatgtct gggaaggtag taggatattc gtaagccttt  300
acagtaaata cttactattt tatctatcct gagttcctta ctactatttt tgttataaaa  360
cgaagaaatt tctggctctt cttctaactt tcaatattat taggattaaa catgtgtaga  420
acttctcggt caaaaaagac actttagaac ttatattttt attttaatta gaatttgatg  480
tataaaaatt aatcattttt acaatgagtg ttatagtaat ataagttgtt atgtgtcttg  540
ttcaatgtgt taattactat agcatgttcc atagaaatac tgtgcaggct gttactaatt  600
ctctcttatt ctgtctttgt ggaaattaca taattactaa acctcatagt aataataata  660
ataactaaga ctccattttt ctgctaacat tacaaccttg atttcaggaa gatcatgaca  720
atatattacg ttcctggtca acaggtaaag gggccctaac atccccttt aagcttctga  780
agtccaacca tctcggtgtg gtgcttacat tcactgtata taaatatgat ctgcctccaa  840
atgcaacacc acaggagcgt attcatgcta cattggggta aaatgttttg caaagtttca  900
agttgaagct atataggaat acactatttt ttctttagga gacttaacct tgtggttatt  960
gacactttgc agctatcttg gtgcctcatt tgatgtccct tctctggttg ataaacgaac  1020
aactcgctag caaacgaaag atagtagtta atttatatga caccacaaat catacctctc  1080
ctattgaaat gtatggttct gattttactc catctggtga tctgcatatt agtagcattg  1140
attttggaga cccaacacgc aaacatgaga tgcattgcag gtagaaaact ttttttgat  1200
gcgaattata caatgctttt gttcttcaga tatgctcagt gctttctctt tcaaacttct  1260
ctttcagatt taaacatgaa ccttcactgc catggtctgc aataataata tcaacagctg  1320
tagctataat tgttttgctt gttggacata ttatttatgc aactctgaac tcccttgaaa  1380
aggctgaaca tgattataga gtaatgagag aacttaaagg acaagctgaa gctgcagata  1440
tagcaaaatc tcaggttcat tctacctctt ccagtgtctt catcctatgc attggtttgt  1500
tatctcattt gttctacttt tctctttttg tcggctgagt cattattgat tgtcttgcag  1560
tttctagcaa ctgtttccca tgagattcgg actccaatga atggtgtttt aggtctgtac  1620
ttctgatatt tctttttttgt ctattaatac ataccgcagt tatttgtgtt tatgttttaa  1680
tcaaagacaa ctaaataaat tttgaaaagg atttcttctt gaattaggta tgctgcagat  1740
gctaatggac actgaacttg atacaactca gcaggatttt gtagtcaccg ctcaagaaag  1800
tggaaaggta ttaataaact taataaatga agtccttgat ctggctaaga tagagtcagg  1860
aaggattgag ctggaagcag tgcctttttga tgtccgtgat attcttgaca atgtgatatc  1920
tcttttctac gataaatcac aagctaaagg catagaggtg agtcctaatt tagaacttgt  1980
attgtttgct aagctctgaa tattgtttgt gccatgggac ctaaaataat gtgtaattct  2040
tttttgaggg tagttggccg tgcttgtatc tgaccaagtt cctgatgtcc taattgggga  2100
tccatggcgg ttccggcaga tcattacgaa ccttgtgggg aattctatga aggttagatt  2160
caaatatgtg gtagcttcat tatttcagct tgctggcaag ttgtaactgt gtctagtcaa  2220
tcccaccatt tagcttatac aacaatatac tttgtaggaa acgtgacaac ttactaaaat  2280
attaatgtca tgagcttttg aatttgagat gtgtagaaga caattggtag aattggtcaa  2340
ttgtgtcgct gagctcgtgg gcagattata catgagtaca ttcacttgga tggcaagaaa  2400
cctccctaaa gataagaagt caggattaca tgaccctaat ctagcatatt taaagatatt  2460
ccaatataat ataccacccc ccatattttt ctcgaacgtg caggaaagct gcacatcttt  2520
atattaagaa gataaaaggt ccaaaatgga ccaaaacagg tatagataca aggcacctca  2580
cgtggccaaa aacaaaagta caaaaaaaac agtccataac tttttttttt tagataatgg  2640
aaaaatcatc cgaccttggc ctcaaatgag gttacggcca tttattacaa gggacggaag  2700
catattgcca aaacacctcc tatgaccact tcagagaacc ccaactagcc aaattaaaga  2760
acttcagcta tcgaaccaca gctactacat atttaaacgc aacgcagacc cccatccaaa  2820
attgctaaag aactgtagta gcaccctctc cacattacga catgaagact ttattaactc  2880
ttggtcctcc cttctaggct gaagctgaga ccagaagcgg caccaatatg ttgccctgaa  2940
ggttacctgc acacatgatt taggagatga attattgaac accacatcat ttctacttaa  3000
ccaaatagcc caacaaattg ccgatgcaac ggttaatagt aagtttcgaa ctctgggaag  3060
cctcccgctc gcccaaaccc caaacaaatc attaacatcc cgaggaggtc tcaaccccgt  3120
gcttatctga atcaaccgcc aaatgaatga cgcatacaaa caactgaaaa ataggtgctt  3180
tattgtctcc ggtctactac aaaagcaaca tatcttatta ccattccaat gcctcctagc  3240
caagttatcc tttgttaatg ttacccctct tttgaggtac cacataaaaa tcttaatttt  3300
cagaggaagc ctaagtttcc aaaggtcctt attatgcacc cccaacccat tgttaagaga  3360
tgccagatac agagacttaa ccgtaaacat cccgttggcg gtcaagttcc atctgaacaa  3420
gtccctgttt gaattcaaat tggtatgcgc aacaagtgag accaattgaa cccattggtc  3480
cctcaattgt tgagccaaac ccctccgaaa ggatatattt aagggcaccg tggagaacac  3540
acaggcaaca gtagagttct tcctcctcgc taggttataa agagacggaa aacgaagttt  3600
taacgttccc gacccgagcc aatcatcctc ccagaaacgc acctgggacc catcatgaat  3660
cacaaaggtt cctttactaa tgaatgtgtc cttaactttc ataagaccac tccagaagtg  3720
tgaatcagtg gccctacgct gcgcctggga taaggttcga ttggccagat atttacgtct  3780
caataatgat tgccacatcc cttcttcatt gagaagttta tacaaccatt tgcttaagag  3840
gcatttattt tgaacctcta aattcaaaat gcctagcccg ccaacctcct taggttgaca  3900
aattacatcc catttggcca gcctatattt tttcttatga ccctcccctt gccagaaaaa  3960
acgcgatctg aaataatcta tcttctccag cacacctttt ggtacctcaa agaaagacat  4020
cataaacatc gctagactgg tcaacacaga attaattaat acgagccgcc ctcctactga  4080
cataagtttt cctttccagc tgctgagctt tttctcgaat ttggcctcca ctgttttcca  4140
ctcaccaatt gtcaatcgac ggtggtgcat aggaatccca agatatctga agggcagccc  4200
accagaactg caaccaaaca gccgtgtgta cctcccttca tcctcttttg ccttccccata  4260
acagaatatc tcactcttgt gaaagtttat tttaagacca gataactgct caaaggcaca  4320
taatatgagc ttcatattcg ttgccttttc cagatcgtga tccataaaca aaattgtatc  4380
atcagcgtat tgcagaatgg atagcccccc atctaccaaa tgcggcacca agccccttgat  4440
ctggccattt tcctttgctc tattaatcag ggtagcaagc atgtccacta ccaagttaaa  4500
gagaatagga gacagcggat cgccctgcct cacccctcta tgggtctgga aaaaaggacc  4560
catgtgatca ttaactctaa ccgcaacatg gcccccccttc atgaaagact cgatccacct  4620
acaccaggta cttgaaaaac ctttcatacg aagggattgt tgaacaaagc tccacttcac  4680
cttatcataa gctttctcga agtcgatttt gaaaatgacc ccatcccttt tcttcgtatg  4740
tagctcatga atagtctcat gtaagaccac cacccccttcc atgatatttc ttcctggcag  4800
```

```
gaacgcagtc tgcaggggac tgattacatt ctgcgcaacc tccgtgatcc tcttagtcgc  4860
cacctttgtg aagattttga aactgacatt tagtagacaa attggtcggt attgttgaac  4920
cgagattgcc tcccgagtct taggaagcaa aatgatagtc ccaaagttaa gactatacaa  4980
agggagattt cctgagtgga actcacgaaa caaagccata agatcatctt taataacatc  5040
ccaacagatt tgataaaatt ccgccgggaa tccatcagga cctggagcct tgttatgttc  5100
catactaaaa accaccgctt ttacttcatc ttcagaaaat ggctgggtga gcttctcgtt  5160
ctcaacttga gtaacttgta ttatatcatc tctaagatcc tcatccagac taaaagacgt  5220
gttttctggg gggccaaaga gatttttata ataaccagtt atatgactct ttaattcttt  5280
ctcgtcgtat aacatacgag ctccatccgt catctggaag atgcgattct tcctgaattt  5340
tccattggct atcatctgaa aatatttagt attactatcc ccctccagga gctccttgac  5400
cttcgctctt tgataccact ttatttcctc ctcccggagt agctgagcaa gcctgttctg  5460
taagtagtta tgcagatcca actccgaagt actcaacaga actacttcag ctctcttatc  5520
taaatcatca agcttagcta tgatctcctt tttttccttt ttcaacaacc ccgaagtgtg  5580
cattgcccaa ccccttaagt gttggcgcac cttcctaatc ctggcttgcc atttctccaa  5640
aggagtagaa ccacttgtct catttaccca aatatctttt accatatcca caaaaccatc  5700
cctcagaaac cagcctagtt ctaacttgaa cggaggaatt gtatgggcgg ttacaacacc  5760
tgtgctaaga agcagaggag tatgatcgga tatatttctc gacaaggcat gtaccgaagc  5820
tctagggtat tttccctccc attctgtagc taccaaaatc cgatccaact tctcataagt  5880
cggaatatcc ctagtattag cccaggtgta ccttcgcccc gacatctgca attctcttag  5940
atcaagacca tcaattaccg cattgaaaag gaacggccaa cgatgatcaa atctatcatt  6000
atttttctca gatggagatc gtaaaatatt aaaatctccc ccaatgagaa taggtaaagt  6060
ttctgtattg ctcacacgga ctagctcaga aaggaattct tgtttgaagc agtcctgggc  6120
agggccatac accgagacaa gagcccattt aaaaccatct gctttatcaa gcaaattaaa  6180
cttaataaag aaatcccctt ccgtgatggc accaacatca aagacatcag cgtcaattcc  6240
taacaacatc cccccagatc taccatgagg ttctttgcaa tgccagataa aatttttccc  6300
agcacacaaa ttccttagta gatgatctgg gaaggatttg cggcctgttt cagagagggc  6360
aataaaattg agaccatgtt ctttggtcag atccgaaatg tatctaagtt ttttcaaatc  6420
cttgaaccca ttgctgttcc aaaagattcc tttcattggt aaacaattaa ttaataatca  6480
agcccgacct tttttcttag aacacaacga accctgacta gatggttttg tacagactga  6540
cttaatcagc ccatcagtgc catccgtctc ttcatgcata atatccccac acaaatgatt  6600
taaaatgaaa tgatcaaact cttcgtcctc tactactccc tttcccataa aatcagataa  6660
atcagcctcg ttcttaccca ctagctgatc ctgaactcta ttaatctcta attttttcaa  6720
ctgaccaata gaggaagcaa ctgaactagg attagaaccc gctaaaatgc caatattttt  6780
aaaagaatcc agaatataat tatcgggtaa actaataaag gaaacattgt tacctttagt  6840
cggctgatcg tccaggttgt atcccgcttt cagccgaatc gctcgaacta gcgagtcttc  6900
actcaccgaa tcagagcggc gcgagctacg acgcagtgca tgcacttttc ctgtcaacgc  6960
ctccgggata ctgcccaact tttcaatact aacagcattg accgagagac aggtaccctg  7020
agattgatcc agatccagct gtgtagggcc agcgcacacc gatttcccac tggacgtgtt  7080
gctgttcagc atagaatccg acaccttatt aactgcccct gctgaatcct ttgatgttcc  7140
cttcaagctc gccccccttat tccctctttc acctatattg tgatccttgt tttgatcctg  7200
aaattcatca tcatcattat ccccgatatg atccatatcc atcggcaaag gctggtcacc  7260
ttcagctgct gactccaccc tgaatttcag ttcatataag tagtctccaa ttaccacatc  7320
aactacttgc ggaatcaaat tcgggtcaag cacggccacc ttcagccttg ccctgtcaaa  7380
cttccgagta aacaacatat ccacctcttt tgagatgcct agcatagaac caaccgccca  7440
gattaccgag tactctctaa gttccttagg taaaccagtg aactgcaccc aagccttagg  7500
catctcatat tttatttcct ctccaaaccc ctcttccttg acaagcatct gtgcaccaaa  7560
ttttgtatga acagttcccc actcgatcat acggtgaagt tcacccctgg aagggaaaca  7620
cgtcgagaac acattgttcc ccacacactt cacacaccag tcccaatcag cagccaccaa  7680
ccttttaagc tcattcaaaa tctgctcttc attcatggaa ccctccacaa tagacactgt  7740
accattgcag ccaccttgcc tctgctttac tggaatgggt tggggtataa agtaaaaccc  7800
caatccctcc accgcatacc cgcaaggtat tgcaaaagtt ttgcaggcac gaaccaccgg  7860
acatttcgaa gttaagtgag ttttgacatc acaaatttca caaaatagct caatattaca  7920
gtcactcaac tgatgacctt tatttttgca cctgaaacaa aacggcactt tctcttttga  7980
acttgaaatc acagaagaac ccaccttgtc atccaagtgg gttggagtag acaattcttt  8040
gatggtctcc aactttgaac tgtgttggga cccaatattc ggacctgctg gattccccct  8100
cgagttctga atgtgctggc tcttccccac agactgctgc agcaaggaaa caatctgttc  8160
catggtacta tctggaacag gcctgacagc gctaccgttg ccaattgatg ttgtaattgc  8220
ctgttggagc aagtccacag cgtttgatac ttgaggagtc accgaagaag cccctgaacc  8280
tcccagaccc tgtccagcga ccatcacaga ggaagcccct ccatttgaaa acctgctgtg  8340
aacacctccg cccccagact gggttggcaa agtacgacca ccatagaacc ggcctccggc  8400
agaagcacct cttccaccac gccacgctcc agcacggccc tgtccacctc cccgacgtcc  8460
aaaaggacgg cgtccgccac cataaccagg atggaacact ggttgggatc caccgcgtcc  8520
aaagtcagtg ttcagtccca aaccagcgac atatcctccc gtgcccccaa gcagttgctg  8580
accggtggaa aaacctgcag cgccctcgga ctgatgctgg ccgcgactgc ctccacgccc  8640
tccagtatca ccaaccggcg ccattgcgtt ccttacagcc tcgacgaagg tgccaggagc  8700
cacaccccgg gaggaaatgt gaaccgccct ggcagcagaa gaactggtgc ctgagcggga  8760
gaacaaggaa gccagcccag cagttggcct ataaggaatc ctaggactga gaatcatatg  8820
ttgggccctc ccattccaac ggggacaagc actaattaag ccaacattcc ttgattccag  8880
cacaggatcc gcatgagaat cccagaatat cgcctgactt gcatccatac caaaatcatt  8940
caaattcaaa ccatcagcta accgctccgc tgataccgct cccattgaag acgtcttctt  9000
caacctttgg ccgtggcacc ttccagggga gcagcgccat tgcgcttttt ctagtgcatg  9060
tccaactgtg aactccggcg aacgtcgtgg cgacggcaat ttgccctgcc atggcttcac  9120
cttattccta gaagaagtgc tcggactagg agaatgcaag catgtactca acgtcggtcc  9180
tggtcccgac ctgcatacac cgccgactac ctctcctacc tgttcgagag cttcattcca  9240
aatagatttt ggtggcgcgg aactgcagtc aattagcttg ccgtcaacac aggacagaga  9300
cccgttcacg aaaacagaga gccgaccacc ctcaggtgtc cgtccgctat ttgccgaacc  9360
ggccagatca ccaacctcct gatccagctg aacctgacaa tcagcaacct ccgccagtgg  9420
gcggacgacc accgcatcgg tgggcgccag cgtctttcga cgacgaccct tccgagcgta  9480
cgtggccaag caacgtcgct gcatagcgca gagaacgaac gaacaaccac tggcgggaga  9540
```

```
ccggcctaga tggccgcctc ccacctctgg tgtcccactc cgccgagaca gagggaagag  9600
cacttaccgg gttacgccgc gcgcctagcc gggacgccca cgcggcctag accgccttgc  9660
cgtggtcacc gcagagaaga aactcgagcg ccagggtcca ccgcggcctg cgatgctctc  9720
tgatgagcag cgggaagttg cggcgtgcga agcgaccggc ccagcagttg agcacggcgt  9780
cgacggcgtc cgcgtcggca cgaggcagcg cgagcaagcg cgcgacgacc tcggacacct  9840
tccagtcccg ctgccaccgg ttgccctcca cgcggaggcg gtgtcacgca atcaaaaaca  9900
gtccataact agagagctaa caacagaaca gctacaaccc tgccagggga gtgtattggg  9960
catcaacacg gactgaggca gggtgatcct ctatcgccta tgctgtttat tcttgtaatg  10020
gatgtcttga atctgcttgt gcagcgagcc tctgaggaag ggtttcttca gcctctttct  10080
tctaggaata tgcagcatcg tatctcgctg tacgcggatg atgcaatgtt atttctatgt  10140
cctactgccc cggatatcag tatggttatg gatattcttc atttatttgg ttcaacttca  10200
ggtctaagga ctaatgtcca gaagagcagt gtgttcccaa tctgatgtgg ggaagaagag  10260
gtgaattgtt tacaggactt gctgctatgc aatatttcag tttttccctg taagtacctc  10320
ggtttgcctt tgtctcccaa gaaactcaca agggaccagg ttcaagccat tgttgaaaga  10380
gtggccagcc ttttgccagg atggaaagct gaacttatga ccagggctgg tagagctatt  10440
catgtgcagt ttgtcatgac ggctaagatg atatatgcag ctctggcact tgaccttcct  10500
gtatgggcca tcaaagcaat cgataagctg aggaagggct tcctctggag gggtaggaaa  10560
gagttccgtg gtggtcactg cctcttggct tggcctaagg ttacccgtcc caaggagttg  10620
ggtggtcttg ggattagtga gttaaagaac ctctgttggg ctttgagagc tcgctggcca  10680
tggctgcaga aaacagaccc cagtaggcct tgggcggact tccccattca tgtttgtaag  10740
gtggttaaaa atctgattgc tgcagccatt attactaagc tcggtgatgg agccaatacc  10800
cttttctgga aggacagatg gttggagggg agatgtatta aggacatagc tcctgcgttg  10860
tttgatttgg tgcccttgcg tcttgccaac aaacggttgg tcaaagatac tctccctaat  10920
ttccattggc tctcagatgt gcaaggggca atctcagtca gagtcattgc tgaattcctg  10980
gaactttgtg aagtgcttga tgcagttgtg ctccagcctg gaataaggga tcgatattta  11040
tggaaattca gcgcttcagg tgattataca tctagttctg cttataatgc tctcttcctt  11100
ggttcagttc agttcgaacc agcagagcgg ctatggaaat cttgggctcc tgggaagtgc  11160
aagttcttta tatggcttgt ggaacataat aggtgctgga ctgctgacag gctcagaaaa  11220
agagggctag accgaccaga gcagtgcccc ttgtgcgacc aagaggttga aaccataaat  11280
catttgctgg tcaagtgtgt ttttgctaag cagttctggt ttgatttcct taattcagtg  11340
gggttgcggg atctgtatcc agctcatgag gaatcctttg agtcgtggtg gaagtctagc  11400
agctccggca tcggatcttg tgagaaaagg tttcaattct ttagtgatcc taggtgcttg  11460
gaccatttgg aagcatagga ataggtgtgt tttttatggt tgtaatccca gcttgctcac  11520
gacccttagg atggctaggg aagaggcggt gctctggtcc atgactggtg ccaaggcctt  11580
gtccttcctc caagtcgatg agttgctggc ttaaaacagc ggtgtgggtc gtgtttcctc  11640
catgttttag tcagtgatcc gtagttagtc tctagtggtg tatgtgctgt attggggttc  11700
tctccccctt tcttttcttc tattaataca aagatgcgca gctctcctgc gtattccaga  11760
aaaaaaagaa aaaaaaaaca accctgggat aggggctgct aggagatcca aattcttggc  11820
cccagccagc acccacaaat ccctctcctc cttagctttt ctaatagccg gtgagagcgg  11880
cacagatggt gagaccagag aagctgaagg ttgtaagacg acgagttgac atcccccaaa  11940
gtcatagtgg tcaatgtgtc gcatatgctg tagctagagt gctcaagcaa ggcagaagct  12000
ctttgtgccg atgttgaggt agtcgagcac gagggtgagt agccatggtt gaggatgcca  12060
tctttacgcc atggtgatgg tcgaggcgcg tcgagacagt ccattgtata agggggtgat  12120
gttgaggtca atgtagtcaa ggccatcgag gatgtcgacg aaaatagcga cacagtcaag  12180
gcaggtcatc atggaggaag catacaccgg atttgctagg cctgagaacg tgtcctggag  12240
aacggcacgc tacactgcca atataagaca tgctagttag agagccccaa caatgtgtca  12300
acatccgagc gaccttggaa gagagtgcct caacgatggt tgattgtggt gcccaaaaca  12360
actgagcaca aggtgtcgat gtatcccaca attgtcaaat tagatgatat atgtgggaaa  12420
gagacaatga tgctggcgat gtggttatgc tgaatgaaga aggaacagtg cgggagtgaa  12480
cgctcctacc cgaaggggag tagtttgggc cgacgtcctt ggccaaggca atggtccaga  12540
cataaggtac agtgtgccca aaggcagtgg tccagaagca aggtatggcg tcaaaaacag  12600
tgttcgctgt tggtgatgaa gagcacaaaa agtttgatga agaccaagtg catcctggtg  12660
gtgcgcaaga ggtgcaacac aattatcgat gtacatggag cgacaatgta gatgcattgt  12720
tgtatgccaa ccatggatag aggcatgcct atgagggtgt ctcaattaga gaatctctaa  12780
cattgcctta aatcaattct ctatcttata atatagtgct taacttataa aaaactgctc  12840
caacagtgct ctattttaca tttttatcaa aaaatatagg gcagaccata aagtgaccaa  12900
aatatactac actctggatt agggcttaac tgttgcaaca caatttgttt ttagtgcctt  12960
aaacacttta aatgatgtag tattgtaatt tttggaacat tattttgagg ggcagcgagt  13020
gtagcgtaga gacagtttat gaggggcagt agcggaagtg ttgggatagc aagcacaacc  13080
aaatacacgg agttgggttg tgtcgtacaa ggcgaagtag gtggtggggt ggctcaccac  13140
cttcgatggg aggcgattga ggaggtgggt ggcggtgtgc aaggcctctg cccagtagtt  13200
ggcagggaga gacgcctgaa agagaaggca acaaatcatg ttggtggtgg tgcgaatcat  13260
tcgctcggcc cgaccgtttt gggcagaggt gtaggggcac gagagatgca attgaacgcc  13320
actggcgagg aagaacgacc gagaggcatg gttgtcgaac tcgcggccat tgtcacactg  13380
cagtgcatgg accgggcgac agaactgggt ggagacccag gcgaagaagt gagtgagggt  13440
ggtaaacgtg tcggatttca ttcgaaaagg aaaagtccat aggaaatggg aaaaatcgtc  13500
caaaatcacc aaatagtatt tgtatcctga cagactgagt accggggagg tccatagatc  13560
acaatgaacc aggtcaaaag cctgttcagc cctagaagaa gatgtagtga aaggaagacg  13620
ggtatgtcgg tcaagctgac atgcatgaca gaggccctca aaatgtcccc tattacaaga  13680
agaatctaaa gtgctggaaa gcttggtcat gacctagatc ctgggtggcc gagacgacga  13740
tgccaagtgg tggaggtggt ggtggagacc aggacgggag gtggagacac gccggtggac  13800
gacgaccgga gtgtgtagag gggcccgacg ctgtcacatc gggcgagtgg ggtcctggtg  13860
gccagatcct ttacagaaaa accagtaggg tcaaactcaa tggaacacga attgtcggtg  13920
gtgaaccaac ggacagaaag aagattgtga gtgatgtgag gggctacgag aacgtcgttg  13980
aggtagaaca gtccagggag aaccgaggca cctactgagg tgactagaag agtggaaccg  14040
tttcgaacga cgatcgaggt agggtgtgtg gggggaggtg ggtgtgagcg agagcatgcc  14100
tagggtgggg gtggtgtgat aggatgcacc ggagtcgatg acccagtcag aaggcggtgg  14160
ggccaacgcc atggtgctgt atgcggcagc gagggcaaca gggtcccaac ctgcaacgaa  14220
cgaggaccat ggtgtcgtgg tagacggtct cgtaggcggg agttgaggcg ggccccgggt  14280
```

```
cggtcggggc acgccgtatg gaggcatgtt gtaggcgggc ggcgtagtca ggagagccgg  14340
aggacgggag gcgctggggg cctgacccag ccacatggag ataatgccgg tccaggggtt  14400
gtagaacgac ggccaactct ggtcgccacc cctatcggtg gaacctccac gagaggagct  14460
gccgccccca tgtccgccct tgtaggggcg acggccgccg tcgatggtgg aatgctgacg  14520
agggtccgta ggagccgcgg tgaagggccg agcgggggtc ctggttgacg gagcgcgggg  14580
ggcgagtcct ccggaagacg cctgggcacc aggggtggcg ctgtagagtg ccggagtggg  14640
agcctcgatc gtcatggtga gctcctcgag aagaagttca ttgcgcacgg cgtggaaggt  14700
gggaaaaggt acggtcctct tgatgagagc cttcaggtgg ccgtagaggg ggctgaggcc  14760
acacaggagg tttagcacca aggtacggtc cgccagcgac tcgccaaggt cgcggaggga  14820
gtctgctagg cccttcatct ggcggcagta ctcccgcaca gagaggtccc cctgggagaa  14880
ttggtggaac tgatcatcga tttgaagggc ccgagcgtcc cggttcccga ggaattgttc  14940
ctcgagggcg agccacgcct ggcgggccgt gtccgccttg tcgcagatga tgtcctggag  15000
ctcgacggtg atagtgtcgt ggagccaaaa gagcacgact gtgtccatca gggaccaggc  15060
catgggcggt ggggtgacga tgtcgtcgag gacgtggtcg gcgagagcgt agcgccgcag  15120
ggtgaggacc tgcccccgac agcgagggta gtgggaggac gccgggtcta gcacgattga  15180
cacgagggac catatgttgt ggagaccggc agcctgcgca tgaagggcgg cgatgtggtc  15240
ggcgtcgagt ccaggggcga tgggtgcctg gggttgggtg gaggtgcctc cggggtgacc  15300
ggaggatgcc cgaggaggag tcgctgagcg gtagccattt gggcggtcag agcagcgctc  15360
atggcacgct cttgctacag ggcgagggtc gcagcgcgct cgcggtcgag ggaagcctcc  15420
acggctgcct ggatagtggc gatggccgtg accagcgccg acgaggccgt cggggggggcg  15480
ggggggggca gtgacgtcag cccatgtggc ggtggtgtgg gcccggagga gaatcgcggc  15540
gtcgttgagc agcgagggtg gcatcgggta ggggcccgag atcggcgatg tgggcccctc  15600
cccaacagcg aggtcgctag gggtgccgag tccggcagtg gcgagggcgg cggtagccgc  15660
ggcgctgcgt gctggtgggg ccacagtggc agtggccgca gggagggccg cgcgtggctg  15720
ctgggcagca gcagtcgtag cggcagccgg ggtgtagggg gaatgaggtg gtgtcgacat  15780
ggcggcacca ggtggttggg cggccgacgc tgcggggttg acggcggcgg tggaggaagg  15840
accggtgcga gcggccgagg tggctggatg gccggcgcgg tgcccagtga gggggtccgg  15900
cgggggcagc ccttgctgct gggcggcggc gcaggaggag gcgccgcggc ggccagcctg  15960
gggaggagcg gcgaccggtg ggaggaaggg gagcggcgat cggcctggg gggagggaga  16020
agggggggagc ggtggctgcc acggactggc ggcggcaggg agggtgggag ggaattagtg  16080
tggctctgat accatgtaga actatggaaa accctaaccc tagaataggg ttgggcagtg  16140
tattaataga ccaaataact gggctaggcc cattacaagg gacgggtatc taaaaaaata  16200
gactgcggct tttttttag ataatggata ctagtccagc ttctcctcgt ttggaggatt  16260
agccaacaca ccaaaagttt ttacatggag tagtcacacg actagctgct ttatttgtcc  16320
ttttcattta tgcaacctag gaattatttg acttgtctcc atcttaatgt gtctgctttt  16380
aaatacagtt tactgaacag ggccacatct ttgttcaagt ccatttggtc aaggaactaa  16440
acaggaaagg aaacaatttt tgtgatgttt ctgctcataa cagagaaatt ctgtatgatt  16500
ctgacaactc gatgctatgg aacacactaa gcggacttga agtagcagat agctggaggt  16560
ccttggagaa ttttacgatg ttcaagaatt caaatggtga aacagataca attaggttag  16620
ctgtcagagt tgaagacacc ggcataggaa taacaaaaga tgctcaaatg cgtattttta  16680
cacctttcat gcaagctgac agttccacct cacgaacata tggtggaact ggaattggct  16740
tgagtattac aaaacgttta gttgaattga tgggtggaga aatagggttt actagtaaat  16800
caggagttgg tagtacattt tcttttactg ccattttcaa ggagaacaga ggatgtcctg  16860
gagatatgaa aagatactat tctgaaccta ctccgttgga ttttcaagga atgagggctc  16920
ttattattga tggaaggagt gcacgtgcag aggttactat gtaccatctt cgtagacttg  16980
gaatacagtg cagtcttgtt gccacatctg aatctgaatc tgcatcttca gctttgatga  17040
aagcctgcac ctcaaggttc atttccttgt gtagtttact gtttgattta cttctacaag  17100
ttttagaaat tagaagttat tttgttcaaa taaatgtaac attccttgca tttataaact  17160
tttgtcatct taacacatgg ctttgctata ttttctttag ttggttgtgt gctatttctt  17220
tgaatatttt ccatattgtc gatcccaaaa caaggtttcg taacttctca tgaactgaag  17280
aaaagtagga gaaacagagt gaaaccttcg ttggtttgag tttagaaact gaaataggat  17340
agttcgattc taaataactt gtgaattcat tcagttgttg ctgtcatcat tataacatat  17400
caatttgttc atggccagca acctacactt gtcctcagta ttacgaccca acaaaatcaa  17460
tgcataatgt cgccatcatc actttccatg tatgcatttt cttttctaag cactgttgat  17520
gccttacttg ttgatgttat catttatatt ttacatgttg agcagcaaaa acaatccgga  17580
catggtcctt gttgatacag aagcttgggg taaaggttca ggtttggcat tctatcatcg  17640
ttttgtagat tgtcaactaa agggcgcaca caagtttct cagcccatgc caaagactat  17700
tcttttggga agctcaataa gccctgttga atctgattat ttaagattga caggatttgg  17760
tgattgcata aggaaacccc tccgtcttag tactattgtt gcctgtcttc gcaaaacctt  17820
aggggttggg gttacaaggc agcagagtag agaccaatct ttggttcttc aaagtgtact  17880
aactggaaaa cagattctgg ttgtggatga taatgcagtc aaccgtaaag ttgcagctgg  17940
ttctttgaag aaatatggat ctaaagttac atgtgttgat agtgggagtg atgcaattga  18000
tatgctcaag ccacctcaca catttgatgc ttgcttcatg gatgttcaga tgcccgagat  18060
ggacgggtaa tgttcctttc caatgagtta ctaatgaaaa agagcgcaga tttgctgccc  18120
aggcgttctc attatctaaa ataccatgtt gcaatatttc aaaaatcatc acaaaaatca  18180
tgtatgcagt acacaaagtt aggtatagcc gcaacacttc agattgaaat ttcttcctag  18240
atgccaagaa ccaaaataga caagcagtca acctggcagt gttcatcatg tgctgacagt  18300
gagactttgt tttttaatct cagcatcaaa gatgaacttt attgaattct tgaggctaca  18360
cttaaggtgt acttgcacac atgtttttg tgatgattgt tgaaacattg caatacggta  18420
ttttagaatg tgggcgccaa tttccctggg cgccatatga tttccaatgg aaaattgtca  18480
tatgttattt acttgcggga tatactataa gagttcaata tgtaaaagat tctttgtgca  18540
gaagtcactc ttggaacatc ttacgttagt tcacatggaa gcatgtcttt agttttaggt  18600
atgtgcttct tttggatttt gtggaatcat cggaacagat gcatctttga tggcctttcc  18660
cctaatgttg ctaattttct aatccatgtg ggggatgagc gccgtctgtg ggagactgcc  18720
ggggccaagg ggttgacatc ccttgttgcc tccctctctc atgtagccta gagttttata  18780
gatgagtcag tctatgctag tttcgttcag gccgccgtaa ggcgtcagtt gtaccccggt  18840
ctattttaga ccttgtttat ttgttctttt aatataatga tacgcagctc tcctgcgtgt  18900
tcgagaaaaa aagagaaagt tattttttgg tcctcaaata acaacacttg tcaaatgtat  18960
gcatctcctc atgttattag caagcactct cataggagta tcactgagga taatctctct  19020
```

```
tttgttttca catccagtcc ttgcttaaaa aaatgcactg tagcctcaca tgcttgtgtt  19080
tgctttccta tgggttataa caagtggttg catctacttt gatcacttgt agatccactg  19140
taggactacc attaacaata ttcacattca attgcaggtt tgaagctaca agattaatcc  19200
ggtccataga gaaaaaaata aacgatatga tcatgatggg tgaaatatcc gctaataatt  19260
atggaaataa ggcccattgg catgtaccaa tattagctat gacggcagat gtaatccaag  19320
cgacttttga aaaatgtatg cagtgtggaa tggatggata tgtgtcaaag ccatttgaag  19380
aacagcagct ctactttgct gttgctcatt tcttagagac tgatgaaaca gaataa      19436

SEQ ID NO: 253          moltype = DNA  length = 19424
FEATURE                 Location/Qualifiers
source                  1..19424
                        mol_type = other DNA
                        organism = synthetic construct
SEQUENCE: 253
aaaacatttg aggacttcac agcaaggaca acatttgaaa ggccattgat gagtggtgtc  60
gcctatgcat tgaaggtatt acacaatgaa agacaacagt ttgaggaaca acatggatgg  120
aagattaaga agatggaaga tggagatcag tcccttgttc atgactacaa ccttgaaaag  180
cttgaaccat caccagttca agatgagtat gcgcctgtta ttttctctca ggaaactgtg  240
aagcacatta tatctgtaga tatgatgtct gggaaggtag taggatattc gtaagccttt  300
acagtaaata cttactattt tatctatcct gagttcctta ctactatttt tgttataaaa  360
cgaagaaatt tctggctctt cttctaactt tcaatattat taggattaaa catgtgtaga  420
acttctcggt caaaaaagac actttagaac ttatattttt attttaatta gaatttgatg  480
tataaaaatt aatcattttt acaatgagtg ttatagtaat ataagttgtt atgtgtcttg  540
ttcaatgtgt taattactat agcatgttcc atagaaatac tgtgcaggct gttactaatt  600
ctctcttatt ctgtctttgt ggaaattaca taattactaa acctcatagt aataataata  660
ataactaaga ctccattttt ctgctaacat tacaaccttg atttcaggaa gatcatgaca  720
atatattacg ttcctggtca acaggtaaag gggccctaac atccccttt aagcttctga  780
agtccaacca tctcggtgtg gtgcttacat tcactgtata taaatatgat ctgcctccaa  840
atgcaacacc acaggagcgt attcatgcta cattggggta aaatgttttg caaagtttca  900
agttgaagct atataggaat acactatttt ttctttagga gacttaacct tgtggttatt  960
gacactttgc agctatcttg gtgcctcatt tgatgtccct tctctggcaa ctcgctagca  1020
aacgaaagat agtagttaat ttatatgaca ccacaaatca tacctctcct attgaaatgt  1080
atggtctga ttttactcca tctggtgatc tgcatattag tagcattgat tttggagacc  1140
caacacgcaa acatgagatg cattgcaggt agaaaacttt tttttgatgc gaattataca  1200
atgcttttgt tcttcagata tgctcagtgc tttctctttc aaacttctct ttcagattta  1260
aacatgaacc ttcactgcca tggtctgcaa taataatatc aacagctgta gctataattg  1320
ttttgcttgt tggacatatt atttatgcaa ctctgaactc ccttgaaaag gctgaacatg  1380
attatagagt aatgagagaa cttaaaggac aagctgaagc tgcagatata gcaaaatctc  1440
aggttcattc tacctcttcc agtgtcttca tcctatgcat tggtttgtta tctcatttgt  1500
tctacttttc tctttttgtc ggctgagtca ttattgattg tcttgcagtt tctagcaact  1560
gtttcccatg agattcggac tccaatgaat ggtgttttag gtctgtactt ctgatatttc  1620
tttttgtct attaatacat accgcagtta tttgtgttta tgttttaatc aaagacaact  1680
aaataaattt tgaaaaggat ttcttcttga attaggtatg ctgcagatgc taatggacac  1740
tgaacttgat acaactcagc aggattttgt agtcaccgct caagaaagtg gaaaggtatt  1800
aataaactta ataaatgaag tccttgatct ggctaagata gagtcaggaa ggattgagct  1860
ggaagcagtg ccttttgatg tccgtgatat tcttgacaat gtgatatctc ttttctacga  1920
taaatcacaa gctaaaggca tagaggtgag tcctaattta gaacttgtat tgtttgctaa  1980
gctctgaata ttgtttgtgc catgggacct aaaataatgt gtaattcttt tttgagggta  2040
gttggccgtg cttgtatctg accaagttcc tgatgtccta attggggatc catggcggtt  2100
ccggcagatc attacgaacc ttgtggggaa ttctatgaag gttagattca aatatgtggt  2160
agcttcatta tttcagcttg ctggcaagtt gtaactgtgt ctagtcaatc ccaccattta  2220
gcttatacaa caatatactt tgtaggaaac gtgacaactt actaaaatat taatgtcatg  2280
agcttttgaa tttgagatgt gtagaagaca attggtagaa ttggtcaatt gtgtcgctga  2340
gctcgtgggc agattataca tgagtacatt cacttggatg gcaagaaacc tccctaaaga  2400
taagaagtca ggattacatg accctaatct agcatattta aagatattcc aatataatat  2460
accaccccc atatttttct cgaacgtgca ggaaagctgc acatctttat attaagaaga  2520
taaaaggtcc aaaatggacc aaaacaggta tagatacaag gcacctcacg tggccaaaaa  2580
caaaagtaca aaaaaaacag tccataactt tttttttta gataatggaa aaatcatccg  2640
accttggcct caaatgaggt tacggccatt tattacaagg gacggaagca tattgccaaa  2700
acacctccta tgaccacttc agagaacccc aactagccaa attaaagaac ttcagctatc  2760
gaaccacagc tactacatat ttaaacgcaa cgcagacccc catccaaaat tgctaaagaa  2820
ctgtagtagc accctctcca cattacgaca tgaagacttt attaactctt ggtcctccct  2880
tctaggctga agctgagacc agaagcggca ccaatatgtt gccctgaagg ttacctgcac  2940
acatgattta ggagatgaat tattgaacac cacatcattt ctacttaacc aaatagccca  3000
acaaattgcc gatgcaacgg ttaatagtaa gtttcgaact ctgggaagcc tcccgctcgc  3060
ccaaacccca aacaaatcat taacatcccg aggaggtctc aaccccgtgc ttatctgaat  3120
caaccgccaa atgaatgacg catacaaaca actgaaaaat aggtgcttta ttgtctccgg  3180
tctactacaa aagcaacata tcttattacc attccaatgc ctcctagcca agttatcctt  3240
tgttaatgtt accccctcttt tgaggtacca cataaaaatc ttaattttca gaggaagcct  3300
aagtttccaa aggtccttat tatgcacccc caacccattg ttaagagatg ccagatacag  3360
agacttaacc gtaaacatcc cgttggcggt caagttccat ctgaacaagt ccctgtttga  3420
attcaaattg gtatgcgcaa caagtgagac caattgaacc cattggtccc tcaattgttg  3480
agccaaaccc ctccgaaagg atatatttaa gggcaccgtg gagaacacac aggcaacagt  3540
agagttcttc ctcctcgcta ggttataaag agacggaaaa cgaagtttta acgttcccga  3600
cccgagccaa tcatcctccc agaaacgcac ctgggaccca tcatgaatca caaaggttcc  3660
tttactaatg aatgtgtcct taactttcat aagaccactc cagaagtgtg aatcagtggc  3720
cctacgctgc gcctgggata aggttcgatt ggccagatat ttacgtctca ataatgattg  3780
ccacatccct tcttcattga gaagtttata caaccatttg cttaagaggc atttattttg  3840
aacctctaaa ttcaaaatgc ctagcccgcc aacctcctta ggttgacaaa ttacatccca  3900
```

```
tttggccagc ctatattttt tcttatgacc ctccccttgc cagaaaaaac gcgatctgaa  3960
ataatctatc ttctccagca caccttttgg tacctcaaag aaagacatca taaacatcgc  4020
tagactggtc aacacagaat taattaatac gagccgccct cctactgaca taagttttcc  4080
tttccagctg ctgagctttt tctcgaattt ggcctccact gttttccact caccaattgt  4140
caatcgacgg tggtgcatag gaatcccaag atatctgaag ggcagcccac cagaactgca  4200
accaaacagc cgtgtgtacc tcccttcatc ctcttttgcc ttcccataac agaatatctc  4260
actcttgtga aagtttattt taagaccaga taactgctca aaggcacata atatgagctt  4320
catattcgtt gccttttcca gatcgtgatc cataaacaaa attgtatcat cagcgtattg  4380
cagaatggat agccccccat ctaccaaatg cggcaccaag cccttgatct ggccattttc  4440
ctttgctcta ttaatcaggg tagcaagcat gtccactacc aagttaaaga gaataggaga  4500
cagcggatcg ccctgcctca cccctctatg ggtctggaaa aaaggaccca tgtgatcatt  4560
aactctaacc gcaacatggc ccccttcat gaaagactcg atccacctac accaggtact  4620
tgaaaaacct ttcatacgaa gggattgttg aacaaagctc cacttcacct tatcataagc  4680
tttctcgaag tcgattttga aaatgacccc atcccttttc ttcgtatgta gctcatgaat  4740
agtctcatgt aagaccacca ccccttccat gatatttctt cctggcagga acgcagtctg  4800
caggggactg attacattct gcgcaacctc cgtgatcctc ttagtcgcca cctttgtgaa  4860
gattttgaaa ctgacattta gtagacaaat tggtcggtat tgttgaaccg agattgcctc  4920
ccgagtctta ggaagcaaaa tgatagtccc aaagttaaga ctatacaaag ggagatttcc  4980
tgagtggaac tcacgaaaca aagccataag atcatcttta ataacatccc aacagatttg  5040
ataaaattcc gccgggaatc catcaggacc tggagccttg ttatgttcca tactaaaaac  5100
caccgctttt acttcatctt cagaaaatgg ctgggtgagc ttctcgttct caacttgagt  5160
aacttgtatt atatcatctc taagatcctc atccagacta aaagacgtgt tttctggggg  5220
gccaaagaga tttttataat aaccagttat atgactcttt aattctttct cgtcgtataa  5280
catacgagct ccatccgtca tctggaagat gcgattcttc ctgaattttc cattggctat  5340
catctgaaaa tatttagtat tactatcccc ctccaggagc tccttgacct tcgctctttg  5400
ataccacttt atttcctcct cccggagtag ctgagcaagc ctgttctgta agtagttatg  5460
cagatccaac tccgaagtac tcaacagaac tacttcagct ctcttatcta aatcatcaag  5520
cttagctatg atctcctttt tttccttttt caacaacccc gaagtgtgca ttgcccaacc  5580
ccttaagtgt tggcgcacct tcctaatcct ggcttgccat ttctccaaag gagtagaacc  5640
acttgtctca tttacccaaa tatcttttac catatccaca aaaccatccc tcagaaacca  5700
gcctagttct aacttgaacg gaggaattgt atgggcggtt acaacacctg tgctaagaag  5760
cagaggagta tgatcggata tatttctcga caaggcatgt accgaagctc tagggtattt  5820
tccctcccat tctgtagcta ccaaaatccg atccaacttc tcataagtcg gaatatccct  5880
agtattagcc caggtgtacc ttcgccccga catctgcaat tctcttagat caagaccatc  5940
aattaccgca ttgaaaagga acggccaacg atgatcaaat ctatcattat ttttctcaga  6000
tggagatcgt aaaatattaa aatctccccc aatgagaata ggtaaagttt ctgtattgct  6060
cacacggact agctcagaaa ggaattcttg tttgaagcag tcctgggcag ggccatacac  6120
cgagacaaga gcccatttaa aaccatctgc tttatcaagc aaattaaact taataaagaa  6180
atccccttcc gtgatggcac caacatcaaa gacatcagcg tcaattccta acaacatccc  6240
cccagatcta ccatgaggtt ctttgcaatg ccagataaaa tttttcccag cacacaaatt  6300
ccttagtaga tgatctggga aggatttgcg gcctgtttca gagagggcaa taaaattgag  6360
accatgttct ttggtcagat ccgaaatgta tctaagtttt ttcaaatcct tgaacccatt  6420
gctgttccaa aagattcctt tcattggtaa acaattaatt aataatcaag cccgaccttt  6480
tttcttagaa cacaacgaac cctgactaga tggttttgta cagactgact taatcagccc  6540
atcagtgcca tccgtctctt catgcataat atccccacac aaatgattta aaatgaaatg  6600
atcaaactct tcgtcctcta ctactccctt tcccataaaa tcagataaat cagcctcgtt  6660
cttacccact agctgatcct gaactctatt aatctctaat tttttcaact gaccaataga  6720
ggaagcaact gaactaggat tagaacccgc taaaatgcca atatttttaa aagaatccag  6780
aatataatta tcgggtaaac taataaagga aacattgtta cctttagtcg gctgatcgtc  6840
caggttgtat cccgctttca gccgaatcgc tcgaactagc gagtcttcac tcaccgaatc  6900
agagcggcgc gagctacgac gcagtgcatg cacttttcct gtcaacgcct ccgggatact  6960
gcccaacttt tcaatactaa cagcattgac cgagagacag gtaccctgag attgatccag  7020
atccagctgt gtagggccag cgcacaccga tttcccactg gacgtgttgc tgttcagcat  7080
agaatccgac accttattaa ctgcccctgc tgaatccttt gatgttccct tcaagctcgc  7140
ccccttattc cctctttcac ctatattgtg atccttgttt tgatcctgaa attcatcatc  7200
atcattatcc ccgatatgat ccatatccat cggcaaaggc tggtcacctt cagctgctga  7260
ctccaccctg aatttcagtt catataagta gtctccaatt accacatcaa ctacttgcgg  7320
aatcaaattc gggtcaagca cggccacctt cagccttgcc ctgtcaaact tccgagtaaa  7380
caacatatcc acctcttttg agatgcctag catagaacca accgcccaga ttaccgagta  7440
ctctctaagt tccttaggta aaccagtgaa ctgcacccaa gccttaggca tctcatattt  7500
tatttcctct ccaaacccct cttccttgac aagcatctgt gcaccaaatt ttgtatgaac  7560
agttccccac tcgatcatac ggtgaagttc accccctggaa gggaaacacg tcgagaacac  7620
attgttcccc acacacttca cacaccagtc ccaatcagca gccaccaacc ttttaagctc  7680
attcaaaatc tgctcttcat tcatggaacc ctccacaata gacactgtac cattgcagcc  7740
accttgcctc tgctttactg gaatgggttg gggtataaag taaaacccca atccctccac  7800
cgcatacccg caaggtattg caaaagtttt gcaggcacga accaccggac atttcgaagt  7860
taagtgagtt ttgacatcac aaatttcaca aaatagctca atattacagt cactcaactg  7920
atgaccttta tttttgcacc tgaaacaaaa cggcactttc tcttttgaac ttgaaatcac  7980
agaagaaccc accttgtcat ccaagtgggt tggagtagac aattctttga tggtctccaa  8040
ctttgaactg tgttgggacc caatattcgg acctgctgga ttccccctcg agttctgaat  8100
gtgctggctc ttccccacag actgctgcag caaggaaaca atctgttcca tggtactatc  8160
tggaacaggc ctgacagcgc taccgttgcc aattgatgtt gtaattgcct gttggagcaa  8220
gtccacagcg tttgatactt gaggagtcac cgaagaagcc cctgaacctc ccagaccctg  8280
tccagcgacc atcacagagg aagcccctcc atttgaaaac ctgctgtgaa cacctccgcc  8340
cccagactgg gttggcaaag tacgaccacc atagaaccgg cctccggcag aagcacctct  8400
tccaccacgc cacgctccag cacggccctg tccacctccc cgacgtccaa aaggacggcg  8460
tccgccacca taaccaggat ggaacactgg ttgggatcca ccgcgtccaa agtcagtgtt  8520
cagtcccaaa ccagcgacat atcctcccgt gcccccaagc agttgctgac cggtggaaaa  8580
acctgcagcg ccctcggact gatgctggcc gcgactgcct ccacgccctc cagtatcacc  8640
```

```
aaccggcgcc attgcgttcc ttacagcctc gacgaaggtg ccaggagcca caccccggga  8700
ggaaatgtga accgccctgg cagcagaaga actggtgcct gagcgggaga acaaggaagc  8760
cagcccagca gttggcctat aaggaatcct aggactgaga atcatatgtt gggccctccc  8820
attccaacgg ggacaagcac taattaagcc aacattcctt gattccagca caggatccgc  8880
atgagaatcc cagaatatcg cctgacttgc atccatacca aaatcattca aattcaaacc  8940
atcagctaac cgctccgctg ataccgctcc cattgaagac gtcttcttca acctttggcc  9000
gtggcacctt ccaggggagc agcgccattg cgctttttct agtgcatgtc caactgtgaa  9060
ctccggcgaa cgtcgtggcg acggcaattt gccctgccat ggcttcacct tattcctaga  9120
agaagtgctc ggactaggag aatgcaagca tgtactcaac gtcggtcctg gtcccgacct  9180
gcatacaccg ccgactacct ctcctacctg ttcgagagct tcattccaaa tagattttgg  9240
tggcgcggaa ctgcagtcaa ttagcttgcc gtcaacacag gacagagacc cgttcacgaa  9300
aacagagagc cgaccaccct caggtgtccg tccgctattt gccgaaccgg ccagatcacc  9360
aacctcctga tccagctgaa cctgacaatc agcaacctcc gccagtgggc ggacgaccac  9420
cgcatcggtg ggcgccagcg tctttcgacg acgacccttc cgagcgtacg tggccaagca  9480
acgtcgctgc atagcgcaga gaacgaacga acaaccactg gcgggagacc ggcctagatg  9540
gccgcctccc acctctggtg tcccactccg ccgagacaga gggaagagca cttaccgggt  9600
tacgccgcgc gcctagccgg gacgcccacg cggcctagac cgccttgccg tggtcaccgc  9660
agagaagaaa ctcgagcgcc agggtccacc gcggcctgcg atgctctctg atgagcagcg  9720
ggaagttgcg gcgtgcgaag cgaccggccc agcagttgag cacggcgtcg acggcgtccg  9780
cgtcggcacg aggcagcgcg agcaagcgcg cgacgacctc ggacaccttc cagtcccgct  9840
gccaccggtt gccctccacg cggaggcggt gtcacgcaat caaaaacagt ccataactag  9900
agagctaaca acagaacagc tacaaccctg ccaggggagt gtattgggca tcaacacgga  9960
ctgaggcagg gtgatcctct atcgcctatg ctgtttattc ttgtaatgga tgtcttgaat  10020
ctgcttgtgc agcgagcctc tgaggaaggg tttcttcagc ctctttcttc taggaatatg  10080
cagcatcgta tctcgctgta cgcggatgat gcaatgttat ttctatgtcc tactgccccg  10140
gatatcagta tggttatgga tattcttcat ttatttggtt caacttcagg tctaaggact  10200
aatgtccaga agagcagtgt gttcccaatc tgatgtgggg aagaagaggt gaattgttta  10260
caggacttgc tgctatgcaa tatttcagtt tttccctgta agtacctcgg tttgcctttg  10320
tctcccaaga aactcacaag ggaccaggtt caagccattg ttgaaagagt ggccagcctt  10380
ttgccaggat ggaaagctga acttatgacc agggctggta gagctattca tgtgcagttt  10440
gtcatgacgg ctaagatgat atatgcagct ctggcacttg accttcctgt atgggccatc  10500
aaagcaatcg ataagctgag gaagggcttc ctctggaggg gtaggaaaga gttccgtggt  10560
ggtcactgcc tcttggcttg gcctaaggtt acccgtccca aggagttggg tggtcttggg  10620
attagtgagt taaagaacct ctgttgggct ttgagagctc gctggccatg gctgcagaaa  10680
acagacccca gtaggccttg ggcggacttc cccattcatg tttgtaaggt ggttaaaaat  10740
ctgattgctg cagccattat tactaagctc ggtgatggag ccaataccct tttctggaag  10800
gacagatggt tggaggggag atgtattaag gacatagctc ctgcgttgtt tgatttggtg  10860
cccttgcgtc ttgccaacaa acggttggtc aaagatactc tccctaattt ccattggctc  10920
tcagatgtgc aaggggcaat ctcagtcaga gtcattgctg aattcctgga actttgtgaa  10980
gtgcttgatg cagttgtgct ccagcctgga ataagggatc gatatttatg gaaattcagc  11040
gcttcaggtg attatacatc tagttctgct tataatgctc tcttccttgg ttcagttcag  11100
ttcgaaccag cagagcggct atggaaatct tgggctcctg ggaagtgcaa gttctttata  11160
tggcttgtgg aacataatag gtgctggact gctgacaggc tcagaaaaag agggctagac  11220
cgaccagagc agtgcccctt gtgcgaccaa gaggttgaaa ccataaatca tttgctggtc  11280
aagtgtgttt ttgctaagca gttctggttt gatttcctta attcagtggg gttgcgggat  11340
ctgtatccag ctcatgagga atcctttgag tcgtggtgga agtctagcag ctccggcatc  11400
ggatcttgtg agaaaaggtt tcaattcttt agtgatccta ggtgcttgga ccatttggaa  11460
gcataggaat aggtgtgttt tttatggttg taatcccagc ttgctcacga cccttaggat  11520
ggctagggaa gaggcggtgc tctggtccat gactggtgcc aaggccttgt ccttcctcca  11580
agtcgatgag ttgctggctt aaaacagcgg tgtgggtcgt gtttcctcca tgttttagtc  11640
agtgatccgt agttagtctc tagtggtgta tgtgctgtat tggggttctc tccccctttc  11700
ttttcttcta ttaatacaaa gatgcgcagc tctcctgcgt attccagaaa aaaaagaaaa  11760
aaaaaacaac cctgggatag gggctgctag gagatccaaa ttcttggccc cagccagcac  11820
ccacaaatcc ctctcctcct tagcttttct aatagccggt gagagcggca cagatggtga  11880
gaccagagaa gctgaaggtt gtaagacgac gagttgacat cccccaaagt catagtggtc  11940
aatgtgtcgc atatgctgta gctagagtgc tcaagcaagg cagaagctct ttgtgccgat  12000
gttgaggtag tcgagcacga gggtgagtag ccatggttga ggatgccatc tttacgccat  12060
ggtgatggtc gaggcgcgtc gagacagtcc attgtataag gggtgatgt tgaggtcaat  12120
gtagtcaagg ccatcgagga tgtcgacgaa aatagcgaca cagtcaaggc aggtcatcat  12180
ggaggaagca tacaccggat ttgctaggcc tgagaacgtg tcctggagaa cggcacgcta  12240
cactgccaat ataagacatg ctagttagag agccccaaca atgtgtcaac atccgagcga  12300
ccttggaaga gagtgcctca acgatggttg attgtggtgc ccaaaacaac tgagcacaag  12360
gtgtcgatgt atcccacaat tgtcaaatta gatgatatat gtgggaaaga gacaatgatg  12420
ctggcgatgt ggttatgctg aatgaagaag gaacagtgcg ggagtgaacg ctcctacccg  12480
aaggggagta gtttgggccg acgtccttgg ccaaggcaat ggtccagaca taaggtacag  12540
tgtgcccaaa ggcagtggtc cagaagcaag gtatggcgtc aaaaacagtg ttcgctgttg  12600
gtgatgaaga gcacaaaaag tttgatgaag accaagtgca tcctggtggt gcgcaagagg  12660
tgcaacacaa ttatcgatgt acatggagcg acaatgtaga tgcattgttg tatgccaacc  12720
atggatagag gcatgcctat gagggtgtct caattagaga atctctaaca ttgccttaaa  12780
tcaattctct atcttataat atagtgctta acttataaaa aactgctcca acagtgctct  12840
attttacatt tttatcaaaa aatatagggc agaccataaa gtgaccaaaa tatactacac  12900
tctggattag ggcttaactg ttgcaacaca atttgttttt agtgccttaa acactttaaa  12960
tgatgtagta ttgtaatttt tggaacatta ttttgagggg cagcgagtgt agcgtagaga  13020
cagtttatga ggggcagtag cggaagtgtt gggatagcaa gcacaaccaa atacacggag  13080
ttgggttgtg tcgtacaagg cgaagtaggt ggtggggtgg ctcaccacct tcgatgggag  13140
gcgattgagg aggtgggtgg cggtgtgcaa ggcctctgcc cagtagttgg cagggagaga  13200
cgcctgaaag agaaggcaac aaatcatgtt ggtggtggtg cgaatcattc gctcggcccg  13260
accgttttgg gcagaggtgt aggggcacga gagatgcaat tgaacgccac tggcgaggaa  13320
gaacgaccga gaggcatggt tgtcgaactc gcggccattg tcacactgca gtgcatggac  13380
```

```
cgggcgacag aactgggtgg agacccaggc gaagaagtga gtgagggtgg taaacgtgtc  13440
ggatttcatt cgaaaaggaa aagtccatag gaaatgggaa aaatcgtcca aaatcaccaa  13500
atagtatttg tatcctgaca gactgagtac cggggaggtc catagatcac aatgaaccag  13560
gtcaaaagcc tgttcagccc tagaagaaga tgtagtgaaa ggaagacggg tatgtcggtc  13620
aagctgacat gcatgacaga ggccctcaaa atgtccccta ttacaagaag aatctaaagt  13680
gctggaaagc ttggtcatga cctagatcct gggtggccga gacgacgatg ccaagtggtg  13740
gaggtggtgg tggagaccag gacgggaggt ggagacacgc cggtggacga cgaccggagt  13800
gtgtagaggg gcccgacgct gtcacatcgg gcgagtgggg tcctggtggc cagatccttt  13860
acagaaaaac cagtagggtc aaactcaatg gaacacgaat tgtcggtggt gaaccaacgg  13920
acagaaagaa gattgtgagt gatgtgaggg gctacgagaa cgtcgttgag gtagaacagt  13980
ccagggagaa ccgaggcacc tactgaggtg actagaagag tggaaccgtt tcgaacgacg  14040
atcgaggtag ggtgtgtggg gggaggtggg tgtgagcgag agcatgccta gggtgggggt  14100
ggtgtgatag gatgcaccgg agtcgatgac ccagtcagaa ggcggtgggg ccaacgccat  14160
ggtgctgtat gcggcagcga gggcaacagg gtcccaacct gcaacgaacg aggaccatgg  14220
tgtcgtggta gacggtctcg taggcgggag ttgaggcggg ccccgggtcg gtcggggcac  14280
gccgtatgga ggcatgttgt aggcgggcgg cgtagtcagg agagccggag gacgggaggc  14340
gctgggggcc tgacccagcc acatggagat aatgccggtc caggggttgt agaacgacgg  14400
ccaactctgg tcgccacccc tatcggtgga acctccacga gaggagctgc cgcccccatg  14460
tccgcccttg taggggcgac ggccgccgtc gatggtggaa tgctgacgag ggtccgtagg  14520
agccgcggtg aagggccgag cgggggtcct ggttgacgga gcgcgggggg cgagtcctcc  14580
ggaagacgcc tgggcaccag gggtggcgct gtagagtgcc ggagtgggag cctcgatcgt  14640
catggtgagc tcctcgagaa gaagttcatt gcgcacggcg tggaaggtgg gaaaaggtac  14700
ggtcctcttg atgagagcct tcaggtggcc gtagaggggg ctgaggccac acaggaggtt  14760
tagcaccaag gtacggtccg ccagcgactc gccaaggtcg cggagggagt ctgctaggcc  14820
cttcatctgg cggcagtact cccgcacaga gaggtccccc tgggagaatt ggtggaactg  14880
atcatcgatt tgaagggccc gagcgtcccg gttcccgagg aattgttcct cgagggcgag  14940
ccacgcctgg cgggccgtgt ccgccttgtc gcagatgatg tcctggagct cgacggtgat  15000
agtgtcgtgg agccaaaaga gcacgactgt gtccatcagg gaccaggcca tgggcggtgg  15060
ggtgacgatg tcgtcgagga cgtggtcggc gagagcgtag cgccgcaggg tgaggacctg  15120
cccccgacag cgagggtagt gggaggacgc cgggtctagc acgattgaca cgagggacca  15180
tatgttgtgg agaccggcag cctgcgcatg aagggcggcg atgtggtcgg cgtcgagtcc  15240
aggggcgatg ggtgcctggg gttgggtgga ggtgcctccg gggtgaccgg aggatgcccg  15300
aggaggagtc gctgagcggt agccatttgg gcggtcagag cagcgctcat ggcacgctct  15360
tgctacaggg cgagggtcgc agcgcgctcg cggtcgaggg aagcctccac ggctgcctgg  15420
atagtggcga tggccgtgac cagcgccgac gaggccgtcg ggggggcggg ggggggcagt  15480
gacgtcagcc catgtggcgg tggtgtgggc ccggaggaga atcgcggcgt cgttgagcag  15540
cgagggtggc atcgggtagg ggcccgagat cggcgatgtg ggcccctccc caacagcgag  15600
gtcgctaggg gtgccgagtc cggcagtggc gagggcggcg gtagccgcgg cgctgcgtgc  15660
tggtggggcc acagtggcag tggccgcagg gagggccgcg cgtggctgct gggcagcagc  15720
agtcgtagcg gcagccgggg tgtaggggga atgaggtggt gtcgacatgg cggcaccagg  15780
tggttgggcg gccgacgctg cggggttgac ggcggcggtg gaggaaggac cggtgcgagc  15840
ggccgaggtg gctggatggc cggcgcggtg cccagtgagg gggtccggcg ggggcagccc  15900
ttgctgctgg gcggcggcgc aggaggaggc gccgcggcgg ccagcctggg gaggagcggc  15960
gaccggtggg aggaagggga gcggcgatcg ggcctggggg gagggagaag gggggagcgg  16020
tggctgccac ggactggcgg cggcagggag ggtgggaggg aattagtgtg gctctgatac  16080
catgtagaac tatggaaaac cctaacccta gaatagggtt gggcagtgta ttaatagacc  16140
aaataactgg gctaggccca ttacaaggga cgggtatcta aaaaaataga ctgcggcttt  16200
ttttttagat aatggatact agtccagctt ctcctcgttt ggaggattag ccaacacacc  16260
aaaagttttt acatggagta gtcacacgac tagctgcttt atttgtcctt ttcatttatg  16320
caacctagga attatttgac ttgtctccat cttaatgtgt ctgcttttaa atacagttta  16380
ctgaacaggg ccacatcttt gttcaagtcc atttggtcaa ggaactaaac aggaaaggaa  16440
acaatttttg tgatgtttct gctcataaca gagaaattct gtatgattct gacaactcga  16500
tgctatggaa cacactaagc ggacttgaag tagcagatag ctggaggtcc ttggagaatt  16560
ttacgatgtt caagaattca aatggtgaaa cagatacaat taggttagct gtcagagttg  16620
aagacaccgg cataggaata acaaaagatg ctcaaatgcg tatttttaca cctttcatgc  16680
aagctgacag ttccacctca cgaacatatg gtggaactgg aattggcttg agtattacaa  16740
aacgtttagt tgaattgatg ggtggagaaa tagggtttac tagtaaatca ggagttggta  16800
gtacattttc ttttactgcc attttcaagg agaacagagg atgtcctgga gatatgaaaa  16860
gatactattc tgaacctact ccgttggatt ttcaaggaat gagggctctt attattgatg  16920
gaaggagtgc acgtgcagag gttactatgt accatcttcg tagacttgga atacagtgca  16980
gtcttgttgc cacatctgaa tctgaatctg catcttcagc tttgatgaaa gcctgcacct  17040
caaggttcat ttccttgtgt agtttactgt ttgatttact tctacaagtt ttagaaatta  17100
gaagttattt tgttcaaata aatgtaacat tccttgcatt tataaacttt tgtcatctta  17160
acacatggct ttgctatatt ttctttagtt ggttgtgtgc tatttctttg aatattttcc  17220
atattgtcga tcccaaaaca aggtttcgta acttctcatg aactgaagaa aagtaggaga  17280
aacagagtga aaccttcgtt ggtttgagtt tagaaactga aataggatag ttcgattcta  17340
aataacttgt gaattcattc agttgttgct gtcatcatta taacatatca atttgttcat  17400
ggccagcaac ctacacttgt cctcagtatt acgacccaac aaaatcaatg cataatgtcg  17460
ccatcatcac tttccatgta tgcattttct tttctaagca ctgttgatgc cttacttgtt  17520
gatgttatca tttatatttt acatgttgag cagcaaaaac aatccggaca tggtccttgt  17580
tgatacagaa gcttggggta aaggttcagg tttggcattc tatcatcgtt ttgtagattg  17640
tcaactaaag ggcgcacaca agttttctca gcccatgcca aagactattc ttttgggaag  17700
ctcaataagc cctgttgaat ctgattattt aagattgaca ggatttggtg attgcataag  17760
gaaacccctc cgtcttagta ctattgttgc ctgtcttcgc aaaaccttag gggttggggt  17820
tacaaggcag cagagtagag accaatcttt ggttcttcaa agtgtactaa ctggaaaaca  17880
gattctggtt gtggatgata atgcagtcaa ccgtaaagtt gcagctggtt ctttgaagaa  17940
atatggatct aaagttacat gtgttgatag tgggagtgat gcaattgata tgctcaagcc  18000
acctcacaca tttgatgctt gcttcatgga tgttcagatg cccgagatgg acgggtaatg  18060
ttcctttcca atgagttact aatgaaaaag agcgcagatt tgctgcccag gcgttctcat  18120
```

```
tatctaaaat accatgttgc aatatttcaa aaatcatcac aaaaatcatg tatgcagtac  18180
acaaagttag gtatagccgc aacacttcag attgaaattt cttcctagat gccaagaacc  18240
aaaatagaca agcagtcaac ctggcagtgt tcatcatgtg ctgacagtga gactttgttt  18300
tttaatctca gcatcaaaga tgaactttat tgaattcttg aggctacact taaggtgtac  18360
ttgcacacat gtttttgtg atgattgttg aaacattgca atacggtatt tttagaatgtg  18420
ggcgccaatt tccctgggcg ccatatgatt tccaatggaa aattgtcata tgttatttac  18480
ttgcgggata tactataaga gttcaatatg taaaagattc tttgtgcaga agtcactctt  18540
ggaacatctt acgttagttc acatggaagc atgtctttag ttttaggtat gtgcttcttt  18600
tggattttgt ggaatcatcg gaacagatgc atctttgatg gcctttcccc taatgttgct  18660
aattttctaa tccatgtggg ggatgagcgc cgtctgtggg agactgccgg ggccaagggg  18720
ttgacatccc ttgttgcctc cctctctcat gtagcctaga gttttataga tgagtcagtc  18780
tatgctagtt tcgttcaggc cgccgtaagg cgtcagttgt accccggtct attttagacc  18840
ttgtttattt gttcttttaa tataatgata cgcagctctc ctgcgtgttc gagaaaaaaa  18900
gagaaagtta ttttttggtc ctcaaataac aacacttgtc aaatgtatgc atctcctcat  18960
gttattagca agcactctca taggagtatc actgaggata atctctcttt tgtttttcaca  19020
tccagtcctt gcttaaaaaa atgcactgta gcctcacatg cttgtgtttg ctttcctatg  19080
ggttataaca agtggttgca tctactttga tcacttgtag atccactgta ggactaccat  19140
taacaatatt cacattcaat tgcaggtttg aagctacaag attaatccgg tccatagaga  19200
aaaaaataaa cgatatgatc atgatgggtg aaatatccgc taataattat ggaaataagg  19260
cccattggca tgtaccaata ttagctatga cggcagatgt aatccaagcg actttgaaa  19320
aatgtatgca gtgtggaatg gatggatatg tgtcaaagcc atttgaagaa cagcagctct  19380
actttgctgt tgctcatttc ttagagactg atgaaacaga ataa                   19424

SEQ ID NO: 254         moltype = DNA  length = 19431
FEATURE                Location/Qualifiers
source                 1..19431
                       mol_type = other DNA
                       organism = synthetic construct
SEQUENCE: 254
aaaacatttg aggacttcac agcaaggaca acatttgaaa ggccattgat gagtggtgtc  60
gcctatgcat tgaaggtatt acacaatgaa agacaacagt ttgaggaaca acatggatgg  120
aagattaaga agatggaaga tggagatcag tcccttgttc atgactacaa ccttgaaaag  180
cttgaaccat caccagttca agatgagtat gcgcctgtta ttttctctca ggaaactgtg  240
aagcacatta tatctgtaga tatgatgtct gggaaggtag taggatattc gtaagccttt  300
acagtaaata cttactattt tatctatcct gagttcctta ctactatttt tgttataaaa  360
cgaagaaatt tctggctctt cttctaactt tcaatattat taggattaaa catgtgtaga  420
acttctcggt caaaaaagac actttagaac ttatattttt attttaatta gaatttgatg  480
tataaaaatt aatcattttt acaatgagtg ttatagtaat ataagttgtt atgtgtcttg  540
ttcaatgtgt taattactat agcatgttcc atagaaatac tgtgcaggct gttactaatt  600
ctctcttatt ctgtctttgt ggaaattaca taattactaa acctcatagt aataataata  660
ataactaaga ctccattttt ctgctaacat tacaaccttg atttcaggaa gatcatgaca  720
atatattacg ttcctggtca acaggtaaag gggccctaac atcccctttt aagcttctga  780
agtccaacca tctcggtgtg gtgcttacat tcactgtata taaatatgat ctgcctccaa  840
atgcaacacc acaggagcgt attcatgcta cattggggta aaatgttttg caaagtttca  900
agttgaagct atataggaat acactatttt ttctttagga gacttaacct tgtggttatt  960
gacactttgc agctatcttg gtgcctcatt tgatgtccct tctctggttg agaacaactc  1020
gctagcaaac gaaagatagt agttaattta tatgacacca caaatcatac ctctcctatt  1080
gaaatgtatg gttctgattt tactccatct ggtgatctgc atattagtag cattgatttt  1140
ggagacccaa cacgcaaaca tgagatgcat tgcaggtaga aaactttttt ttgatgcgaa  1200
ttatacaatg cttttgttct tcagatatgc tcagtgcttt ctctttcaaa cttctctttc  1260
agatttaaac atgaaccttc actgccatgg tctgcaataa taatatcaac agctgtagct  1320
ataattgttt tgcttgttgg acatattatt tatgcaactc tgaactccct tgaaaaggct  1380
gaacatgatt atagagtaat gagagaactt aaaggacaag ctgaagctgc agatatagca  1440
aaatctcagg ttcattctac ctcttccagt gtcttcatcc tatgcattgg tttgttatct  1500
catttgttct acttttctct ttttgtcggc tgagtcatta ttgattgtct tgcagtttct  1560
agcaactgtt tcccatgaga ttcggactcc aatgaatggt gttttaggtc tgtacttctg  1620
atatttcttt tttgtctatt aatacatacc gcagttattt gtgtttatgt tttaatcaaa  1680
gacaactaaa taaattttga aaaggatttc ttcttgaatt aggtatgctg cagatgctaa  1740
tggacactga acttgataca actcagcagg attttgtagt caccgctcaa gaaagtggaa  1800
aggtattaat aaacttaata aatgaagtcc ttgatctggc taagatagag tcaggaagga  1860
ttgagctgga agcagtgcct tttgatgtcc gtgatattct tgacaatgtg atatctcttt  1920
tctacgataa atcacaagct aaaggcatag aggtgagtcc taatttagaa cttgtattgt  1980
ttgctaagct ctgaatattg tttgtgccat gggacctaaa ataatgtgta attctttttt  2040
gagggtagtt ggccgtgctt gtatctgacc aagttcctga tgtcctaatt ggggatccat  2100
ggcggttccg gcagatcatt acgaaccttg tggggaattc tatgaaggtt agattcaaat  2160
atgtggtagc ttcattattt cagcttgctg gcaagttgta actgtgtcta gtcaatccca  2220
ccatttagct tatacaacaa tatactttgt aggaaacgtg acaacttact aaaatattaa  2280
tgtcatgagc ttttgaattt gagatgtgta gaagacaatt ggtagaattg gtcaattgtg  2340
tcgctgagct cgtgggcaga ttatacatga gtacattcac ttggatggca agaaacctcc  2400
ctaaagataa gaagtcagga ttacatgacc ctaatctagc atatttaaag atattccaat  2460
ataatatacc accccccata tttttctcga acgtgcagga aagctgcaca tctttatatt  2520
aagaagataa aaggtccaaa atggaccaaa acaggtatag atacaaggca cctcacgtgg  2580
ccaaaaaacaa aagtacaaaa aaaacagtcc ataacttttt ttttttagat aatggaaaaa  2640
tcatccgacc ttggcctcaa atgaggttac ggccatttat tacaagggac ggaagcatat  2700
tgccaaaaca cctcctatga ccacttcaga gaaccccaac tagccaaatt aaagaacttc  2760
agctatcgaa ccacagctac tacatattta aacgcaacgc agacccccat ccaaaattgc  2820
taaagaactg tagtagcacc ctctccacat tacgacatga agactttatt aactcttggt  2880
cctcccttct aggctgaagc tgagaccaga agcggcacca atatgttgcc ctgaaggtta  2940
cctgcacaca tgatttagga gatgaattat tgaacaccac atcatttcta cttaaccaaa  3000
```

```
tagcccaaca aattgccgat gcaacggtta atagtaagtt tcgaactctg ggaagcctcc  3060
cgctcgccca aaccccaaac aaatcattaa catcccgagg aggtctcaac cccgtgctta  3120
tctgaatcaa ccgccaaatg aatgacgcat acaaacaact gaaaaatagg tgctttattg  3180
tctccggtct actacaaaag caacatatct tattaccatt ccaatgcctc ctagccaagt  3240
tatcctttgt taatgttacc cctcttttga ggtaccacat aaaaatctta attttcagag  3300
gaagcctaag tttccaaagg tccttattat gcacccccaa cccattgtta agagatgcca  3360
gatacagaga cttaaccgta aacatcccgt tggcggtcaa gttccatctg aacaagtccc  3420
tgtttgaatt caaattggta tgcgcaacaa gtgagaccaa ttgaacccat tggtccctca  3480
attgttgagc caaacccctc cgaaaggata tatttaaggg caccgtggag aacacacagg  3540
caacagtaga gttcttcctc ctcgctaggt tataaagaga cggaaaacga agttttaacg  3600
ttcccgaccc gagccaatca tcctcccaga aacgcacctg ggacccatca tgaatcacaa  3660
aggttccttt actaatgaat gtgtccttaa ctttcataag accactccag aagtgtgaat  3720
cagtggccct acgctgcgcc tgggataagg ttcgattggc cagatattta cgtctcaata  3780
atgattgcca catcccttct tcattgagaa gtttatacaa ccatttgctt aagaggcatt  3840
tattttgaac ctctaaattc aaaatgccta gcccgccaac ctccttaggt tgacaaatta  3900
catcccattt ggccagccta tattttttct tatgaccctc cccttgccag aaaaaacgcg  3960
atctgaaata atctatcttc tccagcacac cttttggtac ctcaaagaaa gacatcataa  4020
acatcgctag actggtcaac acagaattaa ttaatacgag ccgccctcct actgacataa  4080
gttttccttt ccagctgctg agctttttct cgaatttggc ctccactgtt ttccactcac  4140
caattgtcaa tcgacggtgg tgcataggaa tcccaagata tctgaagggc agcccaccag  4200
aactgcaacc aaacagccgt gtgtacctcc cttcatcctc ttttgccttc ccataacaga  4260
atatctcact cttgtgaaag tttattttaa gaccagataa ctgctcaaag gcacataata  4320
tgagcttcat attcgttgcc ttttccagat cgtgatccat aaacaaaatt gtatcatcag  4380
cgtattgcag aatggatagc cccccatcta ccaaatgcgg caccaagccc ttgatctggc  4440
cattttcctt tgctctatta atcagggtag caagcatgtc cactaccaag ttaaagagaa  4500
taggagacag cggatcgccc tgcctcaccc ctctatgggt ctggaaaaaa ggacccatgt  4560
gatcattaac tctaaccgca acatggcccc ccttcatgaa agactcgatc cacctacacc  4620
aggtacttga aaaacctttc atacgaaggg attgttgaac aaagctccac ttcaccttat  4680
cataagcttt ctcgaagtcg atttgaaaa tgaccccatc ccttttcttc gtatgtagct  4740
catgaatagt ctcatgtaag accaccaccc cttccatgat atttcttcct ggcaggaacg  4800
cagtctgcag gggactgatt acattctgcg caacctccgt gatcctctta gtcgccacct  4860
ttgtgaagat tttgaaactg acatttagta gacaaattgg tcggtattgt tgaaccgaga  4920
ttgcctcccg agtcttagga agcaaaatga tagtcccaaa gttaagacta tacaaaggga  4980
gatttcctga gtggaactca cgaaacaaag ccataagatc atctttaata acatcccaac  5040
agatttgata aaattccgcc gggaatccat caggacctgg agccttgtta tgttccatac  5100
taaaaaccac cgcttttact tcatcttcag aaaatggctg ggtgagcttc tcgttctcaa  5160
cttgagtaac ttgtattata tcatctctaa gatcctcatc cagactaaaa gacgtgtttt  5220
ctggggggcc aaagagattt ttataataac cagttatatg actctttaat tctttctcgt  5280
cgtataacat acgagctcca tccgtcatct ggaagatgcg attcttcctg aattttccat  5340
tggctatcat ctgaaaatat ttagtattac tatccccctc caggagctcc ttgaccttcg  5400
ctctttgata ccactttatt tcctcctccc ggagtagctg agcaagcctg ttctgtaagt  5460
agttatgcag atccaactcc gaagtactca acagaactac ttcagctctc ttatctaaat  5520
catcaagctt agctatgatc tccttttttt ccttttcaa caaccccgaa gtgtgcattg  5580
cccaacccct taagtgttgg cgcaccttcc taatcctggc ttgccatttc tccaaaggag  5640
tagaaccact tgtctcattt acccaaatat cttttaccat atccacaaaa ccatccctca  5700
gaaaccagcc tagttctaac ttgaacggag gaattgtatg ggcggttaca acacctgtgc  5760
taagaagcag aggagtatga tcggatatat ttctcgacaa ggcatgtacc gaagctctag  5820
ggtattttcc ctcccattct gtagctacca aaatccgatc caacttctca taagtcggaa  5880
tatccctagt attagcccag gtgtaccttc gccccgacat ctgcaattct cttagatcaa  5940
gaccatcaat taccgcattg aaaaggaacg gccaacgatg atcaaatcta tcattatttt  6000
tctcagatgg agatcgtaaa atattaaaat ctcccccaat gagaataggt aaagtttctg  6060
tattgctcac acggactagc tcagaaagga attcttgttt gaagcagtcc tgggcagggc  6120
catacaccga gacaagagcc catttaaaac catctgcttt atcaagcaaa ttaaacttaa  6180
taaagaaatc cccttccgtg atggcaccaa catcaaagac atcagcgtca attcctaaca  6240
acatcccccc agatctacca tgaggttctt tgcaatgcca gataaaattt ttcccagcac  6300
acaaattcct tagtagatga tctgggaagg atttgcggcc tgtttcagag agggcaataa  6360
aattgagacc atgttctttg gtcagatccg aaatgtatct aagtttttc aaatccttga  6420
acccattgct gttccaaaag attcctttca ttggtaaaca attaattaat aatcaagccc  6480
gaccttttt cttagaacac aacgaaccct gactagatgg ttttgtacag actgacttaa  6540
tcagcccatc agtgccatcc gtctcttcat gcataatatc cccacacaaa tgatttaaaa  6600
tgaaatgatc aaactcttcg tcctctacta ctccctttcc cataaaatca gataaatcag  6660
cctcgttctt acccactagc tgatcctgaa ctctattaat ctctaatttt ttcaactgac  6720
caatagagga agcaactgaa ctaggattag aacccgctaa aatgccaata tttttaaaag  6780
aatccagaat ataattatcg ggtaaactaa taaaggaaac attgttacct ttagtcggct  6840
gatcgtccag gttgtatccc gctttcagcc gaatcgctcg aactagcgag tcttcactca  6900
ccgaatcaga gcggcgcgag ctacgacgca gtgcatgcac ttttcctgtc aacgcctccg  6960
ggatactgcc caacttttca atactaacag cattgaccga gagacaggta ccctgagatt  7020
gatccagatc cagctgtgta gggccagcgc acaccgattt cccactggac gtgttgctgt  7080
tcagcataga atccgacacc ttattaactg ccccctgctga atcctttgat gttcccttca  7140
agctcgcccc cttattccct ctttcaccta tattgtgatc cttgttttga tcctgaaatt  7200
catcatcatc attatccccg atatgatcca tatccatcgg caaaggctgg tcaccttcag  7260
ctgctgactc caccctgaat ttcagttcat ataagtagtc tccaattacc acatcaacta  7320
cttgcggaat caaattcggg tcaagcacgg ccaccttcag ccttgccctg tcaaacttcc  7380
gagtaaacaa catatccacc tcttttgaga tgcctagcat agaaccaacc gcccagatta  7440
ccgagtactc tctaagttcc ttaggtaaac cagtgaactg cacccaagcc ttaggcatct  7500
catattttat ttcctctcca aacccctctt ccttgacaag catctgtgca ccaaattttg  7560
tatgaacagt tccccactcg atcatacggt gaagttcacc cctggaaggg aaacacgtcg  7620
agaacacatt gttccccaca cacttcacac accagtccca atcagcagcc accaaccttt  7680
taagctcatt caaaatctgc tcttcattca tggaaccctc cacaatagac actgtaccat  7740
```

```
tgcagccacc ttgcctctgc tttactggaa tgggttgggg tataaagtaa aaccccaatc  7800
cctccaccgc atacccgcaa ggtattgcaa aagttttgca ggcacgaacc accggacatt  7860
tcgaagttaa gtgagtttg  acatcacaaa tttcacaaaa tagctcaata ttacagtcac  7920
tcaactgatg acctttattt ttgcacctga aacaaaacgg cactttctct tttgaacttg  7980
aaatcacaga agaacccacc ttgtcatcca agtgggttgg agtagacaat tctttgatgg  8040
tctccaactt tgaactgtgt tgggacccaa tattcggacc tgctggattc cccctcgagt  8100
tctgaatgtg ctggctcttc cccacagact gctgcagcaa ggaaacaatc tgttccatgg  8160
tactatctgg aacaggcctg acagcgctac cgttgccaat tgatgttgta attgcctgtt  8220
ggagcaagtc cacagcgttt gatacttgag gagtcaccga agaagcccct gaacctccca  8280
gaccctgtcc agcgaccatc acagaggaag cccctccatt tgaaaacctg ctgtgaacac  8340
ctccgccccc agactgggtt ggcaaagtac gaccaccata gaaccggcct ccggcagaag  8400
cacctcttcc accacgccac gctccagcac ggccctgtcc acctccccga cgtccaaaag  8460
gacggcgtcc gccaccataa ccaggatgga acactggttg ggatccaccg cgtccaaagt  8520
cagtgttcag tcccaaacca gcgacatatc ctcccgtgcc cccaagcagt tgctgaccgg  8580
tggaaaaacc tgcagcgccc tcggactgat gctggccgcg actgcctcca cgccctccag  8640
tatcaccaac cggcgccatt gcgttcctta cagcctcgac gaaggtgcca ggagccacac  8700
cccgggagga aatgtgaacc gccctggcag cagaagaact ggtgcctgag cgggagaaca  8760
aggaagccag cccagcagtt ggcctataag gaatcctagg actgagaatc atatgttggg  8820
ccctcccatt ccaacgggga caagcactaa ttaagccaac attccttgat tccagcacag  8880
gatccgcatg agaatcccag aatatcgcct gacttgcatc cataccaaaa tcattcaaat  8940
tcaaaccatc agctaaccgc tccgctgata ccgctcccat tgaagacgtc ttcttcaacc  9000
tttggccgtg gcaccttcca ggggagcagc gccattgcgc tttttctagt gcatgtccaa  9060
ctgtgaactc cggcgaacgt cgtggcgacg gcaatttgcc ctgccatggc ttcaccttat  9120
tcctagaaga agtgctcgga ctaggagaat gcaagcatgt actcaacgtc ggtcctggtc  9180
ccgacctgca tacaccgccg actacctctc ctacctgttc gagagcttca ttccaaatag  9240
attttggtgg cgcggaactg cagtcaatta gcttgccgtc aacacaggac agagacccgt  9300
tcacgaaaac agagagccga ccaccctcag gtgtccgtcc gctatttgcc gaaccggcca  9360
gatcaccaac ctcctgatcc agctgaacct gacaatcagc aacctccgcc agtgggcgga  9420
cgaccaccgc atcggtgggc gccagcgtct ttcgacgacg acccttccga gcgtacgtgg  9480
ccaagcaacg tcgctgcata gcgcagagaa cgaacgaaca accactggcg ggagaccggc  9540
ctagatggcc gcctcccacc tctggtgtcc cactccgccg agacagaggg aagagcactt  9600
accgggttac gccgcgcgcc tagccgggac gcccacgcgg cctagaccgc cttgccgtgg  9660
tcaccgcaga gaagaaactc gagcgccagg gtccaccgcg gcctgcgatg ctctctgatg  9720
agcagcggga agttgcggcg tgcgaagcga ccggcccagc agttgagcac ggcgtcgacg  9780
gcgtccgcgt cggcacgagg cagcgcgagc aagcgcgcga cgacctcgga caccttccag  9840
tcccgctgcc accggttgcc ctccacgcgg aggcggtgtc acgcaatcaa aaacagtcca  9900
taactagaga gctaacaaca gaacagctac aaccctgcca ggggagtgta ttgggcatca  9960
acacggactg aggcagggtg atcctctatc gcctatgctg tttattcttg taatggatgt  10020
cttgaatctg cttgtgcagc gagcctctga ggaagggttt cttcagcctc tttcttctag  10080
gaatatgcag catcgtatct cgctgtacgc ggatgatgca atgttatttc tatgtcctac  10140
tgccccggat atcagtatgg ttatggatat tcttcattta tttggttcaa cttcaggtct  10200
aaggactaat gtccagaaga gcagtgtgtt cccaatctga tgtggggaag aagaggtgaa  10260
ttgtttacag gacttgctgc tatgcaatat ttcagttttt ccctgtaagt acctcggttt  10320
gcctttgtct cccaagaaac tcacaaggga ccaggttcaa gccattgttg aaagagtggc  10380
cagccttttg ccaggatgga aagctgaact tatgaccagg gctggtagag ctattcatgt  10440
gcagtttgtc atgacggcta agatgatata tgcagctctg gcacttgacc ttcctgtatg  10500
ggccatcaaa gcaatcgata agctgaggaa gggcttcctc tggaggggta ggaaagagtt  10560
ccgtggtggt cactgcctct tggcttggcc taaggttacc cgtcccaagg agttgggtgg  10620
tcttgggatt agtgagttaa agaacctctg ttgggctttg agagctcgct ggccatggct  10680
gcagaaaaca gaccccagta ggccttgggc ggacttcccc attcatgttt gtaaggtggt  10740
taaaaatctg attgctgcag ccattattac taagctcggt gatggagcca ataccctttt  10800
ctggaaggac agatggttgg aggggagatg tattaaggac atagctcctg cgttgtttga  10860
tttggtgccc ttgcgtcttg ccaacaaacg gttggtcaaa gatactctcc ctaatttcca  10920
ttggctctca gatgtgcaag gggcaatctc agtcagagtc attgctgaat tcctggaact  10980
ttgtgaagtg cttgatgcag ttgtgctcca gcctggaata agggatcgat atttatggaa  11040
attcagcgct tcaggtgatt atacatctag ttctgcttat aatgctctct tccttggttc  11100
agttcagttc gaaccagcag agcggctatg gaaatcttgg gctcctggga agtgcaagtt  11160
ctttatatgg cttgtggaac ataataggtg ctggactgct gacaggctca gaaaaagagg  11220
gctagaccga ccagagcagt gccccttgtg cgaccaagag gttgaaacca taaatcattt  11280
gctggtcaag tgtgtttttg ctaagcagtt ctggtttgat ttccttaatt cagtggggtt  11340
gcgggatctg tatccagctc atgaggaatc ctttgagtcg tggtggaagt ctagcagctc  11400
cggcatcgga tcttgtgaga aaaggtttca attctttagt gatcctaggt gcttggacca  11460
tttggaagca taggaatagg tgtgtttttt atggttgtaa tcccagcttg ctcacgaccc  11520
ttaggatggc tagggaagag gcggtgctct ggtccatgac tggtgccaag gccttgtcct  11580
tcctccaagt cgatgagttg ctggcttaaa acagcggtgt gggtcgtgtt tcctccatgt  11640
tttagtcagt gatccgtagt tagtctctag tggtgtatgt gctgtattgg ggttctctcc  11700
ccctttcttt tcttctatta atacaaagat gcgcagctct cctgcgtatt ccagaaaaaa  11760
aagaaaaaaa aaacaaccct gggatagggg ctgctaggag atccaaattc ttggccccag  11820
ccagcaccca caaatccctc tcctccttag cttttctaat agccggtgag agcggcacag  11880
atggtgagac cagagaagct gaaggttgta agacgacgag ttgacatccc ccaaagtcat  11940
agtggtcaat gtgtcgcata tgctgtagct agagtgctca agcaaggcag aagctctttg  12000
tgccgatgtt gaggtagtcg agcacgaggg tgagtagcca tggttgagga tgccatcttt  12060
acgccatggt gatggtcgag gcgcgtcgag acagtccatt gtataagggg gtgatgttga  12120
ggtcaatgta gtcaaggcca tcgaggatgt cgacgaaaat agcgacacag tcaaggcagg  12180
tcatcatgga ggaagcatac accggatttg ctaggcctga gaacgtgtcc tggagaacgg  12240
cacgctacac tgccaatata agacatgcta gttagagagc cccaacaatg tgtcaacatc  12300
cgagcgacct tggaagagag tgcctcaacg atggttgatt gtggtgccca aaacaactga  12360
gcacaaggtg tcgatgtatc ccacaattgt caaattagat gatatatgtg ggaaagagac  12420
aatgatgctg gcgatgtggt tatgctgaat gaagaaggaa cagtgcggga gtgaacgctc  12480
```

```
ctacccgaag gggagtagtt tgggccgacg tccttggcca aggcaatggt ccagacataa 12540
ggtacagtgt gcccaaaggc agtggtccag aagcaaggta tggcgtcaaa aacagtgttc 12600
gctgttggtg atgaagagca caaaaagttt gatgaagacc aagtgcatcc tggtggtgcg 12660
caagaggtgc aacacaatta tcgatgtaca tggagcgaca atgtagatgc attgttgtat 12720
gccaaccatg gatagaggca tgcctatgag ggtgtctcaa ttagagaatc tctaacattg 12780
ccttaaatca attctctatc ttataatata gtgcttaact tataaaaaac tgctccaaca 12840
gtgctctatt ttacattttt atcaaaaaat atagggcaga ccataaagtg accaaaatat 12900
actacactct ggattagggc ttaactgttg caacacaatt tgtttttagt gccttaaaca 12960
ctttaaatga tgtagtattg taatttttgg aacattattt tgaggggcag cgagtgtagc 13020
gtagagacag tttatgaggg gcagtagcgg aagtgttggg atagcaagca caaccaaata 13080
cacggagttg ggttgtgtcg tacaaggcga agtaggtggt ggggtggctc accaccttcg 13140
atgggaggcg attgaggagg tgggtggcgg tgtgcaaggc ctctgcccag tagttggcag 13200
ggagagacgc ctgaaagaga aggcaacaaa tcatgttggt ggtggtgcga atcattcgct 13260
cggcccgacc gttttgggca gaggtgtagg ggcacgagag atgcaattga acgccactgg 13320
cgaggaagaa cgaccgagag gcatggttgt cgaactcgcg gccattgtca cactgcagtg 13380
catggaccgg gcgacagaac tgggtggaga cccaggcgaa gaagtgagtg agggtggtaa 13440
acgtgtcgga tttcattcga aaaggaaaag tccataggaa atgggaaaaa tcgtccaaaa 13500
tcaccaaata gtatttgtat cctgacagac tgagtaccgg ggaggtccat agatcacaat 13560
gaaccaggtc aaaagcctgt tcagccctag aagaagatgt agtgaaagga agacgggtat 13620
gtcggtcaag ctgacatgca tgacagaggc cctcaaaatg tcccctatta caagaagaat 13680
ctaaagtgct ggaaagcttg gtcatgacct agatcctggg tggccgagac gacgatgcca 13740
agtggtggag gtggtggtgg agaccaggac gggaggtgga gacacgccgg tggacgacga 13800
ccggagtgtg tagaggggcc cgacgctgtc acatcgggcg agtggggtcc tggtggccag 13860
atcctttaca gaaaaaccag tagggtcaaa ctcaatggaa cacgaattgt cggtggtgaa 13920
ccaacggaca gaaagaagat tgtgagtgat gtgaggggct acgagaacgt cgttgaggta 13980
gaacagtcca gggagaaccg aggcacctac tgaggtgact agaagagtgg aaccgtttcg 14040
aacgacgatc gaggtagggt gtgtgggggg aggtgggtgt gagcgagagc atgcctaggg 14100
tgggggtggt gtgataggat gcaccggagt cgatgaccca gtcagaaggc ggtggggcca 14160
acgccatggt gctgtatgcg gcagcgaggg caacagggtc ccaacctgca acgaacgagg 14220
accatggtgt cgtggtagac ggtctcgtag gcgggagttg aggcgggccc cgggtcggtc 14280
ggggcacgcc gtatggaggc atgttgtagg cgggcggcgt agtcaggaga gccggaggac 14340
gggaggcgct gggggcctga cccagccaca tggagataat gccggtccag gggttgtaga 14400
acgacggcca actctggtcg ccacccctat cggtggaacc tccacgagag gagctgccgc 14460
ccccatgtcc gcccttgtag gggcgacggc cgccgtcgat ggtggaatgc tgacgagggt 14520
ccgtaggagc cgcggtgaag ggccgagcgg gggtcctggt tgacggagcg cggggggcga 14580
gtcctccgga agacgcctgg gcaccagggg tggcgctgta gagtgccgga gtgggagcct 14640
cgatcgtcat ggtgagctcc tcgagaagaa gttcattgcg cacggcgtgg aaggtgggaa 14700
aaggtacggt cctcttgatg agagccttca ggtggccgta gagggggctg aggccacaca 14760
ggaggtttag caccaaggta cggtccgcca gcgactcgcc aaggtcgcgg agggagtctg 14820
ctaggccctt catctggcgg cagtactccc gcacagagag gtccccctgg gagaattggt 14880
ggaactgatc atcgatttga agggcccgag cgtcccggtt cccgaggaat tgttcctcga 14940
gggcgagcca cgcctggcgg gccgtgtccg ccttgtcgca gatgatgtcc tggagctcga 15000
cggtgatagt gtcgtggagc caaaagagca cgactgtgtc catcagggac caggccatgg 15060
gcggtggggt gacgatgtcg tcgaggacgt ggtcggcgag agcgtagcgc cgcagggtga 15120
ggacctgccc ccgacagcga gggtagtggg aggacgccgg gtctagcacg attgacacga 15180
gggaccatat gttgtggaga ccggcagcct gcgcatgaag ggcggcgatg tggtcggcgt 15240
cgagtccagg ggcgatgggt gcctggggtt gggtggaggt gcctccgggg tgaccggagg 15300
atgcccgagg aggagtcgct gagcggtagc catttgggcg gtcagagcag cgctcatggc 15360
acgctcttgc tacagggcga gggtcgcagc gcgctcgcgg tcgagggaag cctccacggc 15420
tgcctggata gtggcgatgg ccgtgaccag cgccgacgag gccgtcgggg gggcgggggg 15480
gggcagtgac gtcagcccat gtggcggtgg tgtgggcccg gaggagaatc gcggcgtcgt 15540
tgagcagcga gggtggcatc gggtaggggc ccgagatcgg cgatgtgggc ccctccccaa 15600
cagcgaggtc gctaggggtg ccgagtccgg cagtggcgag ggcggcggta gccgcggcgc 15660
tgcgtgctgg tggggccaca gtggcagtgg ccgcagggag ggccgcgcgt ggctgctggg 15720
cagcagcagt cgtagcggca gccggggtgt agggggaatg aggtggtgtc gacatggcgg 15780
caccaggtgg ttgggcggcc gacgctgcgg ggttgacggc ggcggtggag gaaggaccgg 15840
tgcgagcggc cgaggtggct ggatggccgg cgcggtgccc agtgaggggg tccggcgggg 15900
gcagcccttg ctgctgggcg gcggcgcagg aggaggcgcc gcggcggcca gcctggggag 15960
gagcggcgac cggtgggagg aaggggagcg gcgatcgggc ctggggggag ggagaagggg 16020
ggagcggtgg ctgccacgga ctggcggcgg cagggagggt gggagggaat tagtgtggct 16080
ctgataccat gtagaactat ggaaaaccct aaccctagaa tagggttggg cagtgtatta 16140
atagaccaaa taactgggct aggcccatta caagggacgg gtatctaaaa aaatagactg 16200
cggctttttt tttagataat ggatactagt ccagcttctc ctcgtttgga ggattagcca 16260
acacaccaaa agtttttaca tggagtagtc acacgactag ctgctttatt tgtccttttc 16320
atttatgcaa cctaggaatt atttgacttg tctccatctt aatgtgtctg cttttaaata 16380
cagtttactg aacaggggcca catctttgtt caagtccatt tggtcaagga actaaacagg 16440
aaaggaaaca atttttgtga tgtttctgct cataacagag aaattctgta tgattctgac 16500
aactcgatgc tatggaacac actaagcgga cttgaagtag cagatagctg gaggtccttg 16560
gagaatttta cgatgttcaa gaattcaaat ggtgaaacag atacaattag gttagctgtc 16620
agagttgaag acaccggcat aggaataaca aaagatgctc aaatgcgtat ttttacacct 16680
ttcatgcaag ctgacagttc cacctcacga acatatggtg gaactggaat tggcttgagt 16740
attacaaaac gtttagttga attgatgggt ggagaaatag ggtttactag taaatcagga 16800
gttggtagta cattttcttt tactgccatt ttcaaggaga acagaggatg tcctggagat 16860
atgaaaagat actattctga acctactccg ttggattttc aaggaatgag ggctcttatt 16920
attgatggaa ggagtgcacg tgcagaggtt actatgtacc atcttcgtag acttggaata 16980
cagtgcagtc ttgttgccac atctgaatct gaatctgcat cttcagcttt gatgaaagcc 17040
tgcacctcaa ggttcatttc cttgtgtagt ttactgtttg atttacttct acaagtttta 17100
gaaattagaa gttattttgt tcaaataaat gtaacattcc ttgcatttat aaacttttgt 17160
catcttaaca catggctttg ctatattttc tttagttggt tgtgtgctat ttctttgaat 17220
```

```
attttccata ttgtcgatcc caaaacaagg tttcgtaact tctcatgaac tgaagaaaag  17280
taggagaaac agagtgaaac cttcgttggt ttgagtttag aaactgaaat aggatagttc  17340
gattctaaat aacttgtgaa ttcattcagt tgttgctgtc atcattataa catatcaatt  17400
tgttcatggc cagcaaccta cacttgtcct cagtattacg acccaacaaa atcaatgcat  17460
aatgtcgcca tcatcacttt ccatgtatgc attttctttt ctaagcactg ttgatgcctt  17520
acttgttgat gttatcattt atattttaca tgttgagcag caaaaacaat ccggacatgg  17580
tccttgttga tacagaagct tggggtaaag gttcaggttt ggcattctat catcgttttg  17640
tagattgtca actaaagggc gcacacaagt tttctcagcc catgccaaag actattcttt  17700
tgggaagctc aataagccct gttgaatctg attatttaag attgacagga tttggtgatt  17760
gcataaggaa acccctccgt cttagtacta ttgttgcctg tcttcgcaaa accttagggg  17820
ttggggttac aaggcagcag agtagagacc aatctttggt tcttcaaagt gtactaactg  17880
gaaaacagat tctggttgtg gatgataatg cagtcaaccg taaagttgca gctggttctt  17940
tgaagaaata tggatctaaa gttacatgtg ttgatagtgg gagtgatgca attgatatgc  18000
tcaagccacc tcacacattt gatgcttgct tcatggatgt tcagatgccc gagatggacg  18060
ggtaatgttc ctttccaatg agttactaat gaaaaagagc gcagatttgc tgcccaggcg  18120
ttctcattat ctaaaatacc atgttgcaat atttcaaaaa tcatcacaaa aatcatgtat  18180
gcagtacaca aagttaggta tagccgcaac acttcagatt gaaatttctt cctagatgcc  18240
aagaaccaaa atagacaagc agtcaacctg gcagtgttca tcatgtgctg acagtgagac  18300
tttgtttttt aatctcagca tcaaagatga actttattga attcttgagg ctacacttaa  18360
ggtgtacttg cacacatgtt ttttgtgatg attgttgaaa cattgcaata cggtatttta  18420
gaatgtgggc gccaatttcc ctgggcgcca tatgatttcc aatggaaaat tgtcatatgt  18480
tatttacttg cgggatatac tataagagtt caatatgtaa aagattcttt gtgcagaagt  18540
cactcttgga acatcttacg ttagttcaca tggaagcatg tctttagttt taggtatgtg  18600
cttcttttgg attttgtgga atcatcggaa cagatgcatc tttgatggcc tttcccctaa  18660
tgttgctaat tttctaatcc atgtggggga tgagcgccgt ctgtgggaga ctgccggggc  18720
caaggggttg acatcccttg ttgcctccct ctctcatgta gcctagagtt ttatagatga  18780
gtcagtctat gctagtttcg ttcaggccgc cgtaaggcgt cagttgtacc ccggtctatt  18840
ttagaccttg tttatttgtt cttttaatat aatgatacgc agctctcctg cgtgttcgag  18900
aaaaaaagag aaagttattt tttggtcctc aaataacaac acttgtcaaa tgtatgcatc  18960
tcctcatgtt attagcaagc actctcatag gagtatcact gaggataatc tctcttttgt  19020
tttcacatcc agtccttgct taaaaaaatg cactgtagcc tcacatgctt gtgtttgctt  19080
tcctatgggt tataacaagt ggttgcatct actttgatca cttgtagatc cactgtagga  19140
ctaccattaa caatattcac attcaattgc aggtttgaag ctacaagatt aatccggtcc  19200
atagagaaaa aaataaacga tatgatcatg atgggtgaaa tatccgctaa taattatgga  19260
aataaggccc attggcatgt accaatatta gctatgacgg cagatgtaat ccaagcgact  19320
tttgaaaaat gtatgcagtg tggaatggat ggatatgtgt caaagccatt tgaagaacag  19380
cagctctact ttgctgttgc tcatttctta gagactgatg aaacagaata a           19431

SEQ ID NO: 255         moltype = DNA  length = 19432
FEATURE                Location/Qualifiers
source                 1..19432
                       mol_type = other DNA
                       organism = synthetic construct
SEQUENCE: 255
aaaacatttg aggacttcac agcaaggaca acatttgaaa ggccattgat gagtggtgtc  60
gcctatgcat tgaaggtatt acacaatgaa agacaacagt ttgaggaaca acatggatgg  120
aagattaaga agatggaaga tggagatcag tcccttgttc atgactacaa ccttgaaaag  180
cttgaaccat caccagttca agatgagtat gcgcctgtta ttttctctca ggaaactgtg  240
aagcacatta tatctgtaga tatgatgtct gggaaggtag taggatattc gtaagccttt  300
acagtaaata cttactattt tatctatcct gagttcctta ctactatttt tgttataaaa  360
cgaagaaatt tctggctctt cttctaactt tcaatattat taggattaaa catgtgtaga  420
acttctcggt caaaaaagac actttagaac ttatattttt attttaatta gaatttgatg  480
tataaaaatt aatcattttt acaatgagtg ttatagtaat ataagttgtt atgtgtcttg  540
ttcaatgtgt taattactat agcatgttcc atagaaatac tgtgcaggct gttactaatt  600
ctctcttatt ctgtctttgt ggaaattaca taattactaa acctcatagt aataataata  660
ataactaaga ctccattttt ctgctaacat tacaaccttg atttcaggaa gatcatgaca  720
atatattacg ttcctggtca acaggtaaag gggccctaac atcccctttt aagcttctga  780
agtccaacca tctcggtgtg gtgcttacat tcactgtata taaatatgat ctgcctccaa  840
atgcaacacc acaggagcgt attcatgcta cattggggta aaatgttttg caaagtttca  900
agttgaagct atataggaat acactatttt ttctttagga gacttaacct tgtggttatt  960
gacactttgc agctatcttg gtgcctcatt tgatgtccct tctctggttg atgaacaact  1020
cgctagcaaa cgaaagatag tagttaattt atatgacacc acaaatcata cctctcctat  1080
tgaaatgtat ggttctgatt ttactccatc tggtgatctg catattagta gcattgattt  1140
tggagaccca acacgcaaac atgagatgca ttgcaggtag aaaacttttt tttgatgcga  1200
attatacaat gcttttgttc ttcagatatg ctcagtgctt tctctttcaa acttctcttt  1260
cagatttaaa catgaacctt cactgccatg gtctgcaata ataatatcaa cagctgtagc  1320
tataattgtt ttgcttgttg gacatattat ttatgcaact ctgaactccc ttgaaaaggc  1380
tgaacatgat tatagagtaa tgagagaact taaaggacaa gctgaagctg cagatatagc  1440
aaaatctcag gttcattcta cctcttccag tgtcttcatc ctatgcattg gtttgttatc  1500
tcatttgttc tacttttctc tttttgtcgg ctgagtcatt attgattgtc ttgcagtttc  1560
tagcaactgt ttcccatgag attcggactc caatgaatgg tgttttaggt ctgtacttct  1620
gatatttctt ttttgtctat taatacatac cgcagttatt tgtgtttatg ttttaatcaa  1680
agacaactaa ataaatttg aaaaggattt cttcttgaat taggtatgct gcagatgcta  1740
atggacactg aacttgatac aactcagcag gatttttgtag tcaccgctca agaaagtgga  1800
aaggtattaa taaacttaat aaatgaagtc cttgatctgg ctaagataga gtcaggaagg  1860
attgagctgg aagcagtgcc ttttgatgtc cgtgatattc ttgacaatgt gatatctctt  1920
ttctacgata aatcacaagc taaaggcata gaggtgagtc ctaatttaga acttgtattg  1980
tttgctaagc tctgaatatt gtttgtgcca tgggacctaa aataatgtgt aattcttttt  2040
tgagggtagt tggccgtgct tgtatctgac caagttcctg atgtcctaat tggggatcca  2100
```

```
tggcggttcc ggcagatcat tacgaacctt gtggggaatt ctatgaaggt tagattcaaa  2160
tatgtggtag cttcattatt tcagcttgct ggcaagttgt aactgtgtct agtcaatccc  2220
accatttagc ttatacaaca atatactttg taggaaacgt gacaacttac taaaatatta  2280
atgtcatgag cttttgaatt tgagatgtgt agaagacaat tggtagaatt ggtcaattgt  2340
gtcgctgagc tcgtgggcag attatacatg agtacattca cttggatggc aagaaacctc  2400
cctaaagata agaagtcagg attacatgac cctaatctag catatttaaa gatattccaa  2460
tataatatac cacccccat atttttctcg aacgtgcagg aaagctgcac atctttatat  2520
taagaagata aaaggtccaa aatggaccaa aacaggtata gatacaaggc acctcacgtg  2580
gccaaaaaca aaagtacaaa aaaaacagtc cataactttt ttttttaga taatggaaaa  2640
atcatccgac cttggcctca aatgaggtta cggccattta ttacaaggga cggaagcata  2700
ttgccaaaac acctcctatg accacttcag agaaccccaa ctagccaaat taaagaactt  2760
cagctatcga accacagcta ctacatattt aaacgcaacg cagaccccca tccaaaattg  2820
ctaaagaact gtagtagcac cctctccaca ttacgacatg aagactttat taactcttgg  2880
tcctcccttc taggctgaag ctgagaccag aagcggcacc aatatgttgc cctgaaggtt  2940
acctgcacac atgatttagg agatgaatta ttgaacacca catcatttct acttaaccaa  3000
atagcccaac aaattgccga tgcaacggtt aatagtaagt ttcgaactct gggaagcctc  3060
ccgctcgccc aaaccccaaa caaatcatta acatcccgag gaggtctcaa ccccgtgctt  3120
atctgaatca accgccaaat gaatgacgca tacaaacaac tgaaaaatag gtgctttatt  3180
gtctccggtc tactacaaaa gcaacatatc ttattaccat tccaatgcct cctagccaag  3240
ttatcctttg ttaatgttac ccctcttttg aggtaccaca taaaaatctt aattttcaga  3300
ggaagcctaa gtttccaaag gtccttatta tgcaccccca acccattgtt aagagatgcc  3360
agatacagag acttaaccgt aaacatcccg ttggcggtca agttccatct gaacaagtcc  3420
ctgtttgaat tcaaattggt atgcgcaaca agtgagacca attgaaccca ttggtccctc  3480
aattgttgag ccaaacccct ccgaaaggat atatttaagg gcaccgtgga gaacacacag  3540
gcaacagtag agttcttcct cctcgctagg ttataaagag acggaaaacg aagttttaac  3600
gttcccgacc cgagccaatc atcctcccag aaacgcacct gggacccatc atgaatcaca  3660
aaggttcctt tactaatgaa tgtgtcctta actttcataa gaccactcca gaagtgtgaa  3720
tcagtggccc tacgctgcgc ctgggataag gttcgattgg ccagatattt acgtctcaat  3780
aatgattgcc acatcccttc ttcattgaga agtttataca accatttgct taagaggcat  3840
ttattttgaa cctctaaatt caaaatgcct agcccgccaa cctccttagg ttgacaaatt  3900
acatcccatt tggccagcct atattttttc ttatgaccct cccccttgcca gaaaaaaacgc  3960
gatctgaaat aatctatctt ctccagcaca ccttttggta cctcaaagaa agacatcata  4020
aacatcgcta gactggtcaa cacagaatta attaatacga gccgccctcc tactgacata  4080
agttttcctt tccagctgct gagctttttc tcgaatttgg cctccactgt tttccactca  4140
ccaattgtca atcgacggtg gtgcatagga atcccaagat atctgaaggg cagcccacca  4200
gaactgcaac caaacagccg tgtgtacctc ccttcatcct cttttgcctt cccataacag  4260
aatatctcac tcttgtgaaa gtttatttta agaccagata actgctcaaa ggcacataat  4320
atgagcttca tattcgttgc cttttccaga tcgtgatcca taaacaaaat tgtatcatca  4380
gcgtattgca gaatggatag ccccccatct accaaatgcg gcaccaagcc cttgatctgg  4440
ccattttcct ttgctctatt aatcagggta gcaagcatgt ccactaccaa gttaaagaga  4500
ataggagaca gcggatcgcc ctgcctcacc cctctatggg tctggaaaaa aggacccatg  4560
tgatcattaa ctctaaccgc aacatggccc cccttcatga aagactcgat ccacctacac  4620
caggtacttg aaaaaccttt catacgaagg gattgttgaa caaagctcca cttcacctta  4680
tcataagctt tctcgaagtc gattttgaaa atgaccccat ccctttttctt cgtatgtagc  4740
tcatgaatag tctcatgtaa gaccaccacc ccttccatga tatttcttcc tggcaggaac  4800
gcagtctgca ggggactgat tacattctgc gcaacctccg tgatcctctt agtcgccacc  4860
tttgtgaaga ttttgaaact gacatttagt agacaaattg gtcggtattg ttgaaccgag  4920
attgcctccc gagtcttagg aagcaaaatg atagtcccaa agttaagact atacaaaggg  4980
agatttcctg agtggaactc acgaaacaaa gccataagat catctttaat aacatcccaa  5040
cagatttgat aaaattccgc cgggaatcca tcaggacctg gagccttgtt atgttccata  5100
ctaaaaacca ccgcttttac ttcatcttca gaaaatggct gggtgagctt ctcgttctca  5160
acttgagtaa cttgtattat atcatctcta agatcctcat ccagactaaa agacgtgttt  5220
tctgggggc caaagagatt tttataataa ccagttatat gactctttaa ttctttctcg  5280
tcgtataaca tacgagctcc atccgtcatc tggaagatgc gattcttcct gaattttcca  5340
ttggctatca tctgaaaata tttagtatta ctatccccct ccaggagctc cttgaccttc  5400
gctctttgat accactttat ttcctcctcc cggagtagct gagcaagcct gttctgtaag  5460
tagttatgca gatccaactc cgaagtactc aacagaacta cttcagctct cttatctaaa  5520
tcatcaagct tagctatgat ctcctttttt tcctttttca acaaccccga agtgtgcatt  5580
gcccaacccc ttaagtgttg gcgcaccttc ctaatcctgg cttgccattt ctccaaagga  5640
gtagaaccac ttgtctcatt tacccaaata tcttttacca tatccacaaa accatccctc  5700
agaaaccagc ctagttctaa cttgaacgga ggaattgtat gggcggttac aacacctgtg  5760
ctaagaagca gaggagtatg atcggatata tttctcgaca aggcatgtac cgaagctcta  5820
gggtattttc cctcccattc tgtagctacc aaaatccgat ccaacttctc ataagtcgga  5880
atatccctag tattagccca ggtgtacctt cgccccgaca tctgcaattc tcttagatca  5940
agaccatcaa ttaccgcatt gaaaaggaac ggccaacgat gatcaaatct atcattattt  6000
ttctcagatg gagatcgtaa aatattaaaa tctcccccaa tgagaatagg taaagtttct  6060
gtattgctca cacggactag ctcagaaagg aattcttgtt tgaagcagtc ctgggcaggg  6120
ccatacaccg agacaagagc ccatttaaaa ccatctgctt tatcaagcaa attaaactta  6180
ataaagaaat ccccttccgt gatggcacca acatcaaaga catcagcgtc aattcctaac  6240
aacatccccc cagatctacc atgaggttct ttgcaatgcc agataaaatt tttcccagca  6300
cacaaattcc ttagtagatg atctgggaag gatttgcggc ctgtttcaga gagggcaata  6360
aaattgagac catgttcttt ggtcagatcc gaaatgtatc taagtttttt caaatccttg  6420
aacccattgc tgttccaaaa gattcctttc attggtaaac aattaattaa taatcaagcc  6480
cgaccttttt tcttagaaca caacgaaccc tgactagatg gttttgtaca gactgactta  6540
atcagcccat cagtgccatc cgtctcttca tgcataatat ccccacacaa atgatttaaa  6600
atgaaatgat caaactcttc gtcctctact actccctttc ccataaaatc agataaatca  6660
gcctcgttct tacccactag ctgatcctga actctattaa tctctaattt tttcaactga  6720
ccaatagagg aagcaactga actaggatta gaacccgcta aaatgccaat atttttaaaa  6780
gaatccagaa tataattatc gggtaaacta ataaaggaaa cattgttacc tttagtcggc  6840
```

```
tgatcgtcca ggttgtatcc cgctttcagc cgaatcgctc gaactagcga gtcttcactc  6900
accgaatcag agcggcgcga gctacgacgc agtgcatgca cttttcctgt caacgcctcc  6960
gggatactgc ccaacttttc aatactaaca gcattgaccg agagacaggt accctgagat  7020
tgatccagat ccagctgtgt agggccagcg cacaccgatt tcccactgga cgtgttgctg  7080
ttcagcatag aatccgacac cttattaact gcccctgctg aatcctttga tgttcccttc  7140
aagctcgccc ccttattccc tctttcacct atattgtgat ccttgttttg atcctgaaat  7200
tcatcatcat cattatcccc gatatgatcc atatccatcg gcaaaggctg gtcaccttca  7260
gctgctgact ccaccctgaa tttcagttca tataagtagt ctccaattac cacatcaact  7320
acttgcggaa tcaaattcgg gtcaagcacg gccaccttca gccttgccct gtcaaacttc  7380
cgagtaaaca acatatccac ctcttttgag atgcctagca tagaaccaac cgcccagatt  7440
accgagtact ctctaagttc cttaggtaaa ccagtgaact gcacccaagc cttaggcatc  7500
tcatatttta tttcctctcc aaacccctct tccttgacaa gcatctgtgc accaaatttt  7560
gtatgaacag ttccccactc gatcatacgg tgaagttcac ccctggaagg gaaacacgtc  7620
gagaacacat tgttccccac acacttcaca caccagtccc aatcagcagc caccaacctt  7680
ttaagctcat tcaaaatctg ctcttcattc atggaaccct ccacaataga cactgtacca  7740
ttgcagccac cttgcctctg ctttactgga atgggttggg gtataaagta aaaccccaat  7800
ccctccaccg catacccgca aggtattgca aaagttttgc aggcacgaac caccggacat  7860
ttcgaagtta agtgagtttt gacatcacaa atttcacaaa atagctcaat attacagtca  7920
ctcaactgat gacctttatt tttgcacctg aaacaaaacg gcactttctc ttttgaactt  7980
gaaatcacag aagaacccac cttgtcatcc aagtgggttg gagtagacaa ttctttgatg  8040
gtctccaact ttgaactgtg ttgggaccca atattcggac ctgctggatt ccccctcgag  8100
ttctgaatgt gctggctctt ccccacagac tgctgcagca aggaaacaat ctgttccatg  8160
gtactatctg gaacaggcct gacagcgcta ccgttgccaa ttgatgttgt aattgcctgt  8220
tggagcaagt ccacagcgtt tgatacttga ggagtcaccg aagaagcccc tgaacctccc  8280
agaccctgtc cagcgaccat cacagaggaa gcccctccat ttgaaaacct gctgtgaaca  8340
cctccgcccc cagactgggt tggcaaagta cgaccaccat agaaccggcc tccggcagaa  8400
gcacctcttc caccacgcca cgctccagca cggccctgtc cacctccccg acgtccaaaa  8460
ggacggcgtc cgccaccata accaggatgg aacactggtt gggatccacc gcgtccaaag  8520
tcagtgttca gtcccaaacc agcgacatat cctcccgtgc ccccaagcag ttgctgaccg  8580
gtggaaaaac ctgcagcgcc ctcggactga tgctggccgc gactgcctcc acgccctcca  8640
gtatcaccaa ccggcgccat tgcgttcctt acagcctcga cgaaggtgcc aggagccaca  8700
ccccgggagg aaatgtgaac cgccctggca gcagaagaac tggtgcctga gcgggagaac  8760
aaggaagcca gcccagcagt tggcctataa ggaatcctag gactgagaat catatgttgg  8820
gccctcccat tccaacgggg acaagcacta attaagccaa cattccttga ttccagcaca  8880
ggatccgcat gagaatccca gaatatcgcc tgacttgcat ccataccaaa atcattcaaa  8940
ttcaaaccat cagctaaccg ctccgctgat accgctccca ttgaagacgt cttcttcaac  9000
ctttggccgt ggcaccttcc aggggagcag cgccattgcg ctttttctag tgcatgtcca  9060
actgtgaact ccggcgaacg tcgtggcgac ggcaatttgc cctgccatgg cttcacctta  9120
ttcctagaag aagtgctcgg actaggagaa tgcaagcatg tactcaacgt cggtcctggt  9180
cccgacctgc atacaccgcc gactacctct cctacctgtt cgagagcttc attccaaata  9240
gattttggtg gcgcggaact gcagtcaatt agcttgccgt caacacagga cagagacccg  9300
ttcacgaaaa cagagagccg accaccctca ggtgtccgtc cgctatttgc cgaaccggcc  9360
agatcaccaa cctcctgatc cagctgaacc tgacaatcag caacctccgc cagtgggcgg  9420
acgaccaccg catcggtggg cgccagcgtc tttcgacgac gacccttccg agcgtacgtg  9480
gccaagcaac gtcgctgcat agcgcagaga acgaacgaac aaccactggc gggagaccgg  9540
cctagatggc cgcctcccac ctctggtgtc ccactccgcc gagacagagg gaagagcact  9600
taccgggtta cgccgcgcgc ctagccggga cgcccacgcg gcctagaccg ccttgccgtg  9660
gtcaccgcag agaagaaact cgagcgccag ggtccaccgc ggcctgcgat gctctctgat  9720
gagcagcggg aagttgcggc gtgcgaagcg accggcccag cagttgagca cggcgtcgac  9780
ggcgtccgcg tcggcacgag gcagcgcgag caagcgcgcg acgacctcgg acaccttcca  9840
gtcccgctgc caccggttgc cctccacgcg gaggcggtgt cacgcaatca aaaacagtcc  9900
ataactagag agctaacaac agaacagcta caaccctgcc aggggagtgt attgggcatc  9960
aacacggact gaggcagggt gatcctctat cgcctatgct gtttattctt gtaatggatg  10020
tcttgaatct gcttgtgcag cgagcctctg aggaagggtt tcttcagcct ctttcttcta  10080
ggaatatgca gcatcgtatc tcgctgtacg cggatgatgc aatgttattt ctatgtccta  10140
ctgccccgga tatcagtatg gttatggata ttcttcattt atttggttca acttcaggtc  10200
taaggactaa tgtccagaag agcagtgtgt tcccaatctg atgtggggaa gaagaggtga  10260
attgtttaca ggacttgctg ctatgcaata tttcagtttt tccctgtaag tacctcggtt  10320
tgcctttgtc tcccaagaaa ctcacaaggg accaggttca agccattgtt gaaagagtgg  10380
ccagcctttt gccaggatgg aaagctgaac ttatgaccag ggctggtaga gctattcatg  10440
tgcagtttgt catgacggct aagatgatat atgcagctct ggcacttgac cttcctgtat  10500
gggccatcaa agcaatcgat aagctgagga agggcttcct ctggaggggt aggaaagagt  10560
tccgtggtgg tcactgcctc ttggcttggc ctaaggttac ccgtcccaag gagttgggtg  10620
gtcttgggat tagtgagtta aagaacctct gttgggcttt gagagctcgc tggccatggc  10680
tgcagaaaac agaccccagt aggccttggg cggacttccc cattcatgtt tgtaaggtgg  10740
ttaaaaatct gattgctgca gccattatta ctaagctcgg tgatggagcc aatacccttt  10800
tctggaagga cagatggttg gaggggagat gtattaagga catagctcct gcgttgtttg  10860
atttggtgcc cttgcgtctt gccaacaaac ggttggtcaa agatactctc cctaatttcc  10920
attggctctc agatgtgcaa ggggcaatct cagtcagagt cattgctgaa ttcctggaac  10980
tttgtgaagt gcttgatgca gttgtgctcc agcctggaat aagggatcga tatttatgga  11040
aattcagcgc ttcaggtgat tatacatcta gttctgctta taatgctctc ttccttggtt  11100
cagttcagtt cgaaccagca gagcggctat ggaaatcttg ggctcctggg aagtgcaagt  11160
tctttatatg gcttgtggaa cataataggt gctggactgc tgacaggctc agaaaaagag  11220
ggctagaccg accagagcag tgccccttgt gcgaccaaga ggttgaaacc ataaatcatt  11280
tgctggtcaa gtgtgttttt gctaagcagt tctggtttga tttccttaat tcagtggggt  11340
tgcgggatct gtatccagct catgaggaat cctttgagtc gtggtggaag tctagcagct  11400
ccggcatcgg atcttgtgag aaaaggtttc aattctttag tgatcctagg tgcttggacc  11460
atttggaagc ataggaatag gtgtgttttt tatggttgta atcccagctt gctcacgacc  11520
cttaggatgg ctagggaaga ggcggtgctc tggtccatga ctggtgccaa ggccttgtcc  11580
```

-continued ttcctccaag tcgatgagtt gctggcttaa aacagcggtg tgggtcgtgt ttcctccatg 11640
ttttagtcag tgatccgtag ttagtctcta gtggtgtatg tgctgtattg gggttctctc 11700
cccctttctt ttcttctatt aatacaaaga tgcgcagctc tcctgcgtat tccagaaaaa 11760
aaagaaaaaa aaaacaaccc tgggataggg gctgctagga gatccaaatt cttggcccca 11820
gccagcaccc acaaatccct ctcctcctta gcttttctaa tagccggtga gagcggcaca 11880
gatggtgaga ccagagaagc tgaaggttgt aagacgacga gttgacatcc cccaaagtca 11940
tagtggtcaa tgtgtcgcat atgctgtagc tagagtgctc aagcaaggca gaagctcttt 12000
gtgccgatgt tgaggtagtc gagcacgagg gtgagtagcc atggttgagg atgccatctt 12060
tacgccatgg tgatggtcga ggcgcgtcga gacagtccat tgtataaggg ggtgatgttg 12120
aggtcaatgt agtcaaggcc atcgaggatg tcgacgaaaa tagcgacaca gtcaaggcag 12180
gtcatcatgg aggaagcata caccggattt gctaggcctg agaacgtgtc ctggagaacg 12240
gcacgctaca ctgccaatat aagacatgct agttagagag ccccaacaat gtgtcaacat 12300
ccgagcgacc ttggaagaga gtgcctcaac gatggttgat tgtggtgccc aaaacaactg 12360
agcacaaggt gtcgatgtat cccacaattg tcaaattaga tgatatatgt gggaaagaga 12420
caatgatgct ggcgatgtgg ttatgctgaa tgaagaagga acagtgcggg agtgaacgct 12480
cctacccgaa ggggagtagt ttgggccgac gtccttggcc aaggcaatgg tccagacata 12540
aggtacagtg tgcccaaagg cagtggtcca gaagcaaggt atggcgtcaa aaacagtgtt 12600
cgctgttggt gatgaagagc acaaaaagtt tgatgaagac caagtgcatc ctggtggtgc 12660
gcaagaggtg caacacaatt atcgatgtac atggagcgac aatgtagatg cattgttgta 12720
tgccaaccat ggatagaggc atgcctatga gggtgtctca attagagaat ctctaacatt 12780
gccttaaatc aattctctat cttataatat agtgcttaac ttataaaaaa ctgctccaac 12840
agtgctctat tttacatttt tatcaaaaaa tatagggcag accataaagt gaccaaaata 12900
tactacactc tggattaggg cttaactgtt gcaacacaat ttgtttttag tgccttaaac 12960
actttaaatg atgtagtatt gtaatttttg gaacattatt ttgaggggca gcgagtgtag 13020
cgtagagaca gtttatgagg ggcagtagcg gaagtgttgg gatagcaagc acaaccaaat 13080
acacggagtt gggttgtgtc gtacaaggcg aagtaggtgg tggggtggct caccaccttc 13140
gatgggaggc gattgaggag gtgggtggcg gtgtgcaagg cctctgccca gtagttggca 13200
gggagagacg cctgaaagag aaggcaacaa atcatgttgg tggtggtgcg aatcattcgc 13260
tcggcccgac cgttttgggc agaggtgtag gggcacgaga gatgcaattg aacgccactg 13320
gcgaggaaga acgaccgaga ggcatggttg tcgaactcgc ggccattgtc acactgcagt 13380
gcatggaccg ggcgacagaa ctgggtggag acccaggcga agaagtgagt gagggtggta 13440
aacgtgtcgg atttcattcg aaaaggaaaa gtccatagga aatgggaaaa atcgtccaaa 13500
atcaccaaat agtatttgta tcctgacaga ctgagtaccg gggaggtcca tagatcacaa 13560
tgaaccaggt caaaagcctg ttcagcccta gaagaagatg tagtgaaagg aagacgggta 13620
tgtcggtcaa gctgacatgc atgacagagg ccctcaaaat gtcccctatt acaagaagaa 13680
tctaaagtgc tggaaagctt ggtcatgacc tagatcctgg gtggccgaga cgacgatgcc 13740
aagtggtgga ggtggtggtg gagaccagga cgggaggtgg agacacgccg gtggacgacg 13800
accggagtgt gtagaggggc ccgacgctgt cacatcgggc gagtggggtc ctggtggcca 13860
gatcctttac agaaaaacca gtagggtcaa actcaatgga acacgaattg tcggtggtga 13920
accaacggac agaaagaaga ttgtgagtga tgtgaggggc tacgagaacg tcgttgaggt 13980
agaacagtcc agggagaacc gaggcaccta ctgaggtgac tagaagagtg gaaccgtttc 14040
gaacgacgat cgaggtaggg tgtgtggggg gaggtgggtg tgagcgagag catgcctagg 14100
gtgggggtgg tgtgatagga tgcaccggag tcgatgaccc agtcagaagg cggtggggcc 14160
aacgccatgg tgctgtatgc ggcagcgagg gcaacagggt cccaacctgc aacgaacgag 14220
gaccatggtg tcgtggtaga cggtctcgta ggcgggagtt gaggcgggcc ccgggtcggt 14280
cggggcacgc cgtatggagg catgttgtag gcgggcggcg tagtcaggag agccggagga 14340
cgggaggcgc tgggggcctg acccagccac atggagataa tgccggtcca ggggttgtag 14400
aacgacggcc aactctggtc gccaccccta tcggtggaac ctccacgaga ggagctgccg 14460
cccccatgtc cgcccttgta ggggcgacgg ccgccgtcga tggtggaatg ctgacgaggg 14520
tccgtaggag ccgcggtgaa gggccgagcg ggggtcctgg ttgacggagc gcggggggcg 14580
agtcctccgg aagacgcctg ggcaccaggg gtggcgctgt agagtgccgg agtgggagcc 14640
tcgatcgtca tggtgagctc ctcgagaaga agttcattgc gcacggcgtg gaaggtggga 14700
aaaggtacgg tcctcttgat gagagccttc aggtggccgt agagggggct gaggccacac 14760
aggaggttta gcaccaaggt acggtccgcc agcgactcgc caaggtcgcg gagggagtct 14820
gctaggccct tcatctggcg gcagtactcc cgcacagaga ggtccccctg ggagaattgg 14880
tggaactgat catcgatttg aagggcccga gcgtcccggt tcccgaggaa ttgttcctcg 14940
agggcgagcc acgcctggcg ggccgtgtcc gccttgtcgc agatgatgtc ctggagctcg 15000
acggtgatag tgtcgtggag ccaaaagagc acgactgtgt ccatcaggga ccaggccatg 15060
ggcggtgggg tgacgatgtc gtcgaggacg tggtcggcga gagcgtagcg ccgcagggtg 15120
aggacctgcc cccgacagcg agggtagtgg gaggacgccg ggtctagcac gattgacacg 15180
agggaccata tgttgtggag accggcagcc tgcgcatgaa gggcggcgat gtggtcggcg 15240
tcgagtccag gggcgatggg tgcctggggt tgggtggagg tgcctccggg gtgaccggag 15300
gatgcccgag gaggagtcgc tgagcggtag ccatttgggc ggtcagagca gcgctcatgg 15360
cacgctcttg ctacagggcg agggtcgcag cgcgctcgcg gtcgagggaa gcctccacgg 15420
ctgcctggat agtggcgatg gccgtgacca gcgccgacga ggccgtcggg ggggcggggg 15480
ggggcagtga cgtcagccca tgtggcggtg gtgtgggccc ggaggagaat cgcggcgtcg 15540
ttgagcagcg agggtggcat cgggtagggg cccgagatcg gcgatgtggg cccctcccca 15600
acagcgaggt cgctaggggt gccgagtccg gcagtggcga gggcggcggt agccgcggcg 15660
ctgcgtgctg gtggggccac agtggcagtg gccgcaggga gggccgcgcg tggctgctgg 15720
gcagcagcag tcgtagcggc agccggggtg taggggggaat gaggtggtgt cgacatggcg 15780
gcaccaggtg gttgggcggc cgacgctgcg gggttgacgg cggcggtgga ggaaggaccg 15840
gtgcgagcgg ccgaggtggc tggatggccg gcgcggtgcc cagtgagggg gtccggcggg 15900
ggcagccctt gctgctgggc ggcggcgcag gaggaggcgc cgcggcggcc agcctgggga 15960
ggagcggcga ccggtgggag gaaggggagc ggcgatcggg cctgggggga gggagaaggg 16020
gggagcggtg gctgccacgg actggcggcg gcagggaggg tgggagggaa ttagtgtggc 16080
tctgatacca tgtagaacta tggaaaaccc taaccctaga atagggttgg gcagtgtatt 16140
aatagaccaa ataactgggc taggcccatt acaagggacg ggtatctaaa aaaatagact 16200
gcggcttttt ttttagataa tggatactag tccagcttct cctcgtttgg aggattagcc 16260
aacacaccaa aagtttttac atggagtagt cacacgacta gctgctttat ttgtcctttt 16320

```
catttatgca acctaggaat tatttgactt gtctccatct taatgtgtct gcttttaaat  16380
acagtttact gaacagggcc acatctttgt tcaagtccat ttggtcaagg aactaaacag  16440
gaaaggaaac aatttttgtg atgtttctgc tcataacaga gaaattctgt atgattctga  16500
caactcgatg ctatggaaca cactaagcgg acttgaagta gcagatagct ggaggtcctt  16560
ggagaatttt acgatgttca agaattcaaa tggtgaaaca gatacaatta ggttagctgt  16620
cagagttgaa gacaccggca taggaataac aaaagatgct caaatgcgta tttttacacc  16680
tttcatgcaa gctgacagtt ccacctcacg aacatatggt ggaactggaa ttggcttgag  16740
tattacaaaa cgtttagttg aattgatggg tggagaaata gggtttacta gtaaatcagg  16800
agttggtagt acattttctt ttactgccat tttcaaggag aacagaggat gtcctggaga  16860
tatgaaaaga tactattctg aacctactcc gttggatttt caaggaatga gggctcttat  16920
tattgatgga aggagtgcac gtgcagaggt tactatgtac catcttcgta gacttggaat  16980
acagtgcagt cttgttgcca catctgaatc tgaatctgca tcttcagctt tgatgaaagc  17040
ctgcacctca aggttcattt ccttgtgtag tttactgttt gatttacttc tacaagtttt  17100
agaaattaga agttattttg ttcaaataaa tgtaacattc cttgcattta taaacttttg  17160
tcatcttaac acatggcttt gctatatttt ctttagttgg ttgtgtgcta tttctttgaa  17220
tattttccat attgtcgatc ccaaaacaag gtttcgtaac ttctcatgaa ctgaagaaaa  17280
gtaggagaaa cagagtgaaa ccttcgttgg tttgagttta gaaactgaaa taggatagtt  17340
cgattctaaa taacttgtga attcattcag ttgttgctgt catcattata acatatcaat  17400
ttgttcatgg ccagcaacct acacttgtcc tcagtattac gacccaacaa aatcaatgca  17460
taatgtcgcc atcatcactt tccatgtatg cattttcttt tctaagcact gttgatgcct  17520
tacttgttga tgttatcatt tatattttac atgttgagca gcaaaaacaa tccggacatg  17580
gtccttgttg atacagaagc ttggggtaaa ggttcaggtt tggcattcta tcatcgtttt  17640
gtagattgtc aactaaaggg cgcacacaag ttttctcagc ccatgccaaa gactattctt  17700
ttgggaagct caataagccc tgttgaatct gattatttaa gattgacagg atttggtgat  17760
tgcataagga aacccctccg tcttagtact attgttgcct gtcttcgcaa aaccttaggg  17820
gttggggtta caaggcagca gagtagagac caatctttgg ttcttcaaag tgtactaact  17880
ggaaaacaga ttctggttgt ggatgataat gcagtcaacc gtaaagttgc agctggttct  17940
ttgaagaaat atggatctaa agttacatgt gttgatagtg ggagtgatgc aattgatatg  18000
ctcaagccac ctcacacatt tgatgcttgc ttcatggatg ttcagatgcc cgagatggac  18060
gggtaatgtt cctttccaat gagttactaa tgaaaaagag cgcagatttg ctgcccaggc  18120
gttctcatta tctaaaatac catgttgcaa tatttcaaaa atcatcacaa aaatcatgta  18180
tgcagtacac aaagttaggt atagccgcaa cacttcagat tgaaatttct tcctagatgc  18240
caagaaccaa aatagacaag cagtcaacct ggcagtgttc atcatgtgct gacagtgaga  18300
ctttgttttt taatctcagc atcaaagatg aactttattg aattcttgag gctacactta  18360
aggtgtactt gcacacatgt tttttgtgat gattgttgaa acattgcaat acggtatttt  18420
agaatgtggg cgccaatttc cctgggcgcc atatgatttc caatggaaaa ttgtcatatg  18480
ttatttactt gcgggatata ctataagagt tcaatatgta aaagattctt tgtgcagaag  18540
tcactcttgg aacatcttac gttagttcac atggaagcat gtctttagtt ttaggtatgt  18600
gcttcttttg gattttgtgg aatcatcgga acagatgcat ctttgatggc ctttccccta  18660
atgttgctaa ttttctaatc catgtggggg atgagcgccg tctgtgggag actgccgggg  18720
ccaaggggtt gacatccctt gttgcctccc tctctcatgt agcctagagt tttatagatg  18780
agtcagtcta tgctagtttc gttcaggccg ccgtaaggcg tcagttgtac cccggtctat  18840
tttagacctt gtttatttgt tcttttaata taatgatacg cagctctcct gcgtgttcga  18900
gaaaaaaaga gaaagttatt ttttggtcct caaataacaa cacttgtcaa atgtatgcat  18960
ctcctcatgt tattagcaag cactctcata ggagtatcac tgaggataat ctctcttttg  19020
ttttcacatc cagtccttgc ttaaaaaaat gcactgtagc ctcacatgct tgtgtttgct  19080
ttcctatggg ttataacaag tggttgcatc tactttgatc acttgtagat ccactgtagg  19140
actaccatta acaatattca cattcaattg caggtttgaa gctacaagat taatccggtc  19200
catagagaaa aaaataaacg atatgatcat gatgggtgaa atatccgcta ataattatgg  19260
aaataaggcc cattggcatg taccaatatt agctatgacg gcagatgtaa tccaagcgac  19320
ttttgaaaaa tgtatgcagt gtggaatgga tggatatgtg tcaaagccat ttgaagaaca  19380
gcagctctac tttgctgttg ctcatttctt agagactgat gaaacagaat aa          19432

SEQ ID NO: 256          moltype = DNA  length = 19433
FEATURE                 Location/Qualifiers
source                  1..19433
                        mol_type = other DNA
                        organism = synthetic construct
SEQUENCE: 256
aaaacatttg aggacttcac agcaaggaca acatttgaaa ggccattgat gagtggtgtc  60
gcctatgcat tgaaggtatt acacaatgaa agacaacagt ttgaggaaca acatggatgg  120
aagattaaga agatggaaga tggagatcag tcccttgttc atgactacaa ccttgaaaag  180
cttgaaccat caccagttca agatgagtat gcgcctgtta ttttctctca ggaaactgtg  240
aagcacatta tatctgtaga tatgatgtct gggaaggtag taggatattc gtaagccttt  300
acagtaaata cttactattt tatctatcct gagttcctta ctactatttt tgttataaaa  360
cgaagaaatt tctggctctt cttctaactt tcaatattat taggattaaa catgtgtaga  420
acttctcggt caaaaaagac actttagaac ttatattttt attttaatta gaatttgatg  480
tataaaaatt aatcattttt acaatgagtg ttatagtaat ataagttgtt atgtgtcttg  540
ttcaatgtgt taattactat agcatgttcc atagaaatac tgtgcaggct gttactaatt  600
ctctcttatt ctgtctttgt ggaaattaca taattactaa acctcatagt aataataata  660
ataactaaga ctccattttt ctgctaacat tacaaccttg atttcaggaa gatcatgaca  720
atatattacg ttcctggtca acaggtaaag gggccctaac atcccctttt aagcttctga  780
agtccaacca tctcggtgtg gtgcttacat tcactgtata taaatatgat ctgcctccaa  840
atgcaacacc acaggagcgt attcatgcta cattggggta aaatgttttg caaagtttca  900
agttgaagct atataggaat acactatttt ttctttagga gacttaacct tgtggttatt  960
gacactttgc agctatcttg gtgcctcatt tgatgtccct tctctggttg atagaacaac  1020
tcgctagcaa acgaaagata gtagttaatt tatatgacac cacaaatcat acctctccta  1080
ttgaaatgta tggttctgat tttactccat ctggtgatct gcatattagt agcattgatt  1140
ttggagaccc aacacgcaaa catgagatgc attgcaggta gaaaactttt ttttgatgcg  1200
```

```
aattatacaa tgcttttgtt cttcagatat gctcagtgct ttctctttca aacttctctt  1260
tcagatttaa acatgaacct tcactgccat ggtctgcaat aataatatca acagctgtag  1320
ctataattgt tttgcttgtt ggacatatta tttatgcaac tctgaactcc cttgaaaagg  1380
ctgaacatga ttatagagta atgagagaac ttaaaggaca agctgaagct gcagatatag  1440
caaaatctca ggttcattct acctcttcca gtgtcttcat cctatgcatt ggtttgttat  1500
ctcatttgtt ctacttttct ctttttgtcg gctgagtcat tattgattgt cttgcagttt  1560
ctagcaactg tttcccatga gattcggact ccaatgaatg gtgttttagg tctgtacttc  1620
tgatatttct tttttgtcta ttaatacata ccgcagttat ttgtgtttat gttttaatca  1680
aagacaacta aataaatttt gaaaaggatt tcttcttgaa ttaggtatgc tgcagatgct  1740
aatggacact gaacttgata caactcagca ggattttgta gtcaccgctc aagaaagtgg  1800
aaaggtatta ataaacttaa taaatgaagt ccttgatctg gctaagatag agtcaggaag  1860
gattgagctg gaagcagtgc cttttgatgt ccgtgatatt cttgacaatg tgatatctct  1920
tttctacgat aaatcacaag ctaaaggcat agaggtgagt cctaatttag aacttgtatt  1980
gtttgctaag ctctgaatat tgtttgtgcc atgggaccta aaataatgtg taattctttt  2040
ttgagggtag ttggccgtgc ttgtatctga ccaagttcct gatgtcctaa ttggggatcc  2100
atggcggttc cggcagatca ttacgaacct tgtggggaat tctatgaagg ttagattcaa  2160
atatgtggta gcttcattat ttcagcttgc tggcaagttg taactgtgtc tagtcaatcc  2220
caccatttag cttatacaac aatatacttt gtaggaaacg tgacaactta ctaaaatatt  2280
aatgtcatga gcttttgaat ttgagatgtg tagaagacaa ttggtagaat tggtcaattg  2340
tgtcgctgag ctcgtgggca gattatacat gagtacattc acttggatgg caagaaacct  2400
ccctaaagat aagaagtcag gattacatga ccctaatcta gcatatttaa agatattcca  2460
atataatata ccacccccca tatttttctc gaacgtgcag gaaagctgca catctttata  2520
ttaagaagat aaaaggtcca aaatggacca aaacaggtat agatacaagg cacctcacgt  2580
ggccaaaaac aaaagtacaa aaaaaacagt ccataacttt tttttttag ataatggaaa  2640
aatcatccga ccttggcctc aaatgaggtt acggccattt attacaaggg acggaagcat  2700
attgccaaaa cacctcctat gaccacttca gagaacccca actagccaaa ttaaagaact  2760
tcagctatcg aaccacagct actacatatt taaacgcaac gcagaccccc atccaaaatt  2820
gctaaagaac tgtagtagca ccctctccac attacgacat gaagacttta ttaactcttg  2880
gtcctccctt ctaggctgaa gctgagacca gaagcggcac caatatgttg ccctgaaggt  2940
tacctgcaca catgatttag gagatgaatt attgaacacc acatcatttc tacttaacca  3000
aatagcccaa caaattgccg atgcaacggt taatagtaag tttcgaactc tgggaagcct  3060
cccgctcgcc caaaccccaa acaaatcatt aacatcccga ggaggtctca accccgtgct  3120
tatctgaatc aaccgccaaa tgaatgacgc atacaaacaa ctgaaaaata ggtgctttat  3180
tgtctccggt ctactacaaa agcaacatat cttattacca ttccaatgcc tcctagccaa  3240
gttatccttt gttaatgtta cccctctttt gaggtaccac ataaaaatct taattttcag  3300
aggaagccta agtttccaaa ggtccttatt atgcaccccc aacccattgt taagagatgc  3360
cagatacaga gacttaaccg taaacatccc gttggcggtc aagttccatc tgaacaagtc  3420
cctgtttgaa ttcaaattgg tatgcgcaac aagtgagacc aattgaaccc attggtccct  3480
caattgttga gccaaacccc tccgaaagga tatatttaag ggcaccgtgg agaacacaca  3540
ggcaacagta gagttcttcc tcctcgctag gttataaaga gacggaaaac gaagttttaa  3600
cgttcccgac ccgagccaat catcctccca gaaacgcacc tgggacccat catgaatcac  3660
aaaggttcct ttactaatga atgtgtcctt aactttcata agaccactcc agaagtgtga  3720
atcagtggcc ctacgctgcg cctgggataa ggttcgattg gccagatatt tacgtctcaa  3780
taatgattgc cacatccctt cttcattgag aagtttatac aaccatttgc ttaagaggca  3840
tttattttga acctctaaat tcaaaatgcc tagcccgcca acctccttag gttgacaaat  3900
tacatcccat ttggccagcc tatatttttt cttatgaccc tccccttgcc agaaaaaacg  3960
cgatctgaaa taatctatct tctccagcac accttttggt acctcaaaga aagacatcat  4020
aaacatcgct agactggtca acacagaatt aattaatacg agccgccctc ctactgacat  4080
aagttttcct ttccagctgc tgagcttttt ctcgaatttg gcctccactg ttttccactc  4140
accaattgtc aatcgacggt ggtgcatagg aatcccaaga tatctgaagg gcagcccacc  4200
agaactgcaa ccaaacagcc gtgtgtacct cccttcatcc tcttttgcct tcccataaca  4260
gaatatctca ctcttgtgaa agtttatttt aagaccagat aactgctcaa aggcacataa  4320
tatgagcttc atattcgttg ccttttccag atcgtgatcc ataaacaaaa ttgtatcatc  4380
agcgtattgc agaatggata gccccccatc taccaaatgc ggcaccaagc ccttgatctg  4440
gccattttcc tttgctctat taatcagggt agcaagcatg tccactacca agttaaagag  4500
aataggagac agcggatcgc cctgcctcac ccctctatgg gtctggaaaa aaggacccat  4560
gtgatcatta actctaaccg caacatggcc ccccttcatg aaagactcga tccacctaca  4620
ccaggtactt gaaaaacctt tcatacgaag ggattgttga acaaagctcc acttcacctt  4680
atcataagct ttctcgaagt cgattttgaa aatgacccca tcccttttct tcgtatgtag  4740
ctcatgaata gtctcatgta agaccaccac cccttccatg atatttcttc ctggcaggaa  4800
cgcagtctgc aggggactga ttacattctg cgcaacctcc gtgatcctct tagtcgccac  4860
ctttgtgaag attttgaaac tgacatttag tagacaaatt ggtcggtatt gttgaaccga  4920
gattgcctcc cgagtcttag gaagcaaaat gatagtccca aagttaagac tatacaaagg  4980
gagatttcct gagtggaact cacgaaacaa agccataaga tcatctttaa taacatccca  5040
acagatttga taaaattccg ccgggaatcc atcaggacct ggagccttgt tatgttccat  5100
actaaaaacc accgctttta cttcatcttc agaaaatggc tgggtgagct tctcgttctc  5160
aacttgagta acttgtatta tatcatctct aagatcctca tccagactaa aagacgtgtt  5220
ttctgggggg ccaaagagat ttttataata accagttata tgactcttta attctttctc  5280
gtcgtataac atacgagctc catccgtcat ctggaagatg cgattcttcc tgaattttcc  5340
attggctatc atctgaaaat atttagtatt actatccccc tccaggagct ccttgacctt  5400
cgctctttga taccacttta tttcctcctc ccggagtagc tgagcaagcc tgttctgtaa  5460
gtagttatgc agatccaact ccgaagtact caacagaact acttcagctc tcttatctaa  5520
atcatcaagc ttagctatga tctccttttt ttcctttttc aacaaccccg aagtgtgcat  5580
tgcccaaccc cttaagtgtt ggcgcacctt cctaatcctg gcttgccatt tctccaaagg  5640
agtagaacca cttgtctcat ttacccaaat atcttttacc atatccacaa aaccatccct  5700
cagaaaccag cctagttcta acttgaacgg aggaattgta tgggcggtta caacacctgt  5760
gctaagaagc agaggagtat gatcggatat atttctcgac aaggcatgta ccgaagctct  5820
agggtatttt ccctcccatt ctgtagctac caaaatccga tccaacttct cataagtcgg  5880
aatatcccta gtattagccc aggtgtacct tcgccccgac atctgcaatt ctcttagatc  5940
```

```
aagaccatca attaccgcat tgaaaaggaa cggccaacga tgatcaaatc tatcattatt  6000
tttctcagat ggagatcgta aaatattaaa atctccccca atgagaatag gtaaagtttc  6060
tgtattgctc acacggacta gctcagaaag gaattcttgt ttgaagcagt cctgggcagg  6120
gccatacacc gagacaagag cccatttaaa accatctgct ttatcaagca aattaaactt  6180
aataaagaaa tccccttccg tgatggcacc aacatcaaag acatcagcgt caattcctaa  6240
caacatcccc ccagatctac catgaggttc tttgcaatgc cagataaaat ttttcccagc  6300
acacaaattc cttagtagat gatctgggaa ggatttgcgg cctgtttcag agagggcaat  6360
aaaattgaga ccatgttctt tggtcagatc cgaaatgtat ctaagttttt tcaaatcctt  6420
gaacccattg ctgttccaaa agattccttt cattggtaaa caattaatta ataatcaagc  6480
ccgacctttt ttcttagaac acaacgaacc ctgactagat ggttttgtac agactgactt  6540
aatcagccca tcagtgccat ccgtctcttc atgcataata tccccacaca aatgatttaa  6600
aatgaaatga tcaaactctt cgtcctctac tactcccttt cccataaaat cagataaatc  6660
agcctcgttc ttacccacta gctgatcctg aactctatta atctctaatt ttttcaactg  6720
accaatagag gaagcaactg aactaggatt agaacccgct aaaatgccaa tatttttaaa  6780
agaatccaga atataattat cgggtaaact aataaaggaa acattgttac ctttagtcgg  6840
ctgatcgtcc aggttgtatc ccgctttcag ccgaatcgct cgaactagcg agtcttcact  6900
caccgaatca gagcggcgcg agctacgacg cagtgcatgc acttttcctg tcaacgcctc  6960
cgggatactg cccaactttt caatactaac agcattgacc gagagacagg taccctgaga  7020
ttgatccaga tccagctgtg tagggccagc gcacaccgat ttcccactgg acgtgttgct  7080
gttcagcata gaatccgaca ccttattaac tgcccctgct gaatcctttg atgttccctt  7140
caagctcgcc cccttattcc ctctttcacc tatattgtga tccttgtttt gatcctgaaa  7200
ttcatcatca tcattatccc cgatatgatc catatccatc ggcaaaggct ggtcaccttc  7260
agctgctgac tccaccctga atttcagttc atataagtag tctccaatta ccacatcaac  7320
tacttgcgga atcaaattcg ggtcaagcac ggccaccttc agccttgccc tgtcaaactt  7380
ccgagtaaac aacatatcca cctcttttga gatgcctagc atagaaccaa ccgcccagat  7440
taccgagtac tctctaagtt ccttaggtaa accagtgaac tgcacccaag ccttaggcat  7500
ctcatatttt atttcctctc caaacccctc ttccttgaca agcatctgtg caccaaattt  7560
tgtatgaaca gttccccact cgatcatacg gtgaagttca cccctggaag ggaaacacgt  7620
cgagaacaca ttgttcccca cacacttcac acaccagtcc caatcagcag ccaccaacct  7680
tttaagctca ttcaaaatct gctcttcatt catggaaccc tccacaatag acactgtacc  7740
attgcagcca ccttgcctct gctttactgg aatgggttgg ggtataaagt aaaaccccaa  7800
tccctccacc gcatacccgc aaggtattgc aaaagttttg caggcacgaa ccaccggaca  7860
tttcgaagtt aagtgagttt tgacatcaca aatttcacaa aatagctcaa tattacagtc  7920
actcaactga tgacctttat ttttgcacct gaaacaaaac ggcactttct cttttgaact  7980
tgaaatcaca gaagaaccca ccttgtcatc caagtgggtt ggagtagaca attctttgat  8040
ggtctccaac tttgaactgt gttgggaccc aatattcgga cctgctggat tccccctcga  8100
gttctgaatg tgctggctct tccccacaga ctgctgcagc aaggaaacaa tctgttccat  8160
ggtactatct ggaacaggcc tgacagcgct accgttgcca attgatgttg taattgcctg  8220
ttggagcaag tccacagcgt ttgatacttg aggagtcacc gaagaagccc ctgaacctcc  8280
cagaccctgt ccagcgacca tcacagagga agcccctcca tttgaaaacc tgctgtgaac  8340
acctccgccc ccagactggg ttggcaaagt acgaccacca tagaaccggc ctccggcaga  8400
agcacctctt ccaccacgcc acgctccagc acggccctgt ccacctcccc gacgtccaaa  8460
aggacggcgt ccgccaccat aaccaggatg gaacactggt tggatccac cgcgtccaaa  8520
gtcagtgttc agtcccaaac cagcgacata tcctcccgtg cccccaagca gttgctgacc  8580
ggtggaaaaa cctgcagcgc cctcggactg atgctggccg cgactgcctc cacgccctcc  8640
agtatcacca accggcgcca ttgcgttcct tacagcctcg acgaaggtgc caggagccac  8700
accccgggag gaaatgtgaa ccgccctggc agcagaagaa ctggtgcctg agcgggagaa  8760
caaggaagcc agcccagcag ttggcctata aggaatccta ggactgagaa tcatatgttg  8820
ggccctccca ttccaacggg gacaagcact aattaagcca acattccttg attccagcac  8880
aggatccgca tgagaatccc agaatatcgc ctgacttgca tccataccaa aatcattcaa  8940
attcaaacca tcagctaacc gctccgctga taccgctccc attgaagacg tcttcttcaa  9000
cctttggccg tggcaccttc caggggagca gcgccattgc gctttttcta gtgcatgtcc  9060
aactgtgaac tccggcgaac gtcgtggcga cggcaatttg ccctgccatg gcttcacctt  9120
attcctagaa gaagtgctcg gactaggaga atgcaagcat gtactcaacg tcggtcctgg  9180
tcccgacctg catacaccgc cgactacctc tcctacctgt tcgagagctt cattccaaat  9240
agattttggt ggcgcggaac tgcagtcaat tagcttgccg tcaacacagg acagagaccc  9300
gttcacgaaa acagagagcc gaccaccctc aggtgtccgt ccgctatttg ccgaaccggc  9360
cagatcacca acctcctgat ccagctgaac ctgacaatca gcaacctccg ccagtgggcg  9420
gacgaccacc gcatcggtgg gcgccagcgt ctttcgacga cgacccttcc gagcgtacgt  9480
ggccaagcaa cgtcgctgca tagcgcagag aacgaacgaa caaccactgg cgggagaccg  9540
gcctagatgg ccgcctccca cctctggtgt cccactccgc cgagacagag ggaagagcac  9600
ttaccgggtt acgccgcgcg cctagccggg acgcccacgc ggcctagacc gccttgccgt  9660
ggtcaccgca gagaagaaac tcgagcgcca gggtccaccg cggcctgcga tgctctctga  9720
tgagcagcgg gaagttgcgg cgtgcgaagc gaccggccca gcagttgagc acggcgtcga  9780
cggcgtccgc gtcggcacga ggcagcgcga gcaagcgcgc gacgacctcg gacaccttcc  9840
agtcccgctg ccaccggttg ccctccacgc ggaggcggtg tcacgcaatc aaaaacagtc  9900
cataactaga gagctaacaa cagaacagct acaaccctgc caggggagtg tattgggcat  9960
caacacggac tgaggcaggg tgatcctcta tcgcctatgc tgtttattct tgtaatggat  10020
gtcttgaatc tgcttgtgca gcgagcctct gaggaagggt ttcttcagcc tctttcttct  10080
aggaatatgc agcatcgtat ctcgctgtac gcggatgatg caatgttatt tctatgtcct  10140
actgccccgg atatcagtat ggttatggat attcttcatt tatttggttc aacttcaggt  10200
ctaaggacta atgtccagaa gagcagtgtg ttcccaatct gatgtgggga agaagaggtg  10260
aattgtttac aggacttgct gctatgcaat atttcagttt ttccctgtaa gtacctcggt  10320
ttgcctttgt ctcccaagaa actcacaagg gaccaggttc aagccattgt tgaaagagtg  10380
gccagccttt tgccaggatg gaaagctgaa cttatgacca gggctggtag agctattcat  10440
gtgcagtttg tcatgacggc taagatgata tatgcagctc tggcacttga ccttcctgta  10500
tgggccatca aagcaatcga taagctgagg aagggcttcc tctggagggg taggaaagag  10560
ttccgtggtg gtcactgcct cttggcttgg cctaaggtta cccgtcccaa ggagttgggt  10620
ggtcttggga ttagtgagtt aaagaacctc tgttgggctt tgagagctcg ctggccatgg  10680
```

```
ctgcagaaaa cagaccccag taggccttgg gcggacttcc ccattcatgt ttgtaaggtg  10740
gttaaaaatc tgattgctgc agccattatt actaagctcg gtgatggagc caataccctt  10800
ttctggaagg acagatggtt ggaggggaga tgtattaagg acatagctcc tgcgttgttt  10860
gatttggtgc ccttgcgtct tgccaacaaa cggttggtca aagatactct ccctaatttc  10920
cattggctct cagatgtgca aggggcaatc tcagtcagag tcattgctga attcctggaa  10980
ctttgtgaag tgcttgatgc agttgtgctc cagcctggaa taagggatcg atatttatgg  11040
aaattcagcg cttcaggtga ttatacatct agttctgctt ataatgctct cttccttggt  11100
tcagttcagt tcgaaccagc agagcggcta tggaaatctt gggctcctgg gaagtgcaag  11160
ttctttatat ggcttgtgga acataatagg tgctggactg ctgacaggct cagaaaaaga  11220
gggctagacc gaccagagca gtgccccttg tgcgaccaag aggttgaaac cataaatcat  11280
ttgctggtca agtgtgtttt tgctaagcag ttctggtttg atttccttaa ttcagtgggg  11340
ttgcgggatc tgtatccagc tcatgaggaa tcctttgagt cgtggtggaa gtctagcagc  11400
tccggcatcg gatcttgtga gaaaaggttt caattcttta gtgatcctag gtgcttggac  11460
catttggaag catagggaata ggtgtgtttt ttatggttgt aatcccagct tgctcacgac  11520
ccttaggatg gctagggaag aggcggtgct ctggtccatg actggtgcca aggccttgtc  11580
cttcctccaa gtcgatgagt tgctggctta aaacagcggt gtgggtcgtg tttcctccat  11640
gttttagtca gtgatccgta gttagtctct agtggtgtat gtgctgtatt ggggttctct  11700
ccccctttct tttcttctat taatacaaag atgcgcagct ctcctgcgta ttccagaaaa  11760
aaaagaaaaa aaaaacaacc ctgggatagg ggctgctagg agatccaaat tcttggcccc  11820
agccagcacc cacaaatccc tctcctcctt agcttttcta atagccggtg agagcggcac  11880
agatggtgag accagagaag ctgaaggttg taagacgacg agttgacatc ccccaaagtc  11940
atagtggtca atgtgtcgca tatgctgtag ctagagtgct caagcaaggc agaagctctt  12000
tgtgccgatg ttgaggtagt cgagcacgag ggtgagtagc catggttgag gatgccatct  12060
ttacgccatg gtgatggtcg aggcgcgtcg agacagtcca ttgtataagg gggtgatgtt  12120
gaggtcaatg tagtcaaggc catcgaggat gtcgacgaaa atagcgacac agtcaaggca  12180
ggtcatcatg gaggaagcat acaccggatt tgctaggcct gagaacgtgt cctggagaac  12240
ggcacgctac actgccaata taagacatgc tagttagaga gccccaacaa tgtgtcaaca  12300
tccgagcgac cttggaagag agtgcctcaa cgatggttga ttgtggtgcc caaaacaact  12360
gagcacaagg tgtcgatgta tcccacaatt gtcaaattag atgatatatg tgggaaagag  12420
acaatgatgc tggcgatgtg gttatgctga atgaagaagg aacagtgcgg gagtgaacgc  12480
tcctacccga aggggagtag tttgggccga cgtccttggc caaggcaatg gtccagacat  12540
aaggtacagt gtgcccaaag gcagtggtcc agaagcaagg tatggcgtca aaaacagtgt  12600
tcgctgttgg tgatgaagag cacaaaaagt ttgatgaaga ccaagtgcat cctggtggtg  12660
cgcaagaggt gcaacacaat tatcgatgta catggagcga caatgtagat gcattgttgt  12720
atgccaacca tggatagagg catgcctatg agggtgtctc aattagagaa tctctaacat  12780
tgccttaaat caattctcta tcttataata tagtgctcaa cttataaaaa actgctccaa  12840
cagtgctcta ttttacattt ttatcaaaaa atatagggca gaccataaag tgaccaaaat  12900
atactacact ctggattagg gcttaactgt tgcaacacaa tttgttttta gtgccttaaa  12960
cactttaaat gatgtagtat tgtaattttt ggaacattat tttgaggggc agcgagtgta  13020
gcgtagagac agtttatgag gggcagtagc ggaagtgttg ggatagcaag cacaaccaaa  13080
tacacggagt tgggttgtgt cgtacaaggc gaagtaggtg gtggggtggc tcaccacctt  13140
cgatgggagg cgattgagga ggtgggtggc ggtgtgcaag gcctctgccc agtagttggc  13200
agggagagac gcctgaaaga gaaggcaaca aatcatgttg gtggtggtgc gaatcattcg  13260
ctcggcccga ccgttttggg cagaggtgta ggggcacgag agatgcaatt gaacgccact  13320
ggcgaggaag aacgaccgag aggcatggtt gtcgaactcg cggccattgt cacactgcag  13380
tgcatggacc gggcgacaga actgggtgga gacccaggcg aagaagtgag tgagggtggt  13440
aaacgtgtcg gatttcattc gaaaaggaaa agtccatagg aaatgggaaa aatcgtccaa  13500
aatcaccaaa tagtatttgt atcctgacag actgagtacc ggggaggtcc atagatcaca  13560
atgaaccagg tcaaaagcct gttcagccct agaagaagat gtagtgaaag gaagacgggt  13620
atgtcggtca agctgacatg catgacagag gccctcaaaa tgtcccctat tacaagaaga  13680
atctaaagtg ctggaaagct tggtcatgac ctagatcctg ggtggccgag acgacgatgc  13740
caagtggtgg aggtggtggt ggagaccagg acgggaggtg gagacacgcc ggtggacgac  13800
gaccggagtg tgtagagggg cccgacgctg tcacatcggg cgagtggggt cctggtggcc  13860
agatccttta cagaaaaacc agtagggtca aactcaatgg aacacgaatt gtcggtggtg  13920
aaccaacgga cagaaagaag attgtgagtg atgtgagggg ctacgagaac gtcgttgagg  13980
tagaacagtc cagggagaac cgaggcacct actgaggtga ctagaagagt ggaaccgttt  14040
cgaacgacga tcgaggtagg gtgtgtgggg ggaggtgggt gtgagcgaga gcatgcctag  14100
ggtgggggtg gtgtgatagg atgcaccgga gtcgatgacc cagtcagaag gcggtggggc  14160
caacgccatg gtgctgtatg cggcagcgag ggcaacaggg tcccaacctg caacgaacga  14220
ggaccatggt gtcgtggtag acggtctcgt aggcgggagt tgaggcgggc cccgggtcgg  14280
tcggggcacg ccgtatggag gcatgttgta ggcgggcggc gtagtcagga gagccggagg  14340
acgggaggcg ctgggggcct gacccagcca catggagata atgccggtcc aggggttgta  14400
gaacgacggc caactctggt cgccacccct atcggtggaa cctccacgag aggagctgcc  14460
gcccccatgt ccgcccttgt aggggcgacg gccgccgtcg atggtggaat gctgacgagg  14520
gtccgtagga gccgcggtga agggccgagc gggggtcctg gttgacggag cgcggggggc  14580
gagtcctccg gaagacgcct gggcaccagg ggtggcgctg tagagtgccg gagtgggagc  14640
ctcgatcgtc atggtgagct cctcgagaag aagttcattg cgcacggcgt ggaaggtggg  14700
aaaaggtacg gtcctcttga tgagagcctt caggtggccg tagagggggc tgaggccaca  14760
caggaggttt agcaccaagg tacggtccgc cagcgactcg ccaaggtcgc ggagggagtc  14820
tgctaggccc ttcatctggc ggcagtactc ccgcacagag aggtccccct gggagaattg  14880
gtggaactga tcatcgattt gaagggcccg agcgtcccgg ttcccgagga attgttcctc  14940
gagggcgagc cacgcctggc gggccgtgtc cgccttgtcg cagatgatgt cctggagctc  15000
gacggtgata gtgtcgtgga gccaaaagag cacgactgtg tccatcaggg accaggccat  15060
gggcggtggg gtgacgatgt cgtcgaggac gtggtcggcg agagcgtagc gccgcagggt  15120
gaggacctgc ccccgacagc gagggtagtg ggaggacgcc gggtctagca cgattgacac  15180
gagggaccat atgttgtgga gaccggcagc ctgcgcatga agggcggcga tgtggtcggc  15240
gtcgagtcca ggggcgatgg gtgcctgggg ttgggtggag gtgcctccgg ggtgaccgga  15300
ggatgcccga ggaggagtcg ctgagcggta gccatttggg cggtcagagc agcgctcatg  15360
gcacgctctt gctacagggc gagggtcgca gcgcgctcgc ggtcgaggga agcctccacg  15420
```

```
gctgcctgga tagtggcgat ggccgtgacc agcgccgacg aggccgtcgg gggggcgggg  15480
gggggcagtg acgtcagccc atgtggcggt ggtgtgggcc cggaggagaa tcgcggcgtc  15540
gttgagcagc gagggtggca tcgggtaggg gcccgagatc ggcgatgtgg gcccctcccc  15600
aacagcgagg tcgctagggg tgccgagtcc ggcagtggcg agggcggcgg tagccgcggc  15660
gctgcgtgct ggtggggcca cagtggcagt ggccgcaggg agggccgcgc gtggctgctg  15720
ggcagcagca gtcgtagcgg cagccggggt gtagggggaa tgaggtggtg tcgacatggc  15780
ggcaccaggt ggttgggcgg ccgacgctgc ggggttgacg gcggcggtgg aggaaggacc  15840
ggtgcgagcg gccgaggtgg ctggatggcc ggcgcggtgc ccagtgaggg ggtccggcgg  15900
gggcagccct tgctgctggg cggcggcgca ggaggaggcg ccgcggcggc cagcctgggg  15960
aggagcggcg accggtggga ggaaggggag cggcgatcgg gcctgggggg agggagaagg  16020
ggggagcggt ggctgccacg gactggcggc ggcagggagg gtgggaggga attagtgtgg  16080
ctctgatacc atgtagaact atggaaaacc ctaaccctag aatagggttg ggcagtgtat  16140
taatagacca aataactggg ctaggcccat tacaagggac gggtatctaa aaaaatagac  16200
tgcggctttt tttttagata atggatacta gtccagcttc tcctcgtttg gaggattagc  16260
caacacacca aaagttttta catggagtag tcacacgact agctgcttta tttgtccttt  16320
tcatttatgc aacctaggaa ttatttgact tgtctccatc ttaatgtgtc tgcttttaaa  16380
tacagtttac tgaacagggc cacatctttg ttcaagtcca tttggtcaag gaactaaaca  16440
ggaaaggaaa caatttttgt gatgtttctg ctcataacag agaaattctg tatgattctg  16500
acaactcgat gctatggaac acactaagcg gacttgaagt agcagatagc tggaggtcct  16560
tggagaattt tacgatgttc aagaattcaa atggtgaaac agatacaatt aggttagctg  16620
tcagagttga agacaccggc ataggaataa caaaagatgc tcaaatgcgt atttttacac  16680
ctttcatgca agctgacagt tccacctcac gaacatatgg tggaactgga attggcttga  16740
gtattacaaa acgtttagtt gaattgatgg gtggagaaat agggtttact agtaaatcag  16800
gagttggtag tacattttct tttactgcca ttttcaagga gaacagagga tgtcctggag  16860
atatgaaaag atactattct gaacctactc cgttggattt tcaaggaatg agggctctta  16920
ttattgatgg aaggagtgca cgtgcagagg ttactatgta ccatcttcgt agacttggaa  16980
tacagtgcag tcttgttgcc acatctgaat ctgaatctgc atcttcagct ttgatgaaag  17040
cctgcacctc aaggttcatt tccttgtgta gtttactgtt tgatttactt ctacaagttt  17100
tagaaattag aagttatttt gttcaaataa atgtaacatt ccttgcattt ataaactttt  17160
gtcatcttaa cacatggctt tgctatattt tctttagttg gttgtgtgct atttctttga  17220
atattttcca tattgtcgat cccaaaacaa ggtttcgtaa cttctcatga actgaagaaa  17280
agtaggagaa acagagtgaa accttcgttg gtttgagttt agaaactgaa ataggatagt  17340
tcgattctaa ataacttgtg aattcattca gttgttgctg tcatcattat aacatatcaa  17400
tttgttcatg gccagcaacc tacacttgtc ctcagtatta cgacccaaca aaatcaatgc  17460
ataatgtcgc catcatcact ttccatgtat gcattttctt ttctaagcac tgttgatgcc  17520
ttacttgttg atgttatcat ttatatttta catgttgagc agcaaaaaca atccggacat  17580
ggtccttgtt gatacagaag cttggggtaa aggttcaggt ttggcattct atcatcgttt  17640
tgtagattgt caactaaagg gcgcacacaa gttttctcag cccatgccaa agactattct  17700
tttgggaagc tcaataagcc ctgttgaatc tgattattta agattgacag gatttggtga  17760
ttgcataagg aaacccctcc gtcttagtac tattgttgcc tgtcttcgca aaaccttagg  17820
ggttggggtt acaaggcagc agagtagaga ccaatctttg gttcttcaaa gtgtactaac  17880
tggaaaacag attctggttg tggatgataa tgcagtcaac cgtaaagttg cagctggttc  17940
tttgaagaaa tatggatcta aagttacatg tgttgatagt gggagtgatg caattgatat  18000
gctcaagcca cctcacacat ttgatgcttg cttcatggat gttcagatgc ccgagatgga  18060
cgggtaatgt tcctttccaa tgagttacta atgaaaaaga gcgcagattt gctgcccagg  18120
cgttctcatt atctaaaata ccatgttgca atatttcaaa aatcatcaca aaaatcatgt  18180
atgcagtaca caaagttagg tatagccgca acacttcaga ttgaaatttc ttcctagatg  18240
ccaagaacca aaatagacaa gcagtcaacc tggcagtgtt catcatgtgc tgacagtgag  18300
actttgtttt ttaatctcag catcaaagat gaactttatt gaattcttga ggctacactt  18360
aaggtgtact tgcacacatg ttttttgtga tgattgttga aacattgcaa tacggtattt  18420
tagaatgtgg gcgccaattt ccctgggcgc catatgattt ccaatggaaa attgtcatat  18480
gttatttact tgcgggatat actataagag ttcaatatgt aaaagattct ttgtgcagaa  18540
gtcactcttg gaacatctta cgttagttca catggaagca tgtctttagt tttaggtatg  18600
tgcttctttt ggattttgtg gaatcatcgg aacagatgca tctttgatgg cctttcccct  18660
aatgttgcta attttctaat ccatgtgggg gatgagcgcc gtctgtggga gactgccggg  18720
gccaaggggt tgacatccct tgttgcctcc ctctctcatg tagcctagag ttttatagat  18780
gagtcagtct atgctagttt cgttcaggcc gccgtaaggc gtcagttgta ccccggtcta  18840
ttttagacct tgtttatttg ttcttttaat ataatgatac gcagctctcc tgcgtgttcg  18900
agaaaaaaag agaaagttat tttttggtcc tcaaataaca acacttgtca aatgtatgca  18960
tctcctcatg ttattagcaa gcactctcat aggagtatca ctgaggataa tctctctttt  19020
gttttcacat ccagtccttg cttaaaaaaa tgcactgtag cctcacatgc ttgtgtttgc  19080
tttcctatgg gttataacaa gtggttgcat ctactttgat cacttgtaga tccactgtag  19140
gactaccatt aacaatattc acattcaatt gcaggtttga agctacaaga ttaatccggt  19200
ccatagagaa aaaaataaac gatatgatca tgatgggtga aatatccgct aataattatg  19260
gaaataaggc ccattggcat gtaccaatat tagctatgac ggcagatgta atccaagcga  19320
cttttgaaaa atgtatgcag tgtggaatgg atggatatgt gtcaaagcca tttgaagaac  19380
agcagctcta ctttgctgtt gctcatttct tagagactga tgaaacagaa taa         19433
```

```
SEQ ID NO: 257          moltype = DNA  length = 9902
FEATURE                 Location/Qualifiers
source                  1..9902
                        mol_type = other DNA
                        organism = synthetic construct
SEQUENCE: 257
gcaacagaaa aaaacaacga aacacgcaac gtgcgggggc agatgcggca attccccgct  60
cacggcgcgc acatggaacg ccttcgcttt cctcctccct ccctccgtcc cgtcccgtgc  120
ccccttctgc cttctctcac cgccacggcc actggcattg gccgcgctcg ccgcccaccg  180
cccaccgccc ccgcgccgct gtaggagcgc gcgcttgctt tagcgtaggc catggcccac  240
tactagcggg tgattagcct tgattagcgg gcaccactcc actgttacgg gaggcgcgtt  300
```

-continued

```
gttttaatcg cgggcgcgcg acgcccgtcg cctgtctcga atatctgctg ccgccgccaa  360
aagtgcggat tcctcctcct ccccgtcggg cggcctcgcc ccccctggtg cctactgggc  420
gctggcggag tgggagtgga tcgacgtgtt gcggccgcgg agtggaggca ataaagggaa  480
agctgggcgg agtgctcggg taccgtagcc ggattagtta ttaatgcccg cgagcagcta  540
gtcgtaggcg taactatttt aaggcagctg tcgccgctgg ggacttgcga aagcttcgcc  600
tcttttgaga agctctgcac cacgcctggc tccgccccgc tccccctcca cctccaggct  660
tccttcacag tctcgctgtt gctagtgctg ccttgctgct agtgataggg gtcccggggc  720
cctcaagttc tgggtgggcg gcaaacatat ggtgggcacc gggcggggga ataaggagga  780
agagaaagag gaggaggagc ggcagtagat ttgggccgca caggcaggga tgggggggcaa  840
gtaccgcgcg gcgaggacga agaggtggtg gaggggggctg gcagcggccg ggtgggtgct  900
aaccgcggtg gtctgctccg cggtgatgca ctggaccctg cgccgggaca gcatggaccg  960
cgccgaggag cgcctcgtca gcatgtgcga ggagagggcc aggatgctgc aggagcagtt  1020
cggggtcacc gtcaaccacg tccacgccat cgccattctc atctccacct tcaacttcga  1080
gaagtcccct ccagccatcg accaggttcg taaccattcg cccccaccct cttctccgcc  1140
attgctcttg tatgttgcaa tgccgcggca tcaattgaca gttggttcag caatggcgga  1200
cggacccccg agatcctgca cgttgttctc ccggttgtct ctgtcttttc tttaaggagc  1260
aaacaaaaaa aaaggaaaag aggagagaga gatgaagatg cgttctggtt tgttgaagct  1320
cacagtcgtt gcggcgctag tcgtctagct ggacatgatt gctgtggttg gctgggagcc  1380
tgggacaggt gctgtccatt gtcttgtgga aagaaaaaaa tgcccattcc tgcggtgggg  1440
aaggcgggga tttttttaggg tttaaagacg tcacggaact gaactactgg gttggtgcca  1500
cattgtttgt tcatagagtg gttagtgtgt tcgttgcaaa caccatctgg aggtcacttt  1560
gacaaccatt gggggcgctc ttttggcaac cttttgatcc cttagtttat tcttagaaag  1620
gtcactgtcg cagagattaa taatgttgca agctgctctc tgcctttctt ttttctttag  1680
cttagattat taatcgtcga agccgtcctt tactgcattt acagttcgtt tctcttcccc  1740
tttttgttga tttaccaata gtttagttta ggctcacagt gccgaaggcc catggtattt  1800
gaagacatgt tcattttttt tgcatactaa agtgatgata caatgaccaa tcaggttcat  1860
tgcatcatta cttttggtaa atcaacaaaa tttcttctgc tggttcttgc aatttatagt  1920
acattgctgc tcactgtttt ttttattctg gattaataaa cattgtccac tacaggacac  1980
ctttgcaaaa tacacggcaa ggacatcatt tgagcgacca ctgctcaatg gggtggcatt  2040
cgcacagcgt gtattccatc atgagaggga aatgtttgaa agccagcagg gatgggttat  2100
gaatacgatg cagcgggagc ctgcacctcc gcaggttgaa tacgccccag tgattttctc  2160
tcaggatacg gtttcctacc ttgcacgcat tgacatgatg tctggggagg tacagttact  2220
tctgtttgat tgttctttgt atccattggg ggggtgtttc tcgcgctttg atgcctcttt  2280
agtgaaatct atctatttat ttccaatata ggaggaccga gaaaacattt tccgggccag  2340
gactactggc aaagctgtgt taacaaacca cttgggagta gttctcacgt ttgctgtgta  2400
ccgccctgat ctccctgctg atgcatcagt tgagcaacgt gtggaagcaa ctattgggtg  2460
agatgttcta actcacttcc ttcgttgttt tatttttttgg accaaatatt tatagtattc  2520
tcacctttaa gacttgtgtg tagcatccat acttcagtaa aatgtggata tgaacaaaat  2580
tacacgcatg attatttgac catgtaatat cttgtcatca tgtatgatac cacatttgtg  2640
gttcactatg atgacctcga catgtttagt aacaggtgat tataggaacg acatgtttct  2700
ttttaacaaa aggcataatg tgttaatgat atagacattt agtaatggca aatactgcgg  2760
tgcaattaac gttcccgtgc aattgccatg caatcaaact accaagggtc atgaaaaact  2820
ctcgaaaatt ttatagatgc acttcattat ttcctctacc aatatatcaa atcttgagtt  2880
ctaattcata ctatgttaag aaatataaaa aatagaaaat tatgcactat gcttatctaa  2940
ttctaaagag aataatttgt tgtgtgttgt acaaaagtat gcatctgttg actattgtgg  3000
taaaatctaa tcaagttccc tactaataga tatcttggtg gagcctttga tgtggagtca  3060
cttgtggaga atttgttgag caaacttgct ggcaatcagg atattgtggt aaatgtctat  3120
gatgtcacaa atgcttcaga tgctatggtt ttgtatggac cttcaagttt ggacgagcaa  3180
gtgcctttct tgcatgttag catgttggat tttggagatc catttaggaa gcatgaaatg  3240
agatgcaggt tggtagtcct taccggtaaa tcttagctgt gttgtctgct tttattttgc  3300
actaacgctg tcaaccatgc aggtatagac aaaaacttcc tatgccgtgg tctgccatca  3360
ccaatccttt gggcacattt gtcatatgga tgcttctagg gtatagcatt gctgctgcat  3420
attctcgata tgacaaagtt actgaagatt gcagaaagat ggaagagcta aaaacacagg  3480
cagaagctgc tgatgttgca aaatctcagg tttggcctat actttagcgc tctcttttgc  3540
taggcattct agcatatgca atcatgtatg acttatctat gtttgtctca ggccttgttc  3600
tgttgtatat ggaattaggg gtcgaaggtg attgaggggg attaaatctt ttctatttaa  3660
ttttgactag caagggattc aattcccttc aatccccttt aatccatccc taaccaaaca  3720
agcccttaga gagtttatat cattccctgt ttaggtgatt ggctggttgc cttatgtgcc  3780
tgatctctcg caccacctcc ctaatctgat ttctataaat caggtagagg aagatcactg  3840
gtaaagatct atatattatg ctcctagtat tcagttgact gcaaacaata ttcacattat  3900
gatggtatca atagaccatc gtgatcatgt gacaattcgc tttcgccaag cctcagctgc  3960
ctgcatcgcc ttcctagcgc cgtgtcatca ccatgccaca tgccattaaa ccttgccgtt  4020
gccgctgatg ccccgcaacg tgcagaggac gaggacgcac aatagaagac ctgctaggac  4080
ttggttggtg tagccgatga ggttgccaag gccaccgtcg ctgctaagga tcttgtacgt  4140
gccgcctagg atgttgttgc aaaggaacaa cataccactg ttctcgcaaa ggaacaacat  4200
acactgccgc ctaggaccct tcaccattga taataattgt tctattgaat ttgacttgtt  4260
tggcctctct gaaggatctc aatcctaggg gtgatcgcca gctgcaatag ttttagaccc  4320
ctttggcctc tacactcacc gtcctgtccc atggagtcat gcgcccttgt tgcaacagct  4380
gccttcacca cttggcatca ttgtttcggg catcctaggc agtccaaact tgttagtacc  4440
tccaccatca attggaaaaa atactagtga ttctctttgt cacatgtgcc aagttgggcg  4500
tcatattaga ttacctttcg gaacctcctc tccttgctaa ctcttaagaa ttttgatttg  4560
attcattgtg atgtgtggac ctcccctatt actagtgtct agttacaaat attatcttgt  4620
tactcttgat tgcttgcact tccttttgac atttccgctt tgagtcaaat ttgagacgtt  4680
tcccgccttg gctcactttt ttctcttatg ggaagacata gttcggctac accattcgaa  4740
atgttcaatg tgacaatggc cgcaagtttg ataactcctc aactcacacc tttctcacca  4800
aaggtgtcct gctcaggatg tcgtgctcct acacaccctc tcaaaacagt aaagtcgact  4860
gtatgattcg ttccattaat aacatcatat gtccatgctc cttcaagcct cccttgcctc  4920
gctatactag gtgaaggtct tcacactgct acataccttg tcaatcgact agccaccaaa  4980
acactgacat ttggcacccc cactttgccc tgtttggttc acgtacctcc tacgaccacc  5040
```

```
tcagtgtgtt tggttgtgca tgctaccaaa acatgttcgc cgtcgtgcct cacaagtcac  5100
aagcttgctt cccggttgag tcaacagaat catgcgggaa gcaagcttgt gacgtgtgag  5160
gcactctgca ggcaacgatg acttgctctc gaacaacaca tgggatcttg tcccatgtcc  5220
tttcggtgcc aacatcgtct ctgacaagtc atttttctgc tacaagttcc acgccgaagg  5280
ttcccttgat aaatatgaat cttgttgggt cctctatggc ttcacacagc cccctagtat  5340
ggattatgac gagactttta gtttagcggt ctagcctacg attgttcata ctattttgta  5400
tttttgttca ttacactctc ttagtaatgg ctagttcatc agctcgatgt caagaatgcc  5460
ttcttgcatg acatgctttg tcgtttgtca tctcaacaag tccatatata tggtccgaag  5520
caggtgcctc gcgcttggtg tagtcgcttt gctgcatgct tgctcacttt ggaattcact  5580
aaggccaggt ttgacacctt gttcatatat ccccacataa cagacaggac acatttactg  5640
ctataggtgg atgatattgt cctcactact ctagttagga tctcctttgt tgcatcatca  5700
ctgcacttta ggaggaattc tccataatga tcttgatgtc atccatcact tcctgggtgt  5760
ggctgttcag cagcgttttg agtgccattt ctttcacaac gacaatacac tttggatgtg  5820
attgagcacg ctggcatgat caactgcaaa tcgtgcagca caccccttcga cactcatgtc  5880
aaggtctcct ccatagtcgg tgcacctatc aatgacccca ctcaggatca tagtttggtt  5940
ggtgcattgc acaccttcat cggcccgcta tctcttatgc ggtccagcag gtgtctccac  6000
atttatgatc ttcatgacat tcacctcttt gttgttaaac ccatcctgcg gctgcaaggg  6060
gtacctagtc atggtcttct tttgtgcttg tcgacgacct ctgctcttct tgtctacgtg  6120
gatgctgatt gggctgtttg tgtggacact cacaagtcta cctcaagcta caccatgttc  6180
cttggtgatg atctggtttt ctagtcctcc aagcagtaga acagtgtcct actccacggc  6240
tctagtgccg aggctgagta ccagacatca ccaatggcgt ggccaaggat tgctgacttc  6300
gacaattgct acgaggacat gccccctaac gaagatcacc ttggtccgtt atgatacttg  6360
tcgaccaacc ctgctcagca tcaacgcaag atcggtctgc acttcatctg caagcgtgtt  6420
gctattggtg atgtttgtgt tctccatgtc ctgaatcctg atgacatacc aattttctga  6480
catcttcacc aaggggcttc tacttatgtc ctatagatgt tctgactatg gggtgtgtgt  6540
gtgtgtgtgt tagagagttt atctccttcc ctctttaggt gattggctgg ttaccttagg  6600
cgccccttct ctgtttaggt gtttggctgg tagtcttatt tccttgttca gttgattgtc  6660
tggttgtttt atgtgcctga tctcctggat cacctccctg atcttgtttc tataaatcag  6720
gtagaggaag atcattggta gaggtctata tattgtactt ctgatattca gttgaatgca  6780
agcaatattc acactctaca tctctcttgc agttcctggc aactgtgtca catgagatca  6840
gaacacctat gaatggcgtc cttggtactt atgcatttat tttgattcta cttaatcttc  6900
agttccatgg gcctggcaat ctaaaatttc tgccttctgg tgtaggaatg ctggatatgc  6960
ttttaggaac agatctaact atgacacaga aggattatgc tcaaactgct caaatgtgtg  7020
gcagagcatt gattacactg ataaatgatg tccttgatcg agcaaagatc gaggctggaa  7080
agttagagct tgaagcggtg ccttttgacc tgcgttctct catggatgat gttgtttcct  7140
tgttttcttc aaagtcacgg gagaagtgca ttgaggtatg ctactgctaa tgcttaaagt  7200
aggaaatgat gtttcctggg ccgtcacttg aatggatgtt gattgctttt agttctagtt  7260
tttggctgat caactgacaa ataatgcagt tctgcatgaa tcaatctgtc actatacttc  7320
tatacttctc tatggcagat actttccctg atttttttcc ttcttgctgc agcttgcagt  7380
atttgtatgt gacaatgttc caaaggttgt tattggagat ccttggaggt ttcgacagat  7440
attgacaaat ttggtcggga atgcagtcaa agtaagcagc caattttggt atttggtatc  7500
ctcacactac aacttcaaat gatgttggtt agaagtattt gataagtctg tcatcaaata  7560
catgcacaaa aatgcactga tatatctatt gtctgttcca gttcacagaa cgaggtcatg  7620
tatttgtgcg ggtctgtttg gctgaaaact caaatgtgga agccaatcag gtcctacatg  7680
gagccatgaa tggcaaaggt ggtagagttg agtcaacaac taatggtgcc ttcaatactt  7740
tgagtgggtt tgaagcagca gacagacgaa atagttggca atattttaaa ctgctcctct  7800
ccgataagga gtcacttttg gatgatcttg agggcgaaaa ttctaatcaa agtgattcaa  7860
atcatgtcac actagcaata agtattgagg acacaggtgt cgggatacca ctgcaagcac  7920
aagatcgtgt ttttacaccg tttatgcagg ctgacagttc aacttcaagg aattatggcg  7980
gtactggcat cggtttaagc atcagcaagt gtctagctga acttatgggt gggcagataa  8040
gtttcactag ccatccttct gttggaagca cgttcacttt ctcagccaca ctgaagcact  8100
catacaaaga tatttcggtc gattcaagta ggagcttgac agaggcacta ccaactgctt  8160
ttaagggaat gaaggccatc ttggtagatg ggagacctgt acgtagtgct gttacaagat  8220
atcacctcaa gaggttggga atacttcttc aagttgtgaa caatatgaat gcagtagtaa  8280
aagctttccc aggacaaaat ggagcaaccg gttctaggtg agtgttctta agttagttta  8340
ttaaatgctg ttcatacaat tggctgagca aggcttcaca ttccagtact ttccctcacg  8400
tggaggctgc ctcaacttca acccttatat gtggaatggg agtagggaac atttctttta  8460
ttaaattgtg tgacaaaaga ttcaaactca gacctggcct tgttaccatg ttgagctgca  8520
tgcactcatg gcctcaacaa aaaccctaag caaggaactc acttataatt tactagatat  8580
catagatatt ctgtctgttt aatcagcttg taccgaataa gctattcgca aattgttttt  8640
gagaatacag aatagcataa aacattatta aaacaccaga tatgcacctt atacttgttt  8700
gtatgacctt cgaaatcatc ccatttattt tcttgtaggg aaaaagcatc aattcttttt  8760
attgagagtg acttctggag gcctgagaca gatgttcagt tattgaacca tctacgcgag  8820
cagaagaacg gtcagttgtc ggatgggcac aaggtagttc ttttggtcac ctctgaagcc  8880
gacaaggaca aatatggatc catatttgat attgtgatgt gtaagcctat aagggcaagc  8940
acaatcgctt catctattca acaactgctc aaagtagaga tagccgaaag aaaagataat  9000
caaaaccggc cgtcgtttct tcgaagcttg ctggttggga agaatatatt ggtcgtagac  9060
gataataaag tcaacctcag agttgctgcg gctgcactca agaaatatgg tgctaatgtt  9120
agctgtgttg aaagcggcaa ggatgctatc agtctacttc aacccccgca tcgcttcgat  9180
gcatgtttta tggatgttca gatgccagag atggacgggt atgtggatga aataaacaaa  9240
gtcgttttcc atttccatcc tgctgtttga agtttgtttg ctagttgaat aaaaaaaatg  9300
tttccactga ccagcagttc tcgattgtta cttttgtagg tttgaggcaa ccggacaaat  9360
aaggcaaatg gagttgaaag cgaacgagga aaggaagaac aagttggctt cgattgaagg  9420
ctcgacaact gccgagtacc atctgcctgt tctggcaatg acagccgatg ttatccaggc  9480
aacttacgaa gagtgcataa aatcgggaat ggatggatac gtatctaaac ccttcgacga  9540
ggagcagcta taccaagcag tctccagatt ggtagtggga acgacggatt cggctgtttg  9600
atgttcaaaa tacgatggac ctgacttctc attcatcgaa gtgaagcatc accatcttgc  9660
ctctgtccag ctgactctat atcccttgac aatgggcctc tgacatggcc tctcacaaga  9720
ctagatgaaa aaagaagatg aaagtgccgt gagttaggta cgtgtcacac atgacatgaa  9780
```

```
gttgctgcgg cagcccagag gagtgtaggt agatcaccct gtaactctct tgttctttga  9840
tgtttatagg ctgttgtgtc ttctgacaat tcattggaaa taccacatct cgttgcaatc  9900
cc                                                                  9902

SEQ ID NO: 258         moltype = DNA  length = 6491
FEATURE                Location/Qualifiers
source                 1..6491
                       mol_type = other DNA
                       organism = synthetic construct
SEQUENCE: 258
gcccgcagcc cgctcttccc cgctccacct ccaggcttcc agtctctcac tctcccgcgc  60
ctcttgctgc tgctgctggc gatagggatc ccagcgcctt caagttcggg tgggcggcta  120
gcgcggcgcg tgtcggcgag catatggtgg gcattgggcg ggggaaggag gaggaggagc  180
ggcaatagat ttgtgggcgc agaggcgggg atggggggca acaagtactg cgcggcgatg  240
acgaagagga gatggagggg gctggcagcg gccgcgtggg tgctagtcgc ggtggcttgc  300
tccgcggtga tgcactggac catgcgccgg gagagcatgg accgcgccga ggagcgcctc  360
gtcagcatgt gcgaggagag ggccaggatg ctgcaggagc agttcggggt caccgtcaac  420
cacgtccacg cgatcgccat tctcatcgcc accttcaact acgataagtc cccttccgct  480
atcgaccagg ttcgtcacca ttcgcccccc tcttctccgc cattgctctt gtagattgct  540
atgccacggt atcaattggc agttggttta gcaatagcgg accccgagat cctacacatt  600
gttctgtggg ttgtctcttt tctttaaagg agcaaacaga aaaaaaaggg gagaaataga  660
gatatagaga tgcgttgttg tttgttgacg cttaccgtcg tttagcacgc catgattgct  720
gtggttggct gggacaggtg ctgttcatag tcttgtggaa agaaaaaaaa tgtccattcc  780
tgcggcggtt aggcggggat tttttaggct tattggagac gtagctgaac tgaactgttg  840
ggttggtggc acattgtttg ttcatagagt gattagtgtg ttcgctgcaa aaccatctgg  900
gggttacttt gacatccatt ggggtgtgct cttttgccaa ccttttgatt ccttgtttat  960
tctgagaaag gtccctgtcg cagagattaa attatgttag aagctgcttt ctgcctctct  1020
tttcttttgc ttagattatt gatcctcaaa gccgtccttt cctgcatcta cacttcgttt  1080
ctcttccccc ccttttttttt tgtcgattta cctatagttt aggcgtgcag tgtcatgggc  1140
ccatgttatt tgaagacgtg ctcgtttttg catacaatga ccaatcttat tcgttgcatc  1200
attacttttg gtaaatcaac aagatgtctt cttctgattc ttgcaattta tagcatatta  1260
ttgtccagta ttctattttg gcttaataat taatgtccga cacaggacac ttttgcaaaa  1320
tacacggcaa ggacatcatt tgagcgaccg ctactcaatg gggtggcata tgcacagcgt  1380
gtattccatc atgagaggga aatgtttgaa agccagcagg gatggattat gaatacaatg  1440
cagcgggagc ctgcaccccc gcaggttgaa tatgctccag tgattttctc tcaggatact  1500
gtttcctacc tcgcacgcat tgacatgatg tctggagagg tatggttcta tttgatcgat  1560
cttagtattc attggggtgt ttatgaccct ttgatgtctc tttagtgaaa gcaatctatt  1620
tatttacgat acaggaggac cgagaaaaca ttttgcgggc caggactact ggcaaagctg  1680
tgttaacaaa cccatttcgg ttggatcaaa ccacttggga gtagttctca cttttgctgt  1740
gtaccgccct gatctccccg ctgatgcatc agttgagcaa cgtgtggaag caactattgg  1800
gtgagatgtt ctaactcaca tcctttgttg ttttattttt aaccaaatat tctagcattg  1860
tcgcctttaa gactcatgtt taacatgtgg gtatgaataa aattttgtgc actattattt  1920
gatcatgtaa tatcttgtca tcgtgtatca tgccacattt gtggttcact gatcaatact  1980
gaatttaggt tgactatgat gaccttaaca tgtctagtaa caggtgataa tagaaacaat  2040
gtgtttcttt tttaaaaaag gtatagcgtg cttatggcag ttatggcagg cacatttagt  2100
aatagatcat gcaggttata atcattgcag cttgtctcaa tttaatcaaa tgatactcta  2160
tgcttatcta attttcaaga gaataatttg ctgtgtgctc ccagatatct tggtggagcg  2220
tttgatgtgg agtcacttgt ggagaatttg ctgagcaaac ttgctggcaa tcaggatatt  2280
gtggtgaatg tctatgatgt cacaaatgct tcagaggcta tggttttgta tggaccttct  2340
agttcggatg agcgcgtgcc tttcttgcat gttagcatgt tggattttgg agatccgttt  2400
aggaggcatg aaatgaggtg caggttggta gtccttatct gtaaatctta attttcttgg  2460
ctgcttttgt tttccactaa tgttgtcaac ctgcaggtat agacaaaagc ttcctatgca  2520
gtggtctgcc ataaccaatc ctttgggcac atttgtcata tggatgcttc tggggtatag  2580
cattgccgct gcatattctc gatatgacaa agttacagaa gattgtagaa agatggaaga  2640
gctaaaaacg caggcagaag ctgctgatgt tgcaaagtct caggtttggc ctgttcttta  2700
gcactctcat ttactaggca ttctagcata tgcatcatgt atggcttagc ttatctatgt  2760
ttgtctctct tgcagttcct ggcaactgtg tcacatgaga tcagaacacc tatgaatggc  2820
gtccttggta cttatgcatt tattttgata ttacttaatc ttcagttccg tgggcctatc  2880
aatctaattt ttttccttct ggcgtaggaa tgctggatat gcttttagga acagatctaa  2940
ctatgacaca gaaggattat gctcaaactg ctcaaatgtg tggcagagca ttgataacgt  3000
tgataaatga tgtccttgat cgagcaaaga ttgaagctgg aaagttagag cttgaagcgg  3060
tgccttttga cctgcgttct ctcatggatg atgttatttc cttattttct tcaaagtcac  3120
gggagaagtg cattgaggta tgttactgtt aatgcttgaa gtaggaaatg atgttgcctg  3180
ggccatcact tgaatggata ttgattgctt ttagtcctag tttttggctg agcaactgac  3240
gaataatgca gttttgcctg aaccaatctg tcactataca ttgtggcata tacttttcct  3300
gatccttttc cttcttgctg cagcttgcag tatttgtatg tgacaatgtt ccgaaggatg  3360
ttcttggaga tccttggagg tttcggcaga tactaacaaa tttggtcggc aatgcagtca  3420
aagtaagcaa ccatttatgg tatttggtat cctcacacta caacttcgaa tgatgttggt  3480
taagtcgtag ataagtctgt catcaaatac attcagaaaa atgcgctgat atatttatcg  3540
tgtgttccag ttcacagaac ggggtcatgt atttgtgcgg gtctgtttgg ctgataactc  3600
aaatatggaa gccggtcagg tcctaaatgg agccatgaat gggaaagatg gtagagttga  3660
ttcaacaact aatggtgcct tcaatactct gagtgggttt gaagcagcag acagacgaaa  3720
tagttggcaa tattttaaga tgctcctctc tgataaggag tcccttttgg atgatcttga  3780
gggaacaaat tctgatcaaa gtgattcaga ccatgtcaca ctagcgataa gtattgagga  3840
cacaggtgtt gggataccat tgcaagcaca agatcgtgtt tttacaccgt ttatgcaggc  3900
tgatagttca acttcaagga attatggtgg tactggcatc ggtttaagca ttagcaagtg  3960
cctagctgaa cttatgggtg ggcagataag ttttgtcagc cgtccttttg ttggaagtac  4020
attcactttc tccaccacac tgaagcgctc atacaaagat atttcagttg attcaagtag  4080
gagcttgtta gaggcactac caactgcttt taagggaatg aaggccatct tgatagatgg  4140
```

```
gagacctgta cgtagtgctg ttacaagata tcacctcaag aggttgggaa taattgttca  4200
agttgtgaac aatatgagtg cagtagtaaa agctttccct ggacaaaatg gagcaactgt  4260
ttctaggtga gtgttcttaa gttagtttat tagatgctgg agatacaatt ggctgagcag  4320
tgattcacat ttcagtactt tccctcacat ggaggctccc tcaaccgcaa gccttatatg  4380
tgaaatggga gctctgtttt aaaggcgacg tctaggcgcc ccaacactcc taggcgttcc  4440
cgtcgcgtag ctaaatcagc aagagggcag agagaaagaa ggggcggcgc cgaatcaggc  4500
cgccggcggc cgattcggcc ccagcgacag ctgaatcagg gcggcggcgg ccgaatcggg  4560
gatggcggca gcaaaatcat gagtggcggc ggctgaatcg tgtgaggaga gaaggaaacc  4620
acggctgaaa aaggggaggg gagaaggaaa gcagcagctc aatcgagggg ggagaggggg  4680
gaaacagggg gagatatagg ctggcttctt tttcttcctc ctccatgctg ctgttttatg  4740
ctgctgtttt gttggttctc atgttgataa ggtgtcacct tgctcgtctt agttgtcgcc  4800
taggcgtcca gaccaggtgg tagttcaacg tcttatcttg ccttaccgct ttaagaacca  4860
taaacgggct agggaacatt tcttttatta aattgtgtga ctaaagattt gaattcgaaa  4920
cctggttttg ttaccagcat gttaagctgc atgcactgac ggcctcaaca aagaccctaa  4980
gggctggttt ggtggacagg gaaatgagat cccctccatt tttctgtcca ccaaaccagc  5040
cctaaactgg tgggaaaggc aggcaactca ttaatatatt ttactacata taatagataa  5100
accgtctatg ccatcagtct gtcctgaata agctattttc ttttttgaaa aagtatagga  5160
ccctaaaatc cttgactgac cttttatccc caaactgttt tggggaatag cataaaacat  5220
tcttaaagca cctgaatatg cactttataa ttgttttgta tgacatctga aatcatcaca  5280
tttattctct tgtagggaaa aggcaaccat tctttttatt gagagtgact tttggaggcc  5340
cgagacagat gttcagttat tgaaccatct acgcgagcac aagaatcgtc agttgtctga  5400
tgggcataag gtagttcttt tggtcacctc cgaagctgat aaggacaagt atggatccat  5460
atttgatatt gtgatgtgca agcctataag ggcaagcatg attgcttcat ctattcaaca  5520
actgctcaaa gtagagatgc ctgaaagaag aaataatcat aatcggccat catttcttcg  5580
cagcctgctg gttgggaaga atatattggt agtagatgat aataaagtca atcttagagt  5640
cgctgcagct gcactcaaaa agtacggtgc taatgttagc tgtgttgaga gtggcaaaga  5700
tgctatcagt ctacttcaac ccccacattg ctttgacgca tgttttatgg atgttcagat  5760
gccagagatg gatgggtatg gattaaataa atataaacac gtttgtcatt tccatcatgt  5820
tgtttgaagt ttgtttgcta ggtgaagtaa atctccccac tgatcatcag ttctcaatta  5880
ttactttttt aggtttgagg caacaagaca aataaggcaa acagagatga gagttaacga  5940
ggaaaggaag aataagttgg tgttgattga aggctcaaca tttgttgagt accatttgcc  6000
tgttttggcg atgacagccg atgttatcca ggcaacttac gagaagtgta taaaatcggg  6060
aatggatgga tacgtgtcta aacccttcga cgaggagcag ctataccaag cagtctccag  6120
attaatagtg ggaacgacag attcgactgt ttaatattta gatggctatg aatctgattt  6180
ctcattcatc gaattgaagc acaccaccat gttgcttctg tccaagtttg actctaaccc  6240
ttaacaattg tctgacctgg cctctcgcag cactagatga aaaggatgaa agtgccacga  6300
gttggctatg tatcagcacc acagatgaag ttgcctcacc ccggagtgta ggttggtaga  6360
tcactctctt ctttgatgtt tataggttgt tgtatatctt ctgacaattc attggaaacc  6420
acatctcgtt gcgacattgg aggacatctt caatgctggt aaatttgtta taggaatatc  6480
ctttaatgct g                                                       6491

SEQ ID NO: 259         moltype = DNA  length = 9919
FEATURE                Location/Qualifiers
source                 1..9919
                       mol_type = other DNA
                       organism = synthetic construct
SEQUENCE: 259
gcaacagaaa aaaacaacga aacacgcaac gtgcgggggc agatgcggca attccccgct  60
cacggcgcgc acatggaacg ccttcgcttt cctcctccct ccctccgtcc cgtcccgtgc  120
ccccttctgc cttctctcac cgccacggcc actggcattg gccgcgctcg ccgcccaccg  180
cccaccgccc ccgcgccgct gtaggagcgc gcgcttgctt tagcgtaggc catggcccac  240
tactagcggg tgattagcct tgattagcgg gcaccactcc actgttacgg gaggcgcgtt  300
gttttaatcg cgggcgcgcg acgcccgtcg cctgtctcga atatctgctg ccgccgccaa  360
aagtgcggat tcctcctcct ccccgtcggg cggcctcgcc ccccctggtg cctactgggc  420
gctggcggag tgggagtgga tcgacgtgtt gcggccgcgg agtggaggca ataaagggaa  480
agctgggcgg agtgctcggg taccgtagcc ggattagtta ttaatgcccg cgagcagcta  540
gtcgtaggcg taactatttt aaggcagctg tcgccgctgg ggacttgcga aagcttcgcc  600
tcttttgaga agctctgcac cacgcctggc tccgccccgc tccccctcca cctccaggct  660
tccttcacag tctcgctgtt gctagtgctg ccttgctgct agtgataggg gtcccggggc  720
cctcaagttc tgggtgggcg gcaaacatat ggtgggcacc gggcggggga ataaggagga  780
agagaaagag gaggaggagc ggcagtagat ttgggccgca caggcaggga tgggggggcaa  840
gtaccgcgcg gcgaggacga agaggtggtg gagggggctg gcagcggccg ggtgggtgct  900
aaccgcggtg gtctgctccg cggtgatgca ctggaccctg cgccgggaca gcatggaccg  960
cgccgaggag cgcctcgtca gcatgtgcga ggagagggcc aggatgctgc aggagcagtt  1020
cggggtcacc gtcaaccacg tccacgccat cgccattctc atctccacct tcaacttcga  1080
gaagtcccct ccagccatcg accaggttcg taaccattcg cccccaccct cttctccgcc  1140
attgctcttg tatgttgcaa tgccgcggca tcaattgaca gttggttcag caatggcgga  1200
cggacccccg agatcctgca cgttgttctc ccggttgtct ctgtcttttc tttaaggagc  1260
aaacaaaaaa aaaggaaaag aggagagaga gatgaagatg cgttctggtt tgttgaagct  1320
cacagtcgtt gcggcgctag tcgtctagct ggacatgatt gctgtggttg gctgggagcc  1380
tgggacaggt gctgtccatt gtcttgtgga aagaaaaaaa tgcccattcc tgcggtgggg  1440
aaggcgggga ttttttaggg tttaaagacg tcacggaact gaactactgg gttggtgcca  1500
cattgtttgt tcatagagtg gttagtgtgt tcgttgcaaa caccatctgg aggtcacttt  1560
gacaaccatt gggggcgctc ttttggcaac cttttgatcc cttagtttat tcttagaaag  1620
gtcactgtcg cagagattaa taatgttgca agctgctctc tgcctttctt ttttctttag  1680
cttagattat taatcgtcga agccgtcctt tactgcattt acagttcgtt tctcttcccc  1740
tttttgttga tttaccaata gtttagttta ggctcacagt gccgaaggcc catggtattt  1800
gaagacatgt tcattttttt tgcatactaa agtgatgata caatgaccaa tcaggttcat  1860
tgcatcatta cttttggtaa atcaacaaaa tttcttctgc tggttcttgc aatttatagt  1920
```

-continued

```
acattgctgc tcactgtttt ttttattctg gattaataaa cattgtccac tacaggacac  1980
ctttgcaaaa tacacggcaa ggacatcatt tgagcgacca ctgctcaatg ggtggcatt   2040
cgcacagcgt gtattccatc atgagaggga aatgtttgaa agccagcagg gatgggttat  2100
gaatacgatg cagcgggagc ctgcacctcc gcaggttgaa tacgccccag tgattttctc  2160
tcaggatacg gtttcctacc ttgcacgcat tgacatgatg tctggggagg tacagttact  2220
tctgtttgat tgttctttgt atccattggg ggggtgtttc tcgcgctttg atgcctcttt  2280
agtgaaatct atctatttat ttccaatata ggaggaccga gaaaacattt tccgggccag  2340
gactactggc aaagctgtgt taacaaaccc attccgggat caaaccactt gggagtagtt  2400
ctcacgtttg ctgtgtaccg ccctgatctc cctgctgatg catcagttga gcaacgtgtg  2460
gaagcaacta ttgggtgaga tgttctaact cacttccttc gttgttttat tttttggacc  2520
aaatatttat agtattctca cctttaagac ttgtgtgtag catccatact tcagtaaaat  2580
gtggatatga acaaaattac acgcatgatt atttgaccat gtaatatctt gtcatcatgt  2640
atgataccac atttgtggtt cactatgatg acctcgacat gtttagtaac aggtgattat  2700
aggaacgaca tgtttctttt taacaaaagg cataatgtgt taatgatata gacatttagt  2760
aatggcaaat actgcggtgc aattaacgtt cccgtgcaat tgccatgcaa tcaaactacc  2820
aagggtcatg aaaaactctc gaaaatttta tagatgcact tcattatttc ctctaccaat  2880
atatcaaatc ttgagttcta attcatacta tgttaagaaa tataaaaaat agaaaattat  2940
gcactatgct tatctaattc taaagagaat aatttgttgt gtgttgtaca aaagtatgca  3000
tctgttgact attgtggtaa aatctaatca agttccctac taatagatat cttggtggag  3060
cctttgatgt ggagtcactt gtggagaatt tgttgagcaa acttgctggc aatcaggata  3120
ttgtggtaaa tgtctatgat gtcacaaatg cttcagatgc tatggttttg tatggacctt  3180
caagtttgga cgagcaagtg cctttcttgc atgttagcat gttggatttt ggagatccat  3240
ttaggaagca tgaaatgaga tgcaggttgg tagtccttac cggtaaatct tagctgtgtt  3300
gtctgctttt attttgcact aacgctgtca accatgcagg tatagacaaa aacttcctat  3360
gccgtggtct gccatcacca atcctttggg cacatttgtc atatggatgc ttctagggta  3420
tagcattgct gctgcatatt ctcgatatga caaagttact gaagattgca gaaagatgga  3480
agagctaaaa acacaggcag aagctgctga tgttgcaaaa tctcaggttt ggcctatact  3540
ttagcgctct cttttgctag gcattctagc atatgcaatc atgtatgact tatctatgtt  3600
tgtctcaggc cttgttctgt tgtatatgga attaggggtc gaaggtgatt gagggggatt  3660
aaatcttttc tatttaattt tgactagcaa gggattcaat tcccttcaat cccctttaat  3720
ccatccctaa ccaaacaagc ccttagagag tttatatcat tccctgttta ggtgattggc  3780
tggttgcctt atgtgcctga tctctcgcac cacctcccta atctgatttc tataaatcag  3840
gtagaggaag atcactggta aagatctata tattatgctc ctagtattca gttgactgca  3900
aacaatattc acattatgat ggtatcaata gaccatcgtg atcatgtgac aattcgcttt  3960
cgccaagcct cagctgcctg catcgccttc ctagcgccgt gtcatcacca tgccacatgc  4020
cattaaacct tgccgttgcc gctgatgccc cgcaacgtgc agaggacgag gacgcacaat  4080
agaagacctg ctaggacttg gttggtgtag ccgatgaggt tgccaaggcc accgtcgctg  4140
ctaaggatct tgtacgtgcc gcctaggatg ttgttgcaaa ggaacaacat accactgttc  4200
tcgcaaagga acaacataca ctgccgccta ggacccttca ccattgataa taattgttct  4260
attgaatttg acttgtttgg cctctctgaa ggatctcaat cctaggggtg atcgccagct  4320
gcaatagttt tagacccctt tggcctctac actcaccgtc ctgtcccatg gagtcatgcg  4380
cccttgttgc aacagctgcc ttcaccactt ggcatcattg tttcgggcat cctaggcagt  4440
ccaaacttgt tagtacctcc accatcaatt ggaaaaaata ctagtgattc tctttgtcac  4500
atgtgccaag ttgggcgtca tattagatta cctttcggaa cctcctctcc ttgctaactc  4560
ttaagaattt tgatttgatt cattgtgatg tgtggacctc ccctattact agtgtctagt  4620
tacaaatatt atcttgttac tcttgattgc ttgcacttcc ttttgacatt tccgctttga  4680
gtcaaatttg agacgtttcc cgccttggct cactttttc tcttatggga agacatagtt   4740
cggctacacc attcgaaatg ttcaatgtga caatggccgc aagtttgata actcctcaac  4800
tcacaccttt ctcaccaaag gtgtcctgct caggatgtcg tgctcctaca caccctctca  4860
aaacagtaaa gtcgactgta tgattcgttc cattaataac atcatatgtc catgctcctt  4920
caagcctccc ttgcctcgct atactaggtg aaggtcttca cactgctaca taccttgtca  4980
atcgactagc caccaaaaca ctgacatttg gcacccccac tttgccctgt ttggttcacg  5040
tacctcctac gaccacctca gtgtgtttgg ttgtgcatgc taccaaaaca tgttcgccgt  5100
cgtgcctcac aagtcacaag cttgcttccc ggttgagtca acagaatcat gcgggaagca  5160
agcttgtgac gtgtgaggca ctctgcaggc aacgatgact tgctctcgaa caacacatgg  5220
gatcttgtcc catgtccttt cggtgccaac atcgtctctg acaagtcatt tttctgctac  5280
aagttccacg ccgaaggttc ccttgataaa tatgaatctt gttgggtcct ctatggcttc  5340
acacagcccc ctagtatgga ttatgacgag actttagtt tagcggtcta gcctacgatt   5400
gttcatacta ttttgtattt ttgttcatta cactctctta gtaatggcta gttcatcagc  5460
tcgatgtcaa gaatgccttc ttgcatgaca tgctttgtcg tttgtcatct caacaagtcc  5520
atatatatgg tccgaagcag gtgcctcgcg cttggtgtag tcgctttgct gcatgcttgc  5580
tcactttgga attcactaag gccaggtttg acaccttgtt catatatccc cacataacag  5640
acaggacaca tttactgcta taggtggatg atattgtcct cactactcta gttaggatct  5700
cctttgttgc atcatcactg cactttagga ggaattctcc ataatgatct tgatgtcatc  5760
catcacttcc tgggtgtggc tgttcagcag cgttttgagt gccatttctt tcacaacgac  5820
aatacacttt ggatgtgatt gagcacgctg gcatgatcaa ctgcaaatcg tgcagcacac  5880
ccttcgacac tcatgtcaag gtctcctcca tagtcggtgc acctatcaat gaccccactc  5940
aggatcatag tttggttggt gcattgcaca ccttcatcgg cccgctatct cttatgcggt  6000
ccagcaggtg tctccacatt tatgatcttc atgacattca cctctttgtt gttaaaccca  6060
tcctgcggct gcaaggggta cctagtcatg gtcttctttt gtgcttgtcg acgacctctg  6120
ctcttcttgt ctacgtggat gctgattggg ctgtttgtgt ggacactcac aagtctacct  6180
caagctacac catgttcctt ggtgatgatc tggttttcta gtcctccaag cagtagaaca  6240
gtgtcctact ccacggctct agtgccgagg ctgagtacca gacatcacca atggcgtggc  6300
caaggattgc tgacttcgac aattgctacg aggacatgcc ccctaacgaa gatcaccttg  6360
gtccgttatg atacttgtcg accaaccctg ctcagcatca acgcaagatc ggtctgcact  6420
tcatctgcaa gcgtgttgct attggtgatg tttgtgttct ccatgtcctg aatcctgatg  6480
acataccaat tttctgacat cttcaccaag gggcttctac ttatgtccta tagatgttct  6540
gactatgggg tgtgtgtgtg tgtgtgttag agagtttatc tccttccctc tttaggtgat  6600
tggctggtta ccttaggcgc cccttctctg tttaggtgtt tggctggtag tcttatttcc  6660
```

```
ttgttcagtt gattgtctgg ttgttttatg tgcctgatct cctggatcac ctccctgatc  6720
ttgtttctat aaatcaggta gaggaagatc attggtagag gtctatatat tgtacttctg  6780
atattcagtt gaatgcaagc aatattcaca ctctacatct ctcttgcagt tcctggcaac  6840
tgtgtcacat gagatcagaa cacctatgaa tggcgtcctt ggtacttatg catttatttt  6900
gattctactt aatcttcagt tccatgggcc tggcaatcta aaatttctgc cttctggtgt  6960
aggaatgctg gatatgcttt taggaacaga tctaactatg acacagaagg attatgctca  7020
aactgctcaa atgtgtggca gagcattgat tacactgata aatgatgtcc ttgatcgagc  7080
aaagatcgag gctggaaagt tagagcttga agcggtgcct tttgacctgc gttctctcat  7140
ggatgatgtt gtttccttgt tttcttcaaa gtcacgggag aagtgcattg aggtatgcta  7200
ctgctaatgc ttaaagtagg aaatgatgtt tcctgggccg tcacttgaat ggatgttgat  7260
tgcttttagt tctagttttt ggctgatcaa ctgacaaata atgcagttct gcatgaatca  7320
atctgtcact atacttctat acttctctat ggcagatact ttccctgatt tttttccttc  7380
ttgctgcagc ttgcagtatt tgtatgtgac aatgttccaa aggttgttat tggagatcct  7440
tggaggtttc gacagatatt gacaaatttg gtcgggaatg cagtcaaagt aagcagccaa  7500
ttttggtatt tggtatcctc acactacaac ttcaaatgat gttggttaga agtatttgat  7560
aagtctgtca tcaaatacat gcacaaaaat gcactgatat atctattgtc tgttccagtt  7620
cacagaacga ggtcatgtat ttgtgcgggt ctgtttggct gaaaactcaa atgtggaagc  7680
caatcaggtc ctacatggag ccatgaatgg caaaggtggt agagttgagt caacaactaa  7740
tggtgccttc aatactttga gtgggtttga agcagcagac agacgaaata gttggcaata  7800
ttttaaactg ctcctctccg ataaggagtc acttttggat gatcttgagg gcgaaaattc  7860
taatcaaagt gattcaaatc atgtcacact agcaataagt attgaggaca caggtgtcgg  7920
gataccactg caagcacaag atcgtgtttt tacaccgttt atgcaggctg acagttcaac  7980
ttcaaggaat tatggcggta ctggcatcgg tttaagcatc agcaagtgtc tagctgaact  8040
tatgggtggg cagataagtt tcactagcca tccttctgtt ggaagcacgt tcactttctc  8100
agccacactg aagcactcat acaaagatat ttcggtcgat tcaagtagga gcttgacaga  8160
ggcactacca actgctttta agggaatgaa ggccatcttg gtagatggga gacctgtacg  8220
tagtgctgtt acaagatatc acctcaagag gttgggaata cttcttcaag ttgtgaacaa  8280
tatgaatgca gtagtaaaag ctttcccagg acaaaatgga gcaaccggtt ctaggtgagt  8340
gttcttaagt tagtttatta aatgctgttc atacaattgg ctgagcaagg cttcacattc  8400
cagtactttc cctcacgtgg aggctgcctc aacttcaacc cttatatgtg gaatgggagt  8460
agggaacatt tcttttatta aattgtgtga caaaagattc aaactcagac ctggccttgt  8520
taccatgttg agctgcatgc actcatggcc tcaacaaaaa ccctaagcaa ggaactcact  8580
tataatttac tagatatcat agatattctg tctgtttaat cagcttgtac cgaataagct  8640
attcgcaaat tgtttttgag aatacagaat agcataaaac attattaaaa caccagatat  8700
gcaccttata cttgtttgta tgaccttcga aatcatccca tttattttct tgtagggaaa  8760
aagcatcaat tctttttatt gagagtgact tctggaggcc tgagacagat gttcagttat  8820
tgaaccatct acgcgagcag aagaacggtc agttgtcgga tgggcacaag gtagttcttt  8880
tggtcacctc tgaagccgac aaggacaaat atggatccat atttgatatt gtgatgtgta  8940
agcctataag ggcaagcaca atcgcttcat ctattcaaca actgctcaaa gtagagatag  9000
ccgaaagaaa agataatcaa aaccggccgt cgtttcttcg aagcttgctg gttgggaaga  9060
atatattggt cgtagacgat aataaagtca acctcagagt tgctgcggct gcactcaaga  9120
aatatggtgc taatgttagc tgtgttgaaa gcggcaagga tgctatcagt ctacttcaac  9180
ccccgcatcg cttcgatgca tgttttatgg atgttcagat gccagagatg gacgggtatg  9240
tggatgaaat aaacaaagtc gttttccatt tccatcctgc tgtttgaagt ttgtttgcta  9300
gttgaataaa aaaaatgttt ccactgacca gcagttctcg attgttactt ttgtaggttt  9360
gaggcaaccg gacaaataag gcaaatggag ttgaaagcga acgaggaaag gaagaacaag  9420
ttggcttcga ttgaaggctc gacaactgcc gagtaccatc tgcctgttct ggcaatgaca  9480
gccgatgtta tccaggcaac ttacgaagag tgcataaaat cgggaatgga tggatacgta  9540
tctaaaccct tcgacgagga gcagctatac caagcagtct ccagattggt agtgggaacg  9600
acggattcgg ctgtttgatg ttcaaaatac gatggacctg acttctcatt catcgaagtg  9660
aagcatcacc atcttgcctc tgtccagctg actctatatc ccttgacaat gggcctctga  9720
catggcctct cacaagacta gatgaaaaaa gaagatgaaa gtgccgtgag ttaggtacgt  9780
gtcacacatg acatgaagtt gctgcggcag cccagaggag tgtaggtaga tcaccctgta  9840
actctcttgt tctttgatgt ttataggctg ttgtgtcttc tgacaattca ttggaaatac  9900
cacatctcgt tgcaatccc                                               9919

SEQ ID NO: 260          moltype = DNA  length = 17
FEATURE                 Location/Qualifiers
source                  1..17
                        mol_type = other DNA
                        organism = Zea mays
SEQUENCE: 260
ttgataaact cctagaa                                                 17

SEQ ID NO: 261          moltype = DNA  length = 10
FEATURE                 Location/Qualifiers
source                  1..10
                        mol_type = other DNA
                        organism = Zea mays
SEQUENCE: 261
taaactccta                                                         10
```

METHODS AND COMPOSITIONS FOR MODIFYING CYTOKININ RECEPTOR HISTIDINE KINASE GENES IN PLANTS

STATEMENT OF PRIORITY

This application claims the benefit, under 35 U.S.C. § 119(e), of U.S. Provisional Application No. 63/234,000 filed on Aug. 17, 2021, the entire contents of which is incorporated by reference herein.

STATEMENT REGARDING ELECTRONIC FILING OF A SEQUENCE LISTING

A Sequence Listing in XML text format, submitted under 37 C.F.R. § 1.831-1.834, entitled 1499_70_ST26.xml, 648,625 bytes in size, generated on Aug. 1, 2022 and filed electronically, is provided in lieu of a paper copy. This Sequence Listing is hereby incorporated herein by reference into the specification for its disclosures.

FIELD OF THE INVENTION

This invention relates to compositions and methods for modifying Cytokinin Receptor Histidine Kinase (HK) genes in plants, optionally to improve yield traits. The invention further relates to plants having increased improved yield traits produced using the methods and compositions of the invention.

BACKGROUND OF THE INVENTION

Intensive breeding across row crops has led to incremental increases in plant yield. However, genetic gain from breeding has started to plateau and assembling multiple small-effect genes in a breeding program has substantially increased research and development costs. Single gene solutions have been challenging for a complex trait such as yield, where background genetics and environment combine to reduce the impact of individual genes. Breeding has been successful by combining many individual genes with small contributing effects but is requiring greater resources to find unique combinations with improved effects. To increase the rate of yield gain, novel variation needs to be introduced in important genes and pathways that contribute to yield.

Transgenic approaches involving stable transformation to increase yield have largely been unsuccessful and there are no commercially relevant single gene approaches that have successfully created a step change in yield. Modifying hormone related pathways through GM approaches has not been fruitful because the simple over- or under-expression through transgene technology is not consistent with the fine-tuning effect required for improving plant yield.

The present invention addresses these shortcomings in the art by providing new compositions and methods for improving/enhancing yield traits in plants, including soybean, corn and other plant species.

SUMMARY OF THE INVENTION

One aspect of the invention provides a plant or plant part thereof comprising at least one mutation in an endogenous Cytokinin Receptor Histidine Kinase (HK) gene encoding a histidine kinase (HK) polypeptide, optionally wherein the mutation may be a non-natural mutation.

A second aspect of the invention provides a plant cell, comprising an editing system comprising: (a) a CRISPR- Cas effector protein; and (b) a guide nucleic acid (e.g., gRNA, gDNA, crRNA, crDNA, sgRNA, sgDNA) comprising a spacer sequence with complementarity to an endogenous target gene encoding a histidine kinase (HK) polypeptide.

A third aspect of the invention provides a plant cell comprising at least one mutation within an endogenous Cytokinin Receptor Histidine Kinase (HK) gene, wherein the at least one mutation is a substitution, insertion, or deletion that is introduced using an editing system that comprises a nucleic acid binding domain that binds to a target site in the endogenous HK gene, optionally wherein the mutation may be a non-natural mutation.

A fourth aspect of the invention provides a method of producing/breeding a transgene-free edited plant, comprising: crossing the plant of the invention with a transgene free plant, thereby introducing the at least one mutation into the plant that is transgene-free; and selecting a progeny plant that comprises the at least one mutation and is transgene-free, thereby producing a transgene free edited plant, optionally wherein the mutation may be a non-natural mutation.

A fifth aspect of the invention provides a method of providing a plurality of plants having one or more improved yield traits, optionally increased seed size (e.g., seed area and/or seed weight) and/or seed oil content, the method comprising planting two or more plants of the invention in a growing area, thereby providing a plurality of plants having one or more improved yield traits as compared to a plurality of control plants not comprising the at least one mutation.

A sixth aspect of the invention provides a method of generating variation in a region of a histidine kinase (HK) polypeptide, comprising: introducing an editing system into a plant cell, wherein the editing system is targeted to a region of a Cytokinin Receptor Histidine Kinase (HK) gene that encodes the region of the HK polypeptide, and contacting the region of the HK gene with the editing system, thereby introducing a mutation into the HK gene and generating variation in the HK polypeptide of the plant cell.

A seventh aspect provides a method for editing a specific site in the genome of a plant cell, the method comprising: cleaving, in a site-specific manner, a target site within an endogenous Cytokinin Receptor Histidine Kinase (HK) gene in the plant cell, the endogenous HK gene: (a) comprising a sequence having at least 80% sequence identity to any one of the nucleotide sequences of SEQ ID NOs:69, 70, 102, 103, 136, 137, 165, 166, 186, 187, 212 or 213, (b) comprising a region having at least 80% sequence identity to any one of the nucleotide sequences of SEQ ID NOs:72-94, 105-120, 139-150, 162-174, 189-205 or 215-222, (c) encoding an amino acid sequence having at least 80% sequence identity to any one of SEQ ID NOs:71, 104, 138, 161, 188 or 214, (d) encoding a region having at least 80% sequence identity to an amino acid sequence of any one of SEQ ID NOs:95-101, 121-135, 151-158, 175-185 or 206-211, thereby generating an edit in the endogenous HK gene of the plant cell and producing a plant cell comprising the edit in the endogenous HK gene.

An eighth aspect provides a method for making a plant, the method comprising: (a) contacting a population of plant cells comprising an endogenous Cytokinin Receptor Histidine Kinase (HK) gene with a nuclease linked to a nucleic acid binding domain (e.g., editing system) that binds to a sequence (i) having at least 80% sequence identity to a nucleotide sequence of any one of SEQ ID NOs:69, 70, 102, 103, 136, 137, 165, 166, 186, 187, 212 or 213, (ii) encoding an amino acid sequence having at least 80% sequence identity to any one of SEQ ID NOs:71, 104, 138, 161, 188 or 214, (iii) encoding an amino acid sequence comprising a region having at least 80% sequence identity to any one of SEQ ID NOs:95-101, 121-135, 151-158, 175-185 or 206-211, and/or (iv) comprising a region having at least 80% identity to any one of SEQ ID NOs:72-94, 105-120, 139-150, 162-174, 189-205 or 215-222; (b) selecting a plant cell from the population in which an endogenous HK gene has been mutated, thereby producing a plant cell comprising a mutation in the endogenous HK gene; and (c) growing the selected plant cell into a plant.

A ninth aspect provides a method for improving one or more yield traits in a plant, comprising: (a) contacting a plant cell comprising an endogenous Cytokinin Receptor Histidine Kinase (HK) gene with a nuclease targeting the endogenous HK gene, wherein the nuclease is linked to a nucleic acid binding domain (e.g., editing system) that binds to a target site in the endogenous HK gene, wherein the endogenous HK gene: (i) comprises a sequence having at least 80% sequence identity to a nucleotide sequence of any one of SEQ ID NOs:69, 70, 102, 103, 136, 137, 165, 166, 186, 187, 212 or 213; (ii) comprises a region having at least 80% identity to any one of SEQ ID NOs:72-94, 105-120, 139-150, 162-174, 189-205 or 215-222; (iii) encodes an amino acid sequence having at least 80% sequence identity to any one of SEQ ID NOs:71, 104, 138, 161, 188 or 214; and/or (iv) encodes an amino acid sequence comprising a region having at least 80% identity to any one of SEQ ID NOs:95-101, 121-135, 151-158, 175-185 or 206-211 to produce a plant cell comprising a mutation in the endogenous HK gene; and (b) growing the plant cell into a plant comprising the mutation in the endogenous HK gene, thereby producing a plant have a mutated endogenous HK gene and one or more improved yield traits.

A tenth aspect provides a method of producing a plant or part thereof comprising at least one cell having a mutated endogenous Cytokinin Receptor Histidine Kinase (HK) gene, the method comprising contacting a target site in an endogenous HK gene in the plant or plant part with a nuclease comprising a cleavage domain and a nucleic acid binding domain, wherein the nucleic acid binding domain binds to a target site in the endogenous HK gene, wherein the endogenous HK gene (a) comprises a sequence having at least 80% sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211, thereby producing the plant or part thereof comprising at least one cell having a mutation in the endogenous HK gene.

An eleventh aspect of the invention provides a method for producing a plant or part thereof comprising a mutated endogenous Cytokinin Receptor Histidine Kinase (HK) gene and exhibiting one or more improved yield traits, the method comprising contacting a target site in an endogenous HK gene in the plant or plant part with a nuclease comprising a cleavage domain and a nucleic acid binding domain, wherein the nucleic acid binding domain binds to a target site in the endogenous HK gene, wherein the endogenous HK gene: (a) comprises a sequence having at least 80% sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs:71, 104, 138, 161, 188 or 214; and/or (d) encodes an amino acid sequence comprising a region having at least 80% identity to any one of SEQ ID NOs: 95-101, 121-135, 151-158, 175-185 or 206-211, thereby producing the plant or part thereof comprising an endogenous HK gene having a mutation and exhibiting one or more improved yield traits.

A twelfth aspect provides a guide nucleic acid that binds to a target site in a Cytokinin Receptor Histidine Kinase (HK) gene, wherein the target site is in a region of the HK gene having at least 80% sequence identity to any one of the nucleotide sequences of SEQ ID NOs:72-94, 105-120, 139-150, 162-174, 189-205 or 215-222.

In a thirteenth aspect, a system is provided that comprises a guide nucleic acid of the invention and a CRISPR-Cas effector protein that associates with the guide nucleic acid.

A fourteenth aspect provides a gene editing system comprising a CRISPR-Cas effector protein in association with a guide nucleic acid, wherein the guide nucleic acid comprises a spacer sequence that binds to an endogenous Cytokinin Receptor Histidine Kinase (HK) gene.

In a fifteenth aspect, a complex comprising a guide nucleic acid and a CRISPR-Cas effector protein comprising a cleavage domain is provided, wherein the guide nucleic acid binds to a target site in an Cytokinin Receptor Histidine Kinase (HK) gene, the endogenous HK gene: (a) comprises a sequence having at least 80% sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211, and the cleavage domain cleaves a target strand in the HK gene.

In a sixteenth aspect, an expression cassette is provided, the expression cassette comprising (a) a polynucleotide encoding CRISPR-Cas effector protein comprising a cleavage domain and (b) a guide nucleic acid that binds to a target site in an endogenous Cytokinin Receptor Histidine Kinase (HK) gene, wherein the guide nucleic acid comprises a spacer sequence that is complementary to and binds to (i) a portion of a nucleic acid having at least 80% sequence identity to any one of the nucleotide sequences of SEQ ID NOs:69, 70, 102, 103, 136, 137, 165, 166, 186, 187, 212 or 213; (ii) a portion of a nucleic acid having at least 80% sequence identity to any one of SEQ ID NOs:72-94, 105-120, 139-150, 162-174, 189-205 or 215-222; (iii) a portion of a nucleic acid encoding an amino acid sequence having at least 80% sequence identity to any one of SEQ ID NOs:71, 104, 138, 161, 188 or 214; and/or (iv) a portion of a nucleic acid encoding an amino acid sequence having at least 80% identity to any one of SEQ ID NOs:95-101, 121-135, 151-158, 175-185 or 206-211; and/or (iv) a portion of a nucleic acid encoding an amino acid sequence having at least 80% identity to any one of SEQ ID NOs:98-104, 124-138, 154-161, 178-188 or 209-213.

In a seventeenth aspect, a modified histidine kinase (HK) polypeptide is provided, the modified HK polypeptide comprising an amino acid sequence having at least 80% sequence identity to any one of SEQ ID NOs:95-101, 121-135, 151-158, 175-185 or 206-211, optionally in a region of the HK polypeptide comprising an amino acid sequence having at least 80% sequence identity to any one of SEQ ID NOs:97, 98, 100, 101, 127, 128, 130, 132-135, 155-158, 180, 181, 183-185 or 210.

In an additional aspect, a method of creating a mutation in an Cytokinin Receptor Histidine Kinase (HK) gene in a plant is provided, the method comprising: (a) targeting a gene editing system to a portion of the HK gene that (i) comprises a sequence having at least 80% sequence identity to any one of SEQ ID NOs:72-94, 105-120, 139-150, 162-174, 189-205 or 215-222; and/or (ii) encodes a sequence having at least 80% identity to any one of SEQ ID NOs:95-101, 121-135, 151-158, 175-185 or 206-211, and (b) selecting a plant that comprises a modified amino acid residue located in a region of the HK gene encoding an amino acid sequence having at least 80% sequence identity to any one of SEQ ID NOs:95-101, 121-135, 151-158, 175-185 or 206-211, optionally located in a region of the HK gene encoding an amino acid sequence having at least 80% sequence identity to any one of SEQ ID NOs:97, 98, 100, 101, 127, 128, 130, 132-135, 155-158, 180, 181, 183-185 or 210.

In another aspect, plants are provided that comprise in their genome one or more mutated Cytokinin Receptor Histidine Kinase (HK) genes produced by the methods of the invention.

A further aspect of the invention provides a corn plant or plant part thereof comprising at least one mutation in at least one endogenous Cytokinin Receptor Histidine Kinase (HK) gene having the gene identification number (gene ID) of Zm00001d014297, Zm00001d017977, and/or Zm00001d051812, optionally wherein the mutation may be a non-natural mutation.

In an additional aspect, a soybean plant or plant part thereof is provided that comprises at least one mutation in at least one endogenous Cytokinin Receptor Histidine Kinase (HK) gene having the gene identification number (gene ID) of Glyma05G148100 (HK2), Glyma08G105000 (HK3) and/or Glyma07G173700 (HK4), optionally wherein the mutation may be a non-natural mutation.

In a further aspect, a guide nucleic acid is provided that binds to a target nucleic acid within a Cytokinin Receptor Histidine Kinase (HK) gene having the gene identification number (gene ID) of Zm00001d014297, Zm00001d017977, Zm00001d051812, Glyma05G148100, Glyma08G105000, and/or Glyma07G173700. Further provided are polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provide example peptide tags and affinity polypeptides useful with this invention.

SEQ ID NOs:45-55 provide example RNA recruiting motifs and corresponding affinity polypeptides useful with this invention.

SEQ ID NOs:56-57 are exemplary Cas9 polypeptide sequences useful with this invention.

SEQ ID NOs:58-68 are exemplary Cas9 polynucleotide sequences useful with this invention.

SEQ ID NO:69 is an example HK3 genomic sequence from soybean.

SEQ ID NO:70 is an example HK3 cDNA sequence from soybean.

SEQ ID NO:71 is an example HK3 polypeptide sequence from soybean.

SEQ ID NOs:72-94 are example portions or regions of soybean HK3 genomic and cDNA sequences.

SEQ ID NOs:95-101 are example portions or regions of a soybean HK2 or HK3 polypeptide sequence.

SEQ ID NO:102 is an example HK4 genomic sequence from soybean.

SEQ ID NO:103 is an example HK4 cDNA sequence from soybean.

SEQ ID NO:104 is an example HK4 polypeptide sequence from soybean.

SEQ ID NOs:105-120 are example portions or regions of soybean HK4 genomic and cDNA sequences.

SEQ ID NOs:121-135 are example portions or regions of a soybean HK4 polypeptide sequence.

SEQ ID NO:136 is an example HK3 genomic sequence from corn.

SEQ ID NO:137 is an example HK3 cDNA sequence from corn.

SEQ ID NO:138 is an example HK3 polypeptide sequence from corn.

SEQ ID NOs:139-150 are example portions or regions of corn HK3 genomic and cDNA sequences.

SEQ ID NOs:151-158 are example portions or regions of a corn HK3 polypeptide sequence.

SEQ ID NO:159 is an example HK1 genomic sequence from corn.

SEQ ID NO:160 is an example HK1 cDNA sequence from corn.

SEQ ID NO:161 is an example HK1 polypeptide sequence from corn.

SEQ ID NOs:162-175 are example portions or regions of corn HK1 genomic and cDNA sequences.

SEQ ID NOs:176-186 are example portions or regions of a corn HK1 polypeptide sequence.

SEQ ID NO:187 is an example HK6 genomic sequence from corn.

SEQ ID NO:188 is an example HK6 cDNA sequence from corn.

SEQ ID NO:189 is an example HK6 polypeptide sequence from corn.

SEQ ID NOs:190-206 are example portions or regions of corn HK6 genomic and cDNA sequences.

SEQ ID NOs:207-211 are example portions or regions of a corn HK6 polypeptide sequence.

SEQ ID NO:212 is an example HK2 genomic sequence from soybean.

SEQ ID NO:213 is an example HK2 cDNA sequence from soybean.

SEQ ID NO:214 is an example HK2 polypeptide sequence from soybean.

SEQ ID NOs:215-222 are example portions or regions of soybean HK2 genomic and cDNA sequences.

SEQ ID NOs:223-243 are example spacer sequences for nucleic acid guides useful with this invention.

SEQ ID NOs:244, 245 and 246 are example genes edited as described herein in soybean.

SEQ ID NOs:247-259 are example genes edited as described herein in corn.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations, and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control. For example, a plant comprising a mutation in a Cytokinin Receptor Histidine Kinase (HK) gene as described herein can exhibit an improved yield trait (e.g., one or more improved yield traits; e.g., optionally an increase in yield (bu/acre), seed size (including kernel size), seed weight (including kernel weight), increased kernel row number (optionally wherein ear length is not substantially reduced), increased number of pods, increased number of seeds per pod and an increase in ear length) as compared to a control plant devoid of the at least one mutation. A control plant is typically the same plant as the edited plant, but the control plant has not been similarly edited and therefore is devoid of the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients, and the like).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence. A "heterologous" nucleotide/polypeptide may originate from a foreign species, or, if from the same species, is substantially modified from its native form in composition and/or genomic locus by deliberate human intervention.

A "native" or "wild type" nucleic acid, nucleotide sequence, polypeptide or amino acid sequence refers to a naturally occurring or endogenous nucleic acid, nucleotide sequence, polypeptide or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous Cytokinin Receptor Histidine Kinase (HK) gene" is a HK gene that is naturally occurring in or endogenous to the reference organism, e.g., a plant, e.g., a soybean plant, a maize plant, and may be subject to modification as described herein, after which, such a modified endogenous gene is no longer wild type. In some embodiments, an endogenous HK gene is an endogenous HK1 gene, an endogenous HK2 gene, an endogenous HK3 gene, an endogenous HK4 gene, or an endogenous HK6 gene.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is nonfunctional.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wild type gene product.

A "hypomorphic mutation" is a mutation that results in a partial loss of gene function, which may occur through reduced expression e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques et Utilisations des Marqueurs Moleculaires les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one (e.g., one or more) progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

A plant in which at least one (e.g., one or more, e.g., 1, 2, 3, or 4, or more) endogenous HK gene (e.g., an endogenous HK1 gene, an endogenous HK2 gene, an endogenous HK3 gene, an endogenous HK4 gene, an endogenous HK6 gene) is modified as described herein (e.g., comprises a modification as described herein) may have improved yield traits as compared to a plant that does not comprise the modification in the at least one HK gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. In some aspects, "improved yield traits" may include, but are not limited to, increased inflorescence production, increased fruit production (e.g., increased number, weight and/or size of fruit; e.g., increase number, weight, and/or length of ears for, e.g., maize), increased fruit quality, increased number, size and/or weight of roots, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a plant that does not comprise a mutated endogenous HK nucleic acid as described herein). In some aspects, improved yield traits can be expressed as quantity of grain produced per area of land (e.g., bushels per acre of land). In some embodiments, the one or more improved yield traits is an increase in seed number.

As used herein, an "increased seed size" can mean a seed that is increased in area. In some embodiments, an seed may be increased in area by up to about 70% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, 50, 51, 52, 53, 54, 55, 56, 57, 58, 59, 60, 61, 62, 63, 64, 65, 66, 67, 68, 69, 70%) as compared to a seed from a control plant (e.g., a plant not comprising the mutation in an endogenous HK gene as described herein). In some embodiments, an seed may be increased in weight by up to about 50% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50%) as compared to a seed from a control plant (e.g., a plant not comprising the mutation in an endogenous HK gene as described herein). In some embodiments, an increase in seed size can include an increase in both seed area and seed size.

As used herein a "control plant" means a plant that does not contain an edited HK gene or genes as described herein that imparts an enhanced/improved trait (e.g., yield trait) or altered phenotype. A control plant is used to identify and select a plant edited as described herein and that has an enhanced trait or altered phenotype as compared to the control plant. A suitable control plant can be a plant of the parental line used to generate a plant comprising a mutated HK gene(s), for example, a wild type plant devoid of an edit in an endogenous HK gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated HK gene as described herein, known as a negative segregant, or a negative isogenic line.

An enhanced trait (e.g., improved yield trait) may include, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant. An altered phenotype may be, for example, plant height, biomass, canopy area, anthocyanin content, chlorophyll content, water applied, water content, and water use efficiency.

In some embodiments, a plant of this invention may comprise one or more improved yield traits including, but not limited to, In some embodiments, the one or more improved yield traits includes higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increase number of seeds, increased seed size, and/or increased seed weight (e.g., increase in 100-seed weight) as compared to a control plant devoid of the at least one mutation. In some embodiments, a plant of this invention may comprise one or more improved yield traits including, but not limited to, optionally an increase in yield (bu/acre), seed size (including kernel size), seed weight (including kernel weight), increased kernel row number (optionally wherein ear length is not substantially reduced), increased number of pods, increased number of seeds per pod and an increase in ear length as compared to a control plant or part thereof.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a HK gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous HK gene as described herein relative to a plant not comprising the mutation, such as a wild-type plant, or a negative segregant. In some cases, the trait modification can be evaluated quantitatively. For example, the trait modification can entail an increase or decrease in an observed trait characteristics or phenotype as compared to a control plant. It is known that there can be natural variations in a modified trait. Therefore, the trait modification observed entails a change of the normal distribution and magnitude of the trait characteristics or phenotype in the plants as compared to a control plant.

The present disclosure relates to a plant with improved economically relevant characteristics, more specifically increased yield. More specifically the present disclosure relates to a plant comprising a mutation(s) in a HK gene(s) as described herein, wherein the plant has increased yield as compared to a control plant devoid of said mutation(s). In some embodiments, plants produced as described herein exhibit increased yield or improved yield trait components as compared to a control plant. In some embodiments, a plant of the present disclosure exhibits an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 285, 290, 300, 310, 320, 330, 340, 350, 360, 370, 380, 390, 395, 396, 397, 398, 399, 400, 410, 411, 412, 413, 414, 415, 420, 425, 430, 435, 440, 445, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, or 1800 or more consecutive nucleotides, or any range or value therein, of a nucleic acid encoding an HK polypeptide, optionally a fragment of an HK gene may be about 10, 20, 30, 35, 40, 45, 50, 55, 60, 65, 70, 75, 80, 85, 90, 95, 100, 110, 115, 120, 125, 130, 135, 140, 145, 150 consecutive nucleotides to about 155, 160, 165, 170, 175, 180, 185, 190, 195, 200, 205, 210, 215, 220, 225, 230, 240, 245, 250, 255, 260, 265, 270, 275, 280, 285, 290, 295, 300, 350, 400, 450, 500, 550, 600, 650, 700, 750, 800, 850, 900, 905, 100, 1100, 120, 1300, 1400, 1500, 1600, or 1700 or more consecutive nucleotides in length, or any range or value therein (e.g., a fragment or portion of any one of SEQ ID NOs:69, 70, 102, 103, 136, 137, 165, 166, 186, 187, 212 or 213 (e.g., SEQ ID NOs:72-94, 105-120, 139-150, 162-174, 189-205 or 215-222).

In some embodiments, a "sequence-specific nucleic acid binding domain" may bind to one or more fragments or portions of nucleotide sequences (e.g., DNA, RNA) encoding, for example, HK polypeptides as described herein.

As used herein, "adjacent to" a region encoding an extracellular cytokinin binding domain means 1 to about 100 nucleotides (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs/nucleotides) located immediately 5' and/or immediately 3' to the region of a Cytokinin Receptor Histidine Kinase (HK) gene encoding an extracellular cytokinin binding domain (e.g., 1 to about 100 nucleotides located immediately 5' and/or immediately 3' to the extracellular cytokinin binding domain of SEQ ID NOs:69, 70, 102, 103, 136, 137, 165, 166, 186, 187, 212 or 213, e.g., the portions that encode the amino acid sequences of SEQ ID NOs:95, 121, 122, 151, 152, 176 or 207). Thus, in some embodiments, a mutation useful with this invention can include a mutation that is within an encoded extracellular cytokinin binding domain (e.g., within a region of a nucleic acid that encodes, for example, any one of the amino acid sequences of SEQ ID NOs:95, 121, 122, 151, 152, 176 or 207), adjacent to an extracellular cytokinin binding domain (e.g., adjacent to a region of a nucleic acid (e.g., SEQ ID NOs:69, 70, 102, 103, 136, 137, 165, 166, 186, 187, 212 or 213) that encodes, for example, any one of the amino acid sequences of SEQ ID NOs:95, 121, 122, 151, 152, 176 or 207), or which mutation may occur both within the region encoding the extracellular cytokinin binding domain and a region that is immediately 5' or immediately 3' of the region encoding the extracellular cytokinin binding domain (e.g., adjacent to and within a region of a nucleic acid that encodes, for example, any one of the amino acid sequences of SEQ ID NOs:95, 121, 122, 151, 152, 176 or 207). Thus, for example, a mutation may be within the region encoding the extracellular cytokinin binding domain. In some embodiments, the mutation may be adjacent to the region encoding the extracellular cytokinin binding domain, for example, in the region immediately 5' to the region encoding the extracellular cytokinin binding domain. In some embodiments, the mutation may be comprised within the region encoding the extracellular cytokinin binding domain and in the region immediately 5' to the region encoding the extracellular cytokinin binding domain.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, a polypeptide fragment may comprise, consist essentially of, or consist of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, or 290 or more consecutive amino acids of a reference polypeptide. In some embodiments, a polypeptide fragment may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 230, 240, or 250 or more consecutive amino acid residues, or any range or value therein, of an HK polypeptide (e.g., a fragment or a portion of SEQ ID NOs:71, 104, 138, 161, 188 or 214 (e.g., SEQ ID NOs:95-101, 121-135, 151-158, 175-185 or 206-211)).

In some embodiments, such a deletion when comprised in a plant can result in the plant exhibiting one or more improved yield traits, as compared to a plant not comprising said deletion. An HK gene may be edited in one or more than one location (and using one or more different editing tools), thereby providing an HK gene comprising one or more than one mutation. In some embodiments, an HK polypeptide mutated as described herein may comprise one or more than one edit that may result in a polypeptide having one or more than one amino acid deletion, optionally wherein the polypeptide comprises 1, 2, 3, 4, 5, 6, 7, 8, or 9 amino acid deletions. In some embodiments, an HK polypeptide mutated as described herein may comprise one or more than one edit that may result in a polypeptide having one or more than one amino acid substitution, optionally wherein the polypeptide comprises 1, 2, 3, 4, 5 or 6, or more amino acid substitutions.

In some embodiments, a "portion" or "region" in reference to a nucleic acid means at least 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 120, 130, 140, 141, 142, 143, 144, 145, 150, 160, 170, 180, 190, 200, 210, 220, 230, 240, 250, 260, 270, 280, 285, 290, 300, 310, 320, 330, 340, 350, 360, 370, 380, 390, 395, 400, 405, 410, 415, 420, 425, 430, 435, 440, 445, 450, 500, 600, 700, 800, 900, 1000, 1100, 1200, 1300, 1400, 1500, 1600, or 1700 or more consecutive nucleotides from a gene (e.g., consecutive nucleotides from a KH gene) (e.g., a fragment or portion of any one of ID NOs:69, 70, 102, 103, 136, 137, 165, 166, 186, 187, 212 or 213 (e.g., SEQ ID NOs:72-94, 105-120, 139-150, 162-174, 189-205 or 215-222).

In some embodiments, a "portion" or "region" of an HK polypeptide sequence may be about 5 to about 250 or more consecutive amino acid residues in length (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 120, 130, 140, 141, 142, 143, 144, 145, 150, 160, 170, 180, 190, 200, 210, 220, 230, 240, or 250, or more consecutive amino acid residues in length (e.g., a portion of any one of SEQ ID NOs:71, 104, 138, 161, 188 or 214 (e.g., SEQ ID NOs:95-101, 121-135, 151-158, 175-185 or 206-211)).

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, inversions and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. A DNA inversion is the result of a rotation of a genetic fragment within a region of a chromosome.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more HK polypeptides may be identical or substantially identical (e.g., at least 70% to 99.9% identical; e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein) over at least 8 consecutive amino acids to about 350 consecutive amino acids. In some embodiments, two or more HK polypeptides may be identical or substantially identical over at least 8, 9, 10, 11, 12, 13, 14, or 15 consecutive amino acids to about 20, 21, 22, 23, 24, 25, 26, 27, 28, 29, 30, 31, 32, 33, 34, 35, 36, 37, 38, 39, or 40 consecutive amino acids).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG WISCONSIN PACKAGE® (Accelrys Inc., San Diego, CA) software suite for sequence analysis. An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain (e.g., DNA binding domain) from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2 USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), $PLA_2$-δ promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean *Glycine* rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) Mol. Gen. Genet. 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one (e.g., one or more) of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering, or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally, included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromosomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

Phytohormones regulate plant growth and development as well as responses to changes in the growing environment, for example, in response to drought or other abiotic stresses. Phytohormone signals can be modulated through biosynthesis or breakdown of the phytohormone at a metabolic level, or through control of phytohormone signaling. Cytokinin is a phytohormone that positively regulates, for example, meristem activity, organ size, seed number, and leaf longevity.

The present invention is directed to modification of Cytokinin Receptor Histidine Kinase (HK) genes (e.g., HK1, HK2, HK3, HK4, HK6) in plants through editing technology to provide plants that exhibit one or more improved yield traits. Mutations that may be useful for producing plants with one or more improved yield traits include, for example, substitutions, deletions, and/or insertions. In some aspects, a mutation generated by the editing technology can be a point mutation.

In some embodiments, the invention provides a plant or plant part thereof comprising at least one mutation in an endogenous Cytokinin Receptor Histidine Kinase (HK) gene encoding a histidine kinase (HK) polypeptide. In some embodiments, the at least one mutation may be a non-natural mutation. In some embodiments, an endogenous HK gene may be an endogenous HK1 gene, an endogenous HK2 gene, an endogenous HK3 gene, an endogenous HK4 gene, or an endogenous HK6 gene, wherein the encoded HK polypeptide is an HK1 polypeptide, an HK2 polypeptide, an HK3 polypeptide, an HK4 polypeptide, or an HK6 polypeptide, respectively. In some embodiments, the HK polypeptide comprises an extracellular cytokinin binding domain, optionally wherein the at least one mutation is within or adjacent to an extracellular cytokinin binding domain. In some embodiments, a mutation within or adjacent to an extracellular cytokinin binding domain of an HK polypeptide as described herein results in a gain of function, such as loss of dependency on the presence of cytokinin for the receptor signaling activity of the HK polypeptide. In some embodiments, the mutation results in hypersignaling by the encoded HK polypeptide, wherein signaling by the HK polypeptide requires cytokinin but the levels of cytokinin are lower than that required for an HK polypeptide devoid of the at least one mutation. Thus, hypersignaling is not constitutive and/or is not entirely independent of cytokinin levels. In some embodiments, the at least one mutation may be a dominant mutation or a semidominant mutation.

As used herein, a "non-natural mutation" refers to a mutation that is generated though human intervention and differs from mutations found in the same gene that have occurred in nature (e.g., occurred naturally)). A natural HK mutation in corn can be, but is not limited to, for example, (1) Hsf1(HK1):1595 (Pro190 to Leu with reference to amino acid position numbering of SEQ ID NO:161 (ZM00001D017977)); (2) Hsf1(HK1):1603 (Glu236 to Lys with reference to amino acid position numbering of SEQ ID NO:161) and/or (3) Hsf1(HK1):AEWL (Leu238 to Phe with reference to amino acid position numbering of SEQ ID NO:161). In some embodiments, a mutated HK polypeptide of the present invention does not comprise, consist essentially of, or consist of a mutation of (1) Hsf1(HK1):1595 (Pro190 to Leu with reference to amino acid position numbering of SEQ ID NO:159); (2) Hsf1(HK1):1603 (Glu236 to Lys with reference to amino acid position numbering of SEQ ID NO:159) or (3) Hsf1(HK1):AEWL (Leu238 to Phe with reference to amino acid position numbering of SEQ ID NO:159).

In some embodiments, a plant cell is provided, the plant cell comprising an editing system, the editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a histidine kinase (HK) polypeptide. The editing system may be used to generate a mutation in the endogenous target gene encoding an HK polypeptide. In some embodiments, the endogenous target gene is an endogenous Cytokinin Receptor Histidine Kinase (HK) gene, optionally an endogenous HK1 gene, an endogenous HK2 gene, an endogenous HK3 gene, an endogenous HK4 gene, or an endogenous HK6 gene, and the HK polypeptide is an HK1 polypeptide, an HK2 polypeptide, an HK3 polypeptide, an HK4 polypeptide, or an HK6 polypeptide. In some embodiments, the mutation is a non-natural mutation. In some embodiments, a guide nucleic acid of an editing system may comprise the nucleotide sequence (a spacer sequence, e.g., one or more spacers) of any of SEQ ID NOs:223-235 (soybean) and/or SEQ ID NOs:236-243 (corn) (e.g., SEQ ID NO:223 (PWsp1205), SEQ ID NO:224 (PWsp1206), SEQ ID NO:225, SEQ ID NO:226, SEQ ID NO:227 (PWsp1502), SEQ ID NO:228 (PWsp734), SEQ ID NO:229 (PWsp1203), SEQ ID NO:230 (PWsp1204), SEQ ID NO:231, SEQ ID NO:232, SEQ ID NO:233 (PWsp733), SEQ ID NO:234 (PWsp1242), SEQ ID NO:235 (PWsp1243), SEQ ID NO:236 (PWsp1219), SEQ ID NO:237 (PWsp1220), SEQ ID NO:238 (PWsp1221), SEQ ID NO:239 (PWsp1222), SEQ ID NO:240 (PWsp1223), SEQ ID NO:241 (PWsp1224), SEQ ID NO:242 (PWsp1225) and/or SEQ ID NO:243 (PWsp1226)).

A mutation in a HK gene of the plant, plant part thereof, or the plant cell useful for this invention may be any type of mutation, including a base substitution, a base deletion, and/or a base insertion. In some embodiments, the at least one mutation may be a non-natural mutation. In some embodiments, a mutation may comprise a base substitution to an A, a T, a G, or a C, optionally the base substitution may be from a C to an A or a T, a G to an A, and/or a T to a C. In some embodiments, a mutation may be a deletion of at least one base pair (e.g., 1 base pair to about 27 base pairs; e.g., 1, 2, 3, 4, 5, 6, 7, 8, 9, 10, 11, 12, 13, 14, 15, 16, 17, 18, 19, 20, 21, 22, 23, 24, 25, 26, or 27 consecutive base pairs) or an insertion of at least one base pair (e.g., 1 base pair to about 27 base pairs; e.g., 1, 2, 3, 4, 5, 6, 7, 8, 9, 10, 11, 12, 13, 14, 15, 16, 17, 18, 19, 20, 21, 22, 23, 24, 25, 26, or 27 consecutive base pairs), optionally wherein the deletion or insertion is an in-frame deletion or in-frame insertion. In some embodiments, a mutation may be a deletion of 3, 6, 9, 12, 15, 18, 21, 24, or 27 consecutive base pairs, optionally resulting in a deletion of one amino acid residue to about 9 consecutive amino acid residues. In some embodiments a mutation in an HK gene as described herein comprises a nucleic acid sequence having at least 90% (e.g., 90%, 91%, 92%, 93%, 94%, 95%, 96%, 97%, 98%, 99%, 99.5%. 99.9% or 100%) sequence identity to any one of SEQ ID NOs: 244-259. In some embodiments, the plant, plant part or plant cell comprising a mutation in a HK gene is soybean and mutated HK gene comprises a nucleic acid sequence having at least 90% sequence identity to any one of SEQ ID NOs:244-246. In some embodiments, the plant, plant part or plant cell comprising a mutation in a HK gene is corn and mutated HK gene comprises a nucleic acid sequence having at least 90% sequence identity to any one of SEQ ID NOs:247-259.

The types of editing tools that may be used to generate these and other mutations in HK genes include any base editors or cutters, which are guided to a target site using spacers having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) complementarity to a portion or a region of a HK gene as described herein.

In some embodiments, a mutation of a HK gene may be within a portion or region of the endogenous HK gene that encodes the HK polypeptide (e.g., the coding regions (exons)). As an example, the mutation may be in or adjacent to the region of the HK gene that encodes the extracellular cytokinin binding domain of the HK polypeptide, optionally wherein the mutation results in the HK polypeptide having an amino acid substitution as compared to a wild type mature HK polypeptide. In some embodiments, the mutation may be an in-frame insertion or in-frame deletion, optionally wherein the mutation is in or adjacent to an extracellular cytokinin binding domain encoded by the endogenous HK gene In some embodiments, a mutation of a HK gene is within a portion or region of the endogenous HK gene having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the amino acid sequences of SEQ ID NOs:95-101, 121-135, 151-158, 175-185 or 206-211.

In some embodiments, the at least one mutation in an endogenous HK gene results in a mutation of one or more amino acid residue(s) located in a region of the HK polypeptide having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the amino acid sequences of SEQ ID NOs:95-101, 121-135, 151-158, 175-185 or 206-211, optionally wherein the mutation may be a non-natural mutation.

In some embodiments, the at least one mutation may result in a substitution of any one or more of the amino acid residues located in a region having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the amino acid sequences of SEQ ID NOs:97, 98, 100, 101, 127, 128, 130, 132-135, 155-158, 180, 181, 183-185 or 210. In some embodiments, the at least one mutation may result in a substitution of an amino acid residue located: at position 172, 178, 325, and/or 332 with reference to amino acid position numbering of SEQ ID NO:71, at position 127, 133, 218, 264, 266, and/or 271 with reference to amino acid position numbering of SEQ ID NO:104, at position 65, 69, 214, and/or 216 with reference to amino acid position numbering of SEQ ID NO:138, at position 102, 105, 190, 236 and/or 238 with reference to amino acid position numbering of SEQ ID NO:161, at position 160 and/or 161 with reference to amino acid position numbering of SEQ ID NO:188, and/or at position 172, 178, 325, and/or 332 with reference to amino acid position numbering of SEQ ID NO:214, optionally wherein the substitution is threonine (T) to isoleucine (I) (T>I), glutamic acid (E) to lysine (K) (E>K), leucine (L) to phenylalanine (F) (L>F), proline (P) to leucine (L) (P>L), and/or serine (S) to leucine (L) (S>L). In some embodiments, the at least one mutation results in an amino acid substitution of T172, E178K, E325K, and/or L332 with reference to amino acid position numbering of SEQ ID NO:71, of T127, E133, P218, E264, L266, and/or L271 with reference to amino acid position numbering of SEQ ID NO:104, of T65, E69, P214, and/or L216 with reference to amino acid position numbering of SEQ ID NO:138, of T102, E105, P190, E236 S237, and/or L238 with reference to amino acid position numbering of SEQ ID NO:161, of S160 and/or L161 with reference to amino acid position numbering of SEQ ID NO:188 and/or of T172, E178K, E325K, and/or L332 with reference to amino acid position numbering of SEQ ID NO:214, optionally an amino acid substitution of T172I, E178K, E325K, and/or L332F with reference to amino acid position numbering of SEQ ID NO:71, of T127I, E133K, P218L, E264K, L266F, and/or L271F with reference to amino acid position numbering of SEQ ID NO:104, of T65I, E69K, P214L, and/or L216F with reference to amino acid position numbering of SEQ ID NO:138, of T102I, E105K, P190L, E236K, S237L, and/or L238F with reference to amino acid position numbering of SEQ ID NO:161, of S160L and/or L161F with reference to amino acid position numbering of SEQ ID NO:188 and/or an amino acid substitution of T172I, E178K, E325K, and/or L332F with reference to amino acid position numbering of SEQ ID NO:214. In some embodiments, a substitution of any one or more of the amino acid residues may be a substitution of one amino acid residue to about six amino acid residues in the HK polypeptide (e.g., 1, 2, 3, 4, 5, or 6 amino acid residues). In some embodiments, the at least one mutation may be a non-natural mutation.

An endogenous HK gene useful with this invention (e.g., an endogenous target gene) encodes a histidine kinase polypeptide and includes an endogenous HK1 gene, an endogenous HK2 gene, an endogenous HK3 gene, an endogenous HK4 gene, or an endogenous HK6 gene, which encode an HK1 polypeptide, an HK2 polypeptide, an HK3 polypeptide, an HK4 polypeptide, or an HK6 polypeptide, respectively. In some embodiments, an endogenous HK gene (e.g., endogenous target gene) (1) may comprise a nucleic acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:69, 70, 102, 103, 136, 137, 165, 166, 186, 187, 212 or 213, (2) may comprise a region having at least 80% sequence identity to any one of SEQ ID NOs:75-97, 108-123, 142-153, 165-177, or 192-208, (3) may encode a polypeptide having at least 80% sequence identity to any one of SEQ NOs:74, 107, 141, 164, or 191 and/or (4) may encode a region of a HK polypeptide having at least 80% sequence identity to any one of SEQ ID NOs:72-94, 105-120, 139-150, 162-174, 189-205 or 215-222.

In some embodiments, a plant (e.g., a corn plant, a soybean plant) comprising at least one (e.g., one or more) mutation, optionally wherein the least one mutation may be a non-natural mutation, in an endogenous HK gene exhibits one or more improved yield traits as compared to a plant devoid of the at least one mutation (e.g., an isogenic plant (e.g., wild type unedited plant (wild type for the target gene(s)) or a null segregant)). In some embodiments, the one or more improved yield traits include but are not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increase number of seeds, increased seed size, and/or increased seed weight (e.g., increase in 100-seed weight). In some embodiments, the one or more improved yield traits may include, but is not limited to, an increase in yield (bu/acre), seed size (including kernel size), seed weight (including kernel weight), increased kernel row number (optionally wherein ear length is not substantially reduced), increased number of pods, increased number of seeds per pod and an increase in ear length. In some embodiments a mutation in an endogenous HK gene as described herein may comprise a nucleic acid sequence having at least 90% (e.g., 90%, 91%, 92%, 93%, 94%, 95%, 96%, 97%, 98%, 99%, 99.5%. 99.9% or 100%) sequence identity to any one of SEQ ID NOs:244-259. In some embodiments, a plant, plant part or plant cell comprising a mutation in a HK gene may be soybean and mutated HK gene may comprise a nucleic acid sequence having at least 90% sequence identity to any one of SEQ ID NOs:244-246. In some embodiments, the plant, plant part or plant cell comprising a mutation in a HK gene may be corn and mutated HK gene may comprise a nucleic acid sequence having at least 90% sequence identity to any one of SEQ ID NOs:247-259.

In some embodiments, a plant may be regenerated from a plant part and/or plant cell of the invention comprising a mutation in a HK gene as described herein, wherein the regenerated plant comprises the mutation in the endogenous HK gene and a phenotype of improvement in one or more yield traits as compared to a plant devoid of the same mutation in the HK gene.

As used herein, the term "without substantially decreasing the length of the ears" or "ear length is not substantially reduced" refers to the length of an ear having increased kernel row number as a result of one or more mutations in one or more HK genes as described herein, wherein the length of the ear is not decreased by more than about 5, 6, 7, 8, 9, 10, 11, 12, 13, 14, 15, 16, 17, 18, 19, 20, 21, 22, 23, 24, 25, 26, 27, 28, 29, or 30% as compared to an ear of a plant devoid of the same mutation(s) in the same HK gene(s).

In some embodiments, a plant cell is provided, the plant cell comprising at least one (e.g., one or more) mutation within an endogenous Cytokinin Receptor Histidine Kinase (HK) gene, wherein the at least one mutation is a substitution, insertion, or deletion that is introduced using an editing system that comprises a nucleic acid binding domain that binds to a target site in the endogenous HK gene. In some embodiments, the substitution, insertion, or deletion results in, for example, an amino acid substitution. In some embodiments, the at least one mutation is a point mutation. In some embodiments, the at least one mutation within the HK gene is an insertion and/or a deletion, optionally the at least one mutation is an in-frame insertion or deletion. In some embodiments, the at least one mutation may be a non-natural mutation. In some embodiments a mutation in an endogenous HK gene as described herein may comprise a nucleic acid sequence having at least 90% (e.g., 90%, 91%, 92%, 93%, 94%, 95%, 96%, 97%, 98%, 99%, 99.5%. 99.9% or 100%) sequence identity to any one of SEQ ID NOs:244-259. In some embodiments, a plant, plant part or plant cell comprising a mutation in a HK gene may be soybean and mutated HK gene may comprise a nucleic acid sequence having at least 90% sequence identity to any one of SEQ ID NOs:244-246. In some embodiments, the plant, plant part or plant cell comprising a mutation in a HK gene may be corn and mutated HK gene may comprise a nucleic acid sequence having at least 90% sequence identity to any one of SEQ ID NOs:247-259.

In some embodiments, the target site in the HK gene of the plant cell is within a region of the endogenous HK gene, the region having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the nucleotide sequences of SEQ ID NOs:72-94, 105-120, 139-150, 162-174, 189-205 or 215-222. In some embodiments, the target site in the HK gene is within a region of the endogenous HK gene that encodes an amino acid sequence having at least 80% sequence identity to any one of SEQ ID NOs:97, 98, 100, 101, 127, 128, 130, 132-135, 155-158, 180, 181, 183-185 or 210.

In some embodiments, a mutation may be made following cleavage by an editing system that comprises a nuclease and a nucleic acid binding domain that binds to a target site within a sequence having least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a sequence encoding of any one of SEQ ID NOs:69, 70, 102, 103, 136, 137, 165, 166, 186, 187, 212 or 213, or a sequence having at least 80% sequence identity to a sequence encoding any one of SEQ ID NOs:72-94, 105-120, 139-150, 162-174, 189-205 or 215-222, optionally any one of SEQ ID NOs:97, 98, 100, 101, 127, 128, 130, 132-135, 155-158, 180, 181, 183-185 or 210, and at least one mutation within a HK gene is made following cleavage by the nuclease. In some embodiments, the at least one mutation results in a modified amino acid residue located: at position 172, 178, 325, and/or 332 with reference to amino acid position numbering of SEQ ID NO:71, at position 127, 133, 218, 264, 266, and/or 271 with reference to amino acid position numbering of SEQ ID NO:104, at position 65, 69, 214, and/or 216 with reference to amino acid position numbering of SEQ ID NO:138, at position 102, 105, 190, 236 and/or 238 with reference to amino acid position numbering of SEQ ID NO:161, at position 160 and/or 161 with reference to amino acid position numbering of SEQ ID NO:188, and/or at position 172, 178, 325, and/or 332 with reference to amino acid position numbering of SEQ ID NO:214, optionally wherein the substitution is threonine (T) to isoleucine (I) (T>I), glutamic acid (E) to lysine (K) (E>K), leucine (L) to phenylalanine (F) (L>F), proline (P) to leucine (L) (P>L), and/or serine (S) to leucine (L) (S>L). In some embodiments, the at least one mutation may be a non-natural mutation.

In some embodiments, the plant cell is regenerated into a plant that comprises the at least one mutation, optionally wherein the plant regenerated from the plant cell exhibits a phenotype of at least one (one or more) improved yield trait when compared to a wild-type plant not comprising/devoid of the allele (e.g., an isogenic wild type plant), optionally wherein the one or more improved yield traits includes, but is not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increase number of seeds, increased seed size, and/or increased seed weight (e.g., increase in 100-seed weight) as compared to a control plant devoid of the at least one mutation. In some embodiments, the one or more improved yield traits resulting from a mutation as described herein includes, but is not limited to, optionally an increase in yield (bu/acre), seed size (including kernel size), seed weight (including kernel weight), increased kernel row number (optionally wherein ear length is not substantially reduced), increased number of pods, increased number of seeds per pod and an increase in ear length as compared to a control plant devoid of the at least one mutation. In some embodiments, the at least one mutation may be a non-natural mutation. In some embodiments, a regenerated plant comprising a mutation in an endogenous HK gene as described herein may comprise a nucleic acid sequence having at least 90% sequence identity to any one of SEQ ID NOs:244-259. In some embodiments, the regenerated plant comprising a mutation in a HK gene may be soybean and mutated HK gene may comprise a nucleic acid sequence having at least 90% sequence identity to any one of SEQ ID NOs:244-246. In some embodiments, the regenerated plant comprising a mutation in a HK gene may be corn and mutated HK gene may comprise a nucleic acid sequence having at least 90% sequence identity to any one of SEQ ID NOs:247-259.

In some embodiments, a method of producing/breeding a transgene-free edited plant (e.g., a corn plant, a soybean plant) is provided, the method comprising: crossing a plant of the present invention (e.g., a plant comprising one or more mutations (e.g., one or more non-natural mutations) in one or more HK genes and having one or more improved yield traits) with a transgene free plant, thereby introducing the mutation into the plant that is transgene-free; and selecting a progeny plant that comprises the mutation and is transgene-free, thereby producing a transgene free edited plant.

Also provided herein is a method of providing a plurality of plants (e.g., corn plants, soybean plants) having one or more improved yield traits, the method comprising planting two or more plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more plants comprising one or more mutations (e.g., one or more non-natural mutations) in one or more HK genes and having one or more improved yield traits) in a growing area (e.g., a field (e.g., a cultivated field, an agricultural field), a growth chamber, a greenhouse, a recreational area, a lawn, and/or a roadside and the like), thereby providing a plurality of plants having one or more improved yield traits as compared to a plurality of control plants devoid of the mutation.

The invention further provides a method of generating variation in a region of a histidine kinase (HK) polypeptide (e.g., HK1, HK2, HK3, HK4, HK6), comprising: introducing an editing system into a plant cell, wherein the editing system is targeted to a region of a Cytokinin Receptor Histidine Kinase (HK) gene (e.g., HK1, HK2, HK3, HK4, HK6) that encodes the region of the HK polypeptide, and contacting the region of the HK gene with the editing system, thereby introducing a mutation into the HK gene and generating variation in the HK polypeptide of the plant cell. In some embodiments, the HK polypeptide is an HK1 polypeptide, an HK2 polypeptide, an HK3 polypeptide, an HK4 polypeptide, or an HK6 polypeptide and the HK gene is an HK1 gene, an HK2 gene, an HK3 gene, an HK4 gene, or an HK6 gene, and the encoded, respectively. In some embodiments, the HK gene comprises a nucleotide sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:69, 70, 102, 103, 136, 137, 165, 166, 186, 187, 212 or 213 and/or encodes an amino acid sequence having at least 80% sequence identity to any one of NOs:71, 104, 138, 161, 188 or 214, and the mutation is made following cleavage by the editing system that comprises a nuclease and a nucleic acid binding domain that binds to a target site within a sequence having at least 80% sequence identity to any one of the nucleotide sequences of SEQ ID NOs:69, 70, 102, 103, 136, 137, 165, 166, 186, 187, 212 or 213. In some embodiments, a mutation in the HK gene that generates variation in the encoded polypeptide may be located adjacent to and/or within a region of the HK gene encoding the extracellular cytokinin binding domain of the HK polypeptide. For example, a mutation for generating variation in the HK polypeptide may be located in a region of the gene that is immediately 5' to the region encoding the extracellular cytokinin binding domain. In some embodiments, the mutation may be comprised within the region of the HK gene that encodes the extracellular cytokinin binding domain. In some embodiments, the variation that is generated in a BBB gene as described herein results in a nucleic acid sequence having at least 90% sequence identity to any one of SEQ ID NOs:244-259.

In some embodiments, the region of the HK gene that is targeted for generating variation in an HK polypeptide comprises at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:72-94, 105-120, 139-150, 162-174, 189-205 or 215-222, optionally comprises at least 80% sequence identity to any one of SEQ ID NOs:77-89, 91-94, 107-118, 144-148, 163-173, 192-203 or 215-222. In some embodiments, the region of the HK polypeptide in which variation is generated comprises an amino acid sequence having at least 80% sequence identity to any one of SEQ ID NOs:95-101, 121-135, 151-158, 175-185 or 206-211, optionally having at least 80% sequence identity to any one of SEQ ID NOs:97, 98, 100, 101, 127, 128, 130, 132-135, 155-158, 180, 181, 183-185 or 210.

In some embodiments, a method for editing a specific site in the genome of a plant cell is provided, the method comprising: cleaving, in a site-specific manner, a target site within an endogenous Cytokinin Receptor Histidine Kinase (HK) gene (e.g., HK1, HK2, HK3, HK4, HK6) in the plant cell, the endogenous HK gene: (a) comprising a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the nucleotide sequences of SEQ ID NOs:69, 70, 102, 103, 136, 137, 165, 166, 186, 187, 212 or 213, (b) comprising a region having at least 80% sequence identity to any one of the nucleotide sequences of SEQ ID NOs:72-94, 105-120, 139-150, 162-174, 189-205 or 215-222, (c) encoding an amino acid sequence having at least 80% sequence identity to any one of SEQ ID NOs:71, 104, 138, 161, 188 or 214, (d) encoding a region having at least 80% sequence identity to an amino acid sequence of any one of SEQ ID NOs:95-101, 121-135, 151-158, 175-185 or 206-211, thereby generating an edit in the endogenous HK gene of the plant cell and producing a plant cell comprising the edit in the endogenous HK gene.

In some embodiments, the endogenous HK gene is an endogenous HK1 gene, an endogenous HK2 gene, an endogenous HK3 gene, an endogenous HK4 gene, or an endogenous HK6 gene from a plant, optionally a soybean plant or a corn plant.

In some embodiments, the edit results in a mutation, optionally a non-natural mutation, that includes but is not limited to a deletion, substitution, or insertion. In some embodiments, the edit may be a nucleotide substitution of a C to an A or a T, a G to an A, and/or a T to a C. In some embodiments, an edit results in variation of amino acids in the coding region of the HK polypeptide, optionally in or adjacent to the extracellular cytokinin binding domain of the HK polypeptide. As an example, an edit may result in variation in a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) identity to any one of SEQ ID NOs:95-101, 121-135, 151-158, 175-185 or 206-211, optionally having at least 80% sequence identity to any one of SEQ ID NOs:97, 98, 100, 101, 127, 128, 130, 132-135, 155-158, 180, 181, 183-185 or 210. In some embodiments, the edit produces an amino acid substitution in a HK polypeptide of a threonine (T) to isoleucine (I) (T>I), glutamic acid (E) to lysine (K) (E>K), leucine (L) to phenylalanine (F) (L>F), proline (P) to leucine (L) (P>L), and/or serine (S) to leucine (L) (S>L). In some embodiments, an edit as described herein results in a mutated HK gene comprising a nucleic acid sequence having at least 90% sequence identity to any one of SEQ ID NOs:244-259.

In some embodiments, a method of editing may further comprise regenerating a plant from the plant cell comprising the edit in the endogenous HK gene, thereby producing a plant comprising the edit in its endogenous HK gene and having a phenotype of one or more improved yield traits when compared to a control plant that is devoid of the edit. In some embodiments, a regenerated plant may comprise a mutated HK gene as described herein, optionally wherein the mutated HK gene comprises a nucleic acid sequence having at least 90% sequence identity to any one of SEQ ID NOs:244-259. In some embodiments, the regenerated plant comprising a mutation in a HK gene is a soybean plant and mutated HK gene comprises a nucleic acid sequence having at least 90% sequence identity to any one of SEQ ID NOs:244-246. In some embodiments, the regenerated plant comprising a mutation in a HK gene is a corn plant and mutated HK gene comprises a nucleic acid sequence having at least 90% sequence identity to any one of SEQ ID NOs:247-259.

In some embodiments, a method for making a plant is provided, the method comprising (a) contacting a population of plant cells comprising an endogenous Cytokinin Receptor Histidine Kinase (HK) gene (e.g., HK1, HK2, HK3, HK4, HK6) with a nuclease linked to a nucleic acid binding domain (e.g., editing system) that binds to a sequence (a) having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213, (b) encoding an amino acid sequence having at least 80% sequence identity to any one of SEQ ID NOs: NOs:71, 104, 138, 161, 188 or 214, (c) encoding an amino acid sequence comprising a region having at least 80% sequence identity to any one of SEQ ID NOs:95-101, 121-135, 151-158, 175-185 or 206-211, and/or (d) comprising a region having at least 80% identity to any one of SEQ ID NOs:72-94, 105-120, 139-150, 162-174, 189-205 or 215-222; (b) selecting a plant cell from the population in which an endogenous HK gene has been mutated, thereby producing a plant cell comprising a mutation in the endogenous HK gene; and (c) growing the selected plant cell into a plant. In some embodiments, the plant that is produced comprises a mutated HK gene comprising a nucleic acid sequence having at least 90% sequence identity to any one of SEQ ID NOs:244-259. In some embodiments, the plant comprising a mutation in a HK gene is a soybean plant and mutated HK gene comprises a nucleic acid sequence having at least 90% sequence identity to any one of SEQ ID NOs:244-246. In some embodiments, the plant comprising a mutation in a HK gene is a corn plant and mutated HK gene comprises a nucleic acid sequence having at least 90% sequence identity to any one of SEQ ID NOs:247-259.

In some embodiments, a method of improving one or more yield traits in a plant is provided, the method comprising (a) contacting a plant cell comprising an endogenous Cytokinin Receptor Histidine Kinase (HK) gene (e.g., HK1, HK2, HK3, HK4, HK6) with a nuclease targeting the endogenous HK gene, wherein the nuclease is linked to a nucleic acid binding domain (e.g., editing system) that binds to a target site in the endogenous HK gene, wherein the endogenous HK gene: (i) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (ii) comprises a region having at least 80% identity to any one of SEQ ID NOs:72-94, 105-120, 139-150, 162-174, 189-205 or 215-222; (iii) encodes an amino acid sequence having at least 80% sequence identity to any one of SEQ ID NOs: NOs:71, 104, 138, 161, 188 or 214; and/or (iv) encodes an amino acid sequence comprising a region having at least 80% identity to any one of SEQ ID NOs:95-101, 121-135, 151-158, 175-185 or 206-211 to produce a plant cell comprising a mutation in the endogenous HK gene; and (b) growing the plant cell into a plant comprising the mutation in the endogenous HK gene, thereby producing a plant have a mutated endogenous HK gene and one or more improved yield traits. In some embodiments, the plant having one or more improved yield traits comprises a mutated endogenous HK gene having at least 90% sequence identity to any one of SEQ ID NOs: 244-259. In some embodiments, the plant having one or more improved yield traits and comprising a mutated HK gene is a soybean plant and the HK gene comprises a nucleic acid sequence having at least 90% sequence identity to any one of SEQ ID NOs:244-246. In some embodiments, the plant having one or more improved yield traits and comprising a mutated HK gene is a corn plant and the HK gene comprises a nucleic acid sequence having at least 90% sequence identity to any one of SEQ ID NOs:247-259.

In some embodiments, a method for producing a plant or part thereof comprising at least one cell having a mutated endogenous Cytokinin Receptor Histidine Kinase (HK) gene (e.g., HK1, HK2, HK3, HK4, HK6), the method comprising contacting a target site in an endogenous HK gene in the plant or plant part with a nuclease comprising a cleavage domain and a nucleic acid binding domain, wherein the nucleic acid binding domain binds to a target site in the endogenous HK gene, wherein the endogenous HK gene (a) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs: NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211, thereby producing the plant or part thereof comprising at least one cell having a mutation in the endogenous HK gene. In some embodiments, the plant or part thereof comprising at least one cell and having a mutation in the endogenous HK gene comprises a mutated HK gene having at least 90% sequence identity to any one of SEQ ID NOs:244-259. In some embodiments, the plant or part thereof comprising at least one cell with a mutated HK gene is a soybean plant and the mutated HK gene comprises a nucleic acid sequence having at least 90% sequence identity to any one of SEQ ID NOs:244-246. In some embodiments, the plant or part thereof comprising at least one cell with a mutated HK gene is a corn plant and the mutated HK gene comprises a nucleic acid sequence having at least 90% sequence identity to any one of SEQ ID NOs:247-259.

Also provided herein is a method for producing a plant or part thereof comprising a mutated Cytokinin Receptor Histidine Kinase (HK) gene (e.g., HK1, HK2, HK3, HK4, HK6) and exhibiting one or more improved yield traits, the method comprising contacting a target site in an endogenous HK gene in the plant or plant part with a nuclease comprising a cleavage domain and a nucleic acid binding domain, wherein the nucleic acid binding domain binds to a target site in the endogenous HK gene, wherein the endogenous HK gene (a) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs: NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211, thereby producing the plant or part thereof comprising an endogenous HK gene having a mutation and exhibiting one or more improved yield traits. In some embodiments, the one or more improved yield traits includes, but is not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increase number of seeds, increased seed size, and/or increased seed weight (e.g., increase in 100-seed weight), optionally wherein the one or more improved yield traits may be, for example, an increase in yield (bu/acre), seed size (including kernel size), seed weight (including kernel weight), increased kernel row number (optionally wherein ear length is not substantially reduced), increased number of pods, increased number of seeds per pod and an increase in ear length, as compared to a control plant devoid of the at least one mutation. In some embodiments, the plant or part thereof comprising a mutated endogenous HK gene as described herein comprises a nucleic acid sequence having at least 90% sequence identity to any one of SEQ ID NOs:244-259. In some embodiments, the plant or part thereof comprising a mutated endogenous HK gene as described herein is a soybean plant and mutated HK gene comprises a nucleic acid sequence having at least 90% sequence identity to any one of SEQ ID NOs:244-246. In some embodiments, the plant or part thereof comprising a mutated endogenous HK gene as described herein is a corn plant and mutated HK gene comprises a nucleic acid sequence having at least 90% sequence identity to any one of SEQ ID NOs:247-259.

In some embodiments, a nuclease may cleave an endogenous HK gene, thereby introducing the mutation into the endogenous HK gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, any nucleic acid binding domain useful with the invention may be any DNA binding domain or RNA binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a nucleic acid binding domain (e.g., DNA binding domain) is comprised in a nucleic acid binding polypeptide. A "nucleic acid binding protein" or "nucleic acid binding polypeptide" as used herein refers to a polypeptide that binds and/or is capable of binding a nucleic acid in a site- and/or sequence-specific manner. In some embodiments, a nucleic acid binding polypeptide may be a sequence-specific nucleic acid binding polypeptide (e.g., a sequence-specific DNA binding domain) such as, but not limited to, a sequence-specific binding polypeptide and/or domain from, for example, a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein. In some embodiments, a nucleic acid binding polypeptide comprises a cleavage polypeptide (e.g., a nuclease polypeptide and/or domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding polypeptide associates with and/or is capable of associating with (e.g., forms a complex with) one or more nucleic acid molecule(s) (e.g., forms a complex with a guide nucleic acid as described herein) that can direct or guide the nucleic acid binding polypeptide to a specific target nucleotide sequence (e.g., a gene locus of a genome) that is complementary to the one or more nucleic acid molecule(s) (or a portion or region thereof), thereby causing the nucleic acid binding polypeptide to bind to the nucleotide sequence at the specific target site. In some embodiments, the nucleic acid binding polypeptide is a CRISPR-Cas effector protein as described herein. In some embodiments, reference is made to specifically to a CRISPR-Cas effector protein for simplicity, but a nucleic acid binding polypeptide as described herein may be used. In some embodiments, a polynucleotide and/or a nucleic acid construct of the invention can be an "expression cassette" or can be comprised within an expression cassette.

In some embodiments, a method of editing an endogenous Cytokinin Receptor Histidine Kinase (HK) gene in a plant or plant part is provided, the method comprising contacting a target site in an endogenous HK gene in the plant or plant part with a cytosine base editing system comprising a cytosine deaminase and a nucleic acid binding domain that binds to a target site in the endogenous HK gene, wherein the endogenous HK gene: (a) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs: NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211, thereby editing the endogenous HK gene in the plant or part thereof and producing a plant or part thereof comprising at least one cell having a mutation in the endogenous HK gene.

In some embodiments, a method of editing an endogenous Cytokinin Receptor Histidine Kinase (HK) gene (e.g., HK1, HK2, HK3, HK4, HK6) in a plant or plant part is provided, the method comprising contacting a target site in an HK gene in the plant or plant part with an adenosine base editing system comprising an adenosine deaminase and a nucleic acid binding domain that binds to a target site in the HK gene, wherein the HK gene (a) comprises a sequence having at least 80% sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs: NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211, thereby editing the endogenous HK gene in the plant or part thereof and producing a plant or part thereof comprising at least one cell having a mutation in the endogenous HK gene.

In some embodiments, a method of creating a mutation in an Cytokinin Receptor Histidine Kinase (HK) gene (e.g., HK1, HK2, HK3, HK4, HK6) in a plant is provided, comprising: (a) targeting a gene editing system to a portion of the HK gene that (i) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:72-94, 105-120, 139-150, 162-174, 189-205 or 215-222; and/or (ii) encodes a sequence having at least 80% identity to any one of SEQ ID NOs:95-101, 121-135, 151-158, 175-185 or 206-211, and (b) selecting a plant that comprises a modified amino acid residue located in a region of the HK gene encoding an amino acid sequence having at least 80% sequence identity to any one of SEQ ID NOs:95-101, 121-135, 151-158, 175-185 or 206-211, optionally located in a region of the HK gene encoding an amino acid sequence having at least 80% sequence identity to any one of SEQ ID NOs:97, 98, 100, 101, 127, 128, 130, 132-135, 155-158, 180, 181, 183-185 or 210, optionally wherein the modification may be a substitution at position 172, 178, 325, and/or 332 with reference to amino acid position numbering of SEQ ID NO:71, at position 127, 133, 218, 264, 266, and/or 271 with reference to amino acid position numbering of SEQ ID NO:104, at position 65, 69, 214, and/or 216 with reference to amino acid position numbering of SEQ ID NO:138, at position 102, 105, 190, 236 and/or 238 with reference to amino acid position numbering of SEQ ID NO:161, at position 160 and/or 161 with reference to amino acid position numbering of SEQ ID NO:188, and/or at position 172, 178, 325, and/or 332 with reference to amino acid position numbering of SEQ ID NO:214. In some embodiments, when the amino acid modification is an amino acid substitution, the substitution is threonine (T) to isoleucine (I) (T>I), glutamic acid (E) to lysine (K) (E>K), leucine (L) to phenylalanine (F) (L>F), proline (P) to leucine (L) (P>L), and/or serine (S) to leucine (L) (S>L). In some embodiments, the selected plant comprises an amino acid substitution: of T172, E178K, E325K, and/or L332 with reference to amino acid position numbering of SEQ ID NO:71, of T127, E133, P218, E264, L266, and/or L271 with reference to amino acid position numbering of SEQ ID NO:104, of T65, E69, P214, and/or L216 with reference to amino acid position numbering of SEQ ID NO:138, of T102, E105, P190, E236 S237, and/or L238 with reference to amino acid position numbering of SEQ ID NO:161, of S160 and/or L161 with reference to amino acid position numbering of SEQ ID NO:188 and/or of T172, E178K, E325K, and/or L332 with reference to amino acid position numbering of SEQ ID NO:214, optionally an amino acid substitution of T172I, E178K, E325K, and/or L332F with reference to amino acid position numbering of SEQ ID NO:71, of T127I, E133K, P218L, E264K, L266F, and/or L271F with reference to amino acid position numbering of SEQ ID NO:104, of T65I, E69K, P214L, and/or L216F with reference to amino acid position numbering of SEQ ID NO:138, of T102I, E105K, P190L, E236K, S237L, and/or L238F with reference to amino acid position numbering of SEQ ID NO:161, of S160L and/or L161F with reference to amino acid position numbering of SEQ ID NO:188 and/or an amino acid substitution of T172I, E178K, E325K, and/or L332F with reference to amino acid position numbering of SEQ ID NO:214. In some embodiments, the mutation in a HK gene may comprise a nucleic acid sequence having at least 90% sequence identity to any one of SEQ ID NOs: 244-259.

A mutation provided by methods of the invention is a mutation, optionally the mutation may be a non-natural mutation. In some embodiments, the mutation may be a substitution, an insertion and/or a deletion, optionally wherein the insertion or deletion is an in-frame insertion or in-frame deletion. In some embodiments, the mutation may be a deletion of about 1 base pair to about 27 consecutive base pairs, optionally a deletion of a 3, 6, 9, 12, 15, 18, 21, 24, or 27 consecutive base pairs. In some embodiments, a deletion of a 3, 6, 9, 12, 15, 18, 21, 24, or 27 consecutive base pairs results in a deletion of one to about nine consecutive amino acid residues from an HK polypeptide (e.g., HK1, HK2, HK3, HK4, HK6). In some embodiments, the mutation is in an HK extracellular cytokinin binding domain encoded by the endogenous HK gene, optionally wherein the mutation in an HK gene is located adjacent to and/or within a region of the HK gene encoding the extracellular cytokinin binding domain of the HK polypeptide. For example, a mutation in the HK gene may be located immediately 5' to the region encoding the extracellular cytokinin binding domain. In some embodiments, the mutation may be located within the region of the HK gene that encodes the extracellular cytokinin binding domain. In some embodiments, the extracellular cytokinin binding domain of the HK polypeptide encoded by the HK gene is located a region of the HK gene having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:72-94, 105-120, 139-150, 162-174, 189-205 or 215-222. In some embodiments, the extracellular cytokinin binding domain of the HK polypeptide is located a region of the HK polypeptide having at least 80% sequence identity to any one of SEQ ID NOs:95-101, 121-135, 151-158, 175-185 or 206-211. In some embodiments, the mutation in a HK gene may comprise a nucleic acid sequence having at least 90% sequence identity to any one of SEQ ID NOs:244-259.

In some embodiments, the mutation results in a modified amino acid residue is located in a region of the HK polypeptide having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:95-101, 121-135, 151-158, 175-185 or 206-211, optionally located in a region having at least 80% sequence identity to any one of the amino acid sequences of SEQ ID NOs:97, 98, 100, 101, 127, 128, 130, 132-135, 155-158, 180, 181, 183-185 or 210. In some embodiments, the mutation results in a modified amino acid residue at position 172, 178, 325, and/or 332 with reference to amino acid position numbering of SEQ ID NO:71, at position 127, 133, 218, 264, 266, and/or 271 with reference to amino acid position numbering of SEQ ID NO:104, at position 65, 69, 214, and/or 216 with reference to amino acid position numbering of SEQ ID NO:138, at position 102, 105, 190, 236 and/or 238 with reference to amino acid position numbering of SEQ ID NO:161, at position 160 and/or 161 with reference to amino acid position numbering of SEQ ID NO:188, and/or at position 172, 178, 325, and/or 332 with reference to amino acid position numbering of SEQ ID NO:214. In some embodiments, the modification is a substitution of one or more amino acids, optionally threonine (T) to isoleucine (I) (T>I), glutamic acid (E) to lysine (K) (E>K), leucine (L) to phenylalanine (F) (L>F), proline (P) to leucine (L) (P>L), and/or serine (S) to leucine (L) (S>L). In some embodiments, the modification is an amino acid substitution of T172, E178K, E325K, and/or L332 with reference to amino acid position numbering of SEQ ID NO:71, of T127, E133, P218, E264, L266, and/or L271 with reference to amino acid position numbering of SEQ ID NO:104, of T65, E69, P214, and/or L216 with reference to amino acid position numbering of SEQ ID NO:138, of T102, E105, P190, E236 S237, and/or L238 with reference to amino acid position numbering of SEQ ID NO:161, of S160 and/or L161 with reference to amino acid position numbering of SEQ ID NO:188 and/or of T172, E178K, E325K, and/or L332 with reference to amino acid position numbering of SEQ ID NO:214, optionally the amino acid substitution may be T172I, E178K, E325K, and/or L332F with reference to amino acid position numbering of SEQ ID NO:71, of T127I, E133K, P218L, E264K, L266F, and/or L271F with reference to amino acid position numbering of SEQ ID NO:104, of T65I, E69K, P214L, and/or L216F with reference to amino acid position numbering of SEQ ID NO:138, of T102I, E105K, P190L, E236K, S237L, and/or L238F with reference to amino acid position numbering of SEQ ID NO:161, of S160L and/or L161F with reference to amino acid position numbering of SEQ ID NO:188 and/or an amino acid substitution of T172I, E178K, E325K, and/or L332F with reference to amino acid position numbering of SEQ ID NO:214. In some embodiments, the at least one mutation may be a non-natural mutation.

In some embodiments, a method of detecting a mutant Cytokinin Receptor Histidine Kinase (HK) gene (e.g., HK1, HK2, HK3, HK4, HK6) is provided, the method comprising detecting in the genome of a plant an endogenous HK gene encoding a HK polypeptide comprising a mutation in an extracellular cytokinin binding domain, optionally wherein the extracellular cytokinin binding domain is located in a region of the HK polypeptide having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the amino acid sequences of SEQ ID NOs:95-101, 121-135, 151-158, 175-185 or 206-211. In some embodiments, a method of detecting a mutant HK gene is provided, the method comprising detecting in the genome of a plant a nucleic acid encoding the amino acid sequence of any one of SEQ ID NOs:71, 104, 138, 161, 188 or 214, wherein the amino acid sequence of any one of SEQ ID NOs:71, 104, 138, 161, 188 or 214 comprises a mutation in one or more of the amino acid residues located in a region of the HK polypeptide having at least 80% sequence identity to any one of SEQ ID NOs:95-101, 121-135, 151-158, 175-185 or 206-211, optionally located in a region having at least 80% sequence identity to any one of the amino acid sequences of SEQ ID NOs:97, 98, 100, 101, 127, 128, 130, 132-135, 155-158, 180, 181, 183-185 or 210. In some embodiments, the mutation is the result of a nucleotide substitution of C to an A or a T, a G to an A, and/or a T to a C. In some embodiments, a mutated HK polypeptide comprises at least one mutation comprising a substitution of threonine (T) to isoleucine (I) (T>I), glutamic acid (E) to lysine (K) (E>K), leucine (L) to phenylalanine (F) (L>F), proline (P) to leucine (L) (P>L), and/or serine (S) to leucine (L) (S>L).

In some embodiments, the present invention provides a method of producing a plant comprising a mutation in an endogenous Cytokinin Receptor Histidine Kinase (HK) gene (e.g., HK1, HK2, HK3, HK4, HK6) and at least one polynucleotide of interest, the method comprising crossing a plant of the invention comprising at least one mutation in an endogenous HK gene (a first plant) with a second plant that comprises the at least one polynucleotide of interest to produce progeny plants; and selecting progeny plants comprising at least one mutation in the HK gene and the at least one polynucleotide of interest, thereby producing the plant comprising a mutation in an endogenous HK gene and at least one polynucleotide of interest.

The present invention further provides a method of producing a plant comprising a mutation in an endogenous HK gene and at least one polynucleotide of interest, the method comprising introducing at least one polynucleotide of interest into a plant of the present invention comprising at least one mutation in a HK gene, thereby producing a plant comprising at least one mutation in a HK gene and at least one polynucleotide of interest. In some embodiments, the plant is a corn plant. In some embodiments, the plant is a soybean plant.

In some embodiments, also provided is a method of producing a plant comprising a mutation in an endogenous HK gene and exhibiting a phenotype of improved yield traits, improved plant architecture and/or improved defense traits, the method comprising crossing a first plant, which is a plant of the present invention comprising at least one mutation in a HK gene, with a second plant that exhibits a phenotype of improved yield traits, improved plant architecture and/or improved defense traits; and selecting progeny plants comprising the mutation in the HK gene and a phenotype of improved yield traits, improved plant architecture and/or improved defense traits, thereby producing the plant comprising a mutation in an endogenous HK gene and exhibiting a phenotype of improved yield traits, improved plant architecture and/or improved defense traits as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) plants of the invention (e.g., a plant comprising at least one mutation in an HK gene (e.g., HK1, HK2, HK3, HK4, HK6) as described herein, optionally wherein the mutation may be a non-natural mutation) growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, the method comprising applying an insecticide to one or more plants of the invention, optionally, wherein the one or more plants are growing in a container, a growth chamber, a greenhouse, a field, a recreational area, a lawn, or on a roadside, thereby reducing insect predation on the one or more plants.

In some embodiments, a method of reducing fungal disease on a plant is provided, the method comprising applying a fungicide to one or more plants of the invention, optionally, wherein the one or more plants are growing in a container, a growth chamber, a greenhouse, a field, a recreational area, a lawn, or on a roadside, thereby reducing fungal disease on the one or more plants.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, nematode resistance, disease resistance, increased yield, increased nutrient use efficiency or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the Cry1A, CryIAb, CryIAc, CryIIA, CryIIIA, CryIIIB2, Cry9c Cry2Ab, Cry3Bb and CryIF proteins or toxic fragments thereof and also hybrids or combinations thereof, especially the Cry1F protein or hybrids derived from a Cry1F protein (e.g. hybrid Cry1A-Cry1F proteins or toxic fragments thereof), the Cry1A-type proteins or toxic fragments thereof, preferably the Cry1Ac protein or hybrids derived from the Cry1Ac protein (e.g. hybrid Cry1Ab-Cry1Ac proteins) or the Cry1Ab or Bt2 protein or toxic fragments thereof, the Cry2Ae, Cry2Af or Cry2Ag proteins or toxic fragments thereof, the Cry1A.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93(11):5389-94, the Cry proteins as described in WO2001/47952, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g., WO2007/024782), a mutated *Arabidopsis* ALS/AHAS gene (e.g., U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV- GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480)); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLINl (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control—herbicide tolerance, deposited as PTA-11507, described in WO2011/084632), Event 4114 (corn, insect control—herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

A Cytokinin Receptor Histidine Kinase (HK) gene useful with this invention includes any HK gene in which a mutation as described herein can confer improvement in one or more yield traits in a plant or part thereof comprising the mutation. In some embodiments, an endogenous HK gene (a) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211.

In some embodiments, the at least one mutation, optionally wherein the at least one mutation may be a non-natural mutation, in an endogenous HK gene in a plant may be a base substitution, a base deletion and/or a base insertion. In some embodiments, the at least one mutation in an endogenous HK gene in a plant may result in a plant having the phenotype of one or more improved yield traits as compared to a control plant devoid of the edit/mutation, optionally wherein the improved yield trait can include but is not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increase number of seeds, increased seed size, and/or increased seed weight (e.g., increase in 100-seed weight). In some embodiments, the one or more improved yield traits includes, but not limited to, an increase in yield (bu/acre), seed size (including kernel size), seed weight (including kernel weight), increased kernel row number (optionally wherein ear length is not substantially reduced), increased number of pods, increased number of seeds per pod and an increase in ear length. In some embodiments, a mutation in an endogenous HK gene may be a base substitution, a base deletion and/or a base insertion of at least 1 nucleotide to about 27 nucleotides (e.g., about 1, 2, 3, 4, 5, 6, 7, 8, 9, 10, 11, 12, 13, 14, 15, 16, 17, 18, 19, 20, 21, 22, 23, 24, 25, 26, or 27 nucleotides, or any range or value therein), optionally where the mutation may result in a substitution, a deletion and/or an insertion of one or more amino acid residues, optionally one amino acid residue to about nine consecutive amino acid residues (e.g., 1, 2, 3, 4, 5, 6, 7, 8, or 9 consecutive amino acid residues) of the HK polypeptide. In some embodiments, the at least one mutation may be a base substitution to an A, a T, a G, or a C. In some embodiments, the at least one mutation may be, for example, a base substitution to from C to an A or a T, a G to an A, and/or a T to a C. A mutation may be a point mutation. In some embodiments, the mutation may result in a substitution of one or more amino acid residues located in a region having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the amino acid sequences of SEQ ID NOs:97, 98, 100, 101, 127, 128, 130, 132-135, 155-158, 180, 181, 183-185 or 210, optionally the mutation may result in a substitution of an amino acid residue located: at position 172, 178, 325, and/or 332 with reference to amino acid position numbering of SEQ ID NO:71, at position 127, 133, 218, 264, 266, and/or 271 with reference to amino acid position numbering of SEQ ID NO:104, at position 65, 69, 214, and/or 216 with reference to amino acid position numbering of SEQ ID NO:138, at position 102, 105, 190, 236 and/or 238 with reference to amino acid position numbering of SEQ ID NO:161, at position 160 and/or 161 with reference to amino acid position numbering of SEQ ID NO:188, and/or at position 172, 178, 325, and/or 332 with reference to amino acid position numbering of SEQ ID NO:214. In some embodiments, a substitution may be a substitution of threonine (T) for isoleucine (I) (T>I), glutamic acid (E) for lysine (K) (E>K), leucine (L) for phenylalanine (F) (L>F), proline (P) for leucine (L) (P>L), and/or serine (S) for leucine (L) (S>L). In some embodiments, a mutation may result in an amino acid substitution of T172, E178K, E325K, and/or L332 with reference to amino acid position numbering of SEQ ID NO:71, of T127, E133, P218, E264, L266, and/or L271 with reference to amino acid position numbering of SEQ ID NO:104, of T65, E69, P214, and/or L216 with reference to amino acid position numbering of SEQ ID NO:138, of T102, E105, P190, E236 S237, and/or L238 with reference to amino acid position numbering of SEQ ID NO:161, of S160 and/or L161 with reference to amino acid position numbering of SEQ ID NO:188 and/or of T172, E178K, E325K, and/or L332 with reference to amino acid position numbering of SEQ ID NO:214, optionally the amino acid substitution may be T172I, E178K, E325K, and/or L332F with reference to amino acid position numbering of SEQ ID NO:71, of T127I, E133K, P218L, E264K, L266F, and/or L271F with reference to amino acid position numbering of SEQ ID NO:104, of T65I, E69K, P214L, and/or L216F with reference to amino acid position numbering of SEQ ID NO:138, of T102I, E105K, P190L, E236K, S237L, and/or L238F with reference to amino acid position numbering of SEQ ID NO:161, of S160L and/or L161F with reference to amino acid position numbering of SEQ ID NO:188 and/or an amino acid substitution of T172I, E178K, E325K, and/or L332F with reference to amino acid position numbering of SEQ ID NO:214. In some embodiments, the mutation in a HK gene may comprise a nucleic acid sequence having at least 90% sequence identity to any one of SEQ ID NOs:244-259.

In some embodiments, a mutation in an endogenous HK gene may be made following cleavage by an editing system that comprises a nuclease and a nucleic acid binding domain that binds to a target site within a target nucleic acid (e.g., a HK gene), the target nucleic acid comprising a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the nucleotide sequences of SEQ ID NOs:69, 70, 102, 103, 136, 137, 165, 166, 186, 187, 212 or 213, and/or encoding an amino acid sequence having at least 80% sequence identity to any one of SEQ ID NOs:71, 104, 138, 161, 188 or 214, optionally wherein the target site is located in a region of the HK gene: the region comprising a sequence having at least 80% identity to any one of SEQ ID NOs:72-94, 105-120, 139-150, 162-174, 189-205 or 215-222 and/or encoding a sequence having at least 80% sequence identity to an amino acid sequence of any one of SEQ ID NOs:95-101, 121-135, 151-158, 175-185 or 206-211.

Further provided are guide nucleic acids (e.g., gRNA, gDNA, crRNA, crDNA) that bind to a target site in a Cytokinin Receptor Histidine Kinase (HK) gene (HK1, HK2, HK3, HK4, HK6), wherein the target site is in a region of the HK gene having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the nucleotide sequences of SEQ ID NOs:72-94, 105-120, 139-150, 162-174, 189-205 or 215-222. In some embodiments, the guide nucleic acid comprises a spacer comprising any one of the nucleotide sequences of SEQ ID NOs:223-235 or SEQ ID NOs:236-243.

In some embodiments, a corn plant or plant part thereof is provided comprising at least one mutation in at least one endogenous Cytokinin Receptor Histidine Kinase (HK) gene having the gene identification number (gene ID) of Zm00001d014297, Zm00001d017977, and/or Zm00001d051812, optionally wherein the at least one mutation may be a non-natural mutation. In some embodiments, the mutation in a HK gene of a corn plant or part thereof may comprise a nucleic acid sequence having at least 90% sequence identity to any one of SEQ ID NOs:247-259.

In some embodiments, a soybean plant or plant part thereof is provided comprising at least one mutation in at least one Cytokinin Receptor Histidine Kinase (HK) gene having the gene identification number (gene ID) of Glyma05G148100 (HK2), Glyma08G105000 (HK3) and/or Glyma07G173700 (HK4), optionally wherein the at least one mutation may be a non-natural mutation. In some embodiments, the mutation in a HK gene of a soybean plant or part thereof may comprise a nucleic acid sequence having at least 90% sequence identity to any one of SEQ ID NOs:244-246.

In some embodiments, a guide nucleic acid is provided that binds to a target nucleic acid in a Cytokinin Receptor Histidine Kinase (HK) gene having the gene identification number (gene ID) of Zm00001d014297, Zm00001d017977, Zm00001d051812, Glyma05G148100, Glyma08G105000, and/or Glyma07G173700.

In some embodiments, a system is provided comprising a guide nucleic acid comprising a spacer (e.g., one or more spacers) having the nucleotide sequence of any one of SEQ ID NOs:223-235 or SEQ ID NOs:236-243, and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The invention further provides a gene editing system comprising a CRISPR-Cas effector protein in association with a guide nucleic acid and the guide nucleic acid comprises a spacer sequence that binds to a Cytokinin Receptor Histidine Kinase (HK) gene, optionally wherein the HK gene (a) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211. In some embodiments, a spacer sequence of the guide nucleic acid may comprise the nucleotide sequence of any of SEQ ID NOs:223-243. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising a CRISPR-Cas effector protein comprising a cleavage domain and a guide nucleic acid, wherein the guide nucleic acid binds to a target site in an endogenous Cytokinin Receptor Histidine Kinase (HK) gene, wherein the endogenous HK gene: (a) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211, and the cleavage domain cleaves a target strand in the HK gene.

In some embodiments, an expression cassette(s) is/are provided that comprise (a) a polynucleotide encoding CRISPR-Cas effector protein comprising a cleavage domain and (b) a guide nucleic acid that binds to a target site in an endogenous Cytokinin Receptor Histidine Kinase (HK) gene, wherein the guide nucleic acid comprises a spacer sequence that is complementary to and binds to (i) a portion of a nucleic acid having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of the nucleotide sequences of SEQ ID NOs:69, 70, 102, 103, 136, 137, 165, 166, 186, 187, 212 or 213; (ii) a portion of a nucleic acid having at least 80% sequence identity to any one of SEQ ID NOs:72-94, 105-120, 139-150, 162-174, 189-205 or 215-222; (iii) a portion of a nucleic acid encoding an amino acid sequence having at least 80% sequence identity to any one of SEQ ID NOs:71, 104, 138, 161, 188 or 214; and/or (iv) a portion of a nucleic acid encoding an amino acid sequence having at least 80% identity to any one of SEQ ID NOs:95-101, 121-135, 151-158, 175-185 or 206-211.

In some embodiments a modified histidine kinase (HK) polypeptide (HK1, HK2, HK3, HK4, HK6) is provided comprising a mutation in an amino acid residue located in a region of the HK polypeptide comprising an amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:95-101, 121-135, 151-158, 175-185 or 206-211, optionally in a region of the HK polypeptide comprising an amino acid sequence having at least 80% sequence identity to any one of SEQ ID NOs:97, 98, 100, 101, 127, 128, 130, 132-135, 155-158, 180, 181, 183-185 or 210, optionally the mutation may result in a substitution of an amino acid residue located: at position 172, 178, 325, and/or 332 with reference to amino acid position numbering of SEQ ID NO:71, of T127, E133, P218, E264, L266, and/or L271 with reference to amino acid position numbering of SEQ ID NO:104, of T65, E69, P214, and/or L216 with reference to amino acid position numbering of SEQ ID NO:138, of T102, E105, P190, E236 S237, and/or L238 with reference to amino acid position numbering of SEQ ID NO:161, of S160 and/or L161 with reference to amino acid position numbering of SEQ ID NO:188 and/or of T172, E178K, E325K, and/or L332 with reference to amino acid position numbering of SEQ ID NO:214. In some embodiments, a substitution may be a substitution of threonine (T) for isoleucine (I) (T>I), glutamic acid (E) for lysine (K) (E>K), leucine (L) for phenylalanine (F) (L>F), proline (P) for leucine (L) (P>L), and/or serine (S) for leucine (L) (S>L). In some embodiments, a mutation may result in an amino acid substitution of T172, E178K, E325K, and/or L332 with reference to amino acid position numbering of SEQ ID NO:71, of T127, E133, P218, E264, L266, and/or L271 with reference to amino acid position numbering of SEQ ID NO:104, of T65, E69, P214, and/or L216 with reference to amino acid position numbering of SEQ ID NO:138, of T102, E105, P190, E236 S237, and/or L238 with reference to amino acid position numbering of SEQ ID NO:161, of S160 and/or L161 with reference to amino acid position numbering of SEQ ID NO:188 and/or of T172, E178K, E325K, and/or L332 with reference to amino acid position numbering of SEQ ID NO:214, optionally the amino acid substitution may be T172I, E178K, E325K, and/or L332F with reference to amino acid position numbering of SEQ ID NO:71, of T127I, E133K, P218L, E264K, L266F, and/or L271F with reference to amino acid position numbering of SEQ ID NO:104, of T65I, E69K, P214L, and/or L216F with reference to amino acid position numbering of SEQ ID NO:138, of T102I, E105K, P190L, E236K, S237L, and/or L238F with reference to amino acid position numbering of SEQ ID NO:161, of S160L and/or L161F with reference to amino acid position numbering of SEQ ID NO:188 and/or an amino acid substitution of T172I, E178K, E325K, and/or L332F with reference to amino acid position numbering of SEQ ID NO:214. In some embodiments, a modified HK polypeptide may be encoded by a nucleic acid sequence having at least 90% sequence identity to any one of SEQ ID NOs:244-259.

Also provided are nucleic acids encoding mutated HK polypeptides, optionally wherein when present in a plant or plant part the mutated HK polypeptide/mutated HK gene results in the plant comprising a phenotype of one or more improved yield traits as compared to a plant or plant part devoid of the mutation.

Nucleic acid constructs of the invention (e.g., a construct comprising a sequence specific nucleic acid binding domain (e.g., sequence specific DNA binding domain), a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous HK genes, e.g., endogenous HK1 gene, endogenous HK2 gene, endogenous HK3 gene, endogenous HK4 gene, endogenous HK6 gene) and/or their expression.

Any plant comprising an endogenous HK gene that is capable of conferring at least one improved yield trait, when modified as described herein, may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to improve one or more yield traits in the plant. A plant exhibiting an improved yield trait may show an improvement of about 5% to about 100% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or more or any range or value therein; e.g., about 5% to about 10%, about 5% to about 15%, about 5% to about 20%, about 10% to about 50%, about 10% to about 80%, about 10% to about 90%, about 10% to about 100%, about 20% to about 50%, about 20% to about 80%, about 20% to about 90%, about 20% to about 100%, about 30% to about 50%, about 30% to about 80%, about 30% to about 90%, about 30% to about 100%, about 50% to about 100%, about 75% to about 100% or more, and any range or value therein) in the yield trait as compared to a plant or part thereof that is devoid of the mutated endogenous HK gene.

An editing system useful with this invention can be any site-specific (sequence-specific) genome editing system now known or later developed, which system can introduce mutations in a target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing Cytokinin Receptor Histidine Kinase (HK) gene may comprise contacting a target nucleic acid (e.g., a nucleic acid encoding an HK polypeptide, e.g., an HK1 polypeptide, an HK2 polypeptide, an HK3 polypeptide, an HK4 polypeptide, an HK6 polypeptide) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a Cytokinin Receptor Histidine Kinase (HK) gene may comprise contacting a target nucleic acid (e.g., a nucleic acid encoding an HK polypeptide) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fused to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous HK gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantages of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Example Cas9 sequences include, but are not limited to, the amino acid sequences of SEQ ID NO:56 and SEQ ID NO:57 or the nucleotide sequences of SEQ ID NOs:58-68.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., amino acid sequences of SEQ ID NOs:1-17, nucleic acid sequences of SEQ ID NOs:18-20). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as dead Cas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26

(e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "–", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made, and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer) (e.g., a portion of consecutive nucleotides of a sequence that (a) comprises a sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to a nucleotide sequence of any one of SEQ ID NOs:69, 70, 102, 103, 136, 137, 165, 166, 186, 187, 212 or 213; (b) comprises a region having at least 80% identity to any one of SEQ ID NOs:72-94, 105-120, 139-150, 162-174, 189-205 or 215-222; (c) encodes an amino acid sequence having at least 80% sequence identity to any one of SEQ ID NOs:71, 104, 138, 161, 188 or 214; and/or (d) encodes an amino acid sequence comprising a region having at least 80% identity to any one of SEQ ID NOs:95-101, 121-135, 151-158, 175-185 or 206-211. In some embodiments, a spacer sequence (e.g., one or more spacers) may include, but is not limited to, the nucleotide sequences of any one of SEQ ID NOs:223-243. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%, or any value or range therein)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic 100% c acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., such as for a Type V CRISPR-Cas system), or the 3' region of a spacer sequence of a guide nucleic acid may be identical to a target DNA, while the 5' region of the spacer may be substantially complementary to the target DNA (e.g., such as for a Type II CRISPR-Cas system), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
 5'-NNNNNNNNNNNNNNNNNNN-3' RNA Spacer
     |||||||||||||||||||
3'AAANNNNNNNNNNNNNNNNNN-5' Target strand
  ||||
5'TTTNNNNNNNNNNNNNNNNNNN-3' Non-target strand
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains (e.g., sequence-specific DNA binding domains), CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:42-44.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide *Pumilio*/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous Cytokinin Receptor Histidine Kinase (HK) gene may be modified as described herein to improve one or more yield traits. Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower.

In some embodiments, a plant that may be modified as described herein may include, but is not limited to, corn, soybean, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleracea, B. rapa, B. juncea*, and/or *B. nigra*). In some embodiments, a plant that may be modified as described herein is a dicot. In some embodiments, a plant that may be modified as described herein is a monocot. In some embodiments, a plant that may be modified as described herein is corn (i.e., *Zea mays*). In some embodiments, a plant that may be modified as described herein is soybean (i.e., *Glycine max*).

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Modification of Cytokinin Receptor Histidine Kinase (HK) Genes in Soybean A strategy to generate edits in soybean Cytokinin Receptor Histidine Kinase (HK) genes (e.g., Glyma05G148100 (HK2), Glyma08G105000 (HK3) and/or Glyma07G173700 (HK4) was developed. Cytokinin Receptor Histidine Kinase (HK) genes from soybean were identified. Editing constructs were designed to target or otherwise affect the function of the CHASE (Cyclases/Histidine kinases Associated Sensory Extracellular) domain (e.g., the extracellular cytokinin binding domain) of the soybean HK genes and generate mutations in or adjacent to the CHASE domain that result in a mutation, for example, a gain of function mutation, in the encoded HK polypeptide. In this example, editing constructs with spacers PWsp733 (SEQ ID NO:233), PWsp1242 (SEQ ID NO:234) and PWsp1243 (SEQ ID NO:235) were transformed into soybean plants and plants regenerated.

Edited plants are identified by Next Generation Sequencing (NGS) and those with confirmed edits in the targeted genes were allowed to self-pollinate to generate seed. The seed was planted and assayed by Next Generation Sequencing to further identify and confirm the edits obtained in HK genes (HK2, HK3, HK4).

Example 2. Modification of Cytokinin Receptor Histidine Kinase (HK) Genes in Corn (HK1 and HK6)

A strategy to generate edits in maize Cytokinin Receptor Histidine Kinase (HK) genes (e.g., HK1, HK6) was developed. The maize genes HK1 (Zm00001d017977) and HK6 (Zm00001d051812) (SEQ ID NO:159, and SEQ ID NO:187, respectively) were identified and editing constructs designed to generate mutations in and adjacent to the CHASE domain that result in a mutation, for example a gain of function mutation, in the encoded HK polypeptide. In one example, the spacer PWsp1223 (SEQ ID NO:240) was employed to generate edits. Maize plants were transformed with the editing construct and plants were recovered.

The resulting edited plants were assayed by Next Generation Sequencing (NGS) and those with confirmed edits in the target genes were allowed to self-pollinate to generate seed. The seed was planted and assayed NGS to further identify and confirm the edits obtained in HK6 and/or HK1.

Example 3. Edited Soybean Alleles

Soybean plant CE62491 was generated as described in Example 1 and transferred to the greenhouse to set E1 seed. The E1 seed of CE62491 was planted and individual plants were evaluated for edited alleles of the HK target genes. E1 plant CE87556 was found to be homozygous for a modified allele of Glyma08G105000 (SEQ ID NO:69), the modified allele having a deletion of 3 bp at position 2122 of SEQ ID NO:69 (deleted sequence is "TGA") resulting in an in-frame deletion of one amino acid (modified genomic sequence of SEQ ID NO:244). Glyma08G105000 was the only HK gene that was edited in CE87556; all of the other HK genes were unmodified.

Soybean plant CE62514 was generated as described in Example 1 and transferred to the greenhouse to set E1 seed. The E1 seed of CE62514 was planted and individual plants were evaluated for edited alleles of the HK target genes. The E1 plant CE87658 was found to be homozygous for modified alleles of two HK genes. The Glyma08G105000 gene contained a 6 bp deletion (TTTGAT) at position 2121 of SEQ ID NO:69 resulting in an in-frame deletion of 2 amino acids (modified genomic sequence of SEQ ID NO:245). The Glyma05G148100 gene contained a 3 bp deletion (ATG) at position 2994 of SEQ ID NO:246 resulting in an in-frame deletion of one amino acid.

Example 4. Soybean Phenotype

Soybean seed was germinated and placed into pots and grown in the greenhouse until the plants reached the R6 stage of growth. The resulting plants were evaluated for phenotypic characteristics associated with yield including direct measurement of plant height (cm), branches per plant, total pods on all branches, nodes on branches, pods on mainstem, nodes on mainstem, nodes on plant, pods per node on branches, pods per node on mainstem, pods per node on plant, pod dry weight, seed dry weight; and image analysis as well as direct analysis of the phenotypes number of pods per plant, seeds on branch, seeds on mainstem, seeds per plant; and calculated values including average seeds per pod, average seed area per plant, average seed diameter, pod length and hundred seed weight (see Table 1).

TABLE 1

| Phenotypic observations | | | | | | | | |
|---|---|---|---|---|---|---|---|---|
| Family | Nodes on Mainstem | Number of branches | Pods on branches | Pods on Mainstem | Pods per node on mainstem | Pods per plant | Seeds per plant | Seeds per pod |
| CE87556 (30 plants) | 24.9 | 9.6 | 107.5 | 54.9 | 2.2 | 162.4 | 314.6 | 1.9 |
| CE87658 (30 plants) | 25.3 | 8.4 | 73.8 | 46.8 | 1.9 | 120.7 | 131.3 | 1.1 |
| Unedited control (29 plants) | 21.1 | 11.1 | 116.9 | 49.2 | 2.3 | 166.1 | 359.9 | 2.2 |

Several architectural changes were observed such as a greater number of nodes along the mainstem, a decrease in branching, a decrease in pods on branches and an increase in pods per node on mainstem in the CE87556 line. Taken together, these results suggest that the edits in the Glyma08G10500 and/or Glyma05G148100 genes in soybean were affecting architectural traits associated with yield.

Example 5. Modification of HK3 Genes in Corn

A strategy to generate edits in maize Cytokinin Receptor Histidine Kinase (HK) gene HK3 (Zm00001d014297) was developed. The spacer PWsp1219 (CAGCAAGGACAA-CATTTGAAAGG SEQ ID NO:236) was employed to generate mutations in the encoded HK polypeptide in the kinase region of HK3. Maize plants were transformed with the editing construct and regenerating plants were recovered.

The genomes of regenerated plants were assayed by Next Generation Sequencing (NGS) and those with confirmed edits in the target gene were allowed to self-pollinate to generate seed. A range of edits were recovered which segregated in the subsequent generation to create a range of edited allele combinations which are further described in Table 2.

TABLE 2

Edited alleles in corn

| HK3 edited allele | Edit description | Notes |
|---|---|---|
| Allele A (SEQ ID NO: 250) (CE98497) | At position 8004 of SEQ ID NO: 136, the base C was converted to a G | In-frame mutation |
| Allele B (SEQ ID NO: 251) (CE98500) | At position 8004 of SEQ ID NO: 136, the base C was converted to a G; at position 8007 of SEQ ID NO: 136, the base C was converted to T | In-frame mutations |

Corn plants were grown under greenhouse conditions to flowering. At flowering, the plants were self-pollinated and the ears permitted to mature and dry down on the plant. The mature ears were harvested and the kernel row number was determined by direct counting of rows by inserting a marker (i.e. paper clip) in between a kernel row to ensure that a row is not counted twice. Kernel row number was determined by counting rows at about the middle of the ear. The harvested ear was directly measured for ear length starting from the base (top of the shank) to the tip, including any tip void. The ear width of the harvested ears was measured directly at the widest part of the ear. In addition to direct measurement, ear length and ear width was calculated based upon image analysis of the harvested ears. The ear phenotype data is outlined in Table 3 below and the asterisk (*) identifies data points sufficiently different from the unedited lines to suggest the edited allele(s) of HK3 are affecting ear architecture and may increase yield.

TABLE 3

Phenotypic analysis

| HK3 allele | KRN | Ear length (cm) | Ear width (cm) |
|---|---|---|---|
| Allele A heterozygous | 15.3 | 13.4 | 3.2 |
| Allele B homozygous | 14.67 | 13.1 | 2.8 |
| Allele B heterozygous | 16 | 14.9 | 3.4 |
| Null segregants | 15.22 | 13.9 | 3.6 |

Example 6. Modification of HK3 Genes in Corn

A strategy to generate edits in maize Cytokinin Receptor Histidine Kinase (HK) gene HK3 (Zm00001d014297) was developed. The spacer PWsp1222 (CTAGCGAGTTGTTCTAGGAGTTT, SEQ ID NO:239) was employed to generate out-of-frame mutations in the encoded HK polypeptide. Maize plants were transformed with the editing construct and regenerating plants were recovered.

The regenerated plants were assayed by NGS and those with confirmed edits in the target gene were allowed to self-pollinate to generate seed. A range of edits were recovered which segregated in the subsequent generation to create a range of edited allele combinations which are further described in Table 4.

TABLE 4

HK3 edits in corn

| HK3 Zm00001d014297 allele | Edit description | Notes |
|---|---|---|
| Allele C (SEQ ID NO: 252) (CE113686) | 5 bp deletion (TCCTA) at position 8992 of SEQ ID NO: 136 | Out of-frame mutation |
| Allele D (SEQ ID NO: 253) (CE113686) | 17 bp deletion (TTGATAAA CTCCTAGAA, SEQ ID NO: 260) at position 8983 of SEQ ID NO: 136 | |
| Allele E (SEQ ID NO: 254) (CE113691 10D version) | 10 bp deletion (TAAACTCCTA, SEQ ID NO: 261) at position 8987 of SEQ ID NO: 136 | Out of-frame mutation |
| Allele F (SEQ ID NO: 255) (CE113691 9D version) | 9 bp deletion (AAACTCCTA) at position 8988 of SEQ ID NO: 136 | In-frame deletion of die amino acids KLL at position 219 of SEQ ID NO: 138 |
| Allele G (SEQ ID NO: 256) (CE13700) | 8 bp deletion (AACTCCTA) at position 8989 of SEQ ID NO: 136 | Out of-frame mutation |

E2 plants were grown to flowering under greenhouse conditions. At flowering, the plants were self-pollinated, and the ears permitted to mature and dry down on the plant. The mature ears were harvested, and the kernel row number was determined by direct counting of rows by inserting a marker (i.e. paper clip) in between a kernel row to ensure that a row is not counted twice. Kernel row number was determined by counting rows at about the middle of the ear. The harvested ear was directly measured for ear length starting from the base (top of the shank) to the tip, including any tip void. The ear width of the harvested ear was measured directly at the widest part of the ear. In addition to direct measurement, ear length and ear width was calculated based upon image analysis of the harvested ears. As outlined in Table 5 below, some of the edited allele combinations showed an increase in ear length and/or ear width as compared to an unedited control plant. These observations suggest that the edited alleles of the HK genes are affecting ear architecture and may lead to an increase in yield.

TABLE 5

| Genotypic and phenotypic analysis | | | |
|---|---|---|---|
| HK3 Allele (genotype) | Ear length (cm) | Ear width (cm) | Sample number |
| Allele E (heterozygous) Allele C (heterozygous) | 17.3 | 3.8 | 1 |
| Allele E (heterozygous) Allele F (heterozygous) | 16 | 3.4 | 2 |
| Allele E (heterozygous) | 15.3 | 3.7 | 2 |
| Allele D (heterozygous) Allele E (heterozygous) | 13.9 | 3.7 | 2 |
| Allele D (heterozygous) Allele C (heterozygous) | 16.8 | 3.4 | 2 |
| Allele C (heterozygous) | 17.5 | 3.7 | 2 |
| Allele G (heterozygous) Allele C (heterozygous) | 17.4 | 3.8 | 5 |
| Allele E (homozygous) | 16.9 | 4.3 | 1 |
| Unedited control | 16.9 | 4.1 | 14 |

Example 7, Modification of HK1 and HK6 Genes in Corn

A strategy to generate edits in maize Cytokinin Receptor Histidine Kinase (HK) genes (e.g., K1, HK6) was developed. The maize genes HK1 (Zm00001d017977) and HK6 (Zm00001d051812) (SEQ ID NO:159, and SEQ ID NO:187, respectively) were identified and editing constructs designed to generate mutations in and adjacent to the kinase domain that result in a mutation, for example, a gain of function mutation, in the encoded HK polypeptide. In one example, the spacer PWsp1226 (AAGTGGTTTGATCCAAGCAACCG, SEQ ID NO:243) was employed to generate edits. Maize plants were transformed with the editing construct and plants were recovered.

The resulting edited plants were assayed by NGS and those with confirmed edits in the target genes were allowed to self-pollinate to generate seed. The seed was planted and assayed by NGS to further identify and confirm the edits obtained in HK6 and/or HK1. The edited alleles are summarized in Table 6 and Table 7 below:

TABLE 6

| HK1 edits in corn | | |
|---|---|---|
| HK1 | Edit description | Notes |
| Allele B (CE114269) | 24 bp deletion (CAAACCCATTCCG GTTGCTTGGAT) at position 2364 in SEQ ID NO: 162 | In frame mutation |
| Allele C (CE114640) | 7 bp deletion (TTGCTTG) at position 2378 of SEQ ID NO: 162 | Out of frame mutation leading to an early stop codon |

TABLE 7

| HK6 edits in corn | | |
|---|---|---|
| HK6 | | |
| Allele C (CE114379) | 4 bp deletion (TTGC) at position 1701 in SEQ ID NO: 189 | Out of frame mutation leading to an early stop codon |

Edited HK genes segregated in each generation giving rise to various combinations of edits in the HK genes, HK6 and HK1. Corn plants were grown to flowering under greenhouse conditions. At flowering, the plants were self-pollinated, and the ears permitted to mature and dry down on the plant. The mature ears were harvested and the kernel row number was determined by direct counting of rows by inserting a marker (i.e. paper clip) in between a kernel row to ensure that a row is not counted twice. Kernel row number was determined by counting rows at about the middle of the ear. The harvested ear was directly measured for ear length starting from the base (top of the shank) to the tip, including any tip void. The ear width of the harvested ear was measured directly at the widest part of the ear. In addition to direct measurement, ear length and ear width was calculated based upon image analysis of the harvested ears. As outlined in Table 8, below, some of the edited allele combinations showed an increase in ear length and/or ear width as compared to an unedited control plant. These observations suggest the edited alleles of the HK genes are affecting ear architecture which may affect yield.

TABLE 8

| Genotypic and phenotypic analysis | | | | |
|---|---|---|---|---|
| Zm00001d051812 edits | Zm00001d017977 edits | Ear length (cm) | Ear width (cm) | Sample number |
| Not edited | Allele B (heterozygous) | 17.7 | 4.2 | 4 |
| Allele C (heterozygous) | Heterozygous 4 bp deletion | 18.5 | 4.1 | 6 |
| Allele C (homozygous) | Heterozygous 4 bp deletion | 18.1 | 4.2 | 5 |
| Not edited | Heterozygous 4 bp deletion | 17.7 | 4.2 | 1 |
| Allele C (heterozygous) | Allele C (heterozygous) | 16.2 | 3.8 | 3 |
| Allele C (homozygous) | Allele C (heterozygous) | 14.4 | 3.3 | 2 |
| Heterozygous 24 bp deletion | Heterozygous 9 bp deletion | 16.9 | 4.3 | 3 |
| Not edited | Heterozygous 9 bp deletion | 16.2 | 4.1 | 2 |
| Not edited | Allele B (homozygous) | 17.5 | 3.9 | 4 |
| Allele C (heterozygous) | Allele C (homozygous) | 17.8 | 3.7 | 1 |
| Allele C (homozygous) | Allele C (homozygous) | 17.2 | 2.9 | 2 |
| Not edited | Allele C (homozygous) | 17.7 | 4.1 | 1 |
| Allele C (homozygous) | Not edited | 17 | 4 | 6 |
| Null segregant (not edited) | Null segregant (not edited) | 17.2 | 3.8 | 5 |
| Unedited control | Unedited control | 16.9 | 4.1 | 14 |

Example 8. Phenotypic Analysis

Regenerated plants produced as described in Example 3 were transferred to the greenhouse to mature and set E1 seed. E1 seed was germinated and the resulting plants analyzed by next generation sequencing for edits in the target HK genes, Zm00001d51812 (HK6) and Zm00001d017977 (HK1). Selected plants were allowed to mature and set E2 seed. Edited HK genes segregated in the E2 population giving rise to various combinations of edits in the HK genes, HK1 and HK6. The edited alleles are summarized in Table 9 below.

TABLE 9

| HK edits in corn | | |
|---|---|---|
| HK edited allele | Genomic change | notes |
| Zm00001d051812 (HK6) allele A (SEQ ID NO: 247) (CE92016) | Base 2238 of SEQ ID NO: 187 changed from C to T | Gave rise to a change from amino acid S to L at position 160 of SEQ ID NO: 189 |
| Zm00001d051812 (HK6) allele B (SEQ ID NO: 248) (CE92008) | Base 2238 of SEQ ID NO: 187 changed from C to T; and base 2240 of SEQ ID NO: 187 changed from C to T | The base change at 2238 and 2240 altered adjacent amino acids from SL to LF at position 160 and 161 of SEQ ID NO: 189 |
| Zm00001d017977 (HK1) allele A (SEQ ID NO: 249) (CE91903) | Base 3083 of SEQ ID NO: 159 change from C to T | Gave rise to a change from amino acid S to L at position 237 of SEQ ID NO: 161 |

E2 plants were grown under greenhouse conditions and grown to flowering. At flowering, the plants were self-pollinated and the ears permitted to mature on the plant and dry down. The mature ears were harvested and the kernel row number was determined by direct counting of rows by inserting a marker (i.e. paper clip) in between a kernel row to ensure that a row is not counted twice. Kernel row number was determined by counting rows at about the middle of the ear. The harvested ear was directly measured for ear length starting from the base (top of the shank) to the tip, including any tip void. The ear width of the harvested ear was measured directly at the widest part of the ear. In addition to direct measurement, ear length and ear width was calculated based upon image analysis of the harvested ears. As outlined in Table 10, below, all of the edited allele combinations as well as the null segregants described above showed an increase in ear length as compared to an unedited control plant. These observations suggest the edits in the HK genes as described herein are affecting ear architecture.

TABLE 10

| Genotype and phenotypic analysis | | | |
|---|---|---|---|
| Genotype | Ear length (cm) | Ear width (cm) | Sample number |
| Heterozygous Zm00001d051812 (HK6) allele A | 17 | 3.8 | 14 |
| Heterozygous Zm00001d051812 (HK6) allele B | 16.7 | 3.8 | 6 |
| Heterozygous Zm00001d017977 (HK1) allele A | 18 | 4 | 3 |
| Homozygous Zm00001d051812 (HK6) allele A | 16.7 | 3.5 | 5 |
| Homozygous Zm00001d051812 (HK6) allele B | 16.2 | 2.6 | 2 |
| Homozygous Zm00001d017977 (HK1) allele A | 16.7 | 4 | 5 |
| Null segregants | 16.7 | 3.8 | 7 |
| Unedited control | 15.4 | 3.6 | 17 |

The foregoing is illustrative of the present invention and is not to be construed as limiting thereof. The invention is defined by the following claims, with equivalents of the claims to be included therein.

That which is claimed is:

1. A corn plant or plant part thereof comprising at least one mutation in an endogenous Cytokinin Receptor Histidine Kinase (HK) gene encoding a histidine kinase (HK) polypeptide, wherein the encoded HK polypeptide comprises an extracellular cytokinin binding domain, wherein the encoded HK polypeptide has at least 85% sequence identity to SEQ ID NO:189, and wherein the at least one mutation is a deletion of about 1 base pair to about 27 consecutive base pairs or wherein the at least one mutation results in a substitution of any one or more amino acid residues located in a region having at least 85% sequence identity to any one of the amino acid sequences of SEQ ID NOs: 183-186 or 210-211.

2. The corn plant or plant part thereof of claim 1, wherein the at least one mutation is the deletion of about 1 base pair to about 27 consecutive base pairs.

3. The corn plant or plant part thereof of claim 1, wherein the endogenous HK gene comprises a nucleotide sequence having at least 85% sequence identity to SEQ ID NO:187 or 188.

4. The corn plant or plant part thereof of claim 1, wherein the substitution is located at position 160 and/or 161 with reference to amino acid position numbering of SEQ ID NO: 189.

5. The corn plant or plant part thereof of claim 4, wherein the substitution is threonine (T) to isoleucine (I) (T>I), glutamic acid (E) to lysine (K) (E>K), leucine (L) to phenylalanine (F) (L>F), proline (P) to leucine (L) (P>L), and/or serine(S) to leucine (L) (S>L).

6. The corn plant or plant part thereof of claim 1, wherein the corn plant comprising the at least one mutation has a phenotype of one or more improved yield traits as compared to a corn plant that is devoid of the at least one mutation.

7. The corn plant or plant part thereof of claim 1, wherein the at least one mutation results in a mutated HK gene comprising a nucleotide sequence having at least 90% sequence identity to SEQ ID NO:247, SEQ ID NO:248, or SEQ ID NO:258.

8. A corn plant cell comprising at least one mutation within an endogenous Cytokinin Receptor Histidine Kinase (HK) gene, wherein the at least one mutation is a substitution or deletion that is introduced using an editing system that comprises a nucleic acid binding domain that binds to a target site in the endogenous HK gene, wherein the target site is within a region of the endogenous HK gene (a) having at least 95% sequence identity to any one of the nucleotide sequences of SEQ ID NOs:190-206 and/or (b) encoding an amino acid sequence having at least 95% sequence identity to any one of SEQ ID NOs:183-186 or 207-211, wherein the at least one mutation is a deletion of about 1 base pair to about 27 consecutive base pairs or wherein the at least one mutation results in a substitution of any one or more amino acid residues located in a region having at least 85% sequence identity to any one of the amino acid sequences of SEQ ID NOs:183-186 or 210-211, and wherein the at least one mutation results in a mutated HK gene comprising a nucleotide sequence having at least 95% sequence identity to any one of SEQ ID NOs: 247-259.

9. The corn plant cell of claim 8, wherein the editing system further comprises a nuclease, wherein the target site is within a sequence having least 80% sequence identity to a sequence encoding of any one of SEQ ID NO:187 or a sequence having at least 80% sequence identity to a sequence encoding any one of SEQ ID NOs:190-206, and wherein the at least one mutation is made following cleavage by the nuclease.

10. The corn plant cell of claim 8, wherein the at least one mutation results in the substitution of any one or more amino acid residues located in a region having at least 85% sequence identity to any one of the amino acid sequences of SEQ ID NOs:183-186 or 210-211.

11. The corn plant cell of claim 10, wherein the substitution is an amino acid substitution of S160 and/or L161 with reference to amino acid position numbering of SEQ ID NO:189.

12. A method for producing a corn plant or plant part thereof comprising at least one cell having a mutated endogenous Cytokinin Receptor Histidine Kinase (HK) gene, the method comprising:

contacting a target site in an endogenous HK gene in the corn plant or plant part with a nuclease comprising a cleavage domain and a nucleic acid binding domain, wherein the nucleic acid binding domain binds to a target site in the endogenous HK gene, wherein the endogenous HK gene:

(a) comprises a sequence having at least 95% sequence identity to a nucleotide sequence of any one of SEQ ID NOs:187 or 188;

(b) comprises a region having at least 95% identity to any one of SEQ ID NOs: 190-206;

(c) encodes an amino acid sequence having at least 95% sequence identity to any one of SEQ ID NOs:189; and/or (d) encodes an amino acid sequence comprising a region having at least 95% identity to any one of SEQ ID NOs:207-211, thereby producing the corn plant or plant part thereof comprising at least one cell having a mutation in the endogenous HK gene, wherein the mutation is a deletion of about 1 base pair to about 27 consecutive base pairs or wherein the mutation results in a substitution of any one or more amino acid residues located in a region having at least 85% sequence identity to any one of the amino acid sequences of SEQ ID NOs:183-186 or 210-211, and wherein the mutated endogenous HK gene comprises a nucleotide sequence having at least 95% sequence identity to any one of SEQ ID NOs:247-259.

13. The method of claim 12, wherein the mutation is the substitution of any one or more amino acid residues located in a region having at least 85% sequence identity to any one of the amino acid sequences of SEQ ID NOs:183-186 or 210-211.

14. The method of claim 12, wherein the mutation is the deletion of about 1 base pair to about 27 consecutive base pairs.

15. The method of claim 12, wherein the mutation results in a modified amino acid residue located in a region having at least 80% sequence identity to any one of the amino acid sequences of SEQ ID NOs:183-186 or 207-211.

16. The corn plant or plant part thereof of claim 1, wherein the at least one mutation results in a mutation in the encoded HK polypeptide that is in or adjacent to the extracellular cytokinin binding domain of the HK polypeptide.

17. A corn plant or plant part thereof comprising at least one mutation in an endogenous Cytokinin Receptor Histidine Kinase (HK) gene encoding a histidine kinase (HK) polypeptide, wherein the encoded HK polypeptide comprises an extracellular cytokinin binding domain, wherein the endogenous HK gene comprises a nucleotide sequence having at least 85% sequence identity to any one of SEQ ID NOs:159, 160, 187, or 188 and encodes a HK polypeptide having at least 85% sequence identity to SEQ ID NO:161 or SEQ ID NO:189, and wherein the at least one mutation is a deletion of about 1 base pair to about 27 consecutive base pairs or wherein the at least one mutation results in a substitution of any one or more amino acid residues located in a region having at least 85% sequence identity to any one of the amino acid sequences of SEQ ID NOs:180, 181, 183-186 or 210-211.

* * * * *